United States Patent [19]

Tseng

[11] Patent Number: 4,838,925
[45] Date of Patent: Jun. 13, 1989

[54] HETEROCYCLIC ACYL SULFONAMIDES

[75] Inventor: Chi-Ping Tseng, Wilmington, Del.

[73] Assignee: E. I. Du Pont de Nemours and Company, Wilmington, Del.

[21] Appl. No.: 101,314

[22] Filed: Sep. 25, 1987

Related U.S. Application Data

[63] Continuation-in-part of Ser. No. 22,949, Mar. 17, 1987, abandoned, which is a continuation-in-part of Ser. No. 892,062, Aug. 1, 1986, abandoned, which is a continuation-in-part of Ser. No. 856,511, Apr. 25, 1986, abandoned.

[51] Int. Cl.$^4$ ............... C07D 401/12; C07D 401/14; C07D 417/12; C07D 487/04; A01N 43/90; A01N 43/54; A01N 43/86; A01N 43/88

[52] U.S. Cl. .................................. 71/90; 71/91; 71/92; 71/93; 544/3; 544/49; 544/235; 544/236; 544/249; 544/250; 544/251; 544/256; 544/254; 544/255; 544/262; 544/263; 544/252; 544/253; 544/278; 544/279; 544/280; 544/281; 544/282; 544/350; 544/349; 544/47; 544/48; 544/115; 544/116; 544/118; 544/119; 544/96; 544/72; 544/117; 544/73; 544/63; 544/66; 544/78; 544/80; 544/81; 544/91; 544/92

[58] Field of Search ............... 71/90, 91, 92; 544/281, 544/49, 3, 235, 250, 254, 263, 278, 282, 47, 116, 119, 73, 78, 91

[56] References Cited

U.S. PATENT DOCUMENTS 4,622,062 11/1986 Wexler .................................. 71/94

FOREIGN PATENT DOCUMENTS 150974 8/1985 European Pat. Off. .
84/8844 5/1985 South Africa .

OTHER PUBLICATIONS

J. Med. Chem., 1974, 17 645, Novinson et al.
Makisumi, Yasuo, Chem. and Pharm. Bulletin 10, (1962), 612–620.

Primary Examiner—John M. Ford

[57] ABSTRACT

This invention relates to novel heterocyclic carbonyl sulfonamides which are particularly useful as agricultural chemicals.

44 Claims, No Drawings

HETEROCYCLIC ACYL SULFONAMIDES

BACKGROUND OF THE INVENTION

This invention relates to heterocyclic carbonyl sulfonamides which are especially useful as agricultural chemicals.

*J. Med. Chem.*, 1974, 17, 645 describes the synthesis of ethyl-5,7-dimethylpyrazolo[1,5-a]pyrimidine-3-carboxylate. No herbicidal use for the compound is disclosed.

Yasuo Nakisumi in *Chem. and Pharm. Bulletin*, 10 (1962), 612 describes the synthesis of 5,7-dimethylpyrazolo[1,5-A]pyrimidine-3-carboxylic acid.

EP-A-No. 150,974, published Aug. 7, 1985, teaches compounds of the following formula to have herbicidal activity.

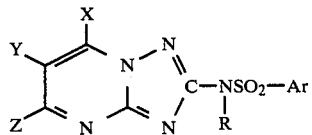

South African Patent Application No. 84/8844, discloses substituted 1,2,4-triazolo[1,5-a]pyrimidine-2-sulfonamides of the following formula as herbicides and plant growth regulants.

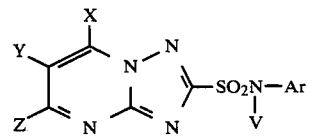

SUMMARY OF THE INVENTION

This invention relates to novel compounds of Formulae Ia and Ib, agriculturally suitable compositions containing them and their method-of-use as preemergent and/or postemergent herbicides or plant growth regulants

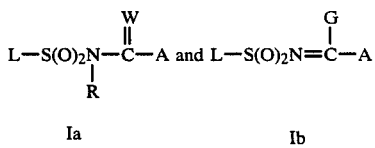

wherein
R is H; $C_1$–$C_3$ alkyl optionally substituted with halogen; $C_1$–$C_3$ thioalkyl optionally substituted with halogen; benzyl optionally substituted with F, Cl, $OCH_3$, $SCH_3$ or $NO_2$; allyl; propargyl; —C(O)(-$C_1$–$C_3$ alkyl); $CO_2CH_3$; or $CO_2CH_2CH_3$;
G is Cl, OR' or SR';
R' is $C_1$–$C_3$ alkyl optionally substituted with halogen;
W is O, S, NR" or NOR";
R" is H or $C_1$–$C_3$ alkyl optionally substituted with halogen;
L is

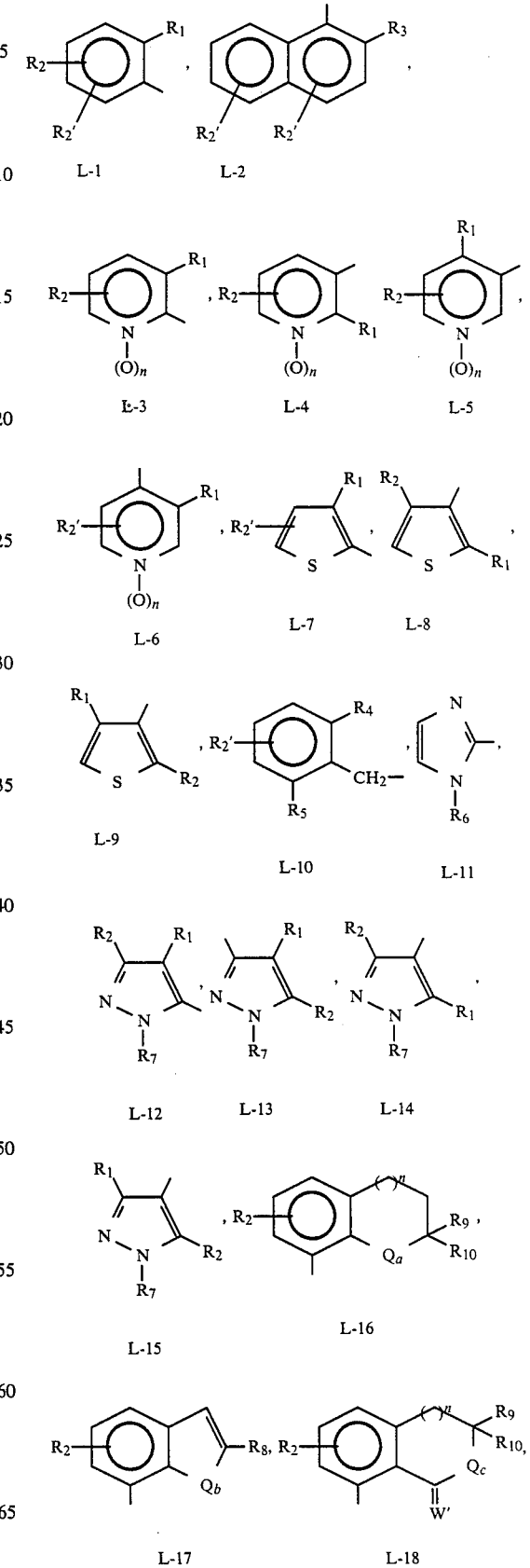

-continued

L-19
L-20
L-21
L-22
L-23
L-24
L-25

$R_1$ is H; halogen; $NO_2$; CN; $C_1$-$C_4$ alkyl optionally substituted with F, Cl, Br, CN, $OCH_3$ or $SCH_3$; $C_2$-$C_4$ alkenyl optionally substituted with F, Cl, Br, $OCH_3$ or SMe; $C_3$-$C_4$ alkynyl; $C_3$-$C_5$ cycloalkyl optionally substituted with F, Cl or $CH_3$; $C(O)R_{16}$; $C(OCH_2CH_2O)R_{16}$; $C(R_{16})(OR_{17})(OR_{18})$; $CO_2R_{19}$; $C(O)NR_{20}R_{21}$; $N_3$; $S(O)_2NR_{22}R_{23}$; $S(O)_2OR_{24}$; $OS(O)_2R_{25}$; phenyl optionally substituted by F, Cl, Br, $CH_3$ or $OCH_3$; $ER_{26}$; $(CH_2)_nQ$ or $(CH_2)_nQ_1$;

$R_2$ is H, halogen, CN, $NO_2$, $C_1$-$C_3$ alkyl optionally substituted with halogen, $CO_2R_{19}$, $S(O)_2NR_{27}R_{28}$, $NR_{29}R_{30}$, $ER_{31}$; or $C_1$-$C_2$ alkyl substituted with $C_1$-$C_2$ alkoxy, $C_1$-$C_2$ haloalkoxy, $C_1$-$C_2$ alkylthio, $C_1$-$C_2$ haloalkylthio, CN, OH or SH;

$R_2'$ is independently H, F, Cl, Br, $CH_3$, $OCH_3$, or $SCH_3$;

$R_3$ is H, $CH_3$, $OCH_3$, $OCF_2H$, F, Cl, Br, $CO_2R_{19}$, $S(O)_2N(CH_3)_2$, $OS(O)_2CH_3$ or $S(O)_pCH_3$;

$R_4$ is Cl, $NO_2$, $CO_2CH_3$, $CO_2CH_2CH_3$, $C(O)N(CH_3)_2$, $OS(O)_2CH_3$, $S(O)_2CH_3$, $S(O)_2CH_2CH_3$, $OCH_3$ or $OCH_2CH_3$;

$R_5$ is H, $C_1$-$C_3$ alkyl, F, Cl, Br, $NO_2$, $S(O)_2NR_{32}R_{33}$, $S(O)_2N(OCH_3)CH_3$ or $S(O)_pR_{34}$;

$R_6$ is $C_1$-$C_3$ alkyl or phenyl;

$R_7$ is H, $C_1$-$C_3$ alkyl optionally substituted with halogen, $C_3$-$C_4$ alkenyl, or phenyl;

$R_8$ is H or $CH_3$;

$R_9$ is H, $CH_3$ or $CH_2CH_3$;

$R_{10}$ is H, $CH_3$ or $CH_2CH_3$;

$R_{11}$ is H, Cl or $C_1$-$C_3$ alkyl;

$R_{12}$ is H, $C_1$-$C_4$ alkyl optionally substituted with F, Cl, Br or $OCH_3$; $C_3$-$C_5$ cycloalkyl optionally substituted with F, Cl or $OCH_3$; $C_3$-$C_4$ alkenyl; or $C_3$-$C_4$ alkynyl;

$R_{13}$ is H or $C_1$-$C_3$ alkyl;

$R_{14}$ is H, F, Cl, Br, $CH_3$ or $CH_2CH_3$;

$R_{15}$ is H, F, Cl, Br, $CH_3$ or $CH_2CH_3$;

$R_{16}$ is $C_1$-$C_4$ alkyl optionally substituted with F, Cl, Br or $OCH_3$; $C_3$-$C_5$ cycloalkyl optionally substituted with F or Cl; or $C_3$-$C_4$ alkenyl;

$R_{17}$ and $R_{18}$ are independently $C_1$-$C_3$ alkyl;

$R_{19}$ is $C_1$-$C_4$ alkyl, $C_3$-$C_4$ alkenyl, $C_3$-$C_4$ alkynyl; $C_2$-$C_4$ haloalkyl, $C_2$-$C_3$ cyanoalkyl, $C_3$-$C_6$ cycloalkyl, $C_4$-$C_7$ cycloalkylalkyl or $C_2$-$C_4$ alkoxyalkyl;

$R_{20}$ is H, $CH_3$ or $CH_2CH_3$;

$R_{21}$ is $CH_3$, $CH_2CH_3$, $CH_2CH_2CH_3$, $OCH_3$ or $OCH_2CH_3$; or $R_{20}$ and $R_{21}$ may be taken together to form $-(CH_2)_2(CH_2)_n(CH_2)_2-$ and $-CH_2CH_2OCH_2CH_2-$;

$R_{22}$ is $C_1$-$C_4$ alkyl, $C_2$-$C_3$ cyanoalkyl, $OCH_3$, $OCH_2CH_3$, $N(CH_3)_2$, $C_3$-$C_4$ alkenyl, $C_3$-$C_4$ alkynyl, cyclopropylmethyl or $C_3$-$C_4$ cycloalkyl;

$R_{23}$ is H, $C_1$-$C_4$ alkyl or $C_3$-$C_4$ alkenyl; or $R_{22}$ and $R_{23}$ may be taken together as $-(CH_2)_3-$, $-(CH_2)_4-$ or $-CH_2CH_2OCH_2CH_2-$;

$R_{24}$ is $C_1$-$C_3$ alkyl or $C_1$-$C_3$ haloalkyl;

$R_{25}$ is $C_1$-$C_3$ alkyl or $N(CH_3)_2$;

$R_{26}$ is $C_1$-$C_4$ alkyl, $C_1$-$C_4$ haloalkyl, $C_2$-$C_4$ alkoxyalkyl, $C_3$-$C_4$ alkenyl, $C_3$-$C_4$ alkynyl, phenyl optionally substituted by F, Cl, Br, $CH_3$ or $OCH_3$, or $C_2$-$C_4$ haloalkenyl;

$R_{27}$ is $C_1$-$C_3$ alkyl;

$R_{28}$ is H, $C_1$-$C_4$ alkyl or methoxy;

$R_{27}$ and $R_{28}$ may be taken together to form $-(CH_2)_4-$, $-(CH_2)_5-$ or $-CH_2CH_2OCH_2CH_2-$;

$R_{29}$ and $R_{30}$ are independently H, $CH_3$ or $CH_2CH_3$;

$R_{31}$ is $C_1$-$C_4$ alkyl optionally substituted with F, Cl or $OCH_3$;

$R_{32}$ is $CH_3$ or $CH_2CH_3$;

$R_{33}$ is H, $CH_3$ or $CH_2CH_3$;

$R_{34}$ is $C_1$-$C_3$ alkyl, $C_3$-$C_4$ alkenyl or $C_3$-$C_4$ alkynyl;

$Q_a$ is O, S, S(O), $S(O)_2$ or $NCH_3$;

$Q_b$ is O, S, or $S(O)_2$;

$Q_c$ is O, S, NH, $N(C_1$-$C_3$ alkyl), $NCH_2CH=CH_2$ or $NCH_2C\equiv CH$;

$Q_d$ is O, NH, $N(C_1$-$C_3$ alkyl), $NCH_2CH=CH_2$ or $NCH_2C\equiv CH$;

$Q_e$ is O or $NR_{12}$;

$Q_f$ is C(O) or $S(O)_2$;

$Q_g$ is O, S, NH or $N(C_1$-$C_3$ alkyl);

n is 0 or 1;

p is 0, 1 or 2;

W' is O or S;

E is O, S, S(O) or $S(O)_2$;

Q is

Q-1, Q-2, Q-3, Q-4

-continued
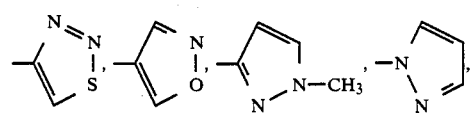
Q-5   Q-6   Q-7   Q-8
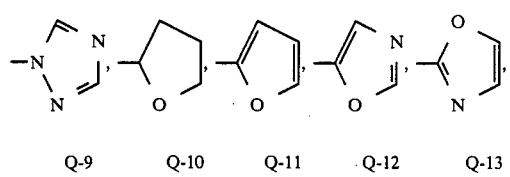
Q-9   Q-10   Q-11   Q-12   Q-13
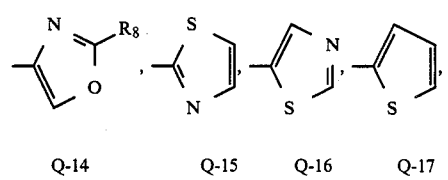
Q-14   Q-15   Q-16   Q-17
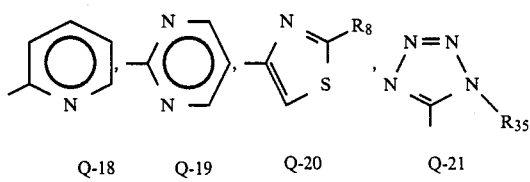
Q-18   Q-19   Q-20   Q-21
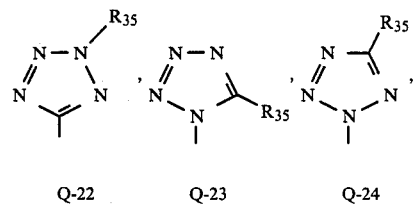
Q-22   Q-23   Q-24
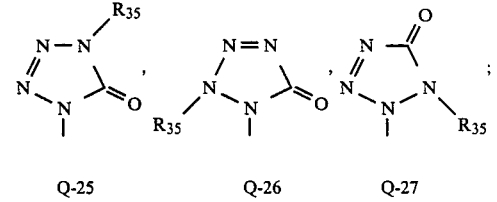
Q-25   Q-26   Q-27
$Q_1$ is
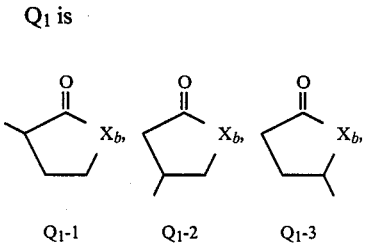
$Q_1$-1   $Q_1$-2   $Q_1$-3
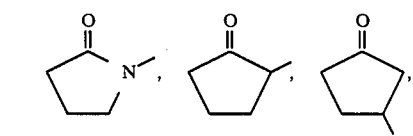
$Q_1$-4   $Q_1$-5   $Q_1$-6
-continued
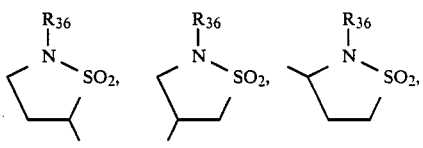
$Q_1$-7   $Q_1$-8   $Q_1$-9
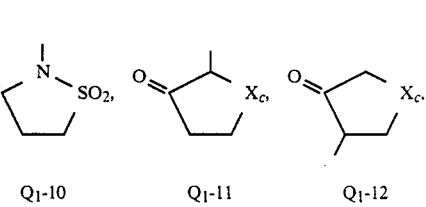
$Q_1$-10   $Q_1$-11   $Q_1$-12
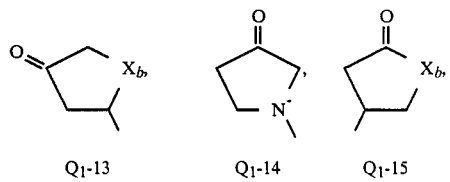
$Q_1$-13   $Q_1$-14   $Q_1$-15
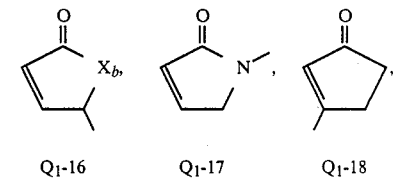
$Q_1$-16   $Q_1$-17   $Q_1$-18
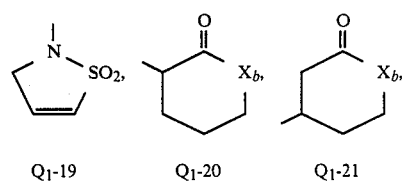
$Q_1$-19   $Q_1$-20   $Q_1$-21
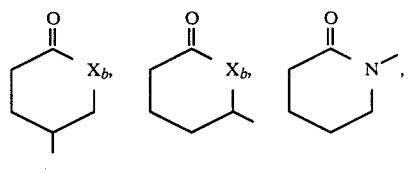
$Q_1$-22   $Q_1$-23   $Q_1$-24
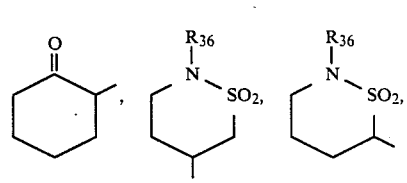
$Q_1$-25   $Q_1$-26   $Q_1$-27
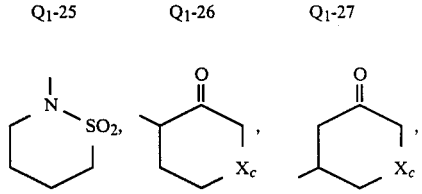
$Q_1$-28   $Q_1$-29   $Q_1$-30

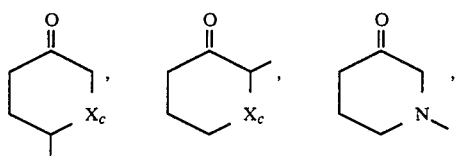

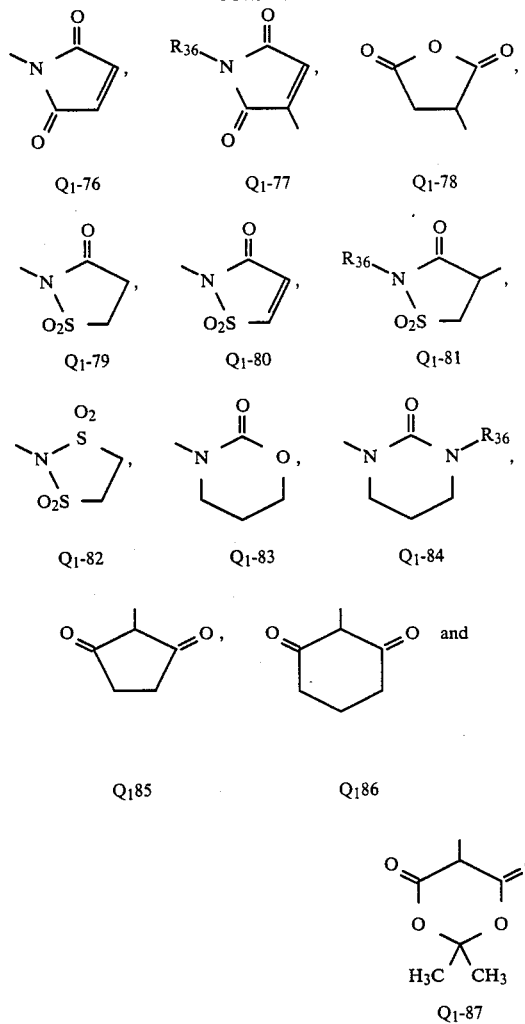
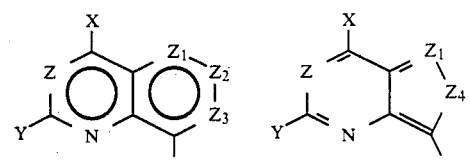
A-5, A-6
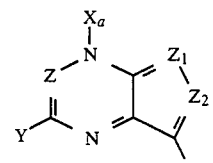
A-7
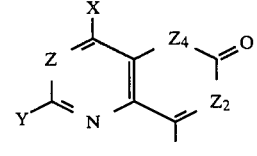
A-9
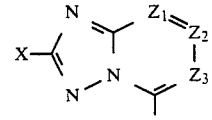
A-11
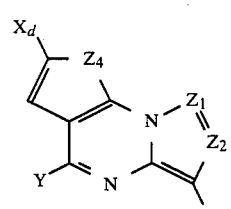
A-12
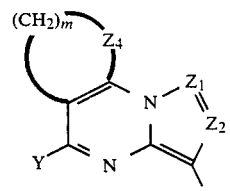
A-13
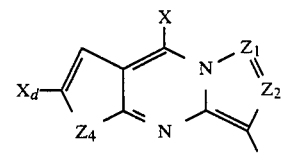
A-14
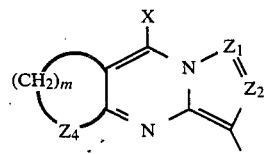
A-15
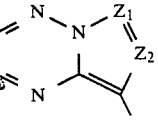
A-16
A-17
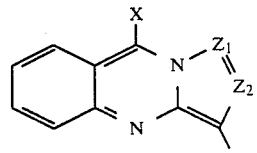
A-18
wherein
$Q_1$-1 through $Q_1$-87 may be optionally substituted with 1 or 2 groups selected from $C_1$–$C_2$ alkyl or $C_1$–$C_2$ haloalkyl;
$R_{35}$ is H, $C_1$–$C_3$ alkyl or allyl;
$R_{36}$ and $R_{37}$ are independently H or $C_1$–$C_3$ alkyl;
$X_b$ is O or $NR_{36}$; and
$X_c$ is O, S, S(O), S(O)$_2$ or $NR_{36}$;
A is
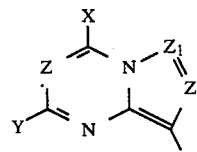
A-1
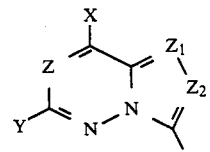
A-2
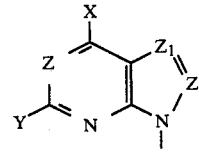
A-3
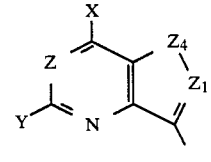
A-4

-continued

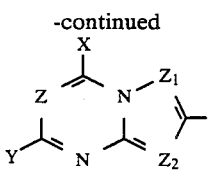

A-19

X or Y is H, halogen, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylsulfinylalkyl, $C_1$-$C_4$ haloalkyl, $C_2$-$C_5$ alkylsulfonylalkyl, $C_3$-$C_5$ cycloalkyl, $C_2$-$C_4$ alkynyl, $C_2$-$C_5$ alkylthioalkyl,

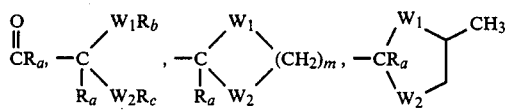

or $N(OCH_3)CH_3$;

$W_1$ and $W_2$ are independently O or S;

m and m' are independently 2 or 3;

$R_a$ is H or $CH_3$;

$R_b$ and $R_c$ are independently $C_1$-$C_2$ alkyl;

Z is CH, N, CCH$_3$, CCH$_2$CH$_3$, CCl or CBr;

$Z_1$ is C—U, N or N—O;

$Z_2$ and $Z_3$ are independently N or C—U;

$Z_4$ is NCH$_3$, O, S or CH$_2$;

U is H, F, Cl, Br, $C_1$-$C_2$ alkyl optionally substituted by F, Cl, Br or OCH$_3$, CN, NO$_2$, NMe$_2$, OR''', SR''' or CO$_2$CH$_3$;

R''' is $C_1$-$C_2$ alkyl optionally substituted with F, Cl, Br or OCH$_3$;

$X_a$ is CH$_3$, C$_2$CH$_3$ or CH$_2$CF$_3$; and $X_d$ is H or CH$_3$;

and their agriculturally suitable salts; provided that (1) the total number of carbon atoms of $R_{22}$ and $R_{23}$ is less than or equal to five;

(2) when X or Y is Cl, F, Br or I, then Z is CH and the remaining X or Y is OCH$_3$, OCH$_2$CH$_3$, N(OCH$_3$)CH$_3$, NHCH$_3$, N(CH$_3$)$_2$ or OCF$_2$H;

(3) when X or Y is C$_1$ haloalkoxy, then Z is CH;

(4) at least one of X or Y is X' where X' is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, $C_2$-$C_5$ alkoxyalkoxy, amino, $C_1$-$C_3$ alkylamino or di($C_1$-$C_3$ alkyl)amino; and (5) the total number of carbon atoms of $R_{27}$ and $R_{28}$ is less than or equal to five.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy, isopropyloxy and the different butyl isomers.

Alkenyl denotes straight chain or branched alkenes, e.g. 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Alkylsulfonyl denotes methylsulfonyl, ethylsulfonyl and the different propylsulfonyl isomers.

Alkylthio, alkylsulfinyl, alkylamino, etc. are defined analogously to the above examples.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms and said halogen atoms may be the same or different. Examples of haloalkyl included CH$_2$CH$_2$F, CF$_2$CF$_3$ and CH$_2$CHFCl.

The total number of carbon atoms in a substituent group is indicated by the $C_i$-$C_j$ prefix where i and j are numbers from 1 to 7. For example, $C_1$-$C_3$ alkylsulfonyl would designate methylsulfonyl through propylsulfonyl, $C_2$ alkoxyalkoxy would designate OCH$_2$OCH$_3$, $C_2$ cyanoalkyl would designate CH$_2$CN and $C_3$ cyanoalkyl would designate CH$_2$C H$_2$CN and CH(CN)CH$_3$.

PREFERRED COMPOUNDS

Preferred for reasons of increased ease of synthesis and/or greater herbicidal efficacy are:

1. Compounds of Formula I where A is A-1, A-2, A-4, A-6, A-7, A-8, A-9, A-11, A-16 or A-19.

2. Compounds of Preferred 1 where
   Formula I is Formula Ia;
   W is O; and
   R is H.

3. Compounds of Preferred 1 where
   Formula I is Formula Ib;
   G is OR' or SR'.

4. Compounds of Preferred 2 where
   $R_2'$ is H;
   X' is $C_1$-$C_2$ alkyl, $C_1$-$C_2$ alkoxy, OCF$_2$H, CH$_2$F, CF$_3$, OCH$_2$CH$_2$F, OCH$_2$CHF$_2$, OCH$_2$CF$_3$, CH$_2$Cl or CH$_2$Br;
   X or Y is H, $C_1$-$C_2$ alkyl, $C_1$-$C_2$ alkoxy, CH$_2$OCH$_3$, Cl, F, Br, I, CH$_2$OCH$_2$CH$_3$, NHCH$_3$, N(OCH$_3$)CH$_3$, N(CH$_3$)$_2$, CF$_3$, SCH$_3$, OCH$_2$CH═CH$_2$, OCH$_2$C≡CH, OCH$_2$CH$_2$OCH$_3$, CH$_2$SCH$_3$,

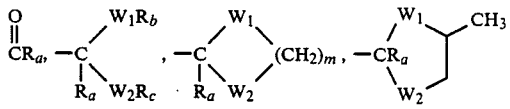

OCF$_2$H, SCF$_2$H, cyclopropyl, C≡CH or C≡CCH$_3$; and
Z is CH.

5. Compounds of Preferred 4 where
   $R_1$ is halogen; NO$_2$; CN; $C_1$-$C_3$ alkyl optionally substituted with F, Cl, Br, CN, OCH$_3$ or SCH$_3$; C$_3$ alkenyl optionally substituted with F, Cl or Br; C$_3$ alkynyl; C$_3$ cycloalkyl optionally substituted with F, Cl or CH$_3$; C(O)R$_{16}$; C(OCH$_2$CH$_2$O)R$_{16}$; C(R$_{16}$)(OR$_{17}$)(OR$_{18}$); CO$_2$R$_{19}$; C(O)NR$_{20}$R$_{21}$; N$_3$; S(O)$_2$NR$_{22}$R$_{23}$; OS(O)$_2$R$_{25}$; ER$_{26}$; (CH$_2$)$_n$Q or (CH$_2$)$_n$Q$_1$;
   R$_{16}$ is $C_1$-$C_3$ alkyl, C$_3$ cycloalkyl or C$_3$ alkenyl;
   R$_{17}$ and R$_{18}$ are $C_1$-$C_2$ alkyl;
   R$_{19}$ is $C_1$-$C_3$ alkyl, C$_3$ alkenyl, CH$_2$CH$_2$F, CH$_2$CH$_2$Cl, CH$_2$CH$_2$OCH$_3$ or cyclopropyl methyl;

$R_{20}$ is H or $CH_3$;
$R_{21}$ is $CH_3$; $CH_2CH_3$ or $OCH_3$;
$R_{22}$ is $C_1-C_3$ alkyl, $OCH_3$, $OCH_2CH_3$, allyl, propargyl or cyclopropyl;
$R_{23}$ is H, $CH_3$ or $CH_2CH_3$;
$R_{26}$ is $C_1-C_3$ alkyl optionally substituted by halogen, $C_2-C_3$ alkoxyalkyl, allyl, propargyl or $C_2-C_3$ haloalkenyl;
n is 0; and
$Q_1$ is $Q_1$-1, $Q_1$-4, $Q_1$-5, $Q_1$-7, $Q_1$-10, $Q_1$-11, $Q_1$-12, $Q_1$-17, $Q_1$-19, $Q_1$-20, $Q_1$-24, $Q_1$-25, $Q_1$-27, $Q_1$-28, $Q_1$-36, $Q_1$-38, $Q_1$-46, $Q_1$-47, $Q_1$-54, $Q_1$-56, $Q_1$-59, $Q_1$-60, $Q_1$-63, $Q_1$-71, $Q_1$-74, $Q_1$-76, $Q_1$-78 or $Q_1$-79.

6. Compounds of Preferred 5 where
   $R_2$ is H; halogen; CN; $NO_2$; $CH_3$; $CF_3$; $ER_{31}$; or $C_1-C_2$ alkyl substituted with $C_1-C_2$ alkoxy, $C_1-C_2$ haloalkoxy, $C_1-C_2$ alkylthio, $C_1-C_2$ haloalkylthio or CN;
   E is O or S; and
   $R_{31}$ is $C_1-C_2$ alkyl optionally substituted with F, Cl or $OCH_3$.

7. Compounds of Preferred 6 where
   W' is O;
   $Q_e$ is $NR_{12}$;
   $Q_c$ is O, NH, $N(C_1-C_3$ alkyl$)$, $NCH_2CH=CH_2$, or $NCH_2C\equiv CH$;
   $Q_f$ is $S(O)_2$;
   $Q_g$ is O or S;
   $R_{11}$ is H or $CH_3$; and
   $R_{13}$ is H or $CH_3$.

8. Compounds of Preferred 7 where
   X' is $CH_3$, $OCH_3$, $OCH_2CH_3$ or $OCF_2H$; and
   X or Y is $CH_3$, $OCH_3$, $C_2H_5$, $CH_2OCH_3$, $NHCH_3$, $CH(OCH_3)_2$, Cl or cyclopropyl.

9. Compounds of Preferred 8 where A is A-1.
10. Compounds of Preferred 8 where A is A-2.
11. Compounds of Preferred 8 where A is A-4.
12. Compounds of Preferred 8 where A is A-6.
13. Compounds of Preferred 8 where A is A-7.
14. Compounds of Preferred 8 where A is A-8.
15. Compounds of Preferred 8 where A is A-9.
16. Compounds of Preferred 8 where A is A-11.
17. Compounds of Preferred 8 where A is A-16.
18. Compounds of Preferred 8 where A is A-19.
19. Compounds of Preferred 8 where
    A is A-1;
    L is L-1, L-3, L-4, L-5, L-6, L-7, L-8, L-9, L-11, L-12, L-13, L-14, L-15 or L-16;
    $Z_1$ is CH or N; and
    $Z_2$ is CH or N.
20. Compounds of Preferred 19 where $Z_1$ and $Z_2$ are N.
21. Compounds of Preferred 8 where
    A is A-4.
    L is L-1, L-3, L-4, L-5, L-6, L-7, L-8, L-9, L-11, L-12, L-13, L-14, L-15 or L-16;
    $Z_4$ is O or S; and
    $Z_1$ is N, CH or $CCH_3$.

Specifically Preferred for reasons of greatest ease of synthesis and/or greatest herbicidal efficacy are:
5,7-Dimethyl-N-[[2-(methylsulfonyl)phenyl]sulfonyl]pyrazolo[1,5-A]pyrimidine-3-carboxamide
Methyl 2-[[[(5,7-dimethylpyrazolo[1,5-A]pyrimidin-3-yl)carbonyl]amino]sulfonyl]benzoate
Methyl 2-[[[(5,7-dimethyl[1,2,3]triazolo[1,5-A]pyrimidin-3-yl)carbonyl]amino]sulfonyl]benzoate
N-[[2-(1-Ethyl-1H-tetrazol-5-yl)phenyl]sulfonyl]-5,7-dimethylpyrazolo[1,5-A]pyrimidine-3-carbamate
N-[[2-[(Dimethylamino)sulfonyl]phenyl]sulfonyl]-5,7-dimethyl[1,2,3]triazolo[1,5-A]pyrimidine-3-carboxamide
N-[(2-Chlorophenyl)sulfonyl]-5,7-dimethyl[1,2,3]triazolo[1,5-A]pyrimidine-3-carboxamide
N-[(2,6-Dibromophenyl)sulfonyl]-5,7-dimethyl[1,2,3]triazolo[1,5-A]pyrimidine-3-carboxamide The compounds disclosed can be variously named using alternative rules of nomenclature. In particular, 5,7-dimethyl-N-[[(2-methylsulfonyl)phenyl]sulfonyl]pyrazolo[1,5-A]pyrimidine-3-carboxamide is alternatively named 5,7-dimethyl-N-((2-(methylsulfonyl)phenylsulfonyl))pyrazolo((1,5-A))pyrimidine-3-carboxamide. Methyl 2-[[[(5,7-dimethylpyrazolo[1,5-A]pyrimidin-3-yl)carbonyl]amino]sulfonyl]benzoate is alternatively named 2-(((((5,7-dimethylpyrazolo((1,5-A))pyrimidine-3-yl)carbonylamino))sulfonyl))benzoic acid, methyl ester. Methyl 2-[[[(5,7-dimethyl[1,2,3]triazolo[1,5-]pyrimidin-3-yl)carbonyl]amino]sulfonyl]benzoate is alternatively named 2-[((((5,7-dimethyl-((1,2,3))triazolo((1,5-A))pyrimidine-3-yl)carbonylamino))sulfonyl]benzoic acid, methyl ester. N-[[2-(1-ethyl-1H-tetrazol-5-yl)phenyl]sulfonyl]-5,7-dimethylpyrazolo[1,5-A]pyrimidine-3-carbamate is alternatively named N-((2-(1-ethyl-1H-tetrazol-5-yl)phenylsulfonyl))-5,7-dimethylpyrazolo((1,5-A))pyrimidine-3-carbamate.

DETAILED DESCRIPTION OF THE INVENTION

Synthesis

Compounds of Formula Ia and Formula Ib can be prepared using one or more of the reactions and techniques described in this section. In some cases, substituents on the starting materials may be incompatible with the reaction conditions described. It will be readily apparent to one skilled in the art to use either standard protecting groups (e.g., ketal as a protecting group for ketone) or one of the alternative methods described.

Equation 1 illustrates the reaction of N-sulfonylheterocyclic carboxamides of Formula Ia (W is O) with Lawesson's Reagent of Formula II to give the desired N-sulfonylthiocarboxamides of Formula Ia (W is S).

Equation 1

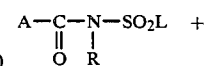

Ia (W is O)

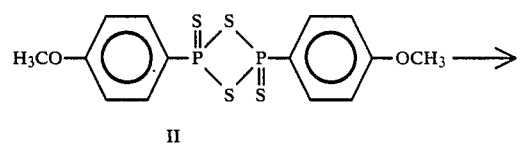

II

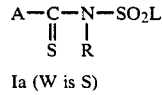

Ia (W is S)

wherein
A, R and L are as previously defined.

The reaction of Equation 1 is best carried out in an inert aprotic solvent such as toluene or xylene at a temperature between about 0° and 145° C. In cases in which the products are insoluble in the reaction solvent, they may be isolated by simple filtration. When the products are soluble, they may be isolated by evaporation of the solvent, followed by crystallization or chromatography of the residue.

Compounds of Formula Ia (W is O and A is not A-3) can be synthesized by the reaction of heterocyclic carboxylic acids or their anion of Formula III with thionyl chloride or oxalyl chloride in the presence of a base such as pyridine, 2,6-lutidine or triethylamine if desired and then by the reaction of the carbonyl chloride of Formula IV which is formed in situ, with a sulfonamide of Formula V in the presence of a base such as pyridine, 2,6-lutidine or triethylamine as shown below in Equation 2.

Equation 2

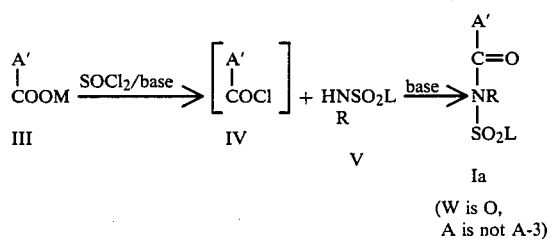

wherein

M is H, Li, K or Na;

R and L are as previously defined; and

A' is A-1, A-2, A-4, A-5, A-6, A-7, A-8, A-9, A-11, A-12, A-13, A-14, A-15, A-16, A-17, A-18 or A-19.

The sequential reactions of Equation 2 are best carried out in an inert aprotic solvent such as methylene chloride or ether. The excess thionyl chloride or oxalyl chloride is evaporated before the carbonyl chloride of Formula IV, is reacted with the sulfonamide of Formula V. The products are readily isolated by evaporation of the solvent, followed by chromatography, or alternatively by extraction of the residue with sodium carbonate aqueous solution, washing the aqueous solution with ether, acidifying the aqueous solution with an inorganic acid such as hydrochloric acid and filtration.

Alternatively, compounds of Formula Ia (W is O, A is not A-3) can be synthesized by the reaction of heterocyclic carboxylic acids of Formula III with 1,1-carbonyldiimidazole of Formula VI and then by the reaction of the carbonylimidazole of Formula VII, which is formed in situ, with a sulfonamide of Formula V in the presence of a base such as pyridine or triethylamine as shown below in Equation 3.

Equation 3

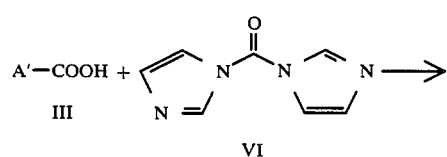

-continued
Equation 3

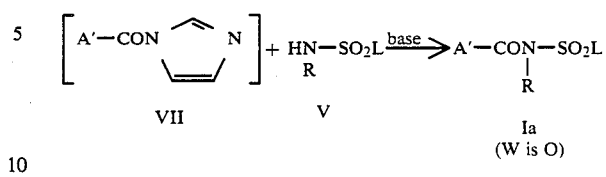

wherein

A', R and L are as previously defined.

The reaction of Equation 3 is best carried out in an inert aprotic solvent such as methylene chloride, chloroform or acetonitrile at a temperature between about 0° C. to 82° C. The product can be isolated by evaporation of solvent, adding the residue to water, acidifying the aqueous solution with hydrochloric acid and filtrating. Crystallization or chromatography may be used for further purification. In cases where the crude products are insoluble in the reaction solvent, the products may be isolated by filtrating, adding the crude products collected to water, acidifying the aqueous solution with hydrochloric acid and filtrating. Crystallization or chromatography may also be used for further purification as would be preferred by one skilled in the art.

Compounds of Formula Ia (W is O, A is not A-3) can also be synthesized by the reaction of heterocyclic carboxylic acid of Formula III with 2-chloro-1-methyl pyridinium iodide of Formula VIa in the presence of a base such as triethylamine and then by the reaction of the 2-(heterocyclic carbonyloxy)-1-methylpyridinium salt of Formula VIIa, which is formed in situ, with a sulfonamide of Formula V in the presence of a base such as triethylamine as shown below in Equation 3a.

Equation 3a

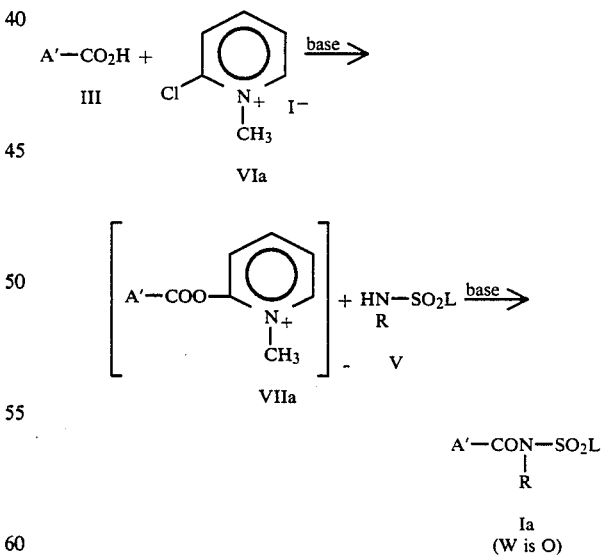

wherein

A', R and L are as previously defined.

The reaction of Equation 3a is best carried out in an inert aprotic solvent such as methylene chloride, chloroform or acetonitrile at a temperature between −30° C. to 82° C. The product can be isolated by evaporation of solvent, adding the residue to water, acidifying the aqueous solution with an acid such as hydrochloric acid and filtration. Crystallization or chromatography may be used for further purification.

Reactions of the heterocycles or their lithium anions of Formula XVII with sulfonyl isocyanates of Formula IX can also afford compounds of Formula Ia (W is O, A is not A-3) as shown below in Equation 3b

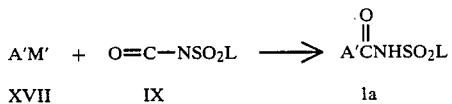

wherein
A' and L are as previously defined
M' is H or Li.

The reaction of Equation 3b is best carried out in an inert aprotic solvent such as tetrahydrofuran or dichloromethane at a temperature between $-78°$ C. and 80° C. The product can be isolated by concentrating the reaction mixture and acidifying (if appropriate) the residue in water followed by filtration. Crystallization or chromatography may be used for further purification.

Compounds of Formula Ia (W is O, A is A-3) can be synthesized by the reaction of compounds of Formula VIII with a sulfonyl isocyanate of Formula IX or a N-phenoxycarbonylsulfonamide of Formula X in the presence of a base such as triethylamine or DBU as shown below in Equation 4.

Equation 4a

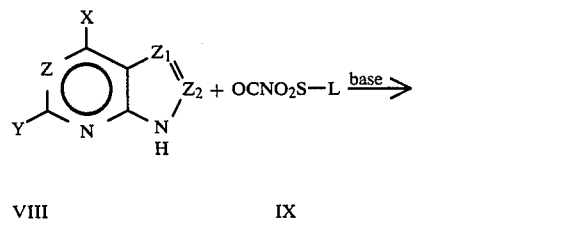

Equation 4b

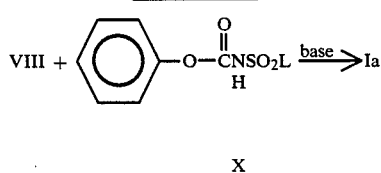

wherein
X, Y, Z, $Z_1$, $Z_2$ and L are as previously defined.

The reaction of Equation 4 is best carried out in an inert aprotic solvent such as acetonitrile, chloroform or methylene chloride at a temperature between about 0° C. to 80° C. In cases where the products are insoluble in the reaction solvents, they can be isolated by simple filtration. Alternatively, the products can be isolated by evaporating the reaction solvents after washing with dilute aqueous acid such as hydrochloric acid, if desired, triturated in a solvent such as ether, n-butylchloride or hexane and then filtrating. The products may be further purified by crystallization or chromatography.

Compounds of Formula Ia (W is S, NR" or NOR" and R is H) can be synthesized by the reaction of imidoyl chlorides of Formula Ib (G is Cl) with an amine, hydroxyamine, alkoxyamine or hydrogen sulfide of Formula XI in the presence of a base such as triethylamine if desired as shown below in Equation 5.

Equation 5

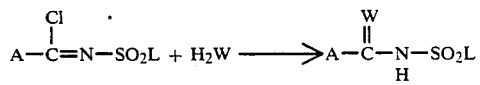

(W is S, NR" or NOR" and R is H)

wherein
W is S, NR" or NOR"; and
A, L and R" are as previously defined.

The reaction of Equation 5 is best carried out in an inert aprotic solvent such as methylene chloride or dichloroethane at a temperature between about 0° C. and 80° C. The products may be isolated by evaporation of the solvent, followed by crystallization or chromatography of the residue.

Compounds of Formula Ia (W is O, NR" or NOR" and R is not H) can be synthesized by contacting compounds of Formula Ia (W is O, NR" or NOR" and R is H) with a base such as n-butyllithium or sodium hydride followed by contacting with an alkylating agent of Formula XII as shown below in Equation 6.

Equation 6

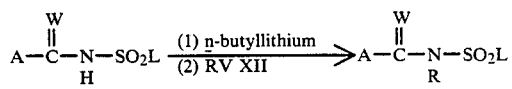

| Ia | Ia |
|---|---|
| (W is O, NR" or NOR" and R is H) | (W is O, NR" or NOR" and R is not H) | wherein
A, R" and L are as previously defined;
R is as previously defined but other than H; and
V is Cl, Br or I.

The reaction of Equation 6 is best carried out in an inert aprotic solvent such as ether or tetrahydrofuran at a temperature between about $-80°$ C. to 70° C. The products may be isolated by evaporation of solvent, followed by crystallization or chromatography of the residue.

Equation 7 illustrates the reaction of imidoyl chlorides or Formula Ib (G is Cl) with an alcohol or a mercaptan of Formula XIII in the presence of a base such as triethylamine to give compounds of Formula Ib (G is OR' or SR').

Equation 7

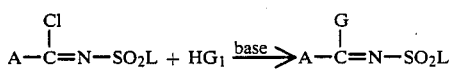

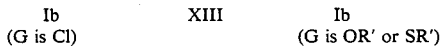

wherein
A and L are as previously defined; and
$G_1$ is OR' or SR'.

The reaction of Equation 7 is best carried out in an inert aprotic solvent such as methylene chloride or dichloroethane at a temperature between about 0° C. and 80° C. The products may be isolated by evaporation of the solvent, followed by crystallization or chromatography of the residue.

The imidoyl chlorides of Formula Ib (G is Cl) can be synthesized by the reaction of carbonyl sulfonamides of Formula Ia (R is H and W is O) with triphenylphosphine/$CCl_4$ or $PCl_5/POCl_3$ as shown below in Equation 8.

Equation 8

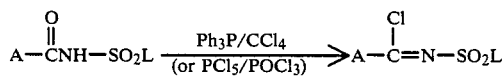

wherein
A and L are as previously defined.

The reaction of Equation 8 is best carried out in $CCl_4$ or $POCl_3$ at a temperature between about 0° C. and 105° C. The products may be isolated by evaporation of the solvent, followed by crystallization or chromatography of the residue as would be apparent to one skilled in the art.

Compounds of Formula Ib (G is SR') may also be prepared by the reaction of N-sulfonylthiocarboxamides of Formula Ia (W is S and R is H), with an alkylating agent of Formula XIV in the presence of a base such as potassium carbonate as shown below in Equation 9.

Equation 9

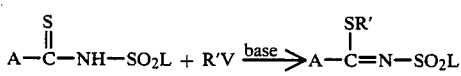

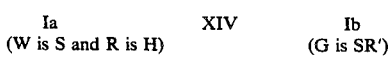

wherein
A, R' and L are as previously defined; and
V is Cl, Br or I.

The reaction of Equation 9 is best carried out in an inert aprotic solvent such as N,N-dimethylformamide at a temperature between about 0° C. and 100° C. The products may be isolated by evaporation of the solvent, followed by crystallization or chromatography of the residue.

The sulfonamides of Formula V, the sulfonyl isocyanates of Formula IX and the N-phenoxycarbonylsulfonamides of Formula X can be prepared by methods known in the art or by obvious modification of these known methods. The anion of heterocyclic carboxylic acid of Formula III (M is K, Li, Na) can be prepared from the acid of Formula III (M is H) by methods known in the art or by modification of these methods.

The heterocyclic carboxylic acid of Formula III (M is H) can be synthesized by the methods shown below in Equations 10, 11, 11a and 12.

Equation 10 illustrates the conversion of the heterocyclic carboxylic acid esters of Formula XV to the acid of Formula III (M is H) by the method taught by Yasuo Makisumi in *Chem. Pharm. Bull.*, 10, 612 (1962) or by modification of this method (e.g., aqueous alcohol instead of water as reaction solvent).

Equation 10

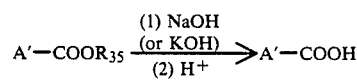

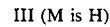

wherein
A' is as previously defined; and
$R_{35}$ is $C_1-C_5$ alkyl or benzyl.

The reaction of Equation 10 is best carried out in an aqueous alcoholic solution or water at a temperature between 0° C. to 100° C. The product can be isolated by concentrating the reaction solution, acidifying it to pH<3 with an acid such as hydrochloric acid followed by filtration. Crystallization or chromatography may be used for further purification.

Alternatively, the heterocyclic acid esters of Formula XV can be converted to the acid of Formula III (M is H) by reaction with acids such as hydrobromic acid or by reaction with trimethylsilyliodide (or boron tribromide) as shown below in Equation 11.

Equation 11

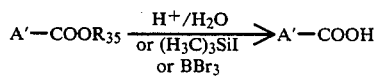

wherein
A' and $R_{35}$ are as previously defined.

The reaction of Equation 11 is best carried out under the conditions taught by C. S. Marvel, et al. in *J. Am. Chem. Soc.*, 62 3495 (1940), A. M. Felix in *J. Org. Chem.*, 39 (10) 1427 (1974) and M. E. Jung, et al. in J. Am. Chem. Soc., 99 968 (1977).

Equation 11a illustrates the conversion of the heterocyclic acid benzyl esters of Formula XV ($R_{35}$ is benzyl) to the acid of Formula III (M is M) by hydrogenation in the presence of a catalyst such as palladium on carbon.

Equation 11a

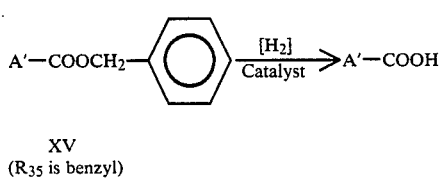

XV
($R_{35}$ is benzyl)

The reaction of Equation 11a is best carried out in an inert solvent such as methanol, ethanol or ethylacetate at a temperature between 0° C.-80° C. The product can be isolated by filtering the reaction solution and concentrating the filtrate. Crystallization or chromatography may be used for further purification.

Equation 12 illustrates the conversion of the bromoheterocycle of Formula XVI to the corresponding lithium anion of Formula XVIIa by reaction of XVI with n-butyllithium or t-butyllithium (two equivalents or more) and the conversion of XVIIa, which is formed in situ, to the acid of Formula III (M is H) by reaction of XVIIa with carbon dioxide followed by acidifying with an acid such as hydrochloric acid.

Equation 12

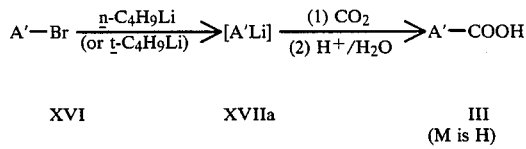

wherein
A' is as previously defined.

The reaction of Equation 12 is best carried out at a temperature between about −110° C. to 70° C. in an inert aprotic solvent such as ether or THF, to which an aqueous acid such as hydrochloric acid is later added. The products may be isolated by evaporation of the solvent followed by washing the residue with water and ether. Crystallization or chromatography may be used for further purification.

The esters of Formula XVa (A is A-1, $Z_1$ is not N—O) can be synthesized by the methods shown below in Equations 13, 14, 15, 16 and 17.

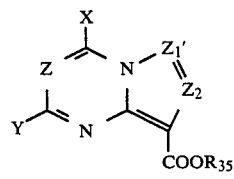

(A' is A-1, $Z_1$ is $Z_1'$)

wherein
$Z_1'$ is C—U or N; and
X, Y, Z, $Z_2$ and $R_{35}$ are as previously defined.

Equation 13 illustrates the reaction of β-dicarbonyl compounds of Formula XVIII (or their equivalent) with an aminoazole ester of Formula XIX to give the desired esters of Formula XVa (X is $X_1$, Y is $Y_1$, Z is C—U, $Z_1$ is not N—O).

Equation 13

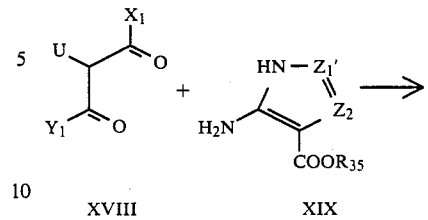

XVIII    XIX

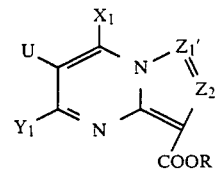

XVa
(X is $X_1$, Y is $Y_1$, Z is C—U)

wherein
$X_1$ or $Y_1$ is H, $C_1$-$C_4$ alkyl, $C_2$-$C_5$ alkoxyalkyl, $C_2$-$C_5$ alkylsulfinylalkyl, $C_1$-$C_4$ haloalkyl, $C_2$-$C_5$ alkylsulfonylalkyl, $C_3$-$C_5$ cycloalkyl, $C_2$-$C_4$ alkynyl, $C_2$-$C_5$ alkylthioalkyl,

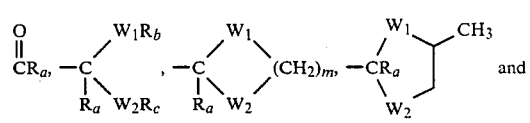

and

U, $Z_1$, $Z_2$ and $R_{35}$ are as previously defined.

The reaction of Equation 13 is best carried out under the conditions taught by D. E. O'Brien, et al., in *J. Med. Chem.*, 17, 645 (1974), P. Guerret, et al., in *Bull. Soc. Chim. Fr.*, (3) 1031 (1971), and Yasuo Makisumi in *Chem. Pharm. Bull.*, 10, 612 (1962).

Equation 14 illustrates the reaction of aminoazole esters of Formula XIX with compounds of Formula XX to give the desired esters of Formula XVa (A is A-1, Z is N and $Z_1$ is not N—O).

Equation 14

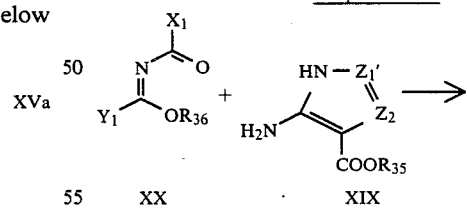

XX    XIX

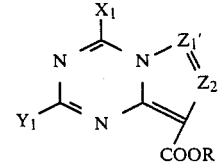

XVa
(X is $X_1$, Y is $Y_1$, Z is N)

wherein $Z_1'$, $Z_2$, $R_{35}$, $X_1$ and $Y_1$ are as previously defined; and $R_{36}$ is $C_1$–$C_4$ alkyl.

The reaction of Equation 14 is best carried out in an inert solvent such as toluene in the presence of an acid such as p-toluenesulfonic acid at a temperature between about 0° C. to 111° C. The products may be isolated by washing the reaction solution with an aqueous sodium carbonate solution, drying (MgSO$_4$) and concentrating the reaction solution. Crystallization and chromatography may be used for further purification of the products.

Equation 15 illustrates the reaction of aminoazole esters of Formula XIX with an imidate of Formula XXI to give the amidines of Formula XXII and the reaction of the amidines of Formula XXII with ortho esters of Formula XXIII to give the desired heterocyclic esters of Formula XVa (X is $X_1$, Y is $Y_1$, Z is N, $Z_1$ is not N—O).

Equation 15

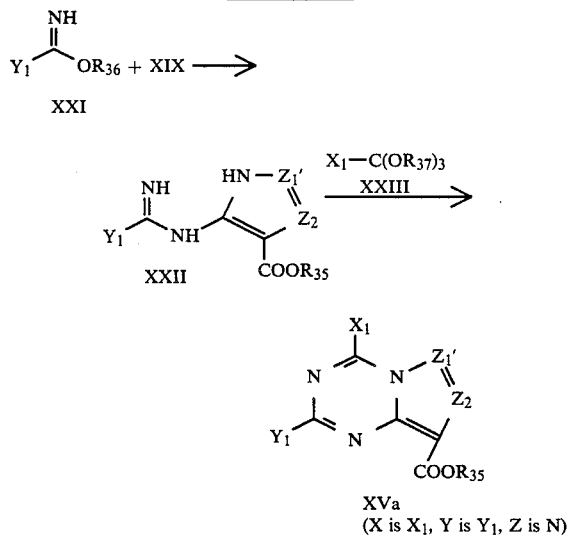

XVa
(X is $X_1$, Y is $Y_1$, Z is N)

wherein
$Z_1'$, $Z_2$, $R_{35}$, $X_1$, $R_{36}$ and $Y_1$ are as previously defined; and
$R_{37}$ is $C_1$–$C_4$ alkyl.

The reaction of Equation 15 is best carried out under the conditions taught by Keitaro Senga, et al., in *J. Med. Chem.*, 25, 243 (1982).

Compounds of Formula XVa (X is $X_2$, $Z_1$ is not N—O) can be prepared as shown below in Equation 16 by reaction of chlorosubstituted heterocyclic carboxylic acid esters of Formula XVa (X is Cl, $Z_1$ is not N—O) with nucleophiles of Formula $^-X_2$.

Equation 16

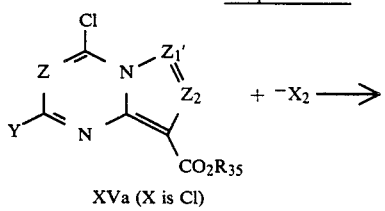

XVa (X is Cl)

-continued
Equation 16

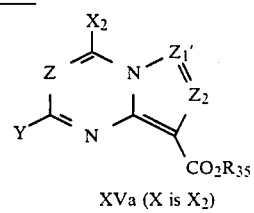

XVa (X is $X_2$)

wherein
Y, Z, $Z_1'$, $Z_2$, and $R_{35}$ are as previously defined;
$X_2$ is $C_1$–$C_4$ alkoxy, $C_1$–$C_4$ haloalkoxy, $C_1$–$C_4$ haloalkylthio, $C_1$–$C_4$ alkylthio, halogen, $C_2$–$C_5$ alkoxyalkoxy, amino, $C_1$–$C_3$ alkylamino, di($C_1$–$C_3$ alkyl)amino, $C_2$–$C_4$ alkynyl, $C_3$–$C_4$ alkenyloxy, $C_3$–$C_4$ alkynyloxy, or N(OCH$_3$)CH$_3$.

The reaction of Equation 16 is best carried out in an inert solvent such as dimethylformamide or an alcohol. The products may be isolated by evaporating the reaction solvent and washing the residue with water. Chromatography may be used for further purification of the products.

Compounds of Formula XVa (Y is $Y_2$, $Z_1$ is not N—O) can be prepared as shown below in Equation 17 by reacting chlorosubstituted heterocyclic carboxylic acid esters of Formula XVa (Y is Cl, $Z_1$ is not N—O) with nucleophiles of Formula $^-Y_2$.

Equation 17

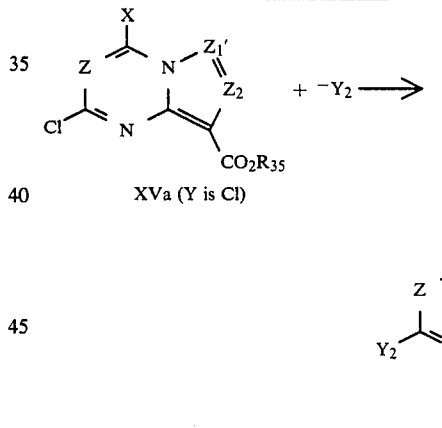

wherein
X, Z, $Z_1'$, $Z_2$ and R are as previously defined;
$Y_2$ is $C_1$–$C_4$ alkoxy, $C_1$–$C_4$ haloalkoxy, $C_1$–$C_4$ haloalkylthio, $C_1$–$C_4$ alkylthio, halogen, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_4$ alkynyl or N(OCH$_3$)CH$_3$.

The reaction of Equation 17 is best carried out in an inert solvent such as dimethylformamide or an alcohol. The products can be isolated by evaporating the reaction solvent and washing the residue with water. Chromatography may be used for further purification of the products.

Compounds XVa (X is Cl and $Z_1$ is not N—O) and XVa (Y is Cl and $Z_1$ is not N—O) can be prepared from dichloroheterocyclic carboxylic acid esters of Formula XVa (X is Cl and Y is Cl, and $Z_1$ is not N—O) by nucleophilic displacement reactions with an appropriate nucleophile by methods known in the art or by obvious modifications of these known methods.

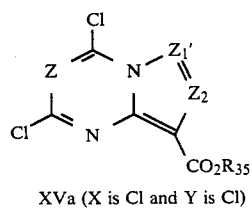

XVa (X is Cl and Y is Cl)

wherein

Z, $Z_1'$, $Z_2$ and $R_{35}$ are as previously defined.

Alternatively, they can be prepared by reacting the corresponding hydroxy compounds of Formula XXIII or XXIV with $POCl_3$ or by other well-known methods or by obvious modification of these known methods.

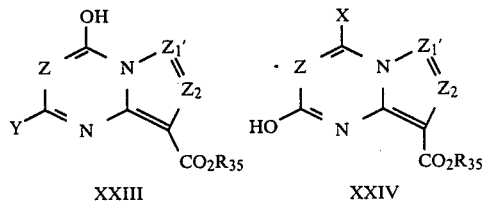

wherein

X, Y, Z, $Z_1'$, $Z_2$ and $R_{35}$ are as previously defined.

Compound XVa (X is Cl, Y is Cl and $Z_1$ is not N—O) can be prepared by reacting the corresponding dihydroxy compounds of Formula XXV with $POCl_3$ by methods well known in the art.

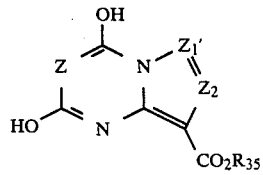

wherein

Z, $Z_1'$, $Z_2$ and $R_{35}$ are as previously defined.

The compounds XXIII (Z is C—U and Z is not N—O), XXIV (Z is C—U and $Z_1$ is not N—O) or XXV (Z is C—U and Z is not N—O) can be prepared by condensation of a β-keto ester, a malonatediester or one of their equivalents with 3-amino-4-carboalkoxypyrazoles as taught by:
1. Yasuo Makisumi in *Chem. Pharm. Bull.*, 10, 612 (1962);
2. Keitaro Senga et al. in *J. Med. Chem.*, 24(5), 61a (1971);
3. Alfred Dornow and Klaus Dehmer in *Chem. Ber.*, 100(8), 2577 (1967);
4. Mohamed Elnagdi in *Arch. Pharm.*, 316(8), 713 (1983);
5. B. B. Gavrilenko in *Zh. Org. Khim.*, 18(5), 1079 (1982);

or by modifications of these methods (e.g., reaction of 3-amino-4-carbethoxypyrazole with diketene).

The compounds XXIII (Z is N, $Z_1$ is not N—O), XXIV (Z is N, $Z_1$ is not N—O) or XXV (Z is N, $Z_1$ is not N—O) can be similarly prepared by condensation of carbonylisocyanates of Formula XXVI or the compounds of Formula XXVII with aminoazole esters of Formula XIX.

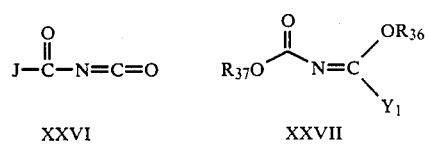

wherein

J is H, Cl, $C_1$–$C_4$ alkyl, $C_1$–$C_4$ alkoxy, $C_2$–$C_5$ alkoxyalkyl, $C_2$–$C_5$ alkylsulfinylalkyl, $C_1$–$C_4$ haloalkyl, $C_2$–$C_5$ alkylsulfonylalkyl, $C_3$–$C_5$ cycloalkyl, $C_2$–$C_4$ alkynyl, $C_2$–$C_5$ alkylthioalkyl,

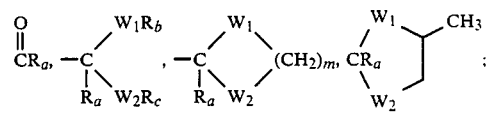

$R_{36}$ and $R_{37}$ are independently $C_1$–$C_4$ alkyl; and $Y_1$ is as previously defined.

The esters of Formula XVa (A is A-1, $Z_1$ is N—O) can be synthesized by oxidation of esters of Formula XVa (A is A-1, $Z_1$ is N) with an oxidizing agent such as m-chloroperoxybenzoic acid.

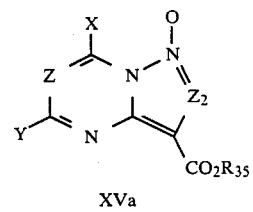

XVa
(A is A-1, $Z_1$ is N—O)

wherein

X, Y, Z, $Z_2$ and $R_{35}$ are as previously defined.

The bromoheterocycles of Formula XVIa (A is A-1) can be synthesized by the same methods as those for the preparation of the esters of Formula XVa (A is A-1) using the aminobromoazoles of Formula XXVIII instead of the aminoazole esters of Formula XIX as starting material.

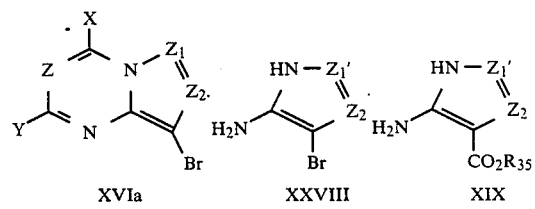

XVIa     XXVIII     XIX wherein

X, Y, Z, $Z_1$, $Z_1'$, $Z_2$ and $R_{35}$ are as previously defined.

Alternatively, the bromoheterocycles of Formula XVIa can be synthesized by bromination of the heterocycles of Formula XXXXV with a brominating agent such as bromine or N-bromosuccinimide as shown in Equation 17b.

Equation 17b

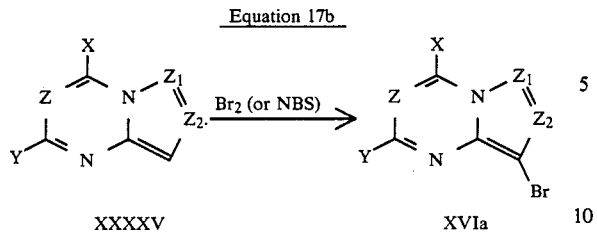

XXXXV     XVIa

Equation 18

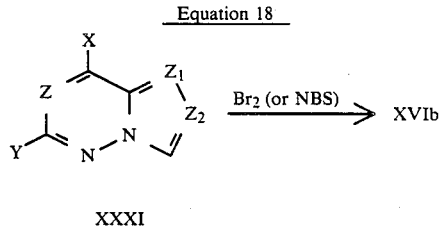

XXXI wherein

X, Y, Z, $Z_1$ and $Z_2$ are as previously defined.

The reaction of Equation 17b is best carried out in an inert solvent such as chloroform or carbon tetrachloride at a temperature between 0° C. to 77° C. The products can then be isolated by filtration, concentration of the filtrate and washing the residue with water. Crystallization or chromatography may be used for further purification if desired.

The bromoheterocycles of Formula XVIb (A is A-2) can be synthesized from aminobromoheterocycle of Formula XXX by similar methods as discussed for the preparation of the heterocyclic esters of Formula XVa (A is A-1) from aminoazole esters of Formula XIX.

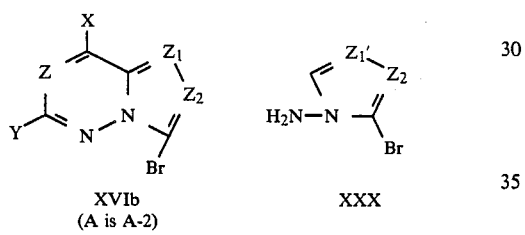

XVIb     XXX
(A is A-2)

wherein

X, Y, Z, $Z_1$, $Z_1'$ and $Z_2$ are as previously defined.

For example, reaction of the aminobromoazoles of Formula XXX with a β-dicarbonyl compounds of Formula XVIII (or its equivalent) should give the bromoheterocycles of Formula XVIb (X is $X_1$, Y is $Y_1$, Z is C—U and $Z_1$ is C—U or N) as shown in Equation 17a.

Equation 17a

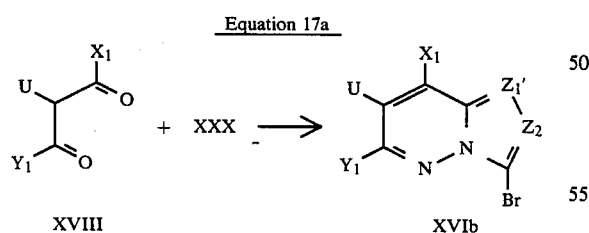

XVIII     XVIb wherein $X_1$, $Y_1$, U, $Z_1'$, $Z_2$ and R are as previously defined.

The reaction of Equation 17a is best carried out under the conditions taught by Takayuki Okabe, et al., in *J. Heterocyclic, Chem.*, 20, 735 (1983).

Alternatively, the bromoheterocycles of Formula XVIb (A is A-2) can be synthesized by bromination of the heterocycles of Formula XXXI with a brominating agent such as bromine or N-bromosuccinimide as shown below in Equation 18.

wherein

X, Y, Z, $Z_1$ and $Z_2$ are as previously defined.

The reaction of Equation 18 is best carried out in an inert solvent such as chloroform or carbontetrachloride at a temperature between about 0° C. to 77° C. The products can then be isolated by filtration, concentration of the filtrate and washing the resulting residue with water. Crystallization or chromatography may be used for further purification, if desired.

The compounds of Formula VIII can be prepared by methods known in the art such as those taught by Tetsuzo Kato, et al. in *Yakugaku Zasshi*, 93, (11), 1437 (1973), Roman Balicki, et al. in *Pol. J. Chem.*, 54, 2175 (1980), Roman Balicki in *Pol. J. Chem.*, 55, 1995 (1981) and 57, 1251 (1983), D. J. Brown, et al. in *J. Chem. Soc., Perkin Trans.* 1, 1819 (1972), Hiroshi Yamamoto, et al. in *Bull. Chem. Soc. Jpn.*, 50 (2), 453 (1977), A. N. Kost, et al. in *Khim. Geterotsikl. Soedin.*, 4, 558 (1977) and Jean Imbach, et al. in *Bull. Soc. Chim. Fr.*, (5) 1929 (1970) or by modifications of these methods.

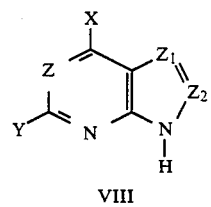

VIII wherein

X, Y, Z, $Z_1$ and $Z_2$ are as previously defined.

The heterocyclic esters of Formula XVb (A is A-4) can be synthesized from the aminoheterocyclic esters of Formula XXXII by similar methods as discussed for the preparation of the heterocyclic esters of Formula XVa (A is A-1) from aminoazole esters of Formula XIX. For example, reaction of the aminoheterocyclic esters of Formula XXXII with a β-dicarbonyl compound of Formula XVIII should give the desired esters of Formula XVb (A is A-4, X is $X_1$, Y is $Y_1$, Z is C—U) as shown below in Equation 19.

Equation 19

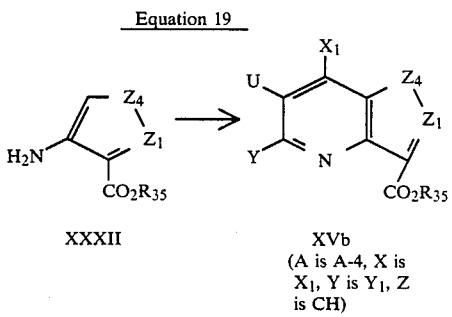

XVIII + XXXII → XVb
(A is A-4, X is $X_1$, Y is $Y_1$, Z is CH)

wherein
X₁, U, Y, Z₄, Z₁ and R₃₅ are as previously defined.

The reaction of Equation 19 is best carried out under the conditions taught by A. Z. Britten, et al. in *Chem. Ind.*, 6, 278 (1973).

The bromoheterocycles of Formula XVIc (A is A-4) can be synthesized from the aminobromoheterocycles in the same way as discussed previously for the preparation of the heterocyclic esters of Formula XVa (A is A-1) from the aminoheterocyclic esters of Formula XIX. Alternatively, compounds of Formula XXXIII can be converted to the bromoheterocycles of Formula XVIc (Z is N). For example, reaction of compounds of formula XXXIII ($X_3$ is $CH_3$, $Y_3$ is $CH_3$) with $HCO_2NH_4$ gives the desired bromoheterocycles of Formula XXIc (Z is N, X is $CH_3$, Y is $CH_3$) as shown below.

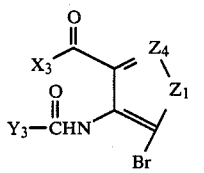
XXXIII

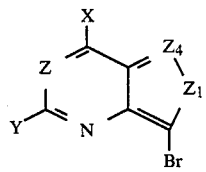
XVIc wherein
X, Y, $Z_4$ and $Z_1$ are as previously defined;
$X_3$ is $X_1$ or $C_1-C_4$ alkoxy; and
$Y_3$ is $Y_1$ or $C_1-C_4$ alkoxy.

Equation 20

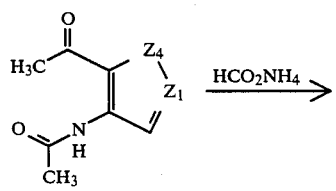
XXXIII
($X_1$ is $CH_3$, $Y_1$ is $CH_3$)

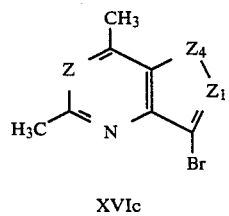
XVIc
(X is $CH_3$, Y is $CH_3$, Z is N)

The reaction of Equation 20 is best carried out under the conditions taught by Guy Ah-Kon, et al., in *C. R. Acad. Sci., Ser. C.*, 278 (26), 1513 (1974).

The compounds of Formula XVc (A is A-6) and Formula XVId (A is A-6) can be prepared from compounds of Formula XXXIV, Formula XXXV and Formula XXXVI by similar chemistry as taught previously for the preparation of compounds of Formula XVb and Formula XVIc.

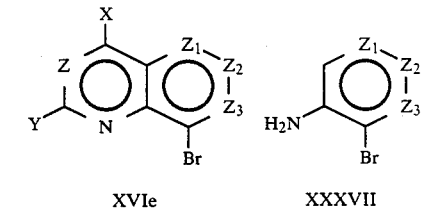

XVc    XVId

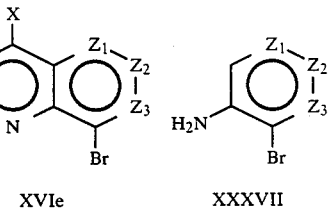

XXXIV    XXXV    XXXVI wherein
X, Y, Z, $X_3$, $Y_3$, $Z_1$, $Z_4$ and $R_{35}$ are as previously defined.

The bromoheterocycles of Formula XVIe (A is A-5) can be prepared from compounds of Formula XXXVII and Formula XXXVIII through similar chemistry as taught previously for the preparation of compounds of Formula XVIC.

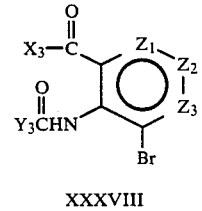

XVIe    XXXVII

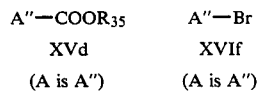

XXXVIII wherein
X, Y, $X_3$, $Y_3$, Z, $Z_1$, $Z_2$ and $Z_3$ are as previously defined.

The heterocyclic esters of Formula XVd (A is A") and the bromoheterocycles of Formula XVIf (A is A") can be prepared by modifications of those methods discussed previously.

| A"—COOR₃₅ | A"—Br |
|---|---|
| XVd | XVIf |
| (A is A") | (A is A") | wherein
A" is A-8, A-9, A-12, A-13, A-14, A-15, A-16, A-17 and A-19; and
$R_{35}$ is as previously defined.

The bromoheterocycles of Formula XVIg (A is A-11) can be prepared from compounds of Formula XXXIX. For example, reaction of compounds of Formula XXXIX with triethylorthoacetate gives the desired bromoheterocycles of Formula XVIg (A is A-11, X is CH$_3$) as shown below.

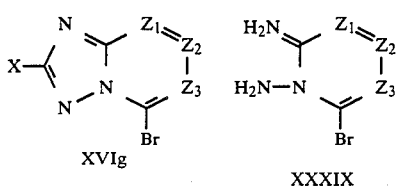

wherein
X, Z$_1$, Z$_2$ and Z$_3$ are as previously defined.

Equation 21

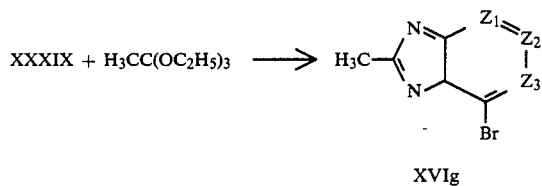

wherein
Z$_1$, Z$_2$ and Z$_3$ are as previously defined.

The reaction of Equation 21 is best carried out in an inert solvent such as acetic acid at a temperature between about 20° C. to 118° C.

The products may be isolated by evaporation of the solvent, followed by chromatography or crystallization of the residue.

The bromoheterocycles of Formula XVIh (A is A-16) can be prepared from compounds of Formula XXXX. For example, reaction of some of the compounds of Formula XXXX with 2,3-butadione gives the desired products of Formula XVIh (X is CH$_3$, Y is CH$_3$) as shown below in Equation 22.

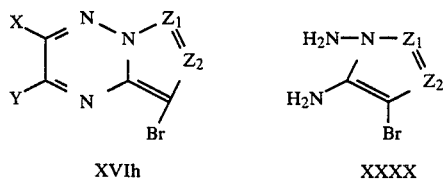

wherein
X, Y, Z$_1$ and Z$_2$ are as previously defined.

Equation 22

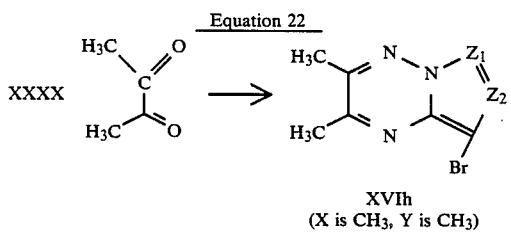

wherein
Z$_1$ and Z$_2$ are as previously defined.

The reaction of Equation 22 is best carried out in an inert solvent such as toluene in the presence of an acid catalyst such as p-toluenesulfonic acid, if necessary, at a temperature between about 0° C. to 120° C. The products may be isolated by evaporation of the solvent, fiollowed by chromatography or recrystallization of the residue.

The bromoheterocycles of Fomrula XVIi (A is A-7) and the heterocyclic esters of Formula XVe (A is A-7) may be prepared by modification of methods taught by H. J. Metz, et al. in *Chem. Ber.*, 115 (8), 2807 (1982).

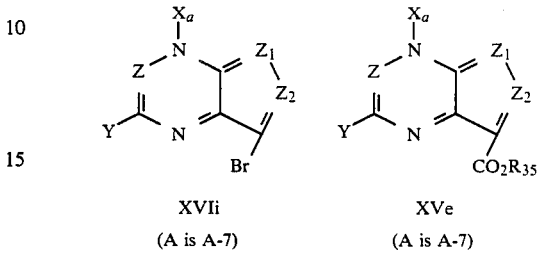

wherein
X$_a$, Y, Z, Z$_1$, Z$_2$ and R$_{35}$ are as previously defined.

The heterocycles of Formula XXXI can be prepared by the methods taught by Takayuki Okabe, et al. in *J. Heterocyclic. Chem.*, 20, 735 (1983), W. Flitsch, et al., in *Liebigs Ann. Chem.*, 735 35 (1970) and M. Zapan, et al., in *J. Heterocyclic Chem.*, 8 1 (1971) or by modification of these methods.

The heterocycles of Formula XXXIa (Z$_1$ is N, Z$_2$ is N) can be prepared by the reaction of compounds of Formula XXXXI with orthoformate of Formula XXXXII as shown below in Equation 23.

Equation 23

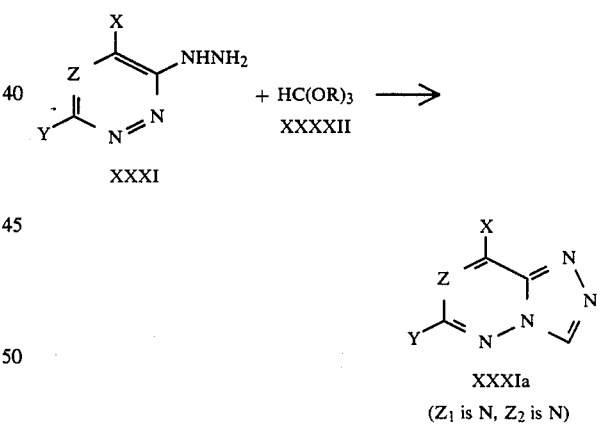

wherein
R is lower alkyl; and
X, Y and Z are as previously defined.

The reaction of Equation 23 is best carried out in an inert solvent such as toluene at a temperature between about 0° C. to 120° C. The product can be isolated by evaporation of the reaction solvent and orthoformate. Crystallization or chromatography may be used for further purification of the products.

The heterocycles of Formula XXXIb (Z$_1$ is N, Z$_2$ is C—U) can be prepared by the reaction of compounds of Formula XXXXIII with an α-halocarbonyl compound of Formula XXXXIV as shown in Equation 24.

Equation 24

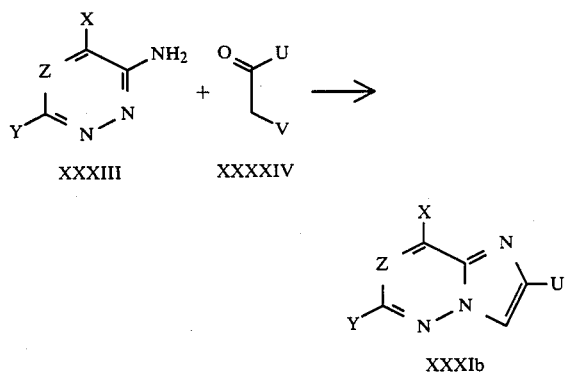

wherein,

X, Y, Z, U and V are as previously defined.

The reaction of Equation 24 is best carried out in an inert solvent such as N,N-dimethylformamide at a temperature between about 0° C. to 160° C. The products can be isolated by evaporation of the reaction solvent and washing the residue with other solvent such as hexane or ether. Crystallization or chromatography may be used for further purification, if desired.

The heterocycles of Formula XXXXV (A is A-1) can be synthesized by the same methods as those for the preparation of the esters of Formula XVa (A is A-1) using the aminoazole of Formula XXXXVI instead of the aminoazole esters of Formula XIX as starting material.

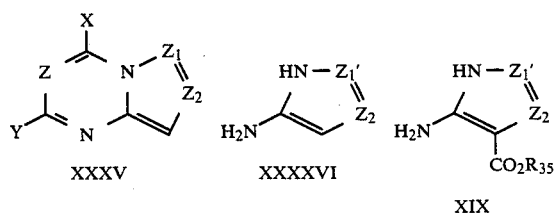

wherein X, Y, Z, $Z_1$, $Z_1'$, $Z_2$ and $R_{35}$ are as previously defined.

The compounds of Formula XVIII, XIX, XX, XXI, XXVI, XXVII, XXVIII, XXX, XXXII, XXXIII, XXXIV, XXXV, XXXVI, XXXVII, XXXVIII, XXXIX, XXXX, XXXXI, XXXXII, XXXXIII, XXXXIV and XXXXVI can be prepared by methods known in the art or by obvious modification of these known methods.

EXAMPLE 1

2-(((((5,7-Dimethylpyrazolo((1,5-A))pyrimidine-3-yl)carbonylamino))sulfonyl))benzoic acid, methyl ester To 1.9 g of 5,7-dimethylpyrazolo(1,5-A)pyrimidine-3-carboxylic acid in 10 mL of methylene chloride at 0° C. was added dropwise 0.5 mL of pyridine and then a solution of 1 mL of thionyl chloride in 3 mL of methylene chloride. The resultant solution was stirred at room temperature for 12 hours. The reaction solution was then concentrated under reduced pressure. To the resultant residue was added 30 mL of anhydrous methylene chloride. To this solution at 5° C. was added portionwise 2.1 g of methyl 2-(aminosulfonyl)benzoate followed by 1.1 g of triethylamine. The resulting mixture was stirred at room temperature for 18 hours followed by concentration under reduced pressure. The resultant residue was stirred in 100 mL of aqueous 1.0M sodium carbonate solution for 0.5 hour. The resultant suspension was then filtered. The filtrate was washed with ether followed by acidification with concentrated hydrochloric acid to pH <3. The mixture was then stirred for 15 minutes and the resultant suspension was filtered. The solid collected was washed with water and then ether to give, after being dried in oven at 80° C. for 2 hours, 1.4 g of the desired product, m.p. 204°–207° C.

NMR(DMSO-$d_6$)δ: 2.67(s, 3H); 2.73 (s, 3H); 3.83 (s, 3H); 7.28 (s, 1H); 7.6–8.36 (m, 4H); 8.63 (s, 1H); and 11.2 (bs, 1H).

EXAMPLE 2

N-((2-Methylsulfonyl)phenylsulfonyl)-5,7-dimethyl-pyrazolo((1,5-A))pyrimidine-3-carboxamide To 1.9 g of 5,7-dimethylpyrazolo(1,5-A)pyrimidine-3-carboxylic acid in 10 mL of methylene chloride at 0° C. was added dropwise 0.5 mL of pyridine and then a solution of 1 mL of thionyl chloride in 3 mL of methylene chloride. The mixture was then stirred at room temperature for 12 hours, and then concentrated under reduced pressure. To the residue was added 30 mL of anhydrous methylene chloride. To the resultant solution at 5° C. was added 2.3 g of 2-(methylsulfonyl)benzenesulfonamide and then 1.1 g of triethylamine. The reaction mixture was stirred at room temperature for 18 hours and then concentrated under reduced pressure. The residue was then stirred in 100 mL of aqueous 1.0M sodium carbonate aqueous solution for 0.5 hour. The resulting suspension was filtered. The filtrate was washed with ether and then acidified with concentrated hydrochloric acid to pH <3. The resulting suspension was filtered. The filtered solid was washed with water and then ether to yield, after being dried in oven at 80° C. for 2 hours, 0.31 g of the desired product, m.p. 230°–233° C.

NMR(DMSO-$d_6$)δ: 2.64 (s, 3H); 2.71 (s, 3H); 3.47 (s, 3H); 7.22 (s, 1H); 8.0–8.5 (m, 4H); 8.57 (s, 1H); and 11.30 (bs, 1H).

EXAMPLE 3

N-((2-(1-Ethyl-1H-tetrazol-5-yl)phenylsulfonyl)-pyrazolo((1,5-A))pyrimidine-3-carboxamide To 0.57 g of 5,7-dimethylpyrazolo(1,5-A)pyrimidine-3-carboxylic acid in 15 ml of chloroform was added 0.53 g of 1,1-carbonyldiimidazole. The resulting mixture was stirred at 55° C. for 3.5 hours. To the reaction solution was then added 0.75 g of 2-(1-ethyl-1H-tetrazol-5-yl)benzenesulfonamide followed by 0.4 g of triethylamine. The resulting solution was stirred at 55° C. for 40 hours and was then heated at reflux for 15 hours. The reaction mixture was then allowed to cool to room temperature and was concentrated under reduced pressure. The residue was added to 21 mL of water. To the aqueous suspension was then added dropwise 10% aqueous hydrochloric acid until the pH of the aqueous solution became ~3. The suspension which formed was stirred at room temperature for another 20 minutes and was then filtered. The solid collected was washed with water and the ether to give, after being dried in an oven at 80° C. for 2 hours, 0.73 g of the desired product, m.p. 233°–236° C.

NMR(DMSO-d$_6$)δ: 1.54 (t, 3H); 2.79 (s, 3H); 2.80 (s, 3H); 4.27 (q, 2H); 6.85 (s, 1H); 7.41 (m, 1H); 7.82 (m, 2H); 8.50 (s, 1H); and 8.65 (m, 1H).

EXAMPLE 4

2-(((2,4-Dimethylimidazo((1,5-a))pyrimidine-8-ylcarbonyl)aminosulfonyl))benzoic acid, methyl ester To 0.55 g of 2,4-dimethylimidazo((1,5-a)pyrimidine-8-carboxylic acid in 21 ml of acetonitrile at room temperature was added 0.8 g of triethylamine and then 0.86 g of 2-chloro-1-methylpyridinium iodide. The mixture was then stirred at room temperature for 30 minutes. To this mixture was then added 0.9 g of methyl 2-(aminosulfonyl)benzoate followed by 0.4 g of triethylamine. The resulting mixture was stirred at room temperature for 12 hours and was then filtered. The solid collected was stirred in ether and was then filtered. The filtrate was combined and was concentrated under reduced pressure. The resultant residue was stirred in 15 ml of water and was acidified with 10% HCl aqueous solution until pH ~2 while being cooled in an ice/water bath. To this suspension was then added 20 ml of ether. The mixture was stirred at room temperature for 1 hour and was then filtered. The solid collected was washed with water and then ether, to give, after being dried in oven at 50° C. for 12 hours, 0.35 g of the desired product, m.p. 228°–230° C.

NMR(DMSO-d$_6$)δ: 2.60 (s, 3H); 2.69 (s, 3H); 3.83 (s, 3H); 6.96 (s, 1H); 7.6–7.9 (m, 3H); 8.2 (m, 1H); and 8.53 (s, 1H).

EXAMPLE 5

2,4-Dimethylimidazo((1,5-a))pyrimidine-8-carboxylic acid

To a suspension of 1.25 g of 2,4-dimethylimidazo((1,5-a))pyrimidine-8-carboxylic acid, ethyl ester in 7 ml of ethanol was added a solution of 1 g of potassium hydroxide in 4 ml of water. The reaction mixture was then heated at reflux for 45 minutes and was then concentrated under reduced pressure. The residue was dissolved in water (~15 ml) and was acidified with 10% HCl until pH ~3 while being cooled in an ice/water bath. The solid formed was collected by filtration and was washed with water and ether to give, after being dried in oven at 50° C. for 12 hours, 0.98 g of the desired product, m.p. 248°–249° C.

NMR(DMSO-d$_6$)δ: 2.49 (s, 3H); 2.64 (s, 3H); 6.8 (s, 1H); 8.34 (s, 1H); and 12.0 (bs, 1H).

EXAMPLE 6

2-(((((5,7-Dimethyl-((1,2,3))-triazolo((1,5-a))pyrimidine-3-yl)carbonylamino))sulfonyl))benzoic acid, methyl ester To 0.55 g of 5,7-dimethyl-((1,2,3))-triazolo((1,5-a))pyrimidine-3-carboxylic acid in 16 ml of acetonitrile was added 1 g of 2-chloro-1-methylpyridinium iodide. To this mixture was then added 0.96 g of triethylamine in 5 ml of acetonitrile dropwise. The mixture was stirred at room temperature for 30 minutes. To this mixture was then added 1.08 g of methyl 2-(aminosulfonyl)benzoate followed by 0.47 g of triethylamine. The resulting mixture was stirred at room temperature for 12 hours and was then filtered. The solid collected was stirred in ether and was then filtered. The filtrate was combined and was concentrated under reduced pressure. The resultant residue was stirred in 15 ml of water and was acidified with 10% HCl aqueous solution until pH ~3 while being cooled in an ice/water bath. To this suspension was then added 30 ml of ether. The mixture was stirred at room temperature for 1 hour and was then filtered. The solid collected was washed with water and then ether to give, after being dried in oven at 50° C. for 12 hours, 0.54 g of a solid, m.p. 228°–230° C. This solid was then further purified by flash column chromatography (silica gel, 4% methanol in methylene chloride as eluent) to give 0.17 g of the desired product, m.p. 193°–195° C.

NMR(DMSO-d$_6$)δ: 2.65 (s, 3H); 2.85 (s, 3H); 3.83 (s, 3H); 7.34 (s, 1H); 7.60–7.85 (m, 3H); 8.21 (m, 1H); and 11.65 (bs, 1H).

EXAMPLE 7

5,7-Dimethyl-((1,2,3))-triazolo((1,5-a))pyrimidine-3-carboxylic acid

To a solution of 4.37 g of 5,7-dimethyl-((1,2,3))triazolo((1,5-a))pyrimidine-3-carboxylic acid, ethyl ester in 30 ml of ethanol was added a solution of 3 g of potassium hydroxide in 12 ml of water. The resulting solution was heated at reflux for 1 hour and was then cooled down to room temperature. The ethanol was then removed under reduced pressure. Water was then added to the residue until the volume reached 50 ml. The aqueous solution was washed with 75 ml of CH$_2$Cl$_2$ and was then acidified with cooling (ice/water bath) with concentrated hydrochloric acid until pH ~3. The resulting suspension was stirred for another 5 minutes and was then filtered. The solid collected was washed with water and then ether to give, after being dried in oven at 50° C. for 12 hours, 3 g of the desired product, m.p. 137°–138° C.

NMR(DMSO-d$_6$)δ: 2.7 (s, 3H); 2.9 (s, 3H); 7.04 (s, 1H); and 13.0 (bs, 1H).

EXAMPLE 8

5,7-Dimethyl-((1,2,3))-triazolo((1,5-a))pyrimidine-3-carboxylic acid, ethyl ester To 300 ml of ethanol was added 23.3 g of 5-amino-1H-((1,2,3))-triazolo-4-carboxylic acid, ethyl ester, 47 g of 2,4-pentanedione and 4 ml of piperidine. The reaction mixture was then heated at reflux for 4 hours. To the reaction solution was then added 47 g of 2,4-pentanedione. The reaction solution was then refluxed for another 12 hours. To the reaction solution was then added another 21 ml of 2,4-pentanedione and the reaction solution was refluxed for another 8 hours. An additional 21 ml of 2,4-pentanedione was then added and refluxing was continued for another 12 hours. The reaction solution was then cooled to room temperature and was concentrated under reduced pressure. The residue was stirred in 300 ml of hexanes for 30 minutes and was filtered. The solid collected was washed with hexanes and was dried in oven at 50° C. for 12 hours to give 30.4 g of the desired product, m.p. 174°–176° C.

NMR(CDCl$_3$)δ: 1.5 (t, 3H); 2.77 (s, 3H); 2.97 (s, 3H); 4.54 (q, 2H); and 6.93 (s, 1H).

EXAMPLE 9

2-(((((5,7-Dimethyl-((1,2,4))-triazolo((1,5-a))pyrimidin-2-yl)carbonylamino))sulfonyl))benzoic acid, methyl ester To a suspension of 0.51 g of 5,7-dimethyl-((1,2,4))-triazolo((1,5-a))pyrimidine-2-carboxylic acid in 16 ml of acetonitrile was added 0.86 g of 2-chloro-1-methylpyridinium iodide. To this mixture was then added 0.8 g of triethylamine in 5 ml of acetonitrile. The reaction mixture was then stirred at room temperature for 30 minutes. To this mixture was then added 0.9 g of methyl 2-(aminosulfonyl)benzoate followed by 0.4 g of triethylamine. The resulting mixture was stirred at room temperature for 2 days and was then concentrated under reduced pressure. The residue was stirred in 15 ml of water and was acidified with 10% HCl aqueous solution until pH ~3 while being cooled in an ice/water bath. The solid formed was collected by filtration, washed with water and then ether, and dried in oven at 50° C. for 12 hours to give 0.65 g of the desired product, m.p. 227°–229° C.

NMR(DMSO-$d_6$)$\delta$: 2.61 (s, 3H); 2.72 (3, 3H); 3.85 (s, 3H); 7.33 (s, 1H); 7.6–7.85 (m, 3H); and 8.2 (m, 1H).

EXAMPLE 10

5,7-Dimethyl-((1,2,4))-triazolo((1,5-a))pyrimidine-2-carboxylic acid

To 4 g of 5,7-dimethyl-((1,2,4))-triazolo(1,5-a)pyrimidine-2-carboxylic acid, ethyl ester, in 20 ml of ethanol was added a solution of 1.3 g of potassium hydroxide in 10 ml of water. An additional 10 ml of ethanol was then added. The reaction mixture was heated at 55° C. for 2 hours and was then concentrated under reduced pressure. The residue was stirred in 20 ml of water and was acidified with 1N HCl aqueous solution until pH ~1 while being cooled in an ice/water bath. The solid formed was collected by filtration, washed with water and then ether, and was dried in oven at 50° C. for 12 hours to give 0.82 g of the desired product, m.p. 188°–189° C.

NMR(DMSO-$d_6$)$\delta$: 2.59 (s, 3H); 2.73 (s, 3H); 7.27 (s, 1H); and 13–14 (bs, 1H).

EXAMPLE 11

5,7-Dimethyl-((1,2,4))-triazolo((1,5-a))pyrimidine-2-carboxylic acid, ethyl ester To 11.7 g of 5-amino-1H-((1,2,4))-triazolo-3-carboxylic acid, methyl ester in 150 ml of ethanol was added 16 g of 2,4-pentanedione and 4 ml of piperidine. The resulting mixture was refluxed for 2.5 days under nitrogen. The mixture was then cooled down to room temperature and was filtered. The solid collected was washed with ether and was dried in oven at 50° C. for 12 hours to give 9.35 g of the desired product, m.p. 180°–181° C.

NMR(CDCl$_3$)$\delta$: 1.47 (t, 3H); 2.70 (s, 3H); 2.86 (s, 3H); 4.56 (q, 2H); and 6.91 (s, 1H).

EXAMPLE 12

N-(((2-Chlorophenyl)-sulfonyl))-5,7-dimethoxypyrazolo((1,5-a))pyrimidine-3-carboxamide To 0.8 g of 3-bromo-5,7-dimethoxypyrazolo(1,5-a)pyrimidine in 40 ml of tetrahydrofuran at −70° C. under nitrogen was added dropwise 4.3 ml of 1.7M t-butyllithium in pentane. The resulting mixture was stirred at −70° C. under N$_2$ for 15 minutes. To this solution at −70° C. was then added 0.75 g of 2-chlorobenzenesulfonyl isocyanate. The resulting mixture was stirred at −60° C. for 30 minutes and was then allowed to warm up to room temperature. The mixture was stirred at room temperature for another 5 minutes and was then concentrated under reduced pressure. The residue was then stirred in 30 ml of water and was then filtered. The filtrate was then acidified with 10% HCl aqueous solution until pH ~2 while being cooled in an ice/water bath. The solid was collected by filtration, washed with water and then a mixture of ether and hexane (1:1), and further purified by flash column chromatography (silica gel; 5%, 10%, 20% ether in CH$_2$Cl$_2$ and then acetonitrile) to give 0.02 g of the desired product, m.p. 186°–190° C.

NMR(CDCl$_3$)$\delta$: 4.17 (s, 3H); 4.21 (s, 3H); 5.9 (s, 1H); 7.6 (m, 3H); 8.38 (s, 1H); and 8.4 (m, 1H).

EXAMPLE 13

3-Bromo-5,7-dimethoxypyrazolo(1,5-a)pyrimidine

To a solution of 1.2 g of sodium dissolved in 60 ml of methanol was added 6.7 g of 3-bromo-5,7-dichloropyrazolo(1,5-a)pyrimidine. The resulting mixture was stirred at room temperature for 12 hours and was then concentrated under reduced pressure. The residue was then stirred in water and was then filtered. The solid collected was washed with ether and was dried in oven at 50° C. for 12 hours to give 5.24 g of the desired product, m.p. 188°–190° C.

NMR(CDCl$_3$)$\delta$: 4.05 (s, 3H); 4.14 (s, 3H); 5.7 (s, 1H); and 7.94 (s, 1H).

EXAMPLE 14

3-Bromo-5,7-dichloropyrazolo(1,5-a)pyrimidine

To a solution of 5.3 g of 5,7-dichloropyrazolo(1,5-a)pyrimidine in 70 ml of chloroform was added portionwise 6 g of N-bromosuccinimide while keeping the temperature below 40° C. The resulting solution was refluxed for 30 minutes and was then stirred at room temperature for 12 hours. The suspension was then filtered. The filtrate was washed with 50 ml of cold 10% sodium hydroxide aqueous solution twice and was then dried over MgSO$_4$. The chloroform solution was then concentrated under reduced pressure to give 7.47 g of the desired product, m.p. 73°–75° C.

NMR(CDCl$_3$)$\delta$: 7.02 (s, 1H) and 8.18 (s, 1H).

EXAMPLE 15

Methyl 2-((6,8-dimethylimidazo[1,2-b]pyridazin-3-ylcarbonyl)aminosulfonyl)benzoate To a solution of 2.0 g (8.8 mmol) of 3-bromo-6,8-dimethylimidazo[1,2-b]pyridazine in 50 mL of tetrahydrofuran at −78° C. was added 6.1 mL (9.7 mmol) of a 1.6M solution of n-butyllithium in hexanes. After 15 min, carbon dioxide was bubbled through the solution for 10 min. After warming to room temperature, the solid material was isolated by filtration and washed with 1 mL of water. After drying overnight in a vacuum desiccator, 1.48 g of a solid was obtained.

To a slurry of 0.5 g (2.5 mmol) of the solid obtained above in 8 mL of dichloromethane was added 1 mL oxalyl chloride. This mixture was heated to reflux for 2 h. After cooling, the volatiles were removed with a rotary evaporator and vacuum pump. The residue was dissolved in 6 mL of dichloromethane and was cooled in an ice bath. To this solution was added 0.55 g (2.5 mmol) of methyl 2-(aminosulfonyl)-benzoate and 0.36 mL (2.6 mmol) of triethylamine. The reaction was stirred 16 h at room temperature. To the reaction mixture was added 1 mL of water and the layers were separated. The organic layer was dried (Na$_2$SO$_4$) and the solvent was removed with a rotary evaporator. The residue was purified by flash chromatography to give 0.33 g of the title compound as a yellow solid, m.p. 210°–212° C.

EXAMPLE 16

3-Bromo-6,8-dimethylimidazo[1,2-b]pyridazine

To a solution of 3.63 g (24.7 mmol) of 6,8-dimethylimidazo[1,2-b]pyridazine in 25 mL of chloroform was added 4.84 g (27.2 mmol) of N-bromosuccinimide. After 2 h, 1 mL of a saturated aqueous solution of sodium bicarbonate was added. The layers were separated. The organic layer was dried ($Na_2SO_4$) and the solvent was removed with a rotary evaporator. The residue was purified by flash chromatography to give 4.66 g of the title compound as a white solid, m.p. 137°–139° C.

EXAMPLE 17

6,8-Dimethylimidazo[1,2-b]pyridazine

A mixture of 25 g (148 mmol) of bromoacetaldehyde dimethyl acetal, 5 mL of water and 5 mL of 48% HBr was refluxed 2 h. After cooling, it was poured into 50 mL of ethanol. Solid sodium bicarbonate was added until bubbling ceased. The mixture was filtered and to the filtrate was added 7.5 g (61 mmol) of 3-amino-4,6-dimethylpyridazine. After stirring 16 h, the ethanol was removed with a rotary evaporator. The residue was triturated with ethanol to give a brown solid which was dissolved in water and washed with dichloromethane. The aqueous layer was brought to pH 9 with sodium bicarbonate and extracted with dichloromethane. Drying ($Na_2SO_4$) and solvent removal with a rotary evaporator gave 4 g of the title compound as a brown solid, m.p. 70°–74° C.

EXAMPLE 18

Methyl 2-((2,4-dimethylpyrrolo[1,2-b]pyridazin-7-ylcarbonyl)aminosulfonyl)benzoate To a solution of 0.40 g (2.7 mmol) of 2,4-dimethylpyrrolo[1,2-b]pyridazine in 15 mL of dichloromethane at −78° C. was added, by syringe pump over a period 70 min, a solution of 0.62 g (2.7 mmol) of methyl 2-(isocyanatosulfonyl)benzoate. The reaction mixture was allowed to warm to room temperature. The residue was purified by flash chromatography to give 0.12 g of a white solid, m.p. 200°–202° C.

The following compounds may be prepared by one skilled in the art by utilizing the procedures and examples shown above and obvious variations thereof.

General Formulae

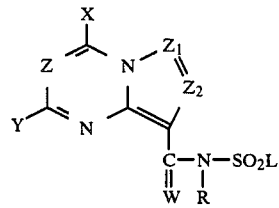

General Formula 1

-continued

General Formulae

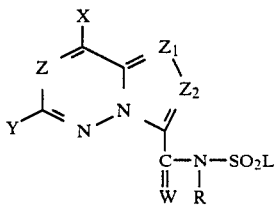

General Formula 2

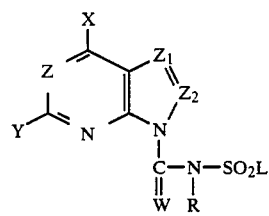

General Formula 3

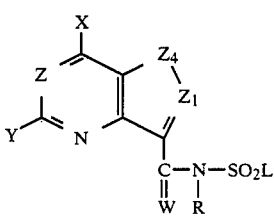

General Formula 4

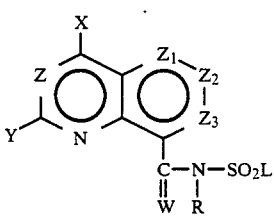

General Formula 5

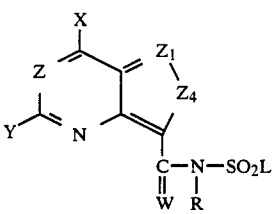

General Formula 6

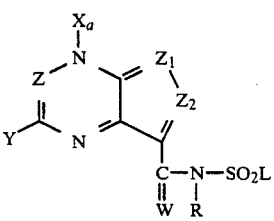

General Formula 7

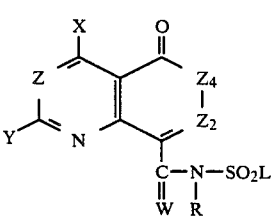

General Formula 8

-continued
General Formulae
General Formula 9
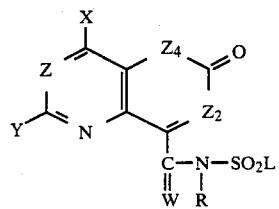
General Formula 10
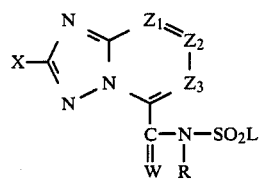
General Formula 11
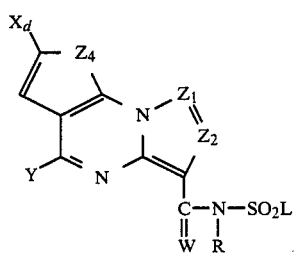
General Formula 12
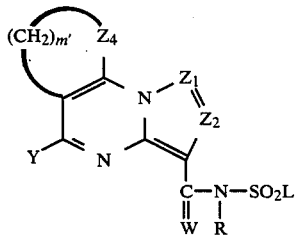
General Formula 13
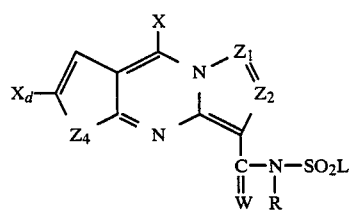
General Formula 14
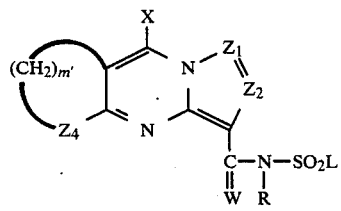
General Formula 15
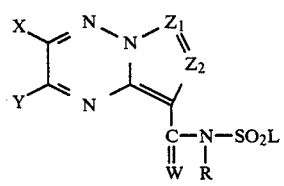
-continued
General Formulae
General Formula 16
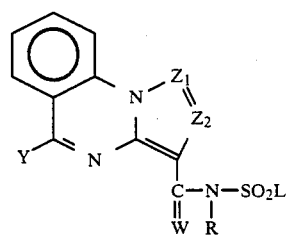
General Formula 17
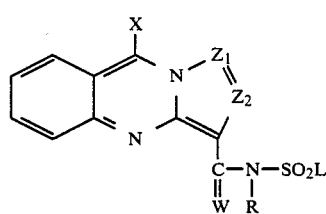
General Formula 18
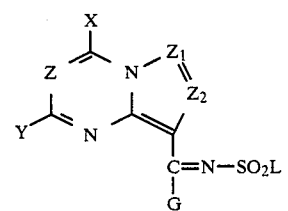
General Formula 19
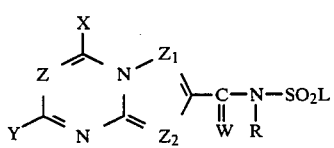
wherein
L-1a is 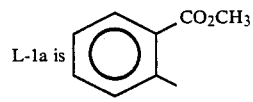
L-1b is 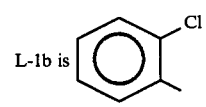
L-1c is 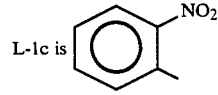
L-1d is 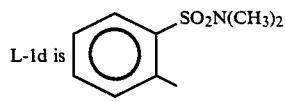
L-1e is 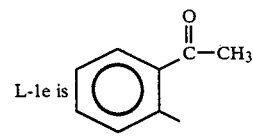

-continued
General Formulae
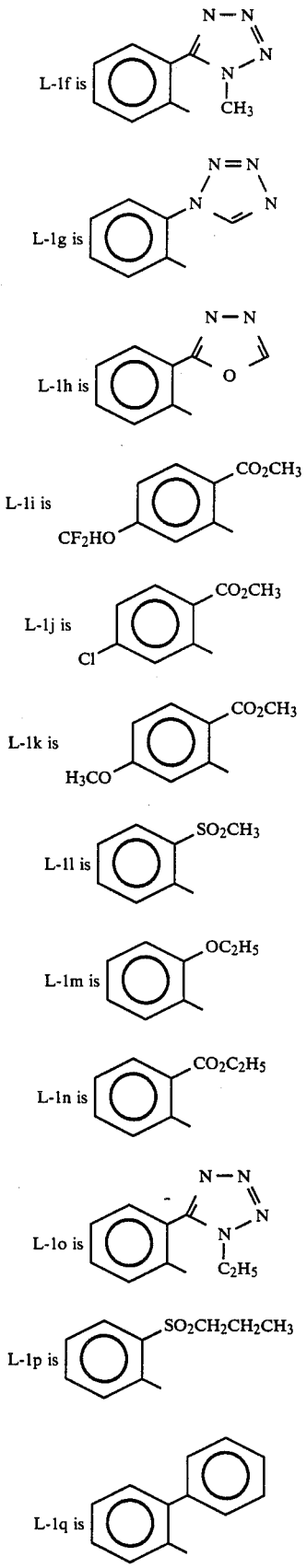
-continued
General Formulae
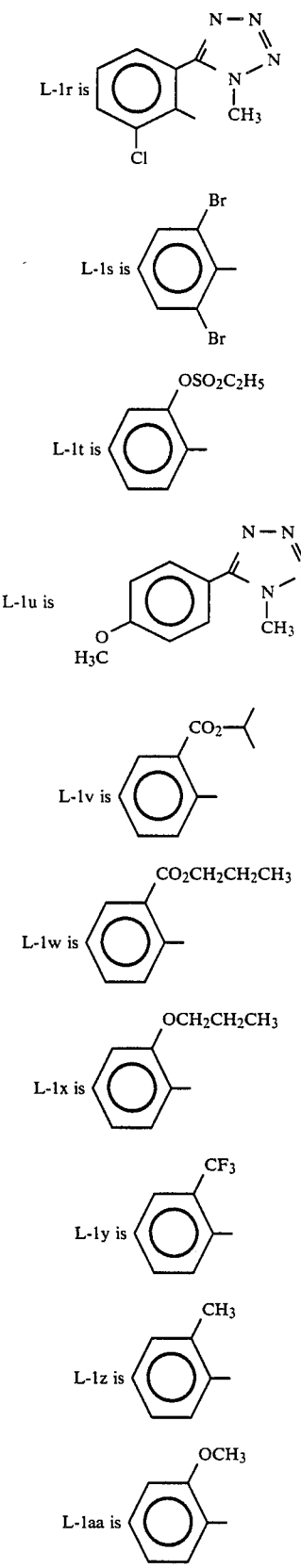

-continued
General Formulae
L-1ab is 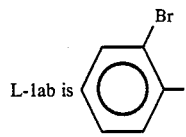
L-1ac is 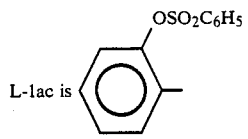
L-1ad is 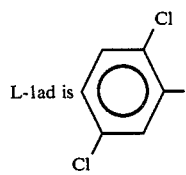
L-1ae is 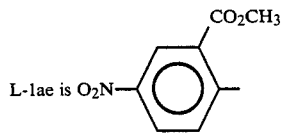
L-1af is 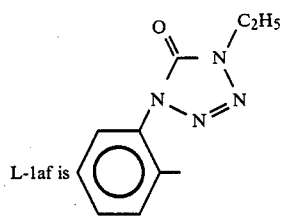
L-3a is 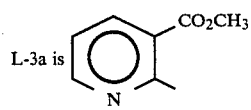
L-3b is 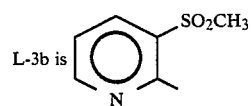
L-4a is 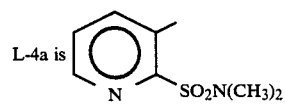
L-7a is 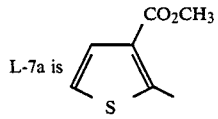
L-8a is 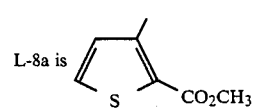
L-8b is 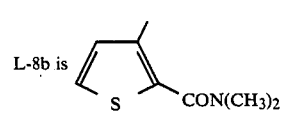
-continued
General Formulae
L-9a is 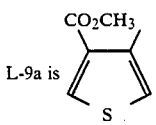
L-10a is 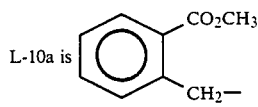
L-12a is 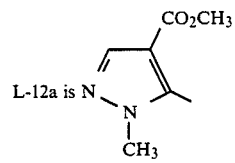
L-12b is 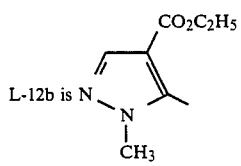
L-12c is 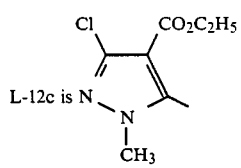
L-14a is 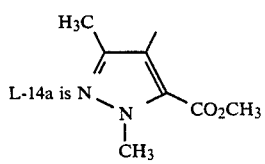
L-15a is 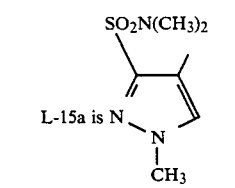
L-16a is 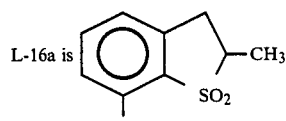
L-16b is 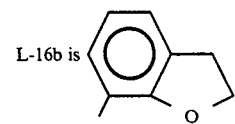
L-18a is 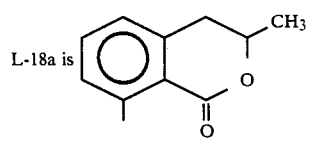

-continued
General Formulae

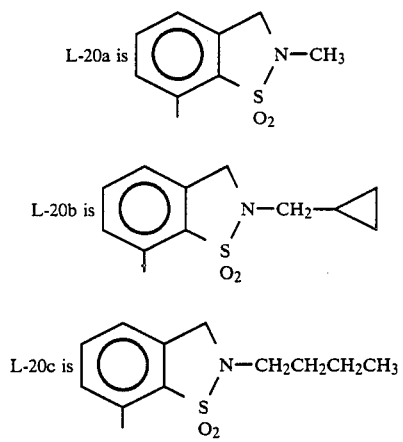

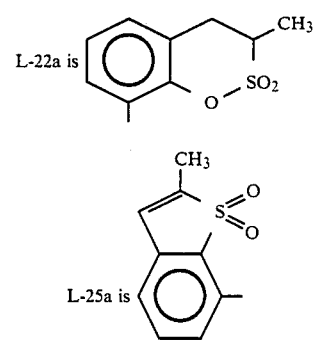

TABLE 1

General Formula 1

| Z | Z₁ | Z₂ | W | X | Y | R | L | m.p. (°C.) |
|---|---|---|---|---|---|---|---|---|
| CH | N | CH | O | CH₃ | CH₃ | H | L-1a | 204–207 |
| CH | N | CH | O | CH₃ | CH₃ | H | L-1b | 250–252 |
| CH | N | CH | O | CH₃ | CH₃ | H | L-1c | 227–232 |
| CH | N | CH | O | CH₃ | CH₃ | H | L-1d | 250–252 |
| CH | N | CH | O | CH₃ | CH₃ | H | L-1e | |
| CH | N | CH | O | CH₃ | CH₃ | H | L-1f | 250–252 |
| CH | N | CH | O | CH₃ | CH₃ | H | L-1g | |
| CH | N | CH | O | CH₃ | CH₃ | H | L-1h | |
| CH | N | CH | O | CH₃ | CH₃ | H | L-1i | |
| CH | N | CH | O | CH₃ | CH₃ | H | L-1j | |
| CH | N | CH | O | CH₃ | CH₃ | H | L-1k | 208–209 |
| CH | N | CH | O | CH₃ | CH₃ | H | L-1l | 230–233 |
| CH | N | CH | O | CH₃ | CH₃ | H | L-1m | 237–239 |
| CH | N | CH | O | CH₃ | CH₃ | H | L-1n | 171–172 |
| CH | N | CH | O | CH₃ | CH₃ | H | L-1o | 233–236 |
| CH | N | CH | O | CH₃ | CH₃ | H | L-1p | 238–240 |
| CH | N | CH | O | CH₃ | CH₃ | H | L-1q | 196–199 |
| CH | N | CH | O | CH₃ | CH₃ | H | L-1r | 304–306 |
| CH | N | CH | O | CH₃ | CH₃ | H | L-1s | 232–234 |
| CH | N | CH | O | CH₃ | CH₃ | H | L-1t | 140–144 |
| CH | N | CH | O | CH₃ | CH₃ | H | L-1u | |
| CH | N | CH | O | CH₃ | CH₃ | H | L-1v | |
| CH | N | CH | O | CH₃ | CH₃ | H | L-3a | |
| CH | N | CH | O | CH₃ | CH₃ | H | L-3b | |
| CH | N | CH | O | CH₃ | CH₃ | H | L-4a | |
| CH | N | CH | O | CH₃ | CH₃ | H | L-7a | |
| CH | N | CH | O | CH₃ | CH₃ | H | L-8a | 203–205 |
| CH | N | CH | O | CH₃ | CH₃ | H | L-8b | |
| CH | N | CH | O | CH₃ | CH₃ | H | L-9a | |
| CH | N | CH | O | CH₃ | CH₃ | H | L-10a | 169–173 |
| CH | N | CH | O | CH₃ | CH₃ | H | L-12a | |
| CH | N | CH | O | C(CH₃)₃ | CH₃ | H | L-1a | 124–125 |
| CH | N | CH | O | Cl | CH₃ | H | L-1d | 257–259 |
| CH | N | CH | O | Cl | CH | H | L-1e | 192–198* |
| CH | N | CH | O | CH₃ | CH₃ | H | L-12b | |
| CH | N | CH | O | CH₃ | CH₃ | H | L-12c | 230–234 |
| CH | N | CH | O | CH₃ | CH₃ | H | L-14a | |
| CH | N | CH | O | CH₃ | CH₃ | H | L-15a | |
| CH | N | CH | O | CH₃ | CH₃ | H | L-16a | 260–262 |
| CH | N | CH | O | CH₃ | CH₃ | H | L-16b | |
| CH | N | CH | O | CH₃ | CH₃ | H | L-18a | |
| CH | N | CH | O | CH₃ | CH₃ | H | L-20a | |
| CH | N | CH | O | CH₃ | CH₃ | H | L-20b | 192–196 |
| CH | N | CH | O | CH₃ | CH₃ | H | L-20c | 210–214 |
| CH | N | CH | O | CH₃ | CH₃ | H | L-22a | |
| CH | N | CH | S | CH₃ | CH₃ | H | L-1a | |
| CH | N | CH | O | CH₃ | CH₃ | CH₃ | L-1a | |
| CH | N | CH | O | OCH₃ | CH₃ | H | L-1a | 184–187 |
| CH | N | CH | O | OCH₃ | CH₃ | H | L-1b | 145–148 |
| CH | N | CH | O | OCH₃ | CH₃ | H | L-1c | |
| CH | N | CH | O | OCH₃ | CH₃ | H | L-1d | 190–192 |
| CH | N | CH | O | OCH₃ | CH₃ | H | L-1e | |
| CH | N | CH | O | OCH₃ | CH₃ | H | L-1f | |
| CH | N | CH | O | OCH₃ | CH₃ | H | L-1g | |

TABLE 1-continued

General Formula 1

| Z | Z₁ | Z₂ | W | X | Y | R | L | m.p. (°C.) |
|---|---|---|---|---|---|---|---|---|
| CH | N | CH | O | OCH₃ | CH₃ | H | L-1h | |
| CH | N | CH | O | OCH₃ | CH₃ | H | L-1i | |
| CH | N | CH | O | OCH₃ | CH₃ | H | L-1j | |
| CH | N | CH | O | OCH₃ | CH₃ | H | L-1k | |
| CH | N | CH | O | OCH₃ | CH₃ | H | L-1n | 181–182(dec) |
| CH | N | CH | O | OCH₃ | CH₃ | H | L-3a | |
| CH | N | CH | O | OCH₃ | CH₃ | H | L-3b | |
| CH | N | CH | O | OCH₃ | CH₃ | H | L-4a | |
| CH | N | CH | O | OCH₃ | CH₃ | H | L-7a | |
| CH | N | CH | O | OCH₃ | CH₃ | H | L-8a | |
| CH | N | CH | O | OCH₃ | CH₃ | H | L-8b | |
| CH | N | CH | O | OCH₃ | CH₃ | H | L-9a | |
| CH | N | CH | O | OCH₃ | CH₃ | H | L-12a | |
| CH | N | CH | O | OCH₃ | CH₃ | H | L-12b | |
| CH | N | CH | O | OCH₃ | CH₃ | H | L-14a | |
| CH | N | CH | O | OCH₃ | CH₃ | H | L-15a | |
| CH | N | CH | O | OCH₃ | CH₃ | H | L-16a | |
| CH | N | CH | O | OCH₃ | CH₃ | H | L-16b | |
| CH | N | CH | O | OCH₃ | CH₃ | H | L-18a | |
| CH | N | CH | O | OCH₃ | CH₃ | H | L-20a | |
| CH | N | CH | O | OCH₃ | CH₃ | H | L-22a | |
| CH | N | CH | S | OCH₃ | CH₃ | H | L-1a | |
| CH | N | CH | O | OCH₃ | CH₃ | CH₃ | L-1a | |
| CH | N | CH | O | CH₃ | OCH₃ | H | L-1a | |
| CH | N | CH | O | OCH₃ | OCH₃ | H | L-1b | 186–190 |
| CH | N | CH | O | CH₃ | OCH₃ | H | L-1c | |
| CH | N | CH | O | CH₃ | OCH₃ | H | L-1d | |
| CH | N | CH | O | CH₃ | OCH₃ | H | L-1e | |
| CH | N | CH | O | CH₃ | OCH₃ | H | L-1f | |
| CH | N | CH | O | CH₃ | OCH₃ | H | L-1g | |
| CH | N | CH | O | CH₃ | OCH₃ | H | L-1h | |
| CH | N | CH | O | CH₃ | OCH₃ | H | L-1i | |
| CH | N | CH | O | CH₃ | OCH₃ | H | L-1j | |
| CH | N | CH | O | CH₃ | OCH₃ | H | L-1k | |
| CH | N | CH | O | CH₃ | OCH₃ | H | L-3a | |
| CH | N | CH | O | CH₃ | OCH₃ | H | L-3b | |
| CH | N | CH | O | CH₃ | OCH₃ | H | L-4a | |
| CH | N | CH | O | CH₃ | OCH₃ | H | L-7a | |
| CH | N | CH | O | CH₃ | OCH₃ | H | L-8a | |
| CH | N | CH | O | CH₃ | OCH₃ | H | L-8b | |
| CH | N | CH | O | CH₃ | OCH₃ | H | L-9a | |
| CH | N | CH | O | CH₃ | OCH₃ | H | L-12a | |
| CH | N | CH | O | CH₃ | OCH₃ | H | L-12b | |
| CH | N | CH | O | CH₃ | OCH₃ | H | L-14a | |
| CH | N | CH | O | CH₃ | OCH₃ | H | L-15a | |
| CH | N | CH | O | CH₃ | OCH₃ | H | L-16a | |
| CH | N | CH | O | CH₃ | OCH₃ | H | L-16b | |
| CH | N | CH | O | CH₃ | OCH₃ | H | L-18a | |
| CH | N | CH | O | CH₃ | OCH₃ | H | L-20a | |
| CH | N | CH | O | CH₃ | OCH₃ | H | L-22a | |
| CH | N | CH | S | CH₃ | OCH₃ | H | L-1a | |
| CH | N | CH | O | CH₃ | OCH₃ | CH₃ | L-1a | |
| CH | N | CH | O | H | CH₃ | H | L-1a | |
| CH | N | CH | O | H | CH₃ | H | L-1b | 236–237 |
| CH | N | CH | O | H | CH₃ | H | L-1c | 249–251 |
| CH | N | CH | O | H | CH₃ | H | L-1d | 240–243 |
| CH | N | CH | O | H | CH₃ | H | L-1e | |
| CH | N | CH | O | H | CH₃ | H | L-1f | |
| CH | N | CH | O | H | CH₃ | H | L-1g | |
| CH | N | CH | O | H | CH₃ | H | L-1h | |
| CH | N | CH | O | H | CH₃ | H | L-1i | |
| CH | N | CH | O | H | CH₃ | H | L-1j | |
| CH | N | CH | O | H | CH₃ | H | L-1k | |
| CH | N | CH | O | H | CH₃ | H | L-1l | 293–294 |
| CH | N | CH | O | H | CH₃ | H | L-1m | |
| CH | N | CH | O | H | CH₃ | H | L-1n | 145–150 |
| CH | N | CH | O | H | CH₃ | H | L-1o | |
| CH | N | CH | O | H | CH₃ | H | L-1p | |
| CH | N | CH | O | H | CH₃ | H | L-1q | |
| CH | N | CH | O | H | CH₃ | H | L-1r | |
| CH | N | CH | O | H | CH₃ | H | L-1s | |
| CH | N | CH | O | H | CH₃ | H | L-1t | |
| CH | N | CH | O | N(CH₃)₂ | CH₃ | H | L-1a | 247–250 |
| CH | N | CH | O | N(CH₃)₂ | CH₃ | H | L-1b | 235–239 |
| CH | N | CH | O | N(CH₃)₂ | CH₃ | H | L-1c | 285–286 |
| CH | N | CH | O | N(CH₃)₂ | CH₃ | H | L-1d | 276–278 |
| CH | N | CH | O | N(CH₃)₂ | CH₃ | H | L-1e | |
| CH | N | CH | O | N(CH₃)₂ | CH | H | L-1f | |
| CH | N | CH | O | N(CH₃)₂ | CH₃ | H | L-1g | |
| CH | N | CH | O | N(CH₃)₂ | CH₃ | H | L-1h | |

TABLE 1-continued

General Formula 1

| Z | Z₁ | Z₂ | W | X | Y | R | L | m.p. (°C.) |
|---|---|---|---|---|---|---|---|---|
| CH | N | CH | O | N(CH₃)₂ | CH₃ | H | L-1i | |
| CH | N | CH | O | N(CH₃)₂ | CH₃ | H | L-1j | |
| CH | N | CH | O | N(CH₃)₂ | CH₃ | H | L-1k | |
| CH | N | CH | O | N(CH₃)₂ | CH₃ | H | L-1l | 270–271 |
| CH | N | CH | O | N(CH₃)₂ | CH₃ | H | L-1m | |
| CH | N | CH | O | N(CH₃)₂ | CH₃ | H | L-1n | |
| CH | N | CH | O | N(CH₃)₂ | CH₃ | H | L-1o | |
| CH | N | CH | O | N(CH₃)₂ | CH₃ | H | L-1p | |
| CH | N | CH | O | N(CH₃)₂ | CH₃ | H | L-1q | |
| CH | N | CH | O | N(CH₃)₂ | CH₃ | H | L-1r | |
| CH | N | CH | O | N(CH₃)₂ | CH₃ | H | L-1s | |
| CH | N | CH | O | N(CH₃)₂ | CH₃ | H | L-1t | |
| CH | CH | N | O | CH₃ | CH₃ | H | L-1a | 228–230 |
| CH | CH | N | O | CH₃ | CH₃ | H | L-1b | 264–266 |
| CH | CH | N | O | CH₃ | CH₃ | H | L-1c | 257–258 |
| CH | CH | N | O | CH₃ | CH₃ | H | L-1d | 288–290 |
| CH | CH | N | O | CH₃ | CH₃ | H | L-1e | |
| CH | CH | N | O | CH₃ | CH₃ | H | L-1f | 277–280 |
| CH | CH | N | O | CH₃ | CH₃ | H | L-1g | |
| CH | CH | N | O | CH₃ | CH₃ | H | L-1h | |
| CH | CH | N | O | CH₃ | CH₃ | H | L-1i | |
| CH | CH | N | O | CH₃ | CH₃ | H | L-1j | |
| CH | CH | N | O | CH₃ | CH₃ | H | L-1k | 258–260 |
| CH | CH | N | O | CH₃ | CH₃ | H | L-1l | 231–233 |
| CH | CH | N | O | CH₃ | CH₃ | H | L-1m | |
| CH | CH | N | O | CH₃ | CH₃ | H | L-1n | 228–232 |
| CH | CH | N | O | CH₃ | CH₃ | H | L-1o | 283–284 |
| CH | CH | N | O | CH₃ | CH₃ | H | L-1p | 270–274 |
| CH | CH | N | O | CH₃ | CH₃ | H | L-1q | 262–264 |
| CH | CH | N | O | CH₃ | CH₃ | H | L-1r | 248–250 |
| CH | CH | N | O | CH₃ | CH₃ | H | L-1s | |
| CH | CH | N | O | CH₃ | CH₃ | H | L-1t | |
| CH | CH | N | O | CH₃ | CH₃ | H | L-1u | 270–272 |
| CH | CH | N | O | CH₃ | CH₃ | H | L-1v | 253–258 |
| CH | CH | N | O | CH₃ | CH₃ | H | L-3a | |
| CH | CH | N | O | CH₃ | CH₃ | H | L-3b | |
| CH | CH | N | O | CH₃ | CH₃ | H | L-4a | |
| CH | CH | N | O | CH₃ | CH₃ | H | L-7a | 233–234 |
| CH | CH | N | O | CH₃ | CH₃ | H | L-8a | |
| CH | CH | N | O | CH₃ | CH₃ | H | L-8b | |
| CH | CH | N | O | CH₃ | CH₃ | H | L-9a | |
| CH | CH | N | O | CH₃ | CH₃ | H | L-10a | |
| CH | CH | N | O | CH₃ | CH₃ | H | L-12a | |
| CH | CH | N | O | CH₃ | CH₃ | H | L-12b | |
| CH | CH | N | O | CH₃ | CH₃ | H | L-12c | |
| CH | CH | N | O | CH₃ | CH₃ | H | L-14a | |
| CH | CH | N | O | CH₃ | CH₃ | H | L-15a | |
| CH | CH | N | O | CH₃ | CH₃ | H | L-16a | 301–303 |
| CH | CH | N | O | CH₃ | CH₃ | H | L-16b | |
| CH | CH | N | O | CH₃ | CH₃ | H | L-18a | |
| CH | CH | N | O | CH₃ | CH₃ | H | L-20a | |
| CH | CH | N | O | CH₃ | CH₃ | H | L-20b | |
| CH | CH | N | O | CH₃ | CH₃ | H | L-20c | |
| CH | CH | N | O | CH₃ | CH₃ | H | L-22a | |
| CH | CH | N | S | CH₃ | CH₃ | H | L-1a | |
| CH | CH | N | O | CH₃ | CH₃ | CH₃ | L-1a | |
| CH | CH | N | O | OCH₃ | CH₃ | H | L-1a | |
| CH | CH | N | O | OCH₃ | CH₃ | H | L-1b | |
| CH | CH | N | O | OCH₃ | CH₃ | H | L-1c | |
| CH | CH | N | O | OCH₃ | CH₃ | H | L-1d | |
| CH | CH | N | O | OCH₃ | CH₃ | H | L-1e | |
| CH | CH | N | O | OCH₃ | CH₃ | H | L-1f | |
| CH | CH | N | O | OCH₃ | CH₃ | H | L-1g | |
| CH | CH | N | O | OCH₃ | CH₃ | H | L-1h | |
| CH | CH | N | O | OCH₃ | CH₃ | H | L-1i | |
| CH | CH | N | O | OCH₃ | CH₃ | H | L-1j | |
| CH | CH | N | O | OCH₃ | CH₃ | H | L-1k | |
| CH | CH | N | O | OCH₃ | CH₃ | H | L-3a | |
| CH | CH | N | O | OCH₃ | CH₃ | H | L-3b | |
| CH | CH | N | O | OCH₃ | CH₃ | H | L-4a | |
| CH | CH | N | O | OCH₃ | CH₃ | H | L-7a | |
| CH | CH | N | O | OCH₃ | CH₃ | H | L-8a | |
| CH | CH | N | O | OCH₃ | CH₃ | H | L-8b | |
| CH | CH | N | O | OCH₃ | CH₃ | H | L-9a | |
| CH | CH | N | O | OCH₃ | CH₃ | H | L-12a | |
| CH | CH | N | O | OCH₃ | CH₃ | H | L-12b | |
| CH | CH | N | O | OCH₃ | CH₃ | H | L-14a | |
| CH | CH | N | O | OCH₃ | CH₃ | H | L-15a | |
| CH | CH | N | O | OCH₃ | CH₃ | H | L-16a | |
| CH | CH | N | O | OCH₃ | CH₃ | H | L-16b | |

TABLE 1-continued

General Formula 1

| Z | $Z_1$ | $Z_2$ | W | X | Y | R | L | m.p. (°C.) |
|---|---|---|---|---|---|---|---|---|
| CH | CH | N | O | OCH$_3$ | CH$_3$ | H | L-18a | |
| CH | CH | N | O | OCH$_3$ | CH$_3$ | H | L-20a | |
| CH | CH | N | O | OCH$_3$ | CH$_3$ | H | L-22a | |
| CH | CH | N | S | OCH$_3$ | CH$_3$ | H | L-1a | |
| CH | CH | N | O | OCH$_3$ | CH$_3$ | CH$_3$ | L-1a | |
| CH | CH | N | O | CH$_3$ | OCH$_3$ | H | L-1a | |
| CH | CH | N | O | CH$_3$ | OCH$_3$ | H | L-1b | |
| CH | CH | N | O | CH$_3$ | OCH$_3$ | H | L-1c | |
| CH | CH | N | O | CH$_3$ | OCH$_3$ | H | L-1d | |
| CH | CH | N | O | CH$_3$ | OCH$_3$ | H | L-1e | |
| CH | CH | N | O | CH$_3$ | OCH$_3$ | H | L-1f | |
| CH | CH | N | O | CH$_3$ | OCH$_3$ | H | L-1g | |
| CH | CH | N | O | CH$_3$ | OCH$_3$ | H | L-1h | |
| CH | CH | N | O | CH$_3$ | OCH$_3$ | H | L-1i | |
| CH | CH | N | O | CH$_3$ | OCH$_3$ | H | L-1j | |
| CH | CH | N | O | CH$_3$ | OCH$_3$ | H | L-1k | |
| CH | CH | N | O | CH$_3$ | OCH$_3$ | H | L-3a | |
| CH | CH | N | O | CH$_3$ | OCH$_3$ | H | L-3b | |
| CH | CH | N | O | CH$_3$ | OCH$_3$ | H | L-4a | |
| CH | CH | N | O | CH$_3$ | OCH$_3$ | H | L-7a | |
| CH | CH | N | O | CH$_3$ | OCH$_3$ | H | L-8a | |
| CH | CH | N | O | CH$_3$ | OCH$_3$ | H | L-8b | |
| CH | CH | N | O | CH$_3$ | OCH$_3$ | H | L-9a | |
| CH | CH | N | O | CH$_3$ | OCH$_3$ | H | L-12a | |
| CH | CH | N | O | CH$_3$ | OCH$_3$ | H | L-12b | |
| CH | CH | N | O | CH$_3$ | OCH$_3$ | H | L-14a | |
| CH | CH | N | O | CH$_3$ | OCH$_3$ | H | L-15a | |
| CH | CH | N | O | CH$_3$ | OCH$_3$ | H | L-16a | |
| CH | CH | N | O | CH$_3$ | OCH$_3$ | H | L-16b | |
| CH | CH | N | O | CH$_3$ | OCH$_3$ | H | L-18a | |
| CH | CH | N | O | CH$_3$ | OCH$_3$ | H | L-20a | |
| CH | CH | N | O | CH$_3$ | OCH$_3$ | H | L-22a | |
| CH | CH | N | S | CH$_3$ | OCH$_3$ | H | L-1a | |
| CH | CH | N | O | CH$_3$ | OCH$_3$ | CH$_3$ | L-1a | |
| CH | CH | N | O | OCH$_3$ | OCH$_3$ | H | L-1a | |
| CH | CH | N | O | OCH$_3$ | OCH$_3$ | H | L-1b | |
| CH | CH | N | O | OCH$_3$ | OCH$_3$ | H | L-1c | |
| CH | CH | N | O | OCH$_3$ | OCH$_3$ | H | L-1d | |
| CH | CH | N | O | OCH$_3$ | OCH$_3$ | H | L-1e | |
| CH | CH | N | O | OCH$_3$ | OCH$_3$ | H | L-1f | |
| CH | CH | N | O | OCH$_3$ | OCH$_3$ | H | L-1g | |
| CH | CH | N | O | OCH$_3$ | OCH$_3$ | H | L-1h | |
| CH | CH | N | O | OCH$_3$ | OCH$_3$ | H | L-1i | |
| CH | CH | N | O | OCH$_3$ | OCH$_3$ | H | L-1j | |
| CH | CH | N | O | OCH$_3$ | OCH$_3$ | H | L-1k | |
| CH | CH | N | O | OCH$_3$ | OCH$_3$ | H | L-3a | |
| CH | CH | N | O | OCH$_3$ | OCH$_3$ | H | L-3b | |
| CH | CH | N | O | OCH$_3$ | OCH$_3$ | H | L-4a | |
| CH | CH | N | O | OCH$_3$ | OCH$_3$ | H | L-7a | |
| CH | CH | N | O | OCH$_3$ | OCH$_3$ | H | L-8a | |
| CH | CH | N | O | OCH$_3$ | OCH$_3$ | H | L-8b | |
| CH | CH | N | O | OCH$_3$ | OCH$_3$ | H | L-9a | |
| CH | CH | N | O | OCH$_3$ | OCH$_3$ | H | L-12a | |
| CH | CH | N | O | OCH$_3$ | OCH$_3$ | H | L-12b | |
| CH | CH | N | O | OCH$_3$ | OCH$_3$ | H | L-14a | |
| CH | CH | N | O | OCH$_3$ | OCH$_3$ | H | L-15a | |
| CH | CH | N | O | OCH$_3$ | OCH$_3$ | H | L-16a | |
| CH | CH | N | O | OCH$_3$ | OCH$_3$ | H | L-16b | |
| CH | CH | N | O | OCH$_3$ | OCH$_3$ | H | L-18a | |
| CH | CH | N | O | OCH$_3$ | OCH$_3$ | H | L-20a | |
| CH | CH | N | O | OCH$_3$ | OCH$_3$ | H | L-22a | |
| CH | CH | N | S | OCH$_3$ | OCH$_3$ | H | L-1a | |
| CH | CH | N | S | OCH$_3$ | OCH$_3$ | CH$_3$ | L-1a | |
| CH | N | N | O | CH$_3$ | CH$_3$ | H | L-1a | 193–195 |
| CH | N | N | O | CH$_3$ | CH$_3$ | H | L-1b | 223–225 |
| CH | N | N | O | CH$_3$ | CH$_3$ | H | L-1c | 172–176 |
| CH | N | N | O | CH$_3$ | CH$_3$ | H | L-1d | 239–242 |
| CH | N | N | O | CH$_3$ | CH$_3$ | H | L-1e | |
| CH | N | N | O | CH$_3$ | CH$_3$ | H | L-1f | 155–157 (d) |
| CH | N | N | O | CH$_3$ | CH$_3$ | H | L-1g | |
| CH | N | N | O | CH$_3$ | CH$_3$ | H | L-1h | |
| CH | N | N | O | CH$_3$ | CH$_3$ | H | L-1i | |
| CH | N | N | O | CH$_3$ | CH$_3$ | H | L-1j | |
| CH | N | N | O | CH$_3$ | CH$_3$ | H | L-1k | 151–153 |
| CH | N | N | O | CH$_3$ | CH$_3$ | H | L-1l | 222–225 |
| CH | N | N | O | CH$_3$ | CH$_3$ | H | L-1m | |
| CH | N | N | O | CH$_3$ | CH$_3$ | H | L-1n | 170–174 |
| CH | N | N | O | CH$_3$ | CH$_3$ | H | L-1o | 197–198 |
| CH | N | N | O | CH$_3$ | CH$_3$ | H | L-1p | 211–213 |
| CH | N | N | O | CH$_3$ | CH$_3$ | H | L-1q | 178–180 |

TABLE 1-continued

General Formula 1

| Z | $Z_1$ | $Z_2$ | W | X | Y | R | L | m.p. (°C.) |
|---|---|---|---|---|---|---|---|---|
| CH | N | N | O | $CH_3$ | $CH_3$ | H | L-1r | |
| CH | N | N | O | $CH_3$ | $CH_3$ | H | L-1s | 215-216 |
| CH | N | N | O | $CH_3$ | $CH_3$ | H | L-1t | 149-153 |
| CH | N | N | O | $CH_3$ | $CH_3$ | H | L-1u | |
| CH | N | N | O | $CH_3$ | $CH_3$ | H | L-1v | |
| CH | N | N | O | $CH_3$ | $CH_3$ | H | L-1w | 152-154 |
| CH | N | N | O | $CH_3$ | $CH_3$ | H | L-3a | 163-164(d) |
| CH | N | N | O | $CH_3$ | $CH_3$ | H | L-3b | 116-118 |
| CH | N | N | O | $CH_3$ | $CH_3$ | H | L-4a | |
| CH | N | N | O | $CH_3$ | $CH_3$ | H | L-7a | |
| CH | N | N | O | $CH_3$ | $CH_3$ | H | L-8a | |
| CH | N | N | O | $CH_3$ | $CH_3$ | H | L-8b | |
| CH | N | N | O | $CH_3$ | $CH_3$ | H | L-9a | |
| CH | N | N | O | $CH_3$ | $CH_3$ | H | L-25a | 183-186 |
| CH | N | N | O | $CH_3$ | $CH_3$ | H | L-1ae | 178-180 |
| CH | N | N | O | $CH_3$ | $CH_3$ | H | L-1ad | 255-256(d) |
| CH | N | N | O | $CH_3$ | $CH_3$ | H | L-1af | 124-125(d) |
| CH | N | N | O | $CH_3$ | $CH_3$ | H | L-10a | |
| CH | N | N | O | $CH_3$ | $CH_3$ | H | L-12a | |
| CH | N | N | O | $CH_3$ | $CH_3$ | H | L-12b | |
| CH | N | N | O | $CH_3$ | $CH_3$ | H | L-12c | |
| CH | N | N | O | $CH_3$ | $CH_3$ | H | L-14a | |
| CH | N | N | O | $CH_3$ | $CH_3$ | H | L-15a | |
| CH | N | N | O | $CH_3$ | $CH_3$ | H | L-16a | 237-238 |
| CH | N | N | O | $CH_3$ | $CH_3$ | H | L-16b | |
| CH | N | N | O | $CH_3$ | $CH_3$ | H | L-18a | |
| CH | N | N | O | $CH_3$ | $CH_3$ | H | L-20a | |
| CH | N | N | O | $CH_3$ | $CH_3$ | H | L-20b | |
| CH | N | N | O | $CH_3$ | $CH_3$ | H | L-20c | |
| CH | N | N | O | $CH_3$ | $CH_3$ | H | L-22a | |
| CH | N | N | S | $CH_3$ | $CH_3$ | H | L-1a | |
| CH | N | N | O | $CH_3$ | $CH_3$ | $CH_3$ | L-1a | |
| CH | N | N | O | $OCH_3$ | $CH_3$ | H | L-1a | |
| CH | N | N | O | $OCH_3$ | $CH_3$ | H | L-1b | |
| CH | N | N | O | $OCH_3$ | $CH_3$ | H | L-1c | |
| CH | N | N | O | $OCH_3$ | $CH_3$ | H | L-1d | |
| CH | N | N | O | $OCH_3$ | $CH_3$ | H | L-1e | |
| CH | N | N | O | $OCH_3$ | $CH_3$ | H | L-1f | |
| CH | N | N | O | $OCH_3$ | $CH_3$ | H | L-1g | |
| CH | N | N | O | $OCH_3$ | $CH_3$ | H | L-1h | |
| CH | N | N | O | $OCH_3$ | $CH_3$ | H | L-1i | |
| CH | N | N | O | $OCH_3$ | $CH_3$ | H | L-1j | |
| CH | N | N | O | $OCH_3$ | $CH_3$ | H | L-1k | |
| CH | N | N | O | $OCH_3$ | $CH_3$ | H | L-3a | |
| CH | N | N | O | $OCH_3$ | $CH_3$ | H | L-3b | |
| CH | N | N | O | $OCH_3$ | $CH_3$ | H | L-4a | |
| CH | N | N | O | $OCH_3$ | $CH_3$ | H | L-7a | |
| CH | N | N | O | $OCH_3$ | $CH_3$ | H | L-8a | |
| CH | N | N | O | $OCH_3$ | $CH_3$ | H | L-8b | |
| CH | N | N | O | $OCH_3$ | $CH_3$ | H | L-9a | |
| CH | N | N | O | $OCH_3$ | $CH_3$ | H | L-12a | |
| CH | N | N | O | $OCH_3$ | $CH_3$ | H | L-12b | |
| CH | N | N | O | $OCH_3$ | $CH_3$ | H | L-14a | |
| CH | N | N | O | $OCH_3$ | $CH_3$ | H | L-15a | |
| CH | N | N | O | $OCH_3$ | $CH_3$ | H | L-16a | |
| CH | N | N | O | $OCH_3$ | $CH_3$ | H | L-16b | |
| CH | N | N | O | $OCH_3$ | $CH_3$ | H | L-18a | |
| CH | N | N | O | $OCH_3$ | $CH_3$ | H | L-20a | |
| CH | N | N | O | $OCH_3$ | $CH_3$ | H | L-22a | |
| CH | N | N | S | $OCH_3$ | $CH_3$ | H | L-1a | |
| CH | N | N | O | $OCH_3$ | $CH_3$ | $CH_3$ | L-1a | |
| CH | N | N | O | $CH_3$ | $OCH_3$ | H | L-1a | |
| CH | N | N | O | $CH_3$ | $OCH_3$ | H | L-1b | |
| CH | N | N | O | $CH_3$ | $OCH_3$ | H | L-1c | |
| CH | N | N | O | $CH_3$ | $OCH_3$ | H | L-1d | |
| CH | N | N | O | $CH_3$ | $OCH_3$ | H | L-1e | |
| CH | N | N | O | $CH_3$ | $OCH_3$ | H | L-1f | |
| CH | N | N | O | $CH_3$ | $OCH_3$ | H | L-1g | |
| CH | N | N | O | $CH_3$ | $OCH_3$ | H | L-1h | |
| CH | N | N | O | $CH_3$ | $OCH_3$ | H | L-1i | |
| CH | N | N | O | $CH_3$ | $OCH_3$ | H | L-1j | |
| CH | N | N | O | $CH_3$ | $OCH_3$ | H | L-1k | |
| CH | N | N | O | $CH_3$ | $OCH_3$ | H | L-3a | |
| CH | N | N | O | $CH_3$ | $OCH_3$ | H | L-3b | |
| CH | N | N | O | $CH_3$ | $OCH_3$ | H | L-4a | |
| CH | N | N | O | $CH_3$ | $OCH_3$ | H | L-7a | |
| CH | N | N | O | $CH_3$ | $OCH_3$ | H | L-8a | |
| CH | N | N | O | $CH_3$ | $OCH_3$ | H | L-8b | |
| CH | N | N | O | $CH_3$ | $OCH_3$ | H | L-9a | |
| CH | N | N | O | $CH_3$ | $OCH_3$ | H | L-12a | |

TABLE 1-continued

General Formula 1

| Z | $Z_1$ | $Z_2$ | W | X | Y | R | L | m.p. (°C.) |
|---|---|---|---|---|---|---|---|---|
| CH | N | N | O | CH$_3$ | OCH$_3$ | H | L-12b | |
| CH | N | N | O | CH$_3$ | OCH$_3$ | H | L-14a | |
| CH | N | N | O | CH$_3$ | OCH$_3$ | H | L-15a | |
| CH | N | N | O | CH$_3$ | OCH$_3$ | H | L-16a | |
| CH | N | N | O | CH$_3$ | OCH$_3$ | H | L-16b | |
| CH | N | N | O | CH$_3$ | OCH$_3$ | H | L-18a | |
| CH | N | N | O | CH$_3$ | OCH$_3$ | H | L-20a | |
| CH | N | N | O | CH$_3$ | OCH$_3$ | H | L-22a | |
| CH | N | N | S | CH$_3$ | OCH$_3$ | H | L-1a | |
| CH | N | N | O | CH$_3$ | OCH$_3$ | CH$_3$ | L-1a | |
| CH | N | N | O | OCH$_3$ | OCH$_3$ | H | L-1a | |
| CH | N | N | O | OCH$_3$ | OCH$_3$ | H | L-1b | |
| CH | N | N | O | OCH$_3$ | OCH$_3$ | H | L-1c | |
| CH | N | N | O | OCH$_3$ | OCH$_3$ | H | L-1d | |
| CH | N | N | O | OCH$_3$ | OCH$_3$ | H | L-1e | |
| CH | N | N | O | OCH$_3$ | OCH$_3$ | H | L-1f | |
| CH | N | N | O | OCH$_3$ | OCH$_3$ | H | L-1g | |
| CH | N | N | O | OCH$_3$ | OCH$_3$ | H | L-1h | |
| CH | N | N | O | OCH$_3$ | OCH$_3$ | H | L-1i | |
| CH | N | N | O | OCH$_3$ | OCH$_3$ | H | L-1j | |
| CH | N | N | O | OCH$_3$ | OCH$_3$ | H | L-1k | |
| CH | N | N | O | OCH$_3$ | OCH$_3$ | H | L-3a | |
| CH | N | N | O | OCH$_3$ | OCH$_3$ | H | L-3b | |
| CH | N | N | O | OCH$_3$ | OCH$_3$ | H | L-4a | |
| CH | N | N | O | OCH$_3$ | OCH$_3$ | H | L-7a | |
| CH | N | N | O | OCH$_3$ | OCH$_3$ | H | L-8a | |
| CH | N | N | O | OCH$_3$ | OCH$_3$ | H | L-8b | |
| CH | N | N | O | OCH$_3$ | OCH$_3$ | H | L-9a | |
| CH | N | N | O | OCH$_3$ | OCH$_3$ | H | L-12a | |
| CH | N | N | O | OCH$_3$ | OCH$_3$ | H | L-12b | |
| CH | N | N | O | OCH$_3$ | OCH$_3$ | H | L-14a | |
| CH | N | N | O | OCH$_3$ | OCH$_3$ | H | L-15a | |
| CH | N | N | O | OCH$_3$ | OCH$_3$ | H | L-16a | |
| CH | N | N | O | OCH$_3$ | OCH$_3$ | H | L-16b | |
| CH | N | N | O | OCH$_3$ | OCH$_3$ | H | L-18a | |
| CH | N | N | O | OCH$_3$ | OCH$_3$ | H | L-20a | |
| CH | N | N | O | OCH$_3$ | OCH$_3$ | H | L-22a | |
| CH | N | N | S | OCH$_3$ | OCH$_3$ | H | L-1a | |
| CH | N | N | S | OCH$_3$ | OCH$_3$ | CH$_3$ | L-1a | |
| CH | CH | CH | O | OCH$_3$ | OCH$_3$ | H | L-1a | |
| CH | CH | CH | O | OCH$_3$ | OCH$_3$ | H | L-1b | |
| CH | CH | CH | O | OCH$_3$ | OCH$_3$ | H | L-1c | |
| CH | CH | CH | O | OCH$_3$ | OCH$_3$ | H | L-1d | |
| CH | CH | CH | O | OCH$_3$ | OCH$_3$ | H | L-1e | |
| CH | CH | CH | O | OCH$_3$ | OCH$_3$ | H | L-1f | |
| CH | CH | CH | O | OCH$_3$ | OCH$_3$ | H | L-1g | |
| CH | CH | CH | O | OCH$_3$ | OCH$_3$ | H | L-1h | |
| CH | CH | CH | O | OCH$_3$ | OCH$_3$ | H | L-1i | |
| CH | CH | CH | O | OCH$_3$ | OCH$_3$ | H | L-1j | |
| CH | CH | CH | O | OCH$_3$ | OCH$_3$ | H | L-1k | |
| CH | CH | CH | O | OCH$_3$ | OCH$_3$ | H | L-3a | |
| CH | CH | CH | O | OCH$_3$ | OCH$_3$ | H | L-3b | |
| CH | CH | CH | O | OCH$_3$ | OCH$_3$ | H | L-4a | |
| CH | CH | CH | O | OCH$_3$ | OCH$_3$ | H | L-7a | |
| CH | CH | CH | O | OCH$_3$ | OCH$_3$ | H | L-8a | |
| CH | CH | CH | O | OCH$_3$ | OCH$_3$ | H | L-8b | |
| CH | CH | CH | O | OCH$_3$ | OCH$_3$ | H | L-9a | |
| CH | CH | CH | O | OCH$_3$ | OCH$_3$ | H | L-12a | |
| CH | CH | CH | O | OCH$_3$ | OCH$_3$ | H | L-12b | |
| CH | CH | CH | O | OCH$_3$ | OCH$_3$ | H | L-14a | |
| CH | CH | CH | O | OCH$_3$ | OCH$_3$ | H | L-15a | |
| CH | CH | CH | O | OCH$_3$ | OCH$_3$ | H | L-16a | |
| CH | CH | CH | O | OCH$_3$ | OCH$_3$ | H | L-16b | |
| CH | CH | CH | O | OCH$_3$ | OCH$_3$ | H | L-18a | |
| CH | CH | CH | O | OCH$_3$ | OCH$_3$ | H | L-20a | |
| CH | CH | CH | O | OCH$_3$ | OCH$_3$ | H | L-22a | |
| CH | CH | CH | S | OCH$_3$ | OCH$_3$ | H | L-1a | |
| CH | CH | CH | O | OCH$_3$ | OCH$_3$ | CH$_3$ | L-1a | |
| CH | CH | CH | O | CH$_3$ | CH$_3$ | H | L-1a | |
| CH | CH | CH | O | CH$_3$ | CH$_3$ | H | L-1b | |
| CH | CH | CH | O | CH$_3$ | CH$_3$ | H | L-1c | |
| CH | CH | CH | O | CH$_3$ | CH$_3$ | H | L-1d | |
| CH | CH | CH | O | CH$_3$ | CH$_3$ | H | L-1e | |
| CH | CH | CH | O | CH$_3$ | CH$_3$ | H | L-1f | |
| CH | CH | CH | O | CH$_3$ | CH$_3$ | H | L-1g | |
| CH | CH | CH | O | CH$_3$ | CH$_3$ | H | L-1h | |
| CH | CH | CH | O | CH$_3$ | CH$_3$ | H | L-1i | |
| CH | CH | CH | O | CH$_3$ | CH$_3$ | H | L-1j | |
| CH | CH | CH | O | CH$_3$ | CH$_3$ | H | L-1k | |
| CH | CH | CH | O | CH$_3$ | CH$_3$ | H | L-3a | |

TABLE 1-continued

General Formula 1

| Z | Z₁ | Z₂ | W | X | Y | R | L | m.p. (°C.) |
|---|---|---|---|---|---|---|---|---|
| CH | CH | CH | O | CH₃ | CH₃ | H | L-3b | |
| CH | CH | CH | O | CH₃ | CH₃ | H | L-4a | |
| CH | CH | CH | O | CH₃ | CH₃ | H | L-7a | |
| CH | CH | CH | O | CH₃ | CH₃ | H | L-8a | |
| CH | CH | CH | O | CH₃ | CH₃ | H | L-8b | |
| CH | CH | CH | O | CH₃ | CH₃ | H | L-9a | |
| CH | CH | CH | O | CH₃ | CH₃ | H | L-12a | |
| CH | CH | CH | O | CH₃ | CH₃ | H | L-12b | |
| CH | CH | CH | O | CH₃ | CH₃ | H | L-14a | |
| CH | CH | CH | O | CH₃ | CH₃ | H | L-15a | |
| CH | CH | CH | O | CH₃ | CH₃ | H | L-16a | |
| CH | CH | CH | O | CH₃ | CH₃ | H | L-16b | |
| CH | CH | CH | O | CH₃ | CH₃ | H | L-18a | |
| CH | CH | CH | O | CH₃ | CH₃ | H | L-20a | |
| CH | CH | CH | O | CH₃ | CH₃ | H | L-22a | |
| CH | CH | CH | S | CH₃ | CH₃ | H | L-1a | |
| CH | CH | CH | O | CH₃ | CH₃ | CH₃ | L-1a | |
| CH | CH | CH | O | OCH₃ | CH₃ | H | L-1a | |
| CH | CH | CH | O | OCH₃ | CH₃ | H | L-1b | |
| CH | CH | CH | O | OCH₃ | CH₃ | H | L-1c | |
| CH | CH | CH | O | OCH₃ | CH₃ | H | L-1d | |
| CH | CH | CH | O | OCH₃ | CH₃ | H | L-1e | |
| CH | CH | CH | O | OCH₃ | CH₃ | H | L-1f | |
| CH | CH | CH | O | OCH₃ | CH₃ | H | L-1g | |
| CH | CH | CH | O | OCH₃ | CH₃ | H | L-1h | |
| CH | CH | CH | O | OCH₃ | CH₃ | H | L-1i | |
| CH | CH | CH | O | OCH₃ | CH₃ | H | L-1j | |
| CH | CH | CH | O | OCH₃ | CH₃ | H | L-1k | |
| CH | CH | CH | O | OCH₃ | CH₃ | H | L-3a | |
| CH | CH | CH | O | OCH₃ | CH₃ | H | L-3b | |
| CH | CH | CH | O | OCH₃ | CH₃ | H | L-4a | |
| CH | CH | CH | O | OCH₃ | CH₃ | H | L-7a | |
| CH | CH | CH | O | OCH₃ | CH₃ | H | L-8a | |
| CH | CH | CH | O | OCH₃ | CH₃ | H | L-8b | |
| CH | CH | CH | O | OCH₃ | CH₃ | H | L-9a | |
| CH | CH | CH | O | OCH₃ | CH₃ | H | L-12a | |
| CH | CH | CH | O | OCH₃ | CH₃ | H | L-12b | |
| CH | CH | CH | O | OCH₃ | CH₃ | H | L-14a | |
| CH | CH | CH | O | OCH₃ | CH₃ | H | L-15a | |
| CH | CH | CH | O | OCH₃ | CH₃ | H | L-16a | |
| CH | CH | CH | O | OCH₃ | CH₃ | H | L-16b | |
| CH | CH | CH | O | OCH₃ | CH₃ | H | L-18a | |
| CH | CH | CH | O | OCH₃ | CH₃ | H | L-20a | |
| CH | CH | CH | O | OCH₃ | CH₃ | H | L-22a | |
| CH | CH | CH | S | OCH₃ | CH₃ | H | L-1a | |
| CH | CH | CH | O | OCH₃ | CH₃ | CH₃ | L-1a | |
| CH | CH | CH | O | CH₃ | OCH₃ | H | L-1a | |
| CH | CH | CH | O | CH₃ | OCH₃ | H | L-1b | |
| CH | CH | CH | O | CH₃ | OCH₃ | H | L-1c | |
| CH | CH | CH | O | CH₃ | OCH₃ | H | L-1d | |
| CH | CH | CH | O | CH₃ | OCH₃ | H | L-1e | |
| CH | CH | CH | O | CH₃ | OCH₃ | H | L-1f | |
| CH | CH | CH | O | CH₃ | OCH₃ | H | L-1g | |
| CH | CH | CH | O | CH₃ | OCH₃ | H | L-1h | |
| CH | CH | CH | O | CH₃ | OCH₃ | H | L-1i | |
| CH | CH | CH | O | CH₃ | OCH₃ | H | L-1j | |
| CH | CH | CH | O | CH₃ | OCH₃ | H | L-1k | |
| CH | CH | CH | O | CH₃ | OCH₃ | H | L-3a | |
| CH | CH | CH | O | CH₃ | OCH₃ | H | L-3b | |
| CH | CH | CH | O | CH₃ | OCH₃ | H | L-4a | |
| CH | CH | CH | O | CH₃ | OCH₃ | H | L-7a | |
| CH | CH | CH | O | CH₃ | OCH₃ | H | L-8a | |
| CH | CH | CH | O | CH₃ | OCH₃ | H | L-8b | |
| CH | CH | CH | O | CH₃ | OCH₃ | H | L-9a | |
| CH | CH | CH | O | CH₃ | OCH₃ | H | L-12a | |
| CH | CH | CH | O | CH₃ | OCH₃ | H | L-12b | |
| CH | CH | CH | O | CH₃ | OCH₃ | H | L-14a | |
| CH | CH | CH | O | CH₃ | OCH₃ | H | L-15a | |
| CH | CH | CH | O | CH₃ | OCH₃ | H | L-16a | |
| CH | CH | CH | O | CH₃ | OCH₃ | H | L-16b | |
| CH | CH | CH | O | CH₃ | OCH₃ | H | L-18a | |
| CH | CH | CH | O | CH₃ | OCH₃ | H | L-20a | |
| CH | CH | CH | O | CH₃ | OCH₃ | H | L-22a | |
| CH | CH | CH | S | CH₃ | OCH₃ | H | L-1a | |
| CH | CH | CH | O | CH₃ | OCH₃ | CH₃ | L-1a | |
| CH | CH | CH | O | OCH₃ | OCH₃ | H | L-1a | |
| CH | CH | CH | O | OCH₃ | OCH₃ | H | L-1b | |
| CH | CH | CH | O | OCH₃ | OCH₃ | H | L-1c | |
| CH | CH | CH | O | OCH₃ | OCH₃ | H | L-1d | |
| CH | CH | CH | O | OCH₃ | OCH₃ | H | L-1e | |

TABLE 1-continued

General Formula 1

| Z | Z₁ | Z₂ | W | X | Y | R | L | m.p. (°C.) |
|---|---|---|---|---|---|---|---|---|
| CH | CH | CH | O | OCH₃ | OCH₃ | H | L-1f | |
| CH | CH | CH | O | OCH₃ | OCH₃ | H | L-1g | |
| CH | CH | CH | O | OCH₃ | OCH₃ | H | L-1h | |
| CH | CH | CH | O | OCH₃ | OCH₃ | H | L-1i | |
| CH | CH | CH | O | OCH₃ | OCH₃ | H | L-1j | |
| CH | CH | CH | O | OCH₃ | OCH₃ | H | L-1k | |
| CH | CH | CH | O | OCH₃ | OCH₃ | H | L-3a | |
| CH | CH | CH | O | OCH₃ | OCH₃ | H | L-3b | |
| CH | CH | CH | O | OCH₃ | OCH₃ | H | L-4a | |
| CH | CH | CH | O | OCH₃ | OCH₃ | H | L-7a | |
| CH | CH | CH | O | OCH₃ | OCH₃ | H | L-8a | |
| CH | CH | CH | O | OCH₃ | OCH₃ | H | L-8b | |
| CH | CH | CH | O | OCH₃ | OCH₃ | H | L-9a | |
| CH | CH | CH | O | OCH₃ | OCH₃ | H | L-12a | |
| CH | CH | CH | O | OCH₃ | OCH₃ | H | L-12b | |
| CH | CH | CH | O | OCH₃ | OCH₃ | H | L-14a | |
| CH | CH | CH | O | OCH₃ | OCH₃ | H | L-15a | |
| CH | CH | CH | O | OCH₃ | OCH₃ | H | L-16a | |
| CH | CH | CH | O | OCH₃ | OCH₃ | H | L-16b | |
| CH | CH | CH | O | OCH₃ | OCH₃ | H | L-18a | |
| CH | CH | CH | O | OCH₃ | OCH₃ | H | L-20a | |
| CH | CH | CH | O | OCH₃ | OCH₃ | H | L-22a | |
| CH | CH | CH | S | OCH₃ | OCH₃ | H | L-1a | |
| CH | CH | CH | O | OCH₃ | OCH₃ | CH₃ | L-1a | |
| N | N | CH | O | CH₃ | CH₃ | H | L-1a | |
| N | N | CH | O | CH₃ | CH₃ | H | L-1b | |
| N | N | CH | O | CH₃ | CH₃ | H | L-1c | |
| N | N | CH | O | CH₃ | CH₃ | H | L-1d | |
| N | N | CH | O | CH₃ | CH₃ | H | L-1e | |
| N | N | CH | O | CH₃ | CH₃ | H | L-1f | |
| N | N | CH | O | CH₃ | CH₃ | H | L-1g | |
| N | N | CH | O | CH₃ | CH₃ | H | L-1h | |
| N | N | CH | O | CH₃ | CH₃ | H | L-1i | |
| N | N | CH | O | CH₃ | CH₃ | H | L-1j | |
| N | N | CH | O | CH₃ | CH₃ | H | L-1k | |
| N | N | CH | O | CH₃ | CH₃ | H | L-3a | |
| N | N | CH | O | CH₃ | CH₃ | H | L-3b | |
| N | N | CH | O | CH₃ | CH₃ | H | L-4a | |
| N | N | CH | O | CH₃ | CH₃ | H | L-7a | |
| N | N | CH | O | CH₃ | CH₃ | H | L-8a | |
| N | N | CH | O | CH₃ | CH₃ | H | L-8b | |
| N | N | CH | O | CH₃ | CH₃ | H | L-9a | |
| N | N | CH | O | CH₃ | CH₃ | H | L-12a | |
| N | N | CH | O | CH₃ | CH₃ | H | L-12b | |
| N | N | CH | O | CH₃ | CH₃ | H | L-14a | |
| N | N | CH | O | CH₃ | CH₃ | H | L-15a | |
| N | N | CH | O | CH₃ | CH₃ | H | L-16a | |
| N | N | CH | O | CH₃ | CH₃ | H | L-16b | |
| N | N | CH | O | CH₃ | CH₃ | H | L-18a | |
| N | N | CH | O | CH₃ | CH₃ | H | L-20a | |
| N | N | CH | O | CH₃ | CH₃ | H | L-22a | |
| N | N | CH | S | CH₃ | CH₃ | H | L-1a | |
| N | N | CH | O | CH₃ | CH₃ | CH₃ | L-1a | |
| N | N | CH | O | CH₃ | CH₃ | H | L-1z | 185–203 |
| N | N | CH | O | CH₃ | CH₃ | H | L-1y | 193–211 |
| N | N | CH | O | CH₃ | CH₃ | H | L-1aa | 192–214 |
| N | N | CH | O | CH₃ | CH₃ | H | L-1q | 197–217 |
| N | N | CH | O | CH₃ | CH₃ | H | L-1ab | 189–198 |
| N | N | CH | O | OCH₃ | CH₃ | H | L-1a | |
| N | N | CH | O | OCH₃ | CH₃ | H | L-1b | |
| N | N | CH | O | OCH₃ | CH₃ | H | L-1c | |
| N | N | CH | O | OCH₃ | CH₃ | H | L-1d | |
| N | N | CH | O | OCH₃ | CH₃ | H | L-1e | |
| N | N | CH | O | OCH₃ | CH₃ | H | L-1f | |
| N | N | CH | O | OCH₃ | CH₃ | H | L-1g | |
| N | N | CH | O | OCH₃ | CH₃ | H | L-1h | |
| N | N | CH | O | OCH₃ | CH₃ | H | L-1i | |
| N | N | CH | O | OCH₃ | CH₃ | H | L-1j | |
| N | N | CH | O | OCH₃ | CH₃ | H | L-1k | |
| N | N | CH | O | OCH₃ | CH₃ | H | L-3a | |
| N | N | CH | O | OCH₃ | CH₃ | H | L-3b | |
| N | N | CH | O | OCH₃ | CH₃ | H | L-4a | |
| N | N | CH | O | OCH₃ | CH₃ | H | L-7a | |
| N | N | CH | O | OCH₃ | CH₃ | H | L-8a | |
| N | N | CH | O | OCH₃ | CH₃ | H | L-8b | |
| N | N | CH | O | OCH₃ | CH₃ | H | L-9a | |
| N | N | CH | O | OCH₃ | CH₃ | H | L-12a | |
| N | N | CH | O | OCH₃ | CH₃ | H | L-12b | |
| N | N | CH | O | OCH₃ | CH₃ | H | L-14a | |
| N | N | CH | O | OCH₃ | CH₃ | H | L-15a | |

TABLE 1-continued

General Formula 1

| Z | Z₁ | Z₂ | W | X | Y | R | L | m.p. (°C.) |
|---|---|---|---|---|---|---|---|---|
| N | N | CH | O | OCH₃ | CH₃ | H | L-16a | |
| N | N | CH | O | OCH₃ | CH₃ | H | L-16b | |
| N | N | CH | O | OCH₃ | CH₃ | H | L-18a | |
| N | N | CH | O | OCH₃ | CH₃ | H | L-20a | |
| N | N | CH | O | OCH₃ | CH₃ | H | L-22a | |
| N | N | CH | S | OCH₃ | CH₃ | H | L-1a | |
| N | N | CH | O | OCH₃ | CH₃ | CH₃ | L-1a | |
| N | N | CH | O | CH₃ | OCH₃ | H | L-1a | |
| N | N | CH | O | CH₃ | OCH₃ | H | L-1b | |
| N | N | CH | O | CH₃ | OCH₃ | H | L-1c | |
| N | N | CH | O | CH₃ | OCH₃ | H | L-1d | |
| N | N | CH | O | CH₃ | OCH₃ | H | L-1e | |
| N | N | CH | O | CH₃ | OCH₃ | H | L-1f | |
| N | N | CH | O | CH₃ | OCH₃ | H | L-1g | |
| N | N | CH | O | CH₃ | OCH₃ | H | L-1h | |
| N | N | CH | O | CH₃ | OCH₃ | H | L-1i | |
| N | N | CH | O | CH₃ | OCH₃ | H | L-1j | |
| N | N | CH | O | CH₃ | OCH₃ | H | L-1k | |
| N | N | CH | O | CH₃ | OCH₃ | H | L-3a | |
| N | N | CH | O | CH₃ | OCH₃ | H | L-3b | |
| N | N | CH | O | CH₃ | OCH₃ | H | L-4a | |
| N | N | CH | O | CH₃ | OCH₃ | H | L-7a | |
| N | N | CH | O | CH₃ | OCH₃ | H | L-8a | |
| N | N | CH | O | CH₃ | OCH₃ | H | L-8b | |
| N | N | CH | O | CH₃ | OCH₃ | H | L-9a | |
| N | N | CH | O | CH₃ | OCH₃ | H | L-12a | |
| N | N | CH | O | CH₃ | OCH₃ | H | L-12b | |
| N | N | CH | O | CH₃ | OCH₃ | H | L-14a | |
| N | N | CH | O | CH₃ | OCH₃ | H | L-15a | |
| N | N | CH | O | CH₃ | OCH₃ | H | L-16a | |
| N | N | CH | O | CH₃ | OCH₃ | H | L-16b | |
| N | N | CH | O | CH₃ | OCH₃ | H | L-18a | |
| N | N | CH | O | CH₃ | OCH₃ | H | L-20a | |
| N | N | CH | O | CH₃ | OCH₃ | H | L-22a | |
| N | N | CH | S | CH₃ | OCH₃ | H | L-1a | |
| N | N | CH | O | CH₃ | OCH₃ | CH₃ | L-1a | |
| N | N | CH | O | OCH₃ | OCH₃ | H | L-1a | 122–157 |
| N | N | CH | O | OCH₃ | OCH₃ | H | L-1b | 237–248 |
| N | N | CH | O | OCH₃ | OCH₃ | H | L-1c | 239–244 |
| N | N | CH | O | OCH₃ | OCH₃ | H | L-1d | 207–236 |
| N | N | CH | O | OCH₃ | OCH₃ | H | L-1e | |
| N | N | CH | O | OCH₃ | OCH₃ | H | L-1f | |
| N | N | CH | O | OCH₃ | OCH₃ | H | L-1g | |
| N | N | CH | O | OCH₃ | OCH₃ | H | L-1h | |
| N | N | CH | O | OCH₃ | OCH₃ | H | L-1i | |
| N | N | CH | O | OCH₃ | OCH₃ | H | L-1j | |
| N | N | CH | O | OCH₃ | OCH₃ | H | L-1k | |
| N | N | CH | O | OCH₃ | OCH₃ | H | L-1e | 239–261 |
| N | N | CH | O | OCH₃ | OCH₃ | H | L-3a | |
| N | N | CH | O | OCH₃ | OCH₃ | H | L-3b | |
| N | N | CH | O | OCH₃ | OCH₃ | H | L-4a | |
| N | N | CH | O | OCH₃ | OCH₃ | H | L-7a | |
| N | N | CH | O | OCH₃ | OCH₃ | H | L-8a | |
| N | N | CH | O | OCH₃ | OCH₃ | H | L-8b | |
| N | N | CH | O | OCH₃ | OCH₃ | H | L-9a | |
| N | N | CH | O | OCH₃ | OCH₃ | H | L-12a | |
| N | N | CH | O | OCH₃ | OCH₃ | H | L-12b | |
| N | N | CH | O | OCH₃ | OCH₃ | H | L-14a | |
| N | N | CH | O | OCH₃ | OCH₃ | H | L-15a | |
| N | N | CH | O | OCH₃ | OCH₃ | H | L-16a | |
| N | N | CH | O | OCH₃ | OCH₃ | H | L-16b | |
| N | N | CH | O | OCH₃ | OCH₃ | H | L-18a | |
| N | N | CH | O | OCH₃ | OCH₃ | H | L-20a | |
| N | N | CH | O | OCH₃ | OCH₃ | H | L-22a | |
| N | N | CH | S | OCH₃ | OCH₃ | H | L-1a | |
| N | N | CH | O | OCH₃ | OCH₃ | CH₃ | L-1a | |
| N | N | CH | O | OCH₃ | OCH₃ | H | L-1t | 114–137 |
| N | N | CH | O | OCH₃ | OCH₃ | H | L-1y | 220–231 |
| N | N | CH | O | OCH₃ | OCH₃ | H | L-1z | 246–253 |
| N | N | CH | O | OCH₃ | OCH₃ | H | L-1aa | 262–270 |
| N | N | CH | O | OCH₃ | OCH₃ | H | L-1ab | 228–244 |
| N | N | CH | O | OCH₃ | OCH₃ | H | L-1ac | 176–178 |
| N | N | CH | O | OCH₃ | OCH₃ | H | L-1ad | 192–238 |
| N | N | CH | O | CH₃ | OCH₃ | H | L-1a | |
| N | N | CH | O | CH₃ | OCH₃ | H | L-1b | |
| N | N | CH | O | CH₃ | OCH₃ | H | L-1c | |
| N | N | CH | O | CH₃ | OCH₃ | H | L-1d | |
| N | N | CH | O | CH₃ | OCH₃ | H | L-1e | |
| N | N | CH | O | CH₃ | OCH₃ | H | L-1f | |
| N | N | CH | O | CH₃ | OCH₃ | H | L-1g | |

TABLE 1-continued

General Formula 1

| Z | Z₁ | Z₂ | W | X | Y | R | L | m.p. (°C.) |
|---|----|----|---|---|---|---|---|------------|
| N | N | CH | O | CH₃ | OCH₃ | H | L-1h | |
| N | N | CH | O | CH₃ | OCH₃ | H | L-1i | |
| N | N | CH | O | CH₃ | OCH₃ | H | L-1j | |
| N | N | CH | O | CH₃ | OCH₃ | H | L-1k | |
| N | N | CH | O | CH₃ | OCH₃ | H | L-3a | |
| N | N | CH | O | CH₃ | OCH₃ | H | L-3b | |
| N | N | CH | O | CH₃ | OCH₃ | H | L-4a | |
| N | N | CH | O | CH₃ | OCH₃ | H | L-7a | |
| N | N | CH | O | CH₃ | OCH₃ | H | L-8a | |
| N | N | CH | O | CH₃ | OCH₃ | H | L-8b | |
| N | N | CH | O | CH₃ | OCH₃ | H | L-9a | |
| N | N | CH | O | CH₃ | OCH₃ | H | L-12a | |
| N | N | CH | O | CH₃ | OCH₃ | H | L-12b | |
| N | N | CH | O | CH₃ | OCH₃ | H | L-14a | |
| N | N | CH | O | CH₃ | OCH₃ | H | L-15a | |
| N | N | CH | O | CH₃ | OCH₃ | H | L-16a | |
| N | N | CH | O | CH₃ | OCH₃ | H | L-16b | |
| N | N | CH | O | CH₃ | OCH₃ | H | L-18a | |
| N | N | CH | O | CH₃ | OCH₃ | H | L-20a | |
| N | N | CH | O | CH₃ | OCH₃ | H | L-22a | |
| N | N | CH | S | CH₃ | OCH₃ | H | L-1a | |
| N | N | CH | O | CH₃ | OCH₃ | CH₃ | L-1a | |
| N | N | CH | O | OCH₃ | OCH₃ | H | L-1a | |
| N | N | CH | O | OCH₃ | OCH₃ | H | L-1b | |
| N | N | CH | O | OCH₃ | OCH₃ | H | L-1c | |
| N | N | CH | O | OCH₃ | OCH₃ | H | L-1d | |
| N | N | CH | O | OCH₃ | OCH₃ | H | L-1e | |
| N | N | CH | O | OCH₃ | OCH₃ | H | L-1f | |
| N | N | CH | O | OCH₃ | OCH₃ | H | L-1g | |
| N | N | CH | O | OCH₃ | OCH₃ | H | L-1h | |
| N | N | CH | O | OCH₃ | OCH₃ | H | L-1i | |
| N | N | CH | O | OCH₃ | OCH₃ | H | L-1j | |
| N | N | CH | O | OCH₃ | OCH₃ | H | L-1k | |
| N | N | CH | O | OCH₃ | OCH₃ | H | L-3a | |
| N | N | CH | O | OCH₃ | OCH₃ | H | L-3b | |
| N | N | CH | O | OCH₃ | OCH₃ | H | L-4a | |
| N | N | CH | O | OCH₃ | OCH₃ | H | L-7a | |
| N | N | CH | O | OCH₃ | OCH₃ | H | L-8a | |
| N | N | CH | O | OCH₃ | OCH₃ | H | L-8b | |
| N | N | CH | O | OCH₃ | OCH₃ | H | L-9a | |
| N | N | CH | O | OCH₃ | OCH₃ | H | L-12a | |
| N | N | CH | O | OCH₃ | OCH₃ | H | L-12b | |
| N | N | CH | O | OCH₃ | OCH₃ | H | L-14a | |
| N | N | CH | O | OCH₃ | OCH₃ | H | L-15a | |
| N | N | CH | O | OCH₃ | OCH₃ | H | L-16a | |
| N | N | CH | O | OCH₃ | OCH₃ | H | L-16b | |
| N | N | CH | O | OCH₃ | OCH₃ | H | L-18a | |
| N | N | CH | O | OCH₃ | OCH₃ | H | L-20a | |
| N | N | CH | O | OCH₃ | OCH₃ | H | L-22a | |
| N | N | CH | S | OCH₃ | OCH₃ | H | L-1a | |
| N | N | CH | O | OCH₃ | OCH₃ | CH₃ | L-1a | |
| N | N | N | O | CH₃ | CH₃ | H | L-1a | |
| N | N | N | O | CH₃ | CH₃ | H | L-1b | |
| N | N | N | O | CH₃ | CH₃ | H | L-1c | |
| N | N | N | O | CH₃ | CH₃ | H | L-1d | |
| N | N | N | O | CH₃ | CH₃ | H | L-1e | |
| N | N | N | O | CH₃ | CH₃ | H | L-1f | |
| N | N | N | O | CH₃ | CH₃ | H | L-1g | |
| N | N | N | O | CH₃ | CH₃ | H | L-1h | |
| N | N | N | O | CH₃ | CH₃ | H | L-1i | |
| N | N | N | O | CH₃ | CH₃ | H | L-1j | |
| N | N | N | O | CH₃ | CH₃ | H | L-1k | |
| N | N | N | O | CH₃ | CH₃ | H | L-3a | |
| N | N | N | O | CH₃ | CH₃ | H | L-3b | |
| N | N | N | O | CH₃ | CH₃ | H | L-4a | |
| N | N | N | O | CH₃ | CH₃ | H | L-7a | |
| N | N | N | O | CH₃ | CH₃ | H | L-8a | |
| N | N | N | O | CH₃ | CH₃ | H | L-8b | |
| N | N | N | O | CH₃ | CH₃ | H | L-9a | |
| N | N | N | O | CH₃ | CH₃ | H | L-12a | |
| N | N | N | O | CH₃ | CH₃ | H | L-12b | |
| N | N | N | O | CH₃ | CH₃ | H | L-14a | |
| N | N | N | O | CH₃ | CH₃ | H | L-15a | |
| N | N | N | O | CH₃ | CH₃ | H | L-16a | |
| N | N | N | O | CH₃ | CH₃ | H | L-16b | |
| N | N | N | O | CH₃ | CH₃ | H | L-18a | |
| N | N | N | O | CH₃ | CH₃ | H | L-20a | |
| N | N | N | O | CH₃ | CH₃ | H | L-22a | |
| N | N | N | S | CH₃ | CH₃ | H | L-1a | |
| N | N | N | O | CH₃ | CH₃ | CH₃ | L-1a | |

TABLE 1-continued

| | | | | General Formula 1 | | | | |
|---|---|---|---|---|---|---|---|---|
| Z | Z₁ | Z₂ | W | X | Y | R | L | m.p. (°C.) |
| N | N | N | O | OCH₃ | CH₃ | H | L-1a | |
| N | N | N | O | OCH₃ | CH₃ | H | L-1b | |
| N | N | N | O | OCH₃ | CH₃ | H | L-1c | |
| N | N | N | O | OCH₃ | CH₃ | H | L-1d | |
| N | N | N | O | OCH₃ | CH₃ | H | L-1e | |
| N | N | N | O | OCH₃ | CH₃ | H | L-1f | |
| N | N | N | O | OCH₃ | CH₃ | H | L-1g | |
| N | N | N | O | OCH₃ | CH₃ | H | L-1h | |
| N | N | N | O | OCH₃ | CH₃ | H | L-1i | |
| N | N | N | O | OCH₃ | CH₃ | H | L-1j | |
| N | N | N | O | OCH₃ | CH₃ | H | L-1k | |
| N | N | N | O | OCH₃ | CH₃ | H | L-3a | |
| N | N | N | O | OCH₃ | CH₃ | H | L-3b | |
| N | N | N | O | OCH₃ | CH₃ | H | L-4a | |
| N | N | N | O | OCH₃ | CH₃ | H | L-7a | |
| N | N | N | O | OCH₃ | CH₃ | H | L-8a | |
| N | N | N | O | OCH₃ | CH₃ | H | L-8b | |
| N | N | N | O | OCH₃ | CH₃ | H | L-9a | |
| N | N | N | O | OCH₃ | CH₃ | H | L-12a | |
| N | N | N | O | OCH₃ | CH₃ | H | L-12b | |
| N | N | N | O | OCH₃ | CH₃ | H | L-14a | |
| N | N | N | O | OCH₃ | CH₃ | H | L-15a | |
| N | N | N | O | OCH₃ | CH₃ | H | L-16a | |
| N | N | N | O | OCH₃ | CH₃ | H | L-16b | |
| N | N | N | O | OCH₃ | CH₃ | H | L-18a | |
| N | N | N | O | OCH₃ | CH₃ | H | L-20a | |
| N | N | N | O | OCH₃ | CH₃ | H | L-22a | |
| N | N | N | S | OCH₃ | CH₃ | H | L-1a | |
| N | N | N | O | OCH₃ | CH₃ | CH₃ | L-1a | |
| N | N | N | O | CH₃ | OCH₃ | H | L-1a | |
| N | N | N | O | CH₃ | OCH₃ | H | L-1b | |
| N | N | N | O | CH₃ | OCH₃ | H | L-1c | |
| N | N | N | O | CH₃ | OCH₃ | H | L-1d | |
| N | N | N | O | CH₃ | OCH₃ | H | L-1e | |
| N | N | N | O | CH₃ | OCH₃ | H | L-1f | |
| N | N | N | O | CH₃ | OCH₃ | H | L-1g | |
| N | N | N | O | CH₃ | OCH₃ | H | L-1h | |
| N | N | N | O | CH₃ | OCH₃ | H | L-1i | |
| N | N | N | O | CH₃ | OCH₃ | H | L-1j | |
| N | N | N | O | CH₃ | OCH₃ | H | L-1k | |
| N | N | N | O | CH₃ | OCH₃ | H | L-3a | |
| N | N | N | O | CH₃ | OCH₃ | H | L-3b | |
| N | N | N | O | CH₃ | OCH₃ | H | L-4a | |
| N | N | N | O | CH₃ | OCH₃ | H | L-7a | |
| N | N | N | O | CH₃ | OCH₃ | H | L-8a | |
| N | N | N | O | CH₃ | OCH₃ | H | L-8b | |
| N | N | N | O | CH₃ | OCH₃ | H | L-9a | |
| N | N | N | O | CH₃ | OCH₃ | H | L-12a | |
| N | N | N | O | CH₃ | OCH₃ | H | L-12b | |
| N | N | N | O | CH₃ | OCH₃ | H | L-14a | |
| N | N | N | O | CH₃ | OCH₃ | H | L-15a | |
| N | N | N | O | CH₃ | OCH₃ | H | L-16a | |
| N | N | N | O | CH₃ | OCH₃ | H | L-16b | |
| N | N | N | O | CH₃ | OCH₃ | H | L-18a | |
| N | N | N | O | CH₃ | OCH₃ | H | L-20a | |
| N | N | N | O | CH₃ | OCH₃ | H | L-22a | |
| N | N | N | S | CH₃ | OCH₃ | H | L-1a | |
| N | N | N | O | CH₃ | OCH₃ | CH₃ | L-1a | |
| N | N | N | O | OCH₃ | OCH₃ | H | L-1a | |
| N | N | N | O | OCH₃ | OCH₃ | H | L-1b | |
| N | N | N | O | OCH₃ | OCH₃ | H | L-1c | |
| N | N | N | O | OCH₃ | OCH₃ | H | L-1d | |
| N | N | N | O | OCH₃ | OCH₃ | H | L-1e | |
| N | N | N | O | OCH₃ | OCH₃ | H | L-1f | |
| N | N | N | O | OCH₃ | OCH₃ | H | L-1g | |
| N | N | N | O | OCH₃ | OCH₃ | H | L-1h | |
| N | N | N | O | OCH₃ | OCH₃ | H | L-1i | |
| N | N | N | O | OCH₃ | OCH₃ | H | L-1j | |
| N | N | N | O | OCH₃ | OCH₃ | H | L-1k | |
| N | N | N | O | OCH₃ | OCH₃ | H | L-3a | |
| N | N | N | O | OCH₃ | OCH₃ | H | L-3b | |
| N | N | N | O | OCH₃ | OCH₃ | H | L-4a | |
| N | N | N | O | OCH₃ | OCH₃ | H | L-7a | |
| N | N | N | O | OCH₃ | OCH₃ | H | L-8a | |
| N | N | N | O | OCH₃ | OCH₃ | H | L-8b | |
| N | N | N | O | OCH₃ | OCH₃ | H | L-9a | |
| N | N | N | O | OCH₃ | OCH₃ | H | L-12a | |
| N | N | N | O | OCH₃ | OCH₃ | H | L-12b | |
| N | N | N | O | OCH₃ | OCH₃ | H | L-14a | |
| N | N | N | O | OCH₃ | OCH₃ | H | L-15a | |

TABLE 1-continued

| | | | | General Formula 1 | | | | |
|---|---|---|---|---|---|---|---|---|
| Z | $Z_1$ | $Z_2$ | W | X | Y | R | L | m.p. (°C.) |
| N | N | N | O | $OCH_3$ | $OCH_3$ | H | L-16a | |
| N | N | N | O | $OCH_3$ | $OCH_3$ | H | L-16b | |
| N | N | N | O | $OCH_3$ | $OCH_3$ | H | L-18a | |
| N | N | N | O | $OCH_3$ | $OCH_3$ | H | L-20a | |
| N | N | N | O | $OCH_3$ | $OCH_3$ | H | L-22a | |
| N | N | N | S | $OCH_3$ | $OCH_3$ | H | L-1a | |
| N | N | N | O | $OCH_3$ | $OCH_3$ | $CH_3$ | L-1a | |
| N | CH | N | O | $CH_3$ | $CH_3$ | H | L-1a | |
| N | CH | N | O | $CH_3$ | $CH_3$ | H | L-1b | |
| N | CH | N | O | $CH_3$ | $CH_3$ | H | L-1c | |
| N | CH | N | O | $CH_3$ | $CH_3$ | H | L-1d | |
| N | CH | N | O | $CH_3$ | $CH_3$ | H | L-1e | |
| N | CH | N | O | $CH_3$ | $CH_3$ | H | L-1f | |
| N | CH | N | O | $CH_3$ | $CH_3$ | H | L-1g | |
| N | CH | N | O | $CH_3$ | $CH_3$ | H | L-1h | |
| N | CH | N | O | $CH_3$ | $CH_3$ | H | L-1i | |
| N | CH | N | O | $CH_3$ | $CH_3$ | H | L-1j | |
| N | CH | N | O | $CH_3$ | $CH_3$ | H | L-1k | |
| N | CH | N | O | $CH_3$ | $CH_3$ | H | L-3a | |
| N | CH | N | O | $CH_3$ | $CH_3$ | H | L-3b | |
| N | CH | N | O | $CH_3$ | $CH_3$ | H | L-4a | |
| N | CH | N | O | $CH_3$ | $CH_3$ | H | L-7a | |
| N | CH | N | O | $CH_3$ | $CH_3$ | H | L-8a | |
| N | CH | N | O | $CH_3$ | $CH_3$ | H | L-8b | |
| N | CH | N | O | $CH_3$ | $CH_3$ | H | L-9a | |
| N | CH | N | O | $CH_3$ | $CH_3$ | H | L-12a | |
| N | CH | N | O | $CH_3$ | $CH_3$ | H | L-12b | |
| N | CH | N | O | $CH_3$ | $CH_3$ | H | L-14a | |
| N | CH | N | O | $CH_3$ | $CH_3$ | H | L-15a | |
| N | CH | N | O | $CH_3$ | $CH_3$ | H | L-16a | |
| N | CH | N | O | $CH_3$ | $CH_3$ | H | L-16b | |
| N | CH | N | O | $CH_3$ | $CH_3$ | H | L-18a | |
| N | CH | N | O | $CH_3$ | $CH_3$ | H | L-20a | |
| N | CH | N | O | $CH_3$ | $CH_3$ | H | L-22a | |
| N | CH | N | S | $CH_3$ | $CH_3$ | H | L-1a | |
| N | CH | N | O | $CH_3$ | $CH_3$ | $CH_3$ | L-1a | |
| N | CH | N | O | $OCH_3$ | $CH_3$ | H | L-1a | |
| N | CH | N | O | $OCH_3$ | $CH_3$ | H | L-1b | |
| N | CH | N | O | $OCH_3$ | $CH_3$ | H | L-1c | |
| N | CH | N | O | $OCH_3$ | $CH_3$ | H | L-1d | |
| N | CH | N | O | $OCH_3$ | $CH_3$ | H | L-1e | |
| N | CH | N | O | $OCH_3$ | $CH_3$ | H | L-1f | |
| N | CH | N | O | $OCH_3$ | $CH_3$ | H | L-1g | |
| N | CH | N | O | $OCH_3$ | $CH_3$ | H | L-1h | |
| N | CH | N | O | $OCH_3$ | $CH_3$ | H | L-1i | |
| N | CH | N | O | $OCH_3$ | $CH_3$ | H | L-1j | |
| N | CH | N | O | $OCH_3$ | $CH_3$ | H | L-1k | |
| N | CH | N | O | $OCH_3$ | $CH_3$ | H | L-3a | |
| N | CH | N | O | $OCH_3$ | $CH_3$ | H | L-3b | |
| N | CH | N | O | $OCH_3$ | $CH_3$ | H | L-4a | |
| N | CH | N | O | $OCH_3$ | $CH_3$ | H | L-7a | |
| N | CH | N | O | $OCH_3$ | $CH_3$ | H | L-8a | |
| N | CH | N | O | $OCH_3$ | $CH_3$ | H | L-8b | |
| N | CH | N | O | $OCH_3$ | $CH_3$ | H | L-9a | |
| N | CH | N | O | $OCH_3$ | $CH_3$ | H | L-12a | |
| N | CH | N | O | $OCH_3$ | $CH_3$ | H | L-12b | |
| N | CH | N | O | $OCH_3$ | $CH_3$ | H | L-14a | |
| N | CH | N | O | $OCH_3$ | $CH_3$ | H | L-15a | |
| N | CH | N | O | $OCH_3$ | $CH_3$ | H | L-16a | |
| N | CH | N | O | $OCH_3$ | $CH_3$ | H | L-16b | |
| N | CH | N | O | $OCH_3$ | $CH_3$ | H | L-18a | |
| N | CH | N | O | $OCH_3$ | $CH_3$ | H | L-20a | |
| N | CH | N | O | $OCH_3$ | $CH_3$ | H | L-22a | |
| N | CH | N | S | $OCH_3$ | $CH_3$ | H | L-1a | |
| N | CH | N | O | $OCH_3$ | $CH_3$ | $CH_3$ | L-1a | |
| N | CH | N | O | $CH_3$ | $OCH_3$ | H | L-1a | |
| N | CH | N | O | $CH_3$ | $OCH_3$ | H | L-1b | |
| N | CH | N | O | $CH_3$ | $OCH_3$ | H | L-1c | |
| N | CH | N | O | $CH_3$ | $OCH_3$ | H | L-1d | |
| N | CH | N | O | $CH_3$ | $OCH_3$ | H | L-1e | |
| N | CH | N | O | $CH_3$ | $OCH_3$ | H | L-1f | |
| N | CH | N | O | $CH_3$ | $OCH_3$ | H | L-1g | |
| N | CH | N | O | $CH_3$ | $OCH_3$ | H | L-1h | |
| N | CH | N | O | $CH_3$ | $OCH_3$ | H | L-1i | |
| N | CH | N | O | $CH_3$ | $OCH_3$ | H | L-1j | |
| N | CH | N | O | $CH_3$ | $OCH_3$ | H | L-1k | |
| N | CH | N | O | $CH_3$ | $OCH_3$ | H | L-3a | |
| N | CH | N | O | $CH_3$ | $OCH_3$ | H | L-3b | |
| N | CH | N | O | $CH_3$ | $OCH_3$ | H | L-4a | |
| N | CH | N | O | $CH_3$ | $OCH_3$ | H | L-7a | |

TABLE 1-continued

General Formula 1

| Z | Z$_1$ | Z$_2$ | W | X | Y | R | L | m.p. (°C.) |
|---|---|---|---|---|---|---|---|---|
| N | CH | N | O | CH$_3$ | OCH$_3$ | H | L-8a | |
| N | CH | N | O | CH$_3$ | OCH$_3$ | H | L-8b | |
| N | CH | N | O | CH$_3$ | OCH$_3$ | H | L-9a | |
| N | CH | N | O | CH$_3$ | OCH$_3$ | H | L-12a | |
| N | CH | N | O | CH$_3$ | OCH$_3$ | H | L-12b | |
| N | CH | N | O | CH$_3$ | OCH$_3$ | H | L-14a | |
| N | CH | N | O | CH$_3$ | OCH$_3$ | H | L-15a | |
| N | CH | N | O | CH$_3$ | OCH$_3$ | H | L-16a | |
| N | CH | N | O | CH$_3$ | OCH$_3$ | H | L-16b | |
| N | CH | N | O | CH$_3$ | OCH$_3$ | H | L-18a | |
| N | CH | N | O | CH$_3$ | OCH$_3$ | H | L-20a | |
| N | CH | N | O | CH$_3$ | OCH$_3$ | H | L-22a | |
| N | CH | N | S | CH$_3$ | OCH$_3$ | H | L-1a | |
| N | CH | N | O | CH$_3$ | OCH$_3$ | CH$_3$ | L-1a | |
| N | CH | N | O | OCH$_3$ | OCH$_3$ | H | L-1a | |
| N | CH | N | O | OCH$_3$ | OCH$_3$ | H | L-1b | |
| N | CH | N | O | OCH$_3$ | OCH$_3$ | H | L-1c | |
| N | CH | N | O | OCH$_3$ | OCH$_3$ | H | L-1d | |
| N | CH | N | O | OCH$_3$ | OCH$_3$ | H | L-1e | |
| N | CH | N | O | OCH$_3$ | OCH$_3$ | H | L-1f | |
| N | CH | N | O | OCH$_3$ | OCH$_3$ | H | L-1g | |
| N | CH | N | O | OCH$_3$ | OCH$_3$ | H | L-1h | |
| N | CH | N | O | OCH$_3$ | OCH$_3$ | H | L-1i | |
| N | CH | N | O | OCH$_3$ | OCH$_3$ | H | L-1j | |
| N | CH | N | O | OCH$_3$ | OCH$_3$ | H | L-1k | |
| N | CH | N | O | OCH$_3$ | OCH$_3$ | H | L-3a | |
| N | CH | N | O | OCH$_3$ | OCH$_3$ | H | L-3b | |
| N | CH | N | O | OCH$_3$ | OCH$_3$ | H | L-4a | |
| N | CH | N | O | OCH$_3$ | OCH$_3$ | H | L-7a | |
| N | CH | N | O | OCH$_3$ | OCH$_3$ | H | L-8a | |
| N | CH | N | O | OCH$_3$ | OCH$_3$ | H | L-8b | |
| N | CH | N | O | OCH$_3$ | OCH$_3$ | H | L-9a | |
| N | CH | N | O | OCH$_3$ | OCH$_3$ | H | L-12a | |
| N | CH | N | O | OCH$_3$ | OCH$_3$ | H | L-12b | |
| N | CH | N | O | OCH$_3$ | OCH$_3$ | H | L-14a | |
| N | CH | N | O | OCH$_3$ | OCH$_3$ | H | L-15a | |
| N | CH | N | O | OCH$_3$ | OCH$_3$ | H | L-16a | |
| N | CH | N | O | OCH$_3$ | OCH$_3$ | H | L-16b | |
| N | CH | N | O | OCH$_3$ | OCH$_3$ | H | L-18a | |
| N | CH | N | O | OCH$_3$ | OCH$_3$ | H | L-20a | |
| N | CH | N | O | OCH$_3$ | OCH$_3$ | H | L-22a | |
| N | CH | N | S | OCH$_3$ | OCH$_3$ | H | L-1a | |
| N | CH | N | O | OCH$_3$ | OCH$_3$ | CH$_3$ | L-1a | |
| N | CH | CH | O | CH$_3$ | CH$_3$ | H | L-1a | |
| N | CH | CH | O | CH$_3$ | CH$_3$ | H | L-1b | |
| N | CH | CH | O | CH$_3$ | CH$_3$ | H | L-1c | |
| N | CH | CH | O | CH$_3$ | CH$_3$ | H | L-1d | |
| N | CH | CH | O | CH$_3$ | CH$_3$ | H | L-1e | |
| N | CH | CH | O | CH$_3$ | CH$_3$ | H | L-1f | |
| N | CH | CH | O | CH$_3$ | CH$_3$ | H | L-1g | |
| N | CH | CH | O | CH$_3$ | CH$_3$ | H | L-1h | |
| N | CH | CH | O | CH$_3$ | CH$_3$ | H | L-1i | |
| N | CH | CH | O | CH$_3$ | CH$_3$ | H | L-1j | |
| N | CH | CH | O | CH$_3$ | CH$_3$ | H | L-1k | |
| N | CH | CH | O | CH$_3$ | CH$_3$ | H | L-3a | |
| N | CH | CH | O | CH$_3$ | CH$_3$ | H | L-3b | |
| N | CH | CH | O | CH$_3$ | CH$_3$ | H | L-4a | |
| N | CH | CH | O | CH$_3$ | CH$_3$ | H | L-7a | |
| N | CH | CH | O | CH$_3$ | CH$_3$ | H | L-8a | |
| N | CH | CH | O | CH$_3$ | CH$_3$ | H | L-8b | |
| N | CH | CH | O | CH$_3$ | CH$_3$ | H | L-9a | |
| N | CH | CH | O | CH$_3$ | CH$_3$ | H | L-12a | |
| N | CH | CH | O | CH$_3$ | CH$_3$ | H | L-12b | |
| N | CH | CH | O | CH$_3$ | CH$_3$ | H | L-14a | |
| N | CH | CH | O | CH$_3$ | CH$_3$ | H | L-15a | |
| N | CH | CH | O | CH$_3$ | CH$_3$ | H | L-16a | |
| N | CH | CH | O | CH$_3$ | CH$_3$ | H | L-16b | |
| N | CH | CH | O | CH$_3$ | CH$_3$ | H | L-18a | |
| N | CH | CH | O | CH$_3$ | CH$_3$ | H | L-20a | |
| N | CH | CH | O | CH$_3$ | CH$_3$ | H | L-22a | |
| N | CH | CH | S | CH$_3$ | CH$_3$ | H | L-1a | |
| N | CH | CH | O | CH$_3$ | CH$_3$ | CH$_3$ | L-1a | |
| N | CH | CH | O | OCH$_3$ | CH$_3$ | H | L-1a | |
| N | CH | CH | O | OCH$_3$ | CH$_3$ | H | L-1b | |
| N | CH | CH | O | OCH$_3$ | CH$_3$ | H | L-1c | |
| N | CH | CH | O | OCH$_3$ | CH$_3$ | H | L-1d | |
| N | CH | CH | O | OCH$_3$ | CH$_3$ | H | L-1e | |
| N | CH | CH | O | OCH$_3$ | CH$_3$ | H | L-1f | |
| N | CH | CH | O | OCH$_3$ | CH$_3$ | H | L-1g | |
| N | CH | CH | O | OCH$_3$ | CH$_3$ | H | L-1h | |

TABLE 1-continued

| | | | | General Formula 1 | | | | |
|---|---|---|---|---|---|---|---|---|
| Z | $Z_1$ | $Z_2$ | W | X | Y | R | L | m.p. (°C.) |
| N | CH | CH | O | OCH$_3$ | CH$_3$ | H | L-1i | |
| N | CH | CH | O | OCH$_3$ | CH$_3$ | H | L-1j | |
| N | CH | CH | O | OCH$_3$ | CH$_3$ | H | L-1k | |
| N | CH | CH | O | OCH$_3$ | CH$_3$ | H | L-3a | |
| N | CH | CH | O | OCH$_3$ | CH$_3$ | H | L-3b | |
| N | CH | CH | O | OCH$_3$ | CH$_3$ | H | L-4a | |
| N | CH | CH | O | OCH$_3$ | CH$_3$ | H | L-7a | |
| N | CH | CH | O | OCH$_3$ | CH$_3$ | H | L-8a | |
| N | CH | CH | O | OCH$_3$ | CH$_3$ | H | L-8b | |
| N | CH | CH | O | OCH$_3$ | CH$_3$ | H | L-9a | |
| N | CH | CH | O | OCH$_3$ | CH$_3$ | H | L-12a | |
| N | CH | CH | O | OCH$_3$ | CH$_3$ | H | L-12b | |
| N | CH | CH | O | OCH$_3$ | CH$_3$ | H | L-14a | |
| N | CH | CH | O | OCH$_3$ | CH$_3$ | H | L-15a | |
| N | CH | CH | O | OCH$_3$ | CH$_3$ | H | L-16a | |
| N | CH | CH | O | OCH$_3$ | CH$_3$ | H | L-16b | |
| N | CH | CH | O | OCH$_3$ | CH$_3$ | H | L-18a | |
| N | CH | CH | O | OCH$_3$ | CH$_3$ | H | L-20a | |
| N | CH | CH | O | OCH$_3$ | CH$_3$ | H | L-22a | |
| N | CH | CH | S | OCH$_3$ | CH$_3$ | H | L-1a | |
| N | CH | CH | O | OCH$_3$ | CH$_3$ | CH$_3$ | L-1a | |
| N | CH | CH | O | CH$_3$ | OCH$_3$ | H | L-1a | |
| N | CH | CH | O | CH$_3$ | OCH$_3$ | H | L-1b | |
| N | CH | CH | O | CH$_3$ | OCH$_3$ | H | L-1c | |
| N | CH | CH | O | CH$_3$ | OCH$_3$ | H | L-1d | |
| N | CH | CH | O | CH$_3$ | OCH$_3$ | H | L-1e | |
| N | CH | CH | O | CH$_3$ | OCH$_3$ | H | L-1f | |
| N | CH | CH | O | CH$_3$ | OCH$_3$ | H | L-1g | |
| N | CH | CH | O | CH$_3$ | OCH$_3$ | H | L-1h | |
| N | CH | CH | O | CH$_3$ | OCH$_3$ | H | L-1i | |
| N | CH | CH | O | CH$_3$ | OCH$_3$ | H | L-1j | |
| N | CH | CH | O | CH$_3$ | OCH$_3$ | H | L-1k | |
| N | CH | CH | O | CH$_3$ | OCH$_3$ | H | L-3a | |
| N | CH | CH | O | CH$_3$ | OCH$_3$ | H | L-3b | |
| N | CH | CH | O | CH$_3$ | OCH$_3$ | H | L-4a | |
| N | CH | CH | O | CH$_3$ | OCH$_3$ | H | L-7a | |
| N | CH | CH | O | CH$_3$ | OCH$_3$ | H | L-8a | |
| N | CH | CH | O | CH$_3$ | OCH$_3$ | H | L-8b | |
| N | CH | CH | O | CH$_3$ | OCH$_3$ | H | L-9a | |
| N | CH | CH | O | CH$_3$ | OCH$_3$ | H | L-12a | |
| N | CH | CH | O | CH$_3$ | OCH$_3$ | H | L-12b | |
| N | CH | CH | O | CH$_3$ | OCH$_3$ | H | L-14a | |
| N | CH | CH | O | CH$_3$ | OCH$_3$ | H | L-15a | |
| N | CH | CH | O | CH$_3$ | OCH$_3$ | H | L-16a | |
| N | CH | CH | O | CH$_3$ | OCH$_3$ | H | L-16b | |
| N | CH | CH | O | CH$_3$ | OCH$_3$ | H | L-18a | |
| N | CH | CH | O | CH$_3$ | OCH$_3$ | H | L-20a | |
| N | CH | CH | O | CH$_3$ | OCH$_3$ | H | L-22a | |
| N | CH | CH | S | CH$_3$ | OCH$_3$ | H | L-1a | |
| N | CH | CH | O | CH$_3$ | OCH$_3$ | CH$_3$ | L-1a | |
| N | CH | CH | O | OCH$_3$ | OCH$_3$ | H | L-1a | |
| N | CH | CH | O | OCH$_3$ | OCH$_3$ | H | L-1b | |
| N | CH | CH | O | OCH$_3$ | OCH$_3$ | H | L-1c | |
| N | CH | CH | O | OCH$_3$ | OCH$_3$ | H | L-1d | |
| N | CH | CH | O | OCH$_3$ | OCH$_3$ | H | L-1e | |
| N | CH | CH | O | OCH$_3$ | OCH$_3$ | H | L-1f | |
| N | CH | CH | O | OCH$_3$ | OCH$_3$ | H | L-1g | |
| N | CH | CH | O | OCH$_3$ | OCH$_3$ | H | L-1h | |
| N | CH | CH | O | OCH$_3$ | OCH$_3$ | H | L-1i | |
| N | CH | CH | O | OCH$_3$ | OCH$_3$ | H | L-1j | |
| N | CH | CH | O | OCH$_3$ | OCH$_3$ | H | L-1k | |
| N | CH | CH | O | OCH$_3$ | OCH$_3$ | H | L-3a | |
| N | CH | CH | O | OCH$_3$ | OCH$_3$ | H | L-3b | |
| N | CH | CH | O | OCH$_3$ | OCH$_3$ | H | L-4a | |
| N | CH | CH | O | OCH$_3$ | OCH$_3$ | H | L-7a | |
| N | CH | CH | O | OCH$_3$ | OCH$_3$ | H | L-8a | |
| N | CH | CH | O | OCH$_3$ | OCH$_3$ | H | L-8b | |
| N | CH | CH | O | OCH$_3$ | OCH$_3$ | H | L-9a | |
| N | CH | CH | O | OCH$_3$ | OCH$_3$ | H | L-12a | |
| N | CH | CH | O | OCH$_3$ | OCH$_3$ | H | L-12b | |
| N | CH | CH | O | OCH$_3$ | OCH$_3$ | H | L-14a | |
| N | CH | CH | O | OCH$_3$ | OCH$_3$ | H | L-15a | |
| N | CH | CH | O | OCH$_3$ | OCH$_3$ | H | L-16a | |
| N | CH | CH | O | OCH$_3$ | OCH$_3$ | H | L-16b | |
| N | CH | CH | O | OCH$_3$ | OCH$_3$ | H | L-18a | |
| N | CH | CH | O | OCH$_3$ | OCH$_3$ | H | L-20a | |
| N | CH | CH | O | OCH$_3$ | OCH$_3$ | H | L-22a | |
| N | CH | CH | S | OCH$_3$ | OCH$_3$ | H | L-1a | |

TABLE 1-continued

General Formula 1

| Z | $Z_1$ | $Z_2$ | W | X | Y | R | L | m.p. (°C.) |
|---|---|---|---|---|---|---|---|---|
| N | CH | CH | O | $OCH_3$ | $OCH_3$ | $CH_3$ | L-1a | |

*N,N—diethylanilinium salt

TABLE 2

General Formula 2

| Z | $Z_1$ | $Z_2$ | W | X | Y | R | L | m.p. (°C.) |
|---|---|---|---|---|---|---|---|---|
| CH | N | CH | O | $CH_3$ | $CH_3$ | H | L-1a | 210–212 |
| CH | N | CH | O | $CH_3$ | $CH_3$ | H | L-1b | |
| CH | N | CH | O | $CH_3$ | $CH_3$ | H | L-1c | |
| CH | N | CH | O | $CH_3$ | $CH_3$ | H | L-1d | |
| CH | N | CH | O | $CH_3$ | $CH_3$ | H | L-1e | |
| CH | N | CH | O | $CH_3$ | $CH_3$ | H | L-1f | |
| CH | N | CH | O | $CH_3$ | $CH_3$ | H | L-1g | |
| CH | N | CH | O | $CH_3$ | $CH_3$ | H | L-1h | |
| CH | N | CH | O | $CH_3$ | $CH_3$ | H | L-1i | |
| CH | N | CH | O | $CH_3$ | $CH_3$ | H | L-1j | |
| CH | N | CH | O | $CH_3$ | $CH_3$ | H | L-1k | |
| CH | N | CH | O | $CH_3$ | $CH_3$ | H | L-1l | 268–272 |
| CH | N | CH | O | $CH_3$ | $CH_3$ | H | L-3a | |
| CH | N | CH | O | $CH_3$ | $CH_3$ | H | L-3b | |
| CH | N | CH | O | $CH_3$ | $CH_3$ | H | L-4a | |
| CH | N | CH | O | $CH_3$ | $CH_3$ | H | L-7a | |
| CH | N | CH | O | $CH_3$ | $CH_3$ | H | L-8a | |
| CH | N | CH | O | $CH_3$ | $CH_3$ | H | L-8b | |
| CH | N | CH | O | $CH_3$ | $CH_3$ | H | L-9a | |
| CH | N | CH | O | $CH_3$ | $CH_3$ | H | L-12a | |
| CH | N | CH | O | $CH_3$ | $CH_3$ | H | L-12b | |
| CH | N | CH | O | $CH_3$ | $CH_3$ | H | L-14a | |
| CH | N | CH | O | $CH_3$ | $CH_3$ | H | L-15a | |
| CH | N | CH | O | $CH_3$ | $CH_3$ | H | L-16a | |
| CH | N | CH | O | $CH_3$ | $CH_3$ | H | L-16b | |
| CH | N | CH | O | $CH_3$ | $CH_3$ | H | L-18a | |
| CH | N | CH | O | $CH_3$ | $CH_3$ | H | L-20a | |
| CH | N | CH | O | $CH_3$ | $CH_3$ | H | L-22a | |
| CH | N | CH | S | $CH_3$ | $CH_3$ | H | L-1a | |
| CH | N | CH | O | $CH_3$ | $CH_3$ | $CH_3$ | L-1a | |
| CH | N | CH | O | $OCH_3$ | $CH_3$ | H | L-1a | |
| CH | N | CH | O | $OCH_3$ | $CH_3$ | H | L-1b | |
| CH | N | CH | O | $OCH_3$ | $CH_3$ | H | L-1c | |
| CH | N | CH | O | $OCH_3$ | $CH_3$ | H | L-1d | |
| CH | N | CH | O | $OCH_3$ | $CH_3$ | H | L-1e | |
| CH | N | CH | O | $OCH_3$ | $CH_3$ | H | L-1f | |
| CH | N | CH | O | $OCH_3$ | $CH_3$ | H | L-1g | |
| CH | N | CH | O | $OCH_3$ | $CH_3$ | H | L-1h | |
| CH | N | CH | O | $OCH_3$ | $CH_3$ | H | L-1i | |
| CH | N | CH | O | $OCH_3$ | $CH_3$ | H | L-1j | |
| CH | N | CH | O | $OCH_3$ | $CH_3$ | H | L-1k | |
| CH | N | CH | O | $OCH_3$ | $CH_3$ | H | L-3a | |
| CH | N | CH | O | $OCH_3$ | $CH_3$ | H | L-3b | |
| CH | N | CH | O | $OCH_3$ | $CH_3$ | H | L-4a | |
| CH | N | CH | O | $OCH_3$ | $CH_3$ | H | L-7a | |
| CH | N | CH | O | $OCH_3$ | $CH_3$ | H | L-8a | |
| CH | N | CH | O | $OCH_3$ | $CH_3$ | H | L-8b | |
| CH | N | CH | O | $OCH_3$ | $CH_3$ | H | L-9a | |
| CH | N | CH | O | $OCH_3$ | $CH_3$ | H | L-12a | |
| CH | N | CH | O | $OCH_3$ | $CH_3$ | H | L-12b | |
| CH | N | CH | O | $OCH_3$ | $CH_3$ | H | L-14a | |
| CH | N | CH | O | $OCH_3$ | $CH_3$ | H | L-15a | |
| CH | N | CH | O | $OCH_3$ | $CH_3$ | H | L-16a | |
| CH | N | CH | O | $OCH_3$ | $CH_3$ | H | L-16b | |
| CH | N | CH | O | $OCH_3$ | $CH_3$ | H | L-18a | |
| CH | N | CH | O | $OCH_3$ | $CH_3$ | H | L-20a | |
| CH | N | CH | O | $OCH_3$ | $CH_3$ | H | L-22a | |
| CH | N | CH | S | $OCH_3$ | $CH_3$ | H | L-1a | |
| CH | N | CH | O | $OCH_3$ | $CH_3$ | $CH_3$ | L-1a | |
| CH | N | CH | O | $CH_3$ | $OCH_3$ | H | L-1a | |
| CH | N | CH | O | $CH_3$ | $OCH_3$ | H | L-1b | |
| CH | N | CH | O | $CH_3$ | $OCH_3$ | H | L-1c | |
| CH | N | CH | O | $CH_3$ | $OCH_3$ | H | L-1d | 262–266 |
| CH | N | CH | O | $CH_3$ | $OCH_3$ | H | L-1e | |
| CH | N | CH | O | $CH_3$ | $OCH_3$ | H | L-1f | |
| CH | N | CH | O | $CH_3$ | $OCH_3$ | H | L-1g | |
| CH | N | CH | O | $CH_3$ | $OCH_3$ | H | L-1h | |
| CH | N | CH | O | $CH_3$ | $OCH_3$ | H | L-1i | |
| CH | N | CH | O | $CH_3$ | $OCH_3$ | H | L-1j | |
| CH | N | CH | O | $CH_3$ | $OCH_3$ | H | L-1k | |
| CH | N | CH | O | $CH_3$ | $OCH_3$ | H | L-1l | 287–292 |
| CH | N | CH | O | $CH_3$ | $OCH_3$ | H | L-3a | |
| CH | N | CH | O | $CH_3$ | $OCH_3$ | H | L-3b | |
| CH | N | CH | O | $CH_3$ | $OCH_3$ | H | L-4a | |
| CH | N | CH | O | $CH_3$ | $OCH_3$ | H | L-7a | |
| CH | N | CH | O | $CH_3$ | $OCH_3$ | H | L-8a | |
| CH | N | CH | O | $CH_3$ | $OCH_3$ | H | L-8b | |
| CH | N | CH | O | $CH_3$ | $OCH_3$ | H | L-9a | |
| CH | N | CH | O | $CH_3$ | $OCH_3$ | H | L-12a | |
| CH | N | CH | O | $CH_3$ | $OCH_3$ | H | L-12b | |
| CH | N | CH | O | $CH_3$ | $OCH_3$ | H | L-14a | |
| CH | N | CH | O | $CH_3$ | $OCH_3$ | H | L-15a | |
| CH | N | CH | O | $CH_3$ | $OCH_3$ | H | L-16a | |
| CH | N | CH | O | $CH_3$ | $OCH_3$ | H | L-16b | |
| CH | N | CH | O | $CH_3$ | $OCH_3$ | H | L-18a | |
| CH | N | CH | O | $CH_3$ | $OCH_3$ | H | L-20a | |
| CH | N | CH | O | $CH_3$ | $OCH_3$ | H | L-22a | |
| CH | N | CH | S | $CH_3$ | $OCH_3$ | H | L-1a | |
| CH | N | CH | O | $CH_3$ | $OCH_3$ | $CH_3$ | L-1a | |
| CH | N | CH | O | $OCH_3$ | $OCH_3$ | H | L-1a | |
| CH | N | CH | O | $OCH_3$ | $OCH_3$ | H | L-1b | |
| CH | N | CH | O | $OCH_3$ | $OCH_3$ | H | L-1c | |
| CH | N | CH | O | $OCH_3$ | $OCH_3$ | H | L-1d | |
| CH | N | CH | O | $OCH_3$ | $OCH_3$ | H | L-1e | |
| CH | N | CH | O | $OCH_3$ | $OCH_3$ | H | L-1f | |
| CH | N | CH | O | $OCH_3$ | $OCH_3$ | H | L-1g | |
| CH | N | CH | O | $OCH_3$ | $OCH_3$ | H | L-1h | |
| CH | N | CH | O | $OCH_3$ | $OCH_3$ | H | L-1i | |
| CH | N | CH | O | $OCH_3$ | $OCH_3$ | H | L-1j | |
| CH | N | CH | O | $OCH_3$ | $OCH_3$ | H | L-1k | |
| CH | N | CH | O | $OCH_3$ | $OCH_3$ | H | L-3a | |
| CH | N | CH | O | $OCH_3$ | $OCH_3$ | H | L-3b | |
| CH | N | CH | O | $OCH_3$ | $OCH_3$ | H | L-4a | |
| CH | N | CH | O | $OCH_3$ | $OCH_3$ | H | L-7a | |
| CH | N | CH | O | $OCH_3$ | $OCH_3$ | H | L-8a | |
| CH | N | CH | O | $OCH_3$ | $OCH_3$ | H | L-8b | |
| CH | N | CH | O | $OCH_3$ | $OCH_3$ | H | L-9a | |
| CH | N | CH | O | $OCH_3$ | $OCH_3$ | H | L-12a | |
| CH | N | CH | O | $OCH_3$ | $OCH_3$ | H | L-12b | |
| CH | N | CH | O | $OCH_3$ | $OCH_3$ | H | L-14a | |
| CH | N | CH | O | $OCH_3$ | $OCH_3$ | H | L-15a | |
| CH | N | CH | O | $OCH_3$ | $OCH_3$ | H | L-16a | |
| CH | N | CH | O | $OCH_3$ | $OCH_3$ | H | L-16b | |
| CH | N | CH | O | $OCH_3$ | $OCH_3$ | H | L-18a | |
| CH | N | CH | O | $OCH_3$ | $OCH_3$ | H | L-20a | |
| CH | N | CH | O | $OCH_3$ | $OCH_3$ | H | L-22a | |
| CH | N | CH | S | $OCH_3$ | $OCH_3$ | H | L-1a | |
| CH | N | CH | O | $OCH_3$ | $OCH_3$ | $CH_3$ | L-1a | |
| CH | N | N | O | $CH_3$ | $CH_3$ | H | L-1a | |
| CH | N | N | O | $CH_3$ | $CH_3$ | H | L-1b | |
| CH | N | N | O | $CH_3$ | $CH_3$ | H | L-1c | |
| CH | N | N | O | $CH_3$ | $CH_3$ | H | L-1d | 242–247 |
| CH | N | N | O | $CH_3$ | $CH_3$ | H | L-1e | |
| CH | N | N | O | $CH_3$ | $CH_3$ | H | L-1f | |
| CH | N | N | O | $CH_3$ | $CH_3$ | H | L-1g | |
| CH | N | N | O | $CH_3$ | $CH_3$ | H | L-1h | |
| CH | N | N | O | $CH_3$ | $CH_3$ | H | L-1i | |
| CH | N | N | O | $CH_3$ | $CH_3$ | H | L-1j | |
| CH | N | N | O | $CH_3$ | $CH_3$ | H | L-1k | |
| CH | N | N | O | $CH_3$ | $CH_3$ | H | L-3a | |
| CH | N | N | O | $CH_3$ | $CH_3$ | H | L-3b | |
| CH | N | N | O | $CH_3$ | $CH_3$ | H | L-4a | |
| CH | N | N | O | $CH_3$ | $CH_3$ | H | L-7a | |
| CH | N | N | O | $CH_3$ | $CH_3$ | H | L-8a | |
| CH | N | N | O | $CH_3$ | $CH_3$ | H | L-8b | |
| CH | N | N | O | $CH_3$ | $CH_3$ | H | L-9a | |
| CH | N | N | O | $CH_3$ | $CH_3$ | H | L-12a | |
| CH | N | N | O | $CH_3$ | $CH_3$ | H | L-12b | |
| CH | N | N | O | $CH_3$ | $CH_3$ | H | L-14a | |
| CH | N | N | O | $CH_3$ | $CH_3$ | H | L-15a | |

TABLE 2-continued

General Formula 2

| Z | Z₁ | Z₂ | W | X | Y | R | L | m.p. (°C.) |
|---|---|---|---|---|---|---|---|---|
| CH | N | N | O | CH₃ | CH₃ | H | L-16a | |
| CH | N | N | O | CH₃ | CH₃ | H | L-16b | |
| CH | N | N | O | CH₃ | CH₃ | H | L-18a | |
| CH | N | N | O | CH₃ | CH₃ | H | L-20a | |
| CH | N | N | O | CH₃ | CH₃ | H | L-22a | |
| CH | N | N | S | CH₃ | CH₃ | H | L-1a | |
| CH | N | N | O | CH₃ | CH₃ | CH₃ | L-1a | |
| CH | N | N | O | OCH₃ | CH₃ | H | L-1a | |
| CH | N | N | O | OCH₃ | CH₃ | H | L-1b | |
| CH | N | N | O | OCH₃ | CH₃ | H | L-1c | |
| CH | N | N | O | OCH₃ | CH₃ | H | L-1d | |
| CH | N | N | O | OCH₃ | CH₃ | H | L-1e | |
| CH | N | N | O | OCH₃ | CH₃ | H | L-1f | |
| CH | N | N | O | OCH₃ | CH₃ | H | L-1g | |
| CH | N | N | O | OCH₃ | CH₃ | H | L-1h | |
| CH | N | N | O | OCH₃ | CH₃ | H | L-1i | |
| CH | N | N | O | OCH₃ | CH₃ | H | L-1j | |
| CH | N | N | O | OCH₃ | CH₃ | H | L-1k | |
| CH | N | N | O | OCH₃ | CH₃ | H | L-3a | |
| CH | N | N | O | OCH₃ | CH₃ | H | L-3b | |
| CH | N | N | O | OCH₃ | CH₃ | H | L-4a | |
| CH | N | N | O | OCH₃ | CH₃ | H | L-7a | |
| CH | N | N | O | OCH₃ | CH₃ | H | L-8a | |
| CH | N | N | O | OCH₃ | CH₃ | H | L-8b | |
| CH | N | N | O | OCH₃ | CH₃ | H | L-9a | |
| CH | N | N | O | OCH₃ | CH₃ | H | L-12a | |
| CH | N | N | O | OCH₃ | CH₃ | H | L-12b | |
| CH | N | N | O | OCH₃ | CH₃ | H | L-14a | |
| CH | N | N | O | OCH₃ | CH₃ | H | L-15a | |
| CH | N | N | O | OCH₃ | CH₃ | H | L-16a | |
| CH | N | N | O | OCH₃ | CH₃ | H | L-16b | |
| CH | N | N | O | OCH₃ | CH₃ | H | L-18a | |
| CH | N | N | O | OCH₃ | CH₃ | H | L-20a | |
| CH | N | N | O | OCH₃ | CH₃ | H | L-22a | |
| CH | N | N | S | OCH₃ | CH₃ | H | L-1a | |
| CH | N | N | O | OCH₃ | CH₃ | CH₃ | L-1a | |
| CH | N | N | O | CH₃ | OCH₃ | H | L-1a | |
| CH | N | N | O | CH₃ | OCH₃ | H | L-1b | |
| CH | N | N | O | CH₃ | OCH₃ | H | L-1c | |
| CH | N | N | O | CH₃ | OCH₃ | H | L-1d | |
| CH | N | N | O | CH₃ | OCH₃ | H | L-1e | |
| CH | N | N | O | CH₃ | OCH₃ | H | L-1f | |
| CH | N | N | O | CH₃ | OCH₃ | H | L-1g | |
| CH | N | N | O | CH₃ | OCH₃ | H | L-1h | |
| CH | N | N | O | CH₃ | OCH₃ | H | L-1i | |
| CH | N | N | O | CH₃ | OCH₃ | H | L-1j | |
| CH | N | N | O | CH₃ | OCH₃ | H | L-1k | |
| CH | N | N | O | CH₃ | OCH₃ | H | L-3a | |
| CH | N | N | O | CH₃ | OCH₃ | H | L-3b | |
| CH | N | N | O | CH₃ | OCH₃ | H | L-4a | |
| CH | N | N | O | CH₃ | OCH₃ | H | L-7a | |
| CH | N | N | O | CH₃ | OCH₃ | H | L-8a | |
| CH | N | N | O | CH₃ | OCH₃ | H | L-8b | |
| CH | N | N | O | CH₃ | OCH₃ | H | L-9a | |
| CH | N | N | O | CH₃ | OCH₃ | H | L-12a | |
| CH | N | N | O | CH₃ | OCH₃ | H | L-12b | |
| CH | N | N | O | CH₃ | OCH₃ | H | L-14a | |
| CH | N | N | O | CH₃ | OCH₃ | H | L-15a | |
| CH | N | N | O | CH₃ | OCH₃ | H | L-16a | |
| CH | N | N | O | CH₃ | OCH₃ | H | L-16b | |
| CH | N | N | O | CH₃ | OCH₃ | H | L-18a | |
| CH | N | N | O | CH₃ | OCH₃ | H | L-20a | |
| CH | N | N | O | CH₃ | OCH₃ | H | L-22a | |
| CH | N | N | S | CH₃ | OCH₃ | H | L-1a | |
| CH | N | N | O | CH₃ | OCH₃ | CH₃ | L-1a | |
| CH | N | N | O | OCH₃ | OCH₃ | H | L-1a | |
| CH | N | N | O | OCH₃ | OCH₃ | H | L-1b | |
| CH | N | N | O | OCH₃ | OCH₃ | H | L-1c | |
| CH | N | N | O | OCH₃ | OCH₃ | H | L-1d | |
| CH | N | N | O | OCH₃ | OCH₃ | H | L-1e | |
| CH | N | N | O | OCH₃ | OCH₃ | H | L-1f | |
| CH | N | N | O | OCH₃ | OCH₃ | H | L-1g | |
| CH | N | N | O | OCH₃ | OCH₃ | H | L-1h | |
| CH | N | N | O | OCH₃ | OCH₃ | H | L-1i | |
| CH | N | N | O | OCH₃ | OCH₃ | H | L-1j | |
| CH | N | N | O | OCH₃ | OCH₃ | H | L-1k | |
| CH | N | N | O | OCH₃ | OCH₃ | H | L-3a | |
| CH | N | N | O | OCH₃ | OCH₃ | H | L-3b | |
| CH | N | N | O | OCH₃ | OCH₃ | H | L-4a | |
| CH | N | N | O | OCH₃ | OCH₃ | H | L-7a | |
| CH | N | N | O | OCH₃ | OCH₃ | H | L-8a | |
| CH | N | N | O | OCH₃ | OCH₃ | H | L-8b | |
| CH | N | N | O | OCH₃ | OCH₃ | H | L-9a | |
| CH | N | N | O | OCH₃ | OCH₃ | H | L-12a | |
| CH | N | N | O | OCH₃ | OCH₃ | H | L-12b | |
| CH | N | N | O | OCH₃ | OCH₃ | H | L-14a | |
| CH | N | N | O | OCH₃ | OCH₃ | H | L-15a | |
| CH | N | N | O | OCH₃ | OCH₃ | H | L-16a | |
| CH | N | N | O | OCH₃ | OCH₃ | H | L-16b | |
| CH | N | N | O | OCH₃ | OCH₃ | H | L-18a | |
| CH | N | N | O | OCH₃ | OCH₃ | H | L-20a | |
| CH | N | N | O | OCH₃ | OCH₃ | H | L-22a | |
| CH | N | N | S | OCH₃ | OCH₃ | H | L-1a | |
| CH | N | N | O | OCH₃ | OCH₃ | CH₃ | L-1a | |
| CH | CH | N | O | CH₃ | CH₃ | H | L-1a | |
| CH | CH | N | O | CH₃ | CH₃ | H | L-1 | 225–228 |
| CH | CH | N | O | CH₃ | CH₃ | H | L-1c | |
| CH | CH | N | O | CH₃ | CH₃ | H | L-1d | 292–297 |
| CH | CH | N | O | CH₃ | CH₃ | H | L-1e | |
| CH | CH | N | O | CH₃ | CH₃ | H | L-1f | |
| CH | CH | N | O | CH₃ | CH₃ | H | L-1g | |
| CH | CH | N | O | CH₃ | CH₃ | H | L-1h | |
| CH | CH | N | O | CH₃ | CH₃ | H | L-1i | |
| CH | CH | N | O | CH₃ | CH₃ | H | L-1j | |
| CH | CH | N | O | CH₃ | CH₃ | H | L-1k | |
| CH | CH | N | O | CH₃ | CH₃ | H | L-1l | 308–311 (d) |
| CH | CH | N | O | CH₃ | CH₃ | H | L-3a | |
| CH | CH | N | O | CH₃ | CH₃ | H | L-3b | |
| CH | CH | N | O | CH₃ | CH₃ | H | L-4a | |
| CH | CH | N | O | CH₃ | CH₃ | H | L-7a | |
| CH | CH | N | O | CH₃ | CH₃ | H | L-8a | |
| CH | CH | N | O | CH₃ | CH₃ | H | L-8b | |
| CH | CH | N | O | CH₃ | CH₃ | H | L-9a | |
| CH | CH | N | O | CH₃ | CH₃ | H | L-12a | |
| CH | CH | N | O | CH₃ | CH₃ | H | L-12b | |
| CH | CH | N | O | CH₃ | CH₃ | H | L-14a | |
| CH | CH | N | O | CH₃ | CH₃ | H | L-15a | |
| CH | CH | N | O | CH₃ | CH₃ | H | L-16a | |
| CH | CH | N | O | CH₃ | CH₃ | H | L-16b | |
| CH | CH | N | O | CH₃ | CH₃ | H | L-18a | |
| CH | CH | N | O | CH₃ | CH₃ | H | L-20a | |
| CH | CH | N | O | CH₃ | CH₃ | H | L-22a | |
| CH | CH | N | S | CH₃ | CH₃ | H | L-1a | |
| CH | CH | N | O | CH₃ | CH₃ | CH₃ | L-1a | |
| CH | CH | N | O | H | CH₃ | H | L-1d | 265–272 |
| CH | CH | N | O | H | CH₃ | H | L-1l | 219–225 |
| CH | CH | N | O | OCH₃ | CH₃ | H | L-1a | |
| CH | CH | N | O | OCH₃ | CH₃ | H | L-1b | |
| CH | CH | N | O | OCH₃ | CH₃ | H | L-1c | |
| CH | CH | N | O | OCH₃ | CH₃ | H | L-1d | |
| CH | CH | N | O | OCH₃ | CH₃ | H | L-1e | |
| CH | CH | N | O | OCH₃ | CH₃ | H | L-1f | |
| CH | CH | N | O | OCH₃ | CH₃ | H | L-1g | |
| CH | CH | N | O | OCH₃ | CH₃ | H | L-1h | |
| CH | CH | N | O | OCH₃ | CH₃ | H | L-1i | |
| CH | CH | N | O | OCH₃ | CH₃ | H | L-1j | |
| CH | CH | N | O | OCH₃ | CH₃ | H | L-1k | |
| CH | CH | N | O | OCH₃ | CH₃ | H | L-3a | |
| CH | CH | N | O | OCH₃ | CH₃ | H | L-3b | |
| CH | CH | N | O | OCH₃ | CH₃ | H | L-4a | |
| CH | CH | N | O | OCH₃ | CH₃ | H | L-7a | |
| CH | CH | N | O | OCH₃ | CH₃ | H | L-8a | |
| CH | CH | N | O | OCH₃ | CH₃ | H | L-8b | |
| CH | CH | N | O | OCH₃ | CH₃ | H | L-9a | |
| CH | CH | N | O | OCH₃ | CH₃ | H | L-12a | |
| CH | CH | N | O | OCH₃ | CH₃ | H | L-12b | |
| CH | CH | N | O | OCH₃ | CH₃ | H | L-14a | |
| CH | CH | N | O | OCH₃ | CH₃ | H | L-15a | |
| CH | CH | N | O | OCH₃ | CH₃ | H | L-16a | |
| CH | CH | N | O | OCH₃ | CH₃ | H | L-16b | |
| CH | CH | N | O | OCH₃ | CH₃ | H | L-18a | |
| CH | CH | N | O | OCH₃ | CH₃ | H | L-20a | |
| CH | CH | N | O | OCH₃ | CH₃ | H | L-22a | |
| CH | CH | N | S | OCH₃ | CH₃ | H | L-1a | |
| CH | CH | N | O | OCH₃ | CH₃ | CH₃ | L-1a | |

TABLE 2-continued

General Formula 2

| Z | $Z_1$ | $Z_2$ | W | X | Y | R | L | m.p. (°C.) |
|---|---|---|---|---|---|---|---|---|
| CH | CH | N | O | CH$_3$ | OCH$_3$ | H | L-1a | |
| CH | CH | N | O | CH$_3$ | OCH$_3$ | H | L-1b | |
| CH | CH | N | O | CH$_3$ | OCH$_3$ | H | L-1c | |
| CH | CH | N | O | CH$_3$ | OCH$_3$ | H | L-1d | |
| CH | CH | N | O | CH$_3$ | OCH$_3$ | H | L-1e | |
| CH | CH | N | O | CH$_3$ | OCH$_3$ | H | L-1f | |
| CH | CH | N | O | CH$_3$ | OCH$_3$ | H | L-1g | |
| CH | CH | N | O | CH$_3$ | OCH$_3$ | H | L-1h | |
| CH | CH | N | O | CH$_3$ | OCH$_3$ | H | L-1i | |
| CH | CH | N | O | CH$_3$ | OCH$_3$ | H | L-1j | |
| CH | CH | N | O | CH$_3$ | OCH$_3$ | H | L-1k | |
| CH | CH | N | O | CH$_3$ | OCH$_3$ | H | L-3a | |
| CH | CH | N | O | CH$_3$ | OCH$_3$ | H | L-3b | |
| CH | CH | N | O | CH$_3$ | OCH$_3$ | H | L-4a | |
| CH | CH | N | O | CH$_3$ | OCH$_3$ | H | L-7a | |
| CH | CH | N | O | CH$_3$ | OCH$_3$ | H | L-8a | |
| CH | CH | N | O | CH$_3$ | OCH$_3$ | H | L-8b | |
| CH | CH | N | O | CH$_3$ | OCH$_3$ | H | L-9a | |
| CH | CH | N | O | CH$_3$ | OCH$_3$ | H | L-12a | |
| CH | CH | N | O | CH$_3$ | OCH$_3$ | H | L-12b | |
| CH | CH | N | O | CH$_3$ | OCH$_3$ | H | L-14a | |
| CH | CH | N | O | CH$_3$ | OCH$_3$ | H | L-15a | |
| CH | CH | N | O | CH$_3$ | OCH$_3$ | H | L-16a | |
| CH | CH | N | O | CH$_3$ | OCH$_3$ | H | L-16b | |
| CH | CH | N | O | CH$_3$ | OCH$_3$ | H | L-18a | |
| CH | CH | N | O | CH$_3$ | OCH$_3$ | H | L-20a | |
| CH | CH | N | O | CH$_3$ | OCH$_3$ | H | L-22a | |
| CH | CH | N | S | CH$_3$ | OCH$_3$ | H | L-1a | |
| CH | CH | N | O | CH$_3$ | OCH$_3$ | CH$_3$ | L-1a | |
| CH | CH | N | O | OCH$_3$ | OCH$_3$ | H | L-1a | |
| CH | CH | N | O | OCH$_3$ | OCH$_3$ | H | L-1b | |
| CH | CH | N | O | OCH$_3$ | OCH$_3$ | H | L-1c | |
| CH | CH | N | O | OCH$_3$ | OCH$_3$ | H | L-1d | |
| CH | CH | N | O | OCH$_3$ | OCH$_3$ | H | L-1e | |
| CH | CH | N | O | OCH$_3$ | OCH$_3$ | H | L-1f | |
| CH | CH | N | O | OCH$_3$ | OCH$_3$ | H | L-1g | |
| CH | CH | N | O | OCH$_3$ | OCH$_3$ | H | L-1h | |
| CH | CH | N | O | OCH$_3$ | OCH$_3$ | H | L-1i | |
| CH | CH | N | O | OCH$_3$ | OCH$_3$ | H | L-1j | |
| CH | CH | N | O | OCH$_3$ | OCH$_3$ | H | L-1k | |
| CH | CH | N | O | OCH$_3$ | OCH$_3$ | H | L-3a | |
| CH | CH | N | O | OCH$_3$ | OCH$_3$ | H | L-3b | |
| CH | CH | N | O | OCH$_3$ | OCH$_3$ | H | L-4a | |
| CH | CH | N | O | OCH$_3$ | OCH$_3$ | H | L-7a | |
| CH | CH | N | O | OCH$_3$ | OCH$_3$ | H | L-8a | |
| CH | CH | N | O | OCH$_3$ | OCH$_3$ | H | L-8b | |
| CH | CH | N | O | OCH$_3$ | OCH$_3$ | H | L-9a | |
| CH | CH | N | O | OCH$_3$ | OCH$_3$ | H | L-12a | |
| CH | CH | N | O | OCH$_3$ | OCH$_3$ | H | L-12b | |
| CH | CH | N | O | OCH$_3$ | OCH$_3$ | H | L-14a | |
| CH | CH | N | O | OCH$_3$ | OCH$_3$ | H | L-15a | |
| CH | CH | N | O | OCH$_3$ | OCH$_3$ | H | L-16a | |
| CH | CH | N | O | OCH$_3$ | OCH$_3$ | H | L-16b | |
| CH | CH | N | O | OCH$_3$ | OCH$_3$ | H | L-18a | |
| CH | CH | N | O | OCH$_3$ | OCH$_3$ | H | L-20a | |
| CH | CH | N | O | OCH$_3$ | OCH$_3$ | H | L-22a | |
| CH | CH | N | S | OCH$_3$ | OCH$_3$ | H | L-1a | |
| CH | CH | N | O | OCH$_3$ | OCH$_3$ | CH$_3$ | L-1a | |
| CH | CH | CH | O | CH$_3$ | CH$_3$ | H | L-1a | 200–202 |
| CH | CH | CH | O | CH$_3$ | CH$_3$ | H | L-1b | 199–202 |
| CH | CH | CH | O | CH$_3$ | CH$_3$ | H | L-1c | |
| CH | CH | CH | O | CH$_3$ | CH$_3$ | H | L-1d | |
| CH | CH | CH | O | CH$_3$ | CH$_3$ | H | L-1e | |
| CH | CH | CH | O | CH$_3$ | CH$_3$ | H | L-1f | |
| CH | CH | CH | O | CH$_3$ | CH$_3$ | H | L-1g | |
| CH | CH | CH | O | CH$_3$ | CH$_3$ | H | L-1h | |
| CH | CH | CH | O | CH$_3$ | CH$_3$ | H | L-1i | |
| CH | CH | CH | O | CH$_3$ | CH$_3$ | H | L-1j | |
| CH | CH | CH | O | CH$_3$ | CH$_3$ | H | L-1k | |
| CH | CH | CH | O | CH$_3$ | CH$_3$ | H | L-3a | |
| CH | CH | CH | O | CH$_3$ | CH$_3$ | H | L-3b | |
| CH | CH | CH | O | CH$_3$ | CH$_3$ | H | L-4a | |
| CH | CH | CH | O | CH$_3$ | CH$_3$ | H | L-7a | |
| CH | CH | CH | O | CH$_3$ | CH$_3$ | H | L-8a | |
| CH | CH | CH | O | CH$_3$ | CH$_3$ | H | L-8b | |
| CH | CH | CH | O | CH$_3$ | CH$_3$ | H | L-9a | |
| CH | CH | CH | O | CH$_3$ | CH$_3$ | H | L-12a | |
| CH | CH | CH | O | CH$_3$ | CH$_3$ | H | L-12b | |
| CH | CH | CH | O | CH$_3$ | CH$_3$ | H | L-14a | |
| CH | CH | CH | O | CH$_3$ | CH$_3$ | H | L-15a | |
| CH | CH | CH | O | CH$_3$ | CH$_3$ | H | L-16a | |
| CH | CH | CH | O | CH$_3$ | CH$_3$ | H | L-16b | |
| CH | CH | CH | O | CH$_3$ | CH$_3$ | H | L-18a | |
| CH | CH | CH | O | CH$_3$ | CH$_3$ | H | L-20a | |
| CH | CH | CH | O | CH$_3$ | CH$_3$ | H | L-22a | |
| CH | CH | CH | S | CH$_3$ | CH$_3$ | H | L-1a | |
| CH | CH | CH | O | CH$_3$ | CH$_3$ | CH$_3$ | L-1a | |
| CH | CH | CH | O | OCH$_3$ | CH$_3$ | H | L-1a | |
| CH | CH | CH | O | OCH$_3$ | CH$_3$ | H | L-1b | |
| CH | CH | CH | O | OCH$_3$ | CH$_3$ | H | L-1c | |
| CH | CH | CH | O | OCH$_3$ | CH$_3$ | H | L-1d | |
| CH | CH | CH | O | OCH$_3$ | CH$_3$ | H | L-1e | |
| CH | CH | CH | O | OCH$_3$ | CH$_3$ | H | L-1f | |
| CH | CH | CH | O | OCH$_3$ | CH$_3$ | H | L-1g | |
| CH | CH | CH | O | OCH$_3$ | CH$_3$ | H | L-1h | |
| CH | CH | CH | O | OCH$_3$ | CH$_3$ | H | L-1i | |
| CH | CH | CH | O | OCH$_3$ | CH$_3$ | H | L-1j | |
| CH | CH | CH | O | OCH$_3$ | CH$_3$ | H | L-1k | |
| CH | CH | CH | O | OCH$_3$ | CH$_3$ | H | L-3a | |
| CH | CH | CH | O | OCH$_3$ | CH$_3$ | H | L-3b | |
| CH | CH | CH | O | OCH$_3$ | CH$_3$ | H | L-4a | |
| CH | CH | CH | O | OCH$_3$ | CH$_3$ | H | L-7a | |
| CH | CH | CH | O | OCH$_3$ | CH$_3$ | H | L-8a | |
| CH | CH | CH | O | OCH$_3$ | CH$_3$ | H | L-8b | |
| CH | CH | CH | O | OCH$_3$ | CH$_3$ | H | L-9a | |
| CH | CH | CH | O | OCH$_3$ | CH$_3$ | H | L-12a | |
| CH | CH | CH | O | OCH$_3$ | CH$_3$ | H | L-12b | |
| CH | CH | CH | O | OCH$_3$ | CH$_3$ | H | L-14a | |
| CH | CH | CH | O | OCH$_3$ | CH$_3$ | H | L-15a | |
| CH | CH | CH | O | OCH$_3$ | CH$_3$ | H | L-16a | |
| CH | CH | CH | O | OCH$_3$ | CH$_3$ | H | L-16b | |
| CH | CH | CH | O | OCH$_3$ | CH$_3$ | H | L-18a | |
| CH | CH | CH | O | OCH$_3$ | CH$_3$ | H | L-20a | |
| CH | CH | CH | O | OCH$_3$ | CH$_3$ | H | L-22a | |
| CH | CH | CH | S | OCH$_3$ | CH$_3$ | H | L-1a | |
| CH | CH | CH | O | OCH$_3$ | CH$_3$ | CH$_3$ | L-1a | |
| CH | CH | CH | O | CH$_3$ | OCH$_3$ | H | L-1a | |
| CH | CH | CH | O | CH$_3$ | OCH$_3$ | H | L-1b | |
| CH | CH | CH | O | CH$_3$ | OCH$_3$ | H | L-1c | |
| CH | CH | CH | O | CH$_3$ | OCH$_3$ | H | L-1d | |
| CH | CH | CH | O | CH$_3$ | OCH$_3$ | H | L-1e | |
| CH | CH | CH | O | CH$_3$ | OCH$_3$ | H | L-1f | |
| CH | CH | CH | O | CH$_3$ | OCH$_3$ | H | L-1g | |
| CH | CH | CH | O | CH$_3$ | OCH$_3$ | H | L-1h | |
| CH | CH | CH | O | CH$_3$ | OCH$_3$ | H | L-1i | |
| CH | CH | CH | O | CH$_3$ | OCH$_3$ | H | L-1j | |
| CH | CH | CH | O | CH$_3$ | OCH$_3$ | H | L-1k | |
| CH | CH | CH | O | CH$_3$ | OCH$_3$ | H | L-3a | |
| CH | CH | CH | O | CH$_3$ | OCH$_3$ | H | L-3b | |
| CH | CH | CH | O | CH$_3$ | OCH$_3$ | H | L-4a | |
| CH | CH | CH | O | CH$_3$ | OCH$_3$ | H | L-7a | |
| CH | CH | CH | O | CH$_3$ | OCH$_3$ | H | L-8a | |
| CH | CH | CH | O | CH$_3$ | OCH$_3$ | H | L-8b | |
| CH | CH | CH | O | CH$_3$ | OCH$_3$ | H | L-9a | |
| CH | CH | CH | O | CH$_3$ | OCH$_3$ | H | L-12a | |
| CH | CH | CH | O | CH$_3$ | OCH$_3$ | H | L-12b | |
| CH | CH | CH | O | CH$_3$ | OCH$_3$ | H | L-14a | |
| CH | CH | CH | O | CH$_3$ | OCH$_3$ | H | L-15a | |
| CH | CH | CH | O | CH$_3$ | OCH$_3$ | H | L-16a | |
| CH | CH | CH | O | CH$_3$ | OCH$_3$ | H | L-16b | |
| CH | CH | CH | O | CH$_3$ | OCH$_3$ | H | L-18a | |
| CH | CH | CH | O | CH$_3$ | OCH$_3$ | H | L-20a | |
| CH | CH | CH | O | CH$_3$ | OCH$_3$ | H | L-22a | |
| CH | CH | CH | S | CH$_3$ | OCH$_3$ | H | L-1a | |
| CH | CH | CH | O | CH$_3$ | OCH$_3$ | CH$_3$ | L-1a | |
| CH | CH | CH | O | OCH$_3$ | OCH$_3$ | H | L-1a | |
| CH | CH | CH | O | OCH$_3$ | OCH$_3$ | H | L-1b | |
| CH | CH | CH | O | OCH$_3$ | OCH$_3$ | H | L-1c | |
| CH | CH | CH | O | OCH$_3$ | OCH$_3$ | H | L-1d | |
| CH | CH | CH | O | OCH$_3$ | OCH$_3$ | H | L-1e | |
| CH | CH | CH | O | OCH$_3$ | OCH$_3$ | H | L-1f | |
| CH | CH | CH | O | OCH$_3$ | OCH$_3$ | H | L-1g | |
| CH | CH | CH | O | OCH$_3$ | OCH$_3$ | H | L-1h | |
| CH | CH | CH | O | OCH$_3$ | OCH$_3$ | H | L-1i | |
| CH | CH | CH | O | OCH$_3$ | OCH$_3$ | H | L-1j | |
| CH | CH | CH | O | OCH$_3$ | OCH$_3$ | H | L-1k | |

TABLE 2-continued

General Formula 2

| Z | Z₁ | Z₂ | W | X | Y | R | L | m.p. (°C.) |
|---|---|---|---|---|---|---|---|---|
| CH | CH | CH | O | OCH₃ | OCH₃ | H | L-3a | |
| CH | CH | CH | O | OCH₃ | OCH₃ | H | L-3b | |
| CH | CH | CH | O | OCH₃ | OCH₃ | H | L-4a | |
| CH | CH | CH | O | OCH₃ | OCH₃ | H | L-7a | |
| CH | CH | CH | O | OCH₃ | OCH₃ | H | L-8a | |
| CH | CH | CH | O | OCH₃ | OCH₃ | H | L-8b | |
| CH | CH | CH | O | OCH₃ | OCH₃ | H | L-9a | |
| CH | CH | CH | O | OCH₃ | OCH₃ | H | L-12a | |
| CH | CH | CH | O | OCH₃ | OCH₃ | H | L-12b | |
| CH | CH | CH | O | OCH₃ | OCH₃ | H | L-14a | |
| CH | CH | CH | O | OCH₃ | OCH₃ | H | L-15a | |
| CH | CH | CH | O | OCH₃ | OCH₃ | H | L-16a | |
| CH | CH | CH | O | OCH₃ | OCH₃ | H | L-16b | |
| CH | CH | CH | O | OCH₃ | OCH₃ | H | L-18a | |
| CH | CH | CH | O | OCH₃ | OCH₃ | H | L-20a | |
| CH | CH | CH | O | OCH₃ | OCH₃ | H | L-22a | |
| CH | CH | CH | S | OCH₃ | OCH₃ | H | L-1a | |
| CH | CH | CH | O | OCH₃ | OCH₃ | CH₃ | L-1a | |
| N | N | CH | O | CH₃ | CH₃ | H | L-1a | |
| N | N | CH | O | CH₃ | CH₃ | H | L-1b | |
| N | N | CH | O | CH₃ | CH₃ | H | L-1c | |
| N | N | CH | O | CH₃ | CH₃ | H | L-1d | |
| N | N | CH | O | CH₃ | CH₃ | H | L-1e | |
| N | N | CH | O | CH₃ | CH₃ | H | L-1f | |
| N | N | CH | O | CH₃ | CH₃ | H | L-1g | |
| N | N | CH | O | CH₃ | CH₃ | H | L-1h | |
| N | N | CH | O | CH₃ | CH₃ | H | L-1i | |
| N | N | CH | O | CH₃ | CH₃ | H | L-1j | |
| N | N | CH | O | CH₃ | CH₃ | H | L-1k | |
| N | N | CH | O | CH₃ | CH₃ | H | L-3a | |
| N | N | CH | O | CH₃ | CH₃ | H | L-3b | |
| N | N | CH | O | CH₃ | CH₃ | H | L-4a | |
| N | N | CH | O | CH₃ | CH₃ | H | L-7a | |
| N | N | CH | O | CH₃ | CH₃ | H | L-8a | |
| N | N | CH | O | CH₃ | CH₃ | H | L-8b | |
| N | N | CH | O | CH₃ | CH₃ | H | L-9a | |
| N | N | CH | O | CH₃ | CH₃ | H | L-12a | |
| N | N | CH | O | CH₃ | CH₃ | H | L-12b | |
| N | N | CH | O | CH₃ | CH₃ | H | L-14a | |
| N | N | CH | O | CH₃ | CH₃ | H | L-15a | |
| N | N | CH | O | CH₃ | CH₃ | H | L-16a | |
| N | N | CH | O | CH₃ | CH₃ | H | L-16b | |
| N | N | CH | O | CH₃ | CH₃ | H | L-18a | |
| N | N | CH | O | CH₃ | CH₃ | H | L-20a | |
| N | N | CH | O | CH₃ | CH₃ | H | L-22a | |
| N | N | CH | S | CH₃ | CH₃ | H | L-1a | |
| N | N | CH | O | CH₃ | CH₃ | CH₃ | L-1a | |
| N | N | CH | O | OCH₃ | CH₃ | H | L-1a | |
| N | N | CH | O | OCH₃ | CH₃ | H | L-1b | |
| N | N | CH | O | OCH₃ | CH₃ | H | L-1c | |
| N | N | CH | O | OCH₃ | CH₃ | H | L-1d | |
| N | N | CH | O | OCH₃ | CH₃ | H | L-1e | |
| N | N | CH | O | OCH₃ | CH₃ | H | L-1f | |
| N | N | CH | O | OCH₃ | CH₃ | H | L-1g | |
| N | N | CH | O | OCH₃ | CH₃ | H | L-1h | |
| N | N | CH | O | OCH₃ | CH₃ | H | L-1i | |
| N | N | CH | O | OCH₃ | CH₃ | H | L-1j | |
| N | N | CH | O | OCH₃ | CH₃ | H | L-1k | |
| N | N | CH | O | OCH₃ | CH₃ | H | L-3a | |
| N | N | CH | O | OCH₃ | CH₃ | H | L-3b | |
| N | N | CH | O | OCH₃ | CH₃ | H | L-4a | |
| N | N | CH | O | OCH₃ | CH₃ | H | L-7a | |
| N | N | CH | O | OCH₃ | CH₃ | H | L-8a | |
| N | N | CH | O | OCH₃ | CH₃ | H | L-8b | |
| N | N | CH | O | OCH₃ | CH₃ | H | L-9a | |
| N | N | CH | O | OCH₃ | CH₃ | H | L-12a | |
| N | N | CH | O | OCH₃ | CH₃ | H | L-12b | |
| N | N | CH | O | OCH₃ | CH₃ | H | L-14a | |
| N | N | CH | O | OCH₃ | CH₃ | H | L-15a | |
| N | N | CH | O | OCH₃ | CH₃ | H | L-16a | |
| N | N | CH | O | OCH₃ | CH₃ | H | L-16b | |
| N | N | CH | O | OCH₃ | CH₃ | H | L-18a | |
| N | N | CH | O | OCH₃ | CH₃ | H | L-20a | |
| N | N | CH | O | OCH₃ | CH₃ | H | L-22a | |
| N | N | CH | S | OCH₃ | CH₃ | H | L-1a | |
| N | N | CH | O | OCH₃ | CH₃ | CH₃ | L-1a | |
| N | N | CH | O | CH₃ | OCH₃ | H | L-1a | |
| N | N | CH | O | CH₃ | OCH₃ | H | L-1b | |
| N | N | CH | O | CH₃ | OCH₃ | H | L-1c | |
| N | N | CH | O | CH₃ | OCH₃ | H | L-1d | |
| N | N | CH | O | CH₃ | OCH₃ | H | L-1e | |
| N | N | CH | O | CH₃ | OCH₃ | H | L-1f | |
| N | N | CH | O | CH₃ | OCH₃ | H | L-1g | |
| N | N | CH | O | CH₃ | OCH₃ | H | L-1h | |
| N | N | CH | O | CH₃ | OCH₃ | H | L-1i | |
| N | N | CH | O | CH₃ | OCH₃ | H | L-1j | |
| N | N | CH | O | CH₃ | OCH₃ | H | L-1k | |
| N | N | CH | O | CH₃ | OCH₃ | H | L-3a | |
| N | N | CH | O | CH₃ | OCH₃ | H | L-3b | |
| N | N | CH | O | CH₃ | OCH₃ | H | L-4a | |
| N | N | CH | O | CH₃ | OCH₃ | H | L-7a | |
| N | N | CH | O | CH₃ | OCH₃ | H | L-8a | |
| N | N | CH | O | CH₃ | OCH₃ | H | L-8b | |
| N | N | CH | O | CH₃ | OCH₃ | H | L-9a | |
| N | N | CH | O | CH₃ | OCH₃ | H | L-12a | |
| N | N | CH | O | CH₃ | OCH₃ | H | L-12b | |
| N | N | CH | O | CH₃ | OCH₃ | H | L-14a | |
| N | N | CH | O | CH₃ | OCH₃ | H | L-15a | |
| N | N | CH | O | CH₃ | OCH₃ | H | L-16a | |
| N | N | CH | O | CH₃ | OCH₃ | H | L-16b | |
| N | N | CH | O | CH₃ | OCH₃ | H | L-18a | |
| N | N | CH | O | CH₃ | OCH₃ | H | L-20a | |
| N | N | CH | O | CH₃ | OCH₃ | H | L-22a | |
| N | N | CH | S | CH₃ | OCH₃ | H | L-1a | |
| N | N | CH | O | CH₃ | OCH₃ | CH₃ | L-1a | |
| N | N | CH | O | OCH₃ | OCH₃ | H | L-1a | |
| N | N | CH | O | OCH₃ | OCH₃ | H | L-1b | |
| N | N | CH | O | OCH₃ | OCH₃ | H | L-1c | |
| N | N | CH | O | OCH₃ | OCH₃ | H | L-1d | |
| N | N | CH | O | OCH₃ | OCH₃ | H | L-1e | |
| N | N | CH | O | OCH₃ | OCH₃ | H | L-1f | |
| N | N | CH | O | OCH₃ | OCH₃ | H | L-1g | |
| N | N | CH | O | OCH₃ | OCH₃ | H | L-1h | |
| N | N | CH | O | OCH₃ | OCH₃ | H | L-1i | |
| N | N | CH | O | OCH₃ | OCH₃ | H | L-1j | |
| N | N | CH | O | OCH₃ | OCH₃ | H | L-1k | |
| N | N | CH | O | OCH₃ | OCH₃ | H | L-3a | |
| N | N | CH | O | OCH₃ | OCH₃ | H | L-3b | |
| N | N | CH | O | OCH₃ | OCH₃ | H | L-4a | |
| N | N | CH | O | OCH₃ | OCH₃ | H | L-7a | |
| N | N | CH | O | OCH₃ | OCH₃ | H | L-8a | |
| N | N | CH | O | OCH₃ | OCH₃ | H | L-8b | |
| N | N | CH | O | OCH₃ | OCH₃ | H | L-9a | |
| N | N | CH | O | OCH₃ | OCH₃ | H | L-12a | |
| N | N | CH | O | OCH₃ | OCH₃ | H | L-12b | |
| N | N | CH | O | OCH₃ | OCH₃ | H | L-14a | |
| N | N | CH | O | OCH₃ | OCH₃ | H | L-15a | |
| N | N | CH | O | OCH₃ | OCH₃ | H | L-16a | |
| N | N | CH | O | OCH₃ | OCH₃ | H | L-16b | |
| N | N | CH | O | OCH₃ | OCH₃ | H | L-18a | |
| N | N | CH | O | OCH₃ | OCH₃ | H | L-20a | |
| N | N | CH | O | OCH₃ | OCH₃ | H | L-22a | |
| N | N | CH | S | OCH₃ | OCH₃ | H | L-1a | |
| N | N | CH | O | OCH₃ | OCH₃ | CH₃ | L-1a | |
| N | N | N | O | CH₃ | CH₃ | H | L-1a | |
| N | N | N | O | CH₃ | CH₃ | H | L-1b | |
| N | N | N | O | CH₃ | CH₃ | H | L-1c | |
| N | N | N | O | CH₃ | CH₃ | H | L-1d | |
| N | N | N | O | CH₃ | CH₃ | H | L-1e | |
| N | N | N | O | CH₃ | CH₃ | H | L-1f | |
| N | N | N | O | CH₃ | CH₃ | H | L-1g | |
| N | N | N | O | CH₃ | CH₃ | H | L-1h | |
| N | N | N | O | CH₃ | CH₃ | H | L-1i | |
| N | N | N | O | CH₃ | CH₃ | H | L-1j | |
| N | N | N | O | CH₃ | CH₃ | H | L-1k | |
| N | N | N | O | CH₃ | CH₃ | H | L-3a | |
| N | N | N | O | CH₃ | CH₃ | H | L-3b | |
| N | N | N | O | CH₃ | CH₃ | H | L-4a | |
| N | N | N | O | CH₃ | CH₃ | H | L-7a | |
| N | N | N | O | CH₃ | CH₃ | H | L-8a | |
| N | N | N | O | CH₃ | CH₃ | H | L-8b | |
| N | N | N | O | CH₃ | CH₃ | H | L-9a | |
| N | N | N | O | CH₃ | CH₃ | H | L-12a | |
| N | N | N | O | CH₃ | CH₃ | H | L-12b | |
| N | N | N | O | CH₃ | CH₃ | H | L-14a | |
| N | N | N | O | CH₃ | CH₃ | H | L-15a | |

TABLE 2-continued

General Formula 2

| Z | Z₁ | Z₂ | W | X | Y | R | L | m.p. (°C.) |
|---|----|----|---|---|---|---|---|-----------|
| N | N | N | O | CH₃ | CH₃ | H | L-16a | |
| N | N | N | O | CH₃ | CH₃ | H | L-16b | |
| N | N | N | O | CH₃ | CH₃ | H | L-18a | |
| N | N | N | O | CH₃ | CH₃ | H | L-20a | |
| N | N | N | O | CH₃ | CH₃ | H | L-22a | |
| N | N | N | S | CH₃ | CH₃ | H | L-1a | |
| N | N | N | O | CH₃ | CH₃ | CH₃ | L-1a | |
| N | N | N | O | OCH₃ | CH₃ | H | L-1a | |
| N | N | N | O | OCH₃ | CH₃ | H | L-1b | |
| N | N | N | O | OCH₃ | CH₃ | H | L-1c | |
| N | N | N | O | OCH₃ | CH₃ | H | L-1d | |
| N | N | N | O | OCH₃ | CH₃ | H | L-1e | |
| N | N | N | O | OCH₃ | CH₃ | H | L-1f | |
| N | N | N | O | OCH₃ | CH₃ | H | L-1g | |
| N | N | N | O | OCH₃ | CH₃ | H | L-1h | |
| N | N | N | O | OCH₃ | CH₃ | H | L-1i | |
| N | N | N | O | OCH₃ | CH₃ | H | L-1j | |
| N | N | N | O | OCH₃ | CH₃ | H | L-1k | |
| N | N | N | O | OCH₃ | CH₃ | H | L-3a | |
| N | N | N | O | OCH₃ | CH₃ | H | L-3b | |
| N | N | N | O | OCH₃ | CH₃ | H | L-4a | |
| N | N | N | O | OCH₃ | CH₃ | H | L-7a | |
| N | N | N | O | OCH₃ | CH₃ | H | L-8a | |
| N | N | N | O | OCH₃ | CH₃ | H | L-8b | |
| N | N | N | O | OCH₃ | CH₃ | H | L-9a | |
| N | N | N | O | OCH₃ | CH₃ | H | L-12a | |
| N | N | N | O | OCH₃ | CH₃ | H | L-12b | |
| N | N | N | O | OCH₃ | CH₃ | H | L-14a | |
| N | N | N | O | OCH₃ | CH₃ | H | L-15a | |
| N | N | N | O | OCH₃ | CH₃ | H | L-16a | |
| N | N | N | O | OCH₃ | CH₃ | H | L-16b | |
| N | N | N | O | OCH₃ | CH₃ | H | L-18a | |
| N | N | N | O | OCH₃ | CH₃ | H | L-20a | |
| N | N | N | O | OCH₃ | CH₃ | H | L-22a | |
| N | N | N | S | OCH₃ | CH₃ | H | L-1a | |
| N | N | N | O | OCH₃ | CH₃ | CH₃ | L-1a | |
| N | N | N | O | CH₃ | OCH₃ | H | L-1a | |
| N | N | N | O | CH₃ | OCH₃ | H | L-1b | |
| N | N | N | O | CH₃ | OCH₃ | H | L-1c | |
| N | N | N | O | CH₃ | OCH₃ | H | L-1d | |
| N | N | N | O | CH₃ | OCH₃ | H | L-1e | |
| N | N | N | O | CH₃ | OCH₃ | H | L-1f | |
| N | N | N | O | CH₃ | OCH₃ | H | L-1g | |
| N | N | N | O | CH₃ | OCH₃ | H | L-1h | |
| N | N | N | O | CH₃ | OCH₃ | H | L-1i | |
| N | N | N | O | CH₃ | OCH₃ | H | L-1j | |
| N | N | N | O | CH₃ | OCH₃ | H | L-1k | |
| N | N | N | O | CH₃ | OCH₃ | H | L-3a | |
| N | N | N | O | CH₃ | OCH₃ | H | L-3b | |
| N | N | N | O | CH₃ | OCH₃ | H | L-4a | |
| N | N | N | O | CH₃ | OCH₃ | H | L-7a | |
| N | N | N | O | CH₃ | OCH₃ | H | L-8a | |
| N | N | N | O | CH₃ | OCH₃ | H | L-8b | |
| N | N | N | O | CH₃ | OCH₃ | H | L-9a | |
| N | N | N | O | CH₃ | OCH₃ | H | L-12a | |
| N | N | N | O | CH₃ | OCH₃ | H | L-12b | |
| N | N | N | O | CH₃ | OCH₃ | H | L-14a | |
| N | N | N | O | CH₃ | OCH₃ | H | L-15a | |
| N | N | N | O | CH₃ | OCH₃ | H | L-16a | |
| N | N | N | O | CH₃ | OCH₃ | H | L-16b | |
| N | N | N | O | CH₃ | OCH₃ | H | L-18a | |
| N | N | N | O | CH₃ | OCH₃ | H | L-20a | |
| N | N | N | O | CH₃ | OCH₃ | H | L-22a | |
| N | N | N | S | CH₃ | OCH₃ | H | L-1a | |
| N | N | N | O | CH₃ | OCH₃ | CH₃ | L-1a | |
| N | N | N | O | OCH₃ | OCH₃ | H | L-1a | |
| N | N | N | O | OCH₃ | OCH₃ | H | L-1b | |
| N | N | N | O | OCH₃ | OCH₃ | H | L-1c | |
| N | N | N | O | OCH₃ | OCH₃ | H | L-1d | |
| N | N | N | O | OCH₃ | OCH₃ | H | L-1e | |
| N | N | N | O | OCH₃ | OCH₃ | H | L-1f | |
| N | N | N | O | OCH₃ | OCH₃ | H | L-1g | |
| N | N | N | O | OCH₃ | OCH₃ | H | L-1h | |
| N | N | N | O | OCH₃ | OCH₃ | H | L-1i | |
| N | N | N | O | OCH₃ | OCH₃ | H | L-1j | |
| N | N | N | O | OCH₃ | OCH₃ | H | L-1k | |
| N | N | N | O | OCH₃ | OCH₃ | H | L-3a | |
| N | N | N | O | OCH₃ | OCH₃ | H | L-3b | |
| N | N | N | O | OCH₃ | OCH₃ | H | L-4a | |
| N | N | N | O | OCH₃ | OCH₃ | H | L-7a | |
| N | N | N | O | OCH₃ | OCH₃ | H | L-8a | |
| N | N | N | O | OCH₃ | OCH₃ | H | L-8b | |
| N | N | N | O | OCH₃ | OCH₃ | H | L-9a | |
| N | N | N | O | OCH₃ | OCH₃ | H | L-12a | |
| N | N | N | O | OCH₃ | OCH₃ | H | L-12b | |
| N | N | N | O | OCH₃ | OCH₃ | H | L-14a | |
| N | N | N | O | OCH₃ | OCH₃ | H | L-15a | |
| N | N | N | O | OCH₃ | OCH₃ | H | L-16a | |
| N | N | N | O | OCH₃ | OCH₃ | H | L-16b | |
| N | N | N | O | OCH₃ | OCH₃ | H | L-18a | |
| N | N | N | O | OCH₃ | OCH₃ | H | L-20a | |
| N | N | N | O | OCH₃ | OCH₃ | H | L-22a | |
| N | N | N | S | OCH₃ | OCH₃ | H | L-1a | |
| N | N | N | O | OCH₃ | OCH₃ | CH₃ | L-1a | |
| N | CH | N | O | CH₃ | CH₃ | H | L-1a | |
| N | CH | N | O | CH₃ | CH₃ | H | L-1b | |
| N | CH | N | O | CH₃ | CH₃ | H | L-1c | |
| N | CH | N | O | CH₃ | CH₃ | H | L-1d | |
| N | CH | N | O | CH₃ | CH₃ | H | L-1e | |
| N | CH | N | O | CH₃ | CH₃ | H | L-1f | |
| N | CH | N | O | CH₃ | CH₃ | H | L-1g | |
| N | CH | N | O | CH₃ | CH₃ | H | L-1h | |
| N | CH | N | O | CH₃ | CH₃ | H | L-1i | |
| N | CH | N | O | CH₃ | CH₃ | H | L-1j | |
| N | CH | N | O | CH₃ | CH₃ | H | L-1k | |
| N | CH | N | O | CH₃ | CH₃ | H | L-3a | |
| N | CH | N | O | CH₃ | CH₃ | H | L-3b | |
| N | CH | N | O | CH₃ | CH₃ | H | L-4a | |
| N | CH | N | O | CH₃ | CH₃ | H | L-7a | |
| N | CH | N | O | CH₃ | CH₃ | H | L-8a | |
| N | CH | N | O | CH₃ | CH₃ | H | L-8b | |
| N | CH | N | O | CH₃ | CH₃ | H | L-9a | |
| N | CH | N | O | CH₃ | CH₃ | H | L-12a | |
| N | CH | N | O | CH₃ | CH₃ | H | L-12b | |
| N | CH | N | O | CH₃ | CH₃ | H | L-14a | |
| N | CH | N | O | CH₃ | CH₃ | H | L-15a | |
| N | CH | N | O | CH₃ | CH₃ | H | L-16a | |
| N | CH | N | O | CH₃ | CH₃ | H | L-16b | |
| N | CH | N | O | CH₃ | CH₃ | H | L-18a | |
| N | CH | N | O | CH₃ | CH₃ | H | L-20a | |
| N | CH | N | O | CH₃ | CH₃ | H | L-22a | |
| N | CH | N | S | CH₃ | CH₃ | H | L-1a | |
| N | CH | N | O | CH₃ | CH₃ | CH₃ | L-1a | |
| N | CH | N | O | OCH₃ | CH₃ | H | L-1a | |
| N | CH | N | O | OCH₃ | CH₃ | H | L-1b | |
| N | CH | N | O | OCH₃ | CH₃ | H | L-1c | |
| N | CH | N | O | OCH₃ | CH₃ | H | L-1d | |
| N | CH | N | O | OCH₃ | CH₃ | H | L-1e | |
| N | CH | N | O | OCH₃ | CH₃ | H | L-1f | |
| N | CH | N | O | OCH₃ | CH₃ | H | L-1g | |
| N | CH | N | O | OCH₃ | CH₃ | H | L-1h | |
| N | CH | N | O | OCH₃ | CH₃ | H | L-1i | |
| N | CH | N | O | OCH₃ | CH₃ | H | L-1j | |
| N | CH | N | O | OCH₃ | CH₃ | H | L-1k | |
| N | CH | N | O | OCH₃ | CH₃ | H | L-3a | |
| N | CH | N | O | OCH₃ | CH₃ | H | L-3b | |
| N | CH | N | O | OCH₃ | CH₃ | H | L-4a | |
| N | CH | N | O | OCH₃ | CH₃ | H | L-7a | |
| N | CH | N | O | OCH₃ | CH₃ | H | L-8a | |
| N | CH | N | O | OCH₃ | CH₃ | H | L-8b | |
| N | CH | N | O | OCH₃ | CH₃ | H | L-9a | |
| N | CH | N | O | OCH₃ | CH₃ | H | L-12a | |
| N | CH | N | O | OCH₃ | CH₃ | H | L-12b | |
| N | CH | N | O | OCH₃ | CH₃ | H | L-14a | |
| N | CH | N | O | OCH₃ | CH₃ | H | L-15a | |
| N | CH | N | O | OCH₃ | CH₃ | H | L-16a | |
| N | CH | N | O | OCH₃ | CH₃ | H | L-16b | |
| N | CH | N | O | OCH₃ | CH₃ | H | L-18a | |
| N | CH | N | O | OCH₃ | CH₃ | H | L-20a | |
| N | CH | N | O | OCH₃ | CH₃ | H | L-22a | |
| N | CH | N | S | OCH₃ | CH₃ | H | L-1a | |
| N | CH | N | O | OCH₃ | CH₃ | CH₃ | L-1a | |
| N | CH | N | O | CH₃ | OCH₃ | H | L-1a | |
| N | CH | N | O | CH₃ | OCH₃ | H | L-1b | |
| N | CH | N | O | CH₃ | OCH₃ | H | L-1c | |
| N | CH | N | O | CH₃ | OCH₃ | H | L-1d | |

TABLE 2-continued

General Formula 2

| Z | Z1 | Z2 | W | X | Y | R | L | m.p. (°C.) |
|---|----|----|---|---|---|---|---|---|
| N | CH | N | O | CH3 | OCH3 | H | L-1e | |
| N | CH | N | O | CH3 | OCH3 | H | L-1f | |
| N | CH | N | O | CH3 | OCH3 | H | L-1g | |
| N | CH | N | O | CH3 | OCH3 | H | L-1h | |
| N | CH | N | O | CH3 | OCH3 | H | L-1i | |
| N | CH | N | O | CH3 | OCH3 | H | L-1j | |
| N | CH | N | O | CH3 | OCH3 | H | L-1k | |
| N | CH | N | O | CH3 | OCH3 | H | L-3a | |
| N | CH | N | O | CH3 | OCH3 | H | L-3b | |
| N | CH | N | O | CH3 | OCH3 | H | L-4a | |
| N | CH | N | O | CH3 | OCH3 | H | L-7a | |
| N | CH | N | O | CH3 | OCH3 | H | L-8a | |
| N | CH | N | O | CH3 | OCH3 | H | L-8b | |
| N | CH | N | O | CH3 | OCH3 | H | L-9a | |
| N | CH | N | O | CH3 | OCH3 | H | L-12a | |
| N | CH | N | O | CH3 | OCH3 | H | L-12b | |
| N | CH | N | O | CH3 | OCH3 | H | L-14a | |
| N | CH | N | O | CH3 | OCH3 | H | L-15a | |
| N | CH | N | O | CH3 | OCH3 | H | L-16a | |
| N | CH | N | O | CH3 | OCH3 | H | L-16b | |
| N | CH | N | O | CH3 | OCH3 | H | L-18a | |
| N | CH | N | O | CH3 | OCH3 | H | L-20a | |
| N | CH | N | O | CH3 | OCH3 | H | L-22a | |
| N | CH | N | S | CH3 | OCH3 | H | L-1a | |
| N | CH | N | O | CH3 | OCH3 | CH3 | L-1a | |
| N | CH | N | O | OCH3 | OCH3 | H | L-1a | |
| N | CH | N | O | OCH3 | OCH3 | H | L-1b | |
| N | CH | N | O | OCH3 | OCH3 | H | L-1c | |
| N | CH | N | O | OCH3 | OCH3 | H | L-1d | |
| N | CH | N | O | OCH3 | OCH3 | H | L-1e | |
| N | CH | N | O | OCH3 | OCH3 | H | L-1f | |
| N | CH | N | O | OCH3 | OCH3 | H | L-1g | |
| N | CH | N | O | OCH3 | OCH3 | H | L-1h | |
| N | CH | N | O | OCH3 | OCH3 | H | L-1i | |
| N | CH | N | O | OCH3 | OCH3 | H | L-1j | |
| N | CH | N | O | OCH3 | OCH3 | H | L-1k | |
| N | CH | N | O | OCH3 | OCH3 | H | L-3a | |
| N | CH | N | O | OCH3 | OCH3 | H | L-3b | |
| N | CH | N | O | OCH3 | OCH3 | H | L-4a | |
| N | CH | N | O | OCH3 | OCH3 | H | L-7a | |
| N | CH | N | O | OCH3 | OCH3 | H | L-8a | |
| N | CH | N | O | OCH3 | OCH3 | H | L-8b | |
| N | CH | N | O | OCH3 | OCH3 | H | L-9a | |
| N | CH | N | O | OCH3 | OCH3 | H | L-12a | |
| N | CH | N | O | OCH3 | OCH3 | H | L-12b | |
| N | CH | N | O | OCH3 | OCH3 | H | L-14a | |
| N | CH | N | O | OCH3 | OCH3 | H | L-15a | |
| N | CH | N | O | OCH3 | OCH3 | H | L-16a | |
| N | CH | N | O | OCH3 | OCH3 | H | L-16b | |
| N | CH | N | O | OCH3 | OCH3 | H | L-18a | |
| N | CH | N | O | OCH3 | OCH3 | H | L-20a | |
| N | CH | N | O | OCH3 | OCH3 | H | L-22a | |
| N | CH | N | S | OCH3 | OCH3 | H | L-1a | |
| N | CH | N | O | OCH3 | OCH3 | CH3 | L-1a | |
| N | CH | CH | O | CH3 | CH3 | H | L-1a | |
| N | CH | CH | O | CH3 | CH3 | H | L-1b | |
| N | CH | CH | O | CH3 | CH3 | H | L-1c | |
| N | CH | CH | O | CH3 | CH3 | H | L-1d | |
| N | CH | CH | O | CH3 | CH3 | H | L-1e | |
| N | CH | CH | O | CH3 | CH3 | H | L-1f | |
| N | CH | CH | O | CH3 | CH3 | H | L-1g | |
| N | CH | CH | O | CH3 | CH3 | H | L-1h | |
| N | CH | CH | O | CH3 | CH3 | H | L-1i | |
| N | CH | CH | O | CH3 | CH3 | H | L-1j | |
| N | CH | CH | O | CH3 | CH3 | H | L-1k | |
| N | CH | CH | O | CH3 | CH3 | H | L-3a | |
| N | CH | CH | O | CH3 | CH3 | H | L-3b | |
| N | CH | CH | O | CH3 | CH3 | H | L-4a | |
| N | CH | CH | O | CH3 | CH3 | H | L-7a | |
| N | CH | CH | O | CH3 | CH3 | H | L-8a | |
| N | CH | CH | O | CH3 | CH3 | H | L-8b | |
| N | CH | CH | O | CH3 | CH3 | H | L-9a | |
| N | CH | CH | O | CH3 | CH3 | H | L-12a | |
| N | CH | CH | O | CH3 | CH3 | H | L-12b | |
| N | CH | CH | O | CH3 | CH3 | H | L-14a | |
| N | CH | CH | O | CH3 | CH3 | H | L-15a | |
| N | CH | CH | O | CH3 | CH3 | H | L-16a | |
| N | CH | CH | O | CH3 | CH3 | H | L-16b | |
| N | CH | CH | O | CH3 | CH3 | H | L-18a | |
| N | CH | CH | O | CH3 | CH3 | H | L-20a | |
| N | CH | CH | O | CH3 | CH3 | H | L-22a | |
| N | CH | CH | S | CH3 | CH3 | H | L-1a | |
| N | CH | CH | O | CH3 | CH3 | CH3 | L-1a | |
| N | CH | CH | O | OCH3 | CH3 | H | L-1a | |
| N | CH | CH | O | OCH3 | CH3 | H | L-1b | |
| N | CH | CH | O | OCH3 | CH3 | H | L-1c | |
| N | CH | CH | O | OCH3 | CH3 | H | L-1d | |
| N | CH | CH | O | OCH3 | CH3 | H | L-1e | |
| N | CH | CH | O | OCH3 | CH3 | H | L-1f | |
| N | CH | CH | O | OCH3 | CH3 | H | L-1g | |
| N | CH | CH | O | OCH3 | CH3 | H | L-1h | |
| N | CH | CH | O | OCH3 | CH3 | H | L-1i | |
| N | CH | CH | O | OCH3 | CH3 | H | L-1j | |
| N | CH | CH | O | OCH3 | CH3 | H | L-1k | |
| N | CH | CH | O | OCH3 | CH3 | H | L-3a | |
| N | CH | CH | O | OCH3 | CH3 | H | L-3b | |
| N | CH | CH | O | OCH3 | CH3 | H | L-4a | |
| N | CH | CH | O | OCH3 | CH3 | H | L-7a | |
| N | CH | CH | O | OCH3 | CH3 | H | L-8a | |
| N | CH | CH | O | OCH3 | CH3 | H | L-8b | |
| N | CH | CH | O | OCH3 | CH3 | H | L-9a | |
| N | CH | CH | O | OCH3 | CH3 | H | L-12a | |
| N | CH | CH | O | OCH3 | CH3 | H | L-12b | |
| N | CH | CH | O | OCH3 | CH3 | H | L-14a | |
| N | CH | CH | O | OCH3 | CH3 | H | L-15a | |
| N | CH | CH | O | OCH3 | CH3 | H | L-16a | |
| N | CH | CH | O | OCH3 | CH3 | H | L-16b | |
| N | CH | CH | O | OCH3 | CH3 | H | L-18a | |
| N | CH | CH | O | OCH3 | CH3 | H | L-20a | |
| N | CH | CH | O | OCH3 | CH3 | H | L-22a | |
| N | CH | CH | S | OCH3 | CH3 | H | L-1a | |
| N | CH | CH | O | OCH3 | CH3 | CH3 | L-1a | |
| N | CH | CH | O | CH3 | OCH3 | H | L-1a | |
| N | CH | CH | O | CH3 | OCH3 | H | L-1b | |
| N | CH | CH | O | CH3 | OCH3 | H | L-1c | |
| N | CH | CH | O | CH3 | OCH3 | H | L-1d | |
| N | CH | CH | O | CH3 | OCH3 | H | L-1e | |
| N | CH | CH | O | CH3 | OCH3 | H | L-1f | |
| N | CH | CH | O | CH3 | OCH3 | H | L-1g | |
| N | CH | CH | O | CH3 | OCH3 | H | L-1h | |
| N | CH | CH | O | CH3 | OCH3 | H | L-1i | |
| N | CH | CH | O | CH3 | OCH3 | H | L-1j | |
| N | CH | CH | O | CH3 | OCH3 | H | L-1k | |
| N | CH | CH | O | CH3 | OCH3 | H | L-3a | |
| N | CH | CH | O | CH3 | OCH3 | H | L-3b | |
| N | CH | CH | O | CH3 | OCH3 | H | L-4a | |
| N | CH | CH | O | CH3 | OCH3 | H | L-7a | |
| N | CH | CH | O | CH3 | OCH3 | H | L-8a | |
| N | CH | CH | O | CH3 | OCH3 | H | L-8b | |
| N | CH | CH | O | CH3 | OCH3 | H | L-9a | |
| N | CH | CH | O | CH3 | OCH3 | H | L-12a | |
| N | CH | CH | O | CH3 | OCH3 | H | L-12b | |
| N | CH | CH | O | CH3 | OCH3 | H | L-14a | |
| N | CH | CH | O | CH3 | OCH3 | H | L-15a | |
| N | CH | CH | O | CH3 | OCH3 | H | L-16a | |
| N | CH | CH | O | CH3 | OCH3 | H | L-16b | |
| N | CH | CH | O | CH3 | OCH3 | H | L-18a | |
| N | CH | CH | O | CH3 | OCH3 | H | L-20a | |
| N | CH | CH | O | CH3 | OCH3 | H | L-22a | |
| N | CH | CH | S | CH3 | OCH3 | H | L-1a | |
| N | CH | CH | O | CH3 | OCH3 | CH3 | L-1a | |
| N | CH | CH | O | OCH3 | OCH3 | H | L-1a | |
| N | CH | CH | O | OCH3 | OCH3 | H | L-1b | |
| N | CH | CH | O | OCH3 | OCH3 | H | L-1c | |
| N | CH | CH | O | OCH3 | OCH3 | H | L-1d | |
| N | CH | CH | O | OCH3 | OCH3 | H | L-1e | |
| N | CH | CH | O | OCH3 | OCH3 | H | L-1f | |
| N | CH | CH | O | OCH3 | OCH3 | H | L-1g | |
| N | CH | CH | O | OCH3 | OCH3 | H | L-1h | |
| N | CH | CH | O | OCH3 | OCH3 | H | L-1i | |
| N | CH | CH | O | OCH3 | OCH3 | H | L-1j | |
| N | CH | CH | O | OCH3 | OCH3 | H | L-1k | |
| N | CH | CH | O | OCH3 | OCH3 | H | L-3a | |
| N | CH | CH | O | OCH3 | OCH3 | H | L-3b | |
| N | CH | CH | O | OCH3 | OCH3 | H | L-4a | |
| N | CH | CH | O | OCH3 | OCH3 | H | L-7a | |

TABLE 2-continued

General Formula 2

| Z | $Z_1$ | $Z_2$ | W | X | Y | R | L | m.p. (°C.) |
|---|---|---|---|---|---|---|---|---|
| N | CH | CH | O | $OCH_3$ | $OCH_3$ | H | L-8a | |
| N | CH | CH | O | $OCH_3$ | $OCH_3$ | H | L-8b | |
| N | CH | CH | O | $OCH_3$ | $OCH_3$ | H | L-9a | |
| N | CH | CH | O | $OCH_3$ | $OCH_3$ | H | L-12a | |
| N | CH | CH | O | $OCH_3$ | $OCH_3$ | H | L-12b | |
| N | CH | CH | O | $OCH_3$ | $OCH_3$ | H | L-14a | |
| N | CH | CH | O | $OCH_3$ | $OCH_3$ | H | L-15a | |
| N | CH | CH | O | $OCH_3$ | $OCH_3$ | H | L-16a | |
| N | CH | CH | O | $OCH_3$ | $OCH_3$ | H | L-16b | |
| N | CH | CH | O | $OCH_3$ | $OCH_3$ | H | L-18a | |
| N | CH | CH | O | $OCH_3$ | $OCH_3$ | H | L-20a | |
| N | CH | CH | O | $OCH_3$ | $OCH_3$ | H | L-22a | |
| N | CH | CH | S | $OCH_3$ | $OCH_3$ | H | L-1a | |
| N | CH | CH | O | $OCH_3$ | $OCH_3$ | $CH_3$ | L-1a | |

TABLE 3

General Formula 3

| Z | $Z_1$ | $Z_2$ | W | X | Y | R | L | m.p. (°C.) |
|---|---|---|---|---|---|---|---|---|
| CH | N | CH | O | $CH_3$ | $CH_3$ | H | L-1a | |
| CH | N | CH | O | $CH_3$ | $CH_3$ | H | L-1b | |
| CH | N | CH | O | $CH_3$ | $CH_3$ | H | L-1c | |
| CH | N | CH | O | $CH_3$ | $CH_3$ | H | L-1d | |
| CH | N | CH | O | $CH_3$ | $CH_3$ | H | L-1e | |
| CH | N | CH | O | $CH_3$ | $CH_3$ | H | L-1f | |
| CH | N | CH | O | $CH_3$ | $CH_3$ | H | L-1g | |
| CH | N | CH | O | $CH_3$ | $CH_3$ | H | L-1h | |
| CH | N | CH | O | $CH_3$ | $CH_3$ | H | L-1i | |
| CH | N | CH | O | $CH_3$ | $CH_3$ | H | L-1j | |
| CH | N | CH | O | $CH_3$ | $CH_3$ | H | L-1k | |
| CH | N | CH | O | $CH_3$ | $CH_3$ | H | L-3a | |
| CH | N | CH | O | $CH_3$ | $CH_3$ | H | L-3b | |
| CH | N | CH | O | $CH_3$ | $CH_3$ | H | L-4a | |
| CH | N | CH | O | $CH_3$ | $CH_3$ | H | L-7a | |
| CH | N | CH | O | $CH_3$ | $CH_3$ | H | L-8a | |
| CH | N | CH | O | $CH_3$ | $CH_3$ | H | L-8b | |
| CH | N | CH | O | $CH_3$ | $CH_3$ | H | L-9a | |
| CH | N | CH | O | $CH_3$ | $CH_3$ | H | L-12a | |
| CH | N | CH | O | $CH_3$ | $CH_3$ | H | L-12b | |
| CH | N | CH | O | $CH_3$ | $CH_3$ | H | L-14a | |
| CH | N | CH | O | $CH_3$ | $CH_3$ | H | L-15a | |
| CH | N | CH | O | $CH_3$ | $CH_3$ | H | L-16a | |
| CH | N | CH | O | $CH_3$ | $CH_3$ | H | L-16b | |
| CH | N | CH | O | $CH_3$ | $CH_3$ | H | L-18a | |
| CH | N | CH | O | $CH_3$ | $CH_3$ | H | L-20a | |
| CH | N | CH | O | $CH_3$ | $CH_3$ | H | L-22a | |
| CH | N | CH | S | $CH_3$ | $CH_3$ | H | L-1a | |
| CH | N | CH | O | $CH_3$ | $CH_3$ | $CH_3$ | L-1a | |
| CH | N | CH | O | $OCH_3$ | $CH_3$ | H | L-1a | |
| CH | N | CH | O | $OCH_3$ | $CH_3$ | H | L-1b | |
| CH | N | CH | O | $OCH_3$ | $CH_3$ | H | L-1c | |
| CH | N | CH | O | $OCH_3$ | $CH_3$ | H | L-1d | |
| CH | N | CH | O | $OCH_3$ | $CH_3$ | H | L-1e | |
| CH | N | CH | O | $OCH_3$ | $CH_3$ | H | L-1f | |
| CH | N | CH | O | $OCH_3$ | $CH_3$ | H | L-1g | |
| CH | N | CH | O | $OCH_3$ | $CH_3$ | H | L-1h | |
| CH | N | CH | O | $OCH_3$ | $CH_3$ | H | L-1i | |
| CH | N | CH | O | $OCH_3$ | $CH_3$ | H | L-1j | |
| CH | N | CH | O | $OCH_3$ | $CH_3$ | H | L-1k | |
| CH | N | CH | O | $OCH_3$ | $CH_3$ | H | L-3a | |
| CH | N | CH | O | $OCH_3$ | $CH_3$ | H | L-3b | |
| CH | N | CH | O | $OCH_3$ | $CH_3$ | H | L-4a | |
| CH | N | CH | O | $OCH_3$ | $CH_3$ | H | L-7a | |
| CH | N | CH | O | $OCH_3$ | $CH_3$ | H | L-8a | |
| CH | N | CH | O | $OCH_3$ | $CH_3$ | H | L-8b | |
| CH | N | CH | O | $OCH_3$ | $CH_3$ | H | L-9a | |
| CH | N | CH | O | $OCH_3$ | $CH_3$ | H | L-12a | |
| CH | N | CH | O | $OCH_3$ | $CH_3$ | H | L-12b | |
| CH | N | CH | O | $OCH_3$ | $CH_3$ | H | L-14a | |
| CH | N | CH | O | $OCH_3$ | $CH_3$ | H | L-15a | |
| CH | N | CH | O | $OCH_3$ | $CH_3$ | H | L-16a | |
| CH | N | CH | O | $OCH_3$ | $CH_3$ | H | L-16b | |
| CH | N | CH | O | $OCH_3$ | $CH_3$ | H | L-18a | |
| CH | N | CH | O | $OCH_3$ | $CH_3$ | H | L-20a | |
| CH | N | CH | O | $OCH_3$ | $CH_3$ | H | L-22a | |
| CH | N | CH | S | $OCH_3$ | $CH_3$ | H | L-1a | |
| CH | N | CH | O | $OCH_3$ | $CH_3$ | $CH_3$ | L-1a | |

TABLE 3-continued

General Formula 3

| Z | $Z_1$ | $Z_2$ | W | X | Y | R | L | m.p.(°C.) |
|---|---|---|---|---|---|---|---|---|
| CH | N | CH | O | $CH_3$ | $OCH_3$ | H | L-1a | |
| CH | N | CH | O | $CH_3$ | $OCH_3$ | H | L-1b | |
| CH | N | CH | O | $CH_3$ | $OCH_3$ | H | L-1c | |
| CH | N | CH | O | $CH_3$ | $OCH_3$ | H | L-1d | |
| CH | N | CH | O | $CH_3$ | $OCH_3$ | H | L-1e | |
| CH | N | CH | O | $CH_3$ | $OCH_3$ | H | L-1f | |
| CH | N | CH | O | $CH_3$ | $OCH_3$ | H | L-1g | |
| CH | N | CH | O | $CH_3$ | $OCH_3$ | H | L-1h | |
| CH | N | CH | O | $CH_3$ | $OCH_3$ | H | L-1i | |
| CH | N | CH | O | $CH_3$ | $OCH_3$ | H | L-1j | |
| CH | N | CH | O | $CH_3$ | $OCH_3$ | H | L-1k | |
| CH | N | CH | O | $CH_3$ | $OCH_3$ | H | L-3a | |
| CH | N | CH | O | $CH_3$ | $OCH_3$ | H | L-3b | |
| CH | N | CH | O | $CH_3$ | $OCH_3$ | H | L-4a | |
| CH | N | CH | O | $CH_3$ | $OCH_3$ | H | L-7a | |
| CH | N | CH | O | $CH_3$ | $OCH_3$ | H | L-8a | |
| CH | N | CH | O | $CH_3$ | $OCH_3$ | H | L-8b | |
| CH | N | CH | O | $CH_3$ | $OCH_3$ | H | L-9a | |
| CH | N | CH | O | $CH_3$ | $OCH_3$ | H | L-12a | |
| CH | N | CH | O | $CH_3$ | $OCH_3$ | H | L-12b | |
| CH | N | CH | O | $CH_3$ | $OCH_3$ | H | L-14a | |
| CH | N | CH | O | $CH_3$ | $OCH_3$ | H | L-15a | |
| CH | N | CH | O | $CH_3$ | $OCH_3$ | H | L-16a | |
| CH | N | CH | O | $CH_3$ | $OCH_3$ | H | L-16b | |
| CH | N | CH | O | $CH_3$ | $OCH_3$ | H | L-18a | |
| CH | N | CH | O | $CH_3$ | $OCH_3$ | H | L-20a | |
| CH | N | CH | O | $CH_3$ | $OCH_3$ | H | L-22a | |
| CH | N | CH | S | $CH_3$ | $OCH_3$ | H | L-1a | |
| CH | N | CH | O | $CH_3$ | $OCH_3$ | $CH_3$ | L-1a | |
| CH | N | CH | O | $OCH_3$ | $OCH_3$ | H | L-1a | |
| CH | N | CH | O | $OCH_3$ | $OCH_3$ | H | L-1b | |
| CH | N | CH | O | $OCH_3$ | $OCH_3$ | H | L-1c | |
| CH | N | CH | O | $OCH_3$ | $OCH_3$ | H | L-1d | |
| CH | N | CH | O | $OCH_3$ | $OCH_3$ | H | L-1e | |
| CH | N | CH | O | $OCH_3$ | $OCH_3$ | H | L-1f | |
| CH | N | CH | O | $OCH_3$ | $OCH_3$ | H | L-1g | |
| CH | N | CH | O | $OCH_3$ | $OCH_3$ | H | L-1h | |
| CH | N | CH | O | $OCH_3$ | $OCH_3$ | H | L-1i | |
| CH | N | CH | O | $OCH_3$ | $OCH_3$ | H | L-1j | |
| CH | N | CH | O | $OCH_3$ | $OCH_3$ | H | L-1k | |
| CH | N | CH | O | $OCH_3$ | $OCH_3$ | H | L-3a | |
| CH | N | CH | O | $OCH_3$ | $OCH_3$ | H | L-3b | |
| CH | N | CH | O | $OCH_3$ | $OCH_3$ | H | L-4a | |
| CH | N | CH | O | $OCH_3$ | $OCH_3$ | H | L-7a | |
| CH | N | CH | O | $OCH_3$ | $OCH_3$ | H | L-8a | |
| CH | N | CH | O | $OCH_3$ | $OCH_3$ | H | L-8b | |
| CH | N | CH | O | $OCH_3$ | $OCH_3$ | H | L-9a | |
| CH | N | CH | O | $OCH_3$ | $OCH_3$ | H | L-12a | |
| CH | N | CH | O | $OCH_3$ | $OCH_3$ | H | L-12b | |
| CH | N | CH | O | $OCH_3$ | $OCH_3$ | H | L-14a | |
| CH | N | CH | O | $OCH_3$ | $OCH_3$ | H | L-15a | |
| CH | N | CH | O | $OCH_3$ | $OCH_3$ | H | L-16a | |
| CH | N | CH | O | $OCH_3$ | $OCH_3$ | H | L-16b | |
| CH | N | CH | O | $OCH_3$ | $OCH_3$ | H | L-18a | |
| CH | N | CH | O | $OCH_3$ | $OCH_3$ | H | L-20a | |
| CH | N | CH | O | $OCH_3$ | $OCH_3$ | H | L-22a | |
| CH | N | CH | S | $OCH_3$ | $OCH_3$ | H | L-1a | |
| CH | N | CH | O | $OCH_3$ | $OCH_3$ | $CH_3$ | L-1a | |
| CH | CH | N | O | $CH_3$ | $CH_3$ | H | L-1a | |
| CH | CH | N | O | $CH_3$ | $CH_3$ | H | L-1b | |
| CH | CH | N | O | $CH_3$ | $CH_3$ | H | L-1c | |
| CH | CH | N | O | $CH_3$ | $CH_3$ | H | L-1d | |
| CH | CH | N | O | $CH_3$ | $CH_3$ | H | L-1e | |
| CH | CH | N | O | $CH_3$ | $CH_3$ | H | L-1f | |
| CH | CH | N | O | $CH_3$ | $CH_3$ | H | L-1g | |
| CH | CH | N | O | $CH_3$ | $CH_3$ | H | L-1h | |
| CH | CH | N | O | $CH_3$ | $CH_3$ | H | L-1i | |
| CH | CH | N | O | $CH_3$ | $CH_3$ | H | L-1j | |
| CH | CH | N | O | $CH_3$ | $CH_3$ | H | L-1k | |
| CH | CH | N | O | $CH_3$ | $CH_3$ | H | L-3a | |
| CH | CH | N | O | $CH_3$ | $CH_3$ | H | L-3b | |
| CH | CH | N | O | $CH_3$ | $CH_3$ | H | L-4a | |
| CH | CH | N | O | $CH_3$ | $CH_3$ | H | L-7a | |
| CH | CH | N | O | $CH_3$ | $CH_3$ | H | L-8a | |
| CH | CH | N | O | $CH_3$ | $CH_3$ | H | L-8b | |
| CH | CH | N | O | $CH_3$ | $CH_3$ | H | L-9a | |
| CH | CH | N | O | $CH_3$ | $CH_3$ | H | L-12a | |
| CH | CH | N | O | $CH_3$ | $CH_3$ | H | L-12b | |
| CH | CH | N | O | $CH_3$ | $CH_3$ | H | L-14a | |

TABLE 3-continued

General Formula 3

| Z | $Z_1$ | $Z_2$ | W | X | Y | R | L | m.p.(°C.) |
|---|---|---|---|---|---|---|---|---|
| CH | CH | N | O | $CH_3$ | $CH_3$ | H | L-15a | |
| CH | CH | N | O | $CH_3$ | $CH_3$ | H | L-16a | |
| CH | CH | N | O | $CH_3$ | $CH_3$ | H | L-16b | |
| CH | CH | N | O | $CH_3$ | $CH_3$ | H | L-18a | |
| CH | CH | N | O | $CH_3$ | $CH_3$ | H | L-20a | |
| CH | CH | N | O | $CH_3$ | $CH_3$ | H | L-22a | |
| CH | CH | N | S | $CH_3$ | $CH_3$ | H | L-1a | |
| CH | CH | N | O | $CH_3$ | $CH_3$ | $CH_3$ | L-1a | |
| CH | CH | N | O | $CH_3$ | Cl | H | L-1a | 114–116 |
| CH | CH | N | O | $CH_3$ | Cl | H | L-1b | 202–205(d) |
| CH | CH | N | O | $CH_3$ | Cl | H | L-1c | 135(d) |
| CH | CH | N | O | $CH_3$ | Cl | H | L-1n | 177–180(d) |
| CH | CH | N | O | $CH_3$ | Cl | H | L-1p | 88–94 |
| CH | CH | N | O | $CH_3$ | Cl | H | L-1x | 94–96 |
| CH | CH | N | O | $CH_3$ | Cl | H | L-1y | 142–145 |
| CH | CH | N | O | $CH_3$ | Cl | H | L-1n | 157–159 |
| CH | CH | N | O | $CH_3$ | Cl | H | L-1b | 178–180 |
| CH | CH | N | O | $CH_3$ | Cl | H | L-1p | 110–112 |
| CH | CH | N | O | $CH_3$ | Cl | H | L-1c | 140–145 |
| CH | CH | N | O | $CH_3$ | Cl | H | L-1x | 105–108 |
| CH | CH | N | O | $CH_3$ | Cl | H | L-1b | 148–152(d) |
| CH | CH | N | O | $CH_3$ | Cl | H | L-1p | 195–197 |
| CH | CH | N | O | $OCH_3$ | $CH_3$ | H | L-1a | |
| CH | CH | N | O | $OCH_3$ | $CH_3$ | H | L-1b | |
| CH | CH | N | O | $OCH_3$ | $CH_3$ | H | L-1c | |
| CH | CH | N | O | $OCH_3$ | $CH_3$ | H | L-1d | |
| CH | CH | N | O | $OCH_3$ | $CH_3$ | H | L-1e | |
| CH | CH | N | O | $OCH_3$ | $CH_3$ | H | L-1f | |
| CH | CH | N | O | $OCH_3$ | $CH_3$ | H | L-1g | |
| CH | CH | N | O | $OCH_3$ | $CH_3$ | H | L-1h | |
| CH | CH | N | O | $OCH_3$ | $CH_3$ | H | L-1i | |
| CH | CH | N | O | $OCH_3$ | $CH_3$ | H | L-1j | |
| CH | CH | N | O | $OCH_3$ | $CH_3$ | H | L-1k | |
| CH | CH | N | O | $OCH_3$ | $CH_3$ | H | L-3a | |
| CH | CH | N | O | $OCH_3$ | $CH_3$ | H | L-3b | |
| CH | CH | N | O | $OCH_3$ | $CH_3$ | H | L-4a | |
| CH | CH | N | O | $OCH_3$ | $CH_3$ | H | L-7a | |
| CH | CH | N | O | $OCH_3$ | $CH_3$ | H | L-8a | |
| CH | CH | N | O | $OCH_3$ | $CH_3$ | H | L-8b | |
| CH | CH | N | O | $OCH_3$ | $CH_3$ | H | L-9a | |
| CH | CH | N | O | $OCH_3$ | $CH_3$ | H | L-12a | |
| CH | CH | N | O | $OCH_3$ | $CH_3$ | H | L-12b | |
| CH | CH | N | O | $OCH_3$ | $CH_3$ | H | L-14a | |
| CH | CH | N | O | $OCH_3$ | $CH_3$ | H | L-15a | |
| CH | CH | N | O | $OCH_3$ | $CH_3$ | H | L-16a | |
| CH | CH | N | O | $OCH_3$ | $CH_3$ | H | L-16b | |
| CH | CH | N | O | $OCH_3$ | $CH_3$ | H | L-18a | |
| CH | CH | N | O | $OCH_3$ | $CH_3$ | H | L-20a | |
| CH | CH | N | O | $OCH_3$ | $CH_3$ | H | L-22a | |
| CH | CH | N | S | $OCH_3$ | $CH_3$ | H | L-1a | |
| CH | CH | N | O | $OCH_3$ | $CH_3$ | $CH_3$ | L-1a | |
| CH | CH | N | O | $CH_3$ | $OCH_3$ | H | L-1a | |
| CH | CH | N | O | $CH_3$ | $OCH_3$ | H | L-1b | |
| CH | CH | N | O | $CH_3$ | $OCH_3$ | H | L-1c | |
| CH | CH | N | O | $CH_3$ | $OCH_3$ | H | L-1d | |
| CH | CH | N | O | $CH_3$ | $OCH_3$ | H | L-1e | |
| CH | CH | N | O | $CH_3$ | $OCH_3$ | H | L-1f | |
| CH | CH | N | O | $CH_3$ | $OCH_3$ | H | L-1g | |
| CH | CH | N | O | $CH_3$ | $OCH_3$ | H | L-1h | |
| CH | CH | N | O | $CH_3$ | $OCH_3$ | H | L-1i | |
| CH | CH | N | O | $CH_3$ | $OCH_3$ | H | L-1j | |
| CH | CH | N | O | $CH_3$ | $OCH_3$ | H | L-1k | |
| CH | CH | N | O | $CH_3$ | $OCH_3$ | H | L-3a | |
| CH | CH | N | O | $CH_3$ | $OCH_3$ | H | L-3b | |
| CH | CH | N | O | $CH_3$ | $OCH_3$ | H | L-4a | |
| CH | CH | N | O | $CH_3$ | $OCH_3$ | H | L-7a | |
| CH | CH | N | O | $CH_3$ | $OCH_3$ | H | L-8a | |
| CH | CH | N | O | $CH_3$ | $OCH_3$ | H | L-8b | |
| CH | CH | N | O | $CH_3$ | $OCH_3$ | H | L-9a | |
| CH | CH | N | O | $CH_3$ | $OCH_3$ | H | L-12a | |
| CH | CH | N | O | $CH_3$ | $OCH_3$ | H | L-12b | |
| CH | CH | N | O | $CH_3$ | $OCH_3$ | H | L-14a | |
| CH | CH | N | O | $CH_3$ | $OCH_3$ | H | L-15a | |
| CH | CH | N | O | $CH_3$ | $OCH_3$ | H | L-16a | |
| CH | CH | N | O | $CH_3$ | $OCH_3$ | H | L-16b | |
| CH | CH | N | O | $CH_3$ | $OCH_3$ | H | L-18a | |
| CH | CH | N | O | $CH_3$ | $OCH_3$ | H | L-20a | |
| CH | CH | N | O | $CH_3$ | $OCH_3$ | H | L-22a | |
| CH | CH | N | S | $CH_3$ | $OCH_3$ | H | L-1a | |
| CH | CH | N | O | $CH_3$ | $OCH_3$ | $CH_3$ | L-1a | |
| CH | CH | N | O | $OCH_3$ | $OCH_3$ | H | L-1b | |
| CH | CH | N | O | $OCH_3$ | $OCH_3$ | H | L-1c | |
| CH | CH | N | O | $OCH_3$ | $OCH_3$ | H | L-1d | |
| CH | CH | N | O | $OCH_3$ | $OCH_3$ | H | L-1e | |
| CH | CH | N | O | $OCH_3$ | $OCH_3$ | H | L-1f | |
| CH | CH | N | O | $OCH_3$ | $OCH_3$ | H | L-1g | |
| CH | CH | N | O | $OCH_3$ | $OCH_3$ | H | L-1h | |
| CH | CH | N | O | $OCH_3$ | $OCH_3$ | H | L-1i | |
| CH | CH | N | O | $OCH_3$ | $OCH_3$ | H | L-1j | |
| CH | CH | N | O | $OCH_3$ | $OCH_3$ | H | L-1k | |
| CH | CH | N | O | $OCH_3$ | $OCH_3$ | H | L-3a | |
| CH | CH | N | O | $OCH_3$ | $OCH_3$ | H | L-3b | |
| CH | CH | N | O | $OCH_3$ | $OCH_3$ | H | L-4a | |
| CH | CH | N | O | $OCH_3$ | $OCH_3$ | H | L-7a | |
| CH | CH | N | O | $OCH_3$ | $OCH_3$ | H | L-8a | |
| CH | CH | N | O | $OCH_3$ | $OCH_3$ | H | L-8b | |
| CH | CH | N | O | $OCH_3$ | $OCH_3$ | H | L-9a | |
| CH | CH | N | O | $OCH_3$ | $OCH_3$ | H | L-12a | |
| CH | CH | N | O | $OCH_3$ | $OCH_3$ | H | L-12b | |
| CH | CH | N | O | $OCH_3$ | $OCH_3$ | H | L-14a | |
| CH | CH | N | O | $OCH_3$ | $OCH_3$ | H | L-15a | |
| CH | CH | N | O | $OCH_3$ | $OCH_3$ | H | L-16a | |
| CH | CH | N | O | $OCH_3$ | $OCH_3$ | H | L-16b | |
| CH | CH | N | O | $OCH_3$ | $OCH_3$ | H | L-18a | |
| CH | CH | N | O | $OCH_3$ | $OCH_3$ | H | L-20a | |
| CH | CH | N | O | $OCH_3$ | $OCH_3$ | H | L-22a | |
| CH | CH | N | S | $OCH_3$ | $OCH_3$ | H | L-1a | |
| CH | CH | N | O | $OCH_3$ | $OCH_3$ | $CH_3$ | L-1a | |
| CH | CH | CH | O | $CH_3$ | $CH_3$ | H | L-1a | |
| CH | CH | CH | O | $CH_3$ | $CH_3$ | H | L-1b | |
| CH | CH | CH | O | $CH_3$ | $CH_3$ | H | L-1c | |
| CH | CH | CH | O | $CH_3$ | $CH_3$ | H | L-1d | |
| CH | CH | CH | O | $CH_3$ | $CH_3$ | H | L-1e | |
| CH | CH | CH | O | $CH_3$ | $CH_3$ | H | L-1f | |
| CH | CH | CH | O | $CH_3$ | $CH_3$ | H | L-1g | |
| CH | CH | CH | O | $CH_3$ | $CH_3$ | H | L-1h | |
| CH | CH | CH | O | $CH_3$ | $CH_3$ | H | L-1i | |
| CH | CH | CH | O | $CH_3$ | $CH_3$ | H | L-1j | |
| CH | CH | CH | O | $CH_3$ | $CH_3$ | H | L-1k | |
| CH | CH | CH | O | $CH_3$ | $CH_3$ | H | L-3a | |
| CH | CH | CH | O | $CH_3$ | $CH_3$ | H | L-3b | |
| CH | CH | CH | O | $CH_3$ | $CH_3$ | H | L-4a | |
| CH | CH | CH | O | $CH_3$ | $CH_3$ | H | L-7a | |
| CH | CH | CH | O | $CH_3$ | $CH_3$ | H | L-8a | |
| CH | CH | CH | O | $CH_3$ | $CH_3$ | H | L-8b | |
| CH | CH | CH | O | $CH_3$ | $CH_3$ | H | L-9a | |
| CH | CH | CH | O | $CH_3$ | $CH_3$ | H | L-12a | |
| CH | CH | CH | O | $CH_3$ | $CH_3$ | H | L-12b | |
| CH | CH | CH | O | $CH_3$ | $CH_3$ | H | L-14a | |
| CH | CH | CH | O | $CH_3$ | $CH_3$ | H | L-15a | |
| CH | CH | CH | O | $CH_3$ | $CH_3$ | H | L-16a | |
| CH | CH | CH | O | $CH_3$ | $CH_3$ | H | L-16b | |
| CH | CH | CH | O | $CH_3$ | $CH_3$ | H | L-18a | |
| CH | CH | CH | O | $CH_3$ | $CH_3$ | H | L-20a | |
| CH | CH | CH | O | $CH_3$ | $CH_3$ | H | L-22a | |
| CH | CH | CH | S | $CH_3$ | $CH_3$ | H | L-1a | |
| CH | CH | CH | O | $CH_3$ | $CH_3$ | $CH_3$ | L-1a | |
| CH | CH | CH | O | $OCH_3$ | $CH_3$ | H | L-1a | |
| CH | CH | CH | O | $OCH_3$ | $CH_3$ | H | L-1b | |
| CH | CH | CH | O | $OCH_3$ | $CH_3$ | H | L-1c | |
| CH | CH | CH | O | $OCH_3$ | $CH_3$ | H | L-1d | |
| CH | CH | CH | O | $OCH_3$ | $CH_3$ | H | L-1e | |
| CH | CH | CH | O | $OCH_3$ | $CH_3$ | H | L-1f | |
| CH | CH | CH | O | $OCH_3$ | $CH_3$ | H | L-1g | |
| CH | CH | CH | O | $OCH_3$ | $CH_3$ | H | L-1h | |
| CH | CH | CH | O | $OCH_3$ | $CH_3$ | H | L-1i | |
| CH | CH | CH | O | $OCH_3$ | $CH_3$ | H | L-1j | |
| CH | CH | CH | O | $OCH_3$ | $CH_3$ | H | L-1k | |
| CH | CH | CH | O | $OCH_3$ | $CH_3$ | H | L-3a | |
| CH | CH | CH | O | $OCH_3$ | $CH_3$ | H | L-3b | |
| CH | CH | CH | O | $OCH_3$ | $CH_3$ | H | L-4a | |
| CH | CH | CH | O | $OCH_3$ | $CH_3$ | H | L-7a | |
| CH | CH | CH | O | $OCH_3$ | $CH_3$ | H | L-8a | |
| CH | CH | CH | O | $OCH_3$ | $CH_3$ | H | L-8b | |
| CH | CH | CH | O | $OCH_3$ | $CH_3$ | H | L-9a | |
| CH | CH | CH | O | $OCH_3$ | $CH_3$ | H | L-12a | |
| CH | CH | CH | O | $OCH_3$ | $CH_3$ | H | L-12b | |

TABLE 3-continued

General Formula 3

| Z | Z₁ | Z₂ | W | X | Y | R | L | m.p.(°C.) |
|---|----|----|---|---|---|---|---|-----------|
| CH | CH | CH | O | OCH₃ | CH₃ | H | L-14a | |
| CH | CH | CH | O | OCH₃ | CH₃ | H | L-15a | |
| CH | CH | CH | O | OCH₃ | CH₃ | H | L-16a | |
| CH | CH | CH | O | OCH₃ | CH₃ | H | L-16b | |
| CH | CH | CH | O | OCH₃ | CH₃ | H | L-18a | |
| CH | CH | CH | O | OCH₃ | CH₃ | H | L-20a | |
| CH | CH | CH | O | OCH₃ | CH₃ | H | L-22a | |
| CH | CH | CH | S | OCH₃ | CH₃ | H | L-1a | |
| CH | CH | CH | O | OCH₃ | CH₃ | CH₃ | L-1a | |
| CH | CH | CH | O | CH₃ | OCH₃ | H | L-1a | |
| CH | CH | CH | O | CH₃ | OCH₃ | H | L-1b | |
| CH | CH | CH | O | CH₃ | OCH₃ | H | L-1c | |
| CH | CH | CH | O | CH₃ | OCH₃ | H | L-1d | |
| CH | CH | CH | O | CH₃ | OCH₃ | H | L-1e | |
| CH | CH | CH | O | CH₃ | OCH₃ | H | L-1f | |
| CH | CH | CH | O | CH₃ | OCH₃ | H | L-1g | |
| CH | CH | CH | O | CH₃ | OCH₃ | H | L-1h | |
| CH | CH | CH | O | CH₃ | OCH₃ | H | L-1i | |
| CH | CH | CH | O | CH₃ | OCH₃ | H | L-1j | |
| CH | CH | CH | O | CH₃ | OCH₃ | H | L-1k | |
| CH | CH | CH | O | CH₃ | OCH₃ | H | L-3a | |
| CH | CH | CH | O | CH₃ | OCH₃ | H | L-3b | |
| CH | CH | CH | O | CH₃ | OCH₃ | H | L-4a | |
| CH | CH | CH | O | CH₃ | OCH₃ | H | L-7a | |
| CH | CH | CH | O | CH₃ | OCH₃ | H | L-8a | |
| CH | CH | CH | O | CH₃ | OCH₃ | H | L-8b | |
| CH | CH | CH | O | CH₃ | OCH₃ | H | L-9a | |
| CH | CH | CH | O | CH₃ | OCH₃ | H | L-12a | |
| CH | CH | CH | O | CH₃ | OCH₃ | H | L-12b | |
| CH | CH | CH | O | CH₃ | OCH₃ | H | L-14a | |
| CH | CH | CH | O | CH₃ | OCH₃ | H | L-15a | |
| CH | CH | CH | O | CH₃ | OCH₃ | H | L-16a | |
| CH | CH | CH | O | CH₃ | OCH₃ | H | L-16b | |
| CH | CH | CH | O | CH₃ | OCH₃ | H | L-18a | |
| CH | CH | CH | O | CH₃ | OCH₃ | H | L-20a | |
| CH | CH | CH | O | CH₃ | OCH₃ | H | L-22a | |
| CH | CH | CH | S | CH₃ | OCH₃ | H | L-1a | |
| CH | CH | CH | O | CH₃ | OCH₃ | CH₃ | L-1a | |
| CH | CH | CH | O | OCH₃ | OCH₃ | H | L-1a | |
| CH | CH | CH | O | OCH₃ | OCH₃ | H | L-1b | |
| CH | CH | CH | O | OCH₃ | OCH₃ | H | L-1c | |
| CH | CH | CH | O | OCH₃ | OCH₃ | H | L-1d | |
| CH | CH | CH | O | OCH₃ | OCH₃ | H | L-1e | |
| CH | CH | CH | O | OCH₃ | OCH₃ | H | L-1f | |
| CH | CH | CH | O | OCH₃ | OCH₃ | H | L-1g | |
| CH | CH | CH | O | OCH₃ | OCH₃ | H | L-1h | |
| CH | CH | CH | O | OCH₃ | OCH₃ | H | L-1i | |
| CH | CH | CH | O | OCH₃ | OCH₃ | H | L-1j | |
| CH | CH | CH | O | OCH₃ | OCH₃ | H | L-1k | |
| CH | CH | CH | O | OCH₃ | OCH₃ | H | L-3a | |
| CH | CH | CH | O | OCH₃ | OCH₃ | H | L-3b | |
| CH | CH | CH | O | OCH₃ | OCH₃ | H | L-4a | |
| CH | CH | CH | O | OCH₃ | OCH₃ | H | L-7a | |
| CH | CH | CH | O | OCH₃ | OCH₃ | H | L-8a | |
| CH | CH | CH | O | OCH₃ | OCH₃ | H | L-8b | |
| CH | CH | CH | O | OCH₃ | OCH₃ | H | L-9a | |
| CH | CH | CH | O | OCH₃ | OCH₃ | H | L-12a | |
| CH | CH | CH | O | OCH₃ | OCH₃ | H | L-12b | |
| CH | CH | CH | O | OCH₃ | OCH₃ | H | L-14a | |
| CH | CH | CH | O | OCH₃ | OCH₃ | H | L-15a | |
| CH | CH | CH | O | OCH₃ | OCH₃ | H | L-16a | |
| CH | CH | CH | O | OCH₃ | OCH₃ | H | L-16b | |
| CH | CH | CH | O | OCH₃ | OCH₃ | H | L-18a | |
| CH | CH | CH | O | OCH₃ | OCH₃ | H | L-20a | |
| CH | CH | CH | O | OCH₃ | OCH₃ | H | L-22a | |
| CH | CH | CH | S | OCH₃ | OCH₃ | H | L-1a | |
| CH | CH | CH | O | OCH₃ | OCH₃ | CH₃ | L-1a | |
| N | N | CH | O | CH₃ | CH₃ | H | L-1a | |
| N | N | CH | O | CH₃ | CH₃ | H | L-1b | |
| N | N | CH | O | CH₃ | CH₃ | H | L-1c | |
| N | N | CH | O | CH₃ | CH₃ | H | L-1d | |
| N | N | CH | O | CH₃ | CH₃ | H | L-1e | |
| N | N | CH | O | CH₃ | CH₃ | H | L-1f | |
| N | N | CH | O | CH₃ | CH₃ | H | L-1g | |
| N | N | CH | O | CH₃ | CH₃ | H | L-1h | |
| N | N | CH | O | CH₃ | CH₃ | H | L-1i | |
| N | N | CH | O | CH₃ | CH₃ | H | L-1j | |
| N | N | CH | O | CH₃ | CH₃ | H | L-1k | |
| N | N | CH | O | CH₃ | CH₃ | H | L-3a | |
| N | N | CH | O | CH₃ | CH₃ | H | L-3b | |
| N | N | CH | O | CH₃ | CH₃ | H | L-4a | |
| N | N | CH | O | CH₃ | CH₃ | H | L-7a | |
| N | N | CH | O | CH₃ | CH₃ | H | L-8a | |
| N | N | CH | O | CH₃ | CH₃ | H | L-8b | |
| N | N | CH | O | CH₃ | CH₃ | H | L-9a | |
| N | N | CH | O | CH₃ | CH₃ | H | L-12a | |
| N | N | CH | O | CH₃ | CH₃ | H | L-12b | |
| N | N | CH | O | CH₃ | CH₃ | H | L-14a | |
| N | N | CH | O | CH₃ | CH₃ | H | L-15a | |
| N | N | CH | O | CH₃ | CH₃ | H | L-16a | |
| N | N | CH | O | CH₃ | CH₃ | H | L-16b | |
| N | N | CH | O | CH₃ | CH₃ | H | L-18a | |
| N | N | CH | O | CH₃ | CH₃ | H | L-20a | |
| N | N | CH | O | CH₃ | CH₃ | H | L-22a | |
| N | N | CH | S | CH₃ | CH₃ | H | L-1a | |
| N | N | CH | O | CH₃ | CH₃ | CH₃ | L-1a | |
| N | N | CH | O | OCH₃ | CH₃ | H | L-1a | |
| N | N | CH | O | OCH₃ | CH₃ | H | L-1b | |
| N | N | CH | O | OCH₃ | CH₃ | H | L-1c | |
| N | N | CH | O | OCH₃ | CH₃ | H | L-1d | |
| N | N | CH | O | OCH₃ | CH₃ | H | L-1e | |
| N | N | CH | O | OCH₃ | CH₃ | H | L-1f | |
| N | N | CH | O | OCH₃ | CH₃ | H | L-1g | |
| N | N | CH | O | OCH₃ | CH₃ | H | L-1h | |
| N | N | CH | O | OCH₃ | CH₃ | H | L-1i | |
| N | N | CH | O | OCH₃ | CH₃ | H | L-1j | |
| N | N | CH | O | OCH₃ | CH₃ | H | L-1k | |
| N | N | CH | O | OCH₃ | CH₃ | H | L-3a | |
| N | N | CH | O | OCH₃ | CH₃ | H | L-3b | |
| N | N | CH | O | OCH₃ | CH₃ | H | L-4a | |
| N | N | CH | O | OCH₃ | CH₃ | H | L-7a | |
| N | N | CH | O | OCH₃ | CH₃ | H | L-8a | |
| N | N | CH | O | OCH₃ | CH₃ | H | L-8b | |
| N | N | CH | O | OCH₃ | CH₃ | H | L-9a | |
| N | N | CH | O | OCH₃ | CH₃ | H | L-12a | |
| N | N | CH | O | OCH₃ | CH₃ | H | L-12b | |
| N | N | CH | O | OCH₃ | CH₃ | H | L-14a | |
| N | N | CH | O | OCH₃ | CH₃ | H | L-15a | |
| N | N | CH | O | OCH₃ | CH₃ | H | L-16a | |
| N | N | CH | O | OCH₃ | CH₃ | H | L-16b | |
| N | N | CH | O | OCH₃ | CH₃ | H | L-18a | |
| N | N | CH | O | OCH₃ | CH₃ | H | L-20a | |
| N | N | CH | O | OCH₃ | CH₃ | H | L-22a | |
| N | N | CH | S | OCH₃ | CH₃ | H | L-1a | |
| N | N | CH | O | OCH₃ | CH₃ | CH₃ | L-1a | |
| N | N | CH | O | CH₃ | OCH₃ | H | L-1a | |
| N | N | CH | O | CH₃ | OCH₃ | H | L-1b | |
| N | N | CH | O | CH₃ | OCH₃ | H | L-1c | |
| N | N | CH | O | CH₃ | OCH₃ | H | L-1d | |
| N | N | CH | O | CH₃ | OCH₃ | H | L-1e | |
| N | N | CH | O | CH₃ | OCH₃ | H | L-1f | |
| N | N | CH | O | CH₃ | OCH₃ | H | L-1g | |
| N | N | CH | O | CH₃ | OCH₃ | H | L-1h | |
| N | N | CH | O | CH₃ | OCH₃ | H | L-1i | |
| N | N | CH | O | CH₃ | OCH₃ | H | L-1j | |
| N | N | CH | O | CH₃ | OCH₃ | H | L-1k | |
| N | N | CH | O | CH₃ | OCH₃ | H | L-3a | |
| N | N | CH | O | CH₃ | OCH₃ | H | L-3b | |
| N | N | CH | O | CH₃ | OCH₃ | H | L-4a | |
| N | N | CH | O | CH₃ | OCH₃ | H | L-7a | |
| N | N | CH | O | CH₃ | OCH₃ | H | L-8a | |
| N | N | CH | O | CH₃ | OCH₃ | H | L-8b | |
| N | N | CH | O | CH₃ | OCH₃ | H | L-9a | |
| N | N | CH | O | CH₃ | OCH₃ | H | L-12a | |
| N | N | CH | O | CH₃ | OCH₃ | H | L-12b | |
| N | N | CH | O | CH₃ | OCH₃ | H | L-14a | |
| N | N | CH | O | CH₃ | OCH₃ | H | L-15a | |
| N | N | CH | O | CH₃ | OCH₃ | H | L-16a | |
| N | N | CH | O | CH₃ | OCH₃ | H | L-16b | |
| N | N | CH | O | CH₃ | OCH₃ | H | L-18a | |
| N | N | CH | O | CH₃ | OCH₃ | H | L-20a | |
| N | N | CH | O | CH₃ | OCH₃ | H | L-22a | |
| N | N | CH | S | CH₃ | OCH₃ | H | L-1a | |
| N | N | CH | O | CH₃ | OCH₃ | CH₃ | L-1a | |
| N | N | CH | O | OCH₃ | OCH₃ | H | L-1a | |
| N | N | CH | O | OCH₃ | OCH₃ | H | L-1b | |
| N | N | CH | O | OCH₃ | OCH₃ | H | L-1c | |
| N | N | CH | O | OCH₃ | OCH₃ | H | L-1d | |

TABLE 3-continued

General Formula 3

| Z | Z₁ | Z₂ | W | X | Y | R | L | m.p.(°C.) |
|---|----|----|---|---|---|---|---|-----------|
| N | N | CH | O | OCH₃ | OCH₃ | H | L-1e | |
| N | N | CH | O | OCH₃ | OCH₃ | H | L-1f | |
| N | N | CH | O | OCH₃ | OCH₃ | H | L-1g | |
| N | N | CH | O | OCH₃ | OCH₃ | H | L-1h | |
| N | N | CH | O | OCH₃ | OCH₃ | H | L-1i | |
| N | N | CH | O | OCH₃ | OCH₃ | H | L-1j | |
| N | N | CH | O | OCH₃ | OCH₃ | H | L-1k | |
| N | N | CH | O | OCH₃ | OCH₃ | H | L-3a | |
| N | N | CH | O | OCH₃ | OCH₃ | H | L-3b | |
| N | N | CH | O | OCH₃ | OCH₃ | H | L-4a | |
| N | N | CH | O | OCH₃ | OCH₃ | H | L-7a | |
| N | N | CH | O | OCH₃ | OCH₃ | H | L-8a | |
| N | N | CH | O | OCH₃ | OCH₃ | H | L-8b | |
| N | N | CH | O | OCH₃ | OCH₃ | H | L-9a | |
| N | N | CH | O | OCH₃ | OCH₃ | H | L-12a | |
| N | N | CH | O | OCH₃ | OCH₃ | H | L-12b | |
| N | N | CH | O | OCH₃ | OCH₃ | H | L-14a | |
| N | N | CH | O | OCH₃ | OCH₃ | H | L-15a | |
| N | N | CH | O | OCH₃ | OCH₃ | H | L-16a | |
| N | N | CH | O | OCH₃ | OCH₃ | H | L-16b | |
| N | N | CH | O | OCH₃ | OCH₃ | H | L-18a | |
| N | N | CH | O | OCH₃ | OCH₃ | H | L-20a | |
| N | N | CH | O | OCH₃ | OCH₃ | H | L-22a | |
| N | N | CH | S | OCH₃ | OCH₃ | H | L-1a | |
| N | N | CH | O | OCH₃ | OCH₃ | CH₃ | L-1a | |
| N | CH | N | O | CH₃ | CH₃ | H | L-1a | |
| N | CH | N | O | CH₃ | CH₃ | H | L-1b | |
| N | CH | N | O | CH₃ | CH₃ | H | L-1c | |
| N | CH | N | O | CH₃ | CH₃ | H | L-1d | |
| N | CH | N | O | CH₃ | CH₃ | H | L-1e | |
| N | CH | N | O | CH₃ | CH₃ | H | L-1f | |
| N | CH | N | O | CH₃ | CH₃ | H | L-1g | |
| N | CH | N | O | CH₃ | CH₃ | H | L-1h | |
| N | CH | N | O | CH₃ | CH₃ | H | L-1i | |
| N | CH | N | O | CH₃ | CH₃ | H | L-1j | |
| N | CH | N | O | CH₃ | CH₃ | H | L-1k | |
| N | CH | N | O | CH₃ | CH₃ | H | L-3a | |
| N | CH | N | O | CH₃ | CH₃ | H | L-3b | |
| N | CH | N | O | CH₃ | CH₃ | H | L-4a | |
| N | CH | N | O | CH₃ | CH₃ | H | L-7a | |
| N | CH | N | O | CH₃ | CH₃ | H | L-8a | |
| N | CH | N | O | CH₃ | CH₃ | H | L-8b | |
| N | CH | N | O | CH₃ | CH₃ | H | L-9a | |
| N | CH | N | O | CH₃ | CH₃ | H | L-12a | |
| N | CH | N | O | CH₃ | CH₃ | H | L-12b | |
| N | CH | N | O | CH₃ | CH₃ | H | L-14a | |
| N | CH | N | O | CH₃ | CH₃ | H | L-15a | |
| N | CH | N | O | CH₃ | CH₃ | H | L-16a | |
| N | CH | N | O | CH₃ | CH₃ | H | L-16b | |
| N | CH | N | O | CH₃ | CH₃ | H | L-18a | |
| N | CH | N | O | CH₃ | CH₃ | H | L-20a | |
| N | CH | N | O | CH₃ | CH₃ | H | L-22a | |
| N | CH | N | S | CH₃ | CH₃ | H | L-1a | |
| N | CH | N | O | CH₃ | CH₃ | CH₃ | L-1a | |
| N | CH | N | O | OCH₃ | CH₃ | H | L-1a | |
| N | CH | N | O | OCH₃ | CH₃ | H | L-1b | |
| N | CH | N | O | OCH₃ | CH₃ | H | L-1c | |
| N | CH | N | O | OCH₃ | CH₃ | H | L-1d | |
| N | CH | N | O | OCH₃ | CH₃ | H | L-1e | |
| N | CH | N | O | OCH₃ | CH₃ | H | L-1f | |
| N | CH | N | O | OCH₃ | CH₃ | H | L-1g | |
| N | CH | N | O | OCH₃ | CH₃ | H | L-1h | |
| N | CH | N | O | OCH₃ | CH₃ | H | L-1i | |
| N | CH | N | O | OCH₃ | CH₃ | H | L-1j | |
| N | CH | N | O | OCH₃ | CH₃ | H | L-1k | |
| N | CH | N | O | OCH₃ | CH₃ | H | L-3a | |
| N | CH | N | O | OCH₃ | CH₃ | H | L-3b | |
| N | CH | N | O | OCH₃ | CH₃ | H | L-4a | |
| N | CH | N | O | OCH₃ | CH₃ | H | L-7a | |
| N | CH | N | O | OCH₃ | CH₃ | H | L-8a | |
| N | CH | N | O | OCH₃ | CH₃ | H | L-8b | |
| N | CH | N | O | OCH₃ | CH₃ | H | L-9a | |
| N | CH | N | O | OCH₃ | CH₃ | H | L-12a | |
| N | CH | N | O | OCH₃ | CH₃ | H | L-12b | |
| N | CH | N | O | OCH₃ | CH₃ | H | L-14a | |
| N | CH | N | O | OCH₃ | CH₃ | H | L-15a | |
| N | CH | N | O | OCH₃ | CH₃ | H | L-16a | |
| N | CH | N | O | OCH₃ | CH₃ | H | L-16b | |
| N | CH | N | O | OCH₃ | CH₃ | H | L-18a | |
| N | CH | N | O | OCH₃ | CH₃ | H | L-20a | |
| N | CH | N | O | OCH₃ | CH₃ | H | L-22a | |
| N | CH | N | S | OCH₃ | CH₃ | H | L-1a | |
| N | CH | N | O | OCH₃ | CH₃ | CH₃ | L-1a | |
| N | CH | N | O | CH₃ | OCH₃ | H | L-1a | |
| N | CH | N | O | CH₃ | OCH₃ | H | L-1b | |
| N | CH | N | O | CH₃ | OCH₃ | H | L-1c | |
| N | CH | N | O | CH₃ | OCH₃ | H | L-1d | |
| N | CH | N | O | CH₃ | OCH₃ | H | L-1e | |
| N | CH | N | O | CH₃ | OCH₃ | H | L-1f | |
| N | CH | N | O | CH₃ | OCH₃ | H | L-1g | |
| N | CH | N | O | CH₃ | OCH₃ | H | L-1h | |
| N | CH | N | O | CH₃ | OCH₃ | H | L-1i | |
| N | CH | N | O | CH₃ | OCH₃ | H | L-1j | |
| N | CH | N | O | CH₃ | OCH₃ | H | L-1k | |
| N | CH | N | O | CH₃ | OCH₃ | H | L-3a | |
| N | CH | N | O | CH₃ | OCH₃ | H | L-3b | |
| N | CH | N | O | CH₃ | OCH₃ | H | L-4a | |
| N | CH | N | O | CH₃ | OCH₃ | H | L-7a | |
| N | CH | N | O | CH₃ | OCH₃ | H | L-8a | |
| N | CH | N | O | CH₃ | OCH₃ | H | L-8b | |
| N | CH | N | O | CH₃ | OCH₃ | H | L-9a | |
| N | CH | N | O | CH₃ | OCH₃ | H | L-12a | |
| N | CH | N | O | CH₃ | OCH₃ | H | L-12b | |
| N | CH | N | O | CH₃ | OCH₃ | H | L-14a | |
| N | CH | N | O | CH₃ | OCH₃ | H | L-15a | |
| N | CH | N | O | CH₃ | OCH₃ | H | L-16a | |
| N | CH | N | O | CH₃ | OCH₃ | H | L-16b | |
| N | CH | N | O | CH₃ | OCH₃ | H | L-18a | |
| N | CH | N | O | CH₃ | OCH₃ | H | L-20a | |
| N | CH | N | O | CH₃ | OCH₃ | H | L-22a | |
| N | CH | N | S | CH₃ | OCH₃ | H | L-1a | |
| N | CH | N | O | CH₃ | OCH₃ | CH₃ | L-1a | |
| N | CH | N | O | OCH₃ | OCH₃ | H | L-1a | |
| N | CH | N | O | OCH₃ | OCH₃ | H | L-1b | |
| N | CH | N | O | OCH₃ | OCH₃ | H | L-1c | |
| N | CH | N | O | OCH₃ | OCH₃ | H | L-1d | |
| N | CH | N | O | OCH₃ | OCH₃ | H | L-1e | |
| N | CH | N | O | OCH₃ | OCH₃ | H | L-1f | |
| N | CH | N | O | OCH₃ | OCH₃ | H | L-1g | |
| N | CH | N | O | OCH₃ | OCH₃ | H | L-1h | |
| N | CH | N | O | OCH₃ | OCH₃ | H | L-1i | |
| N | CH | N | O | OCH₃ | OCH₃ | H | L-1j | |
| N | CH | N | O | OCH₃ | OCH₃ | H | L-1k | |
| N | CH | N | O | OCH₃ | OCH₃ | H | L-3a | |
| N | CH | N | O | OCH₃ | OCH₃ | H | L-3b | |
| N | CH | N | O | OCH₃ | OCH₃ | H | L-4a | |
| N | CH | N | O | OCH₃ | OCH₃ | H | L-7a | |
| N | CH | N | O | OCH₃ | OCH₃ | H | L-8a | |
| N | CH | N | O | OCH₃ | OCH₃ | H | L-8b | |
| N | CH | N | O | OCH₃ | OCH₃ | H | L-9a | |
| N | CH | N | O | OCH₃ | OCH₃ | H | L-12a | |
| N | CH | N | O | OCH₃ | OCH₃ | H | L-12b | |
| N | CH | N | O | OCH₃ | OCH₃ | H | L-14a | |
| N | CH | N | O | OCH₃ | OCH₃ | H | L-15a | |
| N | CH | N | O | OCH₃ | OCH₃ | H | L-16a | |
| N | CH | N | O | OCH₃ | OCH₃ | H | L-16b | |
| N | CH | N | O | OCH₃ | OCH₃ | H | L-18a | |
| N | CH | N | O | OCH₃ | OCH₃ | H | L-20a | |
| N | CH | N | O | OCH₃ | OCH₃ | H | L-22a | |
| N | CH | N | S | OCH₃ | OCH₃ | H | L-1a | |
| N | CH | N | O | OCH₃ | OCH₃ | CH₃ | L-1a | |
| N | CH | CH | O | CH₃ | CH₃ | H | L-1a | |
| N | CH | CH | O | CH₃ | CH₃ | H | L-1b | |
| N | CH | CH | O | CH₃ | CH₃ | H | L-1c | |
| N | CH | CH | O | CH₃ | CH₃ | H | L-1d | |
| N | CH | CH | O | CH₃ | CH₃ | H | L-1e | |
| N | CH | CH | O | CH₃ | CH₃ | H | L-1f | |
| N | CH | CH | O | CH₃ | CH₃ | H | L-1g | |
| N | CH | CH | O | CH₃ | CH₃ | H | L-1h | |
| N | CH | CH | O | CH₃ | CH₃ | H | L-1i | |
| N | CH | CH | O | CH₃ | CH₃ | H | L-1j | |
| N | CH | CH | O | CH₃ | CH₃ | H | L-1k | |
| N | CH | CH | O | CH₃ | CH₃ | H | L-3a | |
| N | CH | CH | O | CH₃ | CH₃ | H | L-3b | |
| N | CH | CH | O | CH₃ | CH₃ | H | L-4a | |
| N | CH | CH | O | CH₃ | CH₃ | H | L-7a | |
| N | CH | CH | O | CH₃ | CH₃ | H | L-8a | |
| N | CH | CH | O | CH₃ | CH₃ | H | L-8b | |

TABLE 3-continued

General Formula 3

| Z | Z₁ | Z₂ | W | X | Y | R | L | m.p.(°C.) |
|---|----|----|----|----|----|----|----|-----|
| N | CH | CH | O | CH₃ | CH₃ | H | L-9a | |
| N | CH | CH | O | CH₃ | CH₃ | H | L-12a | |
| N | CH | CH | O | CH₃ | CH₃ | H | L-12b | |
| N | CH | CH | O | CH₃ | CH₃ | H | L-14a | |
| N | CH | CH | O | CH₃ | CH₃ | H | L-15a | |
| N | CH | CH | O | CH₃ | CH₃ | H | L-16a | |
| N | CH | CH | O | CH₃ | CH₃ | H | L-16b | |
| N | CH | CH | O | CH₃ | CH₃ | H | L-18a | |
| N | CH | CH | O | CH₃ | CH₃ | H | L-20a | |
| N | CH | CH | O | CH₃ | CH₃ | H | L-22a | |
| N | CH | CH | S | CH₃ | CH₃ | H | L-1a | |
| N | CH | CH | O | CH₃ | CH₃ | CH₃ | L-1a | |
| N | CH | CH | O | OCH₃ | CH₃ | H | L-1a | |
| N | CH | CH | O | OCH₃ | CH₃ | H | L-1b | |
| N | CH | CH | O | OCH₃ | CH₃ | H | L-1c | |
| N | CH | CH | O | OCH₃ | CH₃ | H | L-1d | |
| N | CH | CH | O | OCH₃ | CH₃ | H | L-1e | |
| N | CH | CH | O | OCH₃ | CH₃ | H | L-1f | |
| N | CH | CH | O | OCH₃ | CH₃ | H | L-1g | |
| N | CH | CH | O | OCH₃ | CH₃ | H | L-1h | |
| N | CH | CH | O | OCH₃ | CH₃ | H | L-1i | |
| N | CH | CH | O | OCH₃ | CH₃ | H | L-1j | |
| N | CH | CH | O | OCH₃ | CH₃ | H | L-1k | |
| N | CH | CH | O | OCH₃ | CH₃ | H | L-3a | |
| N | CH | CH | O | OCH₃ | CH₃ | H | L-3b | |
| N | CH | CH | O | OCH₃ | CH₃ | H | L-4a | |
| N | CH | CH | O | OCH₃ | CH₃ | H | L-7a | |
| N | CH | CH | O | OCH₃ | CH₃ | H | L-8a | |
| N | CH | CH | O | OCH₃ | CH₃ | H | L-8b | |
| N | CH | CH | O | OCH₃ | CH₃ | H | L-9a | |
| N | CH | CH | O | OCH₃ | CH₃ | H | L-12a | |
| N | CH | CH | O | OCH₃ | CH₃ | H | L-12b | |
| N | CH | CH | O | OCH₃ | CH₃ | H | L-14a | |
| N | CH | CH | O | OCH₃ | CH₃ | H | L-15a | |
| N | CH | CH | O | OCH₃ | CH₃ | H | L-16a | |
| N | CH | CH | O | OCH₃ | CH₃ | H | L-16b | |
| N | CH | CH | O | OCH₃ | CH₃ | H | L-18a | |
| N | CH | CH | O | OCH₃ | CH₃ | H | L-20a | |
| N | CH | CH | O | OCH₃ | CH₃ | H | L-22a | |
| N | CH | CH | S | OCH₃ | CH₃ | H | L-1a | |
| N | CH | CH | O | OCH₃ | CH₃ | CH₃ | L-1a | |
| N | CH | CH | O | CH₃ | OCH₃ | H | L-1a | |
| N | CH | CH | O | CH₃ | OCH₃ | H | L-1b | |
| N | CH | CH | O | CH₃ | OCH₃ | H | L-1c | |
| N | CH | CH | O | CH₃ | OCH₃ | H | L-1d | |
| N | CH | CH | O | CH₃ | OCH₃ | H | L-1e | |
| N | CH | CH | O | CH₃ | OCH₃ | H | L-1f | |
| N | CH | CH | O | CH₃ | OCH₃ | H | L-1g | |
| N | CH | CH | O | CH₃ | OCH₃ | H | L-1h | |
| N | CH | CH | O | CH₃ | OCH₃ | H | L-1i | |
| N | CH | CH | O | CH₃ | OCH₃ | H | L-1j | |
| N | CH | CH | O | CH₃ | OCH₃ | H | L-1k | |
| N | CH | CH | O | CH₃ | OCH₃ | H | L-3a | |
| N | CH | CH | O | CH₃ | OCH₃ | H | L-3b | |
| N | CH | CH | O | CH₃ | OCH₃ | H | L-4a | |
| N | CH | CH | O | CH₃ | OCH₃ | H | L-7a | |
| N | CH | CH | O | CH₃ | OCH₃ | H | L-8a | |
| N | CH | CH | O | CH₃ | OCH₃ | H | L-8b | |
| N | CH | CH | O | CH₃ | OCH₃ | H | L-9a | |
| N | CH | CH | O | CH₃ | OCH₃ | H | L-12a | |
| N | CH | CH | O | CH₃ | OCH₃ | H | L-12b | |
| N | CH | CH | O | CH₃ | OCH₃ | H | L-14a | |
| N | CH | CH | O | CH₃ | OCH₃ | H | L-15a | |
| N | CH | CH | O | CH₃ | OCH₃ | H | L-16a | |
| N | CH | CH | O | CH₃ | OCH₃ | H | L-16b | |
| N | CH | CH | O | CH₃ | OCH₃ | H | L-18a | |
| N | CH | CH | O | CH₃ | OCH₃ | H | L-20a | |
| N | CH | CH | O | CH₃ | OCH₃ | H | L-22a | |
| N | CH | CH | S | CH₃ | OCH₃ | H | L-1a | |
| N | CH | CH | O | CH₃ | OCH₃ | CH₃ | L-1a | |
| N | CH | CH | O | OCH₃ | OCH₃ | H | L-1a | |
| N | CH | CH | O | OCH₃ | OCH₃ | H | L-1b | |
| N | CH | CH | O | OCH₃ | OCH₃ | H | L-1c | |
| N | CH | CH | O | OCH₃ | OCH₃ | H | L-1d | |
| N | CH | CH | O | OCH₃ | OCH₃ | H | L-1e | |
| N | CH | CH | O | OCH₃ | OCH₃ | H | L-1f | |
| N | CH | CH | O | OCH₃ | OCH₃ | H | L-1g | |
| N | CH | CH | O | OCH₃ | OCH₃ | H | L-1h | |
| N | CH | CH | O | OCH₃ | OCH₃ | H | L-1i | |
| N | CH | CH | O | OCH₃ | OCH₃ | H | L-1j | |
| N | CH | CH | O | OCH₃ | OCH₃ | H | L-1k | |
| N | CH | CH | O | OCH₃ | OCH₃ | H | L-3a | |
| N | CH | CH | O | OCH₃ | OCH₃ | H | L-3b | |
| N | CH | CH | O | OCH₃ | OCH₃ | H | L-4a | |
| N | CH | CH | O | OCH₃ | OCH₃ | H | L-7a | |
| N | CH | CH | O | OCH₃ | OCH₃ | H | L-8a | |
| N | CH | CH | O | OCH₃ | OCH₃ | H | L-8b | |
| N | CH | CH | O | OCH₃ | OCH₃ | H | L-9a | |
| N | CH | CH | O | OCH₃ | OCH₃ | H | L-12a | |
| N | CH | CH | O | OCH₃ | OCH₃ | H | L-12b | |
| N | CH | CH | O | OCH₃ | OCH₃ | H | L-14a | |
| N | CH | CH | O | OCH₃ | OCH₃ | H | L-15a | |
| N | CH | CH | O | OCH₃ | OCH₃ | H | L-16a | |
| N | CH | CH | O | OCH₃ | OCH₃ | H | L-16b | |
| N | CH | CH | O | OCH₃ | OCH₃ | H | L-18a | |
| N | CH | CH | O | OCH₃ | OCH₃ | H | L-20a | |
| N | CH | CH | O | OCH₃ | OCH₃ | H | L-22a | |
| N | CH | CH | S | OCH₃ | OCH₃ | H | L-1a | |
| N | CH | CH | O | OCH₃ | OCH₃ | CH₃ | L-1a | |

TABLE 4

General Formula 4

| Z | Z₁ | Z₄ | W | X | Y | R | L | m.p. (°C.) |
|---|----|----|----|----|----|----|----|-----|
| CH | CH | S | O | CH₃ | CH₃ | H | L-1a | |
| CH | CH | S | O | CH₃ | CH₃ | H | L-1b | |
| CH | CH | S | O | CH₃ | CH₃ | H | L-1c | |
| CH | CH | S | O | CH₃ | CH₃ | H | L-1d | |
| CH | CH | S | O | CH₃ | CH₃ | H | L-1e | |
| CH | CH | S | O | CH₃ | CH₃ | H | L-1f | |
| CH | CH | S | O | CH₃ | CH₃ | H | L-1g | |
| CH | CH | S | O | CH₃ | CH₃ | H | L-1h | |
| CH | CH | S | O | CH₃ | CH₃ | H | L-1i | |
| CH | CH | S | O | CH₃ | CH₃ | H | L-1j | |
| CH | CH | S | O | CH₃ | CH₃ | H | L-1k | |
| CH | CH | S | O | CH₃ | CH₃ | H | L-3a | |
| CH | CH | S | O | CH₃ | CH₃ | H | L-3b | |
| CH | CH | S | O | CH₃ | CH₃ | H | L-4a | |
| CH | CH | S | O | CH₃ | CH₃ | H | L-7a | |
| CH | CH | S | O | CH₃ | CH₃ | H | L-8a | |
| CH | CH | S | O | CH₃ | CH₃ | H | L-9a | |
| CH | CH | S | O | CH₃ | CH₃ | H | L-12a | |
| CH | CH | S | O | CH₃ | CH₃ | H | L-12b | |
| CH | CH | S | O | CH₃ | CH₃ | H | L-14a | |
| CH | CH | S | O | CH₃ | CH₃ | H | L-15a | |
| CH | CH | S | O | CH₃ | CH₃ | H | L-16a | |
| CH | CH | S | O | CH₃ | CH₃ | H | L-16b | |
| CH | CH | S | O | CH₃ | CH₃ | H | L-18a | |
| CH | CH | S | O | CH₃ | CH₃ | H | L-20a | |
| CH | CH | S | O | CH₃ | CH₃ | H | L-22a | |
| CH | CH | S | S | CH₃ | CH₃ | H | L-1a | |
| CH | CH | S | O | CH₃ | CH₃ | CH₃ | L-1a | |
| CH | CH | S | O | OCH₃ | CH₃ | H | L-1a | |
| CH | CH | S | O | OCH₃ | CH₃ | H | L-1b | |
| CH | CH | S | O | OCH₃ | CH₃ | H | L-1c | |
| CH | CH | S | O | OCH₃ | CH₃ | H | L-1d | |
| CH | CH | S | O | OCH₃ | CH₃ | H | L-1e | |
| CH | CH | S | O | OCH₃ | CH₃ | H | L-1f | |
| CH | CH | S | O | OCH₃ | CH₃ | H | L-1g | |
| CH | CH | S | O | OCH₃ | CH₃ | H | L-1h | |
| CH | CH | S | O | OCH₃ | CH₃ | H | L-1i | |
| CH | CH | S | O | OCH₃ | CH₃ | H | L-1j | |
| CH | CH | S | O | OCH₃ | CH₃ | H | L-1k | |
| CH | CH | S | O | OCH₃ | CH₃ | H | L-3a | |
| CH | CH | S | O | OCH₃ | CH₃ | H | L-3b | |
| CH | CH | S | O | OCH₃ | CH₃ | H | L-4a | |
| CH | CH | S | O | OCH₃ | CH₃ | H | L-7a | |
| CH | CH | S | O | OCH₃ | CH₃ | H | L-8a | |
| CH | CH | S | O | OCH₃ | CH₃ | H | L-8b | |
| CH | CH | S | O | OCH₃ | CH₃ | H | L-9a | |
| CH | CH | S | O | OCH₃ | CH₃ | H | L-12a | |
| CH | CH | S | O | OCH₃ | CH₃ | H | L-12b | |
| CH | CH | S | O | OCH₃ | CH₃ | H | L-14a | |
| CH | CH | S | O | OCH₃ | CH₃ | H | L-15a | |
| CH | CH | S | O | OCH₃ | CH₃ | H | L-16a | |
| CH | CH | S | O | OCH₃ | CH₃ | H | L-16b | |

TABLE 4-continued

General Formula 4

| Z | Z₁ | Z₄ | W | X | Y | R | L | m.p. (°C.) |
|---|----|----|---|---|---|---|---|-----------|
| CH | CH | S | O | OCH₃ | CH₃ | H | L-18a | |
| CH | CH | S | O | OCH₃ | CH₃ | H | L-20a | |
| CH | CH | S | O | OCH₃ | CH₃ | H | L-22a | |
| CH | CH | S | S | OCH₃ | CH₃ | H | L-1a | |
| CH | CH | S | O | OCH₃ | CH₃ | CH₃ | L-1a | |
| CH | CH | S | O | CH₃ | OCH₃ | H | L-1a | |
| CH | CH | S | O | CH₃ | OCH₃ | H | L-1b | |
| CH | CH | S | O | CH₃ | OCH₃ | H | L-1c | |
| CH | CH | S | O | CH₃ | OCH₃ | H | L-1d | |
| CH | CH | S | O | CH₃ | OCH₃ | H | L-1e | |
| CH | CH | S | O | CH₃ | OCH₃ | H | L-1f | |
| CH | CH | S | O | CH₃ | OCH₃ | H | L-1g | |
| CH | CH | S | O | CH₃ | OCH₃ | H | L-1h | |
| CH | CH | S | O | CH₃ | OCH₃ | H | L-1i | |
| CH | CH | S | O | CH₃ | OCH₃ | H | L-1j | |
| CH | CH | S | O | CH₃ | OCH₃ | H | L-1k | |
| CH | CH | S | O | CH₃ | OCH₃ | H | L-3a | |
| CH | CH | S | O | CH₃ | OCH₃ | H | L-3b | |
| CH | CH | S | O | CH₃ | OCH₃ | H | L-4a | |
| CH | CH | S | O | CH₃ | OCH₃ | H | L-7a | |
| CH | CH | S | O | CH₃ | OCH₃ | H | L-8a | |
| CH | CH | S | O | CH₃ | OCH₃ | H | L-8b | |
| CH | CH | S | O | CH₃ | OCH₃ | H | L-9a | |
| CH | CH | S | O | CH₃ | OCH₃ | H | L-12a | |
| CH | CH | S | O | CH₃ | OCH₃ | H | L-12b | |
| CH | CH | S | O | CH₃ | OCH₃ | H | L-14a | |
| CH | CH | S | O | CH₃ | OCH₃ | H | L-15a | |
| CH | CH | S | O | CH₃ | OCH₃ | H | L-16a | |
| CH | CH | S | O | CH₃ | OCH₃ | H | L-16b | |
| CH | CH | S | O | CH₃ | OCH₃ | H | L-18a | |
| CH | CH | S | O | CH₃ | OCH₃ | H | L-20a | |
| CH | CH | S | O | CH₃ | OCH₃ | H | L-22a | |
| CH | CH | S | S | CH₃ | OCH₃ | H | L-1a | |
| CH | CH | S | O | CH₃ | OCH₃ | CH₃ | L-1a | |
| CH | CH | S | O | OCH₃ | OCH₃ | H | L-1a | |
| CH | CH | S | O | OCH₃ | OCH₃ | H | L-1b | |
| CH | CH | S | O | OCH₃ | OCH₃ | H | L-1c | |
| CH | CH | S | O | OCH₃ | OCH₃ | H | L-1d | |
| CH | CH | S | O | OCH₃ | OCH₃ | H | L-1e | |
| CH | CH | S | O | OCH₃ | OCH₃ | H | L-1f | |
| CH | CH | S | O | OCH₃ | OCH₃ | H | L-1g | |
| CH | CH | S | O | OCH₃ | OCH₃ | H | L-1h | |
| CH | CH | S | O | OCH₃ | OCH₃ | H | L-1i | |
| CH | CH | S | O | OCH₃ | OCH₃ | H | L-1j | |
| CH | CH | S | O | OCH₃ | OCH₃ | H | L-1k | |
| CH | CH | S | O | OCH₃ | OCH₃ | H | L-3a | |
| CH | CH | S | O | OCH₃ | OCH₃ | H | L-3b | |
| CH | CH | S | O | OCH₃ | OCH₃ | H | L-4a | |
| CH | CH | S | O | OCH₃ | OCH₃ | H | L-7a | |
| CH | CH | S | O | OCH₃ | OCH₃ | H | L-8a | |
| CH | CH | S | O | OCH₃ | OCH₃ | H | L-8b | |
| CH | CH | S | O | OCH₃ | OCH₃ | H | L-9a | |
| CH | CH | S | O | OCH₃ | OCH₃ | H | L-12a | |
| CH | CH | S | O | OCH₃ | OCH₃ | H | L-12b | |
| CH | CH | S | O | OCH₃ | OCH₃ | H | L-14a | |
| CH | CH | S | O | OCH₃ | OCH₃ | H | L-15a | |
| CH | CH | S | O | OCH₃ | OCH₃ | H | L-16a | |
| CH | CH | S | O | OCH₃ | OCH₃ | H | L-16b | |
| CH | CH | S | O | OCH₃ | OCH₃ | H | L-18a | |
| CH | CH | S | O | OCH₃ | OCH₃ | H | L-20a | |
| CH | CH | S | O | OCH₃ | OCH₃ | H | L-22a | |
| CH | CH | S | S | OCH₃ | OCH₃ | H | L-1a | |
| CH | CH | S | O | OCH₃ | OCH₃ | CH₃ | L-1a | |
| CH | CH | O | O | CH₃ | CH₃ | H | L-1a | |
| CH | CH | O | O | CH₃ | CH₃ | H | L-1b | |
| CH | CH | O | O | CH₃ | CH₃ | H | L-1c | |
| CH | CH | O | O | CH₃ | CH₃ | H | L-1d | |
| CH | CH | O | O | CH₃ | CH₃ | H | L-1e | |
| CH | CH | O | O | CH₃ | CH₃ | H | L-1f | |
| CH | CH | O | O | CH₃ | CH₃ | H | L-1g | |
| CH | CH | O | O | CH₃ | CH₃ | H | L-1h | |
| CH | CH | O | O | CH₃ | CH₃ | H | L-1i | |
| CH | CH | O | O | CH₃ | CH₃ | H | L-1j | |
| CH | CH | O | O | CH₃ | CH₃ | H | L-1k | |
| CH | CH | O | O | CH₃ | CH₃ | H | L-3a | |
| CH | CH | O | O | CH₃ | CH₃ | H | L-3b | |
| CH | CH | O | O | CH₃ | CH₃ | H | L-4a | |
| CH | CH | O | O | CH₃ | CH₃ | H | L-7a | |
| CH | CH | O | O | CH₃ | CH₃ | H | L-8a | |
| CH | CH | O | O | CH₃ | CH₃ | H | L-8b | |
| CH | CH | O | O | CH₃ | CH₃ | H | L-9a | |
| CH | CH | O | O | CH₃ | CH₃ | H | L-12a | |
| CH | CH | O | O | CH₃ | CH₃ | H | L-12b | |
| CH | CH | O | O | CH₃ | CH₃ | H | L-14a | |
| CH | CH | O | O | CH₃ | CH₃ | H | L-15a | |
| CH | CH | O | O | CH₃ | CH₃ | H | L-16a | |
| CH | CH | O | O | CH₃ | CH₃ | H | L-16b | |
| CH | CH | O | O | CH₃ | CH₃ | H | L-18a | |
| CH | CH | O | O | CH₃ | CH₃ | H | L-20a | |
| CH | CH | O | O | CH₃ | CH₃ | H | L-22a | |
| CH | CH | O | S | CH₃ | CH₃ | H | L-1a | |
| CH | CH | O | O | CH₃ | CH₃ | CH₃ | L-1a | |
| CH | CH | O | O | OCH₃ | CH₃ | H | L-1a | |
| CH | CH | O | O | OCH₃ | CH₃ | H | L-1b | |
| CH | CH | O | O | OCH₃ | CH₃ | H | L-1c | |
| CH | CH | O | O | OCH₃ | CH₃ | H | L-1d | |
| CH | CH | O | O | OCH₃ | CH₃ | H | L-1e | |
| CH | CH | O | O | OCH₃ | CH₃ | H | L-1f | |
| CH | CH | O | O | OCH₃ | CH₃ | H | L-1g | |
| CH | CH | O | O | OCH₃ | CH₃ | H | L-1h | |
| CH | CH | O | O | OCH₃ | CH₃ | H | L-1i | |
| CH | CH | O | O | OCH₃ | CH₃ | H | L-1j | |
| CH | CH | O | O | OCH₃ | CH₃ | H | L-1k | |
| CH | CH | O | O | OCH₃ | CH₃ | H | L-3a | |
| CH | CH | O | O | OCH₃ | CH₃ | H | L-3b | |
| CH | CH | O | O | OCH₃ | CH₃ | H | L-4a | |
| CH | CH | O | O | OCH₃ | CH₃ | H | L-7a | |
| CH | CH | O | O | OCH₃ | CH₃ | H | L-8a | |
| CH | CH | O | O | OCH₃ | CH₃ | H | L-8b | |
| CH | CH | O | O | OCH₃ | CH₃ | H | L-9a | |
| CH | CH | O | O | OCH₃ | CH₃ | H | L-12a | |
| CH | CH | O | O | OCH₃ | CH₃ | H | L-12b | |
| CH | CH | O | O | OCH₃ | CH₃ | H | L-14a | |
| CH | CH | O | O | OCH₃ | CH₃ | H | L-15a | |
| CH | CH | O | O | OCH₃ | CH₃ | H | L-16a | |
| CH | CH | O | O | OCH₃ | CH₃ | H | L-16b | |
| CH | CH | O | O | OCH₃ | CH₃ | H | L-18a | |
| CH | CH | O | O | OCH₃ | CH₃ | H | L-20a | |
| CH | CH | O | O | OCH₃ | CH₃ | H | L-22a | |
| CH | CH | O | S | OCH₃ | CH₃ | H | L-1a | |
| CH | CH | O | O | OCH₃ | CH₃ | CH₃ | L-1a | |
| CH | CH | O | O | CH₃ | OCH₃ | H | L-1a | |
| CH | CH | O | O | CH₃ | OCH₃ | H | L-1b | |
| CH | CH | O | O | CH₃ | OCH₃ | H | L-1c | |
| CH | CH | O | O | CH₃ | OCH₃ | H | L-1d | |
| CH | CH | O | O | CH₃ | OCH₃ | H | L-1e | |
| CH | CH | O | O | CH₃ | OCH₃ | H | L-1f | |
| CH | CH | O | O | CH₃ | OCH₃ | H | L-1g | |
| CH | CH | O | O | CH₃ | OCH₃ | H | L-1h | |
| CH | CH | O | O | CH₃ | OCH₃ | H | L-1i | |
| CH | CH | O | O | CH₃ | OCH₃ | H | L-1j | |
| CH | CH | O | O | CH₃ | OCH₃ | H | L-1k | |
| CH | CH | O | O | CH₃ | OCH₃ | H | L-3a | |
| CH | CH | O | O | CH₃ | OCH₃ | H | L-3b | |
| CH | CH | O | O | CH₃ | OCH₃ | H | L-4a | |
| CH | CH | O | O | CH₃ | OCH₃ | H | L-7a | |
| CH | CH | O | O | CH₃ | OCH₃ | H | L-8a | |
| CH | CH | O | O | CH₃ | OCH₃ | H | L-8b | |
| CH | CH | O | O | CH₃ | OCH₃ | H | L-9a | |
| CH | CH | O | O | CH₃ | OCH₃ | H | L-12a | |
| CH | CH | O | O | CH₃ | OCH₃ | H | L-12b | |
| CH | CH | O | O | CH₃ | OCH₃ | H | L-14a | |
| CH | CH | O | O | CH₃ | OCH₃ | H | L-15a | |
| CH | CH | O | O | CH₃ | OCH₃ | H | L-16a | |
| CH | CH | O | O | CH₃ | OCH₃ | H | L-16b | |
| CH | CH | O | O | CH₃ | OCH₃ | H | L-18a | |
| CH | CH | O | O | CH₃ | OCH₃ | H | L-20a | |
| CH | CH | O | O | CH₃ | OCH₃ | H | L-22a | |
| CH | CH | O | S | CH₃ | OCH₃ | H | L-1a | |
| CH | CH | O | O | CH₃ | OCH₃ | CH₃ | L-1a | |
| CH | CH | O | O | OCH₃ | OCH₃ | H | L-1a | |
| CH | CH | O | O | OCH₃ | OCH₃ | H | L-1b | |
| CH | CH | O | O | OCH₃ | OCH₃ | H | L-1c | |
| CH | CH | O | O | OCH₃ | OCH₃ | H | L-1d | |
| CH | CH | O | O | OCH₃ | OCH₃ | H | L-1e | |
| CH | CH | O | O | OCH₃ | OCH₃ | H | L-1f | |
| CH | CH | O | O | OCH₃ | OCH₃ | H | L-1g | |

TABLE 4-continued

General Formula 4

| Z | Z₁ | Z₄ | W | X | Y | R | L | m.p. (°C.) |
|---|----|----|---|---|---|---|---|------------|
| CH | CH | O | O | OCH₃ | OCH₃ | H | L-1h | |
| CH | CH | O | O | OCH₃ | OCH₃ | H | L-1i | |
| CH | CH | O | O | OCH₃ | OCH₃ | H | L-1j | |
| CH | CH | O | O | OCH₃ | OCH₃ | H | L-1k | |
| CH | CH | O | O | OCH₃ | OCH₃ | H | L-3a | |
| CH | CH | O | O | OCH₃ | OCH₃ | H | L-3b | |
| CH | CH | O | O | OCH₃ | OCH₃ | H | L-4a | |
| CH | CH | O | O | OCH₃ | OCH₃ | H | L-7a | |
| CH | CH | O | O | OCH₃ | OCH₃ | H | L-8a | |
| CH | CH | O | O | OCH₃ | OCH₃ | H | L-8b | |
| CH | CH | O | O | OCH₃ | OCH₃ | H | L-9a | |
| CH | CH | O | O | OCH₃ | OCH₃ | H | L-12a | |
| CH | CH | O | O | OCH₃ | OCH₃ | H | L-12b | |
| CH | CH | O | O | OCH₃ | OCH₃ | H | L-14a | |
| CH | CH | O | O | OCH₃ | OCH₃ | H | L-15a | |
| CH | CH | O | O | OCH₃ | OCH₃ | H | L-16a | |
| CH | CH | O | O | OCH₃ | OCH₃ | H | L-16b | |
| CH | CH | O | O | OCH₃ | OCH₃ | H | L-18a | |
| CH | CH | O | O | OCH₃ | OCH₃ | H | L-20a | |
| CH | CH | O | O | OCH₃ | OCH₃ | H | L-22a | |
| CH | CH | O | S | OCH₃ | OCH₃ | H | L-1a | |
| CH | CH | O | O | OCH₃ | OCH₃ | CH₃ | L-1a | |
| N | CH | S | O | CH₃ | CH₃ | H | L-1a | |
| N | CH | S | O | CH₃ | CH₃ | H | L-1b | |
| N | CH | S | O | CH₃ | CH₃ | H | L-1c | |
| N | CH | S | O | CH₃ | CH₃ | H | L-1d | |
| N | CH | S | O | CH₃ | CH₃ | H | L-1e | |
| N | CH | S | O | CH₃ | CH₃ | H | L-1f | |
| N | CH | S | O | CH₃ | CH₃ | H | L-1g | |
| N | CH | S | O | CH₃ | CH₃ | H | L-1h | |
| N | CH | S | O | CH₃ | CH₃ | H | L-1i | |
| N | CH | S | O | CH₃ | CH₃ | H | L-1j | |
| N | CH | S | O | CH₃ | CH₃ | H | L-1k | |
| N | CH | S | O | CH₃ | CH₃ | H | L-3a | |
| N | CH | S | O | CH₃ | CH₃ | H | L-3b | |
| N | CH | S | O | CH₃ | CH₃ | H | L-4a | |
| N | CH | S | O | CH₃ | CH₃ | H | L-7a | |
| N | CH | S | O | CH₃ | CH₃ | H | L-8a | |
| N | CH | S | O | CH₃ | CH₃ | H | L-8b | |
| N | CH | S | O | CH₃ | CH₃ | H | L-9a | |
| N | CH | S | O | CH₃ | CH₃ | H | L-12a | |
| N | CH | S | O | CH₃ | CH₃ | H | L-12b | |
| N | CH | S | O | CH₃ | CH₃ | H | L-14a | |
| N | CH | S | O | CH₃ | CH₃ | H | L-15a | |
| N | CH | S | O | CH₃ | CH₃ | H | L-16a | |
| N | CH | S | O | CH₃ | CH₃ | H | L-16b | |
| N | CH | S | O | CH₃ | CH₃ | H | L-18a | |
| N | CH | S | O | CH₃ | CH₃ | H | L-20a | |
| N | CH | S | O | CH₃ | CH₃ | H | L-22a | |
| N | CH | S | S | CH₃ | CH₃ | H | L-1a | |
| N | CH | S | O | CH₃ | CH₃ | CH₃ | L-1a | |
| N | CH | S | O | OCH₃ | CH₃ | H | L-1a | |
| N | CH | S | O | OCH₃ | CH₃ | H | L-1b | |
| N | CH | S | O | OCH₃ | CH₃ | H | L-1c | |
| N | CH | S | O | OCH₃ | CH₃ | H | L-1d | |
| N | CH | S | O | OCH₃ | CH₃ | H | L-1e | |
| N | CH | S | O | OCH₃ | CH₃ | H | L-1f | |
| N | CH | S | O | OCH₃ | CH₃ | H | L-1g | |
| N | CH | S | O | OCH₃ | CH₃ | H | L-1h | |
| N | CH | S | O | OCH₃ | CH₃ | H | L-1i | |
| N | CH | S | O | OCH₃ | CH₃ | H | L-1j | |
| N | CH | S | O | OCH₃ | CH₃ | H | L-1k | |
| N | CH | S | O | OCH₃ | CH₃ | H | L-3a | |
| N | CH | S | O | OCH₃ | CH₃ | H | L-3b | |
| N | CH | S | O | OCH₃ | CH₃ | H | L-4a | |
| N | CH | S | O | OCH₃ | CH₃ | H | L-7a | |
| N | CH | S | O | OCH₃ | CH₃ | H | L-8a | |
| N | CH | S | O | OCH₃ | CH₃ | H | L-8b | |
| N | CH | S | O | OCH₃ | CH₃ | H | L-9a | |
| N | CH | S | O | OCH₃ | CH₃ | H | L-12a | |
| N | CH | S | O | OCH₃ | CH₃ | H | L-12b | |
| N | CH | S | O | OCH₃ | CH₃ | H | L-14a | |
| N | CH | S | O | OCH₃ | CH₃ | H | L-15a | |
| N | CH | S | O | OCH₃ | CH₃ | H | L-16a | |
| N | CH | S | O | OCH₃ | CH₃ | H | L-16b | |
| N | CH | S | O | OCH₃ | CH₃ | H | L-18a | |
| N | CH | S | O | OCH₃ | CH₃ | H | L-20a | |
| N | CH | S | O | OCH₃ | CH₃ | H | L-22a | |
| N | CH | S | S | OCH₃ | CH₃ | H | L-1a | |
| N | CH | S | O | OCH₃ | CH₃ | CH₃ | L-1a | |
| N | CH | S | O | CH₃ | OCH₃ | H | L-1a | |
| N | CH | S | O | CH₃ | OCH₃ | H | L-1b | |
| N | CH | S | O | CH₃ | OCH₃ | H | L-1c | |
| N | CH | S | O | CH₃ | OCH₃ | H | L-1d | |
| N | CH | S | O | CH₃ | OCH₃ | H | L-1e | |
| N | CH | S | O | CH₃ | OCH₃ | H | L-1f | |
| N | CH | S | O | CH₃ | OCH₃ | H | L-1g | |
| N | CH | S | O | CH₃ | OCH₃ | H | L-1h | |
| N | CH | S | O | CH₃ | OCH₃ | H | L-1i | |
| N | CH | S | O | CH₃ | OCH₃ | H | L-1j | |
| N | CH | S | O | CH₃ | OCH₃ | H | L-1k | |
| N | CH | S | O | CH₃ | OCH₃ | H | L-3a | |
| N | CH | S | O | CH₃ | OCH₃ | H | L-3b | |
| N | CH | S | O | CH₃ | OCH₃ | H | L-4a | |
| N | CH | S | O | CH₃ | OCH₃ | H | L-7a | |
| N | CH | S | O | CH₃ | OCH₃ | H | L-8a | |
| N | CH | S | O | CH₃ | OCH₃ | H | L-8b | |
| N | CH | S | O | CH₃ | OCH₃ | H | L-9a | |
| N | CH | S | O | CH₃ | OCH₃ | H | L-12a | |
| N | CH | S | O | CH₃ | OCH₃ | H | L-12b | |
| N | CH | S | O | CH₃ | OCH₃ | H | L-14a | |
| N | CH | S | O | CH₃ | OCH₃ | H | L-15a | |
| N | CH | S | O | CH₃ | OCH₃ | H | L-16a | |
| N | CH | S | O | CH₃ | OCH₃ | H | L-16b | |
| N | CH | S | O | CH₃ | OCH₃ | H | L-18a | |
| N | CH | S | O | CH₃ | OCH₃ | H | L-20a | |
| N | CH | S | O | CH₃ | OCH₃ | H | L-22a | |
| N | CH | S | S | CH₃ | OCH₃ | H | L-1a | |
| N | CH | S | O | CH₃ | OCH₃ | CH₃ | L-1a | |
| N | CH | S | O | OCH₃ | OCH₃ | H | L-1a | |
| N | CH | S | O | OCH₃ | OCH₃ | H | L-1b | |
| N | CH | S | O | OCH₃ | OCH₃ | H | L-1c | |
| N | CH | S | O | OCH₃ | OCH₃ | H | L-1d | |
| N | CH | S | O | OCH₃ | OCH₃ | H | L-1e | |
| N | CH | S | O | OCH₃ | OCH₃ | H | L-1f | |
| N | CH | S | O | OCH₃ | OCH₃ | H | L-1g | |
| N | CH | S | O | OCH₃ | OCH₃ | H | L-1h | |
| N | CH | S | O | OCH₃ | OCH₃ | H | L-1i | |
| N | CH | S | O | OCH₃ | OCH₃ | H | L-1j | |
| N | CH | S | O | OCH₃ | OCH₃ | H | L-1k | |
| N | CH | S | O | OCH₃ | OCH₃ | H | L-3a | |
| N | CH | S | O | OCH₃ | OCH₃ | H | L-3b | |
| N | CH | S | O | OCH₃ | OCH₃ | H | L-4a | |
| N | CH | S | O | OCH₃ | OCH₃ | H | L-7a | |
| N | CH | S | O | OCH₃ | OCH₃ | H | L-8a | |
| N | CH | S | O | OCH₃ | OCH₃ | H | L-8b | |
| N | CH | S | O | OCH₃ | OCH₃ | H | L-9a | |
| N | CH | S | O | OCH₃ | OCH₃ | H | L-12a | |
| N | CH | S | O | OCH₃ | OCH₃ | H | L-12b | |
| N | CH | S | O | OCH₃ | OCH₃ | H | L-14a | |
| N | CH | S | O | OCH₃ | OCH₃ | H | L-15a | |
| N | CH | S | O | OCH₃ | OCH₃ | H | L-16a | |
| N | CH | S | O | OCH₃ | OCH₃ | H | L-16b | |
| N | CH | S | O | OCH₃ | OCH₃ | H | L-18a | |
| N | CH | S | O | OCH₃ | OCH₃ | H | L-20a | |
| N | CH | S | O | OCH₃ | OCH₃ | H | L-22a | |
| N | CH | S | S | OCH₃ | OCH₃ | H | L-1a | |
| N | CH | S | O | OCH₃ | OCH₃ | CH₃ | L-1a | |
| N | CH | O | O | CH₃ | CH₃ | H | L-1a | |
| N | CH | O | O | CH₃ | CH₃ | H | L-1b | |
| N | CH | O | O | CH₃ | CH₃ | H | L-1c | |
| N | CH | O | O | CH₃ | CH₃ | H | L-1d | |
| N | CH | O | O | CH₃ | CH₃ | H | L-1e | |
| N | CH | O | O | CH₃ | CH₃ | H | L-1f | |
| N | CH | O | O | CH₃ | CH₃ | H | L-1g | |
| N | CH | O | O | CH₃ | CH₃ | H | L-1h | |
| N | CH | O | O | CH₃ | CH₃ | H | L-1i | |
| N | CH | O | O | CH₃ | CH₃ | H | L-1j | |
| N | CH | O | O | CH₃ | CH₃ | H | L-1k | |
| N | CH | O | O | CH₃ | CH₃ | H | L-3a | |
| N | CH | O | O | CH₃ | CH₃ | H | L-3b | |
| N | CH | O | O | CH₃ | CH₃ | H | L-4a | |
| N | CH | O | O | CH₃ | CH₃ | H | L-7a | |
| N | CH | O | O | CH₃ | CH₃ | H | L-8a | |
| N | CH | O | O | CH₃ | CH₃ | H | L-8b | |
| N | CH | O | O | CH₃ | CH₃ | H | L-9a | |

TABLE 4-continued

General Formula 4

| Z | $Z_1$ | $Z_4$ | W | X | Y | R | L | m.p. (°C.) |
|---|---|---|---|---|---|---|---|---|
| N | CH | O | O | $CH_3$ | $CH_3$ | H | L-12a | |
| N | CH | O | O | $CH_3$ | $CH_3$ | H | L-12b | |
| N | CH | O | O | $CH_3$ | $CH_3$ | H | L-14a | |
| N | CH | O | O | $CH_3$ | $CH_3$ | H | L-15a | |
| N | CH | O | O | $CH_3$ | $CH_3$ | H | L-16a | |
| N | CH | O | O | $CH_3$ | $CH_3$ | H | L-16b | |
| N | CH | O | O | $CH_3$ | $CH_3$ | H | L-18a | |
| N | CH | O | O | $CH_3$ | $CH_3$ | H | L-20a | |
| N | CH | O | O | $CH_3$ | $CH_3$ | H | L-22a | |
| N | CH | O | S | $CH_3$ | $CH_3$ | H | L-1a | |
| N | CH | O | O | $CH_3$ | $CH_3$ | $CH_3$ | L-1a | |
| N | CH | O | O | $OCH_3$ | $CH_3$ | H | L-1a | |
| N | CH | O | O | $OCH_3$ | $CH_3$ | H | L-1b | |
| N | CH | O | O | $OCH_3$ | $CH_3$ | H | L-1c | |
| N | CH | O | O | $OCH_3$ | $CH_3$ | H | L-1d | |
| N | CH | O | O | $OCH_3$ | $CH_3$ | H | L-1e | |
| N | CH | O | O | $OCH_3$ | $CH_3$ | H | L-1f | |
| N | CH | O | O | $OCH_3$ | $CH_3$ | H | L-1g | |
| N | CH | O | O | $OCH_3$ | $CH_3$ | H | L-1h | |
| N | CH | O | O | $OCH_3$ | $CH_3$ | H | L-1i | |
| N | CH | O | O | $OCH_3$ | $CH_3$ | H | L-1j | |
| N | CH | O | O | $OCH_3$ | $CH_3$ | H | L-1k | |
| N | CH | O | O | $OCH_3$ | $CH_3$ | H | L-3a | |
| N | CH | O | O | $OCH_3$ | $CH_3$ | H | L-3b | |
| N | CH | O | O | $OCH_3$ | $CH_3$ | H | L-4a | |
| N | CH | O | O | $OCH_3$ | $CH_3$ | H | L-7a | |
| N | CH | O | O | $OCH_3$ | $CH_3$ | H | L-8a | |
| N | CH | O | O | $OCH_3$ | $CH_3$ | H | L-8b | |
| N | CH | O | O | $OCH_3$ | $CH_3$ | H | L-9a | |
| N | CH | O | O | $OCH_3$ | $CH_3$ | H | L-12a | |
| N | CH | O | O | $OCH_3$ | $CH_3$ | H | L-12b | |
| N | CH | O | O | $OCH_3$ | $CH_3$ | H | L-14a | |
| N | CH | O | O | $OCH_3$ | $CH_3$ | H | L-15a | |
| N | CH | O | O | $OCH_3$ | $CH_3$ | H | L-16a | |
| N | CH | O | O | $OCH_3$ | $CH_3$ | H | L-16b | |
| N | CH | O | O | $OCH_3$ | $CH_3$ | H | L-18a | |
| N | CH | O | O | $OCH_3$ | $CH_3$ | H | L-20a | |
| N | CH | O | O | $OCH_3$ | $CH_3$ | H | L-22a | |
| N | CH | O | S | $OCH_3$ | $CH_3$ | H | L-1a | |
| N | CH | O | O | $OCH_3$ | $CH_3$ | $CH_3$ | L-1a | |
| N | CH | O | O | $CH_3$ | $OCH_3$ | H | L-1a | |
| N | CH | O | O | $CH_3$ | $OCH_3$ | H | L-1b | |
| N | CH | O | O | $CH_3$ | $OCH_3$ | H | L-1c | |
| N | CH | O | O | $CH_3$ | $OCH_3$ | H | L-1d | |
| N | CH | O | O | $CH_3$ | $OCH_3$ | H | L-1e | |
| N | CH | O | O | $CH_3$ | $OCH_3$ | H | L-1f | |
| N | CH | O | O | $CH_3$ | $OCH_3$ | H | L-1h | |
| N | CH | O | O | $CH_3$ | $OCH_3$ | H | L-1i | |
| N | CH | O | O | $CH_3$ | $OCH_3$ | H | L-1j | |
| N | CH | O | O | $CH_3$ | $OCH_3$ | H | L-1k | |
| N | CH | O | O | $CH_3$ | $OCH_3$ | H | L-3a | |
| N | CH | O | O | $CH_3$ | $OCH_3$ | H | L-3b | |
| N | CH | O | O | $CH_3$ | $OCH_3$ | H | L-4a | |
| N | CH | O | O | $CH_3$ | $OCH_3$ | H | L-7a | |
| N | CH | O | O | $CH_3$ | $OCH_3$ | H | L-8a | |
| N | CH | O | O | $CH_3$ | $OCH_3$ | H | L-8b | |
| N | CH | O | O | $CH_3$ | $OCH_3$ | H | L-9a | |
| N | CH | O | O | $CH_3$ | $OCH_3$ | H | L-12a | |
| N | CH | O | O | $CH_3$ | $OCH_3$ | H | L-12b | |
| N | CH | O | O | $CH_3$ | $OCH_3$ | H | L-14a | |
| N | CH | O | O | $CH_3$ | $OCH_3$ | H | L-15a | |
| N | CH | O | O | $CH_3$ | $OCH_3$ | H | L-16a | |
| N | CH | O | O | $CH_3$ | $OCH_3$ | H | L-16b | |
| N | CH | O | O | $CH_3$ | $OCH_3$ | H | L-18a | |
| N | CH | O | O | $CH_3$ | $OCH_3$ | H | L-20a | |
| N | CH | O | O | $CH_3$ | $OCH_3$ | H | L-22a | |
| N | CH | O | S | $CH_3$ | $OCH_3$ | H | L-1a | |
| N | CH | O | O | $CH_3$ | $OCH_3$ | $CH_3$ | L-1a | |
| N | CH | O | O | $OCH_3$ | $OCH_3$ | H | L-1a | |
| N | CH | O | O | $OCH_3$ | $OCH_3$ | H | L-1b | |
| N | CH | O | O | $OCH_3$ | $OCH_3$ | H | L-1c | |
| N | CH | O | O | $OCH_3$ | $OCH_3$ | H | L-1d | |
| N | CH | O | O | $OCH_3$ | $OCH_3$ | H | L-1e | |
| N | CH | O | O | $OCH_3$ | $OCH_3$ | H | L-1f | |
| N | CH | O | O | $OCH_3$ | $OCH_3$ | H | L-1g | |
| N | CH | O | O | $OCH_3$ | $OCH_3$ | H | L-1h | |
| N | CH | O | O | $OCH_3$ | $OCH_3$ | H | L-1i | |
| N | CH | O | O | $OCH_3$ | $OCH_3$ | H | L-1j | |
| N | CH | O | O | $OCH_3$ | $OCH_3$ | H | L-1k | |
| N | CH | O | O | $OCH_3$ | $OCH_3$ | H | L-3a | |
| N | CH | O | O | $OCH_3$ | $OCH_3$ | H | L-3b | |
| N | CH | O | O | $OCH_3$ | $OCH_3$ | H | L-4a | |
| N | CH | O | O | $OCH_3$ | $OCH_3$ | H | L-7a | |
| N | CH | O | O | $OCH_3$ | $OCH_3$ | H | L-8a | |
| N | CH | O | O | $OCH_3$ | $OCH_3$ | H | L-8b | |
| N | CH | O | O | $OCH_3$ | $OCH_3$ | H | L-9a | |
| N | CH | O | O | $OCH_3$ | $OCH_3$ | H | L-12a | |
| N | CH | O | O | $OCH_3$ | $OCH_3$ | H | L-12b | |
| N | CH | O | O | $OCH_3$ | $OCH_3$ | H | L-14a | |
| N | CH | O | O | $OCH_3$ | $OCH_3$ | H | L-15a | |
| N | CH | O | O | $OCH_3$ | $OCH_3$ | H | L-16a | |
| N | CH | O | O | $OCH_3$ | $OCH_3$ | H | L-16b | |
| N | CH | O | O | $OCH_3$ | $OCH_3$ | H | L-18a | |
| N | CH | O | O | $OCH_3$ | $OCH_3$ | H | L-20a | |
| N | CH | O | O | $OCH_3$ | $OCH_3$ | H | L-22a | |
| N | CH | O | S | $OCH_3$ | $OCH_3$ | H | L-1a | |
| N | CH | O | O | $OCH_3$ | $OCH_3$ | $CH_3$ | L-1a | |
| CH | CH | $NCH_3$ | O | $CH_3$ | $CH_3$ | H | L-1a | |
| CH | CH | $NCH_3$ | O | $CH_3$ | $CH_3$ | H | L-1b | |
| CH | CH | $NCH_3$ | O | $CH_3$ | $CH_3$ | H | L-1c | |
| CH | CH | $NCH_3$ | O | $CH_3$ | $CH_3$ | H | L-1d | |
| CH | CH | $NCH_3$ | O | $CH_3$ | $CH_3$ | H | L-1e | |
| CH | CH | $NCH_3$ | O | $CH_3$ | $CH_3$ | H | L-1f | |
| CH | CH | $NCH_3$ | O | $CH_3$ | $CH_3$ | H | L-1g | |
| CH | CH | $NCH_3$ | O | $CH_3$ | $CH_3$ | H | L-1h | |
| CH | CH | $NCH_3$ | O | $CH_3$ | $CH_3$ | H | L-1i | |
| CH | CH | $NCH_3$ | O | $CH_3$ | $CH_3$ | H | L-1j | |
| CH | CH | $NCH_3$ | O | $CH_3$ | $CH_3$ | H | L-1k | |
| CH | CH | $NCH_3$ | O | $CH_3$ | $CH_3$ | H | L-3a | |
| CH | CH | $NCH_3$ | O | $CH_3$ | $CH_3$ | H | L-3b | |
| CH | CH | $NCH_3$ | O | $CH_3$ | $CH_3$ | H | L-4a | |
| CH | CH | $NCH_3$ | O | $CH_3$ | $CH_3$ | H | L-7a | |
| CH | CH | NCH | O | $CH_3$ | $CH_3$ | H | L-8a | |
| CH | CH | $NCH_3$ | O | $CH_3$ | $CH_3$ | H | L-8b | |
| CH | CH | $NCH_3$ | O | $CH_3$ | $CH_3$ | H | L-9a | |
| CH | CH | $NCH_3$ | O | $CH_3$ | $CH_3$ | H | L-12a | |
| CH | CH | $NCH_3$ | O | $CH_3$ | $CH_3$ | H | L-12b | |
| CH | CH | $NCH_3$ | O | $CH_3$ | $CH_3$ | H | L-14a | |
| CH | CH | $NCH_3$ | O | $CH_3$ | $CH_3$ | H | L-15a | |
| CH | CH | $NCH_3$ | O | $CH_3$ | $CH_3$ | H | L-16a | |
| CH | CH | $NCH_3$ | O | $CH_3$ | $CH_3$ | H | L-16b | |
| CH | CH | $NCH_3$ | O | $CH_3$ | $CH_3$ | H | L-18a | |
| CH | CH | $NCH_3$ | O | $CH_3$ | $CH_3$ | H | L-20a | |
| CH | CH | $NCH_3$ | O | $CH_3$ | $CH_3$ | H | L-22a | |
| CH | CH | $NCH_3$ | S | $CH_3$ | $CH_3$ | H | L-1a | |
| CH | CH | $NCH_3$ | O | $CH_3$ | $CH_3$ | $CH_3$ | L-1a | |
| CH | CH | $NCH_3$ | O | $OCH_3$ | $CH_3$ | H | L-1a | |
| CH | CH | $NCH_3$ | O | $OCH_3$ | $CH_3$ | H | L-1b | |
| CH | CH | $NCH_3$ | O | $OCH_3$ | $CH_3$ | H | L-1c | |
| CH | CH | $NCH_3$ | O | $OCH_3$ | $CH_3$ | H | L-1d | |
| CH | CH | $NCH_3$ | O | $OCH_3$ | $CH_3$ | H | L-1e | |
| CH | CH | $NCH_3$ | O | $OCH_3$ | $CH_3$ | H | L-1f | |
| CH | CH | $NCH_3$ | O | $OCH_3$ | $CH_3$ | H | L-1g | |
| CH | CH | $NCH_3$ | O | $OCH_3$ | $CH_3$ | H | L-1h | |
| CH | CH | $NCH_3$ | O | $OCH_3$ | $CH_3$ | H | L-1i | |
| CH | CH | $NCH_3$ | O | $OCH_3$ | $CH_3$ | H | L-1j | |
| CH | CH | $NCH_3$ | O | $OCH_3$ | $CH_3$ | H | L-1k | |
| CH | CH | $NCH_3$ | O | $OCH_3$ | $CH_3$ | H | L-3a | |
| CH | CH | $NCH_3$ | O | $OCH_3$ | $CH_3$ | H | L-3b | |
| CH | CH | $NCH_3$ | O | $OCH_3$ | $CH_3$ | H | L-4a | |
| CH | CH | $NCH_3$ | O | $OCH_3$ | $CH_3$ | H | L-7a | |
| CH | CH | $NCH_3$ | O | $OCH_3$ | $CH_3$ | H | L-8a | |
| CH | CH | $NCH_3$ | O | $OCH_3$ | $CH_3$ | H | L-8b | |
| CH | CH | $NCH_3$ | O | $OCH_3$ | $CH_3$ | H | L-9a | |
| CH | CH | $NCH_3$ | O | $OCH_3$ | $CH_3$ | H | L-12a | |
| CH | CH | $NCH_3$ | O | $OCH_3$ | $CH_3$ | H | L-12b | |
| CH | CH | $NCH_3$ | O | $OCH_3$ | $CH_3$ | H | L-14a | |
| CH | CH | $NCH_3$ | O | $OCH_3$ | $CH_3$ | H | L-15a | |
| CH | CH | $NCH_3$ | O | $OCH_3$ | $CH_3$ | H | L-16a | |
| CH | CH | $NCH_3$ | O | $OCH_3$ | $CH_3$ | H | L-16b | |
| CH | CH | $NCH_3$ | O | $OCH_3$ | $CH_3$ | H | L-18a | |
| CH | CH | $NCH_3$ | O | $OCH_3$ | $CH_3$ | H | L-20a | |
| CH | CH | $NCH_3$ | O | $OCH_3$ | $CH_3$ | H | L-22a | |
| CH | CH | $NCH_3$ | S | $OCH_3$ | $CH_3$ | H | L-1a | |
| CH | CH | $NCH_3$ | O | $OCH_3$ | $CH_3$ | $CH_3$ | L-1a | |
| CH | CH | $NCH_3$ | O | $CH_3$ | $OCH_3$ | H | L-1a | |

TABLE 4-continued

General Formula 4

| Z | Z₁ | Z₄ | W | X | Y | R | L | m.p. (°C.) |
|---|---|---|---|---|---|---|---|---|
| CH | CH | NCH₃ | O | CH₃ | OCH₃ | H | L-1b | |
| CH | CH | NCH₃ | O | CH₃ | OCH₃ | H | L-1c | |
| CH | CH | NCH₃ | O | CH₃ | OCH₃ | H | L-1d | |
| CH | CH | NCH₃ | O | CH₃ | OCH₃ | H | L-1e | |
| CH | CH | NCH₃ | O | CH₃ | OCH₃ | H | L-1f | |
| CH | CH | NCH₃ | O | CH₃ | OCH₃ | H | L-1g | |
| CH | CH | NCH₃ | O | CH₃ | OCH₃ | H | L-1h | |
| CH | CH | NCH₃ | O | CH₃ | OCH₃ | H | L-1i | |
| CH | CH | NCH₃ | O | CH₃ | OCH₃ | H | L-1j | |
| CH | CH | NCH₃ | O | CH₃ | OCH₃ | H | L-1k | |
| CH | CH | NCH₃ | O | CH₃ | OCH₃ | H | L-3a | |
| CH | CH | NCH₃ | O | CH₃ | OCH₃ | H | L-3b | |
| CH | CH | NCH₃ | O | CH₃ | OCH₃ | H | L-4a | |
| CH | CH | NCH₃ | O | CH₃ | OCH₃ | H | L-7a | |
| CH | CH | NCH₃ | O | CH₃ | OCH₃ | H | L-8a | |
| CH | CH | NCH₃ | O | CH₃ | OCH₃ | H | L-8b | |
| CH | CH | NCH₃ | O | CH₃ | OCH₃ | H | L-9a | |
| CH | CH | NCH₃ | O | CH₃ | OCH₃ | H | L-12a | |
| CH | CH | NCH₃ | O | CH₃ | OCH₃ | H | L-12b | |
| CH | CH | NCH₃ | O | CH₃ | OCH₃ | H | L-14a | |
| CH | CH | NCH₃ | O | CH₃ | OCH₃ | H | L-15a | |
| CH | CH | NCH₃ | O | CH₃ | OCH₃ | H | L-16a | |
| CH | CH | NCH₃ | O | CH₃ | OCH₃ | H | L-16b | |
| CH | CH | NCH₃ | O | CH₃ | OCH₃ | H | L-18a | |
| CH | CH | NCH₃ | O | CH₃ | OCH₃ | H | L-20a | |
| CH | CH | NCH₃ | O | CH₃ | OCH₃ | H | L-22a | |
| CH | CH | NCH₃ | S | CH₃ | OCH₃ | H | L-1a | |
| CH | CH | NCH₃ | O | CH₃ | OCH₃ | CH₃ | L-1a | |
| CH | CH | NCH₃ | O | OCH₃ | OCH₃ | H | L-1a | |
| CH | CH | NCH₃ | O | OCH₃ | OCH₃ | H | L-1b | |
| CH | CH | NCH₃ | O | OCH₃ | OCH₃ | H | L-1c | |
| CH | CH | NCH₃ | O | OCH₃ | OCH₃ | H | L-1d | |
| CH | CH | NCH₃ | O | OCH₃ | OCH₃ | H | L-1e | |
| CH | CH | NCH₃ | O | OCH₃ | OCH₃ | H | L-1f | |
| CH | CH | NCH₃ | O | OCH₃ | OCH₃ | H | L-1g | |
| CH | CH | NCH₃ | O | OCH₃ | OCH₃ | H | L-1h | |
| CH | CH | NCH₃ | O | OCH₃ | OCH₃ | H | L-1i | |
| CH | CH | NCH₃ | O | OCH₃ | OCH₃ | H | L-1j | |
| CH | CH | NCH₃ | O | OCH₃ | OCH₃ | H | L-1k | |
| CH | CH | NCH₃ | O | OCH₃ | OCH₃ | H | L-3a | |
| CH | CH | NCH₃ | O | OCH₃ | OCH₃ | H | L-3b | |
| CH | CH | NCH₃ | O | OCH₃ | OCH₃ | H | L-4a | |
| CH | CH | NCH₃ | O | OCH₃ | OCH₃ | H | L-7a | |
| CH | CH | NCH₃ | O | OCH₃ | OCH₃ | H | L-8a | |
| CH | CH | NCH₃ | O | OCH₃ | OCH₃ | H | L-8b | |
| CH | CH | NCH₃ | O | OCH₃ | OCH₃ | H | L-9a | |
| CH | CH | NCH₃ | O | OCH₃ | OCH₃ | H | L-12a | |
| CH | CH | NCH₃ | O | OCH₃ | OCH₃ | H | L-12b | |
| CH | CH | NCH₃ | O | OCH₃ | OCH₃ | H | L-14a | |
| CH | CH | NCH₃ | O | OCH₃ | OCH₃ | H | L-15a | |
| CH | CH | NCH₃ | O | OCH₃ | OCH₃ | H | L-16a | |
| CH | CH | NCH₃ | O | OCH₃ | OCH₃ | H | L-16b | |
| CH | CH | NCH₃ | O | OCH₃ | OCH₃ | H | L-18a | |
| CH | CH | NCH₃ | O | OCH₃ | OCH₃ | H | L-20a | |
| CH | CH | NCH₃ | O | OCH₃ | OCH₃ | H | L-22a | |
| CH | CH | NCH₃ | S | OCH₃ | OCH₃ | H | L-1a | |
| CH | CH | NCH₃ | O | OCH₃ | OCH₃ | CH₃ | L-1a | |
| CH | CH | CH₂ | O | CH₃ | CH₃ | H | L-1a | |
| CH | CH | CH₂ | O | CH₃ | CH₃ | H | L-1b | |
| CH | CH | CH₂ | O | CH₃ | CH₃ | H | L-1c | |
| CH | CH | CH₂ | O | CH₃ | CH₃ | H | L-1d | |
| CH | CH | CH₂ | O | CH₃ | CH₃ | H | L-1e | |
| CH | CH | CH₂ | O | CH₃ | CH₃ | H | L-1f | |
| CH | CH | CH₂ | O | CH₃ | CH₃ | H | L-1g | |
| CH | CH | CH₂ | O | CH₃ | CH₃ | H | L-1h | |
| CH | CH | CH₂ | O | CH₃ | CH₃ | H | L-1i | |
| CH | CH | CH₂ | O | CH₃ | CH₃ | H | L-1j | |
| CH | CH | CH₂ | O | CH₃ | CH₃ | H | L-1k | |
| CH | CH | CH₂ | O | CH₃ | CH₃ | H | L-3a | |
| CH | CH | CH₂ | O | CH₃ | CH₃ | H | L-3b | |
| CH | CH | CH₂ | O | CH₃ | CH₃ | H | L-4a | |
| CH | CH | CH₂ | O | CH₃ | CH₃ | H | L-7a | |
| CH | CH | CH₂ | O | CH₃ | CH₃ | H | L-8a | |
| CH | CH | CH₂ | O | CH₃ | CH₃ | H | L-12a | |
| CH | CH | CH₂ | O | CH₃ | CH₃ | H | L-12b | |
| CH | CH | CH₂ | O | CH₃ | CH₃ | H | L-14a | |
| CH | CH | CH₂ | O | CH₃ | CH₃ | H | L-15a | |
| CH | CH | CH₂ | O | CH₃ | CH₃ | H | L-16a | |
| CH | CH | CH₂ | O | CH₃ | CH₃ | H | L-16b | |
| CH | CH | CH₂ | O | CH₃ | CH₃ | H | L-18a | |
| CH | CH | CH₂ | O | CH₃ | CH₃ | H | L-20a | |
| CH | CH | CH₂ | O | CH₃ | CH₃ | H | L-22a | |
| CH | CH | CH₂ | S | CH₃ | CH₃ | H | L-1a | |
| CH | CH | CH₂ | O | CH₃ | CH₃ | CH₃ | L-1a | |
| CH | CH | CH₂ | O | OCH₃ | CH₃ | H | L-1a | |
| CH | CH | CH₂ | O | OCH₃ | CH₃ | H | L-1b | |
| CH | CH | CH₂ | O | OCH₃ | CH₃ | H | L-1c | |
| CH | CH | CH₂ | O | OCH₃ | CH₃ | H | L-1d | |
| CH | CH | CH₂ | O | OCH₃ | CH₃ | H | L-1e | |
| CH | CH | CH₂ | O | OCH₃ | CH₃ | H | L-1f | |
| CH | CH | CH₂ | O | OCH₃ | CH₃ | H | L-1g | |
| CH | CH | CH₂ | O | OCH₃ | CH₃ | H | L-1h | |
| CH | CH | CH₂ | O | OCH₃ | CH₃ | H | L-1i | |
| CH | CH | CH₂ | O | OCH₃ | CH₃ | H | L-1j | |
| CH | CH | CH₂ | O | OCH₃ | CH₃ | H | L-1k | |
| CH | CH | CH₂ | O | OCH₃ | CH₃ | H | L-3a | |
| CH | CH | CH₂ | O | OCH₃ | CH₃ | H | L-3b | |
| CH | CH | CH₂ | O | OCH₃ | CH₃ | H | L-4a | |
| CH | CH | CH₂ | O | OCH₃ | CH₃ | H | L-7a | |
| CH | CH | CH₂ | O | OCH₃ | CH₃ | H | L-8a | |
| CH | CH | CH₂ | O | OCH₃ | CH₃ | H | L-8b | |
| CH | CH | CH₂ | O | OCH₃ | CH₃ | H | L-9a | |
| CH | CH | CH₂ | O | OCH₃ | CH₃ | H | L-12a | |
| CH | CH | CH₂ | O | OCH₃ | CH₃ | H | L-12b | |
| CH | CH | CH₂ | O | OCH₃ | CH₃ | H | L-14a | |
| CH | CH | CH₂ | O | OCH₃ | CH₃ | H | L-15a | |
| CH | CH | CH₂ | O | OCH₃ | CH₃ | H | L-16a | |
| CH | CH | CH₂ | O | OCH₃ | CH₃ | H | L-16b | |
| CH | CH | CH₂ | O | OCH₃ | CH₃ | H | L-18a | |
| CH | CH | CH₂ | O | OCH₃ | CH₃ | H | L-20a | |
| CH | CH | CH₂ | O | OCH₃ | CH₃ | H | L-22a | |
| CH | CH | CH₂ | S | OCH₃ | CH₃ | H | L-1a | |
| CH | CH | CH₂ | O | OCH₃ | CH₃ | CH₃ | L-1a | |
| CH | CH | CH₂ | O | CH₃ | OCH₃ | H | L-1a | |
| CH | CH | CH₂ | O | CH₃ | OCH₃ | H | L-1b | |
| CH | CH | CH₂ | O | CH₃ | OCH₃ | H | L-1c | |
| CH | CH | CH₂ | O | CH₃ | OCH₃ | H | L-1d | |
| CH | CH | CH₂ | O | CH₃ | OCH₃ | H | L-1e | |
| CH | CH | CH₂ | O | CH₃ | OCH₃ | H | L-1f | |
| CH | CH | CH₂ | O | CH₃ | OCH₃ | H | L-1g | |
| CH | CH | CH₂ | O | CH₃ | OCH₃ | H | L-1h | |
| CH | CH | CH₂ | O | CH₃ | OCH₃ | H | L-1i | |
| CH | CH | CH₂ | O | CH₃ | OCH₃ | H | L-1j | |
| CH | CH | CH₂ | O | CH₃ | OCH₃ | H | L-1k | |
| CH | CH | CH₂ | O | CH₃ | OCH₃ | H | L-3a | |
| CH | CH | CH₂ | O | CH₃ | OCH₃ | H | L-3b | |
| CH | CH | CH₂ | O | CH₃ | OCH₃ | H | L-4a |

TABLE 4-continued

General Formula 4

| Z | $Z_1$ | $Z_4$ | W | X | Y | R | L | m.p. (°C.) |
|---|---|---|---|---|---|---|---|---|
| CH | CH | $CH_2$ | O | $CH_3$ | $OCH_3$ | H | L-7a | |
| CH | CH | $CH_2$ | O | $CH_3$ | $OCH_3$ | H | L-8a | |
| CH | CH | $CH_2$ | O | $CH_3$ | $OCH_3$ | H | L-8b | |
| CH | CH | $CH_2$ | O | $CH_3$ | $OCH_3$ | H | L-9a | |
| CH | CH | $CH_2$ | O | $CH_3$ | $OCH_3$ | H | L-12a | |
| CH | CH | $CH_2$ | O | $CH_3$ | $OCH_3$ | H | L-12b | |
| CH | CH | $CH_2$ | O | $CH_3$ | $OCH_3$ | H | L-14a | |
| CH | CH | $CH_2$ | O | $CH_2$ | $OCH_3$ | H | L-15a | |
| CH | CH | $CH_2$ | O | $CH_3$ | $OCH_3$ | H | L-16a | |
| CH | CH | $CH_2$ | O | $CH_3$ | $OCH_3$ | H | L-16b | |
| CH | CH | $CH_2$ | O | $CH_3$ | $OCH_3$ | H | L-18a | |
| CH | CH | $CH_2$ | O | $CH_3$ | $OCH_3$ | H | L-20a | |
| CH | CH | $CH_2$ | O | $CH_3$ | $OCH_3$ | H | L-22a | |
| CH | CH | $CH_2$ | S | $CH_3$ | $OCH_3$ | H | L-1a | |
| CH | CH | $CH_2$ | O | $CH_3$ | $OCH_3$ | $CH_3$ | L-1a | |
| N | CH | $NCH_3$ | O | $CH_3$ | $CH_3$ | H | L-1a | |
| N | CH | $NCH_3$ | O | $CH_3$ | $CH_3$ | H | L-1b | |
| N | CH | $NCH_3$ | O | $CH_3$ | $CH_3$ | H | L-1c | |
| N | CH | $NCH_3$ | O | $CH_3$ | $CH_3$ | H | L-1d | |
| N | CH | $NCH_3$ | O | $CH_3$ | $CH_3$ | H | L-1e | |
| N | CH | $NCH_3$ | O | $CH_3$ | $CH_3$ | H | L-1f | |
| N | CH | $NCH_3$ | O | $CH_3$ | $CH_3$ | H | L-1g | |
| N | CH | $NCH_3$ | O | $CH_3$ | $CH_3$ | H | L-1h | |
| N | CH | $NCH_3$ | O | $CH_3$ | $CH_3$ | H | L-1i | |
| N | CH | $NCH_3$ | O | $CH_3$ | $CH_3$ | H | L-1j | |
| N | CH | $NCH_3$ | O | $CH_3$ | $CH_3$ | H | L-1k | |
| N | CH | $NCH_3$ | O | $CH_3$ | $CH_3$ | H | L-3a | |
| N | CH | $NCH_3$ | O | $CH_3$ | $CH_3$ | H | L-3b | |
| N | CH | $NCH_3$ | O | $CH_3$ | $CH_3$ | H | L-4a | |
| N | CH | $NCH_3$ | O | $CH_3$ | $CH_3$ | H | L-7a | |
| N | CH | NCH | O | $CH_3$ | $CH_3$ | H | L-8a | |
| N | CH | $NCH_3$ | O | $CH_3$ | $CH_3$ | H | L-8b | |
| N | CH | $NCH_3$ | O | $CH_3$ | $CH_3$ | H | L-9a | |
| N | CH | $NCH_3$ | O | $CH_3$ | $CH_3$ | H | L-12a | |
| N | CH | $NCH_3$ | O | $CH_3$ | $CH_3$ | H | L-12b | |
| N | CH | $NCH_3$ | O | $CH_3$ | $CH_3$ | H | L-14a | |
| N | CH | $NCH_3$ | O | $CH_3$ | $CH_3$ | H | L-15a | |
| N | CH | $NCH_3$ | O | $CH_3$ | $CH_3$ | H | L-16a | |
| N | CH | $NCH_3$ | O | $CH_3$ | $CH_3$ | H | L-16b | |
| N | CH | $NCH_3$ | O | $CH_3$ | $CH_3$ | H | L-18a | |
| N | CH | $NCH_3$ | O | $CH_3$ | $CH_3$ | H | L-20a | |
| N | CH | $NCH_3$ | O | $CH_3$ | $CH_3$ | H | L-22a | |
| N | CH | $NCH_3$ | S | $CH_3$ | $CH_3$ | H | L-1a | |
| N | CH | $NCH_3$ | O | $CH_3$ | $CH_3$ | $CH_3$ | L-1a | |
| N | CH | $NCH_3$ | O | $OCH_3$ | $CH_3$ | H | L-1a | |
| N | CH | $NCH_3$ | O | $OCH_3$ | $CH_3$ | H | L-1b | |
| N | CH | $NCH_3$ | O | $OCH_3$ | $CH_3$ | H | L-1c | |
| N | CH | $NCH_3$ | O | $OCH_3$ | $CH_3$ | H | L-1d | |
| N | CH | $NCH_3$ | O | $OCH_3$ | $CH_3$ | H | L-1e | |
| N | CH | $NCH_3$ | O | $OCH_3$ | $CH_3$ | H | L-1f | |
| N | CH | $NCH_3$ | O | $OCH_3$ | $CH_3$ | H | L-1g | |
| N | CH | $NCH_3$ | O | $OCH_3$ | $CH_3$ | H | L-1h | |
| N | CH | $NCH_3$ | O | $OCH_3$ | $CH_3$ | H | L-1i | |
| N | CH | $NCH_3$ | O | $OCH_3$ | $CH_3$ | H | L-1j | |
| N | CH | $NCH_3$ | O | $OCH_3$ | $CH_3$ | H | L-1k | |
| N | CH | $NCH_3$ | O | $OCH_3$ | $CH_3$ | H | L-3a | |
| N | CH | $NCH_3$ | O | $OCH_3$ | $CH_3$ | H | L-3b | |
| N | CH | $NCH_3$ | O | $OCH_3$ | $CH_3$ | H | L-4a | |
| N | CH | $NCH_3$ | O | $OCH_3$ | $CH_3$ | H | L-7a | |
| N | CH | $NCH_3$ | O | $OCH_3$ | $CH_3$ | H | L-8a | |
| N | CH | $NCH_3$ | O | $OCH_3$ | $CH_3$ | H | L-8b | |
| N | CH | $NCH_3$ | O | $OCH_3$ | $CH_3$ | H | L-9a | |
| N | CH | $NCH_3$ | O | $OCH_3$ | $CH_3$ | H | L-12a | |
| N | CH | $NCH_3$ | O | $OCH_3$ | $CH_3$ | H | L-12b | |
| N | CH | $NCH_3$ | O | $OCH_3$ | $CH_3$ | H | L-14a | |
| N | CH | $NCH_3$ | O | $OCH_3$ | $CH_3$ | H | L-15a | |
| N | CH | $NCH_3$ | O | $OCH_3$ | $CH_3$ | H | L-16a | |
| N | CH | $NCH_3$ | O | $OCH_3$ | $CH_3$ | H | L-16b | |
| N | CH | $NCH_3$ | O | $OCH_3$ | $CH_3$ | H | L-18a | |
| N | CH | $NCH_3$ | O | $OCH_3$ | $CH_3$ | H | L-20a | |
| N | CH | $NCH_3$ | O | $OCH_3$ | $CH_3$ | H | L-22a | |
| N | CH | $NCH_3$ | S | $OCH_3$ | $CH_3$ | H | L-1a | |
| N | CH | $NCH_3$ | O | $OCH_3$ | $CH_3$ | $CH_3$ | L-1a | |
| N | CH | $NCH_3$ | O | $CH_3$ | $OCH_3$ | H | L-1a | |
| N | CH | $NCH_3$ | O | $CH_3$ | $OCH_3$ | H | L-1b | |
| N | CH | $NCH_3$ | O | $CH_3$ | $OCH_3$ | H | L-1c | |
| N | CH | $NCH_3$ | O | $CH_3$ | $OCH_3$ | H | L-1d | |
| N | CH | $NCH_3$ | O | $CH_3$ | $OCH_3$ | H | L-1e | |
| N | CH | $NCH_3$ | O | $CH_3$ | $OCH_3$ | H | L-1f | |
| N | CH | $NCH_3$ | O | $CH_3$ | $OCH_3$ | H | L-1g | |
| N | CH | $NCH_3$ | O | $CH_3$ | $OCH_3$ | H | L-1h | |
| N | CH | $NCH_3$ | O | $CH_3$ | $OCH_3$ | H | L-1i | |
| N | CH | $NCH_3$ | O | $CH_3$ | $OCH_3$ | H | L-1j | |
| N | CH | $NCH_3$ | O | $CH_3$ | $OCH_3$ | H | L-1k | |
| N | CH | $NCH_3$ | O | $CH_3$ | $OCH_3$ | H | L-3a | |
| N | CH | $NCH_3$ | O | $CH_3$ | $OCH_3$ | H | L-3b | |
| N | CH | $NCH_3$ | O | $CH_3$ | $OCH_3$ | H | L-4a | |
| N | CH | $NCH_3$ | O | $CH_3$ | $OCH_3$ | H | L-7a | |
| N | CH | $NCH_3$ | O | $CH_3$ | $OCH_3$ | H | L-8a | |
| N | CH | $NCH_3$ | O | $CH_3$ | $OCH_3$ | H | L-8b | |
| N | CH | $NCH_3$ | O | $CH_3$ | $OCH_3$ | H | L-9a | |
| N | CH | $NCH_3$ | O | $CH_3$ | $OCH_3$ | H | L-12a | |
| N | CH | $NCH_3$ | O | $CH_3$ | $OCH_3$ | H | L-12b | |
| N | CH | $NCH_3$ | O | $CH_3$ | $OCH_3$ | H | L-14a | |
| N | CH | $NCH_3$ | O | $CH_3$ | $OCH_3$ | H | L-15a | |
| N | CH | $NCH_3$ | O | $CH_3$ | $OCH_3$ | H | L-16a | |
| N | CH | $NCH_3$ | O | $CH_3$ | $OCH_3$ | H | L-16b | |
| N | CH | $NCH_3$ | O | $CH_3$ | $OCH_3$ | H | L-18a | |
| N | CH | $NCH_3$ | O | $CH_3$ | $OCH_3$ | H | L-20a | |
| N | CH | $NCH_3$ | O | $CH_3$ | $OCH_3$ | H | L-22a | |
| N | CH | $NCH_3$ | S | $CH_3$ | $OCH_3$ | H | L-1a | |
| N | CH | $NCH_3$ | O | $CH_3$ | $OCH_3$ | $CH_3$ | L-1a | |
| N | CH | $NCH_3$ | O | $OCH_3$ | $OCH_3$ | H | L-1a | |
| N | CH | $NCH_3$ | O | $OCH_3$ | $OCH_3$ | H | L-1b | |
| N | CH | $NCH_3$ | O | $OCH_3$ | $OCH_3$ | H | L-1c | |
| N | CH | $NCH_3$ | O | $OCH_3$ | $OCH_3$ | H | L-1d | |
| N | CH | $NCH_3$ | O | $OCH_3$ | $OCH_3$ | H | L-1e | |
| N | CH | $NCH_3$ | O | $OCH_3$ | $OCH_3$ | H | L-1f | |
| N | CH | $NCH_3$ | O | $OCH_3$ | $OCH_3$ | H | L-1g | |
| N | CH | $NCH_3$ | O | $OCH_3$ | $OCH_3$ | H | L-1h | |
| N | CH | $NCH_3$ | O | $OCH_3$ | $OCH_3$ | H | L-1i | |
| N | CH | $NCH_3$ | O | $OCH_3$ | $OCH_3$ | H | L-1j | |
| N | CH | $NCH_3$ | O | $OCH_3$ | $OCH_3$ | H | L-1k | |
| N | CH | $NCH_3$ | O | $OCH_3$ | $OCH_3$ | H | L-3a | |
| N | CH | $NCH_3$ | O | $OCH_3$ | $OCH_3$ | H | L-3b | |
| N | CH | $NCH_3$ | O | $OCH_3$ | $OCH_3$ | H | L-4a | |
| N | CH | $NCH_3$ | O | $OCH_3$ | $OCH_3$ | H | L-7a | |
| N | CH | $NCH_3$ | O | $OCH_3$ | $OCH_3$ | H | L-8a | |
| N | CH | $NCH_3$ | O | $OCH_3$ | $OCH_3$ | H | L-8b | |
| N | CH | $NCH_3$ | O | $OCH_3$ | $OCH_3$ | H | L-9a | |
| N | CH | $NCH_3$ | O | $OCH_3$ | $OCH_3$ | H | L-12a | |
| N | CH | $NCH_3$ | O | $OCH_3$ | $OCH_3$ | H | L-12b | |
| N | CH | $NCH_3$ | O | $OCH_3$ | $OCH_3$ | H | L-14a | |
| N | CH | $NCH_3$ | O | $OCH_3$ | $OCH_3$ | H | L-15a | |
| N | CH | $NCH_3$ | O | $OCH_3$ | $OCH_3$ | H | L-16a | |
| N | CH | $NCH_3$ | O | $OCH_3$ | $OCH_3$ | H | L-16b | |
| N | CH | $NCH_3$ | O | $OCH_3$ | $OCH_3$ | H | L-18a | |
| N | CH | $NCH_3$ | O | $OCH_3$ | $OCH_3$ | H | L-20a | |
| N | CH | $NCH_3$ | O | $OCH_3$ | $OCH_3$ | H | L-22a | |
| N | CH | $NCH_3$ | S | $OCH_3$ | $OCH_3$ | H | L-1a | |
| N | CH | $NCH_3$ | O | $OCH_3$ | $OCH_3$ | $CH_3$ | L-1a | |
| N | CH | $CH_2$ | O | $CH_3$ | $CH_3$ | H | L-1a | |
| N | CH | $CH_2$ | O | $CH_3$ | $CH_3$ | H | L-1b | |
| N | CH | $CH_2$ | O | $CH_3$ | $CH_3$ | H | L-1c | |
| N | CH | $CH_2$ | O | $CH_3$ | $CH_3$ | H | L-1d | |
| N | CH | $CH_2$ | O | $CH_3$ | $CH_3$ | H | L-1e | |
| N | CH | $CH_2$ | O | $CH_3$ | $CH_3$ | H | L-1f | |
| N | CH | $CH_2$ | O | $CH_3$ | $CH_3$ | H | L-1g | |
| N | CH | $CH_2$ | O | $CH_3$ | $CH_3$ | H | L-1h | |
| N | CH | $CH_2$ | O | $CH_3$ | $CH_3$ | H | L-1i | |
| N | CH | $CH_2$ | O | $CH_3$ | $CH_3$ | H | L-1j | |
| N | CH | $CH_2$ | O | $CH_3$ | $CH_3$ | H | L-1k | |
| N | CH | $CH_2$ | O | $CH_3$ | $CH_3$ | H | L-3a | |
| N | CH | $CH_2$ | O | $CH_3$ | $CH_3$ | H | L-3b | |
| N | CH | $CH_2$ | O | $CH_3$ | $CH_3$ | H | L-4a | |
| N | CH | $CH_2$ | O | $CH_3$ | $CH_3$ | H | L-7a | |
| N | CH | $CH_2$ | O | $CH_3$ | $CH_3$ | H | L-8a | |
| N | CH | $CH_2$ | O | $CH_3$ | $CH_3$ | H | L-8b | |
| N | CH | $CH_2$ | O | $CH_3$ | $CH_3$ | H | L-9a | |
| N | CH | $CH_2$ | O | $CH_3$ | $CH_3$ | H | L-12a | |
| N | CH | $CH_2$ | O | $CH_3$ | $CH_3$ | H | L-12b | |
| N | CH | $CH_2$ | O | $CH_3$ | $CH_3$ | H | L-14a | |
| N | CH | $CH_2$ | O | $CH_3$ | $CH_3$ | H | L-15a | |
| N | CH | $CH_2$ | O | $CH_3$ | $CH_3$ | H | L-16a | |
| N | CH | $CH_2$ | O | $CH_3$ | $CH_3$ | H | L-16b | |
| N | CH | $CH_2$ | O | $CH_3$ | $CH_3$ | H | L-18a | |

TABLE 4-continued

General Formula 4

| Z | Z₁ | Z₄ | W | X | Y | R | L | m.p. (°C.) |
|---|----|----|----|----|----|----|----|----|
| N | CH | CH₂ | O | CH₃ | CH₃ | H | L-20a | |
| N | CH | CH₂ | O | CH₃ | CH₃ | H | L-22a | |
| N | CH | CH₂ | S | CH₃ | CH₃ | H | L-1a | |
| N | CH | CH₂ | O | CH₃ | CH₃ | CH₃ | L-1a | |
| N | CH | CH₂ | O | OCH₃ | CH₃ | H | L-1a | |
| N | CH | CH₂ | O | OCH₃ | CH₃ | H | L-1b | |
| N | CH | CH₂ | O | OCH₃ | CH₃ | H | L-1c | |
| N | CH | CH₂ | O | OCH₃ | CH₃ | H | L-1d | |
| N | CH | CH₂ | O | OCH₃ | CH₃ | H | L-1e | |
| N | CH | CH₂ | O | OCH₃ | CH₃ | H | L-1f | |
| N | CH | CH₂ | O | OCH₃ | CH₃ | H | L-1g | |
| N | CH | CH₂ | O | OCH₃ | CH₃ | H | L-1h | |
| N | CH | CH₂ | O | OCH₃ | CH₃ | H | L-1i | |
| N | CH | CH₂ | O | OCH₃ | CH₃ | H | L-1j | |
| N | CH | CH₂ | O | OCH₃ | CH₃ | H | L-1k | |
| N | CH | CH₂ | O | OCH₃ | CH₃ | H | L-3a | |
| N | CH | CH₂ | O | OCH₃ | CH₃ | H | L-3b | |
| N | CH | CH₂ | O | OCH₃ | CH₃ | H | L-4a | |
| N | CH | CH₂ | O | OCH₃ | CH₃ | H | L-7a | |
| N | CH | CH₂ | O | OCH₃ | CH₃ | H | L-8a | |
| N | CH | CH₂ | O | OCH₃ | CH₃ | H | L-8b | |
| N | CH | CH₂ | O | OCH₃ | CH₃ | H | L-9a | |
| N | CH | CH₂ | O | OCH₃ | CH₃ | H | L-12a | |
| N | CH | CH₂ | O | OCH₃ | CH₃ | H | L-12b | |
| N | CH | CH₂ | O | OCH₃ | CH₃ | H | L-14a | |
| N | CH | CH₂ | O | OCH₃ | CH₃ | H | L-15a | |
| N | CH | CH₂ | O | OCH₃ | CH₃ | H | L-16a | |
| N | CH | CH₂ | O | OCH₃ | CH₃ | H | L-16b | |
| N | CH | CH₂ | O | OCH₃ | CH₃ | H | L-18a | |
| N | CH | CH₂ | O | OCH₃ | CH₃ | H | L-20a | |
| N | CH | CH₂ | O | OCH₃ | CH₃ | H | L-22a | |
| N | CH | CH₂ | S | OCH₃ | CH₃ | H | L-1a | |
| N | CH | CH₂ | O | CH₃ | CH₃ | CH₃ | L-1a | |
| N | CH | CH₂ | O | CH₃ | OCH₃ | H | L-1a | |
| N | CH | CH₂ | O | CH₃ | OCH₃ | H | L-1b | |
| N | CH | CH₂ | O | CH₃ | OCH₃ | H | L-1c | |
| N | CH | CH₂ | O | CH₃ | OCH₃ | H | L-1d | |
| N | CH | CH₂ | O | CH₃ | OCH₃ | H | L-1e | |
| N | CH | CH₂ | O | CH₃ | OCH₃ | H | L-1f | |
| N | CH | CH₂ | O | CH₃ | OCH₃ | H | L-1g | |
| N | CH | CH₂ | O | CH₃ | OCH₃ | H | L-1h | |
| N | CH | CH₂ | O | CH₃ | OCH₃ | H | L-1i | |
| N | CH | CH₂ | O | CH₃ | OCH₃ | H | L-1j | |
| N | CH | CH₂ | O | CH₃ | OCH₃ | H | L-1k | |
| N | CH | CH₂ | O | CH₃ | OCH₃ | H | L-3a | |
| N | CH | CH₂ | O | CH₃ | OCH₃ | H | L-3b | |
| N | CH | CH₂ | O | CH₃ | OCH₃ | H | L-4a | |
| N | CH | CH₂ | O | CH₃ | OCH₃ | H | L-7a | |
| N | CH | CH₂ | O | CH₃ | OCH₃ | H | L-8a | |
| N | CH | CH₂ | O | CH₃ | OCH₃ | H | L-8b | |
| N | CH | CH₂ | O | CH₃ | OCH₃ | H | L-9a | |
| N | CH | CH₂ | O | CH₃ | OCH₃ | H | L-12a | |
| N | CH | CH₂ | O | CH₃ | OCH₃ | H | L-12b | |
| N | CH | CH₂ | O | CH₃ | OCH₃ | H | L-14a | |
| N | CH | CH₂ | O | CH₃ | OCH₃ | H | L-15a | |
| N | CH | CH₂ | O | CH₃ | OCH₃ | H | L-16a | |
| N | CH | CH₂ | O | CH₃ | OCH₃ | H | L-16b | |
| N | CH | CH₂ | O | CH₃ | OCH₃ | H | L-18a | |
| N | CH | CH₂ | O | CH₃ | OCH₃ | H | L-20a | |
| N | CH | CH₂ | O | CH₃ | OCH₃ | H | L-22a | |
| N | CH | CH₂ | S | CH₃ | OCH₃ | H | L-1a | |
| N | CH | CH₂ | O | CH₃ | OCH₃ | CH₃ | L-1a | |
| N | CH | CH₂ | O | OCH₃ | OCH₃ | H | L-1a | |
| N | CH | CH₂ | O | OCH₃ | OCH₃ | H | L-1b | |
| N | CH | CH₂ | O | OCH₃ | OCH₃ | H | L-1c | |
| N | CH | CH₂ | O | OCH₃ | OCH₃ | H | L-1d | |
| N | CH | CH₂ | O | OCH₃ | OCH₃ | H | L-1e | |
| N | CH | CH₂ | O | OCH₃ | OCH₃ | H | L-1f | |
| N | CH | CH₂ | O | OCH₃ | OCH₃ | H | L-1g | |
| N | CH | CH₂ | O | OCH₃ | OCH₃ | H | L-1h | |
| N | CH | CH₂ | O | OCH₃ | OCH₃ | H | L-1i | |
| N | CH | CH₂ | O | OCH₃ | OCH₃ | H | L-1j | |
| N | CH | CH₂ | O | OCH₃ | OCH₃ | H | L-1k | |
| N | CH | CH₂ | O | OCH₃ | OCH₃ | H | L-3a | |
| N | CH | CH₂ | O | OCH₃ | OCH₃ | H | L-3b | |
| N | CH | CH₂ | O | OCH₃ | OCH₃ | H | L-4a | |
| N | CH | CH₂ | O | OCH₃ | OCH₃ | H | L-7a | |
| N | CH | CH₂ | O | OCH₃ | OCH₃ | H | L-8a | |
| N | CH | CH₂ | O | OCH₃ | OCH₃ | H | L-8b | |
| N | CH | CH₂ | O | OCH₃ | OCH₃ | H | L-9a | |
| N | CH | CH₂ | O | OCH₃ | OCH₃ | H | L-12a | |
| N | CH | CH₂ | O | OCH₃ | OCH₃ | H | L-12b | |
| N | CH | CH₂ | O | OCH₃ | OCH₃ | H | L-14a | |
| N | CH | CH₂ | O | OCH₃ | OCH₃ | H | L-15a | |
| N | CH | CH₂ | O | OCH₃ | OCH₃ | H | L-16a | |
| N | CH | CH₂ | O | OCH₃ | OCH₃ | H | L-16b | |
| N | CH | CH₂ | O | OCH₃ | OCH₃ | H | L-18a | |
| N | CH | CH₂ | O | OCH₃ | OCH₃ | H | L-20a | |
| N | CH | CH₂ | O | OCH₃ | OCH₃ | H | L-22a | |
| N | CH | CH₂ | S | OCH₃ | OCH₃ | H | L-1a | |
| N | CH | CH₂ | O | OCH₃ | OCH₃ | CH₃ | L-1a | |

TABLE 5

General Formula 5

| Z | Z₁ | Z₂ | Z₃ | W | X | Y | R | L | m.p. (°C.) |
|---|----|----|----|----|----|----|----|----|----|
| CH | N | CH | CH | O | CH₃ | CH₃ | H | L-1a | |
| CH | N | CH | CH | O | CH₃ | CH₃ | H | L-1b | |
| CH | N | CH | CH | O | CH₃ | CH₃ | H | L-1c | |
| CH | N | CH | CH | O | CH₃ | CH₃ | H | L-1d | |
| CH | N | CH | CH | O | CH₃ | CH₃ | H | L-1e | |
| CH | N | CH | CH | O | CH₃ | CH₃ | H | L-1f | |
| CH | N | CH | CH | O | CH₃ | CH₃ | H | L-1g | |
| CH | N | CH | CH | O | CH₃ | CH₃ | H | L-1h | |
| CH | N | CH | CH | O | CH₃ | CH₃ | H | L-1i | |
| CH | N | CH | CH | O | CH₃ | CH₃ | H | L-1j | |
| CH | N | CH | CH | O | CH₃ | CH₃ | H | L-1k | |
| CH | N | CH | CH | O | CH₃ | CH₃ | H | L-3a | |
| CH | N | CH | CH | O | CH₃ | CH₃ | H | L-3b | |
| CH | N | CH | CH | O | CH₃ | CH₃ | H | L-4a | |
| CH | N | CH | CH | O | CH₃ | CH₃ | H | L-7a | |
| CH | N | CH | CH | O | CH₃ | CH₃ | H | L-8a | |
| CH | N | CH | CH | O | CH₃ | CH₃ | H | L-8b | |
| CH | N | CH | CH | O | CH₃ | CH₃ | H | L-9a | |
| CH | N | CH | CH | O | CH₃ | CH₃ | H | L-12a | |
| CH | N | CH | CH | O | CH₃ | CH₃ | H | L-12b | |
| CH | N | CH | CH | O | CH₃ | CH₃ | H | L-14a | |
| CH | N | CH | CH | O | CH₃ | CH₃ | H | L-15a | |
| CH | N | CH | CH | O | CH₃ | CH₃ | H | L-16a | |
| CH | N | CH | CH | O | CH₃ | CH₃ | H | L-16b | |
| CH | N | CH | CH | O | CH₃ | CH₃ | H | L-18a | |
| CH | N | CH | CH | O | CH₃ | CH₃ | H | L-20a | |
| CH | N | CH | CH | O | CH₃ | CH₃ | H | L-22a | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| CH | N | CH | CH | S | $CH_3$ | $CH_3$ | H | L-1a | |
| CH | N | CH | CH | O | $CH_3$ | $CH_3$ | $CH_3$ | L-1a | |
| CH | N | CH | CH | O | $OCH_3$ | $CH_3$ | H | L-1a | |
| CH | N | CH | CH | O | $OCH_3$ | $CH_3$ | H | L-1b | |
| CH | N | CH | CH | O | $OCH_3$ | $CH_3$ | H | L-1c | |
| CH | N | CH | CH | O | $OCH_3$ | $CH_3$ | H | L-1d | |
| CH | N | CH | CH | O | $OCH_3$ | $CH_3$ | H | L-1e | |
| CH | N | CH | CH | O | $OCH_3$ | $CH_3$ | H | L-1f | |
| CH | N | CH | CH | O | $OCH_3$ | $CH_3$ | H | L-1g | |
| CH | N | CH | CH | O | $OCH_3$ | $CH_3$ | H | L-1h | |
| CH | N | CH | CH | O | $OCH_3$ | $CH_3$ | H | L-1i | |
| CH | N | CH | CH | O | $OCH_3$ | $CH_3$ | H | L-1j | |
| CH | N | CH | CH | O | $OCH_3$ | $CH_3$ | H | L-1k | |
| CH | N | CH | CH | O | $OCH_3$ | $CH_3$ | H | L-3a | |
| CH | N | CH | CH | O | $OCH_3$ | $CH_3$ | H | L-3b | |
| CH | N | CH | CH | O | $OCH_3$ | $CH_3$ | H | L-4a | |
| CH | N | CH | CH | O | $OCH_3$ | $CH_3$ | H | L-7a | |
| CH | N | CH | CH | O | $OCH_3$ | $CH_3$ | H | L-8a | |
| CH | N | CH | CH | O | $OCH_3$ | $CH_3$ | H | L-8b | |
| CH | N | CH | CH | O | $OCH_3$ | $CH_3$ | H | L-9a | |
| CH | N | CH | CH | O | $OCH_3$ | $CH_3$ | H | L-12a | |
| CH | N | CH | CH | O | $OCH_3$ | $CH_3$ | H | L-12b | |
| CH | N | CH | CH | O | $OCH_3$ | $CH_3$ | H | L-14a | |
| CH | N | CH | CH | O | $OCH_3$ | $CH_3$ | H | L-15a | |
| CH | N | CH | CH | O | $OCH_3$ | $CH_3$ | H | L-16a | |
| CH | N | CH | CH | O | $OCH_3$ | $CH_3$ | H | L-16b | |
| CH | N | CH | CH | O | $OCH_3$ | $CH_3$ | H | L-18a | |
| CH | N | CH | CH | O | $OCH_3$ | $CH_3$ | H | L-20a | |
| CH | N | CH | CH | O | $OCH_3$ | $CH_3$ | H | L-22a | |
| CH | N | CH | CH | S | $OCH_3$ | $CH_3$ | H | L-1a | |
| CH | N | CH | CH | O | $OCH_3$ | $CH_3$ | $CH_3$ | L-1a | |
| CH | N | CH | CH | O | $CH_3$ | $OCH_3$ | H | L-1a | |
| CH | N | CH | CH | O | $CH_3$ | $OCH_3$ | H | L-1b | |
| CH | N | CH | CH | O | $CH_3$ | $OCH_3$ | H | L-1c | |
| CH | N | CH | CH | O | $CH_3$ | $OCH_3$ | H | L-1d | |
| CH | N | CH | CH | O | $CH_3$ | $OCH_3$ | H | L-1e | |
| CH | N | CH | CH | O | $CH_3$ | $OCH_3$ | H | L-1f | |
| CH | N | CH | CH | O | $CH_3$ | $OCH_3$ | H | L-1g | |
| CH | N | CH | CH | O | $CH_3$ | $OCH_3$ | H | L-1h | |
| CH | N | CH | CH | O | $CH_3$ | $OCH_3$ | H | L-1i | |
| CH | N | CH | CH | O | $CH_3$ | $OCH_3$ | H | L-1j | |
| CH | N | CH | CH | O | $CH_3$ | $OCH_3$ | H | L-1k | |
| CH | N | CH | CH | O | $CH_3$ | $OCH_3$ | H | L-3a | |
| CH | N | CH | CH | O | $CH_3$ | $OCH_3$ | H | L-3b | |
| CH | N | CH | CH | O | $CH_3$ | $OCH_3$ | H | L-4a | |
| CH | N | CH | CH | O | $CH_3$ | $OCH_3$ | H | L-7a | |
| CH | N | CH | CH | O | $CH_3$ | $OCH_3$ | H | L-8a | |
| CH | N | CH | CH | O | $CH_3$ | $OCH_3$ | H | L-8b | |
| CH | N | CH | CH | O | $CH_3$ | $OCH_3$ | H | L-9a | |
| CH | N | CH | CH | O | $CH_3$ | $OCH_3$ | H | L-12a | |
| CH | N | CH | CH | O | $CH_3$ | $OCH_3$ | H | L-12b | |
| CH | N | CH | CH | O | $CH_3$ | $OCH_3$ | H | L-14a | |
| CH | N | CH | CH | O | $CH_3$ | $OCH_3$ | H | L-15a | |
| CH | N | CH | CH | O | $CH_3$ | $OCH_3$ | H | L-16a | |
| CH | N | CH | CH | O | $CH_3$ | $OCH_3$ | H | L-16b | |
| CH | N | CH | CH | O | $CH_3$ | $OCH_3$ | H | L-18a | |
| CH | N | CH | CH | O | $CH_3$ | $OCH_3$ | H | L-20a | |
| CH | N | CH | CH | O | $CH_3$ | $OCH_3$ | H | L-22a | |
| CH | N | CH | CH | S | $CH_3$ | $OCH_3$ | H | L-1a | |
| CH | N | CH | CH | O | $CH_3$ | $OCH_3$ | $CH_3$ | L-1a | |
| CH | N | CH | CH | O | $OCH_3$ | $OCH_3$ | H | L-1a | |
| CH | N | CH | CH | O | $OCH_3$ | $OCH_3$ | H | L-1b | |
| CH | N | CH | CH | O | $OCH_3$ | $OCH_3$ | H | L-1c | |
| CH | N | CH | CH | O | $OCH_3$ | $OCH_3$ | H | L-1d | |
| CH | N | CH | CH | O | $OCH_3$ | $OCH_3$ | H | L-1e | |
| CH | N | CH | CH | O | $OCH_3$ | $OCH_3$ | H | L-1f | |
| CH | N | CH | CH | O | $OCH_3$ | $OCH_3$ | H | L-1g | |
| CH | N | CH | CH | O | $OCH_3$ | $OCH_3$ | H | L-1h | |
| CH | N | CH | CH | O | $OCH_3$ | $OCH_3$ | H | L-1i | |
| CH | N | CH | CH | O | $OCH_3$ | $OCH_3$ | H | L-1j | |
| CH | N | CH | CH | O | $OCH_3$ | $OCH_3$ | H | L-1k | |
| CH | N | CH | CH | O | $OCH_3$ | $OCH_3$ | H | L-3a | |
| CH | N | CH | CH | O | $OCH_3$ | $OCH_3$ | H | L-3b | |
| CH | N | CH | CH | O | $OCH_3$ | $OCH_3$ | H | L-4a | |
| CH | N | CH | CH | O | $OCH_3$ | $OCH_3$ | H | L-7a | |
| CH | N | CH | CH | O | $OCH_3$ | $OCH_3$ | H | L-8a | |
| CH | N | CH | CH | O | $OCH_3$ | $OCH_3$ | H | L-8b | |
| CH | N | CH | CH | O | $OCH_3$ | $OCH_3$ | H | L-9a | |
| CH | N | CH | CH | O | $OCH_3$ | $OCH_3$ | H | L-12a | |
| CH | N | CH | CH | O | $OCH_3$ | $OCH_3$ | H | L-12b | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| CH | N | CH | CH | O | $OCH_3$ | $OCH_3$ | H | L-14a | |
| CH | N | CH | CH | O | $OCH_3$ | $OCH_3$ | H | L-15a | |
| CH | N | CH | CH | O | $OCH_3$ | $OCH_3$ | H | L-16a | |
| CH | N | CH | CH | O | $OCH_3$ | $OCH_3$ | H | L-16b | |
| CH | N | CH | CH | O | $OCH_3$ | $OCH_3$ | H | L-18a | |
| CH | N | CH | CH | O | $OCH_3$ | $OCH_3$ | H | L-20a | |
| CH | N | CH | CH | O | $OCH_3$ | $OCH_3$ | H | L-22a | |
| CH | N | CH | CH | S | $OCH_3$ | $OCH_3$ | H | L-1a | |
| CH | N | CH | CH | O | $OCH_3$ | $OCH_3$ | $CH_3$ | L-1a | |
| CH | N | N | CH | O | $CH_3$ | $CH_3$ | H | L-1a | |
| CH | N | N | CH | O | $CH_3$ | $CH_3$ | H | L-1b | |
| CH | N | N | CH | O | $CH_3$ | $CH_3$ | H | L-1c | |
| CH | N | N | CH | O | $CH_3$ | $CH_3$ | H | L-1d | |
| CH | N | N | CH | O | $CH_3$ | $CH_3$ | H | L-1e | |
| CH | N | N | CH | O | $CH_3$ | $CH_3$ | H | L-1f | |
| CH | N | N | CH | O | $CH_3$ | $CH_3$ | H | L-1g | |
| CH | N | N | CH | O | $CH_3$ | $CH_3$ | H | L-1h | |
| CH | N | N | CH | O | $CH_3$ | $CH_3$ | H | L-1i | |
| CH | N | N | CH | O | $CH_3$ | $CH_3$ | H | L-1j | |
| CH | N | N | CH | O | $CH_3$ | $CH_3$ | H | L-1k | |
| CH | N | N | CH | O | $CH_3$ | $CH_3$ | H | L-3a | |
| CH | N | N | CH | O | $CH_3$ | $CH_3$ | H | L-3b | |
| CH | N | N | CH | O | $CH_3$ | $CH_3$ | H | L-4a | |
| CH | N | N | CH | O | $CH_3$ | $CH_3$ | H | L-7a | |
| CH | N | N | CH | O | $CH_3$ | $CH_3$ | H | L-8a | |
| CH | N | N | CH | O | $CH_3$ | $CH_3$ | H | L-8b | |
| CH | N | N | CH | O | $CH_3$ | $CH_3$ | H | L-9a | |
| CH | N | N | CH | O | $CH_3$ | $CH_3$ | H | L-12a | |
| CH | N | N | CH | O | $CH_3$ | $CH_3$ | H | L-12b | |
| CH | N | N | CH | O | $CH_3$ | $CH_3$ | H | L-14a | |
| CH | N | N | CH | O | $CH_3$ | $CH_3$ | H | L-15a | |
| CH | N | N | CH | O | $CH_3$ | $CH_3$ | H | L-16a | |
| CH | N | N | CH | O | $CH_3$ | $CH_3$ | H | L-16b | |
| CH | N | N | CH | O | $CH_3$ | $CH_3$ | H | L-18a | |
| CH | N | N | CH | O | $CH_3$ | $CH_3$ | H | L-20a | |
| CH | N | N | CH | O | $CH_3$ | $CH_3$ | H | L-22a | |
| CH | N | N | CH | S | $CH_3$ | $CH_3$ | H | L-1a | |
| CH | N | N | CH | O | $CH_3$ | $CH_3$ | $CH_3$ | L-1a | |
| CH | N | N | CH | O | $OCH_3$ | $CH_3$ | H | L-1a | |
| CH | N | N | CH | O | $OCH_3$ | $CH_3$ | H | L-1b | |
| CH | N | N | CH | O | $OCH_3$ | $CH_3$ | H | L-1c | |
| CH | N | N | CH | O | $OCH_3$ | $CH_3$ | H | L-1d | |
| CH | N | N | CH | O | $OCH_3$ | $CH_3$ | H | L-1e | |
| CH | N | N | CH | O | $OCH_3$ | $CH_3$ | H | L-1f | |
| CH | N | N | CH | O | $OCH_3$ | $CH_3$ | H | L-1g | |
| CH | N | N | CH | O | $OCH_3$ | $CH_3$ | H | L-1h | |
| CH | N | N | CH | O | $OCH_3$ | $CH_3$ | H | L-1i | |
| CH | N | N | CH | O | $OCH_3$ | $CH_3$ | H | L-1j | |
| CH | N | N | CH | O | $OCH_3$ | $CH_3$ | H | L-1k | |
| CH | N | N | CH | O | $OCH_3$ | $CH_3$ | H | L-3a | |
| CH | N | N | CH | O | $OCH_3$ | $CH_3$ | H | L-3b | |
| CH | N | N | CH | O | $OCH_3$ | $CH_3$ | H | L-4a | |
| CH | N | N | CH | O | $OCH_3$ | $CH_3$ | H | L-7a | |
| CH | N | N | CH | O | $OCH_3$ | $CH_3$ | H | L-8a | |
| CH | N | N | CH | O | $OCH_3$ | $CH_3$ | H | L-8b | |
| CH | N | N | CH | O | $OCH_3$ | $CH_3$ | H | L-9a | |
| CH | N | N | CH | O | $OCH_3$ | $CH_3$ | H | L-12a | |
| CH | N | N | CH | O | $OCH_3$ | $CH_3$ | H | L-12b | |
| CH | N | N | CH | O | $OCH_3$ | $CH_3$ | H | L-14a | |
| CH | N | N | CH | O | $OCH_3$ | $CH_3$ | H | L-15a | |
| CH | N | N | CH | O | $OCH_3$ | $CH_3$ | H | L-16a | |
| CH | N | N | CH | O | $OCH_3$ | $CH_3$ | H | L-16b | |
| CH | N | N | CH | O | $OCH_3$ | $CH_3$ | H | L-18a | |
| CH | N | N | CH | O | $OCH_3$ | $CH_3$ | H | L-20a | |
| CH | N | N | CH | O | $OCH_3$ | $CH_3$ | H | L-22a | |
| CH | N | N | CH | S | $OCH_3$ | $CH_3$ | H | L-1a | |
| CH | N | N | CH | O | $OCH_3$ | $CH_3$ | $CH_3$ | L-1a | |
| CH | N | N | CH | O | $CH_3$ | $OCH_3$ | H | L-1a | |
| CH | N | N | CH | O | $CH_3$ | $OCH_3$ | H | L-1b | |
| CH | N | N | CH | O | $CH_3$ | $OCH_3$ | H | L-1c | |
| CH | N | N | CH | O | $CH_3$ | $OCH_3$ | H | L-1d | |
| CH | N | N | CH | O | $CH_3$ | $OCH_3$ | H | L-1e | |
| CH | N | N | CH | O | $CH_3$ | $OCH_3$ | H | L-1f | |
| CH | N | N | CH | O | $CH_3$ | $OCH_3$ | H | L-1g | |
| CH | N | N | CH | O | $CH_3$ | $OCH_3$ | H | L-1h | |
| CH | N | N | CH | O | $CH_3$ | $OCH_3$ | H | L-1i | |
| CH | N | N | CH | O | $CH_3$ | $OCH_3$ | H | L-1j | |
| CH | N | N | CH | O | $CH_3$ | $OCH_3$ | H | L-1k | |
| CH | N | N | CH | O | $CH_3$ | $OCH_3$ | H | L-3a | |
| CH | N | N | CH | O | $CH_3$ | $OCH_3$ | H | L-3b | |

TABLE 5-continued

General Formula 5

| Z | Z₁ | Z₂ | Z₃ | W | X | Y | R | L | m.p. (°C.) |
|---|---|---|---|---|---|---|---|---|---|
| CH | N | N | CH | O | CH₃ | OCH₃ | H | L-4a | |
| CH | N | N | CH | O | CH₃ | OCH₃ | H | L-7a | |
| CH | N | N | CH | O | CH₃ | OCH₃ | H | L-8a | |
| CH | N | N | CH | O | CH₃ | OCH₃ | H | L-8b | |
| CH | N | N | CH | O | CH₃ | OCH₃ | H | L-9a | |
| CH | N | N | CH | O | CH₃ | OCH₃ | H | L-12a | |
| CH | N | N | CH | O | CH₃ | OCH₃ | H | L-12b | |
| CH | N | N | CH | O | CH₃ | OCH₃ | H | L-14a | |
| CH | N | N | CH | O | CH₃ | OCH₃ | H | L-15a | |
| CH | N | N | CH | O | CH₃ | OCH₃ | H | L-16a | |
| CH | N | N | CH | O | CH₃ | OCH₃ | H | L-16b | |
| CH | N | N | CH | O | CH₃ | OCH₃ | H | L-18a | |
| CH | N | N | CH | O | CH₃ | OCH₃ | H | L-20a | |
| CH | N | N | CH | O | CH₃ | OCH₃ | H | L-22a | |
| CH | N | N | CH | S | CH₃ | OCH₃ | H | L-1a | |
| CH | N | N | CH | O | CH₃ | OCH₃ | CH₃ | L-1a | |
| CH | N | N | CH | O | OCH₃ | OCH₃ | H | L-1a | |
| CH | N | N | CH | O | OCH₃ | OCH₃ | H | L-1b | |
| CH | N | N | CH | O | OCH₃ | OCH₃ | H | L-1c | |
| CH | N | N | CH | O | OCH₃ | OCH₃ | H | L-1d | |
| CH | N | N | CH | O | OCH₃ | OCH₃ | H | L-1e | |
| CH | N | N | CH | O | OCH₃ | OCH₃ | H | L-1f | |
| CH | N | N | CH | O | OCH₃ | OCH₃ | H | L-1g | |
| CH | N | N | CH | O | OCH₃ | OCH₃ | H | L-1h | |
| CH | N | N | CH | O | OCH₃ | OCH₃ | H | L-1i | |
| CH | N | N | CH | O | OCH₃ | OCH₃ | H | L-1j | |
| CH | N | N | CH | O | OCH₃ | OCH₃ | H | L-1k | |
| CH | N | N | CH | O | OCH₃ | OCH₃ | H | L-3a | |
| CH | N | N | CH | O | OCH₃ | OCH₃ | H | L-3b | |
| CH | N | N | CH | O | OCH₃ | OCH₃ | H | L-4a | |
| CH | N | N | CH | O | OCH₃ | OCH₃ | H | L-7a | |
| CH | N | N | CH | O | OCH₃ | OCH₃ | H | L-8a | |
| CH | N | N | CH | O | OCH₃ | OCH₃ | H | L-8b | |
| CH | N | N | CH | O | OCH₃ | OCH₃ | H | L-9a | |
| CH | N | N | CH | O | CCH₃ | OCH₃ | H | L-12a | |
| CH | N | N | CH | O | OCH₃ | OCH₃ | H | L-12b | |
| CH | N | N | CH | O | OCH₃ | OCH₃ | H | L-14a | |
| CH | N | N | CH | O | OCH₃ | OCH₃ | H | L-15a | |
| CH | N | N | CH | O | OCH₃ | OCH₃ | H | L-16a | |
| CH | N | N | CH | O | OCH₃ | OCH₃ | H | L-16b | |
| CH | N | N | CH | O | OCH₃ | OCH₃ | H | L-18a | |
| CH | N | N | CH | O | OCH₃ | OCH₃ | H | L-20a | |
| CH | N | N | CH | O | OCH₃ | OCH₃ | H | L-22a | |
| CH | N | N | CH | S | OCH₃ | OCH₃ | H | L-1a | |
| CH | N | N | CH | O | OCH₃ | OCH₃ | CH₃ | L-1a | |
| CH | CH | N | CH | O | CH₃ | CH₃ | H | L-1a | |
| CH | CH | N | CH | O | CH₃ | CH₃ | H | L-1b | |
| CH | CH | N | CH | O | CH₃ | CH₃ | H | L-1c | |
| CH | CH | N | CH | O | CH₃ | CH₃ | H | L-1d | |
| CH | CH | N | CH | O | CH₃ | CH₃ | H | L-1e | |
| CH | CH | N | CH | O | CH₃ | CH₃ | H | L-1f | |
| CH | CH | N | CH | O | CH₃ | CH₃ | H | L-1g | |
| CH | CH | N | CH | O | CH₃ | CH₃ | H | L-1h | |
| CH | CH | N | CH | O | CH₃ | CH₃ | H | L-1i | |
| CH | CH | N | CH | O | CH₃ | CH₃ | H | L-1j | |
| CH | CH | N | CH | O | CH₃ | CH₃ | H | L-1k | |
| CH | CH | N | CH | O | CH₃ | CH₃ | H | L-3a | |
| CH | CH | N | CH | O | CH₃ | CH₃ | H | L-3b | |
| CH | CH | N | CH | O | CH₃ | CH₃ | H | L-4a | |
| CH | CH | N | CH | O | CH₃ | CH₃ | H | L-7a | |
| CH | CH | N | CH | O | CH₃ | CH₃ | H | L-8a | |
| CH | CH | N | CH | O | CH₃ | CH₃ | H | L-8b | |
| CH | CH | N | CH | O | CH₃ | CH₃ | H | L-9a | |
| CH | CH | N | CH | O | CH₃ | CH₃ | H | L-12a | |
| CH | CH | N | CH | O | CH₃ | CH₃ | H | L-12b | |
| CH | CH | N | CH | O | CH₃ | CH₃ | H | L-14a | |
| CH | CH | N | CH | O | CH₃ | CH₃ | H | L-15a | |
| CH | CH | N | CH | O | CH₃ | CH₃ | H | L-16a | |
| CH | CH | N | CH | O | CH₃ | CH₃ | H | L-16b | |
| CH | CH | N | CH | O | CH₃ | CH₃ | H | L-18a | |
| CH | CH | N | CH | O | CH₃ | CH₃ | H | L-20a | |
| CH | CH | N | CH | O | CH₃ | CH₃ | H | L-22a | |
| CH | CH | N | CH | S | CH₃ | CH₃ | H | L-1a | |
| CH | CH | N | CH | O | CH₃ | CH₃ | CH₃ | L-1a | |
| CH | CH | N | CH | O | OCH₃ | CH₃ | H | L-1a | |
| CH | CH | N | CH | O | OCH₃ | CH₃ | H | L-1b | |
| CH | CH | N | CH | O | OCH₃ | CH₃ | H | L-1c | |
| CH | CH | N | CH | O | OCH₃ | CH₃ | H | L-1d | |
| CH | CH | N | CH | O | OCH₃ | CH₃ | H | L-1e | |
| CH | CH | N | CH | O | OCH₃ | CH₃ | H | L-1f | |

TABLE 5-continued

General Formula 5

| Z | Z$_1$ | Z$_2$ | Z$_3$ | W | X | Y | R | L | m.p. (°C.) |
|---|---|---|---|---|---|---|---|---|---|
| CH | CH | N | CH | O | OCH$_3$ | CH$_3$ | H | L-1g | |
| CH | CH | N | CH | O | OCH$_3$ | CH$_3$ | H | L-1h | |
| CH | CH | N | CH | O | OCH$_3$ | CH$_3$ | H | L-1i | |
| CH | CH | N | CH | O | OCH$_3$ | CH$_3$ | H | L-1j | |
| CH | CH | N | CH | O | OCH$_3$ | CH$_3$ | H | L-1k | |
| CH | CH | N | CH | O | OCH$_3$ | CH$_3$ | H | L-3a | |
| CH | CH | N | CH | O | OCH$_3$ | CH$_3$ | H | L-3b | |
| CH | CH | N | CH | O | OCH$_3$ | CH$_3$ | H | L-4a | |
| CH | CH | N | CH | O | OCH$_3$ | CH$_3$ | H | L-7a | |
| CH | CH | N | CH | O | OCH$_3$ | CH$_3$ | H | L-8a | |
| CH | CH | N | CH | O | OCH$_3$ | CH$_3$ | H | L-8b | |
| CH | CH | N | CH | O | OCH$_3$ | CH$_3$ | H | L-9a | |
| CH | CH | N | CH | O | OCH$_3$ | CH$_3$ | H | L-12a | |
| CH | CH | N | CH | O | OCH$_3$ | CH$_3$ | H | L-12b | |
| CH | CH | N | CH | O | OCH$_3$ | CH$_3$ | H | L-14a | |
| CH | CH | N | CH | O | OCH$_3$ | CH$_3$ | H | L-15a | |
| CH | CH | N | CH | O | OCH$_3$ | CH$_3$ | H | L-16a | |
| CH | CH | N | CH | O | OCH$_3$ | CH$_3$ | H | L-16b | |
| CH | CH | N | CH | O | OCH$_3$ | CH$_3$ | H | L-18a | |
| CH | CH | N | CH | O | OCH$_3$ | CH$_3$ | H | L-20a | |
| CH | CH | N | CH | O | OCH$_3$ | CH$_3$ | H | L-22a | |
| CH | CH | N | CH | S | OCH$_3$ | CH$_3$ | H | L-1a | |
| CH | CH | N | CH | O | OCH$_3$ | CH$_3$ | CH$_3$ | L-1a | |
| CH | CH | N | CH | O | CH$_3$ | OCH$_3$ | H | L-1a | |
| CH | CH | N | CH | O | CH$_3$ | OCH$_3$ | H | L-1b | |
| CH | CH | N | CH | O | CH$_3$ | OCH$_3$ | H | L-1c | |
| CH | CH | N | CH | O | CH$_3$ | OCH$_3$ | H | L-1d | |
| CH | CH | N | CH | O | CH$_3$ | OCH$_3$ | H | L-1e | |
| CH | CH | N | CH | O | CH$_3$ | OCH$_3$ | H | L-1f | |
| CH | CH | N | CH | O | CH$_3$ | OCH$_3$ | H | L-1g | |
| CH | CH | N | CH | O | CH$_3$ | OCH$_3$ | H | L-1h | |
| CH | CH | N | CH | O | CH$_3$ | OCH$_3$ | H | L-1i | |
| CH | CH | N | CH | O | CH$_3$ | OCH$_3$ | H | L-1j | |
| CH | CH | N | CH | O | CH$_3$ | OCH$_3$ | H | L-1k | |
| CH | CH | N | CH | O | CH$_3$ | OCH$_3$ | H | L-3a | |
| CH | CH | N | CH | O | CH$_3$ | OCH$_3$ | H | L-3b | |
| CH | CH | N | CH | O | CH$_3$ | OCH$_3$ | H | L-4a | |
| CH | CH | N | CH | O | CH$_3$ | OCH$_3$ | H | L-7a | |
| CH | CH | N | CH | O | CH$_3$ | OCH$_3$ | H | L-8a | |
| CH | CH | N | CH | O | CH$_3$ | OCH$_3$ | H | L-8b | |
| CH | CH | N | CH | O | CH$_3$ | OCH$_3$ | H | L-9a | |
| CH | CH | N | CH | O | CH$_3$ | OCH$_3$ | H | L-12a | |
| CH | CH | N | CH | O | CH$_3$ | OCH$_3$ | H | L-12b | |
| CH | CH | N | CH | O | CH$_3$ | OCH$_3$ | H | L-14a | |
| CH | CH | N | CH | O | CH$_3$ | OCH$_3$ | H | L-15a | |
| CH | CH | N | CH | O | CH$_3$ | OCH$_3$ | H | L-16a | |
| CH | CH | N | CH | O | CH$_3$ | OCH$_3$ | H | L-16b | |
| CH | CH | N | CH | O | CH$_3$ | OCH$_3$ | H | L-18a | |
| CH | CH | N | CH | O | CH$_3$ | OCH$_3$ | H | L-20a | |
| CH | CH | N | CH | O | CH$_3$ | OCH$_3$ | H | L-22a | |
| CH | CH | N | CH | S | CH$_3$ | OCH$_3$ | H | L-1a | |
| CH | CH | N | CH | O | CH$_3$ | OCH$_3$ | CH$_3$ | L-1a | |
| CH | CH | N | CH | O | OCH$_3$ | OCH$_3$ | H | L-1a | |
| CH | CH | N | CH | O | OCH$_3$ | OCH$_3$ | H | L-1b | |
| CH | CH | N | CH | O | OCH$_3$ | OCH$_3$ | H | L-1c | |
| CH | CH | N | CH | O | OCH$_3$ | OCH$_3$ | H | L-1d | |
| CH | CH | N | CH | O | OCH$_3$ | OCH$_3$ | H | L-1e | |
| CH | CH | N | CH | O | OCH$_3$ | OCH$_3$ | H | L-1f | |
| CH | CH | N | CH | O | OCH$_3$ | OCH$_3$ | H | L-1g | |
| CH | CH | N | CH | O | OCH$_3$ | OCH$_3$ | H | L-1h | |
| CH | CH | N | CH | O | OCH$_3$ | OCH$_3$ | H | L-1i | |
| CH | CH | N | CH | O | OCH$_3$ | OCH$_3$ | H | L-1j | |
| CH | CH | N | CH | O | OCH$_3$ | OCH$_3$ | H | L-1k | |
| CH | CH | N | CH | O | OCH$_3$ | OCH$_3$ | H | L-3a | |
| CH | CH | N | CH | O | OCH$_3$ | OCH$_3$ | H | L-3b | |
| CH | CH | N | CH | O | OCH$_3$ | OCH$_3$ | H | L-4a | |
| CH | CH | N | CH | O | OCH$_3$ | OCH$_3$ | H | L-7a | |
| CH | CH | N | CH | O | OCH$_3$ | OCH$_3$ | H | L-8a | |
| CH | CH | N | CH | O | OCH$_3$ | OCH$_3$ | H | L-8b | |
| CH | CH | N | CH | O | OCH$_3$ | OCH$_3$ | H | L-9a | |
| CH | CH | N | CH | O | OCH$_3$ | OCH$_3$ | H | L-12a | |
| CH | CH | N | CH | O | OCH$_3$ | OCH$_3$ | H | L-12b | |
| CH | CH | N | CH | O | OCH$_3$ | OCH$_3$ | H | L-14a | |
| CH | CH | N | CH | O | OCH$_3$ | OCH$_3$ | H | L-15a | |
| CH | CH | N | CH | O | OCH$_3$ | OCH$_3$ | H | L-16a | |
| CH | CH | N | CH | O | OCH$_3$ | OCH$_3$ | H | L-16b | |
| CH | CH | N | CH | O | OCH$_3$ | OCH$_3$ | H | L-18a | |
| CH | CH | N | CH | O | OCH$_3$ | OCH$_3$ | H | L-20a | |
| CH | CH | N | CH | O | OCH$_3$ | OCH$_3$ | H | L-22a | |
| CH | CH | N | CH | S | OCH$_3$ | OCH$_3$ | H | L-1a | |

TABLE 5-continued

General Formula 5

| Z | Z₁ | Z₂ | Z₃ | W | X | Y | R | L | m.p. (°C.) |
|---|---|---|---|---|---|---|---|---|---|
| CH | CH | N | CH | O | OCH₃ | OCH₃ | CH₃ | L-1a | |
| CH | CH | CH | CH | O | CH₃ | CH₃ | H | L-1a | |
| CH | CH | CH | CH | O | CH₃ | CH₃ | H | L-1b | |
| CH | CH | CH | CH | O | CH₃ | CH₃ | H | L-1c | |
| CH | CH | CH | CH | O | CH₃ | CH₃ | H | L-1d | |
| CH | CH | CH | CH | O | CH₃ | CH₃ | H | L-1e | |
| CH | CH | CH | CH | O | CH₃ | CH₃ | H | L-1f | |
| CH | CH | CH | CH | O | CH₃ | CH₃ | H | L-1g | |
| CH | CH | CH | CH | O | CH₃ | CH₃ | H | L-1h | |
| CH | CH | CH | CH | O | CH₃ | CH₃ | H | L-1i | |
| CH | CH | CH | CH | O | CH₃ | CH₃ | H | L-1j | |
| CH | CH | CH | CH | O | CH₃ | CH₃ | H | L-1k | |
| CH | CH | CH | CH | O | CH₃ | CH₃ | H | L-3a | |
| CH | CH | CH | CH | O | CH₃ | CH₃ | H | L-3b | |
| CH | CH | CH | CH | O | CH₃ | CH₃ | H | L-4a | |
| CH | CH | CH | CH | O | CH₃ | CH₃ | H | L-7a | |
| CH | CH | CH | CH | O | CH₃ | CH₃ | H | L-8a | |
| CH | CH | CH | CH | O | CH₃ | CH₃ | H | L-8b | |
| CH | CH | CH | CH | O | CH₃ | CH₃ | H | L-9a | |
| CH | CH | CH | CH | O | CH₃ | CH₃ | H | L-12a | |
| CH | CH | CH | CH | O | CH₃ | CH₃ | H | L-12b | |
| CH | CH | CH | CH | O | CH₃ | CH₃ | H | L-14a | |
| CH | CH | CH | CH | O | CH₃ | CH₃ | H | L-15a | |
| CH | CH | CH | CH | O | CH₃ | CH₃ | H | L-16a | |
| CH | CH | CH | CH | O | CH₃ | CH₃ | H | L-16b | |
| CH | CH | CH | CH | O | CH₃ | CH₃ | H | L-18a | |
| CH | CH | CH | CH | O | CH₃ | CH₃ | H | L-20a | |
| CH | CH | CH | CH | O | CH₃ | CH₃ | H | L-22a | |
| CH | CH | CH | CH | S | CH₃ | CH₃ | H | L-1a | |
| CH | CH | CH | CH | O | CH₃ | CH₃ | CH₃ | L-1a | |
| CH | CH | CH | CH | O | OCH₃ | CH₃ | H | L-1a | |
| CH | CH | CH | CH | O | OCH₃ | CH₃ | H | L-1b | |
| CH | CH | CH | CH | O | OCH₃ | CH₃ | H | L-1c | |
| CH | CH | CH | CH | O | OCH₃ | CH₃ | H | L-1d | |
| CH | CH | CH | CH | O | OCH₃ | CH₃ | H | L-1e | |
| CH | CH | CH | CH | O | OCH₃ | CH₃ | H | L-1f | |
| CH | CH | CH | CH | O | OCH₃ | CH₃ | H | L-1g | |
| CH | CH | CH | CH | O | OCH₃ | CH₃ | H | L-1h | |
| CH | CH | CH | CH | O | OCH₃ | CH₃ | H | L-1i | |
| CH | CH | CH | CH | O | OCH₃ | CH₃ | H | L-1j | |
| CH | CH | CH | CH | O | OCH₃ | CH₃ | H | L-1k | |
| CH | CH | CH | CH | O | OCH₃ | CH₃ | H | L-3a | |
| CH | CH | CH | CH | O | OCH₃ | CH₃ | H | L-3b | |
| CH | CH | CH | CH | O | OCH₃ | CH₃ | H | L-4a | |
| CH | CH | CH | CH | O | OCH₃ | CH₃ | H | L-7a | |
| CH | CH | CH | CH | O | OCH₃ | CH₃ | H | L-8a | |
| CH | CH | CH | CH | O | OCH₃ | CH₃ | H | L-8b | |
| CH | CH | CH | CH | O | OCH₃ | CH₃ | H | L-9a | |
| CH | CH | CH | CH | O | OCH₃ | CH₃ | H | L-12b | |
| CH | CH | CH | CH | O | OCH₃ | CH₃ | H | L-14a | |
| CH | CH | CH | CH | O | OCH₃ | CH₃ | H | L-15a | |
| CH | CH | CH | CH | O | OCH₃ | CH₃ | H | L-16a | |
| CH | CH | CH | CH | O | OCH₃ | CH₃ | H | L-16b | |
| CH | CH | CH | CH | O | OCH₃ | CH₃ | H | L-18a | |
| CH | CH | CH | CH | O | OCH₃ | CH₃ | H | L-20a | |
| CH | CH | CH | CH | O | OCH₃ | CH₃ | H | L-22a | |
| CH | CH | CH | CH | S | OCH₃ | CH₃ | H | L-1a | |
| CH | CH | CH | CH | O | OCH₃ | CH₃ | CH₃ | L-1a | |
| CH | CH | CH | CH | O | CH₃ | OCH₃ | H | L-1a | |
| CH | CH | CH | CH | O | CH₃ | OCH₃ | H | L-1b | |
| CH | CH | CH | CH | O | CH₃ | OCH₃ | H | L-1c | |
| CH | CH | CH | CH | O | CH₃ | OCH₃ | H | L-1d | |
| CH | CH | CH | CH | O | CH₃ | OCH₃ | H | L-1e | |
| CH | CH | CH | CH | O | CH₃ | OCH₃ | H | L-1f | |
| CH | CH | CH | CH | O | CH₃ | OCH₃ | H | L-1g | |
| CH | CH | CH | CH | O | CH₃ | OCH₃ | H | L-1h | |
| CH | CH | CH | CH | O | CH₃ | OCH₃ | H | L-1i | |
| CH | CH | CH | CH | O | CH₃ | OCH₃ | H | L-1j | |
| CH | CH | CH | CH | O | CH₃ | OCH₃ | H | L-1k | |
| CH | CH | CH | CH | O | CH₃ | OCH₃ | H | L-3a | |
| CH | CH | CH | CH | O | CH₃ | OCH₃ | H | L-3b | |
| CH | CH | CH | CH | O | CH₃ | OCH₃ | H | L-4a | |
| CH | CH | CH | CH | O | CH₃ | OCH₃ | H | L-7a | |
| CH | CH | CH | CH | O | CH₃ | OCH₃ | H | L-8a | |
| CH | CH | CH | CH | O | CH₃ | OCH₃ | H | L-8b | |
| CH | CH | CH | CH | O | CH₃ | OCH₃ | H | L-9a | |
| CH | CH | CH | CH | O | CH₃ | OCH₃ | H | L-12b | |
| CH | CH | CH | CH | O | CH₃ | OCH₃ | H | L-14a | |
| CH | CH | CH | CH | O | CH₃ | OCH₃ | H | L-15a | |
| CH | CH | CH | CH | O | CH₃ | OCH₃ | H | L-16a | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| CH | CH | CH | CH | O | $CH_3$ | $OCH_3$ | H | L-16b | |
| CH | CH | CH | CH | O | $CH_3$ | $OCH_3$ | H | L-18a | |
| CH | CH | CH | CH | O | $CH_3$ | $OCH_3$ | H | L-20a | |
| CH | CH | CH | CH | O | $CH_3$ | $OCH_3$ | H | L-22a | |
| CH | CH | CH | CH | S | $CH_3$ | $OCH_3$ | H | L-1a | |
| CH | CH | CH | CH | O | $CH_3$ | $OCH_3$ | $CH_3$ | L-1a | |
| CH | CH | CH | CH | O | $OCH_3$ | $OCH_3$ | H | L-1a | |
| CH | CH | CH | CH | O | $OCH_3$ | $OCH_3$ | H | L-1b | |
| CH | CH | CH | CH | O | $OCH_3$ | $OCH_3$ | H | L-1c | |
| CH | CH | CH | CH | O | $OCH_3$ | $OCH_3$ | H | L-1d | |
| CH | CH | CH | CH | O | $OCH_3$ | $OCH_3$ | H | L-1e | |
| CH | CH | CH | CH | O | $OCH_3$ | $OCH_3$ | H | L-1f | |
| CH | CH | CH | CH | O | $OCH_3$ | $OCH_3$ | H | L-1g | |
| CH | CH | CH | CH | O | $OCH_3$ | $OCH_3$ | H | L-1h | |
| CH | CH | CH | CH | O | $OCH_3$ | $OCH_3$ | H | L-1i | |
| CH | CH | CH | CH | O | $OCH_3$ | $OCH_3$ | H | L-1j | |
| CH | CH | CH | CH | O | $OCH_3$ | $OCH_3$ | H | L-1k | |
| CH | CH | CH | CH | O | $OCH_3$ | $OCH_3$ | H | L-3a | |
| CH | CH | CH | CH | O | $OCH_3$ | $OCH_3$ | H | L-3b | |
| CH | CH | CH | CH | O | $OCH_3$ | $OCH_3$ | H | L-4a | |
| CH | CH | CH | CH | O | $OCH_3$ | $OCH_3$ | H | L-7a | |
| CH | CH | CH | CH | O | $OCH_3$ | $OCH_3$ | H | L-8a | |
| CH | CH | CH | CH | O | $OCH_3$ | $OCH_3$ | H | L-8b | |
| CH | CH | CH | CH | O | $OCH_3$ | $OCH_3$ | H | L-9a | |
| CH | CH | CH | CH | O | $OCH_3$ | $OCH_3$ | H | L-12b | |
| CH | CH | CH | CH | O | $OCH_3$ | $OCH_3$ | H | L-14a | |
| CH | CH | CH | CH | O | $OCH_3$ | $OCH_3$ | H | L-15a | |
| CH | CH | CH | CH | O | $OCH_3$ | $OCH_3$ | H | L-16a | |
| CH | CH | CH | CH | O | $OCH_3$ | $OCH_3$ | H | L-16b | |
| CH | CH | CH | CH | O | $OCH_3$ | $OCH_3$ | H | L-18a | |
| CH | CH | CH | CH | O | $OCH_3$ | $OCH_3$ | H | L-20a | |
| CH | CH | CH | CH | O | $OCH_3$ | $OCH_3$ | H | L-22a | |
| CH | CH | CH | CH | S | $OCH_3$ | $OCH_3$ | H | L-1a | |
| CH | CH | CH | CH | O | $OCH_3$ | $OCH_3$ | $CH_3$ | L-1a | |
| N | N | CH | CH | O | $CH_3$ | $CH_3$ | H | L-1a | |
| N | N | CH | CH | O | $CH_3$ | $CH_3$ | H | L-1b | |
| N | N | CH | CH | O | $CH_3$ | $CH_3$ | H | L-1c | |
| N | N | CH | CH | O | $CH_3$ | $CH_3$ | H | L-1d | |
| N | N | CH | CH | O | $CH_3$ | $CH_3$ | H | L-1e | |
| N | N | CH | CH | O | $CH_3$ | $CH_3$ | H | L-1f | |
| N | N | CH | CH | O | $CH_3$ | $CH_3$ | H | L-1g | |
| N | N | CH | CH | O | $CH_3$ | $CH_3$ | H | L-1h | |
| N | N | CH | CH | O | $CH_3$ | $CH_3$ | H | L-1i | |
| N | N | CH | CH | O | $CH_3$ | $CH_3$ | H | L-1j | |
| N | N | CH | CH | O | $CH_3$ | $CH_3$ | H | L-1k | |
| N | N | CH | CH | O | $CH_3$ | $CH_3$ | H | L-3a | |
| N | N | CH | CH | O | $CH_3$ | $CH_3$ | H | L-3b | |
| N | N | CH | CH | O | $CH_3$ | $CH_3$ | H | L-4a | |
| N | N | CH | CH | O | $CH_3$ | $CH_3$ | H | L-7a | |
| N | N | CH | CH | O | $CH_3$ | $CH_3$ | H | L-8a | |
| N | N | CH | CH | O | $CH_3$ | $CH_3$ | H | L-8b | |
| N | N | CH | CH | O | $CH_3$ | $CH_3$ | H | L-9a | |
| N | N | CH | CH | O | $CH_3$ | $CH_3$ | H | L-12b | |
| N | N | CH | CH | O | $CH_3$ | $CH_3$ | H | L-14a | |
| N | N | CH | CH | O | $CH_3$ | $CH_3$ | H | L-15a | |
| N | N | CH | CH | O | $CH_3$ | $CH_3$ | H | L-16a | |
| N | N | CH | CH | O | $CH_3$ | $CH_3$ | H | L-16b | |
| N | N | CH | CH | O | $CH_3$ | $CH_3$ | H | L-18a | |
| N | N | CH | CH | O | $CH_3$ | $CH_3$ | H | L-20a | |
| N | N | CH | CH | O | $CH_3$ | $CH_3$ | H | L-22a | |
| N | N | CH | CH | S | $CH_3$ | $CH_3$ | H | L-1a | |
| N | N | CH | CH | O | $CH_3$ | $CH_3$ | $CH_3$ | L-1a | |
| N | N | CH | CH | O | $OCH_3$ | $CH_3$ | H | L-1a | |
| N | N | CH | CH | O | $OCH_3$ | $CH_3$ | H | L-1b | |
| N | N | CH | CH | O | $OCH_3$ | $CH_3$ | H | L-1c | |
| N | N | CH | CH | O | $OCH_3$ | $CH_3$ | H | L-1d | |
| N | N | CH | CH | O | $OCH_3$ | $CH_3$ | H | L-1e | |
| N | N | CH | CH | O | $OCH_3$ | $CH_3$ | H | L-1f | |
| N | N | CH | CH | O | $OCH_3$ | $CH_3$ | H | L-1g | |
| N | N | CH | CH | O | $OCH_3$ | $CH_3$ | H | L-1h | |
| N | N | CH | CH | O | $OCH_3$ | $CH_3$ | H | L-1i | |
| N | N | CH | CH | O | $OCH_3$ | $CH_3$ | H | L-1j | |
| N | N | CH | CH | O | $OCH_3$ | $CH_3$ | H | L-1k | |
| N | N | CH | CH | O | $OCH_3$ | $CH_3$ | H | L-3a | |
| N | N | CH | CH | O | $OCH_3$ | $CH_3$ | H | L-3b | |
| N | N | CH | CH | O | $OCH_3$ | $CH_3$ | H | L-4a | |
| N | N | CH | CH | O | $OCH_3$ | $CH_3$ | H | L-7a | |
| N | N | CH | CH | O | $OCH_3$ | $CH_3$ | H | L-8a | |
| N | N | CH | CH | O | $OCH_3$ | $CH_3$ | H | L-8b | |
| N | N | CH | CH | O | $OCH_3$ | $CH_3$ | H | L-9a | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| N | N | CH | CH | O | OCH$_3$ | CH$_3$ | H | L-12a | |
| N | N | CH | CH | O | OCH$_3$ | CH$_3$ | H | L-12b | |
| N | N | CH | CH | O | OCH$_3$ | CH$_3$ | H | L-14a | |
| N | N | CH | CH | O | OCH$_3$ | CH$_3$ | H | L-15a | |
| N | N | CH | CH | O | OCH$_3$ | CH$_3$ | H | L-16a | |
| N | N | CH | CH | O | OCH$_3$ | CH$_3$ | H | L-16b | |
| N | N | CH | CH | O | OCH$_3$ | CH$_3$ | H | L-18a | |
| N | N | CH | CH | O | OCH$_3$ | CH$_3$ | H | L-20a | |
| N | N | CH | CH | O | OCH$_3$ | CH$_3$ | H | L-22a | |
| N | N | CH | CH | S | OCH$_3$ | CH$_3$ | H | L-1a | |
| N | N | CH | CH | O | OCH$_3$ | CH$_3$ | CH$_3$ | L-1a | |
| N | N | CH | CH | O | CH$_3$ | OCH$_3$ | H | L-1a | |
| N | N | CH | CH | O | CH$_3$ | OCH$_3$ | H | L-1b | |
| N | N | CH | CH | O | CH$_3$ | OCH$_3$ | H | L-1c | |
| N | N | CH | CH | O | CH$_3$ | OCH$_3$ | H | L-1d | |
| N | N | CH | CH | O | CH$_3$ | OCH$_3$ | H | L-1e | |
| N | N | CH | CH | O | CH$_3$ | OCH$_3$ | H | L-1f | |
| N | N | CH | CH | O | CH$_3$ | OCH$_3$ | H | L-1g | |
| N | N | CH | CH | O | CH$_3$ | OCH$_3$ | H | L-1h | |
| N | N | CH | CH | O | CH$_3$ | OCH$_3$ | H | L-1i | |
| N | N | CH | CH | O | CH$_3$ | OCH$_3$ | H | L-1j | |
| N | N | CH | CH | O | CH$_3$ | OCH$_3$ | H | L-1k | |
| N | N | CH | CH | O | CH$_3$ | OCH$_3$ | H | L-3a | |
| N | N | CH | CH | O | CH$_3$ | OCH$_3$ | H | L-3b | |
| N | N | CH | CH | O | CH$_3$ | OCH$_3$ | H | L-4a | |
| N | N | CH | CH | O | CH$_3$ | OCH$_3$ | H | L-7a | |
| N | N | CH | CH | O | CH$_3$ | OCH$_3$ | H | L-8a | |
| N | N | CH | CH | O | CH$_3$ | OCH$_3$ | H | L-8b | |
| N | N | CH | CH | O | CH$_3$ | OCH$_3$ | H | L-9a | |
| N | N | CH | CH | O | CH$_3$ | OCH$_3$ | H | L-12a | |
| N | N | CH | CH | O | CH$_3$ | OCH$_3$ | H | L-12b | |
| N | N | CH | CH | O | CH$_3$ | OCH$_3$ | H | L-14a | |
| N | N | CH | CH | O | CH$_3$ | OCH$_3$ | H | L-15a | |
| N | N | CH | CH | O | CH$_3$ | OCH$_3$ | H | L-16a | |
| N | N | CH | CH | O | CH$_3$ | OCH$_3$ | H | L-16b | |
| N | N | CH | CH | O | CH$_3$ | OCH$_3$ | H | L-18a | |
| N | N | CH | CH | O | CH$_3$ | OCH$_3$ | H | L-20a | |
| N | N | CH | CH | O | CH$_3$ | OCH$_3$ | H | L-22a | |
| N | N | CH | CH | S | CH$_3$ | OCH$_3$ | H | L-1a | |
| N | N | CH | CH | O | CH$_3$ | OCH$_3$ | CH$_3$ | L-1a | |
| N | N | CH | CH | O | OCH$_3$ | OCH$_3$ | H | L-1a | |
| N | N | CH | CH | O | OCH$_3$ | OCH$_3$ | H | L-1b | |
| N | N | CH | CH | O | OCH$_3$ | OCH$_3$ | H | L-1c | |
| N | N | CH | CH | O | OCH$_3$ | OCH$_3$ | H | L-1d | |
| N | N | CH | CH | O | OCH$_3$ | OCH$_3$ | H | L-1e | |
| N | N | CH | CH | O | OCH$_3$ | OCH$_3$ | H | L-1f | |
| N | N | CH | CH | O | OCH$_3$ | OCH$_3$ | H | L-1g | |
| N | N | CH | CH | O | OCH$_3$ | OCH$_3$ | H | L-1h | |
| N | N | CH | CH | O | OCH$_3$ | OCH$_3$ | H | L-1i | |
| N | N | CH | CH | O | OCH$_3$ | OCH$_3$ | H | L-1j | |
| N | N | CH | CH | O | OCH$_3$ | OCH$_3$ | H | L-1k | |
| N | N | CH | CH | O | OCH$_3$ | OCH$_3$ | H | L-3a | |
| N | N | CH | CH | O | OCH$_3$ | OCH$_3$ | H | L-3b | |
| N | N | CH | CH | O | OCH$_3$ | OCH$_3$ | H | L-4a | |
| N | N | CH | CH | O | OCH$_3$ | OCH$_3$ | H | L-7a | |
| N | N | CH | CH | O | OCH$_3$ | OCH$_3$ | H | L-8a | |
| N | N | CH | CH | O | OCH$_3$ | OCH$_3$ | H | L-8b | |
| N | N | CH | CH | O | OCH$_3$ | OCH$_3$ | H | L-9a | |
| N | N | CH | CH | O | OCH$_3$ | OCH$_3$ | H | L-12a | |
| N | N | CH | CH | O | OCH$_3$ | OCH$_3$ | H | L-12b | |
| N | N | CH | CH | O | OCH$_3$ | OCH$_3$ | H | L-14a | |
| N | N | CH | CH | O | OCH$_3$ | OCH$_3$ | H | L-15a | |
| N | N | CH | CH | O | OCH$_3$ | OCH$_3$ | H | L-16a | |
| N | N | CH | CH | O | OCH$_3$ | OCH$_3$ | H | L-16b | |
| N | N | CH | CH | O | OCH$_3$ | OCH$_3$ | H | L-18a | |
| N | N | CH | CH | O | OCH$_3$ | OCH$_3$ | H | L-20a | |
| N | N | CH | CH | O | OCH$_3$ | OCH$_3$ | H | L-22a | |
| N | N | CH | CH | S | OCH$_3$ | OCH$_3$ | H | L-1a | |
| N | N | CH | CH | O | OCH$_3$ | OCH$_3$ | CH$_3$ | L-1a | |
| N | N | N | CH | O | CH$_3$ | CH$_3$ | H | L-1a | |
| N | N | N | CH | O | CH$_3$ | CH$_3$ | H | L-1b | |
| N | N | N | CH | O | CH$_3$ | CH$_3$ | H | L-1c | |
| N | N | N | CH | O | CH$_3$ | CH$_3$ | H | L-1d | |
| N | N | N | CH | O | CH$_3$ | CH$_3$ | H | L-1e | |
| N | N | N | CH | O | CH$_3$ | CH$_3$ | H | L-1f | |
| N | N | N | CH | O | CH$_3$ | CH$_3$ | H | L-1g | |
| N | N | N | CH | O | CH$_3$ | CH$_3$ | H | L-1h | |
| N | N | N | CH | O | CH$_3$ | CH$_3$ | H | L-1i | |
| N | N | N | CH | O | CH$_3$ | CH$_3$ | H | L-1j | |
| N | N | N | CH | O | CH$_3$ | CH$_3$ | H | L-1k | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| N | N | N | CH | O | $CH_3$ | $CH_3$ | H | L-3a | |
| N | N | N | CH | O | $CH_3$ | $CH_3$ | H | L-3b | |
| N | N | N | CH | O | $CH_3$ | $CH_3$ | H | L-4a | |
| N | N | N | CH | O | $CH_3$ | $CH_3$ | H | L-7a | |
| N | N | N | CH | O | $CH_3$ | $CH_3$ | H | L-8a | |
| N | N | N | CH | O | $CH_3$ | $CH_3$ | H | L-8b | |
| N | N | N | CH | O | $CH_3$ | $CH_3$ | H | L-9a | |
| N | N | N | CH | O | $CH_3$ | $CH_3$ | H | L-12b | |
| N | N | N | CH | O | $CH_3$ | $CH_3$ | H | L-14a | |
| N | N | N | CH | O | $CH_3$ | $CH_3$ | H | L-15a | |
| N | N | N | CH | O | $CH_3$ | $CH_3$ | H | L-16a | |
| N | N | N | CH | O | $CH_3$ | $CH_3$ | H | L-16b | |
| N | N | N | CH | O | $CH_3$ | $CH_3$ | H | L-18a | |
| N | N | N | CH | O | $CH_3$ | $CH_3$ | H | L-20a | |
| N | N | N | CH | O | $CH_3$ | $CH_3$ | H | L-22a | |
| N | N | N | CH | S | $CH_3$ | $CH_3$ | H | L-1a | |
| N | N | N | CH | O | $CH_3$ | $CH_3$ | $CH_3$ | L-1a | |
| N | N | N | CH | O | $OCH_3$ | $CH_3$ | H | L-1a | |
| N | N | N | CH | O | $OCH_3$ | $CH_3$ | H | L-1b | |
| N | N | N | CH | O | $OCH_3$ | $CH_3$ | H | L-1c | |
| N | N | N | CH | O | $OCH_3$ | $CH_3$ | H | L-1d | |
| N | N | N | CH | O | $OCH_3$ | $CH_3$ | H | L-1e | |
| N | N | N | CH | O | $OCH_3$ | $CH_3$ | H | L-1f | |
| N | N | N | CH | O | $OCH_3$ | $CH_3$ | H | L-1g | |
| N | N | N | CH | O | $OCH_3$ | $CH_3$ | H | L-1h | |
| N | N | N | CH | O | $OCH_3$ | $CH_3$ | H | L-1i | |
| N | N | N | CH | O | $OCH_3$ | $CH_3$ | H | L-1j | |
| N | N | N | CH | O | $OCH_3$ | $CH_3$ | H | L-1k | |
| N | N | N | CH | O | $OCH_3$ | $CH_3$ | H | L-3a | |
| N | N | N | CH | O | $OCH_3$ | $CH_3$ | H | L-3b | |
| N | N | N | CH | O | $OCH_3$ | $CH_3$ | H | L-4a | |
| N | N | N | CH | O | $OCH_3$ | $CH_3$ | H | L-7a | |
| N | N | N | CH | O | $OCH_3$ | $CH_3$ | H | L-8a | |
| N | N | N | CH | O | $OCH_3$ | $CH_3$ | H | L-8b | |
| N | N | N | CH | O | $OCH_3$ | $CH_3$ | H | L-9a | |
| N | N | N | CH | O | $OCH_3$ | $CH_3$ | H | L-12a | |
| N | N | N | CH | O | $OCH_3$ | $CH_3$ | H | L-12b | |
| N | N | N | CH | O | $OCH_3$ | $CH_3$ | H | L-14a | |
| N | N | N | CH | O | $OCH_3$ | $CH_3$ | H | L-15a | |
| N | N | N | CH | O | $OCH_3$ | $CH_3$ | H | L-16a | |
| N | N | N | CH | O | $OCH_3$ | $CH_3$ | H | L-16b | |
| N | N | N | CH | O | $OCH_3$ | $CH_3$ | H | L-18a | |
| N | N | N | CH | O | $OCH_3$ | $CH_3$ | H | L-20a | |
| N | N | N | CH | O | $OCH_3$ | $CH_3$ | H | L-22a | |
| N | N | N | CH | S | $OCH_3$ | $CH_3$ | H | L-1a | |
| N | N | N | CH | O | $OCH_3$ | $CH_3$ | $CH_3$ | L-1a | |
| N | N | N | CH | O | $CH_3$ | $OCH_3$ | H | L-1a | |
| N | N | N | CH | O | $CH_3$ | $OCH_3$ | H | L-1b | |
| N | N | N | CH | O | $CH_3$ | $OCH_3$ | H | L-1c | |
| N | N | N | CH | O | $CH_3$ | $OCH_3$ | H | L-1d | |
| N | N | N | CH | O | $CH_3$ | $OCH_3$ | H | L-1e | |
| N | N | N | CH | O | $CH_3$ | $OCH_3$ | H | L-1f | |
| N | N | N | CH | O | $CH_3$ | $OCH_3$ | H | L-1g | |
| N | N | N | CH | O | $CH_3$ | $OCH_3$ | H | L-1h | |
| N | N | N | CH | O | $CH_3$ | $OCH_3$ | H | L-1i | |
| N | N | N | CH | O | $CH_3$ | $OCH_3$ | H | L-1j | |
| N | N | N | CH | O | $CH_3$ | $OCH_3$ | H | L-1k | |
| N | N | N | CH | O | $CH_3$ | $OCH_3$ | H | L-3a | |
| N | N | N | CH | O | $CH_3$ | $OCH_3$ | H | L-3b | |
| N | N | N | CH | O | $CH_3$ | $OCH_3$ | H | L-4a | |
| N | N | N | CH | O | $CH_3$ | $OCH_3$ | H | L-7a | |
| N | N | N | CH | O | $CH_3$ | $OCH_3$ | H | L-8a | |
| N | N | N | CH | O | $CH_3$ | $OCH_3$ | H | L-8b | |
| N | N | N | CH | O | $CH_3$ | $OCH_3$ | H | L-9a | |
| N | N | N | CH | O | $CH_3$ | $OCH_3$ | H | L-12a | |
| N | N | N | CH | O | $CH_3$ | $OCH_3$ | H | L-12b | |
| N | N | N | CH | O | $CH_3$ | $OCH_3$ | H | L-14a | |
| N | N | N | CH | O | $CH_3$ | $OCH_3$ | H | L-15a | |
| N | N | N | CH | O | $CH_3$ | $OCH_3$ | H | L-16a | |
| N | N | N | CH | O | $CH_3$ | $OCH_3$ | H | L-16b | |
| N | N | N | CH | O | $CH_3$ | $OCH_3$ | H | L-18a | |
| N | N | N | CH | O | $CH_3$ | $OCH_3$ | H | L-20a | |
| N | N | N | CH | O | $CH_3$ | $OCH_3$ | H | L-22a | |
| N | N | N | CH | S | $CH_3$ | $OCH_3$ | H | L-1a | |
| N | N | N | CH | O | $CH_3$ | $OCH_3$ | $CH_3$ | L-1a | |
| N | N | N | CH | O | $OCH_3$ | $OCH_3$ | H | L-1a | |
| N | N | N | CH | O | $OCH_3$ | $OCH_3$ | H | L-1b | |
| N | N | N | CH | O | $OCH_3$ | $OCH_3$ | H | L-1c | |
| N | N | N | CH | O | $OCH_3$ | $OCH_3$ | H | L-1d | |
| N | N | N | CH | O | $OCH_3$ | $OCH_3$ | H | L-1e | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| N | N | N | CH | O | $OCH_3$ | $OCH_3$ | H | L-1f | |
| N | N | N | CH | O | $OCH_3$ | $OCH_3$ | H | L-1g | |
| N | N | N | CH | O | $OCH_3$ | $OCH_3$ | H | L-1h | |
| N | N | N | CH | O | $OCH_3$ | $OCH_3$ | H | L-1i | |
| N | N | N | CH | O | $OCH_3$ | $OCH_3$ | H | L-1j | |
| N | N | N | CH | O | $OCH_3$ | $OCH_3$ | H | L-1k | |
| N | N | N | CH | O | $OCH_3$ | $OCH_3$ | H | L-3a | |
| N | N | N | CH | O | $OCH_3$ | $OCH_3$ | H | L-3b | |
| N | N | N | CH | O | $OCH_3$ | $OCH_3$ | H | L-4a | |
| N | N | N | CH | O | $OCH_3$ | $OCH_3$ | H | L-7a | |
| N | N | N | CH | O | $OCH_3$ | $OCH_3$ | H | L-8a | |
| N | N | N | CH | O | $OCH_3$ | $OCH_3$ | H | L-8b | |
| N | N | N | CH | O | $OCH_3$ | $OCH_3$ | H | L-9a | |
| N | N | N | CH | O | $OCH_3$ | $OCH_3$ | H | L-12a | |
| N | N | N | CH | O | $OCH_3$ | $OCH_3$ | H | L-12b | |
| N | N | N | CH | O | $OCH_3$ | $OCH_3$ | H | L-14a | |
| N | N | N | CH | O | $OCH_3$ | $OCH_3$ | H | L-15a | |
| N | N | N | CH | O | $OCH_3$ | $OCH_3$ | H | L-16a | |
| N | N | N | CH | O | $OCH_3$ | $OCH_3$ | H | L-16b | |
| N | N | N | CH | O | $OCH_3$ | $OCH_3$ | H | L-18a | |
| N | N | N | CH | O | $OCH_3$ | $OCH_3$ | H | L-20a | |
| N | N | N | CH | O | $OCH_3$ | $OCH_3$ | H | L-22a | |
| N | N | N | CH | S | $OCH_3$ | $OCH_3$ | H | L-1a | |
| N | N | N | CH | O | $OCH_3$ | $OCH_3$ | $CH_3$ | L-1a | |
| N | CH | N | CH | O | $CH_3$ | $CH_3$ | H | L-1a | |
| N | CH | N | CH | O | $CH_3$ | $CH_3$ | H | L-1b | |
| N | CH | N | CH | O | $CH_3$ | $CH_3$ | H | L-1c | |
| N | CH | N | CH | O | $CH_3$ | $CH_3$ | H | L-1d | |
| N | CH | N | CH | O | $CH_3$ | $CH_3$ | H | L-1e | |
| N | CH | N | CH | O | $CH_3$ | $CH_3$ | H | L-1f | |
| N | CH | N | CH | O | $CH_3$ | $CH_3$ | H | L-1g | |
| N | CH | N | CH | O | $CH_3$ | $CH_3$ | H | L-1h | |
| N | CH | N | CH | O | $CH_3$ | $CH_3$ | H | L-1i | |
| N | CH | N | CH | O | $CH_3$ | $CH_3$ | H | L-1j | |
| N | CH | N | CH | O | $CH_3$ | $CH_3$ | H | L-1k | |
| N | CH | N | CH | O | $CH_3$ | $CH_3$ | H | L-3a | |
| N | CH | N | CH | O | $CH_3$ | $CH_3$ | H | L-3b | |
| N | CH | N | CH | O | $CH_3$ | $CH_3$ | H | L-4a | |
| N | CH | N | CH | O | $CH_3$ | $CH_3$ | H | L-7a | |
| N | CH | N | CH | O | $CH_3$ | $CH_3$ | H | L-8a | |
| N | CH | N | CH | O | $CH_3$ | $CH_3$ | H | L-8b | |
| N | CH | N | CH | O | $CH_3$ | $CH_3$ | H | L-9a | |
| N | CH | N | CH | O | $CH_3$ | $CH_3$ | H | L-12b | |
| N | CH | N | CH | O | $CH_3$ | $CH_3$ | H | L-14a | |
| N | CH | N | CH | O | $CH_3$ | $CH_3$ | H | L-15a | |
| N | CH | N | CH | O | $CH_3$ | $CH_3$ | H | L-16a | |
| N | CH | N | CH | O | $CH_3$ | $CH_3$ | H | L-16b | |
| N | CH | N | CH | O | $CH_3$ | $CH_3$ | H | L-18a | |
| N | CH | N | CH | O | $CH_3$ | $CH_3$ | H | L-20a | |
| N | CH | N | CH | O | $CH_3$ | $CH_3$ | H | L-22a | |
| N | CH | N | CH | S | $CH_3$ | $CH_3$ | H | L-1a | |
| N | CH | N | CH | O | $CH_3$ | $CH_3$ | $CH_3$ | L-1a | |
| N | CH | N | CH | O | $OCH_3$ | $CH_3$ | H | L-1a | |
| N | CH | N | CH | O | $OCH_3$ | $CH_3$ | H | L-1b | |
| N | CH | N | CH | O | $OCH_3$ | $CH_3$ | H | L-1c | |
| N | CH | N | CH | O | $OCH_3$ | $CH_3$ | H | L-1d | |
| N | CH | N | CH | O | $OCH_3$ | $CH_3$ | H | L-1e | |
| N | CH | N | CH | O | $OCH_3$ | $CH_3$ | H | L-1f | |
| N | CH | N | CH | O | $OCH_3$ | $CH_3$ | H | L-1g | |
| N | CH | N | CH | O | $OCH_3$ | $CH_3$ | H | L-1h | |
| N | CH | N | CH | O | $OCH_3$ | $CH_3$ | H | L-1i | |
| N | CH | N | CH | O | $OCH_3$ | $CH_3$ | H | L-1j | |
| N | CH | N | CH | O | $OCH_3$ | $CH_3$ | H | L-1k | |
| N | CH | N | CH | O | $OCH_3$ | $CH_3$ | H | L-3a | |
| N | CH | N | CH | O | $OCH_3$ | $CH_3$ | H | L-3b | |
| N | CH | N | CH | O | $OCH_3$ | $CH_3$ | H | L-4a | |
| N | CH | N | CH | O | $OCH_3$ | $CH_3$ | H | L-7a | |
| N | CH | N | CH | O | $OCH_3$ | $CH_3$ | H | L-8a | |
| N | CH | N | CH | O | $OCH_3$ | $CH_3$ | H | L-8b | |
| N | CH | N | CH | O | $OCH_3$ | $CH_3$ | H | L-9a | |
| N | CH | N | CH | O | $OCH_3$ | $CH_3$ | H | L-12a | |
| N | CH | N | CH | O | $OCH_3$ | $CH_3$ | H | L-12b | |
| N | CH | N | CH | O | $OCH_3$ | $CH_3$ | H | L-14a | |
| N | CH | N | CH | O | $OCH_3$ | $CH_3$ | H | L-15a | |
| N | CH | N | CH | O | $OCH_3$ | $CH_3$ | H | L-16a | |
| N | CH | N | CH | O | $OCH_3$ | $CH_3$ | H | L-16b | |
| N | CH | N | CH | O | $OCH_3$ | $CH_3$ | H | L-18a | |
| N | CH | N | CH | O | $OCH_3$ | $CH_3$ | H | L-20a | |
| N | CH | N | CH | O | $OCH_3$ | $CH_3$ | H | L-22a | |
| N | CH | N | CH | S | $OCH_3$ | $CH_3$ | H | L-1a | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| N | CH | N | CH | O | $OCH_3$ | $CH_3$ | $CH_3$ | L-1a | |
| N | CH | N | CH | O | $CH_3$ | $OCH_3$ | H | L-1a | |
| N | CH | N | CH | O | $CH_3$ | $OCH_3$ | H | L-1b | |
| N | CH | N | CH | O | $CH_3$ | $OCH_3$ | H | L-1c | |
| N | CH | N | CH | O | $CH_3$ | $OCH_3$ | H | L-1d | |
| N | CH | N | CH | O | $CH_3$ | $OCH_3$ | H | L-1e | |
| N | CH | N | CH | O | $CH_3$ | $OCH_3$ | H | L-1f | |
| N | CH | N | CH | O | $CH_3$ | $OCH_3$ | H | L-1g | |
| N | CH | N | CH | O | $CH_3$ | $OCH_3$ | H | L-1h | |
| N | CH | N | CH | O | $CH_3$ | $OCH_3$ | H | L-1i | |
| N | CH | N | CH | O | $CH_3$ | $OCH_3$ | H | L-1j | |
| N | CH | N | CH | O | $CH_3$ | $OCH_3$ | H | L-1k | |
| N | CH | N | CH | O | $CH_3$ | $OCH_3$ | H | L-3a | |
| N | CH | N | CH | O | $CH_3$ | $OCH_3$ | H | L-3b | |
| N | CH | N | CH | O | $CH_3$ | $OCH_3$ | H | L-4a | |
| N | CH | N | CH | O | $CH_3$ | $OCH_3$ | H | L-7a | |
| N | CH | N | CH | O | $CH_3$ | $OCH_3$ | H | L-8a | |
| N | CH | N | CH | O | $CH_3$ | $OCH_3$ | H | L-8b | |
| N | CH | N | CH | O | $CH_3$ | $OCH_3$ | H | L-9a | |
| N | CH | N | CH | O | $CH_3$ | $OCH_3$ | H | L-12a | |
| N | CH | N | CH | O | $CH_3$ | $OCH_3$ | H | L-12b | |
| N | CH | N | CH | O | $CH_3$ | $OCH_3$ | H | L-14a | |
| N | CH | N | CH | O | $CH_3$ | $OCH_3$ | H | L-15a | |
| N | CH | N | CH | O | $CH_3$ | $OCH_3$ | H | L-16a | |
| N | CH | N | CH | O | $CH_3$ | $OCH_3$ | H | L-16b | |
| N | CH | N | CH | O | $CH_3$ | $OCH_3$ | H | L-18a | |
| N | CH | N | CH | O | $CH_3$ | $OCH_3$ | H | L-20a | |
| N | CH | N | CH | O | $CH_3$ | $OCH_3$ | H | L-22a | |
| N | CH | N | CH | S | $CH_3$ | $OCH_3$ | H | L-1a | |
| N | CH | N | CH | O | $CH_3$ | $OCH_3$ | $CH_3$ | L-1a | |
| N | CH | N | CH | O | $OCH_3$ | $OCH_3$ | H | L-1a | |
| N | CH | N | CH | O | $OCH_3$ | $OCH_3$ | H | L-1b | |
| N | CH | N | CH | O | $OCH_3$ | $OCH_3$ | H | L-1c | |
| N | CH | N | CH | O | $OCH_3$ | $OCH_3$ | H | L-1d | |
| N | CH | N | CH | O | $OCH_3$ | $OCH_3$ | H | L-1e | |
| N | CH | N | CH | O | $OCH_3$ | $OCH_3$ | H | L-1f | |
| N | CH | N | CH | O | $OCH_3$ | $OCH_3$ | H | L-1g | |
| N | CH | N | CH | O | $OCH_3$ | $OCH_3$ | H | L-1h | |
| N | CH | N | CH | O | $OCH_3$ | $OCH_3$ | H | L-1i | |
| N | CH | N | CH | O | $OCH_3$ | $OCH_3$ | H | L-1j | |
| N | CH | N | CH | O | $OCH_3$ | $OCH_3$ | H | L-1k | |
| N | CH | N | CH | O | $OCH_3$ | $OCH_3$ | H | L-3a | |
| N | CH | N | CH | O | $OCH_3$ | $OCH_3$ | H | L-3b | |
| N | CH | N | CH | O | $OCH_3$ | $OCH_3$ | H | L-4a | |
| N | CH | N | CH | O | $OCH_3$ | $OCH_3$ | H | L-7a | |
| N | CH | N | CH | O | $OCH_3$ | $OCH_3$ | H | L-8a | |
| N | CH | N | CH | O | $OCH_3$ | $OCH_3$ | H | L-8b | |
| N | CH | N | CH | O | $OCH_3$ | $OCH_3$ | H | L-9a | |
| N | CH | N | CH | O | $OCH_3$ | $OCH_3$ | H | L-12a | |
| N | CH | N | CH | O | $OCH_3$ | $OCH_3$ | H | L-12b | |
| N | CH | N | CH | O | $OCH_3$ | $OCH_3$ | H | L-14a | |
| N | CH | N | CH | O | $OCH_3$ | $OCH_3$ | H | L-15a | |
| N | CH | N | CH | O | $OCH_3$ | $OCH_3$ | H | L-16a | |
| N | CH | N | CH | O | $OCH_3$ | $OCH_3$ | H | L-16b | |
| N | CH | N | CH | O | $OCH_3$ | $OCH_3$ | H | L-18a | |
| N | CH | N | CH | O | $OCH_3$ | $OCH_3$ | H | L-20a | |
| N | CH | N | CH | O | $OCH_3$ | $OCH_3$ | H | L-22a | |
| N | CH | N | CH | S | $OCH_3$ | $OCH_3$ | H | L-1a | |
| N | CH | N | CH | O | $OCH_3$ | $OCH_3$ | $CH_3$ | L-1a | |
| N | CH | CH | CH | O | $CH_3$ | $CH_3$ | H | L-1a | |
| N | CH | CH | CH | O | $CH_3$ | $CH_3$ | H | L-1b | |
| N | CH | CH | CH | O | $CH_3$ | $CH_3$ | H | L-1c | |
| N | CH | CH | CH | O | $CH_3$ | $CH_3$ | H | L-1d | |
| N | CH | CH | CH | O | $CH_3$ | $CH_3$ | H | L-1e | |
| N | CH | CH | CH | O | $CH_3$ | $CH_3$ | H | L-1f | |
| N | CH | CH | CH | O | $CH_3$ | $CH_3$ | H | L-1g | |
| N | CH | CH | CH | O | $CH_3$ | $CH_3$ | H | L-1h | |
| N | CH | CH | CH | O | $CH_3$ | $CH_3$ | H | L-1i | |
| N | CH | CH | CH | O | $CH_3$ | $CH_3$ | H | L-1j | |
| N | CH | CH | CH | O | $CH_3$ | $CH_3$ | H | L-1k | |
| N | CH | CH | CH | O | $CH_3$ | $CH_3$ | H | L-3a | |
| N | CH | CH | CH | O | $CH_3$ | $CH_3$ | H | L-3b | |
| N | CH | CH | CH | O | $CH_3$ | $CH_3$ | H | L-4a | |
| N | CH | CH | CH | O | $CH_3$ | $CH_3$ | H | L-7a | |
| N | CH | CH | CH | O | $CH_3$ | $CH_3$ | H | L-8a | |
| N | CH | CH | CH | O | $CH_3$ | $CH_3$ | H | L-8b | |
| N | CH | CH | CH | O | $CH_3$ | $CH_3$ | H | L-9a | |
| N | CH | CH | CH | O | $CH_3$ | $CH_3$ | H | L-12b | |
| N | CH | CH | CH | O | $CH_3$ | $CH_3$ | H | L-14a | |
| N | CH | CH | CH | O | $CH_3$ | $CH_3$ | H | L-15a | |

TABLE 5-continued

General Formula 5

| Z | Z₁ | Z₂ | Z₃ | W | X | Y | R | L | m.p. (°C.) |
|---|---|---|---|---|---|---|---|---|---|
| N | CH | CH | CH | O | CH₃ | CH₃ | H | L-16a | |
| N | CH | CH | CH | O | CH₃ | CH₃ | H | L-16b | |
| N | CH | CH | CH | O | CH₃ | CH₃ | H | L-18a | |
| N | CH | CH | CH | O | CH₃ | CH₃ | H | L-20a | |
| N | CH | CH | CH | O | CH₃ | CH₃ | H | L-22a | |
| N | CH | CH | CH | S | CH₃ | CH₃ | H | L-1a | |
| N | CH | CH | CH | O | CH₃ | CH₃ | CH₃ | L-1a | |
| N | CH | CH | CH | O | OCH₃ | CH₃ | H | L-1a | |
| N | CH | CH | CH | O | OCH₃ | CH₃ | H | L-1b | |
| N | CH | CH | CH | O | OCH₃ | CH₃ | H | L-1c | |
| N | CH | CH | CH | O | OCH₃ | CH₃ | H | L-1d | |
| N | CH | CH | CH | O | OCH₃ | CH₃ | H | L-1e | |
| N | CH | CH | CH | O | OCH₃ | CH₃ | H | L-1f | |
| N | CH | CH | CH | O | OCH₃ | CH₃ | H | L-1g | |
| N | CH | CH | CH | O | OCH₃ | CH₃ | H | L-1h | |
| N | CH | CH | CH | O | OCH₃ | CH₃ | H | L-1i | |
| N | CH | CH | CH | O | OCH₃ | CH₃ | H | L-1j | |
| N | CH | CH | CH | O | OCH₃ | CH₃ | H | L-1k | |
| N | CH | CH | CH | O | OCH₃ | CH₃ | H | L-3a | |
| N | CH | CH | CH | O | OCH₃ | CH₃ | H | L-3b | |
| N | CH | CH | CH | O | OCH₃ | CH₃ | H | L-4a | |
| N | CH | CH | CH | O | OCH₃ | CH₃ | H | L-7a | |
| N | CH | CH | CH | O | OCH₃ | CH₃ | H | L-8a | |
| N | CH | CH | CH | O | OCH₃ | CH₃ | H | L-8b | |
| N | CH | CH | CH | O | OCH₃ | CH₃ | H | L-9a | |
| N | CH | CH | CH | O | OCH₃ | CH₃ | H | L-12a | |
| N | CH | CH | CH | O | OCH₃ | CH₃ | H | L-12b | |
| N | CH | CH | CH | O | OCH₃ | CH₃ | H | L-14a | |
| N | CH | CH | CH | O | OCH₃ | CH₃ | H | L-15a | |
| N | CH | CH | CH | O | OCH₃ | CH₃ | H | L-16a | |
| N | CH | CH | CH | O | OCH₃ | CH₃ | H | L-16b | |
| N | CH | CH | CH | O | OCH₃ | CH₃ | H | L-18a | |
| N | CH | CH | CH | O | OCH₃ | CH₃ | H | L-20a | |
| N | CH | CH | CH | O | OCH₃ | CH₃ | H | L-22a | |
| N | CH | CH | CH | S | OCH₃ | CH₃ | H | L-1a | |
| N | CH | CH | CH | O | OCH₃ | CH₃ | CH₃ | L-1a | |
| N | CH | CH | CH | O | CH₃ | OCH₃ | H | L-1a | |
| N | CH | CH | CH | O | CH₃ | OCH₃ | H | L-1b | |
| N | CH | CH | CH | O | CH₃ | OCH₃ | H | L-1c | |
| N | CH | CH | CH | O | CH₃ | OCH₃ | H | L-1d | |
| N | CH | CH | CH | O | CH₃ | OCH₃ | H | L-1e | |
| N | CH | CH | CH | O | CH₃ | OCH₃ | H | L-1f | |
| N | CH | CH | CH | O | CH₃ | OCH₃ | H | L-1g | |
| N | CH | CH | CH | O | CH₃ | OCH₃ | H | L-1h | |
| N | CH | CH | CH | O | CH₃ | OCH₃ | H | L-1i | |
| N | CH | CH | CH | O | CH₃ | OCH₃ | H | L-1j | |
| N | CH | CH | CH | O | CH₃ | OCH₃ | H | L-1k | |
| N | CH | CH | CH | O | CH₃ | OCH₃ | H | L-3a | |
| N | CH | CH | CH | O | CH₃ | OCH₃ | H | L-3b | |
| N | CH | CH | CH | O | CH₃ | OCH₃ | H | L-4a | |
| N | CH | CH | CH | O | CH₃ | OCH₃ | H | L-7a | |
| N | CH | CH | CH | O | CH₃ | OCH₃ | H | L-8a | |
| N | CH | CH | CH | O | CH₃ | OCH₃ | H | L-8b | |
| N | CH | CH | CH | O | CH₃ | OCH₃ | H | L-9a | |
| N | CH | CH | CH | O | CH₃ | OCH₃ | H | L-12a | |
| N | CH | CH | CH | O | CH₃ | OCH₃ | H | L-12b | |
| N | CH | CH | CH | O | CH₃ | OCH₃ | H | L-14a | |
| N | CH | CH | CH | O | CH₃ | OCH₃ | H | L-15a | |
| N | CH | CH | CH | O | CH₃ | OCH₃ | H | L-16a | |
| N | CH | CH | CH | O | CH₃ | OCH₃ | H | L-16b | |
| N | CH | CH | CH | O | CH₃ | OCH₃ | H | L-18a | |
| N | CH | CH | CH | O | CH₃ | OCH₃ | H | L-20a | |
| N | CH | CH | CH | O | CH₃ | OCH₃ | H | L-22a | |
| N | CH | CH | CH | S | CH₃ | OCH₃ | H | L-1a | |
| N | CH | CH | CH | O | CH₃ | OCH₃ | CH₃ | L-1a | |
| N | CH | CH | CH | O | OCH₃ | OCH₃ | H | L-1a | |
| N | CH | CH | CH | O | OCH₃ | OCH₃ | H | L-1b | 284–287 |
| N | CH | CH | CH | O | OCH₃ | OCH₃ | H | L-1c | 223–226 |
| N | CH | CH | CH | O | OCH₃ | OCH₃ | H | L-1d | 277–279 |
| N | CH | CH | CH | O | OCH₃ | OCH₃ | H | L-1e | |
| N | CH | CH | CH | O | OCH₃ | OCH₃ | H | L-1f | |
| N | CH | CH | CH | O | OCH₃ | OCH₃ | H | L-1g | |
| N | CH | CH | CH | O | OCH₃ | OCH₃ | H | L-1h | |
| N | CH | CH | CH | O | OCH₃ | OCH₃ | H | L-1i | |
| N | CH | CH | CH | O | OCH₃ | OCH₃ | H | L-1j | |
| N | CH | CH | CH | O | OCH₃ | OCH₃ | H | L-1k | |
| N | CH | CH | CH | O | OCH₃ | OCH₃ | H | L-3a | |
| N | CH | CH | CH | O | OCH₃ | OCH₃ | H | L-3b | |
| N | CH | CH | CH | O | OCH₃ | OCH₃ | H | L-4a | |
| N | CH | CH | CH | O | OCH₃ | OCH₃ | H | L-7a | |

TABLE 5-continued

General Formula 5

| Z | Z$_1$ | Z$_2$ | Z$_3$ | W | X | Y | R | L | m.p. (°C.) |
|---|---|---|---|---|---|---|---|---|---|
| N | CH | CH | CH | O | OCH$_3$ | OCH$_3$ | H | L-8a | |
| N | CH | CH | CH | O | OCH$_3$ | OCH$_3$ | H | L-8b | |
| N | CH | CH | CH | O | OCH$_3$ | OCH$_3$ | H | L-9a | |
| N | CH | CH | CH | O | OCH$_3$ | OCH$_3$ | H | L-12a | |
| N | CH | CH | CH | O | OCH$_3$ | OCH$_3$ | H | L-12b | |
| N | CH | CH | CH | O | OCH$_3$ | OCH$_3$ | H | L-14a | |
| N | CH | CH | CH | O | OCH$_3$ | OCH$_3$ | H | L-15a | |
| N | CH | CH | CH | O | OCH$_3$ | OCH$_3$ | H | L-16a | 295–296 |
| N | CH | CH | CH | O | OCH$_3$ | OCH$_3$ | H | L-16b | |
| N | CH | CH | CH | O | OCH$_3$ | OCH$_3$ | H | L-18a | |
| N | CH | CH | CH | O | OCH$_3$ | OCH$_3$ | H | L-20a | |
| N | CH | CH | CH | O | OCH$_3$ | OCH$_3$ | H | L-22a | |
| N | CH | CH | CH | S | OCH$_3$ | OCH$_3$ | H | L-1a | |
| N | CH | CH | CH | O | OCH$_3$ | OCH$_3$ | CH$_3$ | L-1a | |
| CH | N | CH | N | O | CH$_3$ | CH$_3$ | H | L-1a | |
| CH | N | CH | N | O | CH$_3$ | CH$_3$ | H | L-1b | |
| CH | N | CH | N | O | CH$_3$ | CH$_3$ | H | L-1c | |
| CH | N | CH | N | O | CH$_3$ | CH$_3$ | H | L-1d | |
| CH | N | CH | N | O | CH$_3$ | CH$_3$ | H | L-1e | |
| CH | N | CH | N | O | CH$_3$ | CH$_3$ | H | L-1f | |
| CH | N | CH | N | O | CH$_3$ | CH$_3$ | H | L-1g | |
| CH | N | CH | N | O | CH$_3$ | CH$_3$ | H | L-1h | |
| CH | N | CH | N | O | CH$_3$ | CH$_3$ | H | L-1i | |
| CH | N | CH | N | O | CH$_3$ | CH$_3$ | H | L-1j | |
| CH | N | CH | N | O | CH$_3$ | CH$_3$ | H | L-1k | |
| CH | N | CH | N | O | CH$_3$ | CH$_3$ | H | L-3a | |
| CH | N | CH | N | O | CH$_3$ | CH$_3$ | H | L-3b | |
| CH | N | CH | N | O | CH$_3$ | CH$_3$ | H | L-4a | |
| CH | N | CH | N | O | CH$_3$ | CH$_3$ | H | L-7a | |
| CH | N | CH | N | O | CH$_3$ | CH$_3$ | H | L-8a | |
| CH | N | CH | N | O | CH$_3$ | CH$_3$ | H | L-8b | |
| CH | N | CH | N | O | CH$_3$ | CH$_3$ | H | L-9a | |
| CH | N | CH | N | O | CH$_3$ | CH$_3$ | H | L-12a | |
| CH | N | CH | N | O | CH$_3$ | CH$_3$ | H | L-12b | |
| CH | N | CH | N | O | CH$_3$ | CH$_3$ | H | L-14a | |
| CH | N | CH | N | O | CH$_3$ | CH$_3$ | H | L-15a | |
| CH | N | CH | N | O | CH$_3$ | CH$_3$ | H | L-16a | |
| CH | N | CH | N | O | CH$_3$ | CH$_3$ | H | L-16b | |
| CH | N | CH | N | O | CH$_3$ | CH$_3$ | H | L-18a | |
| CH | N | CH | N | O | CH$_3$ | CH$_3$ | H | L-20a | |
| CH | N | CH | N | O | CH$_3$ | CH$_3$ | H | L-22a | |
| CH | N | CH | N | S | CH$_3$ | CH$_3$ | H | L-1a | |
| CH | N | CH | N | O | CH$_3$ | CH$_3$ | CH$_3$ | L-1a | |
| CH | N | CH | N | O | OCH$_3$ | CH$_3$ | H | L-1a | |
| CH | N | CH | N | O | OCH$_3$ | CH$_3$ | H | L-1b | |
| CH | N | CH | N | O | OCH$_3$ | CH$_3$ | H | L-1c | |
| CH | N | CH | N | O | OCH$_3$ | CH$_3$ | H | L-1d | |
| CH | N | CH | N | O | OCH$_3$ | CH$_3$ | H | L-1e | |
| CH | N | CH | N | O | OCH$_3$ | CH$_3$ | H | L-1f | |
| CH | N | CH | N | O | OCH$_3$ | CH$_3$ | H | L-1g | |
| CH | N | CH | N | O | OCH$_3$ | CH$_3$ | H | L-1h | |
| CH | N | CH | N | O | OCH$_3$ | CH$_3$ | H | L-1i | |
| CH | N | CH | N | O | OCH$_3$ | CH$_3$ | H | L-1j | |
| CH | N | CH | N | O | OCH$_3$ | CH$_3$ | H | L-1k | |
| CH | N | CH | N | O | OCH$_3$ | CH$_3$ | H | L-3a | |
| CH | N | CH | N | O | OCH$_3$ | CH$_3$ | H | L-3b | |
| CH | N | CH | N | O | OCH$_3$ | CH$_3$ | H | L-4a | |
| CH | N | CH | N | O | OCH$_3$ | CH$_3$ | H | L-7a | |
| CH | N | CH | N | O | OCH$_3$ | CH$_3$ | H | L-8a | |
| CH | N | CH | N | O | OCH$_3$ | CH$_3$ | H | L-8b | |
| CH | N | CH | N | O | OCH$_3$ | CH$_3$ | H | L-9a | |
| CH | N | CH | N | O | OCH$_3$ | CH$_3$ | H | L-12a | |
| CH | N | CH | N | O | OCH$_3$ | CH$_3$ | H | L-12b | |
| CH | N | CH | N | O | OCH$_3$ | CH$_3$ | H | L-14a | |
| CH | N | CH | N | O | OCH$_3$ | CH$_3$ | H | L-15a | |
| CH | N | CH | N | O | OCH$_3$ | CH$_3$ | H | L-16a | |
| CH | N | CH | N | O | OCH$_3$ | CH$_3$ | H | L-16b | |
| CH | N | CH | N | O | OCH$_3$ | CH$_3$ | H | L-18a | |
| CH | N | CH | N | O | OCH$_3$ | CH$_3$ | H | L-20a | |
| CH | N | CH | N | O | OCH$_3$ | CH$_3$ | H | L-22a | |
| CH | N | CH | N | S | OCH$_3$ | CH$_3$ | H | L-1a | |
| CH | N | CH | N | O | OCH$_3$ | CH$_3$ | CH$_3$ | L-1a | |
| CH | N | CH | N | O | CH$_3$ | OCH$_3$ | H | L-1a | |
| CH | N | CH | N | O | CH$_3$ | OCH$_3$ | H | L-1b | |
| CH | N | CH | N | O | CH$_3$ | OCH$_3$ | H | L-1c | |
| CH | N | CH | N | O | CH$_3$ | OCH$_3$ | H | L-1d | |
| CH | N | CH | N | O | CH$_3$ | OCH$_3$ | H | L-1e | |
| CH | N | CH | N | O | CH$_3$ | OCH$_3$ | H | L-1f | |
| CH | N | CH | N | O | CH$_3$ | OCH$_3$ | H | L-1g | |
| CH | N | CH | N | O | CH$_3$ | OCH$_3$ | H | L-1h | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| CH | N | CH | N | O | $CH_3$ | $OCH_3$ | H | L-1i | |
| CH | N | CH | N | O | $CH_3$ | $OCH_3$ | H | L-1j | |
| CH | N | CH | N | O | $CH_3$ | $OCH_3$ | H | L-1k | |
| CH | N | CH | N | O | $CH_3$ | $OCH_3$ | H | L-3a | |
| CH | N | CH | N | O | $CH_3$ | $OCH_3$ | H | L-3b | |
| CH | N | CH | N | O | $CH_3$ | $OCH_3$ | H | L-4a | |
| CH | N | CH | N | O | $CH_3$ | $OCH_3$ | H | L-7a | |
| CH | N | CH | N | O | $CH_3$ | $OCH_3$ | H | L-8a | |
| CH | N | CH | N | O | $CH_3$ | $OCH_3$ | H | L-8b | |
| CH | N | CH | N | O | $CH_3$ | $OCH_3$ | H | L-9a | |
| CH | N | CH | N | O | $CH_3$ | $OCH_3$ | H | L-12a | |
| CH | N | CH | N | O | $CH_3$ | $OCH_3$ | H | L-12b | |
| CH | N | CH | N | O | $CH_3$ | $OCH_3$ | H | L-14a | |
| CH | N | CH | N | O | $CH_3$ | $OCH_3$ | H | L-15a | |
| CH | N | CH | N | O | $CH_3$ | $OCH_3$ | H | L-16a | |
| CH | N | CH | N | O | $CH_3$ | $OCH_3$ | H | L-16b | |
| CH | N | CH | N | O | $CH_3$ | $OCH_3$ | H | L-18a | |
| CH | N | CH | N | O | $CH_3$ | $OCH_3$ | H | L-20a | |
| CH | N | CH | N | O | $CH_3$ | $OCH_3$ | H | L-22a | |
| CH | N | CH | N | S | $CH_3$ | $OCH_3$ | H | L-1a | |
| CH | N | CH | N | O | $CH_3$ | $OCH_3$ | $CH_3$ | L-1a | |
| CH | N | CH | N | O | $OCH_3$ | $OCH_3$ | H | L-1a | |
| CH | N | CH | N | O | $OCH_3$ | $OCH_3$ | H | L-1b | |
| CH | N | CH | N | O | $OCH_3$ | $OCH_3$ | H | L-1c | |
| CH | N | CH | N | O | $OCH_3$ | $OCH_3$ | H | L-1d | |
| CH | N | CH | N | O | $OCH_3$ | $OCH_3$ | H | L-1e | |
| CH | N | CH | N | O | $OCH_3$ | $OCH_3$ | H | L-1f | |
| CH | N | CH | N | O | $OCH_3$ | $OCH_3$ | H | L-1g | |
| CH | N | CH | N | O | $OCH_3$ | $OCH_3$ | H | L-1h | |
| CH | N | CH | N | O | $OCH_3$ | $OCH_3$ | H | L-1i | |
| CH | N | CH | N | O | $OCH_3$ | $OCH_3$ | H | L-1j | |
| CH | N | CH | N | O | $OCH_3$ | $OCH_3$ | H | L-1k | |
| CH | N | CH | N | O | $OCH_3$ | $OCH_3$ | H | L-3a | |
| CH | N | CH | N | O | $OCH_3$ | $OCH_3$ | H | L-3b | |
| CH | N | CH | N | O | $OCH_3$ | $OCH_3$ | H | L-4a | |
| CH | N | CH | N | O | $OCH_3$ | $OCH_3$ | H | L-7a | |
| CH | N | CH | N | O | $OCH_3$ | $OCH_3$ | H | L-8a | |
| CH | N | CH | N | O | $OCH_3$ | $OCH_3$ | H | L-8b | |
| CH | N | CH | N | O | $OCH_3$ | $OCH_3$ | H | L-9a | |
| CH | N | CH | N | O | $OCH_3$ | $OCH_3$ | H | L-12a | |
| CH | N | CH | N | O | $OCH_3$ | $OCH_3$ | H | L-12b | |
| CH | N | CH | N | O | $OCH_3$ | $OCH_3$ | H | L-14a | |
| CH | N | CH | N | O | $OCH_3$ | $OCH_3$ | H | L-15a | |
| CH | N | CH | N | O | $OCH_3$ | $OCH_3$ | H | L-16a | |
| CH | N | CH | N | O | $OCH_3$ | $OCH_3$ | H | L-16b | |
| CH | N | CH | N | O | $OCH_3$ | $OCH_3$ | H | L-18a | |
| CH | N | CH | N | O | $OCH_3$ | $OCH_3$ | H | L-20a | |
| CH | N | CH | N | O | $OCH_3$ | $OCH_3$ | H | L-22a | |
| CH | N | CH | N | S | $OCH_3$ | $OCH_3$ | H | L-1a | |
| CH | N | CH | N | O | $OCH_3$ | $OCH_3$ | $CH_3$ | L-1a | |
| CH | CH | N | N | O | $CH_3$ | $CH_3$ | H | L-1a | |
| CH | CH | N | N | O | $CH_3$ | $CH_3$ | H | L-1b | |
| CH | CH | N | N | O | $CH_3$ | $CH_3$ | H | L-1c | |
| CH | CH | N | N | O | $CH_3$ | $CH_3$ | H | L-1d | |
| CH | CH | N | N | O | $CH_3$ | $CH_3$ | H | L-1e | |
| CH | CH | N | N | O | $CH_3$ | $CH_3$ | H | L-1f | |
| CH | CH | N | N | O | $CH_3$ | $CH_3$ | H | L-1g | |
| CH | CH | N | N | O | $CH_3$ | $CH_3$ | H | L-1h | |
| CH | CH | N | N | O | $CH_3$ | $CH_3$ | H | L-1i | |
| CH | CH | N | N | O | $CH_3$ | $CH_3$ | H | L-1j | |
| CH | CH | N | N | O | $CH_3$ | $CH_3$ | H | L-1k | |
| CH | CH | N | N | O | $CH_3$ | $CH_3$ | H | L-3a | |
| CH | CH | N | N | O | $CH_3$ | $CH_3$ | H | L-3b | |
| CH | CH | N | N | O | $CH_3$ | $CH_3$ | H | L-4a | |
| CH | CH | N | N | O | $CH_3$ | $CH_3$ | H | L-7a | |
| CH | CH | N | N | O | $CH_3$ | $CH_3$ | H | L-8a | |
| CH | CH | N | N | O | $CH_3$ | $CH_3$ | H | L-8b | |
| CH | CH | N | N | O | $CH_3$ | $CH_3$ | H | L-9a | |
| CH | CH | N | N | O | $CH_3$ | $CH_3$ | H | L-12a | |
| CH | CH | N | N | O | $CH_3$ | $CH_3$ | H | L-12b | |
| CH | CH | N | N | O | $CH_3$ | $CH_3$ | H | L-14a | |
| CH | CH | N | N | O | $CH_3$ | $CH_3$ | H | L-15a | |
| CH | CH | N | N | O | $CH_3$ | $CH_3$ | H | L-16a | |
| CH | CH | N | N | O | $CH_3$ | $CH_3$ | H | L-16b | |
| CH | CH | N | N | O | $CH_3$ | $CH_3$ | H | L-18a | |
| CH | CH | N | N | O | $CH_3$ | $CH_3$ | H | L-20a | |
| CH | CH | N | N | O | $CH_3$ | $CH_3$ | H | L-22a | |
| CH | CH | N | N | S | $CH_3$ | $CH_3$ | H | L-1a | |
| CH | CH | N | N | O | $CH_3$ | $CH_3$ | $CH_3$ | L-1a | |
| CH | CH | N | N | O | $OCH_3$ | $CH_3$ | H | L-1a | |

TABLE 5-continued

General Formula 5

| Z | Z₁ | Z₂ | Z₃ | W | X | Y | R | L | m.p. (°C.) |
|---|---|---|---|---|---|---|---|---|---|
| CH | CH | N | N | O | OCH₃ | CH₃ | H | L-1b | |
| CH | CH | N | N | O | OCH₃ | CH₃ | H | L-1c | |
| CH | CH | N | N | O | OCH₃ | CH₃ | H | L-1d | |
| CH | CH | N | N | O | OCH₃ | CH₃ | H | L-1e | |
| CH | CH | N | N | O | OCH₃ | CH₃ | H | L-1f | |
| CH | CH | N | N | O | OCH₃ | CH₃ | H | L-1g | |
| CH | CH | N | N | O | OCH₃ | CH₃ | H | L-1h | |
| CH | CH | N | N | O | OCH₃ | CH₃ | H | L-1i | |
| CH | CH | N | N | O | OCH₃ | CH₃ | H | L-1j | |
| CH | CH | N | N | O | OCH₃ | CH₃ | H | L-1k | |
| CH | CH | N | N | O | OCH₃ | CH₃ | H | L-3a | |
| CH | CH | N | N | O | OCH₃ | CH₃ | H | L-3b | |
| CH | CH | N | N | O | OCH₃ | CH₃ | H | L-4a | |
| CH | CH | N | N | O | OCH₃ | CH₃ | H | L-7a | |
| CH | CH | N | N | O | OCH₃ | CH₃ | H | L-8a | |
| CH | CH | N | N | O | OCH₃ | CH₃ | H | L-8b | |
| CH | CH | N | N | O | OCH₃ | CH₃ | H | L-9a | |
| CH | CH | N | N | O | OCH₃ | CH₃ | H | L-12b | |
| CH | CH | N | N | O | OCH₃ | CH₃ | H | L-14a | |
| CH | CH | N | N | O | OCH₃ | CH₃ | H | L-15a | |
| CH | CH | N | N | O | OCH₃ | CH₃ | H | L-16a | |
| CH | CH | N | N | O | OCH₃ | CH₃ | H | L-16b | |
| CH | CH | N | N | O | OCH₃ | CH₃ | H | L-18a | |
| CH | CH | N | N | O | OCH₃ | CH₃ | H | L-20a | |
| CH | CH | N | N | O | OCH₃ | CH₃ | H | L-22a | |
| CH | CH | N | N | S | OCH₃ | CH₃ | H | L-1a | |
| CH | CH | N | N | O | OCH₃ | CH₃ | CH₃ | L-1a | |
| CH | CH | N | N | O | CH₃ | OCH₃ | H | L-1a | |
| CH | CH | N | N | O | CH₃ | OCH₃ | H | L-1b | |
| CH | CH | N | N | O | CH₃ | OCH₃ | H | L-1c | |
| CH | CH | N | N | O | CH₃ | OCH₃ | H | L-1d | |
| CH | CH | N | N | O | CH₃ | OCH₃ | H | L-1e | |
| CH | CH | N | N | O | CH₃ | OCH₃ | H | L-1f | |
| CH | CH | N | N | O | CH₃ | OCH₃ | H | L-1g | |
| CH | CH | N | N | O | CH₃ | OCH₃ | H | L-1h | |
| CH | CH | N | N | O | CH₃ | OCH₃ | H | L-1i | |
| CH | CH | N | N | O | CH₃ | OCH₃ | H | L-1j | |
| CH | CH | N | N | O | CH₃ | OCH₃ | H | L-1k | |
| CH | CH | N | N | O | CH₃ | OCH₃ | H | L-3a | |
| CH | CH | N | N | O | CH₃ | OCH₃ | H | L-3b | |
| CH | CH | N | N | O | CH₃ | OCH₃ | H | L-4a | |
| CH | CH | N | N | O | CH₃ | OCH₃ | H | L-7a | |
| CH | CH | N | N | O | CH₃ | OCH₃ | H | L-8a | |
| CH | CH | N | N | O | CH₃ | OCH₃ | H | L-8b | |
| CH | CH | N | N | O | CH₃ | OCH₃ | H | L-9a | |
| CH | CH | N | N | O | CH₃ | OCH₃ | H | L-12b | |
| CH | CH | N | N | O | CH₃ | OCH₃ | H | L-14a | |
| CH | CH | N | N | O | CH₃ | OCH₃ | H | L-15a | |
| CH | CH | N | N | O | CH₃ | OCH₃ | H | L-16a | |
| CH | CH | N | N | O | CH₃ | OCH₃ | H | L-16b | |
| CH | CH | N | N | O | CH₃ | OCH₃ | H | L-18a | |
| CH | CH | N | N | O | CH₃ | OCH₃ | H | L-20a | |
| CH | CH | N | N | O | CH₃ | OCH₃ | H | L-22a | |
| CH | CH | N | N | S | CH₃ | OCH₃ | H | L-1a | |
| CH | CH | N | N | O | CH₃ | OCH₃ | CH₃ | L-1a | |
| CH | CH | N | N | O | OCH₃ | OCH₃ | H | L-1a | |
| CH | CH | N | N | O | OCH₃ | OCH₃ | H | L-1b | |
| CH | CH | N | N | O | OCH₃ | OCH₃ | H | L-1c | |
| CH | CH | N | N | O | OCH₃ | OCH₃ | H | L-1d | |
| CH | CH | N | N | O | OCH₃ | OCH₃ | H | L-1e | |
| CH | CH | N | N | O | OCH₃ | OCH₃ | H | L-1f | |
| CH | CH | N | N | O | OCH₃ | OCH₃ | H | L-1g | |
| CH | CH | N | N | O | OCH₃ | OCH₃ | H | L-1h | |
| CH | CH | N | N | O | OCH₃ | OCH₃ | H | L-1i | |
| CH | CH | N | N | O | OCH₃ | OCH₃ | H | L-1j | |
| CH | CH | N | N | O | OCH₃ | OCH₃ | H | L-1k | |
| CH | CH | N | N | O | OCH₃ | OCH₃ | H | L-3a | |
| CH | CH | N | N | O | OCH₃ | OCH₃ | H | L-3b | |
| CH | CH | N | N | O | OCH₃ | OCH₃ | H | L-4a | |
| CH | CH | N | N | O | OCH₃ | OCH₃ | H | L-7a | |
| CH | CH | N | N | O | OCH₃ | OCH₃ | H | L-8a | |
| CH | CH | N | N | O | OCH₃ | OCH₃ | H | L-8b | |
| CH | CH | N | N | O | OCH₃ | OCH₃ | H | L-9a | |
| CH | CH | N | N | O | OCH₃ | OCH₃ | H | L-12a | |
| CH | CH | N | N | O | OCH₃ | OCH₃ | H | L-12b | |
| CH | CH | N | N | O | OCH₃ | OCH₃ | H | L-14a | |
| CH | CH | N | N | O | OCH₃ | OCH₃ | H | L-15a | |
| CH | CH | N | N | O | OCH₃ | OCH₃ | H | L-16a | |
| CH | CH | N | N | O | OCH₃ | OCH₃ | H | L-16b | |
| CH | CH | N | N | O | OCH₃ | OCH₃ | H | L-18a | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| CH | CH | N | N | O | OCH$_3$ | OCH$_3$ | H | L-20a | |
| CH | CH | N | N | O | OCH$_3$ | OCH$_3$ | H | L-22a | |
| CH | CH | N | N | S | OCH$_3$ | OCH$_3$ | H | L-1a | |
| CH | CH | N | N | O | OCH$_3$ | OCH$_3$ | CH$_3$ | L-1a | |
| CH | CH | CH | N | O | CH$_3$ | CH$_3$ | H | L-1a | |
| CH | CH | CH | N | O | CH$_3$ | CH$_3$ | H | L-1b | |
| CH | CH | CH | N | O | CH$_3$ | CH$_3$ | H | L-1c | |
| CH | CH | CH | N | O | CH$_3$ | CH$_3$ | H | L-1d | |
| CH | CH | CH | N | O | CH$_3$ | CH$_3$ | H | L-1e | |
| CH | CH | CH | N | O | CH$_3$ | CH$_3$ | H | L-1f | |
| CH | CH | CH | N | O | CH$_3$ | CH$_3$ | H | L-1g | |
| CH | CH | CH | N | O | CH$_3$ | CH$_3$ | H | L-1h | |
| CH | CH | CH | N | O | CH$_3$ | CH$_3$ | H | L-1i | |
| CH | CH | CH | N | O | CH$_3$ | CH$_3$ | H | L-1j | |
| CH | CH | CH | N | O | CH$_3$ | CH$_3$ | H | L-1k | |
| CH | CH | CH | N | O | CH$_3$ | CH$_3$ | H | L-3a | |
| CH | CH | CH | N | O | CH$_3$ | CH$_3$ | H | L-3b | |
| CH | CH | CH | N | O | CH$_3$ | CH$_3$ | H | L-4a | |
| CH | CH | CH | N | O | CH$_3$ | CH$_3$ | H | L-7a | |
| CH | CH | CH | N | O | CH$_3$ | CH$_3$ | H | L-8a | |
| CH | CH | CH | N | O | CH$_3$ | CH$_3$ | H | L-8b | |
| CH | CH | CH | N | O | CH$_3$ | CH$_3$ | H | L-9a | |
| CH | CH | CH | N | O | CH$_3$ | CH$_3$ | H | L-12a | |
| CH | CH | CH | N | O | CH$_3$ | CH$_3$ | H | L-12b | |
| CH | CH | CH | N | O | CH$_3$ | CH$_3$ | H | L-14a | |
| CH | CH | CH | N | O | CH$_3$ | CH$_3$ | H | L-15a | |
| CH | CH | CH | N | O | CH$_3$ | CH$_3$ | H | L-16a | |
| CH | CH | CH | N | O | CH$_3$ | CH$_3$ | H | L-16b | |
| CH | CH | CH | N | O | CH$_3$ | CH$_3$ | H | L-18a | |
| CH | CH | CH | N | O | CH$_3$ | CH$_3$ | H | L-20a | |
| CH | CH | CH | N | O | CH$_3$ | CH$_3$ | H | L-22a | |
| CH | CH | CH | N | S | CH$_3$ | CH$_3$ | H | L-1a | |
| CH | CH | CH | N | O | CH$_3$ | CH$_3$ | CH$_3$ | L-1a | |
| CH | CH | CH | N | O | OCH$_3$ | CH$_3$ | H | L-1a | |
| CH | CH | CH | N | O | OCH$_3$ | CH$_3$ | H | L-1b | |
| CH | CH | CH | N | O | OCH$_3$ | CH$_3$ | H | L-1c | |
| CH | CH | CH | N | O | OCH$_3$ | CH$_3$ | H | L-1d | |
| CH | CH | CH | N | O | OCH$_3$ | CH$_3$ | H | L-1e | |
| CH | CH | CH | N | O | OCH$_3$ | CH$_3$ | H | L-1f | |
| CH | CH | CH | N | O | OCH$_3$ | CH$_3$ | H | L-1g | |
| CH | CH | CH | N | O | OCH$_3$ | CH$_3$ | H | L-1h | |
| CH | CH | CH | N | O | OCH$_3$ | CH$_3$ | H | L-1i | |
| CH | CH | CH | N | O | OCH$_3$ | CH$_3$ | H | L-1j | |
| CH | CH | CH | N | O | OCH$_3$ | CH$_3$ | H | L-1k | |
| CH | CH | CH | N | O | OCH$_3$ | CH$_3$ | H | L-3a | |
| CH | CH | CH | N | O | OCH$_3$ | CH$_3$ | H | L-3b | |
| CH | CH | CH | N | O | OCH$_3$ | CH$_3$ | H | L-4a | |
| CH | CH | CH | N | O | OCH$_3$ | CH$_3$ | H | L-7a | |
| CH | CH | CH | N | O | OCH$_3$ | CH$_3$ | H | L-8a | |
| CH | CH | CH | N | O | OCH$_3$ | CH$_3$ | H | L-8b | |
| CH | CH | CH | N | O | OCH$_3$ | CH$_3$ | H | L-9a | |
| CH | CH | CH | N | O | OCH$_3$ | CH$_3$ | H | L-12b | |
| CH | CH | CH | N | O | OCH$_3$ | CH$_3$ | H | L-14a | |
| CH | CH | CH | N | O | OCH$_3$ | CH$_3$ | H | L-15a | |
| CH | CH | CH | N | O | OCH$_3$ | CH$_3$ | H | L-16a | |
| CH | CH | CH | N | O | OCH$_3$ | CH$_3$ | H | L-16b | |
| CH | CH | CH | N | O | OCH$_3$ | CH$_3$ | H | L-18a | |
| CH | CH | CH | N | O | OCH$_3$ | CH$_3$ | H | L-20a | |
| CH | CH | CH | N | O | OCH$_3$ | CH$_3$ | H | L-22a | |
| CH | CH | CH | N | S | OCH$_3$ | CH$_3$ | H | L-1a | |
| CH | CH | CH | N | O | OCH$_3$ | CH$_3$ | CH$_3$ | L-1a | |
| CH | CH | CH | N | O | CH$_3$ | OCH$_3$ | H | L-1a | |
| CH | CH | CH | N | O | CH$_3$ | OCH$_3$ | H | L-1b | |
| CH | CH | CH | N | O | CH$_3$ | OCH$_3$ | H | L-1c | |
| CH | CH | CH | N | O | CH$_3$ | OCH$_3$ | H | L-1d | |
| CH | CH | CH | N | O | CH$_3$ | OCH$_3$ | H | L-1e | |
| CH | CH | CH | N | O | CH$_3$ | OCH$_3$ | H | L-1f | |
| CH | CH | CH | N | O | CH$_3$ | OCH$_3$ | H | L-1g | |
| CH | CH | CH | N | O | CH$_3$ | OCH$_3$ | H | L-1h | |
| CH | CH | CH | N | O | CH$_3$ | OCH$_3$ | H | L-1i | |
| CH | CH | CH | N | O | CH$_3$ | OCH$_3$ | H | L-1j | |
| CH | CH | CH | N | O | CH$_3$ | OCH$_3$ | H | L-1k | |
| CH | CH | CH | N | O | CH$_3$ | OCH$_3$ | H | L-3a | |
| CH | CH | CH | N | O | CH$_3$ | OCH$_3$ | H | L-3b | |
| CH | CH | CH | N | O | CH$_3$ | OCH$_3$ | H | L-4a | |
| CH | CH | CH | N | O | CH$_3$ | OCH$_3$ | H | L-7a | |
| CH | CH | CH | N | O | CH$_3$ | OCH$_3$ | H | L-8a | |
| CH | CH | CH | N | O | CH$_3$ | OCH$_3$ | H | L-8b | |
| CH | CH | CH | N | O | CH$_3$ | OCH$_3$ | H | L-9a | |
| CH | CH | CH | N | O | CH$_3$ | OCH$_3$ | H | L-12b | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| CH | CH | CH | N | O | $CH_3$ | $OCH_3$ | H | L-14a | |
| CH | CH | CH | N | O | $CH_3$ | $OCH_3$ | H | L-15a | |
| CH | CH | CH | N | O | $CH_3$ | $OCH_3$ | H | L-16a | |
| CH | CH | CH | N | O | $CH_3$ | $OCH_3$ | H | L-16b | |
| CH | CH | CH | N | O | $CH_3$ | $OCH_3$ | H | L-18a | |
| CH | CH | CH | N | O | $CH_3$ | $OCH_3$ | H | L-20a | |
| CH | CH | CH | N | O | $CH_3$ | $OCH_3$ | H | L-22a | |
| CH | CH | CH | N | S | $CH_3$ | $OCH_3$ | H | L-1a | |
| CH | CH | CH | N | O | $CH_3$ | $OCH_3$ | $CH_3$ | L-1a | |
| CH | CH | CH | N | O | $OCH_3$ | $OCH_3$ | H | L-1a | |
| CH | CH | CH | N | O | $OCH_3$ | $OCH_3$ | H | L-1b | |
| CH | CH | CH | N | O | $OCH_3$ | $OCH_3$ | H | L-1c | |
| CH | CH | CH | N | O | $OCH_3$ | $OCH_3$ | H | L-1d | |
| CH | CH | CH | N | O | $OCH_3$ | $OCH_3$ | H | L-1e | |
| CH | CH | CH | N | O | $OCH_3$ | $OCH_3$ | H | L-1f | |
| CH | CH | CH | N | O | $OCH_3$ | $OCH_3$ | H | L-1g | |
| CH | CH | CH | N | O | $OCH_3$ | $OCH_3$ | H | L-1h | |
| CH | CH | CH | N | O | $OCH_3$ | $OCH_3$ | H | L-1i | |
| CH | CH | CH | N | O | $OCH_3$ | $OCH_3$ | H | L-1j | |
| CH | CH | CH | N | O | $OCH_3$ | $OCH_3$ | H | L-1k | |
| CH | CH | CH | N | O | $OCH_3$ | $OCH_3$ | H | L-3a | |
| CH | CH | CH | N | O | $OCH_3$ | $OCH_3$ | H | L-3b | |
| CH | CH | CH | N | O | $OCH_3$ | $OCH_3$ | H | L-4a | |
| CH | CH | CH | N | O | $OCH_3$ | $OCH_3$ | H | L-7a | |
| CH | CH | CH | N | O | $OCH_3$ | $OCH_3$ | H | L-8a | |
| CH | CH | CH | N | O | $OCH_3$ | $OCH_3$ | H | L-8b | |
| CH | CH | CH | N | O | $OCH_3$ | $OCH_3$ | H | L-9a | |
| CH | CH | CH | N | O | $OCH_3$ | $OCH_3$ | H | L-12b | |
| CH | CH | CH | N | O | $OCH_3$ | $OCH_3$ | H | L-14a | |
| CH | CH | CH | N | O | $OCH_3$ | $OCH_3$ | H | L-15a | |
| CH | CH | CH | N | O | $OCH_3$ | $OCH_3$ | H | L-16a | |
| CH | CH | CH | N | O | $OCH_3$ | $OCH_3$ | H | L-16b | |
| CH | CH | CH | N | O | $OCH_3$ | $OCH_3$ | H | L-18a | |
| CH | CH | CH | N | O | $OCH_3$ | $OCH_3$ | H | L-20a | |
| CH | CH | CH | N | O | $OCH_3$ | $OCH_3$ | H | L-22a | |
| CH | CH | CH | N | S | $OCH_3$ | $OCH_3$ | H | L-1a | |
| CH | CH | CH | N | O | $OCH_3$ | $OCH_3$ | $CH_3$ | L-1a | |
| N | N | CH | N | O | $CH_3$ | $CH_3$ | H | L-1a | |
| N | N | CH | N | O | $CH_3$ | $CH_3$ | H | L-1b | |
| N | N | CH | N | O | $CH_3$ | $CH_3$ | H | L-1c | |
| N | N | CH | N | O | $CH_3$ | $CH_3$ | H | L-1d | |
| N | N | CH | N | O | $CH_3$ | $CH_3$ | H | L-1e | |
| N | N | CH | N | O | $CH_3$ | $CH_3$ | H | L-1f | |
| N | N | CH | N | O | $CH_3$ | $CH_3$ | H | L-1g | |
| N | N | CH | N | O | $CH_3$ | $CH_3$ | H | L-1h | |
| N | N | CH | N | O | $CH_3$ | $CH_3$ | H | L-1i | |
| N | N | CH | N | O | $CH_3$ | $CH_3$ | H | L-1j | |
| N | N | CH | N | O | $CH_3$ | $CH_3$ | H | L-1k | |
| N | N | CH | N | O | $CH_3$ | $CH_3$ | H | L-3a | |
| N | N | CH | N | O | $CH_3$ | $CH_3$ | H | L-3b | |
| N | N | CH | N | O | $CH_3$ | $CH_3$ | H | L-4a | |
| N | N | CH | N | O | $CH_3$ | $CH_3$ | H | L-7a | |
| N | N | CH | N | O | $CH_3$ | $CH_3$ | H | L-8a | |
| N | N | CH | N | O | $CH_3$ | $CH_3$ | H | L-8b | |
| N | N | CH | N | O | $CH_3$ | $CH_3$ | H | L-9a | |
| N | N | CH | N | O | $CH_3$ | $CH_3$ | H | L-12a | |
| N | N | CH | N | O | $CH_3$ | $CH_3$ | H | L-12b | |
| N | N | CH | N | O | $CH_3$ | $CH_3$ | H | L-14a | |
| N | N | CH | N | O | $CH_3$ | $CH_3$ | H | L-15a | |
| N | N | CH | N | O | $CH_3$ | $CH_3$ | H | L-16a | |
| N | N | CH | N | O | $CH_3$ | $CH_3$ | H | L-16b | |
| N | N | CH | N | O | $CH_3$ | $CH_3$ | H | L-18a | |
| N | N | CH | N | O | $CH_3$ | $CH_3$ | H | L-20a | |
| N | N | CH | N | O | $CH_3$ | $CH_3$ | H | L-22a | |
| N | N | CH | N | S | $CH_3$ | $CH_3$ | H | L-1a | |
| N | N | CH | N | O | $CH_3$ | $CH_3$ | $CH_3$ | L-1a | |
| N | N | CH | N | O | $OCH_3$ | $CH_3$ | H | L-1a | |
| N | N | CH | N | O | $OCH_3$ | $CH_3$ | H | L-1b | |
| N | N | CH | N | O | $OCH_3$ | $CH_3$ | H | L-1c | |
| N | N | CH | N | O | $OCH_3$ | $CH_3$ | H | L-1d | |
| N | N | CH | N | O | $OCH_3$ | $CH_3$ | H | L-1e | |
| N | N | CH | N | O | $OCH_3$ | $CH_3$ | H | L-1f | |
| N | N | CH | N | O | $OCH_3$ | $CH_3$ | H | L-1g | |
| N | N | CH | N | O | $OCH_3$ | $CH_3$ | H | L-1h | |
| N | N | CH | N | O | $OCH_3$ | $CH_3$ | H | L-1i | |
| N | N | CH | N | O | $OCH_3$ | $CH_3$ | H | L-1j | |
| N | N | CH | N | O | $OCH_3$ | $CH_3$ | H | L-1k | |
| N | N | CH | N | O | $OCH_3$ | $CH_3$ | H | L-3a | |
| N | N | CH | N | O | $OCH_3$ | $CH_3$ | H | L-3b | |
| N | N | CH | N | O | $OCH_3$ | $CH_3$ | H | L-4a | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| N | N | CH | N | O | $OCH_3$ | $CH_3$ | H | L-7a | |
| N | N | CH | N | O | $OCH_3$ | $CH_3$ | H | L-8a | |
| N | N | CH | N | O | $OCH_3$ | $CH_3$ | H | L-8b | |
| N | N | CH | N | O | $OCH_3$ | $CH_3$ | H | L-9a | |
| N | N | CH | N | O | $OCH_3$ | $CH_3$ | H | L-12a | |
| N | N | CH | N | O | $OCH_3$ | $CH_3$ | H | L-12b | |
| N | N | CH | N | O | $OCH_3$ | $CH_3$ | H | L-14a | |
| N | N | CH | N | O | $OCH_3$ | $CH_3$ | H | L-15a | |
| N | N | CH | N | O | $OCH_3$ | $CH_3$ | H | L-16a | |
| N | N | CH | N | O | $OCH_3$ | $CH_3$ | H | L-16b | |
| N | N | CH | N | O | $OCH_3$ | $CH_3$ | H | L-18a | |
| N | N | CH | N | O | $OCH_3$ | $CH_3$ | H | L-20a | |
| N | N | CH | N | O | $OCH_3$ | $CH_3$ | H | L-22a | |
| N | N | CH | N | S | $OCH_3$ | $CH_3$ | H | L-1a | |
| N | N | CH | N | O | $OCH_3$ | $CH_3$ | $CH_3$ | L-1a | |
| N | N | CH | N | O | $CH_3$ | $OCH_3$ | H | L-1a | |
| N | N | CH | N | O | $CH_3$ | $OCH_3$ | H | L-1b | |
| N | N | CH | N | O | $CH_3$ | $OCH_3$ | H | L-1c | |
| N | N | CH | N | O | $CH_3$ | $OCH_3$ | H | L-1d | |
| N | N | CH | N | O | $CH_3$ | $OCH_3$ | H | L-1e | |
| N | N | CH | N | O | $CH_3$ | $OCH_3$ | H | L-1f | |
| N | N | CH | N | O | $CH_3$ | $OCH_3$ | H | L-1g | |
| N | N | CH | N | O | $CH_3$ | $OCH_3$ | H | L-1h | |
| N | N | CH | N | O | $CH_3$ | $OCH_3$ | H | L-1i | |
| N | N | CH | N | O | $CH_3$ | $OCH_3$ | H | L-1j | |
| N | N | CH | N | O | $CH_3$ | $OCH_3$ | H | L-1k | |
| N | N | CH | N | O | $CH_3$ | $OCH_3$ | H | L-3a | |
| N | N | CH | N | O | $CH_3$ | $OCH_3$ | H | L-3b | |
| N | N | CH | N | O | $CH_3$ | $OCH_3$ | H | L-4a | |
| N | N | CH | N | O | $CH_3$ | $OCH_3$ | H | L-7a | |
| N | N | CH | N | O | $CH_3$ | $OCH_3$ | H | L-8a | |
| N | N | CH | N | O | $CH_3$ | $OCH_3$ | H | L-8b | |
| N | N | CH | N | O | $CH_3$ | $OCH_3$ | H | L-9a | |
| N | N | CH | N | O | $CH_3$ | $OCH_3$ | H | L-12a | |
| N | N | CH | N | O | $CH_3$ | $OCH_3$ | H | L-12b | |
| N | N | CH | N | O | $CH_3$ | $OCH_3$ | H | L-14a | |
| N | N | CH | N | O | $CH_3$ | $OCH_3$ | H | L-15a | |
| N | N | CH | N | O | $CH_3$ | $OCH_3$ | H | L-16a | |
| N | N | CH | N | O | $CH_3$ | $OCH_3$ | H | L-16b | |
| N | N | CH | N | O | $CH_3$ | $OCH_3$ | H | L-18a | |
| N | N | CH | N | O | $CH_3$ | $OCH_3$ | H | L-20a | |
| N | N | CH | N | O | $CH_3$ | $OCH_3$ | H | L-22a | |
| N | N | CH | N | S | $CH_3$ | $OCH_3$ | H | L-1a | |
| N | N | CH | N | O | $CH_3$ | $OCH_3$ | $CH_3$ | L-1a | |
| N | N | CH | N | O | $OCH_3$ | $OCH_3$ | H | L-1a | |
| N | N | CH | N | O | $OCH_3$ | $OCH_3$ | H | L-1b | |
| N | N | CH | N | O | $OCH_3$ | $OCH_3$ | H | L-1c | |
| N | N | CH | N | O | $OCH_3$ | $OCH_3$ | H | L-1d | |
| N | N | CH | N | O | $OCH_3$ | $OCH_3$ | H | L-1e | |
| N | N | CH | N | O | $OCH_3$ | $OCH_3$ | H | L-1f | |
| N | N | CH | N | O | $OCH_3$ | $OCH_3$ | H | L-1g | |
| N | N | CH | N | O | $OCH_3$ | $OCH_3$ | H | L-1h | |
| N | N | CH | N | O | $OCH_3$ | $OCH_3$ | H | L-1i | |
| N | N | CH | N | O | $OCH_3$ | $OCH_3$ | H | L-1j | |
| N | N | CH | N | O | $OCH_3$ | $OCH_3$ | H | L-1k | |
| N | N | CH | N | O | $OCH_3$ | $OCH_3$ | H | L-3a | |
| N | N | CH | N | O | $OCH_3$ | $OCH_3$ | H | L-3b | |
| N | N | CH | N | O | $OCH_3$ | $OCH_3$ | H | L-4a | |
| N | N | CH | N | O | $OCH_3$ | $OCH_3$ | H | L-7a | |
| N | N | CH | N | O | $OCH_3$ | $OCH_3$ | H | L-8a | |
| N | N | CH | N | O | $OCH_3$ | $OCH_3$ | H | L-8b | |
| N | N | CH | N | O | $OCH_3$ | $OCH_3$ | H | L-9a | |
| N | N | CH | N | O | $OCH_3$ | $OCH_3$ | H | L-12a | |
| N | N | CH | N | O | $OCH_3$ | $OCH_3$ | H | L-12b | |
| N | N | CH | N | O | $OCH_3$ | $OCH_3$ | H | L-14a | |
| N | N | CH | N | O | $OCH_3$ | $OCH_3$ | H | L-15a | |
| N | N | CH | N | O | $OCH_3$ | $OCH_3$ | H | L-16a | |
| N | N | CH | N | O | $OCH_3$ | $OCH_3$ | H | L-16b | |
| N | N | CH | N | O | $OCH_3$ | $OCH_3$ | H | L-18a | |
| N | N | CH | N | O | $OCH_3$ | $OCH_3$ | H | L-20a | |
| N | N | CH | N | O | $OCH_3$ | $OCH_3$ | H | L-22a | |
| N | N | CH | N | S | $OCH_3$ | $OCH_3$ | H | L-1a | |
| N | N | CH | N | O | $OCH_3$ | $OCH_3$ | $CH_3$ | L-1a | |
| N | CH | N | N | O | $CH_3$ | $CH_3$ | H | L-1a | |
| N | CH | N | N | O | $CH_3$ | $CH_3$ | H | L-1b | |
| N | CH | N | N | O | $CH_3$ | $CH_3$ | H | L-1c | |
| N | CH | N | N | O | $CH_3$ | $CH_3$ | H | L-1d | |
| N | CH | N | N | O | $CH_3$ | $CH_3$ | H | L-1e | |
| N | CH | N | N | O | $CH_3$ | $CH_3$ | H | L-1f | |
| N | CH | N | N | O | $CH_3$ | $CH_3$ | H | L-1g | |

TABLE 5-continued

General Formula 5

| Z | Z₁ | Z₂ | Z₃ | W | X | Y | R | L | m.p. (°C.) |
|---|---|---|---|---|---|---|---|---|---|
| N | CH | N | N | O | CH₃ | CH₃ | H | L-1h | |
| N | CH | N | N | O | CH₃ | CH₃ | H | L-1i | |
| N | CH | N | N | O | CH₃ | CH₃ | H | L-1j | |
| N | CH | N | N | O | CH₃ | CH₃ | H | L-1k | |
| N | CH | N | N | O | CH₃ | CH₃ | H | L-3a | |
| N | CH | N | N | O | CH₃ | CH₃ | H | L-3b | |
| N | CH | N | N | O | CH₃ | CH₃ | H | L-4a | |
| N | CH | N | N | O | CH₃ | CH₃ | H | L-7a | |
| N | CH | N | N | O | CH₃ | CH₃ | H | L-8a | |
| N | CH | N | N | O | CH₃ | CH₃ | H | L-8b | |
| N | CH | N | N | O | CH₃ | CH₃ | H | L-9a | |
| N | CH | N | N | O | CH₃ | CH₃ | H | L-12a | |
| N | CH | N | N | O | CH₃ | CH₃ | H | L-12b | |
| N | CH | N | N | O | CH₃ | CH₃ | H | L-14a | |
| N | CH | N | N | O | CH₃ | CH₃ | H | L-15a | |
| N | CH | N | N | O | CH₃ | CH₃ | H | L-16a | |
| N | CH | N | N | O | CH₃ | CH₃ | H | L-16b | |
| N | CH | N | N | O | CH₃ | CH₃ | H | L-18a | |
| N | CH | N | N | O | CH₃ | CH₃ | H | L-20a | |
| N | CH | N | N | O | CH₃ | CH₃ | H | L-22a | |
| N | CH | N | N | S | CH₃ | CH₃ | H | L-1a | |
| N | CH | N | N | O | CH₃ | CH₃ | CH₃ | L-1a | |
| N | CH | N | N | O | OCH₃ | CH₃ | H | L-1a | |
| N | CH | N | N | O | OCH₃ | CH₃ | H | L-1b | |
| N | CH | N | N | O | OCH₃ | CH₃ | H | L-1c | |
| N | CH | N | N | O | OCH₃ | CH₃ | H | L-1d | |
| N | CH | N | N | O | OCH₃ | CH₃ | H | L-1e | |
| N | CH | N | N | O | OCH₃ | CH₃ | H | L-1f | |
| N | CH | N | N | O | OCH₃ | CH₃ | H | L-1g | |
| N | CH | N | N | O | OCH₃ | CH₃ | H | L-1h | |
| N | CH | N | N | O | OCH₃ | CH₃ | H | L-1i | |
| N | CH | N | N | O | OCH₃ | CH₃ | H | L-1j | |
| N | CH | N | N | O | OCH₃ | CH₃ | H | L-1k | |
| N | CH | N | N | O | OCH₃ | CH₃ | H | L-3a | |
| N | CH | N | N | O | OCH₃ | CH₃ | H | L-3b | |
| N | CH | N | N | O | OCH₃ | CH₃ | H | L-4a | |
| N | CH | N | N | O | OCH₃ | CH₃ | H | L-7a | |
| N | CH | N | N | O | OCH₃ | CH₃ | H | L-8a | |
| N | CH | N | N | O | OCH₃ | CH₃ | H | L-8b | |
| N | CH | N | N | O | OCH₃ | CH₃ | H | L-9a | |
| N | CH | N | N | O | OCH₃ | CH₃ | H | L-12a | |
| N | CH | N | N | O | OCH₃ | CH₃ | H | L-12b | |
| N | CH | N | N | O | OCH₃ | CH₃ | H | L-14a | |
| N | CH | N | N | O | OCH₃ | CH₃ | H | L-15a | |
| N | CH | N | N | O | OCH₃ | CH₃ | H | L-16a | |
| N | CH | N | N | O | OCH₃ | CH₃ | H | L-16b | |
| N | CH | N | N | O | OCH₃ | CH₃ | H | L-18a | |
| N | CH | N | N | O | OCH₃ | CH₃ | H | L-20a | |
| N | CH | N | N | O | OCH₃ | CH₃ | H | L-22a | |
| N | CH | N | N | S | OCH₃ | CH₃ | H | L-1a | |
| N | CH | N | N | O | OCH₃ | CH₃ | CH₃ | L-1a | |
| N | CH | N | N | O | CH₃ | OCH₃ | H | L-1a | |
| N | CH | N | N | O | CH₃ | OCH₃ | H | L-1b | |
| N | CH | N | N | O | CH₃ | OCH₃ | H | L-1c | |
| N | CH | N | N | O | CH₃ | OCH₃ | H | L-1d | |
| N | CH | N | N | O | CH₃ | OCH₃ | H | L-1e | |
| N | CH | N | N | O | CH₃ | OCH₃ | H | L-1f | |
| N | CH | N | N | O | CH₃ | OCH₃ | H | L-1g | |
| N | CH | N | N | O | CH₃ | OCH₃ | H | L-1h | |
| N | CH | N | N | O | CH₃ | OCH₃ | H | L-1i | |
| N | CH | N | N | O | CH₃ | OCH₃ | H | L-1j | |
| N | CH | N | N | O | CH₃ | OCH₃ | H | L-1k | |
| N | CH | N | N | O | CH₃ | OCH₃ | H | L-3a | |
| N | CH | N | N | O | CH₃ | OCH₃ | H | L-3b | |
| N | CH | N | N | O | CH₃ | OCH₃ | H | L-4a | |
| N | CH | N | N | O | CH₃ | OCH₃ | H | L-7a | |
| N | CH | N | N | O | CH₃ | OCH₃ | H | L-8a | |
| N | CH | N | N | O | CH₃ | OCH₃ | H | L-8b | |
| N | CH | N | N | O | CH₃ | OCH₃ | H | L-9a | |
| N | CH | N | N | O | CH₃ | OCH₃ | H | L-12a | |
| N | CH | N | N | O | CH₃ | OCH₃ | H | L-12b | |
| N | CH | N | N | O | CH₃ | OCH₃ | H | L-14a | |
| N | CH | N | N | O | CH₃ | OCH₃ | H | L-15a | |
| N | CH | N | N | O | CH₃ | OCH₃ | H | L-16a | |
| N | CH | N | N | O | CH₃ | OCH₃ | H | L-16b | |
| N | CH | N | N | O | CH₃ | OCH₃ | H | L-18a | |
| N | CH | N | N | O | CH₃ | OCH₃ | H | L-20a | |
| N | CH | N | N | O | CH₃ | OCH₃ | H | L-22a | |
| N | CH | N | N | S | CH₃ | OCH₃ | H | L-1a | |
| N | CH | N | N | O | CH₃ | OCH₃ | CH₃ | L-1a | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| N | CH | N | N | O | OCH$_3$ | OCH$_3$ | H | L-1a | |
| N | CH | N | N | O | OCH$_3$ | OCH$_3$ | H | L-1b | |
| N | CH | N | N | O | OCH$_3$ | OCH$_3$ | H | L-1c | |
| N | CH | N | N | O | OCH$_3$ | OCH$_3$ | H | L-1d | |
| N | CH | N | N | O | OCH$_3$ | OCH$_3$ | H | L-1e | |
| N | CH | N | N | O | OCH$_3$ | OCH$_3$ | H | L-1f | |
| N | CH | N | N | O | OCH$_3$ | OCH$_3$ | H | L-1g | |
| N | CH | N | N | O | OCH$_3$ | OCH$_3$ | H | L-1h | |
| N | CH | N | N | O | OCH$_3$ | OCH$_3$ | H | L-1i | |
| N | CH | N | N | O | OCH$_3$ | OCH$_3$ | H | L-1j | |
| N | CH | N | N | O | OCH$_3$ | OCH$_3$ | H | L-1k | |
| N | CH | N | N | O | OCH$_3$ | OCH$_3$ | H | L-3a | |
| N | CH | N | N | O | OCH$_3$ | OCH$_3$ | H | L-3b | |
| N | CH | N | N | O | OCH$_3$ | OCH$_3$ | H | L-4a | |
| N | CH | N | N | O | OCH$_3$ | OCH$_3$ | H | L-7a | |
| N | CH | N | N | O | OCH$_3$ | OCH$_3$ | H | L-8a | |
| N | CH | N | N | O | OCH$_3$ | OCH$_3$ | H | L-8b | |
| N | CH | N | N | O | OCH$_3$ | OCH$_3$ | H | L-9a | |
| N | CH | N | N | O | OCH$_3$ | OCH$_3$ | H | L-12a | |
| N | CH | N | N | O | OCH$_3$ | OCH$_3$ | H | L-12b | |
| N | CH | N | N | O | OCH$_3$ | OCH$_3$ | H | L-14a | |
| N | CH | N | N | O | OCH$_3$ | OCH$_3$ | H | L-15a | |
| N | CH | N | N | O | OCH$_3$ | OCH$_3$ | H | L-16a | |
| N | CH | N | N | O | OCH$_3$ | OCH$_3$ | H | L-16b | |
| N | CH | N | N | O | OCH$_3$ | OCH$_3$ | H | L-18a | |
| N | CH | N | N | O | OCH$_3$ | OCH$_3$ | H | L-20a | |
| N | CH | N | N | O | OCH$_3$ | OCH$_3$ | H | L-22a | |
| N | CH | N | N | S | OCH$_3$ | OCH$_3$ | H | L-1a | |
| N | CH | N | N | O | OCH$_3$ | OCH$_3$ | CH$_3$ | L-1a | |
| N | CH | CH | N | O | CH$_3$ | CH$_3$ | H | L-1a | |
| N | CH | CH | N | O | CH$_3$ | CH$_3$ | H | L-1b | |
| N | CH | CH | N | O | CH$_3$ | CH$_3$ | H | L-1c | |
| N | CH | CH | N | O | CH$_3$ | CH$_3$ | H | L-1d | |
| N | CH | CH | N | O | CH$_3$ | CH$_3$ | H | L-1e | |
| N | CH | CH | N | O | CH$_3$ | CH$_3$ | H | L-1f | |
| N | CH | CH | N | O | CH$_3$ | CH$_3$ | H | L-1g | |
| N | CH | CH | N | O | CH$_3$ | CH$_3$ | H | L-1h | |
| N | CH | CH | N | O | CH$_3$ | CH$_3$ | H | L-1i | |
| N | CH | CH | N | O | CH$_3$ | CH$_3$ | H | L-1j | |
| N | CH | CH | N | O | CH$_3$ | CH$_3$ | H | L-1k | |
| N | CH | CH | N | O | CH$_3$ | CH$_3$ | H | L-3a | |
| N | CH | CH | N | O | CH$_3$ | CH$_3$ | H | L-3b | |
| N | CH | CH | N | O | CH$_3$ | CH$_3$ | H | L-4a | |
| N | CH | CH | N | O | CH$_3$ | CH$_3$ | H | L-7a | |
| N | CH | CH | N | O | CH$_3$ | CH$_3$ | H | L-8a | |
| N | CH | CH | N | O | CH$_3$ | CH$_3$ | H | L-8b | |
| N | CH | CH | N | O | CH$_3$ | CH$_3$ | H | L-9a | |
| N | CH | CH | N | O | CH$_3$ | CH$_3$ | H | L-12a | |
| N | CH | CH | N | O | CH$_3$ | CH$_3$ | H | L-12b | |
| N | CH | CH | N | O | CH$_3$ | CH$_3$ | H | L-14a | |
| N | CH | CH | N | O | CH$_3$ | CH$_3$ | H | L-15a | |
| N | CH | CH | N | O | CH$_3$ | CH$_3$ | H | L-16a | |
| N | CH | CH | N | O | CH$_3$ | CH$_3$ | H | L-16b | |
| N | CH | CH | N | O | CH$_3$ | CH$_3$ | H | L-18a | |
| N | CH | CH | N | O | CH$_3$ | CH$_3$ | H | L-20a | |
| N | CH | CH | N | O | CH$_3$ | CH$_3$ | H | L-22a | |
| N | CH | CH | N | S | CH$_3$ | CH$_3$ | H | L-1a | |
| N | CH | CH | N | O | CH$_3$ | CH$_3$ | CH$_3$ | L-1a | |
| N | CH | CH | N | O | OCH$_3$ | CH$_3$ | H | L-1a | |
| N | CH | CH | N | O | OCH$_3$ | CH$_3$ | H | L-1b | |
| N | CH | CH | N | O | OCH$_3$ | CH$_3$ | H | L-1c | |
| N | CH | CH | N | O | OCH$_3$ | CH$_3$ | H | L-1d | |
| N | CH | CH | N | O | OCH$_3$ | CH$_3$ | H | L-1e | |
| N | CH | CH | N | O | OCH$_3$ | CH$_3$ | H | L-1f | |
| N | CH | CH | N | O | OCH$_3$ | CH$_3$ | H | L-1g | |
| N | CH | CH | N | O | OCH$_3$ | CH$_3$ | H | L-1h | |
| N | CH | CH | N | O | OCH$_3$ | CH$_3$ | H | L-1i | |
| N | CH | CH | N | O | OCH$_3$ | CH$_3$ | H | L-1j | |
| N | CH | CH | N | O | OCH$_3$ | CH$_3$ | H | L-1k | |
| N | CH | CH | N | O | OCH$_3$ | CH$_3$ | H | L-3a | |
| N | CH | CH | N | O | OCH$_3$ | CH$_3$ | H | L-3b | |
| N | CH | CH | N | O | OCH$_3$ | CH$_3$ | H | L-4a | |
| N | CH | CH | N | O | OCH$_3$ | CH$_3$ | H | L-7a | |
| N | CH | CH | N | O | OCH$_3$ | CH$_3$ | H | L-8a | |
| N | CH | CH | N | O | OCH$_3$ | CH$_3$ | H | L-8b | |
| N | CH | CH | N | O | OCH$_3$ | CH$_3$ | H | L-9a | |
| N | CH | CH | N | O | OCH$_3$ | CH$_3$ | H | L-12a | |
| N | CH | CH | N | O | OCH$_3$ | CH$_3$ | H | L-12b | |
| N | CH | CH | N | O | OCH$_3$ | CH$_3$ | H | L-14a | |
| N | CH | CH | N | O | OCH$_3$ | CH$_3$ | H | L-15a | |

TABLE 5-continued

General Formula 5

| Z | $Z_1$ | $Z_2$ | $Z_3$ | W | X | Y | R | L | m.p. (°C.) |
|---|---|---|---|---|---|---|---|---|---|
| N | CH | CH | N | O | OCH$_3$ | CH$_3$ | H | L-16a | |
| N | CH | CH | N | O | OCH$_3$ | CH$_3$ | H | L-16b | |
| N | CH | CH | N | O | OCH$_3$ | CH$_3$ | H | L-18a | |
| N | CH | CH | N | O | OCH$_3$ | CH$_3$ | H | L-20a | |
| N | CH | CH | N | O | OCH$_3$ | CH$_3$ | H | L-22a | |
| N | CH | CH | N | S | OCH$_3$ | CH$_3$ | H | L-1a | |
| N | CH | CH | N | O | OCH$_3$ | CH$_3$ | CH$_3$ | L-1a | |
| N | CH | CH | N | O | CH$_3$ | OCH$_3$ | H | L-1a | |
| N | CH | CH | N | O | CH$_3$ | OCH$_3$ | H | L-1b | |
| N | CH | CH | N | O | CH$_3$ | OCH$_3$ | H | L-1c | |
| N | CH | CH | N | O | CH$_3$ | OCH$_3$ | H | L-1d | |
| N | CH | CH | N | O | CH$_3$ | OCH$_3$ | H | L-1e | |
| N | CH | CH | N | O | CH$_3$ | OCH$_3$ | H | L-1f | |
| N | CH | CH | N | O | CH$_3$ | OCH$_3$ | H | L-1g | |
| N | CH | CH | N | O | CH$_3$ | OCH$_3$ | H | L-1h | |
| N | CH | CH | N | O | CH$_3$ | OCH$_3$ | H | L-1i | |
| N | CH | CH | N | O | CH$_3$ | OCH$_3$ | H | L-1j | |
| N | CH | CH | N | O | CH$_3$ | OCH$_3$ | H | L-1k | |
| N | CH | CH | N | O | CH$_3$ | OCH$_3$ | H | L-3a | |
| N | CH | CH | N | O | CH$_3$ | OCH$_3$ | H | L-3b | |
| N | CH | CH | N | O | CH$_3$ | OCH$_3$ | H | L-4a | |
| N | CH | CH | N | O | CH$_3$ | OCH$_3$ | H | L-7a | |
| N | CH | CH | N | O | CH$_3$ | OCH$_3$ | H | L-8a | |
| N | CH | CH | N | O | CH$_3$ | OCH$_3$ | H | L-8b | |
| N | CH | CH | N | O | CH$_3$ | OCH$_3$ | H | L-9a | |
| N | CH | CH | N | O | CH$_3$ | OCH$_3$ | H | L-12a | |
| N | CH | CH | N | O | CH$_3$ | OCH$_3$ | H | L-12b | |
| N | CH | CH | N | O | CH$_3$ | OCH$_3$ | H | L-14a | |
| N | CH | CH | N | O | CH$_3$ | OCH$_3$ | H | L-15a | |
| N | CH | CH | N | O | CH$_3$ | OCH$_3$ | H | L-16a | |
| N | CH | CH | N | O | CH$_3$ | OCH$_3$ | H | L-16b | |
| N | CH | CH | N | O | CH$_3$ | OCH$_3$ | H | L-18a | |
| N | CH | CH | N | O | CH$_3$ | OCH$_3$ | H | L-20a | |
| N | CH | CH | N | O | CH$_3$ | OCH$_3$ | H | L-22a | |
| N | CH | CH | N | S | CH$_3$ | OCH$_3$ | H | L-1a | |
| N | CH | CH | N | O | CH$_3$ | OCH$_3$ | CH$_3$ | L-1a | |
| N | CH | CH | N | O | OCH$_3$ | OCH$_3$ | H | L-1a | |
| N | CH | CH | N | O | OCH$_3$ | OCH$_3$ | H | L-1b | |
| N | CH | CH | N | O | OCH$_3$ | OCH$_3$ | H | L-1c | |
| N | CH | CH | N | O | OCH$_3$ | OCH$_3$ | H | L-1d | |
| N | CH | CH | N | O | OCH$_3$ | OCH$_3$ | H | L-1e | |
| N | CH | CH | N | O | OCH$_3$ | OCH$_3$ | H | L-1f | |
| N | CH | CH | N | O | OCH$_3$ | OCH$_3$ | H | L-1g | |
| N | CH | CH | N | O | OCH$_3$ | OCH$_3$ | H | L-1h | |
| N | CH | CH | N | O | OCH$_3$ | OCH$_3$ | H | L-1i | |
| N | CH | CH | N | O | OCH$_3$ | OCH$_3$ | H | L-1j | |
| N | CH | CH | N | O | OCH$_3$ | OCH$_3$ | H | L-1k | |
| N | CH | CH | N | O | OCH$_3$ | OCH$_3$ | H | L-3a | |
| N | CH | CH | N | O | OCH$_3$ | OCH$_3$ | H | L-3b | |
| N | CH | CH | N | O | OCH$_3$ | OCH$_3$ | H | L-4a | |
| N | CH | CH | N | O | OCH$_3$ | OCH$_3$ | H | L-7a | |
| N | CH | CH | N | O | OCH$_3$ | OCH$_3$ | H | L-8a | |
| N | CH | CH | N | O | OCH$_3$ | OCH$_3$ | H | L-8b | |
| N | CH | CH | N | O | OCH$_3$ | OCH$_3$ | H | L-9a | |
| N | CH | CH | N | O | OCH$_3$ | OCH$_3$ | H | L-12a | |
| N | CH | CH | N | O | OCH$_3$ | OCH$_3$ | H | L-12b | |
| N | CH | CH | N | O | OCH$_3$ | OCH$_3$ | H | L-14a | |
| N | CH | CH | N | O | OCH$_3$ | OCH$_3$ | H | L-15a | |
| N | CH | CH | N | O | OCH$_3$ | OCH$_3$ | H | L-16a | |
| N | CH | CH | N | O | OCH$_3$ | OCH$_3$ | H | L-16b | |
| N | CH | CH | N | O | OCH$_3$ | OCH$_3$ | H | L-18a | |
| N | CH | CH | N | O | OCH$_3$ | OCH$_3$ | H | L-20a | |
| N | CH | CH | N | O | OCH$_3$ | OCH$_3$ | H | L-22a | |
| N | CH | CH | N | S | OCH$_3$ | OCH$_3$ | H | L-1a | |
| N | CH | CH | N | O | OCH$_3$ | OCH$_3$ | CH$_3$ | L-1a | |

TABLE 6

General Formula 6

| Z | $Z_1$ | $Z_4$ | W | X | Y | R | L | m.p. (°C.) |
|---|---|---|---|---|---|---|---|---|
| CH | CH | S | O | CH$_3$ | CH$_3$ | H | L-1a | |
| CH | CH | S | O | CH$_3$ | CH$_3$ | H | L-1b | |
| CH | CH | S | O | CH$_3$ | CH$_3$ | H | L-1c | |
| CH | CH | S | O | CH$_3$ | CH$_3$ | H | L-1d | |
| CH | CH | S | O | CH$_3$ | CH$_3$ | H | L-1e | |
| CH | CH | S | O | CH$_3$ | CH$_3$ | H | L-1f | |
| CH | CH | S | O | CH$_3$ | CH$_3$ | H | L-1g | |
| CH | CH | S | O | CH$_3$ | CH$_3$ | H | L-1h | |
| CH | CH | S | O | CH$_3$ | CH$_3$ | H | L-1i | |
| CH | CH | S | O | CH$_3$ | CH$_3$ | H | L-1j | |
| CH | CH | S | O | CH$_3$ | CH$_3$ | H | L-1k | |
| CH | CH | S | O | CH$_3$ | CH$_3$ | H | L-3a | |
| CH | CH | S | O | CH$_3$ | CH$_3$ | H | L-3b | |
| CH | CH | S | O | CH$_3$ | CH$_3$ | H | L-4a | |

TABLE 6-continued

General Formula 6

| Z | $Z_1$ | $Z_4$ | W | X | Y | R | L | m.p. (°C.) |
|---|---|---|---|---|---|---|---|---|
| CH | CH | S | O | $CH_3$ | $CH_3$ | H | L-7a | |
| CH | CH | S | O | $CH_3$ | $CH_3$ | H | L-8a | |
| CH | CH | S | O | $CH_3$ | $CH_3$ | H | L-8b | |
| CH | CH | S | O | $CH_3$ | $CH_3$ | H | L-9a | |
| CH | CH | S | O | $CH_3$ | $CH_3$ | H | L-12a | |
| CH | CH | S | O | $CH_3$ | $CH_3$ | H | L-12b | |
| CH | CH | S | O | $CH_3$ | $CH_3$ | H | L-14a | |
| CH | CH | S | O | $CH_3$ | $CH_3$ | H | L-15a | |
| CH | CH | S | O | $CH_3$ | $CH_3$ | H | L-16a | |
| CH | CH | S | O | $CH_3$ | $CH_3$ | H | L-16b | |
| CH | CH | S | O | $CH_3$ | $CH_3$ | H | L-18a | |
| CH | CH | S | O | $CH_3$ | $CH_3$ | H | L-20a | |
| CH | CH | S | O | $CH_3$ | $CH_3$ | H | L-22a | |
| CH | CH | S | S | $CH_3$ | $CH_3$ | H | L-1a | |
| CH | CH | S | O | $CH_3$ | $CH_3$ | $CH_3$ | L-1a | |
| CH | CH | S | O | $OCH_3$ | $CH_3$ | H | L-1a | |
| CH | CH | S | O | $OCH_3$ | $CH_3$ | H | L-1b | |
| CH | CH | S | O | $OCH_3$ | $CH_3$ | H | L-1c | |
| CH | CH | S | O | $OCH_3$ | $CH_3$ | H | L-1d | |
| CH | CH | S | O | $OCH_3$ | $CH_3$ | H | L-1e | |
| CH | CH | S | O | $OCH_3$ | $CH_3$ | H | L-1f | |
| CH | CH | S | O | $OCH_3$ | $CH_3$ | H | L-1g | |
| CH | CH | S | O | $OCH_3$ | $CH_3$ | H | L-1h | |
| CH | CH | S | O | $OCH_3$ | $CH_3$ | H | L-1i | |
| CH | CH | S | O | $OCH_3$ | $CH_3$ | H | L-1j | |
| CH | CH | S | O | $OCH_3$ | $CH_3$ | H | L-1k | |
| CH | CH | S | O | $OCH_3$ | $CH_3$ | H | L-3a | |
| CH | CH | S | O | $OCH_3$ | $CH_3$ | H | L-3b | |
| CH | CH | S | O | $OCH_3$ | $CH_3$ | H | L-4a | |
| CH | CH | S | O | $OCH_3$ | $CH_3$ | H | L-7a | |
| CH | CH | S | O | $OCH_3$ | $CH_3$ | H | L-8a | |
| CH | CH | S | O | $OCH_3$ | $CH_3$ | H | L-8b | |
| CH | CH | S | O | $OCH_3$ | $CH_3$ | H | L-9a | |
| CH | CH | S | O | $OCH_3$ | $CH_3$ | H | L-12a | |
| CH | CH | S | O | $OCH_3$ | $CH_3$ | H | L-12b | |
| CH | CH | S | O | $OCH_3$ | $CH_3$ | H | L-14a | |
| CH | CH | S | O | $OCH_3$ | $CH_3$ | H | L-15a | |
| CH | CH | S | O | $OCH_3$ | $CH_3$ | H | L-16a | |
| CH | CH | S | O | $OCH_3$ | $CH_3$ | H | L-16b | |
| CH | CH | S | O | $OCH_3$ | $CH_3$ | H | L-18a | |
| CH | CH | S | O | $OCH_3$ | $CH_3$ | H | L-20a | |
| CH | CH | S | O | $OCH_3$ | $CH_3$ | H | L-22a | |
| CH | CH | S | S | $OCH_3$ | $CH_3$ | H | L-1a | |
| CH | CH | S | O | $OCH_3$ | $CH_3$ | $CH_3$ | L-1a | |
| CH | CH | S | O | $CH_3$ | $OCH_3$ | H | L-1a | |
| CH | CH | S | O | $CH_3$ | $OCH_3$ | H | L-1b | |
| CH | CH | S | O | $CH_3$ | $OCH_3$ | H | L-1c | |
| CH | CH | S | O | $CH_3$ | $OCH_3$ | H | L-1d | |
| CH | CH | S | O | $CH_3$ | $OCH_3$ | H | L-1e | |
| CH | CH | S | O | $CH_3$ | $OCH_3$ | H | L-1f | |
| CH | CH | S | O | $CH_3$ | $OCH_3$ | H | L-1g | |
| CH | CH | S | O | $CH_3$ | $OCH_3$ | H | L-1h | |
| CH | CH | S | O | $CH_3$ | $OCH_3$ | H | L-1i | |
| CH | CH | S | O | $CH_3$ | $OCH_3$ | H | L-1j | |
| CH | CH | S | O | $CH_3$ | $OCH_3$ | H | L-1k | |
| CH | CH | S | O | $CH_3$ | $OCH_3$ | H | L-3a | |
| CH | CH | S | O | $CH_3$ | $OCH_3$ | H | L-3b | |
| CH | CH | S | O | $CH_3$ | $OCH_3$ | H | L-4a | |
| CH | CH | S | O | $CH_3$ | $OCH_3$ | H | L-7a | |
| CH | CH | S | O | $CH_3$ | $OCH_3$ | H | L-8a | |
| CH | CH | S | O | $CH_3$ | $OCH_3$ | H | L-8b | |
| CH | CH | S | O | $CH_3$ | $OCH_3$ | H | L-9a | |
| CH | CH | S | O | $CH_3$ | $OCH_3$ | H | L-12a | |
| CH | CH | S | O | $CH_3$ | $OCH_3$ | H | L-12b | |
| CH | CH | S | O | $CH_3$ | $OCH_3$ | H | L-14a | |
| CH | CH | S | O | $CH_3$ | $OCH_3$ | H | L-15a | |
| CH | CH | S | O | $CH_3$ | $OCH_3$ | H | L-16a | |
| CH | CH | S | O | $CH_3$ | $OCH_3$ | H | L-16b | |
| CH | CH | S | O | $CH_3$ | $OCH_3$ | H | L-18a | |
| CH | CH | S | O | $CH_3$ | $OCH_3$ | H | L-20a | |
| CH | CH | S | O | $CH_3$ | $OCH_3$ | H | L-22a | |
| CH | CH | S | S | $CH_3$ | $OCH_3$ | H | L-1a | |
| CH | CH | S | O | $CH_3$ | $OCH_3$ | $CH_3$ | L-1a | |
| CH | CH | S | O | $OCH_3$ | $OCH_3$ | H | L-1a | |
| CH | CH | S | O | $OCH_3$ | $OCH_3$ | H | L-1b | |
| CH | CH | S | O | $OCH_3$ | $OCH_3$ | H | L-1c | |
| CH | CH | S | O | $OCH_3$ | $OCH_3$ | H | L-1d | |
| CH | CH | S | O | $OCH_3$ | $OCH_3$ | H | L-1e | |
| CH | CH | S | O | $OCH_3$ | $OCH_3$ | H | L-1f | |
| CH | CH | S | O | $OCH_3$ | $OCH_3$ | H | L-1g | |
| CH | CH | S | O | $OCH_3$ | $OCH_3$ | H | L-1h | |
| CH | CH | S | O | $OCH_3$ | $OCH_3$ | H | L-1i | |
| CH | CH | S | O | $OCH_3$ | $OCH_3$ | H | L-1j | |
| CH | CH | S | O | $OCH_3$ | $OCH_3$ | H | L-1k | |
| CH | CH | S | O | $OCH_3$ | $OCH_3$ | H | L-3a | |
| CH | CH | S | O | $OCH_3$ | $OCH_3$ | H | L-3b | |
| CH | CH | S | O | $OCH_3$ | $OCH_3$ | H | L-4a | |
| CH | CH | S | O | $OCH_3$ | $OCH_3$ | H | L-7a | |
| CH | CH | S | O | $OCH_3$ | $OCH_3$ | H | L-8a | |
| CH | CH | S | O | $OCH_3$ | $OCH_3$ | H | L-8b | |
| CH | CH | S | O | $OCH_3$ | $OCH_3$ | H | L-9a | |
| CH | CH | S | O | $OCH_3$ | $OCH_3$ | H | L-12a | |
| CH | CH | S | O | $OCH_3$ | $OCH_3$ | H | L-12b | |
| CH | CH | S | O | $OCH_3$ | $OCH_3$ | H | L-14a | |
| CH | CH | S | O | $OCH_3$ | $OCH_3$ | H | L-15a | |
| CH | CH | S | O | $OCH_3$ | $OCH_3$ | H | L-16a | |
| CH | CH | S | O | $OCH_3$ | $OCH_3$ | H | L-16b | |
| CH | CH | S | O | $OCH_3$ | $OCH_3$ | H | L-18a | |
| CH | CH | S | O | $OCH_3$ | $OCH_3$ | H | L-20a | |
| CH | CH | S | O | $OCH_3$ | $OCH_3$ | H | L-22a | |
| CH | CH | S | O | $OCH_3$ | $OCH_3$ | H | L-1a | |
| CH | CH | S | O | $OCH_3$ | $OCH_3$ | $CH_3$ | L-1a | |
| CH | CH | O | O | $CH_3$ | $CH_3$ | H | L-1a | |
| CH | CH | O | O | $CH_3$ | $CH_3$ | H | L-1b | |
| CH | CH | O | O | $CH_3$ | $CH_3$ | H | L-1c | |
| CH | CH | O | O | $CH_3$ | $CH_3$ | H | L-1d | |
| CH | CH | O | O | $CH_3$ | $CH_3$ | H | L-1e | |
| CH | CH | O | O | $CH_3$ | $CH_3$ | H | L-1f | |
| CH | CH | O | O | $CH_3$ | $CH_3$ | H | L-1g | |
| CH | CH | O | O | $CH_3$ | $CH_3$ | H | L-1h | |
| CH | CH | O | O | $CH_3$ | $CH_3$ | H | L-1i | |
| CH | CH | O | O | $CH_3$ | $CH_3$ | H | L-1j | |
| CH | CH | O | O | $CH_3$ | $CH_3$ | H | L-1k | |
| CH | CH | O | O | $CH_3$ | $CH_3$ | H | L-3a | |
| CH | CH | O | O | $CH_3$ | $CH_3$ | H | L-3b | |
| CH | CH | O | O | $CH_3$ | $CH_3$ | H | L-4a | |
| CH | CH | O | O | $CH_3$ | $CH_3$ | H | L-7a | |
| CH | CH | O | O | $CH_3$ | $CH_3$ | H | L-8a | |
| CH | CH | O | O | $CH_3$ | $CH_3$ | H | L-8b | |
| CH | CH | O | O | $CH_3$ | $CH_3$ | H | L-9a | |
| CH | CH | O | O | $CH_3$ | $CH_3$ | H | L-12a | |
| CH | CH | O | O | $CH_3$ | $CH_3$ | H | L-12b | |
| CH | CH | O | O | $CH_3$ | $CH_3$ | H | L-14a | |
| CH | CH | O | O | $CH_3$ | $CH_3$ | H | L-15a | |
| CH | CH | O | O | $CH_3$ | $CH_3$ | H | L-16a | |
| CH | CH | O | O | $CH_3$ | $CH_3$ | H | L-16b | |
| CH | CH | O | O | $CH_3$ | $CH_3$ | H | L-18a | |
| CH | CH | O | O | $CH_3$ | $CH_3$ | H | L-20a | |
| CH | CH | O | O | $CH_3$ | $CH_3$ | H | L-22a | |
| CH | CH | O | S | $CH_3$ | $CH_3$ | H | L-1a | |
| CH | CH | O | O | $CH_3$ | $CH_3$ | $CH_3$ | L-1a | |
| CH | CH | O | O | $OCH_3$ | $CH_3$ | H | L-1a | |
| CH | CH | O | O | $OCH_3$ | $CH_3$ | H | L-1b | |
| CH | CH | O | O | $OCH_3$ | $CH_3$ | H | L-1c | |
| CH | CH | O | O | $OCH_3$ | $CH_3$ | H | L-1d | |
| CH | CH | O | O | $OCH_3$ | $CH_3$ | H | L-1e | |
| CH | CH | O | O | $OCH_3$ | $CH_3$ | H | L-1f | |
| CH | CH | O | O | $OCH_3$ | $CH_3$ | H | L-1g | |
| CH | CH | O | O | $OCH_3$ | $CH_3$ | H | L-1h | |
| CH | CH | O | O | $OCH_3$ | $CH_3$ | H | L-1i | |
| CH | CH | O | O | $OCH_3$ | $CH_3$ | H | L-1j | |
| CH | CH | O | O | $OCH_3$ | $CH_3$ | H | L-1k | |
| CH | CH | O | O | $OCH_3$ | $CH_3$ | H | L-3a | |
| CH | CH | O | O | $OCH_3$ | $CH_3$ | H | L-3b | |
| CH | CH | O | O | $OCH_3$ | $CH_3$ | H | L-4a | |
| CH | CH | O | O | $OCH_3$ | $CH_3$ | H | L-7a | |
| CH | CH | O | O | $OCH_3$ | $CH_3$ | H | L-8a | |
| CH | CH | O | O | $OCH_3$ | $CH_3$ | H | L-8b | |
| CH | CH | O | O | $OCH_3$ | $CH_3$ | H | L-9a | |
| CH | CH | O | O | $OCH_3$ | $CH_3$ | H | L-12a | |
| CH | CH | O | O | $OCH_3$ | $CH_3$ | H | L-12b | |
| CH | CH | O | O | $OCH_3$ | $CH_3$ | H | L-14a | |
| CH | CH | O | O | $OCH_3$ | $CH_3$ | H | L-15a | |
| CH | CH | O | O | $OCH_3$ | $CH_3$ | H | L-16a | |
| CH | CH | O | O | $OCH_3$ | $CH_3$ | H | L-16b | |
| CH | CH | O | O | $OCH_3$ | $CH_3$ | H | L-18a | |

TABLE 6-continued

General Formula 6

| Z | Z₁ | Z₄ | W | X | Y | R | L | m.p. (°C.) |
|---|----|----|---|---|---|---|---|------------|
| CH | CH | O | O | OCH₃ | CH₃ | H | L-20a | |
| CH | CH | O | O | OCH₃ | CH₃ | H | L-22a | |
| CH | CH | O | S | OCH₃ | CH₃ | H | L-1a | |
| CH | CH | O | O | OCH₃ | CH₃ | CH₃ | L-1a | |
| CH | CH | O | O | CH₃ | OCH₃ | H | L-1a | |
| CH | CH | O | O | CH₃ | OCH₃ | H | L-1b | |
| CH | CH | O | O | CH₃ | OCH₃ | H | L-1c | |
| CH | CH | O | O | CH₃ | OCH₃ | H | L-1d | |
| CH | CH | O | O | CH₃ | OCH₃ | H | L-1e | |
| CH | CH | O | O | CH₃ | OCH₃ | H | L-1f | |
| CH | CH | O | O | CH₃ | OCH₃ | H | L-1g | |
| CH | CH | O | O | CH₃ | OCH₃ | H | L-1h | |
| CH | CH | O | O | CH₃ | OCH₃ | H | L-1i | |
| CH | CH | O | O | CH₃ | OCH₃ | H | L-1j | |
| CH | CH | O | O | CH₃ | OCH₃ | H | L-1k | |
| CH | CH | O | O | CH₃ | OCH₃ | H | L-3a | |
| CH | CH | O | O | CH₃ | OCH₃ | H | L-3b | |
| CH | CH | O | O | CH₃ | OCH₃ | H | L-4a | |
| CH | CH | O | O | CH₃ | OCH₃ | H | L-7a | |
| CH | CH | O | O | CH₃ | OCH₃ | H | L-8a | |
| CH | CH | O | O | CH₃ | OCH₃ | H | L-8b | |
| CH | CH | O | O | CH₃ | OCH₃ | H | L-9a | |
| CH | CH | O | O | CH₃ | OCH₃ | H | L-12a | |
| CH | CH | O | O | CH₃ | OCH₃ | H | L-12b | |
| CH | CH | O | O | CH₃ | OCH₃ | H | L-14a | |
| CH | CH | O | O | CH₃ | OCH₃ | H | L-15a | |
| CH | CH | O | O | CH₃ | OCH₃ | H | L-16a | |
| CH | CH | O | O | CH₃ | OCH₃ | H | L-16b | |
| CH | CH | O | O | CH₃ | OCH₃ | H | L-18a | |
| CH | CH | O | O | CH₃ | OCH₃ | H | L-20a | |
| CH | CH | O | O | CH₃ | OCH₃ | H | L-22a | |
| CH | CH | O | S | CH₃ | OCH₃ | H | L-1a | |
| CH | CH | O | O | CH₃ | OCH₃ | CH₃ | L-1a | |
| CH | CH | O | O | OCH₃ | OCH₃ | H | L-1a | |
| CH | CH | O | O | OCH₃ | OCH₃ | H | L-1b | |
| CH | CH | O | O | OCH₃ | OCH₃ | H | L-1c | |
| CH | CH | O | O | OCH₃ | OCH₃ | H | L-1d | |
| CH | CH | O | O | OCH₃ | OCH₃ | H | L-1e | |
| CH | CH | O | O | OCH₃ | OCH₃ | H | L-1f | |
| CH | CH | O | O | OCH₃ | OCH₃ | H | L-1g | |
| CH | CH | O | O | OCH₃ | OCH₃ | H | L-1h | |
| CH | CH | O | O | OCH₃ | OCH₃ | H | L-1i | |
| CH | CH | O | O | OCH₃ | OCH₃ | H | L-1j | |
| CH | CH | O | O | OCH₃ | OCH₃ | H | L-1k | |
| CH | CH | O | O | OCH₃ | OCH₃ | H | L-3a | |
| CH | CH | O | O | OCH₃ | OCH₃ | H | L-3b | |
| CH | CH | O | O | OCH₃ | OCH₃ | H | L-4a | |
| CH | CH | O | O | OCH₃ | OCH₃ | H | L-7a | |
| CH | CH | O | O | OCH₃ | OCH₃ | H | L-8a | |
| CH | CH | O | O | OCH₃ | OCH₃ | H | L-8b | |
| CH | CH | O | O | OCH₃ | OCH₃ | H | L-9a | |
| CH | CH | O | O | OCH₃ | OCH₃ | H | L-12a | |
| CH | CH | O | O | OCH₃ | OCH₃ | H | L-12b | |
| CH | CH | O | O | OCH₃ | OCH₃ | H | L-14a | |
| CH | CH | O | O | OCH₃ | OCH₃ | H | L-15a | |
| CH | CH | O | O | OCH₃ | OCH₃ | H | L-16a | |
| CH | CH | O | O | OCH₃ | OCH₃ | H | L-16b | |
| CH | CH | O | O | OCH₃ | OCH₃ | H | L-18a | |
| CH | CH | O | O | OCH₃ | OCH₃ | H | L-20a | |
| CH | CH | O | O | OCH₃ | OCH₃ | H | L-22a | |
| CH | CH | O | S | OCH₃ | OCH₃ | H | L-1a | |
| CH | CH | O | O | OCH₃ | OCH₃ | CH₃ | L-1a | |
| N | CH | S | O | CH₃ | CH₃ | H | L-1a | |
| N | CH | S | O | CH₃ | CH₃ | H | L-1b | |
| N | CH | S | O | CH₃ | CH₃ | H | L-1c | |
| N | CH | S | O | CH₃ | CH₃ | H | L-1d | |
| N | CH | S | O | CH₃ | CH₃ | H | L-1e | |
| N | CH | S | O | CH₃ | CH₃ | H | L-1f | |
| N | CH | S | O | CH₃ | CH₃ | H | L-1g | |
| N | CH | S | O | CH₃ | CH₃ | H | L-1h | |
| N | CH | S | O | CH₃ | CH₃ | H | L-1i | |
| N | CH | S | O | CH₃ | CH₃ | H | L-1j | |
| N | CH | S | O | CH₃ | CH₃ | H | L-1k | |
| N | CH | S | O | CH₃ | CH₃ | H | L-3a | |
| N | CH | S | O | CH₃ | CH₃ | H | L-3b | |
| N | CH | S | O | CH₃ | CH₃ | H | L-4a | |
| N | CH | S | O | CH₃ | CH₃ | H | L-7a | |
| N | CH | S | O | CH₃ | CH₃ | H | L-8a | |
| N | CH | S | O | CH₃ | CH₃ | H | L-8b | |
| N | CH | S | O | CH₃ | CH₃ | H | L-9a | |
| N | CH | S | O | CH₃ | CH₃ | H | L-12a | |
| N | CH | S | O | CH₃ | CH₃ | H | L-12b | |
| N | CH | S | O | CH₃ | CH₃ | H | L-14a | |
| N | CH | S | O | CH₃ | CH₃ | H | L-15a | |
| N | CH | S | O | CH₃ | CH₃ | H | L-16a | |
| N | CH | S | O | CH₃ | CH₃ | H | L-16b | |
| N | CH | S | O | CH₃ | CH₃ | H | L-18a | |
| N | CH | S | O | CH₃ | CH₃ | H | L-20a | |
| N | CH | S | O | CH₃ | CH₃ | H | L-22a | |
| N | CH | S | S | CH₃ | CH₃ | H | L-1a | |
| N | CH | S | O | CH₃ | CH₃ | CH₃ | L-1a | |
| N | CH | S | O | OCH₃ | CH₃ | H | L-1a | |
| N | CH | S | O | OCH₃ | CH₃ | H | L-1b | |
| N | CH | S | O | OCH₃ | CH₃ | H | L-1c | |
| N | CH | S | O | OCH₃ | CH₃ | H | L-1d | |
| N | CH | S | O | OCH₃ | CH₃ | H | L-1e | |
| N | CH | S | O | OCH₃ | CH₃ | H | L-1f | |
| N | CH | S | O | OCH₃ | CH₃ | H | L-1g | |
| N | CH | S | O | OCH₃ | CH₃ | H | L-1h | |
| N | CH | S | O | OCH₃ | CH₃ | H | L-1i | |
| N | CH | S | O | OCH₃ | CH₃ | H | L-1j | |
| N | CH | S | O | OCH₃ | CH₃ | H | L-1k | |
| N | CH | S | O | OCH₃ | CH₃ | H | L-3a | |
| N | CH | S | O | OCH₃ | CH₃ | H | L-3b | |
| N | CH | S | O | OCH₃ | CH₃ | H | L-4a | |
| N | CH | S | O | OCH₃ | CH₃ | H | L-7a | |
| N | CH | S | O | OCH₃ | CH₃ | H | L-8a | |
| N | CH | S | O | OCH₃ | CH₃ | H | L-8b | |
| N | CH | S | O | OCH₃ | CH₃ | H | L-9a | |
| N | CH | S | O | OCH₃ | CH₃ | H | L-12a | |
| N | CH | S | O | OCH₃ | CH₃ | H | L-12b | |
| N | CH | S | O | OCH₃ | CH₃ | H | L-14a | |
| N | CH | S | O | OCH₃ | CH₃ | H | L-15a | |
| N | CH | S | O | OCH₃ | CH₃ | H | L-16a | |
| N | CH | S | O | OCH₃ | CH₃ | H | L-16b | |
| N | CH | S | O | OCH₃ | CH₃ | H | L-18a | |
| N | CH | S | O | OCH₃ | CH₃ | H | L-20a | |
| N | CH | S | O | OCH₃ | CH₃ | H | L-22a | |
| N | CH | S | S | OCH₃ | CH₃ | H | L-1a | |
| N | CH | S | O | OCH₃ | CH₃ | CH₃ | L-1a | |
| N | CH | S | O | CH₃ | OCH₃ | H | L-1a | |
| N | CH | S | O | CH₃ | OCH₃ | H | L-1b | |
| N | CH | S | O | CH₃ | OCH₃ | H | L-1c | |
| N | CH | S | O | CH₃ | OCH₃ | H | L-1d | |
| N | CH | S | O | CH₃ | OCH₃ | H | L-1e | |
| N | CH | S | O | CH₃ | OCH₃ | H | L-1f | |
| N | CH | S | O | CH₃ | OCH₃ | H | L-1g | |
| N | CH | S | O | CH₃ | OCH₃ | H | L-1h | |
| N | CH | S | O | CH₃ | OCH₃ | H | L-1i | |
| N | CH | S | O | CH₃ | OCH₃ | H | L-1j | |
| N | CH | S | O | CH₃ | OCH₃ | H | L-1k | |
| N | CH | S | O | CH₃ | OCH₃ | H | L-3a | |
| N | CH | S | O | CH₃ | OCH₃ | H | L-3b | |
| N | CH | S | O | CH₃ | OCH₃ | H | L-4a | |
| N | CH | S | O | CH₃ | OCH₃ | H | L-7a | |
| N | CH | S | O | CH₃ | OCH₃ | H | L-8a | |
| N | CH | S | O | CH₃ | OCH₃ | H | L-8b | |
| N | CH | S | O | CH₃ | OCH₃ | H | L-9a | |
| N | CH | S | O | CH₃ | OCH₃ | H | L-12a | |
| N | CH | S | O | CH₃ | OCH₃ | H | L-12b | |
| N | CH | S | O | CH₃ | OCH₃ | H | L-14a | |
| N | CH | S | O | CH₃ | OCH₃ | H | L-15a | |
| N | CH | S | O | CH₃ | OCH₃ | H | L-16a | |
| N | CH | S | O | CH₃ | OCH₃ | H | L-16b | |
| N | CH | S | O | CH₃ | OCH₃ | H | L-18a | |
| N | CH | S | O | CH₃ | OCH₃ | H | L-20a | |
| N | CH | S | O | CH₃ | OCH₃ | H | L-22a | |
| N | CH | S | S | CH₃ | OCH₃ | H | L-1a | |
| N | CH | S | O | CH₃ | OCH₃ | CH₃ | L-1a | |
| N | CH | S | O | OCH₃ | OCH₃ | H | L-1a | |
| N | CH | S | O | OCH₃ | OCH₃ | H | L-1b | |
| N | CH | S | O | OCH₃ | OCH₃ | H | L-1c | |
| N | CH | S | O | OCH₃ | OCH₃ | H | L-1d | |
| N | CH | S | O | OCH₃ | OCH₃ | H | L-1e | |
| N | CH | S | O | OCH₃ | OCH₃ | H | L-1f | |
| N | CH | S | O | OCH₃ | OCH₃ | H | L-1g | |

TABLE 6-continued

General Formula 6

| Z | Z₁ | Z₄ | W | X | Y | R | L | m.p. (°C.) |
|---|----|----|---|---|---|---|---|------------|
| N | CH | S | O | OCH₃ | OCH₃ | H | L-1h | |
| N | CH | S | O | OCH₃ | OCH₃ | H | L-1i | |
| N | CH | S | O | OCH₃ | OCH₃ | H | L-1j | |
| N | CH | S | O | OCH₃ | OCH₃ | H | L-1k | |
| N | CH | S | O | OCH₃ | OCH₃ | H | L-3a | |
| N | CH | S | O | OCH₃ | OCH₃ | H | L-3b | |
| N | CH | S | O | OCH₃ | OCH₃ | H | L-4a | |
| N | CH | S | O | OCH₃ | OCH₃ | H | L-7a | |
| N | CH | S | O | OCH₃ | OCH₃ | H | L-8a | |
| N | CH | S | O | OCH₃ | OCH₃ | H | L-8b | |
| N | CH | S | O | OCH₃ | OCH₃ | H | L-9a | |
| N | CH | S | O | OCH₃ | OCH₃ | H | L-12a | |
| N | CH | S | O | OCH₃ | OCH₃ | H | L-12b | |
| N | CH | S | O | OCH₃ | OCH₃ | H | L-14a | |
| N | CH | S | O | OCH₃ | OCH₃ | H | L-15a | |
| N | CH | S | O | OCH₃ | OCH₃ | H | L-16a | |
| N | CH | S | O | OCH₃ | OCH₃ | H | L-16b | |
| N | CH | S | O | OCH₃ | OCH₃ | H | L-18a | |
| N | CH | S | O | OCH₃ | OCH₃ | H | L-20a | |
| N | CH | S | O | OCH₃ | OCH₃ | H | L-22a | |
| N | CH | S | S | OCH₃ | OCH₃ | H | L-1a | |
| N | CH | S | O | OCH₃ | OCH₃ | CH₃ | L-1a | |
| N | CH | O | O | CH₃ | CH₃ | H | L-1a | |
| N | CH | O | O | CH₃ | CH₃ | H | L-1b | |
| N | CH | O | O | CH₃ | CH₃ | H | L-1c | |
| N | CH | O | O | CH₃ | CH₃ | H | L-1d | |
| N | CH | O | O | CH₃ | CH₃ | H | L-1e | |
| N | CH | O | O | CH₃ | CH₃ | H | L-1f | |
| N | CH | O | O | CH₃ | CH₃ | H | L-1g | |
| N | CH | O | O | CH₃ | CH₃ | H | L-1h | |
| N | CH | O | O | CH₃ | CH₃ | H | L-1i | |
| N | CH | O | O | CH₃ | CH₃ | H | L-1j | |
| N | CH | O | O | CH₃ | CH₃ | H | L-1k | |
| N | CH | O | O | CH₃ | CH₃ | H | L-3a | |
| N | CH | O | O | CH₃ | CH₃ | H | L-3b | |
| N | CH | O | O | CH₃ | CH₃ | H | L-4a | |
| N | CH | O | O | CH₃ | CH₃ | H | L-7a | |
| N | CH | O | O | CH₃ | CH₃ | H | L-8a | |
| N | CH | O | O | CH₃ | CH₃ | H | L-8b | |
| N | CH | O | O | CH₃ | CH₃ | H | L-9a | |
| N | CH | O | O | CH₃ | CH₃ | H | L-12a | |
| N | CH | O | O | CH₃ | CH₃ | H | L-12b | |
| N | CH | O | O | CH₃ | CH₃ | H | L-14a | |
| N | CH | O | O | CH₃ | CH₃ | H | L-15a | |
| N | CH | O | O | CH₃ | CH₃ | H | L-16a | |
| N | CH | O | O | CH₃ | CH₃ | H | L-16b | |
| N | CH | O | O | CH₃ | CH₃ | H | L-18a | |
| N | CH | O | O | CH₃ | CH₃ | H | L-20a | |
| N | CH | O | O | CH₃ | CH₃ | H | L-22a | |
| N | CH | O | S | CH₃ | CH₃ | H | L-1a | |
| N | CH | O | O | CH₃ | CH₃ | CH₃ | L-1a | |
| N | CH | O | O | OCH₃ | CH₃ | H | L-1a | |
| N | CH | O | O | OCH₃ | CH₃ | H | L-1b | |
| N | CH | O | O | OCH₃ | CH₃ | H | L-1c | |
| N | CH | O | O | OCH₃ | CH₃ | H | L-1d | |
| N | CH | O | O | OCH₃ | CH₃ | H | L-1e | |
| N | CH | O | O | OCH₃ | CH₃ | H | L-1f | |
| N | CH | O | O | OCH₃ | CH₃ | H | L-1g | |
| N | CH | O | O | OCH₃ | CH₃ | H | L-1h | |
| N | CH | O | O | OCH₃ | CH₃ | H | L-1i | |
| N | CH | O | O | OCH₃ | CH₃ | H | L-1j | |
| N | CH | O | O | OCH₃ | CH₃ | H | L-1k | |
| N | CH | O | O | OCH₃ | CH₃ | H | L-3a | |
| N | CH | O | O | OCH₃ | CH₃ | H | L-3b | |
| N | CH | O | O | OCH₃ | CH₃ | H | L-4a | |
| N | CH | O | O | OCH₃ | CH₃ | H | L-7a | |
| N | CH | O | O | OCH₃ | CH₃ | H | L-8a | |
| N | CH | O | O | OCH₃ | CH₃ | H | L-8b | |
| N | CH | O | O | OCH₃ | CH₃ | H | L-9a | |
| N | CH | O | O | OCH₃ | CH₃ | H | L-12a | |
| N | CH | O | O | OCH₃ | CH₃ | H | L-12b | |
| N | CH | O | O | OCH₃ | CH₃ | H | L-14a | |
| N | CH | O | O | OCH₃ | CH₃ | H | L-15a | |
| N | CH | O | O | OCH₃ | CH₃ | H | L-16a | |
| N | CH | O | O | OCH₃ | CH₃ | H | L-16b | |
| N | CH | O | O | OCH₃ | CH₃ | H | L-18a | |
| N | CH | O | O | OCH₃ | CH₃ | H | L-20a | |
| N | CH | O | O | OCH₃ | CH₃ | H | L-22a | |
| N | CH | O | S | OCH₃ | CH₃ | H | L-1a | |
| N | CH | O | O | OCH₃ | CH₃ | CH₃ | L-1a | |
| N | CH | O | O | CH₃ | OCH₃ | H | L-1a | |
| N | CH | O | O | CH₃ | OCH₃ | H | L-1b | |
| N | CH | O | O | CH₃ | OCH₃ | H | L-1c | |
| N | CH | O | O | CH₃ | OCH₃ | H | L-1d | |
| N | CH | O | O | CH₃ | OCH₃ | H | L-1e | |
| N | CH | O | O | CH₃ | OCH₃ | H | L-1f | |
| N | CH | O | O | CH₃ | OCH₃ | H | L-1g | |
| N | CH | O | O | CH₃ | OCH₃ | H | L-1h | |
| N | CH | O | O | CH₃ | OCH₃ | H | L-1i | |
| N | CH | O | O | CH₃ | OCH₃ | H | L-1j | |
| N | CH | O | O | CH₃ | OCH₃ | H | L-1k | |
| N | CH | O | O | CH₃ | OCH₃ | H | L-3a | |
| N | CH | O | O | CH₃ | OCH₃ | H | L-3b | |
| N | CH | O | O | CH₃ | OCH₃ | H | L-4a | |
| N | CH | O | O | CH₃ | OCH₃ | H | L-7a | |
| N | CH | O | O | CH₃ | OCH₃ | H | L-8a | |
| N | CH | O | O | CH₃ | OCH₃ | H | L-8b | |
| N | CH | O | O | CH₃ | OCH₃ | H | L-9a | |
| N | CH | O | O | CH₃ | OCH₃ | H | L-12a | |
| N | CH | O | O | CH₃ | OCH₃ | H | L-12b | |
| N | CH | O | O | CH₃ | OCH₃ | H | L-14a | |
| N | CH | O | O | CH₃ | OCH₃ | H | L-15a | |
| N | CH | O | O | CH₃ | OCH₃ | H | L-16a | |
| N | CH | O | O | CH₃ | OCH₃ | H | L-16b | |
| N | CH | O | O | CH₃ | OCH₃ | H | L-18a | |
| N | CH | O | O | CH₃ | OCH₃ | H | L-20a | |
| N | CH | O | O | CH₃ | OCH₃ | H | L-22a | |
| N | CH | O | S | CH₃ | OCH₃ | H | L-1a | |
| N | CH | O | O | CH₃ | OCH₃ | CH₃ | L-1a | |
| N | CH | O | O | OCH₃ | OCH₃ | H | L-1a | |
| N | CH | O | O | OCH₃ | OCH₃ | H | L-1b | |
| N | CH | O | O | OCH₃ | OCH₃ | H | L-1c | |
| N | CH | O | O | OCH₃ | OCH₃ | H | L-1d | |
| N | CH | O | O | OCH₃ | OCH₃ | H | L-1e | |
| N | CH | O | O | OCH₃ | OCH₃ | H | L-1f | |
| N | CH | O | O | OCH₃ | OCH₃ | H | L-1g | |
| N | CH | O | O | OCH₃ | OCH₃ | H | L-1h | |
| N | CH | O | O | OCH₃ | OCH₃ | H | L-1i | |
| N | CH | O | O | OCH₃ | OCH₃ | H | L-1j | |
| N | CH | O | O | OCH₃ | OCH₃ | H | L-1k | |
| N | CH | O | O | OCH₃ | OCH₃ | H | L-3a | |
| N | CH | O | O | OCH₃ | OCH₃ | H | L-3b | |
| N | CH | O | O | OCH₃ | OCH₃ | H | L-4a | |
| N | CH | O | O | OCH₃ | OCH₃ | H | L-7a | |
| N | CH | O | O | OCH₃ | OCH₃ | H | L-8a | |
| N | CH | O | O | OCH₃ | OCH₃ | H | L-8b | |
| N | CH | O | O | OCH₃ | OCH₃ | H | L-9a | |
| N | CH | O | O | OCH₃ | OCH₃ | H | L-12a | |
| N | CH | O | O | OCH₃ | OCH₃ | H | L-12b | |
| N | CH | O | O | OCH₃ | OCH₃ | H | L-14a | |
| N | CH | O | O | OCH₃ | OCH₃ | H | L-15a | |
| N | CH | O | O | OCH₃ | OCH₃ | H | L-16a | |
| N | CH | O | O | OCH₃ | OCH₃ | H | L-16b | |
| N | CH | O | O | OCH₃ | OCH₃ | H | L-18a | |
| N | CH | O | O | OCH₃ | OCH₃ | H | L-20a | |
| N | CH | O | O | OCH₃ | OCH₃ | H | L-22a | |
| N | CH | O | S | OCH₃ | OCH₃ | H | L-1a | |
| N | CH | O | O | OCH₃ | OCH₃ | CH₃ | L-1a | |
| CH | CH | NCH₃ | O | CH₃ | CH₃ | H | L-1a | |
| CH | CH | NCH₃ | O | CH₃ | CH₃ | H | L-1b | |
| CH | CH | NCH₃ | O | CH₃ | CH₃ | H | L-1c | |
| CH | CH | NCH₃ | O | CH₃ | CH₃ | H | L-1d | |
| CH | CH | NCH₃ | O | CH₃ | CH₃ | H | L-1e | |
| CH | CH | NCH₃ | O | CH₃ | CH₃ | H | L-1f | |
| CH | CH | NCH₃ | O | CH₃ | CH₃ | H | L-1g | |
| CH | CH | NCH₃ | O | CH₃ | CH₃ | H | L-1h | |
| CH | CH | NCH₃ | O | CH₃ | CH₃ | H | L-1i | |
| CH | CH | NCH₃ | O | CH₃ | CH₃ | H | L-1j | |
| CH | CH | NCH₃ | O | CH₃ | CH₃ | H | L-1k | |
| CH | CH | NCH₃ | O | CH₃ | CH₃ | H | L-3a | |
| CH | CH | NCH₃ | O | CH₃ | CH₃ | H | L-3b | |
| CH | CH | NCH₃ | O | CH₃ | CH₃ | H | L-4a | |
| CH | CH | NCH₃ | O | CH₃ | CH₃ | H | L-7a | |
| CH | CH | NCH₃ | O | CH₃ | CH₃ | H | L-8a | |
| CH | CH | NCH₃ | O | CH₃ | CH₃ | H | L-8b | |
| CH | CH | NCH₃ | O | CH₃ | CH₃ | H | L-9a | |

TABLE 6-continued

General Formula 6

| Z | Z₁ | Z₄ | W | X | Y | R | L | m.p. (°C.) |
|---|---|---|---|---|---|---|---|---|
| CH | CH | NCH₃ | O | CH₃ | CH₃ | H | L-12a | |
| CH | CH | NCH₃ | O | CH₃ | CH₃ | H | L-12b | |
| CH | CH | NCH₃ | O | CH₃ | CH₃ | H | L-14a | |
| CH | CH | NCH₃ | O | CH₃ | CH₃ | H | L-15a | |
| CH | CH | NCH₃ | O | CH₃ | CH₃ | H | L-16a | |
| CH | CH | NCH₃ | O | CH₃ | CH₃ | H | L-16b | |
| CH | CH | NCH₃ | O | CH₃ | CH₃ | H | L-18a | |
| CH | CH | NCH₃ | O | CH₃ | CH₃ | H | L-20a | |
| CH | CH | NCH₃ | O | CH₃ | CH₃ | H | L-22a | |
| CH | CH | NCH₃ | S | CH₃ | CH₃ | H | L-1a | |
| CH | CH | NCH₃ | O | CH₃ | CH₃ | CH₃ | L-1a | |
| CH | CH | NCH₃ | O | OCH₃ | CH₃ | H | L-1a | |
| CH | CH | NCH₃ | O | OCH₃ | CH₃ | H | L-1b | |
| CH | CH | NCH₃ | O | OCH₃ | CH₃ | H | L-1c | |
| CH | CH | NCH₃ | O | OCH₃ | CH₃ | H | L-1d | |
| CH | CH | NCH₃ | O | OCH₃ | CH₃ | H | L-1e | |
| CH | CH | NCH₃ | O | OCH₃ | CH₃ | H | L-1f | |
| CH | CH | NCH₃ | O | OCH₃ | CH₃ | H | L-1g | |
| CH | CH | NCH₃ | O | OCH₃ | CH₃ | H | L-1h | |
| CH | CH | NCH₃ | O | OCH₃ | CH₃ | H | L-1i | |
| CH | CH | NCH₃ | O | OCH₃ | CH₃ | H | L-1j | |
| CH | CH | NCH₃ | O | OCH₃ | CH₃ | H | L-1k | |
| CH | CH | NCH₃ | O | OCH₃ | CH₃ | H | L-3a | |
| CH | CH | NCH₃ | O | OCH₃ | CH₃ | H | L-3b | |
| CH | CH | NCH₃ | O | OCH₃ | CH₃ | H | L-4a | |
| CH | CH | NCH₃ | O | OCH₃ | CH₃ | H | L-7a | |
| CH | CH | NCH₃ | O | OCH₃ | CH₃ | H | L-8a | |
| CH | CH | NCH₃ | O | OCH₃ | CH₃ | H | L-8b | |
| CH | CH | NCH₃ | O | OCH₃ | CH₃ | H | L-9a | |
| CH | CH | NCH₃ | O | OCH₃ | CH₃ | H | L-12a | |
| CH | CH | NCH₃ | O | OCH₃ | CH₃ | H | L-12b | |
| CH | CH | NCH₃ | O | OCH₃ | CH₃ | H | L-14a | |
| CH | CH | NCH₃ | O | OCH₃ | CH₃ | H | L-15a | |
| CH | CH | NCH₃ | O | OCH₃ | CH₃ | H | L-16a | |
| CH | CH | NCH₃ | O | OCH₃ | CH₃ | H | L-16b | |
| CH | CH | NCH₃ | O | OCH₃ | CH₃ | H | L-18a | |
| CH | CH | NCH₃ | O | OCH₃ | CH₃ | H | L-20a | |
| CH | CH | NCH₃ | O | OCH₃ | CH₃ | H | L-22a | |
| CH | CH | NCH₃ | S | OCH₃ | CH₃ | H | L-1a | |
| CH | CH | NCH₃ | O | OCH₃ | CH₃ | CH₃ | L-1a | |
| CH | CH | NCH₃ | O | CH₃ | OCH₃ | H | L-1a | |
| CH | CH | NCH₃ | O | CH₃ | OCH₃ | H | L-1b | |
| CH | CH | NCH₃ | O | CH₃ | OCH₃ | H | L-1c | |
| CH | CH | NCH₃ | O | CH₃ | OCH₃ | H | L-1d | |
| CH | CH | NCH₃ | O | CH₃ | OCH₃ | H | L-1e | |
| CH | CH | NCH₃ | O | CH₃ | OCH₃ | H | L-1f | |
| CH | CH | NCH₃ | O | CH₃ | OCH₃ | H | L-1g | |
| CH | CH | NCH₃ | O | CH₃ | OCH₃ | H | L-1h | |
| CH | CH | NCH₃ | O | CH₃ | OCH₃ | H | L-1i | |
| CH | CH | NCH₃ | O | CH₃ | OCH₃ | H | L-1j | |
| CH | CH | NCH₃ | O | CH₃ | OCH₃ | h | L-1k | |
| CH | CH | NCH₃ | O | CH₃ | OCH₃ | H | L-3a | |
| CH | CH | NCH₃ | O | CH₃ | OCH₃ | H | L-3b | |
| CH | CH | NCH₃ | O | CH₃ | OCH₃ | H | L-4a | |
| CH | CH | NCH₃ | O | CH₃ | OCH₃ | H | L-7a | |
| CH | CH | NCH₃ | O | CH₃ | OCH₃ | H | L-8a | |
| CH | CH | NCH₃ | O | CH₃ | OCH₃ | H | L-8b | |
| CH | CH | NCH₃ | O | CH₃ | OCH₃ | H | L-9a | |
| CH | CH | NCH₃ | O | CH₃ | OCH₃ | H | L-12a | |
| CH | CH | NCH₃ | O | CH₃ | OCH₃ | H | L-12b | |
| CH | CH | NCH₃ | O | CH₃ | OCH₃ | H | L-14a | |
| CH | CH | NCH₃ | O | CH₃ | OCH₃ | H | L-15a | |
| CH | CH | NCH₃ | O | CH₃ | OCH₃ | H | L-16a | |
| CH | CH | NCH₃ | O | CH₃ | OCH₃ | H | L-16b | |
| CH | CH | NCH₃ | O | CH₃ | OCH₃ | H | L-18a | |
| CH | CH | NCH₃ | O | CH₃ | OCH₃ | H | L-20a | |
| CH | CH | NCH₃ | O | CH₃ | OCH₃ | H | L-22a | |
| CH | CH | NCH₃ | S | CH₃ | OCH₃ | H | L-1a | |
| CH | CH | NCH₃ | O | CH₃ | OCH₃ | CH₃ | L-1a | |
| CH | CH | NCH₃ | O | OCH₃ | OCH₃ | H | L-1a | |
| CH | CH | NCH₃ | O | OCH₃ | OCH₃ | H | L-1b | |
| CH | CH | NCH₃ | O | OCH₃ | OCH₃ | H | L-1c | |
| CH | CH | NCH₃ | O | OCH₃ | OCH₃ | H | L-1d | |
| CH | CH | NCH₃ | O | OCH₃ | OCH₃ | H | L-1e | |
| CH | CH | NCH₃ | O | OCH₃ | OCH₃ | H | L-1f | |
| CH | CH | NCH₃ | O | OCH₃ | OCH₃ | H | L-1g | |
| CH | CH | NCH₃ | O | OCH₃ | OCH₃ | H | L-1h | |
| CH | CH | NCH₃ | O | OCH₃ | OCH₃ | H | L-1i | |
| CH | CH | NCH₃ | O | OCH₃ | OCH₃ | H | L-1j | |
| CH | CH | NCH₃ | O | OCH₃ | OCH₃ | H | L-1k | |
| CH | CH | NCH₃ | O | OCH₃ | OCH₃ | H | L-3a | |
| CH | CH | NCH₃ | O | OCH₃ | OCH₃ | H | L-3b | |
| CH | CH | NCH₃ | O | OCH₃ | OCH₃ | H | L-4a | |
| CH | CH | NCH₃ | O | OCH₃ | OCH₃ | H | L-7a | |
| CH | CH | NCH₃ | O | OCH₃ | OCH₃ | H | L-8a | |
| CH | CH | NCH₃ | O | OCH₃ | OCH₃ | H | L-8b | |
| CH | CH | NCH₃ | O | OCH₃ | OCH₃ | H | L-9a | |
| CH | CH | NCH₃ | O | OCH₃ | OCH₃ | H | L-12a | |
| CH | CH | NCH₃ | O | OCH₃ | OCH₃ | H | L-12b | |
| CH | CH | NCH₃ | O | OCH₃ | OCH₃ | H | L-14a | |
| CH | CH | NCH₃ | O | OCH₃ | OCH₃ | H | L-15a | |
| CH | CH | NCH₃ | O | OCH₃ | OCH₃ | H | L-16a | |
| CH | CH | NCH₃ | O | OCH₃ | OCH₃ | H | L-16b | |
| CH | CH | NCH₃ | O | OCH₃ | OCH₃ | H | L-18a | |
| CH | CH | NCH₃ | O | OCH₃ | OCH₃ | H | L-20a | |
| CH | CH | NCH₃ | O | OCH₃ | OCH₃ | H | L-22a | |
| CH | CH | NCH₃ | S | OCH₃ | OCH₃ | H | L-1a | |
| CH | CH | NCH₃ | O | OCH₃ | OCH₃ | CH₃ | L-1a | |
| N | CH | NCH₃ | O | CH₃ | CH₃ | H | L-1a | |
| N | CH | NCH₃ | O | CH₃ | CH₃ | H | L-1b | |
| N | CH | NCH₃ | O | CH₃ | CH₃ | H | L-1c | |
| N | CH | NCH₃ | O | CH₃ | CH₃ | H | L-1d | |
| N | CH | NCH₃ | O | CH₃ | CH₃ | H | L-1e | |
| N | CH | NCH₃ | O | CH₃ | CH₃ | H | L-1f | |
| N | CH | NCH₃ | O | CH₃ | CH₃ | H | L-1g | |
| N | CH | NCH₃ | O | CH₃ | CH₃ | H | L-1h | |
| N | CH | NCH₃ | O | CH₃ | CH₃ | H | L-1i | |
| N | CH | NCH₃ | O | CH₃ | CH₃ | H | L-1j | |
| N | CH | NCH₃ | O | CH₃ | CH₃ | H | L-1k | |
| N | CH | NCH₃ | O | CH₃ | CH₃ | H | L-3a | |
| N | CH | NCH₃ | O | CH₃ | CH₃ | H | L-3b | |
| N | CH | NCH₃ | O | CH₃ | CH₃ | H | L-4a | |
| N | CH | NCH₃ | O | CH₃ | CH₃ | H | L-7a | |
| N | CH | NCH₃ | O | CH₃ | CH₃ | H | L-8a | |
| N | CH | NCH₃ | O | CH₃ | CH₃ | H | L-8b | |
| N | CH | NCH₃ | O | CH₃ | CH₃ | H | L-9a | |
| N | CH | NCH₃ | O | CH₃ | CH₃ | H | L-12a | |
| N | CH | NCH₃ | O | CH₃ | CH₃ | H | L-12b | |
| N | CH | NCH₃ | O | CH₃ | CH₃ | H | L-14a | |
| N | CH | NCH₃ | O | CH₃ | CH₃ | H | L-15a | |
| N | CH | NCH₃ | O | CH₃ | CH₃ | H | L-16a | |
| N | CH | NCH₃ | O | CH₃ | CH₃ | H | L-16b | |
| N | CH | NCH₃ | O | CH₃ | CH₃ | H | L-18a | |
| N | CH | NCH₃ | O | CH₃ | CH₃ | H | L-20a | |
| N | CH | NCH₃ | O | CH₃ | CH₃ | H | L-22a | |
| N | CH | NCH₃ | S | CH₃ | CH₃ | H | L-1a | |
| N | CH | NCH₃ | O | CH₃ | CH₃ | CH₃ | L-1a | |
| N | CH | NCH₃ | O | OCH₃ | CH₃ | H | L-1a | |
| N | CH | NCH₃ | O | OCH₃ | CH₃ | H | L-1b | |
| N | CH | NCH₃ | O | OCH₃ | CH₃ | H | L-1c | |
| N | CH | NCH₃ | O | OCH₃ | CH₃ | H | L-1d | |
| N | CH | NCH₃ | O | OCH₃ | CH₃ | H | L-1e | |
| N | CH | NCH₃ | O | OCH₃ | CH₃ | H | L-1f | |
| N | CH | NCH₃ | O | OCH₃ | CH₃ | H | L-1g | |
| N | CH | NCH₃ | O | OCH₃ | CH₃ | H | L-1h | |
| N | CH | NCH₃ | O | OCH₃ | CH₃ | H | L-1i | |
| N | CH | NCH₃ | O | OCH₃ | CH₃ | H | L-1j | |
| N | CH | NCH₃ | O | OCH₃ | CH₃ | H | L-1k | |
| N | CH | NCH₃ | O | OCH₃ | CH₃ | H | L-3a | |
| N | CH | NCH₃ | O | OCH₃ | CH₃ | H | L-3b | |
| N | CH | NCH₃ | O | OCH₃ | CH₃ | H | L-4a | |
| N | CH | NCH₃ | O | OCH₃ | CH₃ | H | L-7a | |
| N | CH | NCH₃ | O | OCH₃ | CH₃ | H | L-8a | |
| N | CH | NCH₃ | O | OCH₃ | CH₃ | H | L-8b | |
| N | CH | NCH₃ | O | OCH₃ | CH₃ | H | L-9a | |
| N | CH | NCH₃ | O | OCH₃ | CH₃ | H | L-12a | |
| N | CH | NCH₃ | O | OCH₃ | CH₃ | H | L-12b | |
| N | CH | NCH₃ | O | OCH₃ | CH₃ | H | L-14a | |
| N | CH | NCH₃ | O | OCH₃ | CH₃ | H | L-15a | |
| N | CH | NCH₃ | O | OCH₃ | CH₃ | H | L-16a | |
| N | CH | NCH₃ | O | OCH₃ | CH₃ | H | L-16b | |
| N | CH | NCH₃ | O | OCH₃ | CH₃ | H | L-18a | |
| N | CH | NCH₃ | O | OCH₃ | CH₃ | H | L-20a | |
| N | CH | NCH₃ | O | OCH₃ | CH₃ | H | L-22a | |
| N | CH | NCH₃ | S | OCH₃ | CH₃ | H | L-1a | |
| N | CH | NCH₃ | O | OCH₃ | CH₃ | CH₃ | L-1a | |

TABLE 6-continued

General Formula 6

| Z | Z₁ | Z₄ | W | X | Y | R | L | m.p. (°C.) |
|---|---|---|---|---|---|---|---|---|
| N | CH | NCH₃ | O | CH₃ | OCH₃ | H | L-1a | |
| N | CH | NCH₃ | O | CH₃ | OCH₃ | H | L-1b | |
| N | CH | NCH₃ | O | CH₃ | OCH₃ | H | L-1c | |
| N | CH | NCH₃ | O | CH₃ | OCH₃ | H | L-1d | |
| N | CH | NCH₃ | O | CH₃ | OCH₃ | H | L-1e | |
| N | CH | NCH₃ | O | CH₃ | OCH₃ | H | L-1f | |
| N | CH | NCH₃ | O | CH₃ | OCH₃ | H | L-1g | |
| N | CH | NCH₃ | O | CH₃ | OCH₃ | H | L-1h | |
| N | CH | NCH₃ | O | CH₃ | OCH₃ | H | L-1i | |
| N | CH | NCH₃ | O | CH₃ | OCH₃ | H | L-1j | |
| N | CH | NCH₃ | O | CH₃ | OCH₃ | H | L-1k | |
| N | CH | NCH₃ | O | CH₃ | OCH₃ | H | L-3a | |
| N | CH | NCH₃ | O | CH₃ | OCH₃ | H | L-3b | |
| N | CH | NCH₃ | O | CH₃ | OCH₃ | H | L-4a | |
| N | CH | NCH₃ | O | CH₃ | OCH₃ | H | L-7a | |
| N | CH | NCH₃ | O | CH₃ | OCH₃ | H | L-8a | |
| N | CH | NCH₃ | O | CH₃ | OCH₃ | H | L-8b | |
| N | CH | NCH₃ | O | CH₃ | OCH₃ | H | L-9a | |
| N | CH | NCH₃ | O | CH₃ | OCH₃ | H | L-12a | |
| N | CH | NCH₃ | O | CH₃ | OCH₃ | H | L-12b | |
| N | CH | NCH₃ | O | CH₃ | OCH₃ | H | L-14a | |
| N | CH | NCH₃ | O | CH₃ | OCH₃ | H | L-15a | |
| N | CH | NCH₃ | O | CH₃ | OCH₃ | H | L-16a | |
| N | CH | NCH₃ | O | CH₃ | OCH₃ | H | L-16b | |
| N | CH | NCH₃ | O | CH₃ | OCH₃ | H | L-18a | |
| N | CH | NCH₃ | O | CH₃ | OCH₃ | H | L-20a | |
| N | CH | NCH₃ | O | CH₃ | OCH₃ | H | L-22a | |
| N | CH | NCH₃ | S | CH₃ | OCH₃ | H | L-1a | |
| N | CH | NCH₃ | O | CH₃ | OCH₃ | CH₃ | L-1a | |
| N | CH | NCH₃ | O | OCH₃ | OCH₃ | H | L-1a | |
| N | CH | NCH₃ | O | OCH₃ | OCH₃ | H | L-1b | |
| N | CH | NCH₃ | O | OCH₃ | OCH₃ | H | L-1c | |
| N | CH | NCH₃ | O | OCH₃ | OCH₃ | H | L-1d | |
| N | CH | NCH₃ | O | OCH₃ | OCH₃ | H | L-1e | |
| N | CH | NCH₃ | O | OCH₃ | OCH₃ | H | L-1f | |
| N | CH | NCH₃ | O | OCH₃ | OCH₃ | H | L-1g | |
| N | CH | NCH₃ | O | OCH₃ | OCH₃ | H | L-1h | |
| N | CH | NCH₃ | O | OCH₃ | OCH₃ | H | L-1i | |
| N | CH | NCH₃ | O | OCH₃ | OCH₃ | H | L-1j | |
| N | CH | NCH₃ | O | OCH₃ | OCH₃ | H | L-1k | |
| N | CH | NCH₃ | O | OCH₃ | OCH₃ | H | L-3a | |
| N | CH | NCH₃ | O | OCH₃ | OCH₃ | H | L-3b | |
| N | CH | NCH₃ | O | OCH₃ | OCH₃ | H | L-4a | |
| N | CH | NCH₃ | O | OCH₃ | OCH₃ | H | L-7a | |
| N | CH | NCH₃ | O | OCH₃ | OCH₃ | H | L-8a | |
| N | CH | NCH₃ | O | OCH₃ | OCH₃ | H | L-8b | |
| N | CH | NCH₃ | O | OCH₃ | OCH₃ | H | L-9a | |
| N | CH | NCH₃ | O | OCH₃ | OCH₃ | H | L-12a | |
| N | CH | NCH₃ | O | OCH₃ | OCH₃ | H | L-12b | |
| N | CH | NCH₃ | O | OCH₃ | OCH₃ | H | L-14a | |
| N | CH | NCH₃ | O | OCH₃ | OCH₃ | H | L-15a | |
| N | CH | NCH₃ | O | OCH₃ | OCH₃ | H | L-16a | |
| N | CH | NCH₃ | O | OCH₃ | OCH₃ | H | L-16b | |
| N | CH | NCH₃ | O | OCH₃ | OCH₃ | H | L-18a | |
| N | CH | NCH₃ | O | OCH₃ | OCH₃ | H | L-20a | |
| N | CH | NCH₃ | O | OCH₃ | OCH₃ | H | L-22a | |
| N | CH | NCH₃ | S | OCH₃ | OCH₃ | H | L-1a | |
| N | CH | NCH₃ | O | OCH₃ | OCH₃ | CH₃ | L-1a | |

TABLE 7

General Formula 7

| Z | Z₁ | Z₂ | W | Xₐ | Y | R | L | m.p.(°C.) |
|---|---|---|---|---|---|---|---|---|
| CH | N | CH | O | CH₃ | CH₃ | H | L-1a | |
| CH | N | CH | O | CH₃ | OCH₃ | H | L-1a | |
| N | N | CH | O | CH₃ | CH₃ | H | L-1a | |
| N | N | CH | O | CH₃ | OCH₃ | H | L-1a | |
| CH | N | N | O | CH₃ | OCH₃ | H | L-1a | |
| CH | N | N | O | CH₃ | OCH₃ | H | L-1a | |
| N | N | N | O | CH₃ | CH₃ | H | L-1a | |
| N | N | N | O | CH₃ | OCH₃ | H | L-1a | |
| CH | CH | CH | O | CH₃ | CH₃ | H | L-1a | |
| CH | CH | CH | O | CH₃ | OCH₃ | H | L-1a | |
| N | CH | CH | O | CH₃ | CH₃ | H | L-1a | |
| N | CH | CH | O | CH₃ | OCH₃ | H | L-1a | |
| CH | CH | N | O | CH₃ | CH₃ | H | L-1a | |
| CH | CH | N | O | CH₃ | OCH₃ | H | L-1a | |

TABLE 7-continued

General Formula 7

| Z | Z₁ | Z₂ | W | Xₐ | Y | R | L | m.p.(°C.) |
|---|---|---|---|---|---|---|---|---|
| N | CH | N | O | CH₃ | CH₃ | H | L-1a | |
| N | CH | N | O | CH₃ | OCH₃ | H | L-1a | |

TABLE 8

General Formula 8

| Z | Z₄ | Z₂ | W | X | Y | R | L | m.p.(°C.) |
|---|---|---|---|---|---|---|---|---|
| CH | NCH₃ | CH | O | CH₃ | CH₃ | H | L-1a | |
| CH | NCH₃ | CH | O | OCH₃ | CH₃ | H | L-1a | |
| CH | NCH₃ | CH | O | CH₃ | OCH₃ | H | L-1a | |
| CH | NCH₃ | CH | O | OCH₃ | OCH₃ | H | L-1a | |
| N | NCH₃ | CH | O | CH₃ | CH₃ | H | L-1a | |
| N | NCH₃ | CH | O | OCH₃ | CH₃ | H | L-1a | |
| N | NCH₃ | CH | O | CH₃ | OCH₃ | H | L-1a | |
| N | NCH₃ | CH | O | OCH₃ | OCH₃ | H | L-1a | |
| CH | NCH₃ | N | O | CH₃ | CH₃ | H | L-1a | |
| CH | NCH₃ | N | O | OCH₃ | CH₃ | H | L-1a | |
| CH | NCH₃ | N | O | CH₃ | OCH₃ | H | L-1a | |
| CH | NCH₃ | N | O | OCH₃ | OCH₃ | H | L-1a | |
| N | NCH₃ | CH | O | CH₃ | CH₃ | H | L-1a | |
| N | NCH₃ | CH | O | OCH₃ | CH₃ | H | L-1a | |
| N | NCH₃ | CH | O | CH₃ | OCH₃ | H | L-1a | |
| N | NCH₃ | CH | O | OCH₃ | OCH₃ | H | L-1a | |
| CH | O | CH | O | CH₃ | CH₃ | H | L-1a | |
| CH | O | CH | O | OCH₃ | CH₃ | H | L-1a | |
| CH | O | CH | O | OCH₃ | OCH₃ | H | L-1a | |
| N | NCH₃ | CH | O | CH₃ | CH₃ | H | L-1a | |
| N | NCH₃ | CH | O | OCH₃ | CH₃ | H | L-1a | |
| N | NCH₃ | CH | O | CH₃ | OCH₃ | H | L-1a | |
| N | NCH₃ | CH | O | OCH₃ | OCH₃ | H | L-1a | |

TABLE 9

General Formula 9

| Z | Z₄ | Z₂ | W | X | Y | R | L | m.p.(°C.) |
|---|---|---|---|---|---|---|---|---|
| CH | NCH₃ | CH | O | CH₃ | CH₃ | H | L-1a | |
| CH | NCH₃ | CH | O | OCH₃ | CH₃ | H | L-1a | |
| CH | NCH₃ | CH | O | CH₃ | OCH₃ | H | L-1a | |
| CH | NCH₃ | CH | O | OCH₃ | OCH₃ | H | L-1a | |
| N | NCH₃ | CH | O | CH₃ | CH₃ | H | L-1a | |
| N | NCH₃ | CH | O | OCH₃ | CH₃ | H | L-1a | |
| N | NCH₃ | CH | O | CH₃ | OCH₃ | H | L-1a | |
| N | NCH₃ | CH | O | OCH₃ | OCH₃ | H | L-1a | |
| CH | NCH₃ | N | O | CH₃ | CH₃ | H | L-1a | |
| CH | NCH₃ | N | O | OCH₃ | CH₃ | H | L-1a | |
| CH | NCH₃ | N | O | CH₃ | OCH₃ | H | L-1a | |
| CH | NCH₃ | N | O | OCH₃ | OCH₃ | H | L-1a | |
| N | NCH₃ | CH | O | CH₃ | CH₃ | H | L-1a | |
| N | NCH₃ | CH | O | OCH₃ | CH₃ | H | L-1a | |
| N | NCH₃ | CH | O | CH₃ | OCH₃ | H | L-1a | |
| N | NCH₃ | CH | O | OCH₃ | OCH₃ | H | L-1a | |
| CH | O | CH | O | CH₃ | CH₃ | H | L-1a | |
| CH | O | CH | O | OCH₃ | CH₃ | H | L-1a | |
| CH | O | CH | O | OCH₃ | OCH₃ | H | L-1a | |
| N | NCH₃ | CH | O | CH₃ | CH₃ | H | L-1a | |
| N | NCH₃ | CH | O | OCH₃ | CH₃ | H | L-1a | |
| N | NCH₃ | CH | O | CH₃ | OCH₃ | H | L-1a | |
| N | NCH₃ | CH | O | OCH₃ | OCH₃ | H | L-1a | |

TABLE 10

General Formula 10

| Z₁ | Z₂ | Z₃ | X | W | R | L | m.p.(°C.) |
|---|---|---|---|---|---|---|---|
| N | CH | CH | CH₃ | O | H | L-1a | |
| N | CH | N | CH₃ | O | H | L-1a | |
| N | N | CH | CH₃ | O | H | L-1a | |
| N | N | N | CH₃ | O | H | L-1a | |
| CH | CH | CH | CH₃ | O | H | L-1a | |
| CH | CH | N | CH₃ | O | H | L-1a | |
| CH | N | CH | CH₃ | O | H | L-1a | |
| CH | N | N | CH₃ | O | H | L-1a | |
| N | CH | CH | OCH₃ | O | H | L-1a | |

TABLE 10-continued

General Formula 10

| $Z_1$ | $Z_2$ | $Z_3$ | X | W | R | L | m.p.(°C.) |
|---|---|---|---|---|---|---|---|
| N | CH | N | OCH$_3$ | O | H | L-1a | |
| N | N | CH | OCH$_3$ | O | H | L-1a | |
| N | N | N | OCH$_3$ | O | H | L-1a | |
| CH | CH | CH | OCH$_3$ | O | H | L-1a | |
| CH | CH | N | OCH$_3$ | O | H | L-1a | |
| CH | N | CH | OCH$_3$ | O | H | L-1a | |
| CH | N | N | OCH$_3$ | O | H | L-1a | |

TABLE 11

General Formula 11

| $Z_4$ | $Z_1$ | $Z_2$ | $X_d$ | Y | W | R | L | m.p.(°C.) |
|---|---|---|---|---|---|---|---|---|
| O | CH | N | H | CH$_3$ | O | H | L-1a | |
| O | CH | CH | H | CH$_3$ | O | H | L-1a | |
| O | N | N | H | CH$_3$ | O | H | L-1a | |
| O | N | CH | H | CH$_3$ | O | H | L-1a | |
| S | CH | N | H | CH$_3$ | O | H | L-1a | |
| S | CH | CH | H | CH$_3$ | O | H | L-1a | |
| S | N | N | H | CH$_3$ | O | H | L-1a | |
| S | N | CH | H | CH$_3$ | O | H | L-1a | |
| NCH$_3$ | CH | N | H | CH$_3$ | O | H | L-1a | |
| NCH$_3$ | CH | CH | H | CH$_3$ | O | H | L-1a | |
| NCH$_3$ | N | N | H | CH$_3$ | O | H | L-1a | |
| NCH$_3$ | N | CH | H | CH$_3$ | O | H | L-a | |
| CH$_2$ | CH | N | H | CH$_3$ | O | H | L-1a | |
| CH$_2$ | CH | CH | H | CH$_3$ | O | H | L-1a | |
| CH$_2$ | N | N | H | CH$_3$ | O | H | L-1a | |
| CH$_2$ | N | CH | H | CH$_3$ | O | H | L-1a | |
| O | CH | N | CH$_3$ | CH$_3$ | O | H | L-1a | |
| O | CH | CH | CH$_3$ | CH$_3$ | O | H | L-1a | |
| O | N | N | CH$_3$ | CH$_3$ | O | H | L-1a | |
| O | N | CH | CH$_3$ | CH$_3$ | O | H | L-1a | |
| S | CH | N | CH$_3$ | CH$_3$ | O | H | L-1a | |
| S | CH | CH | CH$_3$ | CH$_3$ | O | H | L-1a | |
| S | N | N | CH$_3$ | CH$_3$ | O | H | L-1a | |
| S | N | CH | CH$_3$ | CH$_3$ | O | H | L-1a | |
| NCH$_3$ | CH | N | CH$_3$ | CH$_3$ | O | H | L-1a | |
| NCH$_3$ | CH | CH | CH$_3$ | CH$_3$ | O | H | L-1a | |
| NCH$_3$ | N | N | CH$_3$ | CH$_3$ | O | H | L-1a | |
| NCH$_3$ | N | CH | CH$_3$ | CH$_3$ | O | H | L-1a | |
| CH$_2$ | CH | N | CH$_3$ | CH$_3$ | O | H | L-1a | |
| CH$_2$ | CH | CH | CH$_3$ | CH$_3$ | O | H | L-1a | |
| CH$_2$ | N | N | CH$_3$ | CH$_3$ | O | H | L-1a | |
| CH$_2$ | N | CH | CH$_3$ | CH$_3$ | O | H | L-1a | |
| O | CH | N | H | OCH$_3$ | O | H | L-1a | |
| O | CH | CH | H | OCH$_3$ | O | H | L-1a | |
| O | N | N | H | OCH$_3$ | O | H | L-1a | |
| O | N | CH | H | OCH$_3$ | O | H | L-1a | |
| S | CH | N | H | OCH$_3$ | O | H | L-1a | |
| S | CH | CH | H | OCH$_3$ | O | H | L-1a | |
| S | N | N | H | OCH$_3$ | O | H | L-1a | |
| S | N | CH | H | OCH$_3$ | O | H | L-1a | |
| NCH$_3$ | CH | N | H | OCH$_3$ | O | H | L-1a | |
| NCH$_3$ | CH | CH | H | OCH$_3$ | O | H | L-1a | |
| NCH$_3$ | N | N | H | OCH$_3$ | O | H | L-1a | |
| NCH$_3$ | N | CH | H | OCH$_3$ | O | H | L-1a | |
| CH$_2$ | CH | N | H | OCH$_3$ | O | H | L-1a | |
| CH$_2$ | CH | CH | H | OCH$_3$ | O | H | L-1a | |
| CH$_2$ | N | N | H | OCH$_3$ | O | H | L-1a | |
| CH$_2$ | N | CH | H | OCH$_3$ | O | H | L-1a | |
| O | CH | N | CH$_3$ | OCH$_3$ | O | H | L-1a | |
| O | CH | CH | CH$_3$ | OCH$_3$ | O | H | L-1a | |
| O | N | N | CH$_3$ | OCH$_3$ | O | H | L-1a | |
| O | N | CH | CH$_3$ | OCH$_3$ | O | H | L-1a | |
| S | CH | N | CH$_3$ | OCH$_3$ | O | H | L-1a | |
| S | CH | CH | CH$_3$ | OCH$_3$ | O | H | L-1a | |
| S | N | N | CH$_3$ | OCH$_3$ | O | H | L-1a | |
| S | N | CH | CH$_3$ | OCH$_3$ | O | H | L-1a | |
| NCH$_3$ | CH | N | CH$_3$ | OCH$_3$ | O | H | L-1a | |
| NCH$_3$ | CH | CH | CH$_3$ | OCH$_3$ | O | H | L-1a | |
| NCH$_3$ | N | N | CH$_3$ | OCH$_3$ | O | H | L-1a | |
| NCH$_3$ | N | CH | CH$_3$ | OCH$_3$ | O | H | L-1a | |
| CH$_2$ | CH | N | CH$_3$ | OCH$_3$ | O | H | L-1a | |
| CH$_2$ | CH | CH | CH$_3$ | OCH$_3$ | O | H | L-1a | |
| CH$_2$ | N | N | CH$_3$ | OCH$_3$ | O | H | L-1a | |
| CH$_2$ | N | CH | CH$_3$ | OCH$_3$ | O | H | L-1a | |

TABLE 12

General Formula 12

| $Z_4$ | $Z_1$ | $Z_2$ | m' | Y | W | R | L | m.p.(°C.) |
|---|---|---|---|---|---|---|---|---|
| O | CH | N | 2 | CH$_3$ | O | H | L-1a | |
| O | CH | CH | 2 | CH$_3$ | O | H | L-1a | |
| O | N | N | 2 | CH$_3$ | O | H | L-1a | |
| O | N | CH | 2 | CH$_3$ | O | H | L-1a | |
| S | CH | N | 2 | CH$_3$ | O | H | L-1a | |
| S | CH | CH | 2 | CH$_3$ | O | H | L-1a | |
| S | N | N | 2 | CH$_3$ | O | H | L-1a | |
| S | N | CH | 2 | CH$_3$ | O | H | L-1a | |
| NCH$_3$ | CH | N | 2 | CH$_3$ | O | H | L-1a | |
| NCH$_3$ | CH | CH | 2 | CH$_3$ | O | H | L-1a | |
| NCH$_3$ | N | N | 2 | CH$_3$ | O | H | L-1a | |
| NCH$_3$ | N | CH | 2 | CH$_3$ | O | H | L-1a | |
| CH$_2$ | CH | N | 2 | CH$_3$ | O | H | L-1a | |
| CH$_2$ | CH | CH | 2 | CH$_3$ | O | H | L-1a | |
| CH$_2$ | N | N | 2 | CH$_3$ | O | H | L-1a | |
| CH$_2$ | N | CH | 2 | CH$_3$ | O | H | L-1a | |
| O | CH | N | 3 | CH$_3$ | O | H | L-1a | |
| O | CH | CH | 3 | CH$_3$ | O | H | L-1a | |
| O | N | N | 3 | CH$_3$ | O | H | L-1a | |
| O | N | CH | 3 | CH$_3$ | O | H | L-1a | |
| S | CH | N | 3 | CH$_3$ | O | H | L-1a | |
| S | CH | CH | 3 | CH$_3$ | O | H | L-1a | |
| S | N | N | 3 | CH$_3$ | O | H | L-1a | |
| S | N | CH | 3 | CH$_3$ | O | H | L-1a | |
| NCH$_3$ | CH | N | 3 | CH$_3$ | O | H | L-1a | |
| NCH$_3$ | CH | CH | 3 | CH$_3$ | O | H | L-1a | |
| NCH$_3$ | N | N | 3 | CH$_3$ | O | H | L-1a | |
| NCH$_3$ | N | CH | 3 | CH$_3$ | O | H | L-1a | |
| CH$_2$ | CH | N | 3 | CH$_3$ | O | H | L-1a | |
| CH$_2$ | CH | CH | 3 | CH$_3$ | O | H | L-1a | |
| CH$_2$ | N | N | 3 | CH$_3$ | O | H | L-1a | |
| CH$_2$ | N | CH | 3 | CH$_3$ | O | H | L-1a | |
| O | CH | N | 2 | OCH$_3$ | O | H | L-1a | |
| O | CH | CH | 2 | OCH$_3$ | O | H | L-1a | |
| O | N | N | 2 | OCH$_3$ | O | H | L-1a | |
| O | N | CH | 2 | OCH$_3$ | O | H | L-1a | |
| S | CH | N | 2 | OCH$_3$ | O | H | L-1a | |
| S | CH | CH | 2 | OCH$_3$ | O | H | L-1a | |
| S | N | N | 2 | OCH$_3$ | O | H | L-1a | |
| S | N | CH | 2 | OCH$_3$ | O | H | L-1a | |
| NCH$_3$ | CH | N | 2 | OCH$_3$ | O | H | L-1a | |
| NCH$_3$ | CH | CH | 2 | OCH$_3$ | O | H | L-1a | |
| NCH$_3$ | N | N | 2 | OCH$_3$ | O | H | L-1a | |
| NCH$_3$ | N | CH | 2 | OCH$_3$ | O | H | L-1a | |
| CH$_2$ | CH | N | 2 | OCH$_3$ | O | H | L-1a | |
| CH$_2$ | CH | CH | 2 | OCH$_3$ | O | H | L-1a | |
| CH$_2$ | N | N | 2 | OCH$_3$ | O | H | L-1a | |
| CH$_2$ | N | CH | 2 | OCH$_3$ | O | H | L-1a | |
| O | CH | N | 3 | OCH$_3$ | O | H | L-1a | |
| O | CH | CH | 3 | OCH$_3$ | O | H | L-1a | |
| O | N | N | 3 | OCH$_3$ | O | H | L-1a | |
| O | N | CH | 3 | OCH$_3$ | O | H | L-1a | |
| S | CH | N | 3 | OCH$_3$ | O | H | L-1a | |
| S | CH | CH | 3 | OCH$_3$ | O | H | L-1a | |
| S | N | N | 3 | OCH$_3$ | O | H | L-1a | |
| S | N | CH | 3 | OCH$_3$ | O | H | L-1a | |
| NCH$_3$ | CH | N | 3 | OCH$_3$ | O | H | L-1a | |
| NCH$_3$ | CH | CH | 3 | OCH$_3$ | O | H | L-1a | |
| NCH$_3$ | N | N | 3 | OCH$_3$ | O | H | L-1a | |
| NCH$_3$ | N | CH | 3 | OCH$_3$ | O | H | L-1a | |
| CH$_2$ | CH | N | 3 | OCH$_3$ | O | H | L-1a | |
| CH$_2$ | CH | CH | 3 | OCH$_3$ | O | H | L-1a | |
| CH$_2$ | N | N | 3 | OCH$_3$ | O | H | L-1a | |
| CH$_2$ | N | CH | 3 | OCH$_3$. | O | H | L-1a | |

TABLE 13

General Formula 13

| $Z_4$ | $Z_1$ | $Z_2$ | $X_d$ | X | W | R | L | m.p.(°C.) |
|---|---|---|---|---|---|---|---|---|
| O | CH | N | H | CH$_3$ | O | H | L-1a | |
| O | CH | CH | H | CH$_3$ | O | H | L-1a | |
| O | N | N | H | CH$_3$ | O | H | L-1a | |
| O | N | CH | H | CH$_3$ | O | H | L-1a | |
| S | CH | N | H | CH$_3$ | O | H | L-1a | |
| S | CH | CH | H | CH$_3$ | O | H | L-1a | |
| S | N | N | H | CH$_3$ | O | H | L-1a | |
| S | N | CH | H | CH$_3$ | O | H | L-1a | |
| NCH$_3$ | CH | N | H | CH$_3$ | O | H | L-1a | |

TABLE 13-continued

General Formula 13

| Z4 | Z1 | Z2 | Xd | X | W | R | L | m.p.(°C.) |
|---|---|---|---|---|---|---|---|---|
| NCH3 | CH | CH | H | CH3 | O | H | L-1a | |
| NCH3 | N | N | H | CH3 | O | H | L-1a | |
| NCH3 | N | CH | H | CH3 | O | H | L-1a | |
| CH2 | CH | N | H | CH3 | O | H | L-1a | |
| CH2 | CH | CH | H | CH3 | O | H | L-1a | |
| CH2 | N | N | H | CH3 | O | H | L-1a | |
| CH2 | N | CH | H | CH3 | O | H | L-1a | |
| O | CH | N | CH3 | CH3 | O | H | L-1a | |
| O | CH | CH | CH3 | CH3 | O | H | L-1a | |
| O | N | N | CH3 | CH3 | O | H | L-1a | |
| O | N | CH | CH3 | CH3 | O | H | L-1a | |
| S | CH | N | CH3 | CH3 | O | H | L-1a | |
| S | CH | CH | CH3 | CH3 | O | H | L-1a | |
| S | N | N | CH3 | CH3 | O | H | L-1a | |
| S | N | CH | CH3 | CH3 | O | H | L-1a | |
| NCH3 | CH | N | CH3 | CH3 | O | H | L-1a | |
| NCH3 | CH | CH | CH3 | CH3 | O | H | L-1a | |
| NCH3 | N | N | CH3 | CH3 | O | H | L-1a | |
| NCH3 | N | CH | CH3 | CH3 | O | H | L-1a | |
| CH2 | CH | N | CH3 | CH3 | O | H | L-1a | |
| CH2 | CH | CH | CH3 | CH3 | O | H | L-1a | |
| CH2 | N | N | CH3 | CH3 | O | H | L-1a | |
| CH2 | N | CH | CH3 | CH3 | O | H | L-1a | |
| O | CH | N | H | OCH3 | O | H | L-1a | |
| O | CH | CH | H | OCH3 | O | H | L-1a | |
| O | N | N | H | OCH3 | O | H | L-1a | |
| O | N | CH | H | OCH3 | O | H | L-1a | |
| S | CH | N | H | OCH3 | O | H | L-1a | |
| S | CH | CH | H | OCH3 | O | H | L-1a | |
| S | N | N | H | OCH3 | O | H | L-1a | |
| S | N | CH | H | OCH3 | O | H | L-1a | |
| NCH3 | CH | N | H | OCH3 | O | H | L-1a | |
| NCH3 | CH | CH | H | OCH3 | O | H | L-1a | |
| NCH3 | N | N | H | OCH3 | O | H | L-1a | |
| NCH3 | N | CH | H | OCH3 | O | H | L-1a | |
| CH2 | CH | N | H | OCH3 | O | H | L-1a | |
| CH2 | CH | CH | H | OCH3 | O | H | L-1a | |
| CH2 | N | N | H | OCH3 | O | H | L-1a | |
| CH2 | N | CH | H | OCH3 | O | H | L-1a | |
| O | CH | N | CH3 | OCH3 | O | H | L-1a | |
| O | CH | CH | CH3 | OCH3 | O | H | L-1a | |
| O | N | N | CH3 | OCH3 | O | H | L-1a | |
| O | N | CH | CH3 | OCH3 | O | H | L-1a | |
| S | CH | N | CH3 | OCH3 | O | H | L-1a | |
| S | CH | CH | CH3 | OCH3 | O | H | L-1a | |
| S | N | N | CH3 | OCH3 | O | H | L-1a | |
| S | N | CH | CH3 | OCH3 | O | H | L-1a | |
| NCH3 | CH | N | CH3 | OCH3 | O | H | L-1a | |
| NCH3 | CH | CH | CH3 | OCH3 | O | H | L-1a | |
| NCH3 | N | N | CH3 | OCH3 | O | H | L-1a | |
| NCH3 | N | CH | CH3 | OCH3 | O | H | L-1a | |
| CH2 | CH | N | CH3 | OCH3 | O | H | L-1a | |
| CH2 | CH | CH | CH3 | OCH3 | O | H | L-1a | |
| CH2 | N | N | CH3 | OCH3 | O | H | L-1a | |
| CH2 | N | CH | CH3 | OCH3 | O | H | L-1a | |

TABLE 14

General Formula 14

| Z4 | Z1 | Z2 | m' | X | W | R | L | m.p.(°C.) |
|---|---|---|---|---|---|---|---|---|
| O | CH | N | 2 | CH3 | O | H | L-1a | |
| O | CH | CH | 2 | CH3 | O | H | L-1a | |
| O | N | N | 2 | CH3 | O | H | L-1a | |
| O | N | CH | 2 | CH3 | O | H | L-1a | |
| S | CH | N | 2 | CH3 | O | H | L-1a | |
| S | CH | CH | 2 | CH3 | O | H | L-1a | |
| S | N | N | 2 | CH3 | O | H | L-1a | |
| S | N | CH | 2 | CH3 | O | H | L-1a | |
| NCH3 | CH | N | 2 | CH3 | O | H | L-1a | |
| NCH3 | CH | CH | 2 | CH3 | O | H | L-1a | |
| NCH3 | N | N | 2 | CH3 | O | H | L-1a | |
| NCH3 | N | CH | 2 | CH3 | O | H | L-1a | |
| CH2 | CH | N | 2 | CH3 | O | H | L-1a | |
| CH2 | CH | CH | 2 | CH3 | O | H | L-1a | |
| CH2 | N | N | 2 | CH3 | O | H | L-1a | |
| CH2 | N | CH | 2 | CH3 | O | H | L-1a | |
| O | CH | N | 3 | CH3 | O | H | L-1a | |
| O | CH | CH | 3 | CH3 | O | H | L-1a | |
| O | N | N | 3 | CH3 | O | H | L-1a | |
| O | N | CH | 3 | CH3 | O | H | L-1a | |
| S | CH | N | 3 | CH3 | O | H | L-1a | |
| S | CH | CH | 3 | CH3 | O | H | L-1a | |
| S | N | N | 3 | CH3 | O | H | L-1a | |
| S | N | CH | 3 | CH3 | O | H | L-1a | |
| NCH3 | CH | N | 3 | CH3 | O | H | L-1a | |
| NCH3 | CH | CH | 3 | CH3 | O | H | L-1a | |
| NCH3 | N | N | 3 | CH3 | O | H | L-1a | |
| NCH3 | N | CH | 3 | CH3 | O | H | L-1a | |
| CH2 | CH | N | 3 | CH3 | O | H | L-1a | |
| CH2 | CH | CH | 3 | CH3 | O | H | L-1a | |
| CH2 | N | N | 3 | CH3 | O | H | L-1a | |
| CH2 | N | CH | 3 | CH3 | O | H | L-1a | |

TABLE 15

General Formula 15

| Z1 | Z2 | W | X | Y | R | L | m.p. (°C.) |
|---|---|---|---|---|---|---|---|
| N | CH | O | CH3 | CH3 | H | L-1a | |
| N | CH | O | CH3 | CH3 | H | L-1b | |
| N | CH | O | CH3 | CH3 | H | L-1c | |
| N | CH | O | CH3 | CH3 | H | L-1d | |
| N | CH | O | CH3 | CH3 | H | L-1e | |
| N | CH | O | CH3 | CH3 | H | L-1f | |
| N | CH | O | CH3 | CH3 | H | L-1g | |
| N | CH | O | CH3 | CH3 | H | L-1h | |
| N | CH | O | CH3 | CH3 | H | L-1i | |
| N | CH | O | CH3 | CH3 | H | L-3a | |
| N | CH | O | CH3 | CH3 | H | L-3b | |
| N | CH | O | CH3 | CH3 | H | L-4a | |
| N | CH | O | CH3 | CH3 | H | L-7a | |
| N | CH | O | CH3 | CH3 | H | L-8a | |
| N | CH | O | CH3 | CH3 | H | L-8b | |
| N | CH | O | CH3 | CH3 | H | L-9a | |
| N | CH | O | CH3 | CH3 | H | L-12a | |
| N | CH | O | CH3 | CH3 | H | L-12b | |
| N | CH | O | CH3 | CH3 | H | L-14a | |
| N | CH | O | CH3 | CH3 | H | L-15a | |
| N | CH | O | CH3 | CH3 | H | L-16a | |
| N | CH | O | CH3 | CH3 | H | L-16b | |
| N | CH | O | CH3 | CH3 | H | L-18a | |
| N | CH | O | CH3 | CH3 | H | L-20a | |
| N | CH | O | CH3 | CH3 | H | L-22a | |
| N | CH | S | CH3 | CH3 | H | L-1a | |
| N | CH | O | CH3 | CH3 | CH3 | L-1a | |
| N | CH | O | OCH3 | CH3 | H | L-1a | |
| N | CH | O | OCH3 | CH3 | H | L-1b | |
| N | CH | O | OCH3 | CH3 | H | L-1c | |
| N | CH | O | OCH3 | CH3 | H | L-1d | |
| N | CH | O | OCH3 | CH3 | H | L-1e | |
| N | CH | O | OCH3 | CH3 | H | L-1f | |
| N | CH | O | OCH3 | CH3 | H | L-1g | |
| N | CH | O | OCH3 | CH3 | H | L-1h | |
| N | CH | O | OCH3 | CH3 | H | L-1i | |
| N | CH | O | OCH3 | CH3 | H | L-3a | |
| N | CH | O | OCH3 | CH3 | H | L-3b | |
| N | CH | O | OCH3 | CH3 | H | L-4a | |
| N | CH | O | OCH3 | CH3 | H | L-7a | |
| N | CH | O | OCH3 | CH3 | H | L-8a | |
| N | CH | O | OCH3 | CH3 | H | L-8b | |
| N | CH | O | OCH3 | CH3 | H | L-9a | |
| N | CH | O | OCH3 | CH3 | H | L-12a | |
| N | CH | O | OCH3 | CH3 | H | L-12b | |
| N | CH | O | OCH3 | CH3 | H | L-14a | |
| N | CH | O | OCH3 | CH3 | H | L-15a | |
| N | CH | O | OCH3 | CH3 | H | L-16a | |
| N | CH | O | OCH3 | CH3 | H | L-16b | |
| N | CH | O | OCH3 | CH3 | H | L-18a | |
| N | CH | O | OCH3 | CH3 | H | L-20a | |
| N | CH | O | OCH3 | CH3 | H | L-22a | |
| N | CH | S | OCH3 | CH3 | H | L-1a | |
| N | CH | O | OCH3 | CH3 | CH3 | L-1a | |
| N | CH | O | CH3 | OCH3 | H | L-1a | |
| N | CH | O | CH3 | OCH3 | H | L-1b | |
| N | CH | O | CH3 | OCH3 | H | L-1c | |
| N | CH | O | CH3 | OCH3 | H | L-1d | |
| N | CH | O | CH3 | OCH3 | H | L-1e | |

TABLE 15-continued

General Formula 15

| $Z_1$ | $Z_2$ | W | X | Y | R | L | m.p. (°C.) |
|---|---|---|---|---|---|---|---|
| N | CH | O | CH₃ | OCH₃ | H | L-1f | |
| N | CH | O | CH₃ | OCH₃ | H | L-1g | |
| N | CH | O | CH₃ | OCH₃ | H | L-1h | |
| N | CH | O | CH₃ | OCH₃ | H | L-1i | |
| N | CH | O | CH₃ | OCH₃ | H | L-3a | |
| N | CH | O | CH₃ | OCH₃ | H | L-3b | |
| N | CH | O | CH₃ | OCH₃ | H | L-4a | |
| N | CH | O | CH₃ | OCH₃ | H | L-7a | |
| N | CH | O | CH₃ | OCH₃ | H | L-8a | |
| N | CH | O | CH₃ | OCH₃ | H | L-8b | |
| N | CH | O | CH₃ | OCH₃ | H | L-9a | |
| N | CH | O | CH₃ | OCH₃ | H | L-12a | |
| N | CH | O | CH₃ | OCH₃ | H | L-12b | |
| N | CH | O | CH₃ | OCH₃ | H | L-14a | |
| N | CH | O | CH₃ | OCH₃ | H | L-15a | |
| N | CH | O | CH₃ | OCH₃ | H | L-16a | |
| N | CH | O | CH₃ | OCH₃ | H | L-16b | |
| N | CH | O | CH₃ | OCH₃ | H | L-18a | |
| N | CH | O | CH₃ | OCH₃ | H | L-20a | |
| N | CH | O | CH₃ | OCH₃ | H | L-22a | |
| N | CH | S | CH₃ | OCH₃ | H | L-1a | |
| N | CH | O | CH₃ | OCH₃ | CH₃ | L-1a | |
| N | CH | O | OCH₃ | OCH₃ | H | L-1a | |
| N | CH | O | OCH₃ | OCH₃ | H | L-1b | |
| N | CH | O | OCH₃ | OCH₃ | H | L-1c | |
| N | CH | O | OCH₃ | OCH₃ | H | L-1d | |
| N | CH | O | OCH₃ | OCH₃ | H | L-1e | |
| N | CH | O | OCH₃ | OCH₃ | H | L-1f | |
| N | CH | O | OCH₃ | OCH₃ | H | L-1g | |
| N | CH | O | OCH₃ | OCH₃ | H | L-1h | |
| N | CH | O | OCH₃ | OCH₃ | H | L-1i | |
| N | CH | O | OCH₃ | OCH₃ | H | L-3a | |
| N | CH | O | OCH₃ | OCH₃ | H | L-3b | |
| N | CH | O | OCH₃ | OCH₃ | H | L-4a | |
| N | CH | O | OCH₃ | OCH₃ | H | L-7a | |
| N | CH | O | OCH₃ | OCH₃ | H | L-8a | |
| N | CH | O | OCH₃ | OCH₃ | H | L-8b | |
| N | CH | O | OCH₃ | OCH₃ | H | L-9a | |
| N | CH | O | OCH₃ | OCH₃ | H | L-12a | |
| N | CH | O | OCH₃ | OCH₃ | H | L-12b | |
| N | CH | O | OCH₃ | OCH₃ | H | L-14a | |
| N | CH | O | OCH₃ | OCH₃ | H | L-15a | |
| N | CH | O | OCH₃ | OCH₃ | H | L-16a | |
| N | CH | O | OCH₃ | OCH₃ | H | L-16b | |
| N | CH | O | OCH₃ | OCH₃ | H | L-18a | |
| N | CH | O | OCH₃ | OCH₃ | H | L-20a | |
| N | CH | O | OCH₃ | OCH₃ | H | L-22a | |
| N | CH | S | OCH₃ | OCH₃ | H | L-1a | |
| N | CH | O | OCH₃ | OCH₃ | CH₃ | L-1a | |
| N | N | O | CH₃ | CH₃ | H | L-1a | |
| N | N | O | CH₃ | CH₃ | H | L-1b | |
| N | N | O | CH₃ | CH₃ | H | L-1c | |
| N | N | O | CH₃ | CH₃ | H | L-1d | |
| N | N | O | CH₃ | CH₃ | H | L-1e | |
| N | N | O | CH₃ | CH₃ | H | L-1f | |
| N | N | O | CH₃ | CH₃ | H | L-1g | |
| N | N | O | CH₃ | CH₃ | H | L-1h | |
| N | N | O | CH₃ | CH₃ | H | L-1i | |
| N | N | O | CH₃ | CH₃ | H | L-3a | |
| N | N | O | CH₃ | CH₃ | H | L-3b | |
| N | N | O | CH₃ | CH₃ | H | L-4a | |
| N | N | O | CH₃ | CH₃ | H | L-7a | |
| N | N | O | CH₃ | CH₃ | H | L-8a | |
| N | N | O | CH₃ | CH₃ | H | L-8b | |
| N | N | O | CH₃ | CH₃ | H | L-9a | |
| N | N | O | CH₃ | CH₃ | H | L-12a | |
| N | N | O | CH₃ | CH₃ | H | L-12b | |
| N | N | O | CH₃ | CH₃ | H | L-14a | |
| N | N | O | CH₃ | CH₃ | H | L-15a | |
| N | N | O | CH₃ | CH₃ | H | L-16a | |
| N | N | O | CH₃ | CH₃ | H | L-16b | |
| N | N | O | CH₃ | CH₃ | H | L-18a | |
| N | N | O | CH₃ | CH₃ | H | L-20a | |
| N | N | O | CH₃ | CH₃ | H | L-22a | |
| N | N | S | CH₃ | CH₃ | H | L-1a | |
| N | N | O | CH₃ | CH₃ | CH₃ | L-1a | |
| N | N | O | OCH₃ | CH₃ | H | L-1a | |
| N | N | O | OCH₃ | CH₃ | H | L-1b | |
| N | N | O | OCH₃ | CH₃ | H | L-1c | |
| N | N | O | OCH₃ | CH₃ | H | L-1d | |
| N | N | O | OCH₃ | CH₃ | H | L-1e | |
| N | N | O | OCH₃ | CH₃ | H | L-1f | |
| N | N | O | OCH₃ | CH₃ | H | L-1g | |
| N | N | O | OCH₃ | CH₃ | H | L-1h | |
| N | N | O | OCH₃ | CH₃ | H | L-1i | |
| N | N | O | OCH₃ | CH₃ | H | L-3a | |
| N | N | O | OCH₃ | CH₃ | H | L-3b | |
| N | N | O | OCH₃ | CH₃ | H | L-4a | |
| N | N | O | OCH₃ | CH₃ | H | L-7a | |
| N | N | O | OCH₃ | CH₃ | H | L-8a | |
| N | N | O | OCH₃ | CH₃ | H | L-8b | |
| N | N | O | OCH₃ | CH₃ | H | L-9a | |
| N | N | O | OCH₃ | CH₃ | H | L-12a | |
| N | N | O | OCH₃ | CH₃ | H | L-12b | |
| N | N | O | OCH₃ | CH₃ | H | L-14a | |
| N | N | O | OCH₃ | CH₃ | H | L-15a | |
| N | N | O | OCH₃ | CH₃ | H | L-16a | |
| N | N | O | OCH₃ | CH₃ | H | L-16b | |
| N | N | O | OCH₃ | CH₃ | H | L-18a | |
| N | N | O | OCH₃ | CH₃ | H | L-20a | |
| N | N | O | OCH₃ | CH₃ | H | L-22a | |
| N | N | S | OCH₃ | CH₃ | H | L-1a | |
| N | N | O | OCH₃ | CH₃ | CH₃ | L-1a | |
| N | N | O | CH₃ | OCH₃ | H | L-1a | |
| N | N | O | CH₃ | OCH₃ | H | L-1b | |
| N | N | O | CH₃ | OCH₃ | H | L-1c | |
| N | N | O | CH₃ | OCH₃ | H | L-1d | |
| N | N | O | CH₃ | OCH₃ | H | L-1e | |
| N | N | O | CH₃ | OCH₃ | H | L-1f | |
| N | N | O | CH₃ | OCH₃ | H | L-1g | |
| N | N | O | CH₃ | OCH₃ | H | L-1h | |
| N | N | O | CH₃ | OCH₃ | H | L-1i | |
| N | N | O | CH₃ | OCH₃ | H | L-3a | |
| N | N | O | CH₃ | OCH₃ | H | L-3b | |
| N | N | O | CH₃ | OCH₃ | H | L-4a | |
| N | N | O | CH₃ | OCH₃ | H | L-7a | |
| N | N | O | CH₃ | OCH₃ | H | L-8a | |
| N | N | O | CH₃ | OCH₃ | H | L-8b | |
| N | N | O | CH₃ | OCH₃ | H | L-9a | |
| N | N | O | CH₃ | OCH₃ | H | L-12a | |
| N | N | O | CH₃ | OCH₃ | H | L-12b | |
| N | N | O | CH₃ | OCH₃ | H | L-14a | |
| N | N | O | CH₃ | OCH₃ | H | L-15a | |
| N | N | O | CH₃ | OCH₃ | H | L-16a | |
| N | N | O | CH₃ | OCH₃ | H | L-16b | |
| N | N | O | CH₃ | OCH₃ | H | L-18a | |
| N | N | O | CH₃ | OCH₃ | H | L-20a | |
| N | N | O | CH₃ | OCH₃ | H | L-22a | |
| N | N | S | CH₃ | OCH₃ | H | L-1a | |
| N | N | O | CH₃ | OCH₃ | CH₃ | L-1a | |
| N | N | O | OCH₃ | OCH₃ | H | L-1a | |
| N | N | O | OCH₃ | OCH₃ | H | L-1b | |
| N | N | O | OCH₃ | OCH₃ | H | L-1c | |
| N | N | O | OCH₃ | OCH₃ | H | L-1d | |
| N | N | O | OCH₃ | OCH₃ | H | L-1e | |
| N | N | O | OCH₃ | OCH₃ | H | L-1f | |
| N | N | O | OCH₃ | OCH₃ | H | L-1g | |
| N | N | O | OCH₃ | OCH₃ | H | L-1h | |
| N | N | O | OCH₃ | OCH₃ | H | L-1i | |
| N | N | O | OCH₃ | OCH₃ | H | L-3a | |
| N | N | O | OCH₃ | OCH₃ | H | L-3b | |
| N | N | O | OCH₃ | OCH₃ | H | L-4a | |
| N | N | O | OCH₃ | OCH₃ | H | L-7a | |
| N | N | O | OCH₃ | OCH₃ | H | L-8a | |
| N | N | O | OCH₃ | OCH₃ | H | L-8b | |
| N | N | O | OCH₃ | OCH₃ | H | L-9a | |
| N | N | O | OCH₃ | OCH₃ | H | L-12a | |
| N | N | O | OCH₃ | OCH₃ | H | L-12b | |
| N | N | O | OCH₃ | OCH₃ | H | L-14a | |
| N | N | O | OCH₃ | OCH₃ | H | L-15a | |
| N | N | O | OCH₃ | OCH₃ | H | L-16a | |
| N | N | O | OCH₃ | OCH₃ | H | L-16b | |
| N | N | O | OCH₃ | OCH₃ | H | L-18a | |
| N | N | O | OCH₃ | OCH₃ | H | L-20a | |
| N | N | O | OCH₃ | OCH₃ | H | L-22a | |
| N | N | S | OCH₃ | OCH₃ | H | L-1a | |
| N | N | O | OCH₃ | OCH₃ | CH₃ | L-1a | |
| CH | N | O | CH₃ | CH₃ | H | L-1a | |

TABLE 15-continued

General Formula 15

| $Z_1$ | $Z_2$ | W | X | Y | R | L | m.p. (°C.) |
|---|---|---|---|---|---|---|---|
| CH | N | O | CH$_3$ | CH$_3$ | H | L-1b | |
| CH | N | O | CH$_3$ | CH$_3$ | H | L-1c | |
| CH | N | O | CH$_3$ | CH$_3$ | H | L-1d | |
| CH | N | O | CH$_3$ | CH$_3$ | H | L-1e | |
| CH | N | O | CH$_3$ | CH$_3$ | H | L-1f | |
| CH | N | O | CH$_3$ | CH$_3$ | H | L-1g | |
| CH | N | O | CH$_3$ | CH$_3$ | H | L-1h | |
| CH | N | O | CH$_3$ | CH$_3$ | H | L-1i | |
| CH | N | O | CH$_3$ | CH$_3$ | H | L-3a | |
| CH | N | O | CH$_3$ | CH$_3$ | H | L-3b | |
| CH | N | O | CH$_3$ | CH$_3$ | H | L-4a | |
| CH | N | O | CH$_3$ | CH$_3$ | H | L-7a | |
| CH | N | O | CH$_3$ | CH$_3$ | H | L-8a | |
| CH | N | O | CH$_3$ | CH$_3$ | H | L-8b | |
| CH | N | O | CH$_3$ | CH$_3$ | H | L-9a | |
| CH | N | O | CH$_3$ | CH$_3$ | H | L-12a | |
| CH | N | O | CH$_3$ | CH$_3$ | H | L-12b | |
| CH | N | O | CH$_3$ | CH$_3$ | H | L-14a | |
| CH | N | O | CH$_3$ | CH$_3$ | H | L-15a | |
| CH | N | O | CH$_3$ | CH$_3$ | H | L-16a | |
| CH | N | O | CH$_3$ | CH$_3$ | H | L-16b | |
| CH | N | O | CH$_3$ | CH$_3$ | H | L-18a | |
| CH | N | O | CH$_3$ | CH$_3$ | H | L-20a | |
| CH | N | O | CH$_3$ | CH$_3$ | H | L-22a | |
| CH | N | S | CH$_3$ | CH$_3$ | H | L-1a | |
| CH | N | O | CH$_3$ | CH$_3$ | CH$_3$ | L-1a | |
| CH | N | O | OCH$_3$ | CH$_3$ | H | L-1a | |
| CH | N | O | OCH$_3$ | CH$_3$ | H | L-1b | |
| CH | N | O | OCH$_3$ | CH$_3$ | H | L-1c | |
| CH | N | O | OCH$_3$ | CH$_3$ | H | L-1d | |
| CH | N | O | OCH$_3$ | CH$_3$ | H | L-1e | |
| CH | N | O | OCH$_3$ | CH$_3$ | H | L-1f | |
| CH | N | O | OCH$_3$ | CH$_3$ | H | L-1g | |
| CH | N | O | OCH$_3$ | CH$_3$ | H | L-1h | |
| CH | N | O | OCH$_3$ | CH$_3$ | H | L-1i | |
| CH | N | O | OCH$_3$ | CH$_3$ | H | L-3a | |
| CH | N | O | OCH$_3$ | CH$_3$ | H | L-3b | |
| CH | N | O | OCH$_3$ | CH$_3$ | H | L-4a | |
| CH | N | O | OCH$_3$ | CH$_3$ | H | L-7a | |
| CH | N | O | OCH$_3$ | CH$_3$ | H | L-8a | |
| CH | N | O | OCH$_3$ | CH$_3$ | H | L-8b | |
| CH | N | O | OCH$_3$ | CH$_3$ | H | L-9a | |
| CH | N | O | OCH$_3$ | CH$_3$ | H | L-12a | |
| CH | N | O | OCH$_3$ | CH$_3$ | H | L-12b | |
| CH | N | O | OCH$_3$ | CH$_3$ | H | L-14a | |
| CH | N | O | OCH$_3$ | CH$_3$ | H | L-15a | |
| CH | N | O | OCH$_3$ | CH$_3$ | H | L-16a | |
| CH | N | O | OCH$_3$ | CH$_3$ | H | L-16b | |
| CH | N | O | OCH$_3$ | CH$_3$ | H | L-18a | |
| CH | N | O | OCH$_3$ | CH$_3$ | H | L-20a | |
| CH | N | O | OCH$_3$ | CH$_3$ | H | L-22a | |
| CH | N | S | OCH$_3$ | CH$_3$ | H | L-1a | |
| CH | N | O | OCH$_3$ | CH$_3$ | CH$_3$ | L-1a | |
| CH | N | O | CH$_3$ | OCH$_3$ | H | L-1a | |
| CH | N | O | CH$_3$ | OCH$_3$ | H | L-1b | |
| CH | N | O | CH$_3$ | OCH$_3$ | H | L-1c | |
| CH | N | O | CH$_3$ | OCH$_3$ | H | L-1d | |
| CH | N | O | CH$_3$ | OCH$_3$ | H | L-1e | |
| CH | N | O | CH$_3$ | OCH$_3$ | H | L-1f | |
| CH | N | O | CH$_3$ | OCH$_3$ | H | L-1g | |
| CH | N | O | CH$_3$ | OCH$_3$ | H | L-1h | |
| CH | N | O | CH$_3$ | OCH$_3$ | H | L-1i | |
| CH | N | O | CH$_3$ | OCH$_3$ | H | L-3a | |
| CH | N | O | CH$_3$ | OCH$_3$ | H | L-3b | |
| CH | N | O | CH$_3$ | OCH$_3$ | H | L-4a | |
| CH | N | O | CH$_3$ | OCH$_3$ | H | L-7a | |
| CH | N | O | CH$_3$ | OCH$_3$ | H | L-8a | |
| CH | N | O | CH$_3$ | OCH$_3$ | H | L-8b | |
| CH | N | O | CH$_3$ | OCH$_3$ | H | L-9a | |
| CH | N | O | CH$_3$ | OCH$_3$ | H | L-12a | |
| CH | N | O | CH$_3$ | OCH$_3$ | H | L-12b | |
| CH | N | O | CH$_3$ | OCH$_3$ | H | L-14a | |
| CH | N | O | CH$_3$ | OCH$_3$ | H | L-15a | |
| CH | N | O | CH$_3$ | OCH$_3$ | H | L-16a | |
| CH | N | O | CH$_3$ | OCH$_3$ | H | L-16b | |
| CH | N | O | CH$_3$ | OCH$_3$ | H | L-18a | |
| CH | N | O | CH$_3$ | OCH$_3$ | H | L-20a | |
| CH | N | O | CH$_3$ | OCH$_3$ | H | L-22a | |
| CH | N | S | CH$_3$ | OCH$_3$ | H | L-1a | |
| CH | N | O | CH$_3$ | OCH$_3$ | CH$_3$ | L-1a | |
| CH | N | O | OCH$_3$ | OCH$_3$ | H | L-1a | |
| CH | N | O | OCH$_3$ | OCH$_3$ | H | L-1b | |
| CH | N | O | OCH$_3$ | OCH$_3$ | H | L-1c | |
| CH | N | O | OCH$_3$ | OCH$_3$ | H | L-1d | |
| CH | N | O | OCH$_3$ | OCH$_3$ | H | L-1e | |
| CH | N | O | OCH$_3$ | OCH$_3$ | H | L-1f | |
| CH | N | O | OCH$_3$ | OCH$_3$ | H | L-1g | |
| CH | N | O | OCH$_3$ | OCH$_3$ | H | L-1h | |
| CH | N | O | OCH$_3$ | OCH$_3$ | H | L-1i | |
| CH | N | O | OCH$_3$ | OCH$_3$ | H | L-3a | |
| CH | N | O | OCH$_3$ | OCH$_3$ | H | L-3b | |
| CH | N | O | OCH$_3$ | OCH$_3$ | H | L-4a | |
| CH | N | O | OCH$_3$ | OCH$_3$ | H | L-7a | |
| CH | N | O | OCH$_3$ | OCH$_3$ | H | L-8a | |
| CH | N | O | OCH$_3$ | OCH$_3$ | H | L-8b | |
| CH | N | O | OCH$_3$ | OCH$_3$ | H | L-9a | |
| CH | N | O | OCH$_3$ | OCH$_3$ | H | L-12a | |
| CH | N | O | OCH$_3$ | OCH$_3$ | H | L-12b | |
| CH | N | O | OCH$_3$ | OCH$_3$ | H | L-14a | |
| CH | N | O | OCH$_3$ | OCH$_3$ | H | L-15a | |
| CH | N | O | OCH$_3$ | OCH$_3$ | H | L-16a | |
| CH | N | O | OCH$_3$ | OCH$_3$ | H | L-16b | |
| CH | N | O | OCH$_3$ | OCH$_3$ | H | L-18a | |
| CH | N | O | OCH$_3$ | OCH$_3$ | H | L-20a | |
| CH | N | O | OCH$_3$ | OCH$_3$ | H | L-22a | |
| CH | N | S | OCH$_3$ | OCH$_3$ | H | L-1a | |
| CH | N | O | OCH$_3$ | OCH$_3$ | CH$_3$ | L-1a | |
| CH | CH | O | CH$_3$ | CH$_3$ | H | L-1a | |
| CH | CH | O | CH$_3$ | CH$_3$ | H | L-1b | |
| CH | CH | O | CH$_3$ | CH$_3$ | H | L-1c | |
| CH | CH | O | CH$_3$ | CH$_3$ | H | L-1d | |
| CH | CH | O | CH$_3$ | CH$_3$ | H | L-1e | |
| CH | CH | O | CH$_3$ | CH$_3$ | H | L-1f | |
| CH | CH | O | CH$_3$ | CH$_3$ | H | L-1g | |
| CH | CH | O | CH$_3$ | CH$_3$ | H | L-1h | |
| CH | CH | O | CH$_3$ | CH$_3$ | H | L-1i | |
| CH | CH | O | CH$_3$ | CH$_3$ | H | L-3a | |
| CH | CH | O | CH$_3$ | CH$_3$ | H | L-3b | |
| CH | CH | O | CH$_3$ | CH$_3$ | H | L-4a | |
| CH | CH | O | CH$_3$ | CH$_3$ | H | L-7a | |
| CH | CH | O | CH$_3$ | CH$_3$ | H | L-8a | |
| CH | CH | O | CH$_3$ | CH$_3$ | H | L-8b | |
| CH | CH | O | CH$_3$ | CH$_3$ | H | L-9a | |
| CH | CH | O | CH$_3$ | CH$_3$ | H | L-12a | |
| CH | CH | O | CH$_3$ | CH$_3$ | H | L-12b | |
| CH | CH | O | CH$_3$ | CH$_3$ | H | L-14a | |
| CH | CH | O | CH$_3$ | CH$_3$ | H | L-15a | |
| CH | CH | O | CH$_3$ | CH$_3$ | H | L-16a | |
| CH | CH | O | CH$_3$ | CH$_3$ | H | L-16b | |
| CH | CH | O | CH$_3$ | CH$_3$ | H | L-18a | |
| CH | CH | O | CH$_3$ | CH$_3$ | H | L-20a | |
| CH | CH | O | CH$_3$ | CH$_3$ | H | L-22a | |
| CH | CH | S | CH$_3$ | CH$_3$ | H | L-1a | |
| CH | CH | O | CH$_3$ | CH$_3$ | CH$_3$ | L-1a | |
| CH | CH | O | OCH$_3$ | CH$_3$ | H | L-1a | |
| CH | CH | O | OCH$_3$ | CH$_3$ | H | L-1b | |
| CH | CH | O | OCH$_3$ | CH$_3$ | H | L-1c | |
| CH | CH | O | OCH$_3$ | CH$_3$ | H | L-1d | |
| CH | CH | O | OCH$_3$ | CH$_3$ | H | L-1e | |
| CH | CH | O | OCH$_3$ | CH$_3$ | H | L-1f | |
| CH | CH | O | OCH$_3$ | CH$_3$ | H | L-1g | |
| CH | CH | O | OCH$_3$ | CH$_3$ | H | L-1h | |
| CH | CH | O | OCH$_3$ | CH$_3$ | H | L-1i | |
| CH | CH | O | OCH$_3$ | CH$_3$ | H | L-3a | |
| CH | CH | O | OCH$_3$ | CH$_3$ | H | L-3b | |
| CH | CH | O | OCH$_3$ | CH$_3$ | H | L-4a | |
| CH | CH | O | OCH$_3$ | CH$_3$ | H | L-7a | |
| CH | CH | O | OCH$_3$ | CH$_3$ | H | L-8a | |
| CH | CH | O | OCH$_3$ | CH$_3$ | H | L-8b | |
| CH | CH | O | OCH$_3$ | CH$_3$ | H | L-9a | |
| CH | CH | O | OCH$_3$ | CH$_3$ | H | L-12a | |
| CH | CH | O | OCH$_3$ | CH$_3$ | H | L-12b | |
| CH | CH | O | OCH$_3$ | CH$_3$ | H | L-14a | |
| CH | CH | O | OCH$_3$ | CH$_3$ | H | L-15a | |
| CH | CH | O | OCH$_3$ | CH$_3$ | H | L-16a | |
| CH | CH | O | OCH$_3$ | CH$_3$ | H | L-16b | |
| CH | CH | O | OCH$_3$ | CH$_3$ | H | L-18a | |
| CH | CH | O | OCH$_3$ | CH$_3$ | H | L-20a | |

TABLE 15-continued

General Formula 15

| $Z_1$ | $Z_2$ | W | X | Y | R | L | m.p. (°C.) |
|---|---|---|---|---|---|---|---|
| CH | CH | O | $OCH_3$ | $CH_3$ | H | L-22a | |
| CH | CH | S | $OCH_3$ | $CH_3$ | H | L-1a | |
| CH | CH | O | $OCH_3$ | $CH_3$ | $CH_3$ | L-1a | |
| CH | CH | O | $CH_3$ | $OCH_3$ | H | L-1a | |
| CH | CH | O | $CH_3$ | $OCH_3$ | H | L-1b | |
| CH | CH | O | $CH_3$ | $OCH_3$ | H | L-1c | |
| CH | CH | O | $CH_3$ | $OCH_3$ | H | L-1d | |
| CH | CH | O | $CH_3$ | $OCH_3$ | H | L-1e | |
| CH | CH | O | $CH_3$ | $OCH_3$ | H | L-1f | |
| CH | CH | O | $CH_3$ | $OCH_3$ | H | L-1g | |
| CH | CH | O | $CH_3$ | $OCH_3$ | H | L-1h | |
| CH | CH | O | $CH_3$ | $OCH_3$ | H | L-1i | |
| CH | CH | O | $CH_3$ | $OCH_3$ | H | L-3a | |
| CH | CH | O | $CH_3$ | $OCH_3$ | H | L-3b | |
| CH | CH | O | $CH_3$ | $OCH_3$ | H | L-4a | |
| CH | CH | O | $CH_3$ | $OCH_3$ | H | L-7a | |
| CH | CH | O | $CH_3$ | $OCH_3$ | H | L-8a | |
| CH | CH | O | $CH_3$ | $OCH_3$ | H | L-8b | |
| CH | CH | O | $CH_3$ | $OCH_3$ | H | L-9a | |
| CH | CH | O | $CH_3$ | $OCH_3$ | H | L-12a | |
| CH | CH | O | $CH_3$ | $OCH_3$ | H | L-12b | |
| CH | CH | O | $CH_3$ | $OCH_3$ | H | L-14a | |
| CH | CH | O | $CH_3$ | $OCH_3$ | H | L-15a | |
| CH | CH | O | $CH_3$ | $OCH_3$ | H | L-16a | |
| CH | CH | O | $CH_3$ | $OCH_3$ | H | L-16b | |
| CH | CH | O | $CH_3$ | $OCH_3$ | H | L-18a | |
| CH | CH | O | $CH_3$ | $OCH_3$ | H | L-20a | |
| CH | CH | O | $CH_3$ | $OCH_3$ | H | L-22a | |
| CH | CH | S | $CH_3$ | $OCH_3$ | H | L-1a | |
| CH | CH | O | $CH_3$ | $OCH_3$ | $CH_3$ | L-1a | |
| CH | CH | O | $OCH_3$ | $OCH_3$ | H | L-1a | |
| CH | CH | O | $OCH_3$ | $OCH_3$ | H | L-1b | |
| CH | CH | O | $OCH_3$ | $OCH_3$ | H | L-1c | |
| CH | CH | O | $OCH_3$ | $OCH_3$ | H | L-1d | |
| CH | CH | O | $OCH_3$ | $OCH_3$ | H | L-1e | |
| CH | CH | O | $OCH_3$ | $OCH_3$ | H | L-1f | |
| CH | CH | O | $OCH_3$ | $OCH_3$ | H | L-1g | |
| CH | CH | O | $OCH_3$ | $OCH_3$ | H | L-1h | |
| CH | CH | O | $OCH_3$ | $OCH_3$ | H | L-1i | |
| CH | CH | O | $OCH_3$ | $OCH_3$ | H | L-3a | |
| CH | CH | O | $OCH_3$ | $OCH_3$ | H | L-3b | |
| CH | CH | O | $OCH_3$ | $OCH_3$ | H | L-4a | |
| CH | CH | O | $OCH_3$ | $OCH_3$ | H | L-7a | |
| CH | CH | O | $OCH_3$ | $OCH_3$ | H | L-8a | |
| CH | CH | O | $OCH_3$ | $OCH_3$ | H | L-8b | |
| CH | CH | O | $OCH_3$ | $OCH_3$ | H | L-9a | |
| CH | CH | O | $OCH_3$ | $OCH_3$ | H | L-12a | |
| CH | CH | O | $OCH_3$ | $OCH_3$ | H | L-12b | |
| CH | CH | O | $OCH_3$ | $OCH_3$ | H | L-14a | |
| CH | CH | O | $OCH_3$ | $OCH_3$ | H | L-15a | |
| CH | CH | O | $OCH_3$ | $OCH_3$ | H | L-16a | |
| CH | CH | O | $OCH_3$ | $OCH_3$ | H | L-16b | |
| CH | CH | O | $OCH_3$ | $OCH_3$ | H | L-18a | |
| CH | CH | O | $OCH_3$ | $OCH_3$ | H | L-20a | |
| CH | CH | O | $OCH_3$ | $OCH_3$ | H | L-22a | |
| CH | CH | S | $OCH_3$ | $OCH_3$ | H | L-1a | |
| CH | CH | O | $OCH_3$ | $OCH_3$ | $CH_3$ | L-1a | |

TABLE 16

General Formula 16

| $Z_1$ | $Z_2$ | Y | W | R | L | m.p. (°C.) |
|---|---|---|---|---|---|---|
| CH | CH | $CH_3$ | O | H | L-1a | |
| CH | N | $CH_3$ | O | H | L-1a | |
| N | CH | $CH_3$ | O | H | L-1a | |
| N | N | $CH_3$ | O | H | L-1a | |
| CH | CH | $OCH_3$ | O | H | L-1a | |
| CH | N | $OCH_3$ | O | H | L-1a | |
| N | CH | $OCH_3$ | O | H | L-1a | |
| N | N | $OCH_3$ | O | H | L-1a | |

TABLE 17

General Formula 17

| $Z_1$ | $Z_2$ | X | W | R | L | m.p. (°C.) |
|---|---|---|---|---|---|---|
| CH | CH | $CH_3$ | O | H | L-1a | |

TABLE 17-continued

General Formula 17

| $Z_1$ | $Z_2$ | X | W | R | L | m.p. (°C.) |
|---|---|---|---|---|---|---|
| CH | N | $CH_3$ | O | H | L-1a | |
| N | CH | $CH_3$ | O | H | L-1a | |
| N | N | $CH_3$ | O | H | L-1a | |
| CH | CH | $OCH_3$ | O | H | L-1a | |
| CH | N | $OCH_3$ | O | H | L-1a | |
| N | CH | $OCH_3$ | O | H | L-1a | |
| N | N | $OCH_3$ | O | H | L-1a | |

TABLE 18

General Formula 18

| Z | $Z_1$ | $Z_2$ | G | X | Y | L | m.p. (°C.) |
|---|---|---|---|---|---|---|---|
| CH | N | CH | $OCH_3$ | $CH_3$ | $CH_3$ | L-1a | |
| CH | N | CH | $OCH_3$ | $CH_3$ | $CH_3$ | L-1b | |
| CH | N | CH | $OCH_3$ | $CH_3$ | $CH_3$ | L-1c | |
| CH | N | CH | $OCH_3$ | $CH_3$ | $CH_3$ | L-1d | |
| CH | N | CH | $OCH_3$ | $CH_3$ | $CH_3$ | L-1e | |
| CH | N | CH | $OCH_3$ | $CH_3$ | $CH_3$ | L-1f | |
| CH | N | CH | $OCH_3$ | $CH_3$ | $CH_3$ | L-1g | |
| CH | N | CH | $OCH_3$ | $CH_3$ | $CH_3$ | L-1h | |
| CH | N | CH | $OCH_3$ | $CH_3$ | $CH_3$ | L-1i | |
| CH | N | CH | $OCH_3$ | $CH_3$ | $CH_3$ | L-3a | |
| CH | N | CH | $OCH_3$ | $CH_3$ | $CH_3$ | L-3b | |
| CH | N | CH | $OCH_3$ | $CH_3$ | $CH_3$ | L-4a | |
| CH | N | CH | $OCH_3$ | $CH_3$ | $CH_3$ | L-7a | |
| CH | N | CH | $OCH_3$ | $CH_3$ | $CH_3$ | L-8a | |
| CH | N | CH | $OCH_3$ | $CH_3$ | $CH_3$ | L-8b | |
| CH | N | CH | $OCH_3$ | $CH_3$ | $CH_3$ | L-9a | |
| CH | N | CH | $OCH_3$ | $CH_3$ | $CH_3$ | L-12a | |
| CH | N | CH | $OCH_3$ | $CH_3$ | $CH_3$ | L-12b | |
| CH | N | CH | $OCH_3$ | $CH_3$ | $CH_3$ | L-14a | |
| CH | N | CH | $OCH_3$ | $CH_3$ | $CH_3$ | L-15a | |
| CH | N | CH | $OCH_3$ | $CH_3$ | $CH_3$ | L-16a | |
| CH | N | CH | $OCH_3$ | $CH_3$ | $CH_3$ | L-16b | |
| CH | N | CH | $OCH_3$ | $CH_3$ | $CH_3$ | L-18a | |
| CH | N | CH | $OCH_3$ | $CH_3$ | $CH_3$ | L-20a | |
| CH | N | CH | $OCH_3$ | $CH_3$ | $CH_3$ | L-22a | |
| CH | N | CH | $SCH_3$ | $CH_3$ | $CH_3$ | L-1a | |
| CH | N | CH | $OCH_3$ | $OCH_3$ | $CH_3$ | L-1a | |
| CH | N | CH | $OCH_3$ | $OCH_3$ | $CH_3$ | L-1b | |
| CH | N | CH | $OCH_3$ | $OCH_3$ | $CH_3$ | L-1c | |
| CH | N | CH | $OCH_3$ | $OCH_3$ | $CH_3$ | L-1d | |
| CH | N | CH | $OCH_3$ | $OCH_3$ | $CH_3$ | L-1e | |
| CH | N | CH | $OCH_3$ | $OCH_3$ | $CH_3$ | L-1f | |
| CH | N | CH | $OCH_3$ | $OCH_3$ | $CH_3$ | L-1g | |
| CH | N | CH | $OCH_3$ | $OCH_3$ | $CH_3$ | L-1h | |
| CH | N | CH | $OCH_3$ | $OCH_3$ | $CH_3$ | L-1i | |
| CH | N | CH | $OCH_3$ | $OCH_3$ | $CH_3$ | L-3a | |
| CH | N | CH | $OCH_3$ | $OCH_3$ | $CH_3$ | L-3b | |
| CH | N | CH | $OCH_3$ | $OCH_3$ | $CH_3$ | L-4a | |
| CH | N | CH | $OCH_3$ | $OCH_3$ | $CH_3$ | L-7a | |
| CH | N | CH | $OCH_3$ | $OCH_3$ | $CH_3$ | L-8a | |
| CH | N | CH | $OCH_3$ | $OCH_3$ | $CH_3$ | L-8b | |
| CH | N | CH | $OCH_3$ | $OCH_3$ | $CH_3$ | L-9a | |
| CH | N | CH | $OCH_3$ | $OCH_3$ | $CH_3$ | L-12a | |
| CH | N | CH | $OCH_3$ | $OCH_3$ | $CH_3$ | L-12b | |
| CH | N | CH | $OCH_3$ | $OCH_3$ | $CH_3$ | L-14a | |
| CH | N | CH | $OCH_3$ | $OCH_3$ | $CH_3$ | L-15a | |
| CH | N | CH | $OCH_3$ | $OCH_3$ | $CH_3$ | L-16a | |
| CH | N | CH | $OCH_3$ | $OCH_3$ | $CH_3$ | L-16b | |
| CH | N | CH | $OCH_3$ | $OCH_3$ | $CH_3$ | L-18a | |
| CH | N | CH | $OCH_3$ | $OCH_3$ | $CH_3$ | L-20a | |
| CH | N | CH | $OCH_3$ | $OCH_3$ | $CH_3$ | L-22a | |
| CH | N | CH | $SCH_3$ | $OCH_3$ | $CH_3$ | L-1a | |
| CH | N | CH | $OCH_3$ | $CH_3$ | $OCH_3$ | L-1a | |
| CH | N | CH | $OCH_3$ | $CH_3$ | $OCH_3$ | L-1b | |
| CH | N | CH | $OCH_3$ | $CH_3$ | $OCH_3$ | L-1c | |
| CH | N | CH | $OCH_3$ | $CH_3$ | $OCH_3$ | L-1d | |
| CH | N | CH | $OCH_3$ | $CH_3$ | $OCH_3$ | L-1e | |
| CH | N | CH | $OCH_3$ | $CH_3$ | $OCH_3$ | L-1f | |
| CH | N | CH | $OCH_3$ | $CH_3$ | $OCH_3$ | L-1g | |
| CH | N | CH | $OCH_3$ | $CH_3$ | $OCH_3$ | L-1h | |
| CH | N | CH | $OCH_3$ | $CH_3$ | $OCH_3$ | L-1i | |
| CH | N | CH | $OCH_3$ | $CH_3$ | $OCH_3$ | L-3a | |
| CH | N | CH | $OCH_3$ | $CH_3$ | $OCH_3$ | L-3b | |
| CH | N | CH | $OCH_3$ | $CH_3$ | $OCH_3$ | L-4a | |
| CH | N | CH | $OCH_3$ | $CH_3$ | $OCH_3$ | L-7a | |
| CH | N | CH | $OCH_3$ | $CH_3$ | $OCH_3$ | L-8a | |

TABLE 18-continued

General Formula 18

| Z | Z₁ | Z₂ | G | X | Y | L | m.p. (°C.) |
|---|----|----|----|----|----|----|----|
| CH | N | CH | OCH₃ | CH₃ | OCH₃ | L-8b | |
| CH | N | CH | OCH₃ | CH₃ | OCH₃ | L-9a | |
| CH | N | CH | OCH₃ | CH₃ | OCH₃ | L-12a | |
| CH | N | CH | OCH₃ | CH₃ | OCH₃ | L-12b | |
| CH | N | CH | OCH₃ | CH₃ | OCH₃ | L-14a | |
| CH | N | CH | OCH₃ | CH₃ | OCH₃ | L-15a | |
| CH | N | CH | OCH₃ | CH₃ | OCH₃ | L-16a | |
| CH | N | CH | OCH₃ | CH₃ | OCH₃ | L-16b | |
| CH | N | CH | OCH₃ | CH₃ | OCH₃ | L-18a | |
| CH | N | CH | OCH₃ | CH₃ | OCH₃ | L-20a | |
| CH | N | CH | OCH₃ | CH₃ | OCH₃ | L-22a | |
| CH | N | CH | SCH₃ | CH₃ | OCH₃ | L-1a | |
| CH | N | CH | OCH₃ | OCH₃ | OCH₃ | L-1a | |
| CH | N | CH | OCH₃ | OCH₃ | OCH₃ | L-1b | |
| CH | N | CH | OCH₃ | OCH₃ | OCH₃ | L-1c | |
| CH | N | CH | OCH₃ | OCH₃ | OCH₃ | L-1d | |
| CH | N | CH | OCH₃ | OCH₃ | OCH₃ | L-1e | |
| CH | N | CH | OCH₃ | OCH₃ | OCH₃ | L-1f | |
| CH | N | CH | OCH₃ | OCH₃ | OCH₃ | L-1g | |
| CH | N | CH | OCH₃ | OCH₃ | OCH₃ | L-1h | |
| CH | N | CH | OCH₃ | OCH₃ | OCH₃ | L-1i | |
| CH | N | CH | OCH₃ | OCH₃ | OCH₃ | L-3a | |
| CH | N | CH | OCH₃ | OCH₃ | OCH₃ | L-3b | |
| CH | N | CH | OCH₃ | OCH₃ | OCH₃ | L-4a | |
| CH | N | CH | OCH₃ | OCH₃ | OCH₃ | L-7a | |
| CH | N | CH | OCH₃ | OCH₃ | OCH₃ | L-8a | |
| CH | N | CH | OCH₃ | OCH₃ | OCH₃ | L-8b | |
| CH | N | CH | OCH₃ | OCH₃ | OCH₃ | L-9a | |
| CH | N | CH | OCH₃ | OCH₃ | OCH₃ | L-12a | |
| CH | N | CH | OCH₃ | OCH₃ | OCH₃ | L-12b | |
| CH | N | CH | OCH₃ | OCH₃ | OCH₃ | L-14a | |
| CH | N | CH | OCH₃ | OCH₃ | OCH₃ | L-15a | |
| CH | N | CH | OCH₃ | OCH₃ | OCH₃ | L-16a | |
| CH | N | CH | OCH₃ | OCH₃ | OCH₃ | L-16b | |
| CH | N | CH | OCH₃ | OCH₃ | OCH₃ | L-18a | |
| CH | N | CH | OCH₃ | OCH₃ | OCH₃ | L-20a | |
| CH | N | CH | OCH₃ | OCH₃ | OCH₃ | L-22a | |
| CH | N | CH | SCH₃ | OCH₃ | OCH₃ | L-1a | |

TABLE 19

General Formula 19

| Z | Z₁ | Z₂ | W | X | Y | L | m.p. (°C.) |
|---|----|----|---|---|---|---|----|
| CH | N | N | O | CH₃ | CH₃ | L-1a | 227–229 |
| CH | N | N | O | CH₃ | CH₃ | L-1b | 207–209 |
| CH | N | N | O | CH₃ | CH₃ | L-1c | 194–196 |
| CH | N | N | O | CH₃ | CH₃ | L-1d | 244–246 |
| CH | N | N | O | CH₃ | CH₃ | L-1e | |
| CH | N | N | O | CH₃ | CH₃ | L-1f | |
| CH | N | N | O | CH₃ | CH₃ | L-1g | |
| CH | N | N | O | CH₃ | CH₃ | L-1h | |
| CH | N | N | O | CH₃ | CH₃ | L-1i | |
| CH | N | N | O | CH₃ | CH₃ | L-1j | |
| CH | N | N | O | CH₃ | CH₃ | L-1k | |
| CH | N | N | O | CH₃ | CH₃ | L-1l | 303–306 |
| CH | N | N | O | CH₃ | CH₃ | L-1m | |
| CH | N | N | O | CH₃ | CH₃ | L-1n | |
| CH | N | N | O | CH₃ | CH₃ | L-1o | |
| CH | N | N | O | CH₃ | CH₃ | L-1p | 282–284 |
| CH | N | N | O | CH₃ | CH₃ | L-1q | |
| CH | N | N | O | CH₃ | CH₃ | L-1r | |
| CH | N | N | O | CH₃ | CH₃ | L-1s | |
| CH | N | N | O | CH₃ | CH₃ | L-1t | |
| CH | N | N | O | CH₃ | CH₃ | L-1u | |
| CH | N | N | O | CH₃ | CH₃ | L-1v | |
| CH | N | N | O | CH₃ | CH₃ | L-3a | |
| CH | N | N | O | CH₃ | CH₃ | L-3b | |
| CH | N | N | O | CH₃ | CH₃ | L-4a | |
| CH | N | N | O | CH₃ | CH₃ | L-7a | |
| CH | N | N | O | CH₃ | CH₃ | L-8a | |
| CH | N | N | O | CH₃ | CH₃ | L-8b | |
| CH | N | N | O | CH₃ | CH₃ | L-9a | |
| CH | N | N | O | CH₃ | CH₃ | L-10a | |
| CH | N | N | O | CH₃ | CH₃ | L-12a | |
| CH | N | N | O | CH₃ | CH₃ | L-12b | |
| CH | N | N | O | CH₃ | CH₃ | L-12c | |
| CH | N | N | O | CH₃ | CH₃ | L-14a | |
| CH | N | N | O | CH₃ | CH₃ | L-15a | |

TABLE 19-continued

General Formula 19

| Z | Z₁ | Z₂ | W | X | Y | L | m.p. (°C.) |
|---|----|----|---|---|---|---|----|
| CH | N | N | O | CH₃ | CH₃ | L-16a | |
| CH | N | N | O | CH₃ | CH₃ | L-16b | |
| CH | N | N | O | CH₃ | CH₃ | L-18a | |
| CH | N | N | O | CH₃ | CH₃ | L-20a | |
| CH | N | N | O | CH₃ | CH₃ | L-20b | |
| CH | N | N | O | CH₃ | CH₃ | L-22a | |
| CH | N | CH | O | CH₃ | CH₃ | L-1a | |
| CH | N | CH | O | CH₃ | CH₃ | L-1b | |
| CH | N | CH | O | CH₃ | CH₃ | L-1c | |
| CH | N | CH | O | CH₃ | CH₃ | L-1d | |
| CH | N | CH | O | CH₃ | CH₃ | L-1e | |
| CH | N | CH | O | CH₃ | CH₃ | L-1f | |
| CH | N | CH | O | CH₃ | CH₃ | L-1g | |
| CH | N | CH | O | CH₃ | CH₃ | L-1h | |
| CH | N | CH | O | CH₃ | CH₃ | L-1i | |
| CH | N | CH | O | CH₃ | CH₃ | L-1j | |
| CH | N | CH | O | CH₃ | CH₃ | L-1k | |
| CH | N | CH | O | CH₃ | CH₃ | L-1l | |
| CH | N | CH | O | CH₃ | CH₃ | L-1m | |
| CH | N | CH | O | CH₃ | CH₃ | L-1n | |
| CH | N | CH | O | CH₃ | CH₃ | L-1o | |
| CH | N | CH | O | CH₃ | CH₃ | L-1p | |
| CH | N | CH | O | CH₃ | CH₃ | L-1q | |
| CH | N | CH | O | CH₃ | CH₃ | L-1r | |
| CH | N | CH | O | CH₃ | CH₃ | L-1s | |
| CH | N | CH | O | CH₃ | CH₃ | L-1t | |
| CH | N | CH | O | CH₃ | CH₃ | L-1u | |
| CH | N | CH | O | CH₃ | CH₃ | L-1v | |
| CH | N | CH | O | CH₃ | CH₃ | L-3a | |
| CH | N | CH | O | CH₃ | CH₃ | L-3b | |
| CH | N | CH | O | CH₃ | CH₃ | L-4a | |
| CH | N | CH | O | CH₃ | CH₃ | L-7a | |
| CH | N | CH | O | CH₃ | CH₃ | L-8a | |
| CH | N | CH | O | CH₃ | CH₃ | L-8b | |
| CH | N | CH | O | CH₃ | CH₃ | L-9a | |
| CH | N | CH | O | CH₃ | CH₃ | L-10a | |
| CH | N | CH | O | CH₃ | CH₃ | L-12a | |
| CH | N | CH | O | CH₃ | CH₃ | L-12b | |
| CH | N | CH | O | CH₃ | CH₃ | L-12c | |
| CH | N | CH | O | CH₃ | CH₃ | L-14a | |
| CH | N | CH | O | CH₃ | CH₃ | L-15a | |
| CH | N | CH | O | CH₃ | CH₃ | L-16a | |
| CH | N | CH | O | CH₃ | CH₃ | L-16b | |
| CH | N | CH | O | CH₃ | CH₃ | L-18a | |
| CH | N | CH | O | CH₃ | CH₃ | L-20a | |
| CH | N | CH | O | CH₃ | CH₃ | L-20b | |
| CH | N | CH | O | CH₃ | CH₃ | L-22a | |
| CH | CH | N | O | CH₃ | CH₃ | L-1a | |
| CH | CH | N | O | CH₃ | CH₃ | L-1b | |
| CH | CH | N | O | CH₃ | CH₃ | L-1c | |
| CH | CH | N | O | CH₃ | CH₃ | L-1d | |
| CH | CH | N | O | CH₃ | CH₃ | L-1e | |
| CH | CH | N | O | CH₃ | CH₃ | L-1f | |
| CH | CH | N | O | CH₃ | CH₃ | L-1g | |
| CH | CH | N | O | CH₃ | CH₃ | L-1h | |
| CH | CH | N | O | CH₃ | CH₃ | L-1i | |
| CH | CH | N | O | CH₃ | CH₃ | L-1j | |
| CH | CH | N | O | CH₃ | CH₃ | L-1k | |
| CH | CH | N | O | CH₃ | CH₃ | L-1l | |
| CH | CH | N | O | CH₃ | CH₃ | L-1m | |
| CH | CH | N | O | CH₃ | CH₃ | L-1n | |
| CH | CH | N | O | CH₃ | CH₃ | L-1o | |
| CH | CH | N | O | CH₃ | CH₃ | L-1p | |
| CH | CH | N | O | CH₃ | CH₃ | L-1q | |
| CH | CH | N | O | CH₃ | CH₃ | L-1r | |
| CH | CH | N | O | CH₃ | CH₃ | L-1s | |
| CH | CH | N | O | CH₃ | CH₃ | L-1t | |
| CH | CH | N | O | CH₃ | CH₃ | L-1u | |
| CH | CH | N | O | CH₃ | CH₃ | L-1v | |
| CH | CH | N | O | CH₃ | CH₃ | L-3a | |
| CH | CH | N | O | CH₃ | CH₃ | L-3b | |
| CH | CH | N | O | CH₃ | CH₃ | L-4a | |
| CH | CH | N | O | CH₃ | CH₃ | L-7a | |
| CH | CH | N | O | CH₃ | CH₃ | L-8a | |
| CH | CH | N | O | CH₃ | CH₃ | L-8b | |
| CH | CH | N | O | CH₃ | CH₃ | L-9a | |
| CH | CH | N | O | CH₃ | CH₃ | L-10a | |
| CH | CH | N | O | CH₃ | CH₃ | L-12a | |
| CH | CH | N | O | CH₃ | CH₃ | L-12b | |

TABLE 19-continued

| | | | General Formula 19 | | | | |
|---|---|---|---|---|---|---|---|
| Z | $Z_1$ | $Z_2$ | W | X | Y | L | m.p. (°C.) |
| CH | CH | N | O | $CH_3$ | $CH_3$ | L-12c | |
| CH | CH | N | O | $CH_3$ | $CH_3$ | L-14a | |
| CH | CH | N | O | $CH_3$ | $CH_3$ | L-15a | |
| CH | CH | N | O | $CH_3$ | $CH_3$ | L-16a | |
| CH | CH | N | O | $CH_3$ | $CH_3$ | L-16b | |
| CH | CH | N | O | $CH_3$ | $CH_3$ | L-18a | |
| CH | CH | N | O | $CH_3$ | $CH_3$ | L-20a | |
| CH | CH | N | O | $CH_3$ | $CH_3$ | L-20b | |
| CH | CH | N | O | $CH_3$ | $CH_3$ | L-22a | |

FORMULATIONS

Useful formulations of the compounds of Formulae Ia and Ib can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 20

| | Active Ingredient | Weight Percent* | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants are recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 19

Wettable Powder

| | |
|---|---|
| Methyl 2-[[[(5,7-dimethylpyrazolo[1,5-A]pyrimidin-3-yl)carbonyl]amino]sulfonyl]benzoate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 20

Wettable Powder

| | |
|---|---|
| Methyl 2-[[[(5,7-dimethyl[1,2,3]triazolo[1,5-A]-pyrimidin-3-yl)carbonyl]amino]sulfonyl]benzoate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 21

Granule

| | |
|---|---|
| Wettable Powder of Example 20 | 5% |
| attapulgite granules | 95% |

A slurry of wettable powder containing 25% solids is sprayed on the surface of attapulgite granules in a double-cone blender. The granules are dried and packaged.

EXAMPLE 22

Extruded Pellet

| | |
|---|---|
| 5,7-Dimethyl-N—[[2-(methylsulfonyl)phenyl]sulfonyl]-pyrazolo[1,5-A]pyrimidine-3-carboxamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 23

Oil Suspension

| | |
|---|---|
| N—[[2-(1-ethyl-1H—tetrazol-5-yl)phenyl]sulfonyl]-5,7-dimethylpyrazolo[1,5-A]pyrimidine-3-carbamate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 24

Wettable Powder

| | |
|---|---|
| 5,7-Dimethyl-N—[[2-(methylsulfonyl)phenyl]sulfonyl]-pyrazolo[1,5-A]pyrimidine-3-carboxamide | 20% |
| sodium alkylnaphthalenesulfonte | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 25

Low Strength Granule

| | |
|---|---|
| Methyl 2-[[[(5,7-dimethylpyrazolo[1,5-A]pyrimidin-3-yl)carbonyl]amino]sulfonyl]benzoate | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blended. After spraying of the solution has been completed, the blender is allowed to run for a short period and then the granules are packaged.

EXAMPLE 26

Aqueous Suspension

| | |
|---|---|
| Methyl 2-[[[(5,7-dimethyl[1,2,3]triazolo[1,5-A]-pyrimidin-3-yl)carbonyl]amino]sulfonyl]benzoate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 27

Solution

| | |
|---|---|
| N—[[2-(1-ethyl-1H—tetrazol-5-yl)phenyl]sulfonyl]-5,7-dimethylpyrazolo[1,5-A]pyrimidine-3-carbamate | 5% |
| water | 95% |

The salt is added directly to the water with stirring to produce the solution, which may then be packaged for use.

EXAMPLE 28

Low Strength Granule

| | |
|---|---|
| 5,7-Dimethyl-N—[[2-(methylsulfonyl)phenyl]sulfonyl]-pyrazolo[1,5-A]pyrimidine-3-carboxamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 29

Granule

| | |
|---|---|
| Methyl 2-[[[(5,7-dimethylpyrazolo[1,5-A]pyrimidin-3-yl)carbonyl]amino]sulfonyl]benzoate | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 30

High Strength Concentrate

| | |
|---|---|
| Methyl 2-[[[(5,7-dimethyl[1,2,3]triazolo[1,5-A]pyrimidin-3-yl)-carbonyl]amino]sulfonyl]benzoate | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 31

Wettable Powder

| | |
|---|---|
| 5,7-Dimethyl-N—[[2-(methylsulfonyl)phenyl]sulfonyl]-pyrazolo[1,5-A]pyrimidine-3-carboxamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 32

Wettable Powder

| | |
|---|---|
| Methyl 2-[[[(5,7-dimethylpyrazolo[1,5-A]pytimidin-3-yl)-carbonyl]amino]sulfonyl]benzoate | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 33

Oil Suspension

| | |
|---|---|
| N—[[2-(ethyl-1H—tetrazol-5-yl)phenyl]sulfonyl]-5,7-dimethylpyrazolo[1,5-A]pyrimidine-3-carbamate | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 34

Dust

| | |
|---|---|
| Methyl 2-[[[(5,7-dimethyl[1,2,3]triazolo[1,5-A]-pyrimidin-3-yl)carbonyl]amino]sulfonyl]benzoate | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 35

Emulsifiable Concentrate

| | |
|---|---|
| 5,7-Dimethyl-N—[[2-(methylsulfonyl)phenyl]sulfonyl]-pyrazolo[1,5-A]pyrimidine-3-carboxamide | 10% |
| chlorobenzene | 84% |
| sorbitan monostearate and polyoxyethylene condensates thereof | 6% |

The ingredients are combined and stirred to produce a solution which can be emulsified in water for application.

UTILITY

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as rice, wheat, barley, corn, soybeans, sugarbeets and cotton. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.010 to 20 kg/ha, the lower rates being suggested for use on lighter soils and/or those having a low organic matter content, for plant growth modification or for situations where only short-term persistence is required, such as a herbicide for fallow land.

The compounds of the invention may be used in combination with any other commercial herbicide, non-limiting examples of which are those of the sulfonylurea, triazine, triazole, uracil, urea, amide, diphenyl ether, carbamate, imidazolinone, cineole and bipyridylium types.

The herbicidal properties of the subject compounds were discovered in a number of greenhouse tests. The test procedures and results follow.

It is noted that several of the compounds exhibit little herbicidal activity at the rates tested; it is believed that these compounds would have activity at application rates not exceeding 20 kg/ha.

Compounds
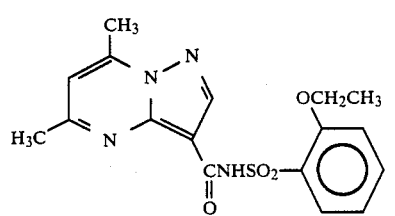 Compound 1
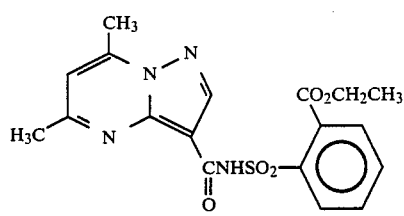 Compound 2
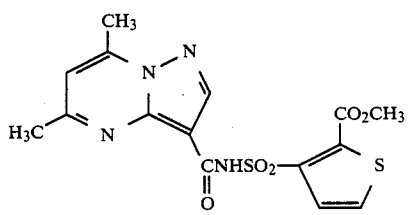 Compound 3
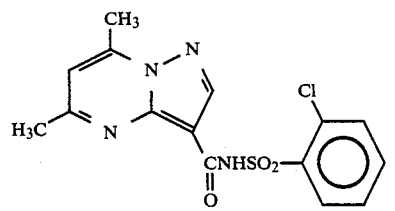 Compound 4
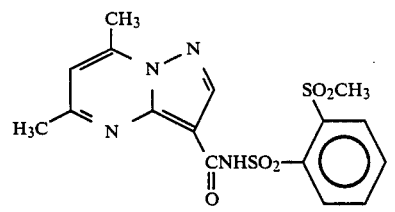 Compound 5
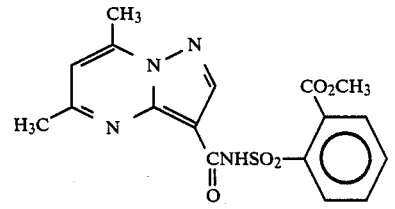 Compound 6
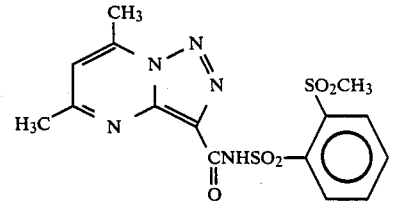 Compound 7
-continued
Compounds
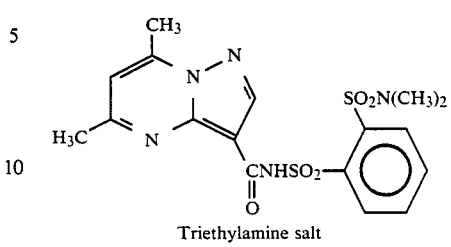 Compound 8
Triethylamine salt
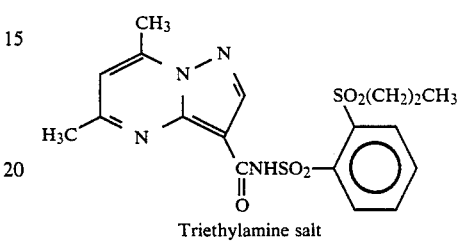 Compound 9
Triethylamine salt
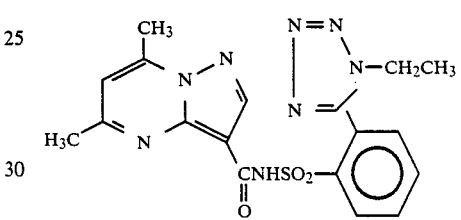 Compound 10
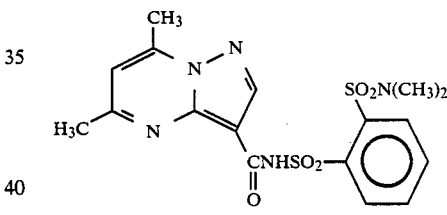 Compound 11
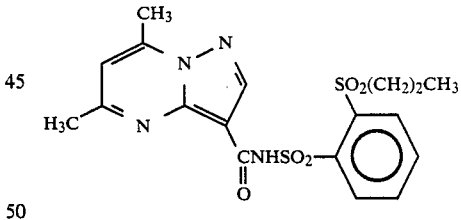 Compound 12
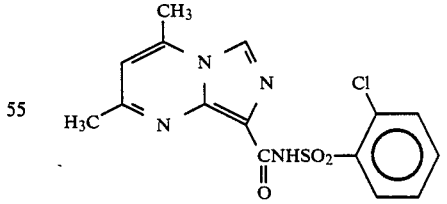 Compound 13
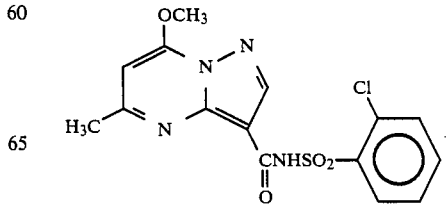 Compound 14

-continued
Compounds
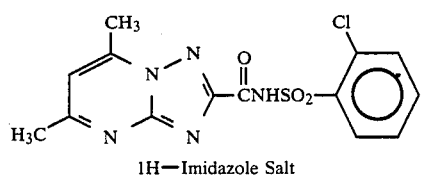
Compound 15
1H—Imidazole Salt
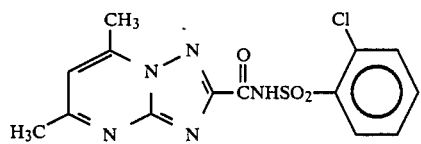
Compound 16
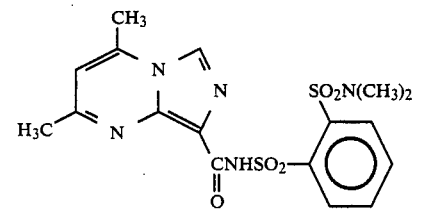
Compound 17
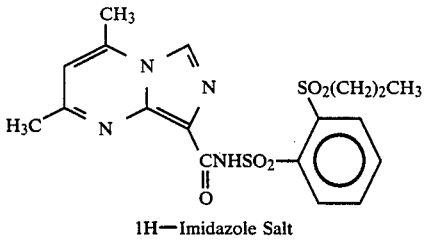
Compound 18
1H—Imidazole Salt
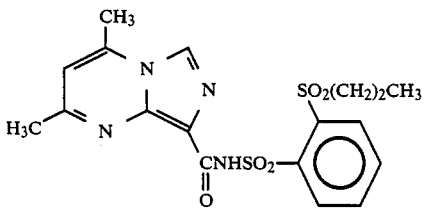
Compound 19
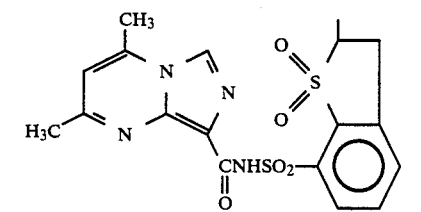
Compound 20
1H—Imidazole Salt
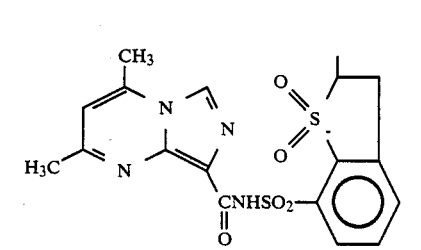
Compound 21
-continued
Compounds
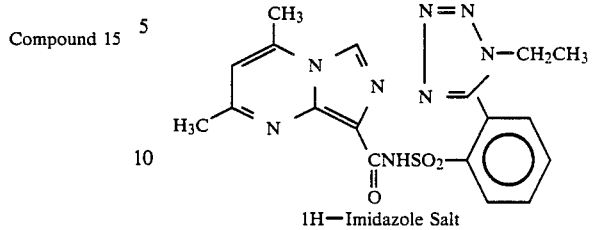
Compound 22
1H—Imidazole Salt
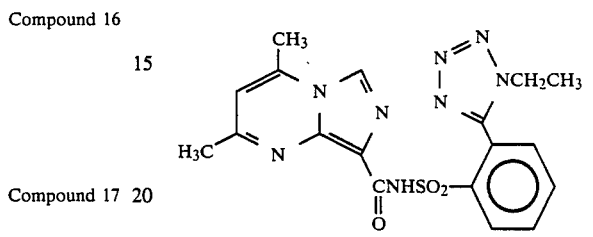
Compound 23
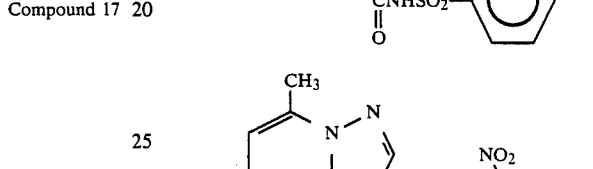
Compound 24
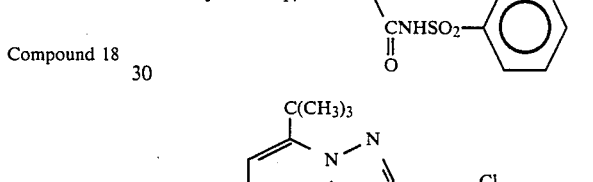
Compound 25
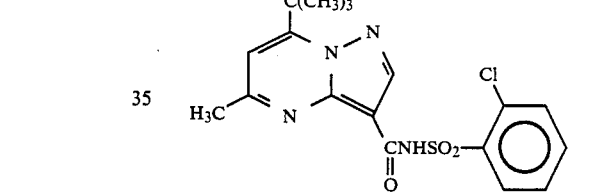
Compound 26
1H—Imidazole Salt
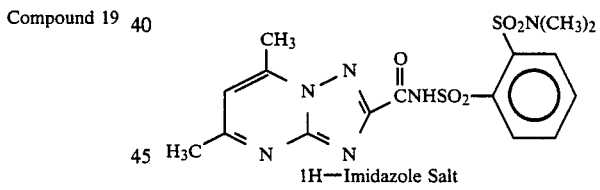
Compound 27
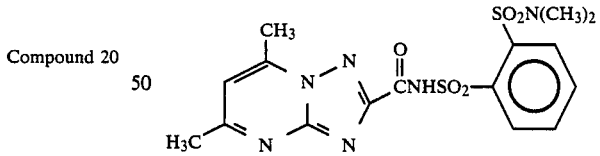
Compound 28
1H—Imidazole Salt
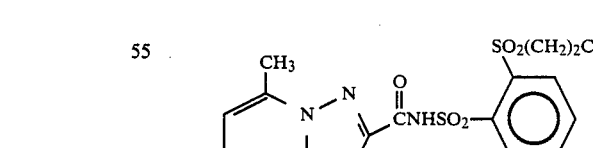
Compound 29

-continued
Compounds
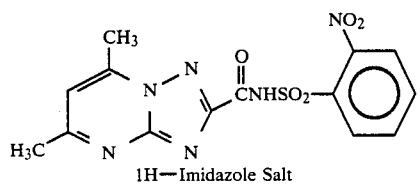
Compound 30
1H—Imidazole Salt
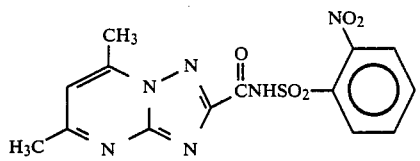
Compound 31
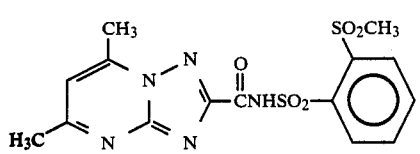
Compound 32
1H—Imidazole Salt
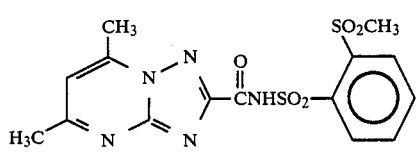
Compound 33
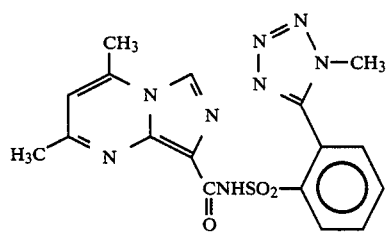
Compound 34
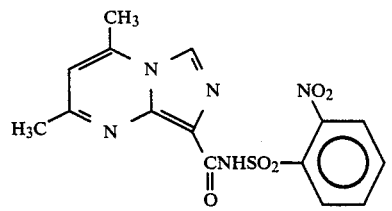
Compound 35
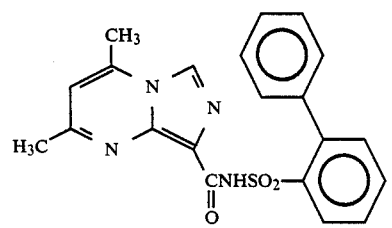
Compound 36
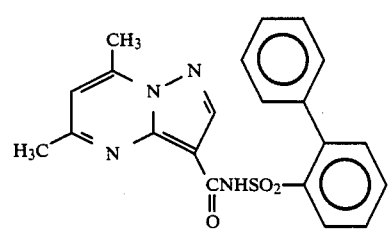
Compound 37
-continued
Compounds
1H—Imidazole Salt
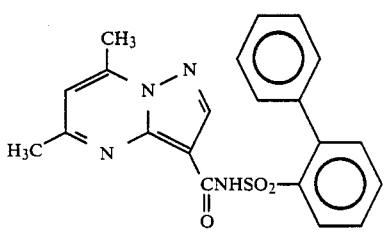
Compound 38
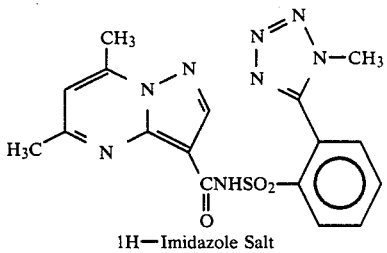
Compound 39
1H—Imidazole Salt
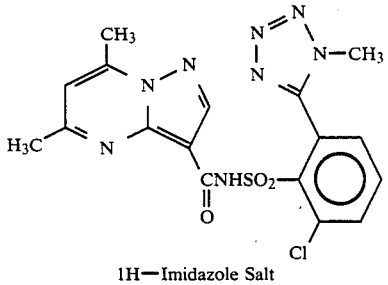
Compound 40
1H—Imidazole Salt
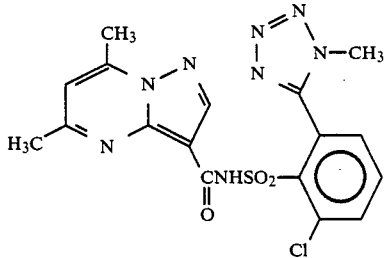
Compound 41
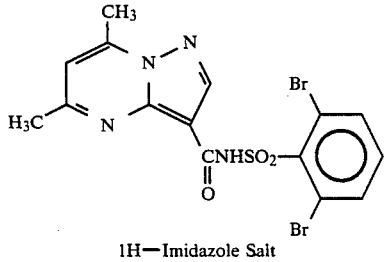
Compound 42
1H—Imidazole Salt
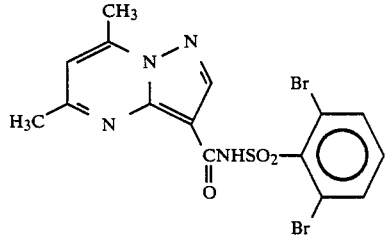
Compound 43

-continued
Compounds
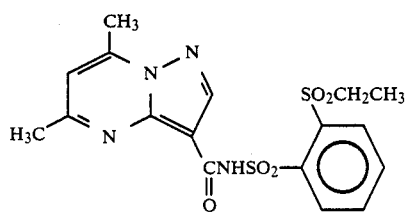
Compound 44
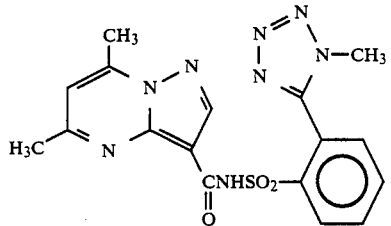
Compound 45
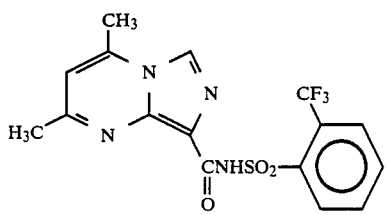
Compound 46
1H—Imidazole Salt
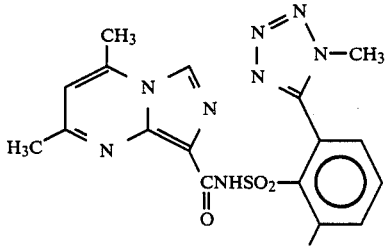
Compound 47
1H—Imidazole Salt
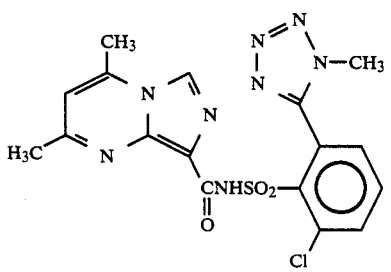
Compound 48
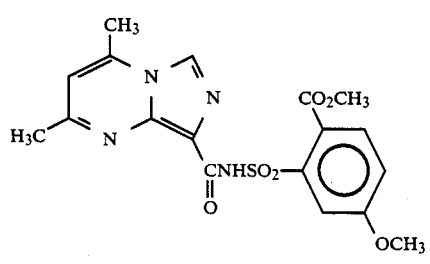
Compound 49
1H—Imidazole Salt
-continued
Compounds
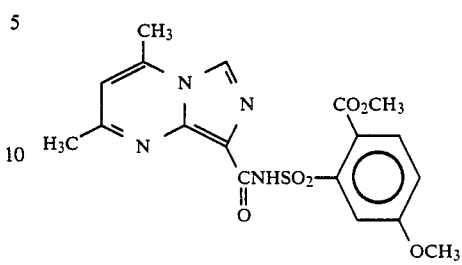
Compound 50
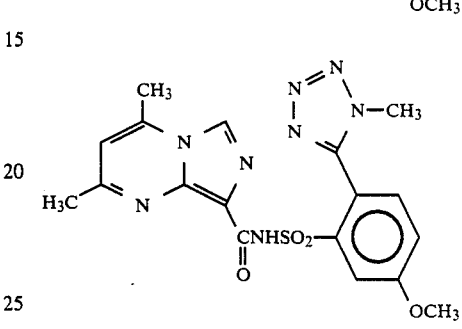
Compound 51
1H—Imidazole Salt
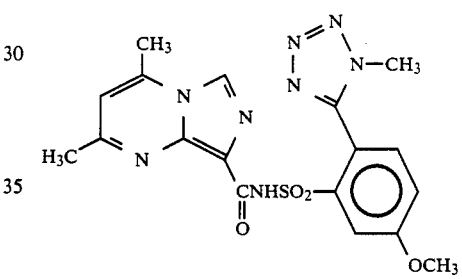
Compound 52
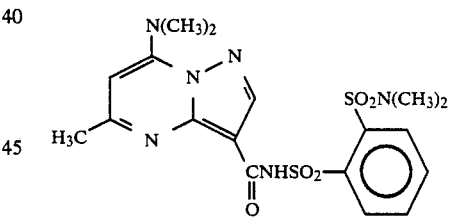
Compound 53
1H—Imidazole Salt
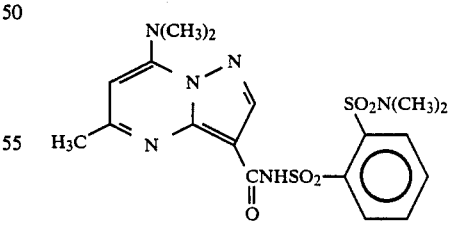
Compound 54
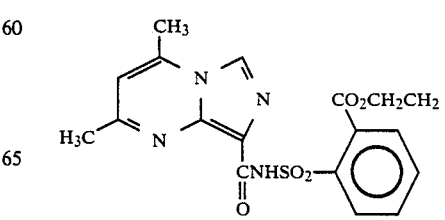
Compound 55

-continued
Compounds
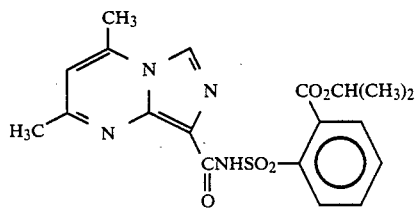
Compound 56
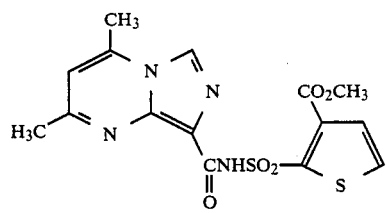
Compound 57
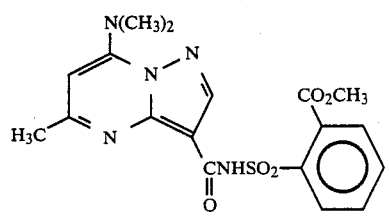
Compound 58
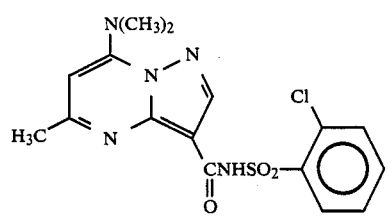
Compound 59
Triethylamine Salt
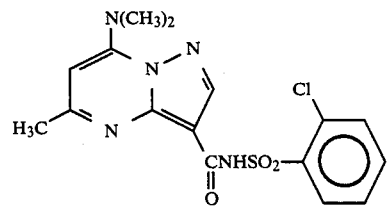
Compound 60
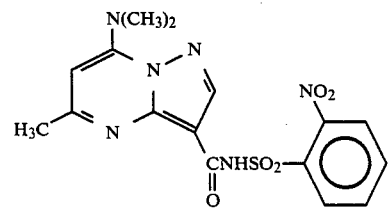
Compound 61
1H—Imidazole Salt
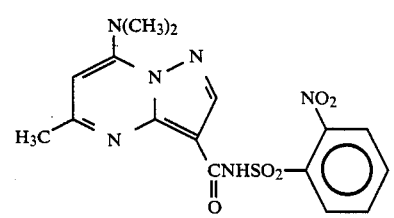
Compound 62
-continued
Compounds
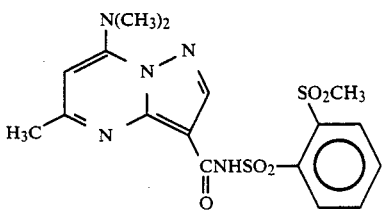
Compound 63
1H—Imidazole Salt
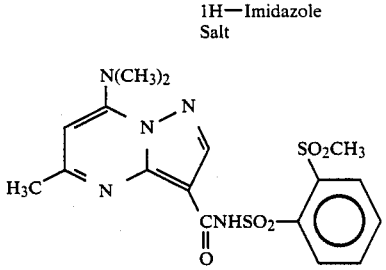
Compound 64
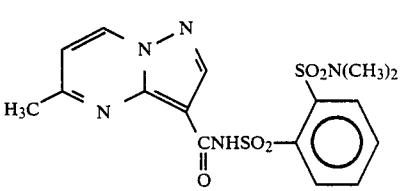
Compound 65
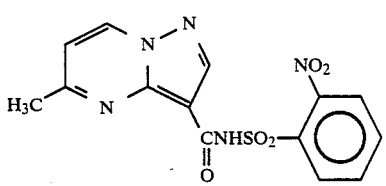
Compound 66
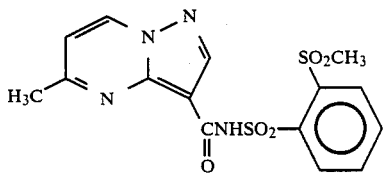
Compound 67
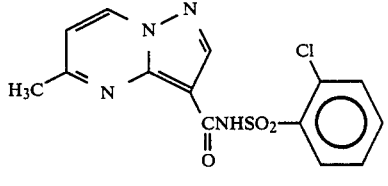
Compound 68
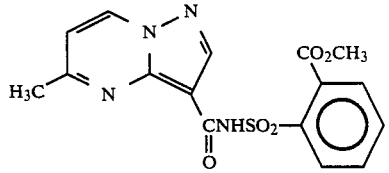
Compound 69
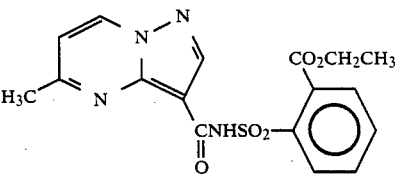
Compound 70

-continued
Compounds
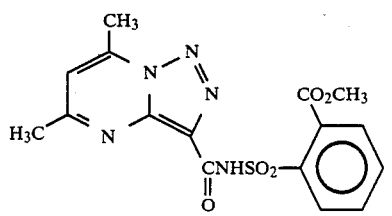
Compound 71
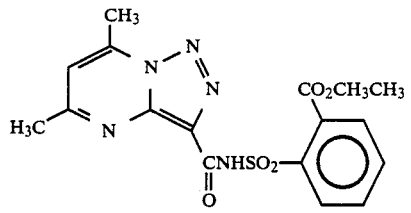
Compound 72
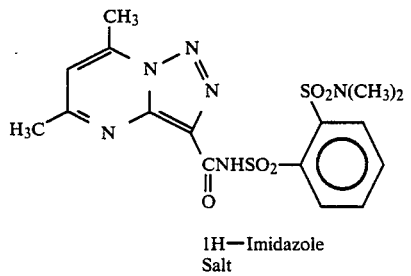
Compound 73
1H—Imidazole
Salt
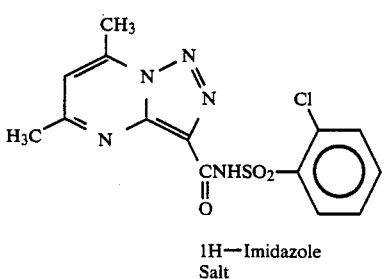
Compound 74
1H—Imidazole
Salt
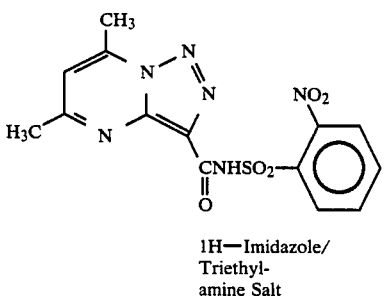
Compound 75
1H—Imidazole/
Triethyl-
amine Salt
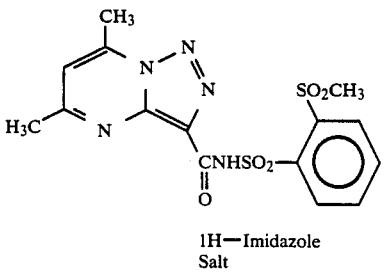
Compound 76
1H—Imidazole
Salt
-continued
Compounds
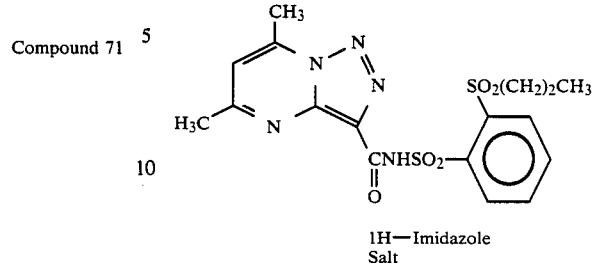
Compound 77
1H—Imidazole
Salt
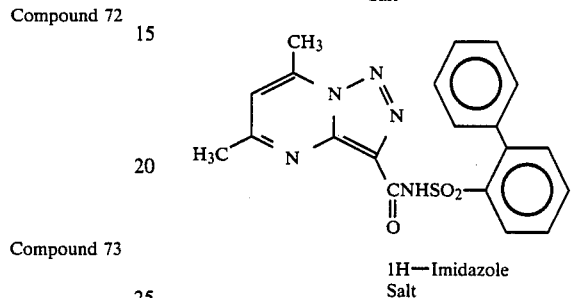
Compound 78
1H—Imidazole
Salt
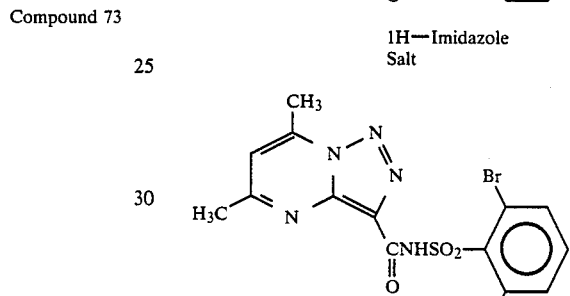
Compound 79
1H—Imidazole
Salt
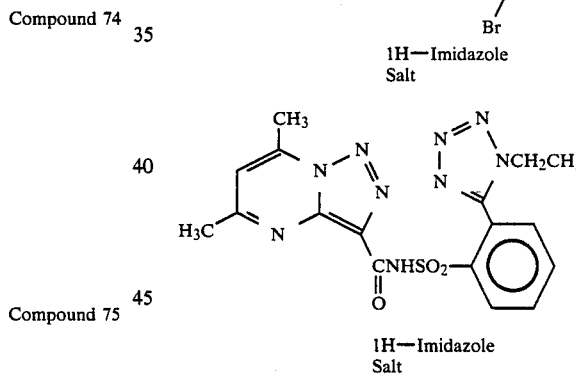
Compound 80
1H—Imidazole
Salt
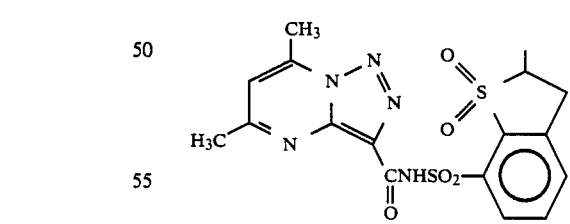
Compound 81
1H—Imidazole
Salt
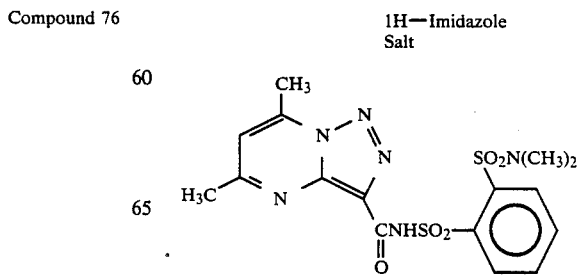
Compound 82

-continued
Compounds

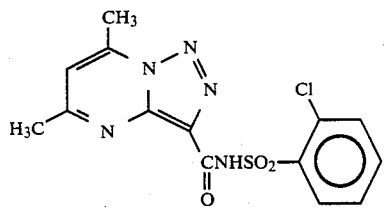
Compound 83

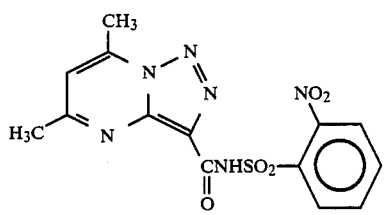
Compound 84

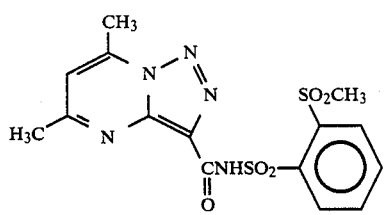
Compound 85

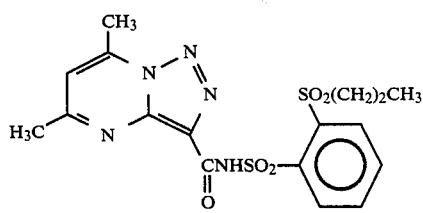
Compound 86

-continued
Compounds

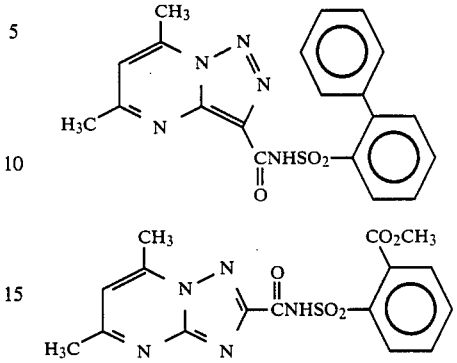
Compound 87

Compound 88

TEST A

Seeds of crabgrass (Digitaria spp.), barynard-grass (Echinochloa cruss-galli), giant foxtail (Setaria faberii), wild oats (Avena fatua), cheatgrass (Bromus secalinus), velvetleaf (Abutilon theophrasti), morningglory (Ipomoea spp.), cocklebur (Xanthium pensylvanicum), sorghum, corn, soybean, sugarbeet, cotton, rice, wheat, barley and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
Y=abscised buds or flowers.

TABLE A

| | CMPD 1 | | CMPD 2 | | CMPD 3 | | CMPD 4 | | CMPD 5 | | CMPD 6 | | CMPD 7 | | CMPD 8 | | CMPD 9 | | CMPD 10 | | CMPD 11 | | CMPD 12 | |
|---|---|---|---|---|---|---|---|---|---|---|---|---|---|---|---|---|---|---|---|---|---|---|---|---|
| RATE RATE = KG/HA | 0.4 | | 0.4 | | 0.4 | | 0.4 | | 0.4 | | 0.4 | | 0.05 | 0.4 | 0.05 | 0.4 | 0.05 | 0.4 | 0.05 | 0.4 | 0.05 | 0.4 | 0.05 | 0.4 | |
| POSTEMERGENCE |
| COTTON | 10C | | 6C,9G | | 10C | | 10C | | | | 9C | | 5S | 5C,9G | 10C | 10C | 4C,9G | 5C,9G | 5C,9G | 5C,9G | 5C,9G | 9C | 9H | 5C,9G | |
| MORNING GLORY | 2C,6G | | 10C | | 10C | | 10C | | 10C | | 10C | | 9C | 10C | 10C | 10C | 6G | 9C | 10C | 10C | 10C | 10C | 3C,8H | 5C,9G | |
| COCKLEBUR | 4C,9H | | 10C | | 9C | | 10C | | 9C | | 10C | | 10C | 10C | 10C | 10C | 4C,9H | 10C | 10C | 10C | 10C | 10C | 4C,9G | 10C | |
| NUTSEDGE | 5C,9G | | 5C,9G | | 2C,9G | | 9C | | 2C,9G | | 5C,9G | | 9C | 4C,9G | 4C,9G | 5C,9G | 3C,9G | 9G | 5C,9G | 5C,9G | 5C,9G | 5C,9G | 9G | 4C,9G | |
| CRABGRASS | 4C,9H | | 4C,9G | | 5G | | 9G | | 9C | | 2C,8G | | 3C,6G | 3C,7G | 4C,9G | 4C,9G | 2G | 8H | 6C,9G | 4G | 3C,8G | 10C | 9G | 3C,8G | |
| BARNYARD GRASS | 9C | | 9C | | 9C | | 9C | | 9C | | 10C | | 5C,9G | 10C | 10C | 10C | 7H | 10C | 2C,6G | 3C,6G | 10C | 10C | 1H | 9C | |
| WILD OATS | 5C,9G | | 5C,9G | | 0 | | 5C,9G | | 5C,9G | | 9C | | 9C | 2C,8G | 9C | 5C,9G | 2G | 5G | 10C | 9C | 3C,7H | 4C,9G | 3C,7H | 3C,6G | |
| WHEAT | 5C,9G | | 5C,9G | | 8G | | 9G | | 9G | | 9C | | 9C | 9C | 9C | 9C | 8G | 2C,9G | 9C | 3C,8H | 2C,4G | 10C | 1H | 9C | |
| CORN | 2C,9G | | 9C | | 5C,9G | | 5C,9G | | 3C,9G | | 9C | | 9C | 9C | 9C | 9C | 2C,6G | 3C,9H | 3C,8H | 3C,9H | 2C,9G | 9C | 2C,9G | 5C,9G | |
| SOYBEAN | 9G | | 9C | | 4C,9G | | 5C,9G | | 3C,9G | | 5C,9G | | 9C | 10C | 9C | 9C | 3C,7H | 3C,9G | 2C,8H | 3C,6G | 5C,9G | 9C | 3C,8H | 3C,9G | |
| RICE | 4C,9G | | 9C | | 5C,9G | | 6C,9G | | 3C,9G | | 9C | | 10C | 10C | 10C | 9C | 5C,9G | 4C,9G | 9C | 9C | 3C,8H | 9C | 9C | 9C | |
| SORGHUM | 6C,9G | | 9C | | 9G | | 9C | | 9C | | 9C | | 9C | 9C | 9C | 9C | 5C,9H | 9C | 3C,8H | 3C,7H | 9C | 9C | 5C,9G | 9C | |
| CHEATGRASS | 2C,9G | | 9C | | 6G | | 9C | | 9C | | 10C | | 9C | 10C | 10C | 9C | 9G | 4C,9G | 9C | 3G | 9C | 9C | 9C | 1H | |
| SUGAR BEETS | 9G | | 9C | | 10C | | 9C | | 5C,9G | | 10C | | 4C,9G | 10C | 10C | 10C | 0 | 2G | 10C | 5C,7G | 10C | 10C | 0 | 10C | |
| VELVETLEAF | 4C,8H | | 5C,9G | | 10C | | 9C | | 10C | | 10C | | 2H,7G | 9C | 10C | 10C | 5C,9H | 10C | 1C | 10C | 10C | 10C | 9C | 5C,9G | |
| GIANT FOXTAIL | 10C | | 10C | | 10C | | 10C | | 10C | | 5C,9G | | 9C | 5C,9G | 9C | 9C | 2C,6G | 3C,8G | 9C | 9C | 6C,9G | 9C | 3C,7G | 5C,9G | |
| BARLEY | 6G | | 4C,9G | | 2C,8G | | 2C,8H | | 6C,9G | | 6C,9G | | 10C | 9C | 9C | 9C | 7G | 4C,9G | 3C,9G | 3C,9G | 10C | 10C | 9H | 9C | |
| | 9G | | 9C | | 5G | | 9H | | | | | | | | | | | | | | | | | | |

| | CMPD 13 | | CMPD 14 | | CMPD 15 | | CMPD 16 | | CMPD 17 | | CMPD 18 | | CMPD 19 | | CMPD 20 | | CMPD 21 | | CMPD 22 | |
|---|---|---|---|---|---|---|---|---|---|---|---|---|---|---|---|---|---|---|---|---|---|
| RATE RATE = KG/HA | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | |
| PREEMERGENCE |
| COTTON | 8G | 9G | 0 | 0 | 8G | 2C,9H | 2C,9G | 2C,9G | 1C | 0 | 2G | 2C,9G | 0 | 0 | 0 | 5H | 4G | 1C | 2G | 2C,9G | |
| MORNING GLORY | 5G | 9H | 1C | 1C | 4G | 8H | 8H | 3C,8G | 0 | 0 | 2C,4G | 3C,8G | 2C,3G | 0 | 0 | 1C | 8G | 0 | 2C,7G | 3C,7H | |
| COCKLEBUR | 9H | 9H | 10E | 10E | 2C,4H | 9H | 10C | 10C | 1C | 0 | 3C,3H | 10C | 3C,4H | 1H | 2C | 3C,8H | 3C,3H | 1H | 3C,8H | 9C | |
| NUTSEDGE | 7G | 10E | 0 | 0 | 0 | 10E | 3C,8G | 10C | 0 | 0 | 7G | 10C | 3G | 10C | 0 | 0 | 3C,8G | 5G | 6G | 7G | |
| CRABGRASS | 7G | 9H | 2C,8G | 2C,8G | 2C,9H | 3C,9G | 2C,7G | 3C,8G | 2C | 0 | 5G | 2C,8G | 2G | 4G | 2G | 0 | 4C,9G | 0 | 5G | 9G | |
| BARNYARD GRASS | 9H | 9H | 3G | 3G | 3G | 9H | 3C,5G | 6G | 0 | 0 | 3G | 9H | 2C,7H | 3C,6G | 2G | 3C,7G | 2C,2H | 3C,5G | 2C,7G | 5G | |
| WILD OATS | 2C,8H | 3C,9H | 5G | 5G | 3G | 4C,8H | 2C,7G | 5C,9G | 0 | 0 | 2C,4G | 4C,8H | 8G | 3C,8H | 2G | 5C,9H | 2C,5H | 3C,5G | 9C | 3C,8H | |
| WHEAT | 4C,9G | 3C,9H | 7G | 2G | 4G | 2C,9H | 3C,8G | 4C,8G | 2C | 0 | 8H | 5C,9G | 3C,7H | 3C,8G | 4G | 6C,9G | 3C,9G | 2C,5G | 6C,9G | 9C | |
| CORN | 6C,9H | 2C,9H | 0 | 2G | 2C,9G | 3C,9G | 4C,9G | 3C,8G | 2C | 2C,9H | 3C,8H | 5C,9G | 4C,6G | 2C,9G | 2G | 6C,9G | 3C,8G | 3C,9G | 6C,9G | 9C | |
| SOYBEAN | 2C,8H | 2C,2H | 6H | 0 | 9C | 9G | 3C,8H | 9C | 0 | 3C,4H | 3C,6G | 9C | 3C,8H | 9H | 2G | 5C,9G | 3C,9G | 7H | 4C,9G | 3U,9C | |
| RICE | 4C,9H | 9H | 7H | 6H | 5C,9H | 10E | 5U,9C | 10E | 2G | 3C,9G | 9H | 9H | 9H | 10E | 2C,2H | 9H | 7H | 9H | 3C,9G | 5C,9G | |
| SORGHUM | 9H | 10H | 9H | 10E | 7G | 10E | 6C,9G | 3C,9G | 3G | 3C,9G | 9H | 9H | 8H | 3C,7G | 2C,5G | 9H | 9H | 10E | | | |
| CHEATGRASS | 9G | 9H | 6G | 5C,9H | 9G | 3C,9H | 9G | 8G | 1C | 0 | 8G | 3C,9G | 8G | 10H | 5G | 9H | 8G | 3C,9G | | | |
| SUGAR BEETS | 7G | 10H | 8H | 7G | 9G | 5H | 3G | 10C | 0 | 8G | 7G | 9G | 3G | 3G | 2G | 9G | 3G | 10E | | | |
| VELVETLEAF | 8H | 5C,9G | 2H | 9H | 7H | 9H | 6C,9G | 4C,8G | 2G | 0 | 5G | 8H | 1H | 9G | 1H | 8H | 1H | 3C,9G | | | |
| GIANT FOXTAIL | 6G | 3C,9G | 0 | 0 | 3C,8H | 5G | 5U,9C | 9C | 0 | 2G | 2C,9G | 6G | 4G | 4G | 5G | 4C,9H | 9G | 6C,9G | | | |
| BARLEY | 2C,9H | 4C,9H | 3G | 4C,9H | 5G | 9G | 4C,9G | 9G | 1C | 0 | 8G | 4C,9G | 9G | 3G | 7G | 3C,8H | 5G | 3C,9G | | | |

| | CMPD 13 | | CMPD 14 | | CMPD 15 | | CMPD 16 | | CMPD 17 | | CMPD 18 | | CMPD 19 | | CMPD 20 | | CMPD 21 | | CMPD 22 | |
|---|---|---|---|---|---|---|---|---|---|---|---|---|---|---|---|---|---|---|---|---|---|
| RATE RATE = KG/HA | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | |
| POSTEMERGENCE |
| COTTON | 8G | 10C | 4C,9G | 4C,9G | 5G | 2C,9H | 9G | 3C,9G | 2C,9G | 2C,9G | 2C,9G | 10C | 2C,9H | 10C | | 5H | | 1C | | 2C,9G | |
| MORNING GLORY | 9C | 10C | 4C,9G | 4C,9G | | | 1C | 4C,9G | | 5C,9G | 3C,8G | 3C,8G | 4C,8H | 5C,9G | | 1C | | 0 | | 3C,7H | |
| COCKLEBUR | 9C | 10C | 10C | 10C | 2C,5G | | 3C,8H | 9C | 10C | 10C | 10C | 10C | 9C | 9C | | 3C,7H | | 1H | | 9C | |
| NUTSEDGE | 9C | 9C | 2C,8G | 2C,8G | 0 | 2C,9G | 2C,7G | 6G | 3C,8G | 3C,8G | 10C | 10C | 7G | 3C,6G | | 0 | | 5G | | 6G | |
| CRABGRASS | 8G | 9C | 3G | 3G | 2C,5G | 2C,5G | 3C,5G | 3G | 7G | 6G | 7G | 6G | 5G | 7G | | 3C,7G | | 0 | | 2C,7G | |
| BARNYARD GRASS | 10C | 9C | 5G | 5G | 9C | | | 4C,9G | 5C,9G | 5C,9G | 4C,8H | 4C,9H | 5C,9G | 5C,9G | | 5C,9H | | 3C,5G | | 9C | |
| WILD OATS | 6C,9G | 10C | 2G | 2G | 4G | 4G | | 3C,8G | 9C | 4C,9G | 5C,9G | 4C,9G | 5C,9G | 5C,9G | | 6C,9G | | 2C,8G | | 6C,9G | |
| WHEAT | 6C,9G | 6C,9G | 7G | 7G | 8G | 4G | 3C,8G | 6C,9G | 9C | 9C | 8G | 9C | 6G | 6G | | 6C,9G | | 5C,9G | | 6C,9G | |
| CORN | 10C | 10C | 0 | 0 | 9C | 4U,9G | 5U,9C | 3C,9G | 3C,9G | 3C,9G | 2C,9G | 2C,9G | 2C,9G | 5U,9G | | 4C,9H | | 3C,7H | | 3U,9C | |
| SOYBEAN | 9C | 9C | 3G | 3G | 3C,9H | 3C,9H | 2C,8H | 4C,9G | 4C,9G | 4C,9G | 4C,9H | 9C | 5C,9G | 5C,9G | | 3C,8H | | 0 | | 5C,9G | |

TABLE A-continued

| | CMPD 23 | | CMPD 24 | | CMPD 25 | | CMPD 26 | | CMPD 27 | | CMPD 28 | | CMPD 29 | | CMPD 30 | | CMPD 31 | | CMPD 32 | | CMPD 33 | |
|---|---|---|---|---|---|---|---|---|---|---|---|---|---|---|---|---|---|---|---|---|---|---|
| RATE RATE = KG/HA | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 |
| RICE | 9C | 9C | 9C | 3C,9G | 9C | 5C,9G | 9C | 10C | 9C | 10C | 9C | 9C | 9C | 9C | 2C,8G | 5C,9H | 3C,7G | 2C,8G | 9C | 9C | 9C | 6C,9G |
| SORGHUM | 10C | 10C | 3C,4G | 3C,6G | 3C,8H | 3C,8H | 3C,8G | 9C | 10C | 5C,9G | 10C | 5C,9G | 5C,9G | 4C,9G | 3C,6G | 3C,9H | 3C,8G | 3C,6G | 6C,9G | 6C,9G | 6C,9G | 9C |
| CHEATGRASS | 10C | 3C,8H | 3C,9G | 4C,9G | 9C | 5C,9G | 9C | 9C | 9C | 5C,9G | 9C | 5C,9G | 9C | 4C,9G | 2C,8G | 6C,9G | 2C,7G | 6C,9G | 6C,9G | 6C,9G | 9C |
| SUGAR BEETS | 9C | 3C,8H | 10C | 3C,4H | 3C,7H | 3C,5H | 9C | 10C | 1H | 3C,5H | 9C | 4C,8G | 4C,8G | 9C | 3C,7G | 3C,5H | 1H | 2H | 1H | 3C,8G | 3C,7G | 9C |
| VELVETLEAF | 5C,9G | 5G | 10C | 3C,8G | 2G | 3G | 9C | 4C,9G | 0 | 2C,4H | 2C,8H | 9C | 4C,9G | 5C,9H | 0 | 2C,4H | 0 | 2C,5G | 0 | 2C,2H | 6H | 3C,8H |
| GIANT FOXTAIL | 5C,9H | 9C | 9C | 3C,8G | 9G | 4C,9G | 3C,7G | 3C,9G | 4C,9G | 4C,9G | 4C,9G | 4C,9G | 4C,9G | 5C,9H | 3C,7G | 4C,9G | 3C,8G | 3C,7G | 3C,9G | 3C,7G | 9C | 3C,9G |
| BARLEY | 6C,9G | 10C | 3C,4G | 3C,8G | 2C,9G | 2C,8G | 4C,9G | 2C,9G | 2C,9G | 3C,9G | 9C | 2C,9G | 2C,9G | 3C,9G | 3C,8G | 4C,9H | 2C,9G | 2C,5G | 9G | 3C,9G | 6H | 4C,9G |

PREEMERGENCE

| COTTON | 0 | 1H | 0 | 0 | 0 | 0 | 0 | 0 | 0 | 0 | 0 | 3C,7H | 0 | 0 | 0 | 0 | 0 | 0 | 0 | 0 | 0 | 0 |
| MORNING GLORY | 2G | 4G | 2C | 0 | 0 | 0 | 2G | 0 | 2G | 0 | 0 | 3G | 0 | 1C | 0 | 2C,3G | 0 | 0 | 2H | 0 | 0 | 0 |
| COCKLEBUR | | 3C,4H | 1C | 0 | 0 | 0 | 0 | 0 | 0 | 1C | 0 | 0 | 0 | 3C,3H | 0 | 0 | 0 | 0 | 0 | 0 | 0 | 0 |
| NUTSEDGE | | 4C,6G | 0 | 0 | 0 | 0 | 0 | 0 | 0 | 0 | 0 | 4G | 0 | 0 | 0 | 0 | 0 | 0 | 0 | 0 | 0 | 0 |
| CRABGRASS | | 9G | 0 | 2G | 0 | 0 | 5G | 0 | 0 | 0 | 0 | 8G | 0 | 0 | 0 | 0 | 0 | 0 | 0 | 0 | 0 | 0 |
| BARNYARD GRASS | 1H | 3C,5H | 0 | 2G | 0 | 0 | 2G | 0 | 0 | 0 | 0 | 1H | 0 | 0 | 0 | 0 | 0 | 0 | 0 | 0 | 0 | 0 |
| WILD OATS | 2C | 3C,7G | 4G | 0 | 0 | 0 | 4G | 0 | 0 | 0 | 0 | 4G | 0 | 7G | 0 | 0 | 0 | 0 | 0 | 0 | 0 | 0 |
| WHEAT | 0 | 3C,9H | 0 | 0 | 0 | 0 | 7G | 0 | 0 | 0 | 0 | 0 | 0 | 0 | 0 | 0 | 0 | 0 | 0 | 0 | 0 | 0 |
| CORN | 2G | 3C,9H | 0 | 3C,6G | 2C,8G | 0 | 2C,8G | 0 | 4C,9H | 2C | 2C,4G | 4C,9H | 0 | 0 | 0 | 0 | 0 | 0 | 0 | 0 | 0 | 0 |
| SOYBEAN | 3C,3G | 3C,8G | 2G | 0 | 0 | 0 | 2G | 0 | 0 | 0 | 0 | 3C,3H | 0 | 2H | 0 | 0 | 0 | 0 | 0 | 0 | 0 | 0 |
| RICE | 8G | 5C,9G | 2C | 3G | 8G | 5G | 9H | 0 | 2G | 0 | 2G | 9H | 0 | 0 | 0 | 0 | 0 | 0 | 0 | 0 | 0 | 0 |
| SORGHUM | 3C,7G | 9H | 2C | 1C | 3C,7G | 0 | 3C,7G | 0 | 1C | 0 | 3C,7H | 3C,9H | 0 | 0 | 0 | 0 | 0 | 0 | 0 | 0 | 0 | 0 |
| CHEATGRASS | 8G | 9G | 5G | 2G | 7G | 0 | 3G | 0 | 0 | 1H | 2G | 5G | 0 | 0 | 0 | 0 | 0 | 0 | 0 | 0 | 0 | 0 |
| SUGAR BEETS | 0 | 8G | 2H | 0 | 6G | 1H | 8G | 0 | 0 | 0 | 0 | 3G | 0 | 0 | 0 | 2H | 0 | 0 | 0 | 0 | 0 | 0 |
| VELVETLEAF | 2G | 3H | 0 | 0 | 0 | 0 | 0 | 0 | 0 | 0 | 0 | 2C,2G | 0 | 0 | 0 | 0 | 0 | 0 | 0 | 0 | 0 | 0 |
| GIANT FOXTAIL | 0 | | 0 | 0 | 7G | 3G | 8G | 0 | 0 | 0 | 0 | 4G | 0 | 0 | 0 | 0 | 0 | 0 | 0 | 0 | 0 | 0 |
| BARLEY | 1C | 7G | 3G | 0 | 3C,7G | 0 | 1C | 0 | 2C | 0 | 0 | 3C,6G | 0 | 0 | 0 | 0 | 0 | 0 | 0 | 0 | 0 | 0 |

POSTEMERGENCE

| COTTON | 3C,8H | 2C,9H | 9C | 10C | 1C | 0 | 0 | 0 | 3G | 0 | 4H | 0 | 1H | 0 | 0 | 0 | 2G | 0 | 0 | 0 | 0 | 0 |
| MORNING GLORY | 3C,7G | 3C,6H | 3C,8G | 5C,9G | 1H | 0 | 0 | 0 | 3G | 0 | 3G | 0 | 0 | 0 | 0 | 0 | 0 | 0 | 2G | 0 | 0 | 0 |
| COCKLEBUR | 3C,8H | 3C,8H | 10C | 10C | 2H | 0 | 0 | 0 | 1H | 0 | 0 | 0 | 2H | 0 | 3G | 2G | 0 | 0 | 0 | 0 | 0 | 0 |
| NUTSEDGE | 7G | 5G | 10C | 9C | 2C,3G | 0 | 0 | 0 | 0 | 0 | 0 | 0 | 0 | 0 | 0 | 0 | 0 | 0 | 0 | 0 | 0 | 0 |
| CRABGRASS | 3G | 5G | 5G | 8G | 0 | 0 | 0 | 0 | 4G | 0 | 0 | 0 | 0 | 0 | 3G | 3G | 3G | 0 | 0 | 0 | 0 | 0 |
| BARNYARD GRASS | 5C,9H | 4C,8G | 2C,8G | 9C | 0 | 0 | 3H | 1H | 4C,9G | 0 | 4G | 0 | 2G | 0 | 2C,5G | 0 | 7H | 0 | 0 | 0 | 0 | 0 |
| WILD OATS | 4C,8G | 3C,8G | 9G | 9G | 0 | 0 | 0 | 0 | 3G | 0 | 0 | 0 | 0 | 0 | 8G | 0 | 3C,5G | 0 | 0 | 0 | 0 | 0 |
| WHEAT | 4C,9G | 9G | 5U,9G | 4U,9C | 0 | 0 | 4G | 0 | 2G | 0 | 0 | 0 | 0 | 0 | 3C,7G | 8G | 3C,8G | 0 | 0 | 0 | 0 | 0 |
| CORN | 3C,9G | 3C,9G | 9C | 9C | 0 | 0 | 2C,8H | 0 | 2C,9G | 0 | 3C,7G | 3C,7G | 1H | 2G | 3C,8H | 3C,7G | 2C,5G | 0 | 0 | 0 | 0 | 0 |
| SOYBEAN | 3C,8G | 3C,9G | 9C | 9C | 2H | 0 | 4H | 0 | 2C,7H | 0 | 3H | 3H | 0 | 1H | 3C,7G | 8G | 0 | 0 | 0 | 0 | 0 | 0 |
| RICE | 9C | 6C,9G | 9C | 9C | 2G | 0 | 3C,9G | 0 | 4C,9G | 0 | 3G | 3G | 0 | 1H | 3C,7G | 3C,7G | 8G | 0 | 0 | 0 | 0 | 0 |
| SORGHUM | 5C,9G | 5C,9G | 9G | 5C,9G | 1C | 0 | 2C | 0 | 4C,8G | 2G | 2C,5G | 3G | 0 | 1H | 2C | 2C | 2C,2G | 0 | 0 | 0 | 0 | 0 |
| CHEATGRASS | 4C,9G | 4C,9G | 8G | 9C | 3C,8G | 0 | 3C,8G | 2G | 2C,9G | 2H | 5G | 2C,5G | 0 | 0 | 3C,8G | 7G | 3G | 0 | 0 | 0 | 0 | 0 |
| SUGAR BEETS | 4C,8G | 3C,7H | 9C | 10C | 2H | 0 | 3H | 2H | 4G | 0 | 1H | 5G | 0 | 0 | 3H | 2C,5H | 3C,6G | 0 | 0 | 0 | 0 | 0 |
| VELVETLEAF | 7U | 4C,8H | 10C | 10C | 0 | 0 | 3G | 0 | 0 | 0 | 0 | 1H | 0 | 0 | 0 | 0 | 2G | 0 | 0 | 0 | 0 | 0 |
| GIANT FOXTAIL | 4C,9G | 4C,9H | 10C | 4C,9G | 3C,8G | 3C,8G | 3C,7G | 0 | 5C,9G | 2G | 3C,8G | 3H | 3H | 3C,7H | 3C,8G | 3C,8G | 0 | 0 | 0 | 0 | 0 |
| BARLEY | 2C,8G | 3C,9G | 3C,8G | 3C,9G | 0 | 0 | 2G | 0 | 3C,8G | 0 | 0 | 0 | 0 | 2G | 2G | 4G | 0 | 0 | 0 | 0 | 0 |

PREEMERGENCE

| COTTON | 0 | 0 | 0 | 9G | 0 | 0 | 0 | 0 | 0 | 0 | 0 | 2G | 0 | 5G | 6G | 2G | 0 | 2G | 0 | 0 | 0 | 0 |
| MORNING GLORY | 0 | 0 | 2G | 9G | 0 | 0 | 0 | 0 | 0 | 0 | 0 | 0 | 2G | 0 | 2G | 0 | 2G | 0 | 0 | 0 | 0 |
| COCKLEBUR | 0 | 0 | 6H | 9H | 0 | 0 | 0 | 0 | 0 | 0 | 0 | 2G | 0 | 2G | 2G | 0 | 2H | 0 | 0 | 0 | 0 | 0 |
| NUTSEDGE | 0 | 0 | 4C,9G | 10E | 0 | 0 | 0 | 0 | 0 | 0 | 0 | 2G | 0 | 3H | 0 | 0 | 0 | 0 | 0 | 0 | 0 | 0 |
| CRABGRASS | 0 | 0 | 4G | 8G | 0 | 0 | 0 | 0 | 0 | 0 | 0 | 0 | 0 | 0 | 3G | 3G | 0 | 0 | 0 | 0 | 0 | 0 |

TABLE A-continued

| | CMPD 34 | | CMPD 35 | | CMPD 36 | | CMPD 37 | | CMPD 38 | | CMPD 39 | |
|---|---|---|---|---|---|---|---|---|---|---|---|---|
| RATE RATE = KG/HA | 0.05 | 0.4 | 0.05 | 0.4 | 0.05 | 0.4 | 0.05 | 0.4 | 0.05 | 0.4 | 0.05 | 0.4 |
| BARNYARD GRASS | 0 | 0 | 0 | 0 | 0 | 0 | 0 | 0 | 0 | 0 | 0 | 0 |
| WILD OATS | 0 | 0 | 0 | 0 | 0 | 0 | 0 | 0 | 0 | 0 | 0 | 0 |
| WHEAT | 0 | 0 | 0 | 9H | 0 | 0 | 0 | 0 | 0 | 0 | 0 | 0 |
| CORN | 0 | 0 | 0 | 4C,8G | 0 | 0 | 0 | 0 | 0 | 2G | 0 | 0 |
| SOYBEAN | 0 | 0 | 0 | 9H | 0 | 0 | 0 | 0 | 0 | 2G | 0 | 0 |
| RICE | 0 | 0 | 0 | 5C,9G | 0 | 0 | 0 | 0 | 0 | 0 | 3H | 2C,6G |
| SORGHUM | 0 | 0 | 0 | 9H | 0 | 0 | 0 | 0 | 0 | 0 | 0 | 6G |
| CHEATGRASS | 0 | 0 | 0 | 10E | 0 | 0 | 0 | 0 | 0 | 0 | 0 | 4G |
| SUGAR BEETS | 0 | 0 | 0 | 10E | 0 | 0 | 0 | 0 | 0 | 2G | 0 | 0 |
| VELVETLEAF | 0 | 0 | 0 | 9H | 0 | 0 | 0 | 0 | 3G | 3G | 0 | 5G |
| GIANT FOXTAIL | 0 | 0 | 0 | 4C,8G | 0 | 0 | 0 | 0 | 0 | 2G | 0 | 2G |
| BARLEY | 0 | 0 | 0 | 9H | 0 | 0 | 0 | 0 | 0 | 0 | 0 | 0 |

POSTEMERGENCE

| | CMPD 34 | | CMPD 35 | | CMPD 36 | | CMPD 37 | | CMPD 38 | | CMPD 39 | |
|---|---|---|---|---|---|---|---|---|---|---|---|---|
| | 0.05 | 0.4 | 0.05 | 0.4 | 0.05 | 0.4 | 0.05 | 0.4 | 0.05 | 0.4 | 0.05 | 0.4 |
| COTTON | 0 | 3C,8H | 8G | 10C | 6G | 2C,9G | 7G | 8G | 9H | 10C | 9C |
| MORNING GLORY | 0 | 0 | 4C,8G | 10C | 3C,3H | 3C,8G | 1H | 3C,8G | 2C,6G | 3C,7H | 9C | 10C |
| COCKLEBUR | 0 | 1C | 10C | 10C | 4C,9H | 5C,9G | 3H | 7H | 2C,6G | 7H | 10C | 10C |
| NUTSEDGE | 0 | 0 | 5C,9G | 4C,9G | 3C,8G | 2C,8G | 0 | 7G | 0 | 2C,4G | 9G | 2C,9G |
| CRABGRASS | 2G | 6G | 7G | 3C,8G | 2G | 5G | 0 | 3G | 0 | 0 | 6G | 3C,9G |
| BARNYARD GRASS | 3C,8H | 4C,9H | 9C | 9C | 3C,7H | 3C,7H | 0 | 2G | 4C,8H | 10C | 10C |
| WILD OATS | 2C,7G | 5G | 4C,9G | 9C | 3G | 4G | 0 | 3G | 9G | 4C,9G |
| WHEAT | 3C,9G | 8G | 9G | 9G | 7G | 5G | 0 | 3G | 9G | 4C,9G |
| CORN | 3C,9G | 2C,7H | 50,9C | 10C | 3C,9H | 3C,9H | 0 | 2G | 6G | 9G |
| SOYBEAN | 2C,7H | 4H | 9C | 9C | 5C,9G | 4C,9G | 3C,6G | 2C,8G | 2C,5G | 6G | 4C,9G |
| RICE | 9C | 9C | 9C | 9C | 3G | 4C,9G | 2C,4G | 5G | 5G | 4C,9G |
| SORGHUM | 3C,7G | 2C,3G | 5C,9G | 9C | 3C,8H | 3C,7G | 2G | 6G | 2G | 4C,9G |
| CHEATGRASS | 3C,8G | 3C,7G | 9C | 9C | 8G | 3C,8G | 2G | 5G | 2C,8G | 5G | 3C,8G |
| SUGAR BEETS | 5G | 3C,6H | 9C | 10C | 3C,6H | 4C,8H | 0 | 3G | 2G | 6G |
| VELVETLEAF | 0 | 1H | 6C,9G | 10C | 8G | 6C,9G | 0 | 3G | 0 | 3G | 9C |
| GIANT FOXTAIL | 3C,8G | 3C,8G | 4C,8G | 4C,9G | 3C,7G | 4C,8G | 1H | 3G | 6G | 9C |
| BARLEY | 2C,8G | 3C,7G | 3C,9G | 5C,9G | 5G | 2C,5G | 0 | 6G | 6G | 9C |

PREEMERGENCE

| | CMPD 34 | | CMPD 35 | | CMPD 36 | | CMPD 37 | | CMPD 38 | | CMPD 39 | |
|---|---|---|---|---|---|---|---|---|---|---|---|---|
| | 0.05 | 0.4 | 0.05 | 0.4 | 0.05 | 0.4 | 0.05 | 0.4 | 0.05 | 0.4 | 0.05 | 0.4 |
| COTTON | 0 | 0 | 3G | 7G | 0 | 0 | 0 | 0 | 0 | 0 | 7G | 9G |
| MORNING GLORY | 0 | 0 | 0 | 5G | 0 | 3C,3H | 0 | 0 | 0 | 0 | 3C,7H | 8G |
| COCKLEBUR | 0 | 0 | 0 | 0 | 2H | 0 | 0 | 2G | 0 | 2G | 0 | 8H |
| NUTSEDGE | 0 | 0 | 0 | 9G | 0 | 0 | 0 | 0 | 0 | 2G | 9C | 10E |
| CRABGRASS | 0 | 0 | 0 | 3C,6G | 0 | 0 | 0 | 0 | 0 | 0 | 3C,3G | 9H |
| BARNYARD GRASS | 0 | 0 | 0 | 7H | 0 | 2C,7G | 0 | 0 | 0 | 7G | 0 | 3C,7H |
| WILD OATS | 0 | 0 | 0 | 4G | 0 | 0 | 0 | 5G | 0 | 3G | 2C,6G | 3C,8G |
| WHEAT | 0 | 0 | 0 | 7G | 0 | 0 | 0 | 2G | 0 | 0 | 2C,8G | 2C,8H |
| CORN | 0 | 0 | 0 | 9H | 0 | 3C,7G | 0 | 3C,7G | 0 | 2C,5G | 3C,5G | 8G |
| SOYBEAN | 0 | 0 | 0 | 9H | 0 | 2C,2H | 0 | 2C,2H | 0 | 1C | 2C,5H | 9H |
| RICE | 0 | 0 | 8G | 4C,9H | 0 | 2G | 0 | 2C,7G | 2H | 3G | 9H | 10H |
| SORGHUM | 0 | 0 | 9G | 3C,9H | 0 | 3C,7G | 0 | 2C,7G | 2C,2G | 2G | 3C,7G | 9H |
| CHEATGRASS | 0 | 0 | 9G | 9G | 0 | 8G | 0 | 8G | 3C,3G | 2G | 0 | 7G |
| SUGAR BEETS | 0 | 0 | 3H | 9C | 0 | 0 | 0 | 6H | 7G | 8G | 6G | 7G |
| VELVETLEAF | 0 | 0 | 0 | 6H | 0 | 0 | 0 | 0 | 0 | 8G | 3C,6H | 5C,9G |
| GIANT FOXTAIL | 0 | 0 | 0 | 3G | 0 | 2G | 0 | 2G | 1H | 0 | 3C,7G | 9H |
| BARLEY | 0 | 0 | 0 | 7G | 0 | 0 | 0 | 2C,3G | 0 | 0 | 5G | 8G |

| | CMPD 40 | | CMPD 41 | | CMPD 42 | | CMPD 43 | |
|---|---|---|---|---|---|---|---|---|
| | 0.05 | 0.4 | 0.05 | 0.4 | 0.05 | 0.4 | 0.05 | 0.4 |
| BARNYARD GRASS | 0 | 0 | 0 | 0 | 0 | 0 | 0 | 0 |
| WILD OATS | 0 | 0 | 0 | 0 | 0 | 0 | 0 | 0 |
| WHEAT | 0 | 0 | 0 | 0 | 0 | 0 | 0 | 0 |
| CORN | 0 | 0 | 0 | 0 | 0 | 0 | 0 | 0 |
| SOYBEAN | 0 | 0 | 0 | 0 | 0 | 0 | 0 | 0 |
| RICE | 0 | 0 | 0 | 0 | 0 | 0 | 0 | 0 |
| SORGHUM | 0 | 0 | 2C,6G | 0 | 0 | 0 | 0 | 0 |
| CHEATGRASS | 0 | 0 | 6G | 0 | 0 | 0 | 2G | 2G |
| SUGAR BEETS | 0 | 0 | 4G | 0 | 0 | 0 | 0 | 3G |
| VELVETLEAF | 3G | 3G | 5G | 0 | 0 | 0 | 2G | 2G |
| GIANT FOXTAIL | 0 | 0 | 2G | 0 | 0 | 0 | 2G | 0 |
| BARLEY | 0 | 0 | 0 | 0 | 0 | 0 | 0 | 0 |

POSTEMERGENCE

| | CMPD 40 | | CMPD 41 | | CMPD 42 | | CMPD 43 | |
|---|---|---|---|---|---|---|---|---|
| | 0.05 | 0.4 | 0.05 | 0.4 | 0.05 | 0.4 | 0.05 | 0.4 |
| COTTON | 4C,8H | 9H | 9H | 9H | 10C | 9C | 10C | 9C |
| MORNING GLORY | 3C,7H | 5C,9H | 4C,8H | 4C,9H | 3H,6G | 5C,9G | 3C,7G | 4C,8G |
| COCKLEBUR | 3C,7H | 9C | 4C,8H | 5C,9H | 4C,9H | 4C,9H | 5C,9H | 10C |
| NUTSEDGE | 3G | 9G | 2G | 9G | 3C,9G | 4C,9G | 4C,9G | 9G |
| CRABGRASS | 0 | 2G | 4C,7H | 2G | 4G | 5G | 3C,5G | 7G |
| BARNYARD GRASS | 3C,5H | 9H | 4C,7H | 3C,7H | 2C,9H | 4C,9H | 3C,9H | 3C,9H |
| WILD OATS | 9G | 2C,9G | 7G | 7G | 2C,5G | 3C,8G | 3C,5G | 4C,9G |
| WHEAT | 7G | 9G | 9G | 9G | 4G | 5G | 4G | 8G |
| CORN | 2G | 2G | 0 | 0 | 3C,9H | 2C,9G | 3C,9H | 2C,9G |
| SOYBEAN | 3C,7H | 5C,9G | 4C,8G | 4C,9G | 5C,9G | 6C,9G | 4C,9G | 4C,9H |
| RICE | 4C,9G | 5C,9G | 5C,9G | 4C,9G | 5C,9G | 3C,9H | 6C,9G | 5C,9G |
| SORGHUM | 4C,9G | 3C,9G | 4C,8G | 3C,9G | 4C,9G | 3C,9H | 4C,9G | 4C,9G |
| CHEATGRASS | 3C,9G | 2C,9G | 3C,6G | 9C | 2C,8G | 9C | 2G | 3C,9G |
| SUGAR BEETS | 5C,8G | 9C | 4C,9G | 4C,8H | 9C | 3C,8H | 9C | 9C |
| VELVETLEAF | 3C,7H | 4C,8H | 3C,6G | 3C,9G | 4C,8H | 4C,9G | 4C,8G | 3C,9H |
| GIANT FOXTAIL | 3C,8G | 5C,9G | 4C,9G | 4C,9G | 3C,9G | 3C,9H | 4C,8G | 8G |
| BARLEY | 5G | 5G | 0 | 2G | 3G | 6G | 2G | 8G |

PREEMERGENCE

| | CMPD 44 | | CMPD 45 | | CMPD 46 | | CMPD 47 | | CMPD 48 | | CMPD 49 | | CMPD 50 | | CMPD 51 | | CMPD 52 | | CMPD 53 | | CMPD 54 |
|---|---|---|---|---|---|---|---|---|---|---|---|---|---|---|---|---|---|---|---|

(Table continuation - additional compound data for CMPD 44-54)

COTTON, MORNING GLORY, COCKLEBUR, NUTSEDGE, CRABGRASS, BARNYARD GRASS, WILD OATS, WHEAT, CORN, SOYBEAN, RICE, SORGHUM, CHEATGRASS, SUGAR BEETS, VELVETLEAF, GIANT FOXTAIL, BARLEY

TABLE A-continued

POSTEMERGENCE

| RATE RATE = KG/HA | CMPD 55 | | CMPD 56 | | | CMPD 57 | | | CMPD 58 | | | CMPD 59 | | | CMPD 60 | | | CMPD 61 | | | CMPD 62 | | | CMPD 63 | | | CMPD 64 | |
|---|---|---|---|---|---|---|---|---|---|---|---|---|---|---|---|---|---|---|---|---|---|---|---|---|---|---|---|
| | 0.05 | 0.4 | 0.05 | 0.4 | | 0.05 | 0.4 | | 0.05 | 0.4 | | 0.05 | 0.4 | | 0.05 | 0.4 | | 0.05 | 0.4 | | 0.05 | 0.4 | | 0.05 | 0.4 | | 0.05 | 0.4 |
| COTTON | 9C | 10C | 9H | 10C | | 0 | 0 | | 0 | 0 | | 0 | 2C,9G | | 5C,9G | 5C,9G | | 0 | 0 | | 0 | 2C,4G | | 0 | 2C,2G | | 2G | 1C |
| MORNING GLORY | 5C,9G | 4C,9G | 4C,9G | 10C | | 1H | 0 | | 0 | 0 | | 0 | 4G | | 2H,5G | 9C | | 2H | 1C | | 0 | 2G | | 2C,3G | 3C,8G | | 3C,6G | 3C,7H |
| COCKLEBUR | 10C | 10C | 10C | 10C | | 1H | 0 | | 0 | 0 | | 0 | 10C | | 10C | 10C | | 5G | 0 | | 2H | 2C,5G | | 2G | 2C,5G | | 1H | 2C,5G |
| NUTSEDGE | 9G | 9G | 9G | 4C,9G | | 0 | 0 | | 0 | 0 | | 0 | 0 | | 9G | 9G | | 9G | 0 | | 8G | 0 | | 0 | 0 | | 0 | 0 |
| CRABGRASS | 2C,8G | 4C,9H | 6G | 6C,9G | | 0 | 0 | | 0 | 0 | | 0 | 3C,7G | | 2G | 2C,5G | | 2H | 1C | | 3C,7G | 1H | | 1H | 3G | | 0 | 2C,2G |
| BARNYARD GRASS | 4C,8H | 5C,9H | 4C,8H | 9C | | 0 | 0 | | 0 | 0 | | 0 | 0 | | 3C,9H | 4C,9H | | 0 | 0 | | 0 | 1H | | 0 | 2C,4H | | 0 | 3C,3H |
| WILD OATS | 8G | 3C,9G | 2C,9G | 6C,9G | | 0 | 0 | | 0 | 0 | | 3G | 2H | | 2C,9G | 5C,9G | | 8G | 2C,2G | | 0 | 0 | | 0 | 1C | | 0 | 2C |
| WHEAT | 5G | 8G | 9G | 2C,9G | | 0 | 0 | | 0 | 0 | | 0 | 3G | | 9G | 9G | | 0 | 7G | | 0 | 8G | | 3G | 8G | | 0 | 4G |
| CORN | 3C,8H | 9G | 3G | 3C,8G | | 0 | 0 | | 0 | 0 | | 0 | 0 | | 10C | 3U,9G | | 1H | 2G | | 0 | 2G | | 0 | 0 | | 0 | 3C,4G |
| SOYBEAN | 5C,9G | 9C | 5C,9G | 9C | | 0 | 0 | | 0 | 0 | | 0 | 2G | | 9C | 6C,9G | | 4G | 2C,2H | | 1H | 2C,2H | | 2C,2G | 3C,3G | | 0 | 2C,2G |
| RICE | 5C,9G | 6C,9G | 3C,9G | 9C | | 0 | 0 | | 1H | 0 | | 0 | 2C | | 9C | 9C | | 0 | 8G | | 4G | 5G | | 2G | 3C,4G | | 0 | 3C,7G |
| SORGHUM | 4C,9G | 5C,9G | 3C,9G | 6C,9G | | 0 | 0 | | 0 | 0 | | 0 | 0 | | 9C | 5C,9G | | 0 | 5G | | 0 | 0 | | 0 | 3C,6G | | 0 | 1C |
| CHEATGRASS | 3C,5G | 9C | 1C | 9C | | 0 | 0 | | 0 | 0 | | 0 | 2G | | 9C | 9C | | 2G | 3C,4G | | 2G | 3C,4G | | 3C,7G | 3C,8H | | 3C,7G | 3C,7H |
| SUGAR BEETS | 9G | 10C | 3C,8H | 10C | | 0 | 0 | | 1H | 0 | | 2H | 2H | | 2C,7G | 9C | | 0 | 4H | | 0 | 0 | | 2G | 2C,6G | | 4G | 3C,7G |
| VELVETLEAF | 3C,8G | 5C,9H | 4C,9H | 10C | | 0 | 0 | | 0 | 0 | | 3G | 3G | | 9C | 5C,9G | | 3C,4G | 2C,5G | | 0 | 3G | | 0 | 3C,5G | | 0 | 2C,2G |
| GIANT FOXTAIL | 2C,9G | 2C,9G | 9G | 6C,9G | | 0 | 0 | | 0 | 0 | | 0 | 0 | | 9C | 9C | | 2H | 2G | | 0 | 2G | | 0 | 0 | | 0 | 3C,6G |
| BARLEY | | | | | | | | | | | | | | | | | | 0 | 2G | | | | | | | | | 2G |

PREEMERGENCE

| RATE RATE = KG/HA | CMPD 55 | | CMPD 56 | | CMPD 57 | | CMPD 58 | | CMPD 59 | | CMPD 60 | | CMPD 61 | | CMPD 62 | | CMPD 63 | | CMPD 64 | |
|---|---|---|---|---|---|---|---|---|---|---|---|---|---|---|---|---|---|---|---|---|
| | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 |
| COTTON | 8G | 9G | 5G | 9G | 0 | 5G | 0 | 0 | 0 | 0 | 0 | 2C,8G | 0 | 0 | 0 | 0 | 0 | 1C | 0 | 3C,3H |
| MORNING GLORY | 2G | 6H | 2G,3H | 9H | 2G | 0 | 0 | 0 | 0 | 0 | 0 | 0 | 0 | 2G | 0 | 0 | 0 | 2C | 0 | 3C,2H |
| COCKLEBUR | 3C,3H | 9H | 2H | 9H | 0 | 2C,2H | 0 | 0 | 0 | 0 | 0 | 3C,6H | 0 | 0 | 0 | 0 | 0 | 0 | 0 | 0 |
| NUTSEDGE | 8G | 10E | 9H | 10E | 2G | 0 | 0 | 0 | 0 | 0 | 0 | 8G | 0 | 2G | 0 | 2H | 0 | 0 | 0 | 0 |
| CRABGRASS | 5G | 10E | 7G | 3C,9G | 0 | 0 | 0 | 0 | 0 | 0 | 0 | 2G | 0 | 2G | 0 | 2H | 0 | 0 | 0 | 1C |
| BARNYARD GRASS | 5G | 4C,9H | 2G | 3C,7H | 0 | 2G | 0 | 0 | 0 | 0 | 0 | 0 | 0 | 2G | 0 | 3G | 0 | 0 | 0 | 0 |
| WILD OATS | 2C,5G | 2C,8G | 2C,5G | 3C,7H | 0 | 1S | 0 | 0 | 0 | 0 | 0 | 0 | 0 | 0 | 0 | 0 | 0 | 0 | 0 | 0 |
| WHEAT | 0 | 5G | 5G | 4C,9H | 0 | 0 | 0 | 0 | 0 | 0 | 0 | 0 | 0 | 0 | 0 | 0 | 0 | 0 | 0 | 2C |
| CORN | 3C,6G | 3C,9G | 1C | 4C,9G | 0 | 2C,2G | 0 | 0 | 0 | 0 | 0 | 2C,2G | 0 | 2G | 0 | 0 | 0 | 3C,3G | 0 | 2C |
| SOYBEAN | 3G | 3C,8H | 2C,4G | 9H | 0 | 2C,5G | 2G | 0 | 0 | 0 | 0 | 3C,7G | 0 | 0 | 0 | 0 | 0 | 0 | 0 | 2G |
| RICE | 8H | 10H | 3C,9H | 10H | 0 | 2C,8H | 0 | 0 | 0 | 0 | 0 | 2C,8H | 0 | 0 | 0 | 0 | 0 | 3C,7G | 0 | 3C,4G |
| SORGHUM | 3C,7G | 9H | 3C,7H | 10H | 0 | 3C,8H | 0 | 0 | 0 | 2C | 0 | 3C,8H | 0 | 0 | 0 | 0 | 0 | 0 | 0 | 0 |
| CHEATGRASS | 7G | 3C,8G | 2G | 6G | 0 | 7G | 0 | 0 | 0 | 0 | 0 | 7G | 0 | 0 | 0 | 0 | 0 | 1H | 0 | 3H |
| SUGAR BEETS | 7G | 8G | 4H | 9G | 0 | 3H | 0 | 2G | 0 | 0 | 0 | 4H | 3C,4G | 0 | 0 | 3G | 0 | 0 | 0 | 1C |
| VELVETLEAF | 0 | 4C,8G | 2C,3G | 4C,7H | 0 | 3G | 0 | 0 | 0 | 0 | 0 | 2C,5G | 2H | 0 | 0 | 0 | 0 | 0 | 0 | 0 |
| GIANT FOXTAIL | 2G | 4C,9H | 5G | 4C,8H | 0 | 0 | 0 | 0 | 0 | 0 | 0 | 2G | 0 | 0 | 0 | 0 | 0 | 0 | 0 | 7G |
| BARLEY | 4G | 8G | 8G | 4C,9G | 0 | 0 | 0 | 2G | 0 | 0 | 0 | 0 | 0 | 0 | 0 | 0 | 0 | 0 | 0 | 3C,6G |

POSTEMERGENCE

| | CMPD 55 | | CMPD 56 | | CMPD 57 | | CMPD 58 | | CMPD 59 | | CMPD 60 | | CMPD 61 | | CMPD 62 | | CMPD 63 | | CMPD 64 | |
|---|---|---|---|---|---|---|---|---|---|---|---|---|---|---|---|---|---|---|---|---|
| RATE RATE = KG/HA | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 |
| COTTON | 5C,9G | 9C | 9C | 9C | 4C,9H | 9C | 7G | 0 | 0 | 3G | 0 | 0 | 0 | 2C,5G | 2G | 2C,3G | 2G | 3C,5G | 2G | 3C,5G |
| MORNING GLORY | 3C,6G | 4C,9G | 9C | 10C | 9C | 10C | 2C,4G | 0 | 3G | 3G | 3G | 3G | 2H | 0 | 1C | 2G | 1C,1H | 2C,4G | 2C,3G | 3C,7G |
| COCKLEBUR | 10C | 10C | 10C | 10C | 10C | 10C | 3C,8H | 0 | 0 | 1H | 0 | 0 | 5G | 2G | 2H | 2H | 2G | 2C,3G | 2G | 2C,3G |
| NUTSEDGE | 9G | | 8G | | 8G | | 9G | | 0 | 0 | 5G | 5G | 9G | 8G | 3G | 8G | 3G | 8G | 0 | 2C,8G |
| CRABGRASS | 2C,7G | 4C,9G | 6G | 4C,9G | 4C,9G | 4C,9G | 4C,9G | 3G | 3G | 3G | 5G | 2C,4G | 4G | 2C,8H | 0 | 3C,7G | 0 | 2C,5G | 0 | 2C,8G |
| BARNYARD GRASS | 5C,9G | 5C,9G | 4C,9G | 5C,9G | 5C,9G | 5C,9G | 3C,8G | 3C,5G | 3C,5G | 3C,5G | 2C,4G | 3G | 2H | 2C,8H | 2G | 3C,5G | 0 | 3C,7G | 0 | 3C,7G |
| WILD OATS | 3C,9G | 3C,9G | 2C,9G | 9G | 2C,9G | 4C,9G | 3C,8G | 3G | 0 | 0 | 3G | 5G | 3C,4G | 4G | 3G | 4G | 0 | 0 | 0 | 0 |
| WHEAT | 9G | 9G | 9G | 4C,9G | 9G | 9G | 2C,9G | 2G | 3G | 3G | 5G | 5G | 0 | 5G | 3G | 3G | 0 | 2C | 0 | 7G |
| CORN | 3C,9G | 5C,9G | 4C,9G | 3C,9G | 4C,9G | 4C,9G | 3C,9H | 3C,4G | 3C,5G | 3C,4G | 1C,1H | 3C,8G | 3C,4G | 2C,3H | 2C,2G | 2C,8G | 2C | 3C,5H | 3C,5G | 2C,2G |
| SOYBEAN | 9C | 9C | 5C,9G | 9C | 9C | 9C | 3C,8G | 0 | 1C | 1C | 3C,4G | 2C,2G | 2H | 0 | 1C | 5C,9H | 3C,5H | 0 | 3C,5G | 3C,6G |
| RICE | 5C,9G | 9C | | 9C | 9C | 9C | 4C,9G | 2G | 3C,5G | 3C,5G | 3C,4G | 5C,8G | 0 | 0 | 1C | 0 | 0 | 0 | 1C | 2G |

TABLE A-continued

| | CMPD 65 | | CMPD 66 | | CMPD 67 | | CMPD 68 | | CMPD 69 | | CMPD 70 | | CMPD 71 | | CMPD 72 | | CMPD 73 | | CMPD 74 | |
|---|---|---|---|---|---|---|---|---|---|---|---|---|---|---|---|---|---|---|---|---|
| RATE RATE = KG/HA | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 |
| SORGHUM | 4C,9G | 4C,9G | 3C,9G | 4C,9G | 5C,9G | 4C,9G | 5C,9G | 0 | 0 | 2G | 0 | 2G | 0 | 2G | 0 | 2G | 0 | 3C,5G | 0 | 3C,6G |
| CHEATGRASS | 9C | 5C,9G | 5C,9G | 5C,9G | 4C,9G | 8G | 2C,8G | 0 | 0 | 3G | 0 | 3G | 2C,4G | 5C,9H | 6G | 2C,5G | 0 | 2C,5G | 0 | 2C,5G |
| SUGAR BEETS | 9C | 9C | 9C | 9C | 9C | 4C,8H | 5C,9G | 3C,9G | 3C,7G | 4C,8H | 4C,8H | 4C,8H | 5C,9H | 5C,9G | 9C | 3C,8G | 3C,8G | 3C,8G | 3C,8G | 4C,8H |
| VELVETLEAF | 9C | 9C | 3C,8G | 9C | 9C | 2C,7G | 3C,7G | 3C,8G | 0 | 2G | 0 | 2G | 3C,7G | 3C,7G | 2C,9G | 2C,5G | 2C,5G | 3G | 3C,6G |
| GIANT FOXTAIL | 5C,9G | 3C,8G | 3C,9G | 9C | 3C,7G | 7G | 3C,7G | 0 | 3G | 4G | 4G | 4G | 2G | 2G | 4G | 3C,7G | 5G | 5G |
| BARLEY | 5C,9G | 9C | 3C,9G | 3C,9G | 2C,7G | 8G | 3G | 0 | 0 | 2G | 2G | 2G | 0 | 0 | 0 | 0 | 0 | 0 | 0 |
| | | | | | | | | | | | | | | | | | | | | |
| COTTON | 8G | 7G | 4G | 8G | 9G | 3G | 3C,7G | 2G | 2G | 0 | 0 | 0 | 2C,2G | 2C,2G | 0 | 0 | 2G |
| MORNING GLORY | 4G | 3G | 1C | 0 | 2G | 0 | 0 | 0 | 2G | 0 | 9H | 1H | 6G | 1H | 0 | 2H | 2G |
| COCKLEBUR | 0 | 8H | 3C,4G | 8H | 3C,5H | 2H | 2C,2H | 1C | 1C | 0 | 0 | 1C | 0 | 2C,3H | 0 | 2G |
| NUTSEDGE | 10E | 10E | 10E | 10E | 10E | 0 | 0 | 0 | 0 | 4G | 4G | 5G | 5G | 0 | 1C | 0 |
| CRABGRASS | 3C,8G | 9H | 2G | 3C,8H | 9H | 6G | 3C,8G | 3C,7G | 3G | 0 | 0 | 2H | 7G | 4C,8G | 4C,9G | 3C,5G | 2C,5G |
| BARNYARD GRASS | 3C,6G | 9H | 3G | 4C,9H | 2G | 0 | 3C,7G | 3C,7G | 4G | 3H | 3H | 3H | 3C,8G | 3C,8G | 5G | 3C,5G | 3C,5G |
| WILD OATS | 3G | 3C,6H | 3G | 3C,7G | 0 | 0 | 2G | 2G | 0 | 0 | 0 | 0 | 5G | 7G | 2C,2G | 0 | 3G |
| WHEAT | 3G | 0 | 0 | 3G | 7G | 6G | 7G | 7G | 3G | 0 | 0 | 0 | 2C,2G | 2C,2G | 0 | 0 | 0 |
| CORN | 1C | 9G | 4C,9G | 4C,8G | 2C,3G | 2G | 2C,3G | 3C,7G | 2G | 4C,7G | 4C,7G | 4C,7G | 3C,5G | 4C,8H | 5G | 0 | 2C,2G |
| SOYBEAN | 1C,2H | 4C,8H | 3C,6H | 3C,8H | 3C,3G | 2G | 2C,3G | 3C,7G | 2G | 0 | 0 | 0 | 5G | 4C,8H | 5G | 0 | 5G |
| RICE | 7G | 10E | 3C,8G | 9H | 9H | 3C,5H | 8H | 3C,8H | 7G | 3C,8H | 3C,8H | 3C,8H | 3C,8H | 4C,9H | 0 | 2H | 0 |
| SORGHUM | 3C,4G | 4C,9H | 3C,9G | 4C,9H | 4C,8G | 2C,2G | 3C,8G | 0 | 0 | 2G | 2G | 2G | 2C,3G | 0 | 2G | 3C,4G | 3C,3G |
| CHEATGRASS | 9G | 4G | 9G | 3G | 4C,8G | 3G | 8G | 3C,7G | 7G | 0 | 0 | 0 | 2C,3G | 3C,8G | 5G | 2G | 2G |
| SUGAR BEETS | 3G | 8G | 7G | 3C,7G | 4C,8G | 7G | 0 | 3C,8G | 3C,7G | 4C,9G | 4C,9G | 4C,9G | 7G | 5C,9G | 2C | 5G | 2H |
| VELVETLEAF | 3G | 2C,7G | 4G | 9G | 2G | 3C,8G | 2G | 3C,7G | 4G | 2C,3G | 2C,3G | 2C,3G | 0 | 3C,7G | 0 | 3G | 1C |
| GIANT FOXTAIL | 1C | 9H | 3G | 3C,9H | 6H | 3G | 2G | 3C,6G | 2G | 3C,7H | 3C,7H | 3C,7H | 6G | 4C,8G | 2G | 4C,4G | 2C,6G |
| BARLEY | 0 | 2C,7G | 2C,5G | 3C,8G | 2C,4G | 0 | 3G | 2G | 0 | 0 | 0 | 0 | 0 | 2G | 0 | 0 | 0 |

POSTEMERGENCE

| | CMPD 65 | | CMPD 66 | | CMPD 67 | | CMPD 68 | | CMPD 69 | | CMPD 70 | | CMPD 71 | | CMPD 72 | | CMPD 73 | | CMPD 74 | |
|---|---|---|---|---|---|---|---|---|---|---|---|---|---|---|---|---|---|---|---|---|
| RATE | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 |
| COTTON | 4C,9G | 5C,9G | 3C,8G | 9G | 3C,9H | 2G | 8G | 3C,8H | 9C | 5G | 9G | 9C | 9C | 10C | 9C | 10C | 10C |
| MORNING GLORY | 10C | 10C | 4C,9H | 4C,9G | 3C,8H | 3C,6G | 3C,8G | 1C,1H | 5C,9G | 2C,5G | 3C,8G | 10C | 10C | 9C | 10C | 10C | 10C |
| COCKLEBUR | 5C,9G | 9C | 3C,8G | 4C,9G | 2C,6G | 2H | 3C,7G | 0 | 5C,9G | 4G | 3C,7H | 10C | 10C | 10C | 2C,8G | 2C,9G | 10C |
| NUTSEDGE | 6G | 2C,9G | 0 | 9C | 2G | 0 | 7G | 0 | 5G | 0 | 0 | 9C | 9C | 9C | 9C | 3C,9G | 4C,9G |
| CRABGRASS | 9H | 9G | 3G | 0 | 3C,8H | 0 | 0 | 2C,7G | 3C,9H | 0 | 1H | 10C | 9C | 9C | 9C | 10C | 10C |
| BARNYARD GRASS | 8G | 9H | 3G | 3C,6G | 9G | 3C,8G | 0 | 6G | 2C,8G | 0 | 1H | 9C | 9C | 5C,9G | 4C,9G | 5C,9G | 9C |
| WILD OATS | 9G | 3C,7G | 5C,9G | 0 | 3C,8H | 3G | 0 | 0 | 3C,9H | 0 | 1C | 5C,9G | 5C,9G | 9C | 9G | 10C | 9C |
| WHEAT | 2C,5G | 3C,9G | 5C,9G | 2C,4G | 3C,7G | 0 | 0 | 0 | 2C,8G | 0 | 1C | 9C | 9C | 9C | 4C,9G | 5C,9G | 9C |
| CORN | 5C,9G | 5C,9G | 3C,7G | 3C,8G | 3C,7G | 3C,5H | 0 | 0 | 4C,9G | 0 | 3C,7G | 10C | 10C | 10C | 9G | 9C | 9C |
| SOYBEAN | 2C,8G | 3C,9G | 3C,7G | 9G | 3C,7G | 0 | 0 | 3C,7G | 9G | 3G | 7G | 9C | 9C | 9C | 4C,7H | 5C,9G | 9C |
| RICE | 3C,7G | 9G | 4C,9H | 2G | 2C,8G | 3C,8G | 5G | 2G | 3C,6G | 1C | 1C | 9C | 9C | 9C | 9C | 9C | 9C |
| SORGHUM | 9G | 3C,8H | 5C,9G | 0 | 5C,9H | 3C,8G | 3C,8G | 0 | 2C,6G | 3C,7G | 3C,7G | 10C | 10C | 10C | 9C | 10C | 9C |
| CHEATGRASS | 3C,8H | 3C,8G | 3C,7H | 3C,7H | 3C,8G | 3C,7G | 3C,7G | 4C,7H | 3G | 2C,7G | 2C,7G | 10C | 10C | 10C | 2C,7G | 5C,8G | 9C |
| SUGAR BEETS | 4C,9G | 3C,8G | 3C,6G | 4C,9G | 3C,8G | 4G | 4C,7H | 0 | 2C,8G | 3C,7H | 3C,7H | 10C | 10C | 10C | 10C | 10C | 9C |
| VELVETLEAF | 3C,8G | 3C,9G | 2C,6G | 3C,8G | 3C,8G | 2G | 3C,6G | 0 | 5G | 0 | 0 | 9C | 9C | 9C | 2C,7G | 5C,9G | 9C |
| GIANT FOXTAIL | 3G | 5G | 0 | 0 | 2G | 0 | 2G | 0 | 0 | 0 | 0 | 5C,9G | 5C,9G | 5C,9G | 5C,9G | 5C,9G | 9C |

PREEMERGENCE

| | CMPD 65 | | CMPD 66 | | CMPD 67 | | CMPD 68 | | CMPD 69 | | CMPD 70 | | CMPD 71 | | CMPD 72 | | CMPD 73 | | CMPD 74 | |
|---|---|---|---|---|---|---|---|---|---|---|---|---|---|---|---|---|---|---|---|---|
| COTTON | 6G | 8G | 4G | 9G | 7G | 2C,8G | 0 | 0 | 2G | 7G | 8G | 9G | 7G | 2C,8G | 5G | 5G |
| MORNING GLORY | 7G | 0 | 0 | 7G | 2C,8G | 0 | 0 | 1C,1H | 7G | 3C,7G | 9G | 3C,7G | 3C,7G | 9G | 9G |
| COCKLEBUR | 0 | 8H | 7G | 0 | 9G | 0 | 0 | 3C,8H | 0 | 3C,3H | 9H | 9H | 8H | 8H | 3C,7H | 10E |
| NUTSEDGE | 5G | 9G | 3G | 7G | 6G | 0 | 0 | 10E | 10E | 2G | 10E | 10E | 10E | 10E | 10E |
| CRABGRASS | 2C,5G | 3C,8G | 7G | 3G | 4C,8G | 3G | 0 | 0 | 3G | 5C,9G | 5C,9G | 6C,9G | 4C,8G | 5C,9G | 5C,9H |
| BARNYARD GRASS | 8H | 9H | 0 | 7G | 2C,4G | 6H | 0 | 0 | 9H | 9H | 9H | 3C,7G | 9H | 9H |

TABLE A-continued

| | CMPD 75 | | CMPD 76 | | CMPD 77 | | CMPD 78 | | CMPD 79 | | CMPD 80 | | CMPD 81 | | CMPD 82 | | CMPD 83 | | CMPD 84 | |
|---|---|---|---|---|---|---|---|---|---|---|---|---|---|---|---|---|---|---|---|---|
| RATE RATE = KG/HA | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 |
| WILD OATS | 2C,7G | 3C,7G | 0 | 3G | 2G | 5G | 0 | 0 | 0 | 3G | 0 | 0 | 4C,9H | 5C,9H | 3C,8G | 3C,9H | 2C,7G | 3C,9H | 4C,8G | 5C,9H |
| WHEAT | 7G | 9H | 0 | 3G | 0 | 7G | 0 | 0 | 0 | 0 | 0 | 0 | 9H | 10H | 9H | 10E | 2C,8H | 10E | 9H | 9H |
| CORN | 3C,5G | 3C,9G | 0 | 3C,5G | 2G | 2C,5G | 2G | 0 | 0 | 1C | 0 | 0 | 9H | 9H | 9C | 9H | 3C,9G | 9H | 4C,9G | 10E |
| SOYBEAN | 2G | 3C,6G | 0 | 2C,3G | 2G | 2C,3G | 2G | 0 | 0 | 3C,3H | 0 | 0 | 9H | 10E | 9H | 10E | 3C,8H | 10E | 9H | 9H |
| RICE | 8G | 9H | 2G | 9H | 8G | 9H | 2G | 0 | 0 | 9H | 0 | 2G | 10E | 10E | 5C,9H | 10H | 3C,9H | 10E | 5C,9G | 10E |
| SORGHUM | 3G | 3C,9H | 0 | 0 | 3G | 3C,7G | 0 | 0 | 2G | 0 | 0 | 0 | 4C,9H | 5C,9H | 9H | 9H | 3C,8G | 10H | 5C,9G | 10E |
| CHEATGRASS | 5G | 8G | 0 | 2G | 0 | 6G | 0 | 0 | 0 | 0 | 0 | 0 | 9H | 10E | 9C | 9H | 7G | 9H | 9G | 10E |
| SUGAR BEETS | 8G | 3C,8G | 0 | 8G | 2G | 3C,8G | 0 | 0 | 0 | 8G | 0 | 3G | 3C,9G | 5C,9G | 9C | 9G | 5G | 9C | 9C | 10E |
| VELVETLEAF | 4G | 4C,9G | 0 | 6G | 7G | 2C,5H | 0 | 0 | 0 | 8G | 0 | 0 | 3C,8H | 10E | 8G | 9G | 5G | 3C,6G | 7G | 5C,9G |
| GIANT FOXTAIL | 7G | 9H | 0 | 8G | 2G | 9H | 0 | 0 | 0 | 0 | 2C,3H | 2C,3H | 9H | 10E | 4C,9G | 10E | 3C,9G | 9H | 9H | 9H |
| BARLEY | 2G | 7G | 0 | 0 | 0 | 7G | 0 | 0 | 0 | 3G | 0 | 0 | 4C,9H | 5C,9H | 4C,9G | 5C,9H | 3C,9G | 5C,9H | 4C,9G | 4C,9H |

POSTEMERGENCE

| | CMPD 85 | | CMPD 86 | | CMPD 87 | | CMPD 88 | |
|---|---|---|---|---|---|---|---|---|
| RATE RATE = KG/HA | 0.05 | 0.4 | 0.05 | 0.4 | 0.05 | 0.4 | 0.05 | 0.4 |
| COTTON | 1H | 9C | 2G | 10C | 1H | 10C | 9C | 10C |
| MORNING GLORY | 0 | 4C,9G | 2C,2G | 5C,9G | 2C,5G | 10C | 5C,9G | 10C |
| COCKLEBUR | 5G | 4C,9G | 2C,5G | 10C | 2C,3H | 10C | 5C,9G | 10C |
| NUTSEDGE | 2C,9G | 0 | 3G | 9C | 4H | 9C | 3C,8G | 9G |
| CRABGRASS | 5C,9G | 5C,9G | 3C,5G | 5C,9H | 2G | 3C,8G | 5C,9G | 9C |
| BARNYARD GRASS | 1H | 9H | 3C,6G | 4C,9G | 3C,6H | 4C,9G | 9C | 9C |
| WILD OATS | 3C,7G | 4C,9H | 3C,6G | 4C,8H | 3C,8H | 3C,8G | 5C,9G | 9C |
| WHEAT | 9H | 5C,9H | 3C,8G | 9H | 3C,9G | 4C,9G | 5C,9G | 10C |
| CORN | 3C,9G | 9H | 3C,7H | 10H | 3C,9H | 9C | 10C | 10C |
| SOYBEAN | 3C,6G | 9H | 4C,9G | 10H | 2H | 5C,9G | 10C | 10C |
| RICE | 5C,9H | 10E | 3C,7H | 9H | 4C,9G | 5C,9G | 4C,9G | 10C |
| SORGHUM | 4C,5G | 5C,9H | 3C,9H | 5C,9H | 4C,9G | 5C,9G | 10C | 9C |
| CHEATGRASS | 9G | 9H | 9H | 9H | 9C | 9C | 9C | 9C |
| SUGAR BEETS | 8G | 9G | 3C,6G | 5C,9G | 9G | 10C | 10C | 10C |
| VELVETLEAF | 2G | 3C,6G | 2G | 2C,4G | 2G | 2C,6G | 2C,4H | 9G |
| GIANT FOXTAIL | 9H | 9H | 4C,9H | 9H | 9C | 9C | 9C | 9C |
| BARLEY | 8G | 5C,9H | 3C,9G | 3C,9H | 3C,9G | 3C,9G | 9C | 9C |

PREEMERGENCE

| | CMPD 75 | | CMPD 76 | | CMPD 77 | | CMPD 78 | | CMPD 79 | | CMPD 80 | | CMPD 81 | | CMPD 82 | | CMPD 83 | | CMPD 84 | |
|---|---|---|---|---|---|---|---|---|---|---|---|---|---|---|---|---|---|---|---|---|
| RATE RATE = KG/HA | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 |
| COTTON | 1H | 8G | 2G | 9G | 2C,5G | 9G | 9H | 2G | 9C | 2C,7G | 0 | 0 | 3C,8G | 3C,8G | 9C | 10C | 9C | 10C | 9C | 10C |
| MORNING GLORY | 0 | 9G | 2C,2G | 9G | 8H | 8H | 9G | 6G | 10C | 8G | 2C,2H | 0 | 3C,8G | 10H | 10C | 10C | 10C | 10C | 5C,9G | 10C |
| COCKLEBUR | 5G | 3C,8H | 2C,5G | 3C,7H | 3C,5H | 3C,8H | 9H | 2C,5G | 10C | 2C,8H | 2H | 0 | 2C,3H | 2C,3H | 10C | 10C | 10C | 10C | 5C,9G | 10C |
| NUTSEDGE | 2C,9G | 10E | 3G | 4G | 4C,9G | 10E | 9H | 9C | 9C | 10E | 0 | 2H | 5G | 5G | 2C,8G | 9C | 9C | 10C | 3C,8G | 9C |
| CRABGRASS | 5C,9G | 5C,9G | 3C,5G | 5C,9H | 4C,8G | 4C,9G | 4C,9G | 5C,9G | 5C,9H | 5C,9H | 1C | 0 | 9C | 9C | 4C,9G | 9C | 5C,9H | 9C | 5C,9G | 9H |
| BARNYARD GRASS | 1H | 4C,9H | 3C,6G | 4C,9H | 4C,8G | 9H | 9H | 4C,8H | 9H | 9H | 3C,6G | 2G | 9C | 9C | 4C,9G | 9C | 4C,9H | 9C | 9C | 9C |
| WILD OATS | 3C,7G | 4C,9H | 3C,6G | 4C,8H | 2C,7G | 2C,3G | 4C,4H | 2G | 9H | 9H | 0 | 1H | 4C,9G | 4C,9G | 4C,9G | 9G | 6C,9G | 9C | 5C,9G | 4C,8H |
| WHEAT | 9H | 5C,9H | 3C,8G | 9H | 2C,8G | 7G | 5C,9G | 8G | 3C,8H | 3C,9G | 2G | 3G | 5C,9G | 5C,9G | 4C,9G | 10C | 6C,9G | 9C | 4C,9G | 9H |
| CORN | 3C,9G | 9H | 4C,9G | 10H | 3C,9G | 9G | 5C,9H | 3C,8G | 3C,9G | 3C,9H | 3C,9H | 3C,6G | 2C,2H | 5C,9G | 9C | 10C | 9C | 9C | 10C | 9H |
| SOYBEAN | 3C,6G | 3C,7H | 4C,9G | 10H | 3C,6G | 2C,5H | 5C,9G | 3C,9H | 10C | 3C,8G | 3C,1H | 0 | 2C,2H | 4C,9G | 9C | 10C | 10C | 10C | 10C | 9H |
| RICE | 5C,9H | 10E | 3C,7H | 9H | 3C,8H | 3C,8H | 5C,9H | 3C,9H | 3C,9H | 5C,9H | 8G | 4C,9G | 5C,9G | 4C,9G | 9C | 9C | 9C | 10C | 9C | 10E |
| SORGHUM | 4C,5G | 5C,9H | 3C,9H | 5C,9H | 3C,5G | 3C,8G | 5C,9G | 3C,9H | 10E | 5C,9H | 8G | 3C,6G | 2C,2H | 4C,9G | 9C | 10C | 9C | 10C | 9C | 9H |
| CHEATGRASS | 9G | 9H | 9H | 9H | 9C | 3C,8G | 9C | 3C,8H | 10E | 3C,9H | 3C,8G | 5C,9G | 9G | 9C | 10C | 10C | 10C | 9C | 10C | 9H |
| SUGAR BEETS | 8G | 9G | 3C,6G | 5C,9G | 10C | 4C,9G | 3C,5G | 5C,9G | 10C | 3C,8H | 1C,1H | 1H | 3C,8H | 10C | 9C | 9C | 9C | 10C | 9C | 9H |
| VELVETLEAF | 2G | 3C,6G | 2G | 2C,4G | 2C,6G | 2C,9H | 3C,8G | 3C,8H | 10C | 5C,9G | 9C | 3C,8G | 3C,8G | 3C,3G | 2C,6G | 5C,9G | 5C,9G | 9C | 2C,4H | 9H |
| GIANT FOXTAIL | 9H | 9H | 4C,9H | 9H | 9C | 9C | 5C,9G | 5C,9G | 5C,9G | 5C,9G | 2C,8G | 3C,8G | 3C,8G | 5C,9G | 9C | 10C | 6C,9G | 10C | 9C | 10H |
| BARLEY | 8G | 5C,9H | 3C,9G | 3C,9H | 3C,9H | 4C,9G | 3C,9G | 5C,9G | 4C,9H | 6C,9G | 3C,8G | 2C,5G | 3C,8G | 3C,8G | 9C | 9C | 9C | 9C | 9C | 9H |

| | CMPD 85 | | CMPD 86 | | CMPD 87 | | CMPD 88 | |
|---|---|---|---|---|---|---|---|---|
| RATE RATE = KG/HA | 0.05 | 0.4 | 0.05 | 0.4 | 0.05 | 0.4 | 0.05 | 0.4 |
| COTTON | 1H | 0 | 2G | 2C,7G | 0 | 9C | 6G | 4G |
| MORNING GLORY | 0 | 2C,2H | 6G | 8G | 0 | 9C | 3C,6H | 2G |
| COCKLEBUR | 5G | 2H | 2C,5G | 10E | 0 | 9H | 9H | 1C,1H |
| NUTSEDGE | 2C,9G | 0 | 9G | 10E | 10E | 10C | 10E | 10E |
| CRABGRASS | 5C,9G | 1C | 5C,9G | 5C,9H | 5C,9H | 9C | 4C,9G | 5C,9G |
| BARNYARD GRASS | 1H | 3C,6G | 4C,8H | 9H | 9H | 4C,9H | 4C,8H | 9H |
| WILD OATS | 3C,7G | 0 | 2G | 9H | 2C,3G | 9C | 4C,8H | 4C,9H |
| WHEAT | 9H | 2G | 8G | 3C,8H | 7G | 9C | 3C,9H | 9H |
| CORN | 3C,9G | 3G | 8G | 3C,9G | 9G | 9H | 3C,8H | 3C,9G |
| SOYBEAN | 3C,6G | 2G | 3C,6G | 3C,7H | 3C,9G | 10E | 10H | 10H |
| RICE | 5C,9H | 3C,6G | 7H | 1H | 3C,9H | 10E | 9C | 9H |
| SORGHUM | 4C,5G | 0 | 8G | 0 | 3C,9H | 10E | 4C,9H | 10E |
| CHEATGRASS | 0 | 0 | 4G | 4C,9H | 3C,9H | 9C | 9C | 9C |
| SUGAR BEETS | 6G | 2G | 7G | 5C,9H | 6G | 10E | 3C,7H | 10E |
| VELVETLEAF | 9C | 2G | 4G | 9H | 2C,9G | 9C | 1C,2H | 9C |
| GIANT FOXTAIL | 0 | 5G | 3C,7G | 2C,6G | 2C,9G | 5C,9G | 8G | 10E |
| BARLEY | 6G | 2C,8G | 9G | 3C,9G | 2C,7G | 9H | 3C,9G | 4C,9H |

TABLE A-continued

| RATE RATE = KG/HA | 0.05 | 0.4 | 0.05 | 0.4 | 0.05 | 0.4 | 0.05 | 0.4 |
|---|---|---|---|---|---|---|---|---|
| | | | POSTEMERGENCE | | | | | |
| COTTON | 2C,9H | 9C | 4C,9G | 10C | | 9C | 0 | 2G |
| MORNING GLORY | 5C,8H | 9C | 5C,9G | 9C | | 10C | 0 | 2C,4G |
| COCKLEBUR | 9C | 9C | 5C,9G | 9C | | 10C | 4H | 3C,7G |
| NUTSEDGE | 3G | 9G | 2C,9G | 9C | | 9G | 0 | 3C,5G |
| CRABGRASS | 9C | 4U,9C | 6C,9G | 6C,9G | | 5C,9G | 1H | 2G |
| BARNYARD GRASS | 9C | 9C | 3C,9G | 4C,9G | | 9C | 3C,5G | 4C,9H |
| WILD OATS | 5C,9G | 9C | 9G | 9G | | 4C,8G | 2C,5G | 4C,8G |
| WHEAT | 9C | 9C | 3C,9G | 9G | | 9G | 8G | 4C,9G |
| CORN | 9C | 10C | 4C,8G | 3C,8G | | 9C | 3C,8G | 2C,9H |
| SOYBEAN | 4C,9G | 9C | 5C,9G | 6C,9G | | 9C | 1C,1H | 3C,9G |
| RICE | 9C | 9C | 5C,9G | 9C | | 9C | 5C,9G | 9C |
| SORGHUM | 9C | 9C | 5C,9G | 9C | | 4C,9G | 0 | 0 |
| CHEATGRASS | 9C | 9C | 3C,9G | 9C | | 5C,9G | 3C,9G | 9C |
| SUGAR BEETS | 9C | 10C | 10C | 10C | | 3C,7G | 2G | 4C,9G |
| VELVETLEAF | 4C,6G | 3C,7H | 3C,7G | 9C | | 10C | 0 | 1C |
| GIANT FOXTAIL | 9C | 10C | 9C | 9C | | 9C | 3C,8G | 5C,9H |
| BARLEY | 9C | 9C | 6C,9G | 6C,9G | | 6C,9G | 5G | 3C,9H |
| | | | PREEMERGENCE | | | | | |
| COTTON | 6G | 7G | 5G | 2C,8G | | 8G | 0 | 5G |
| MORNING GLORY | 3C,6H | 9G | 5G | 9G | | 9G | 2C,2H | 0 |
| COCKLEBUR | 3C,3G | 3C,7H | 3C,3H | 8H | | 9H | 2H | |
| NUTSEDGE | 2G | 9G | 3C,9G | 10E | | 10E | 0 | 0 |
| CRABGRASS | 5C,9G | 5C,9G | 4C,8H | 5C,9G | | 4C,9H | 0 | 3C,6G |
| BARNYARD GRASS | 4C,8H | 9H | 4C,9H | 9H | | 9H | 0 | 6G |
| WILD OATS | 3C,9H | 4C,9H | 4C,8H | 3C,8H | | 4C,8G | 0 | 6G |
| WHEAT | 4C,9G | 5C,9H | 4C,9H | 9H | | 9H | 0 | 8G |
| CORN | 9H | 9H | 5C,9G | 4C,9G | | 9H | 0 | 3C,7G |
| SOYBEAN | 4C,9G | 9H | 3C,8H | 9H | | 9H | 0 | 2C,4G |
| RICE | 3C,9G | 10E | 9G | 10E | | 9H | 2G | 8H |
| SORGHUM | 4C,9H | 5C,9H | 3C,8H | 9H | | 3C,9H | 0 | 0 |
| CHEATGRASS | 4C,9G | 9H | 3C,9H | 3C,9H | | 9H | 0 | 6G |
| SUGAR BEETS | 7H | 9C | 3C,7G | 3C,8G | | 8G | 2H | 5G |
| VELVETLEAF | 1C | 3C,6G | 2C,2G | 3C,7G | | 4C,9G | 0 | 0 |
| GIANT FOXTAIL | 4C,9H | 9H | 4C,9H | 9H | | 9H | 0 | 2C,4G |
| BARLEY | 3C,9G | 4C,9G | 9H | 9H | | 3C,9H | 0 | 2C,2G |

TEST B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*), and teaweed (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crus-galli*), corn (*Zea mays*), soybean (*Glycine max*), and giant foxtail (*Setaria faberi*). The third pot was planted with wheat (*Triticum aestivum*), barley (*Hordeum vulgare*), wild buckwheat (*Polygonum convolvulus* L.), cheatgrass (*Bromus secalinus* L.), sugarbeet (*Beta vulgaris*), wild oat (*Avena fatua* L.), viola (*Viola arvensis*), blackgrass (*Alopecurus myosuroides*), and rape (*Brassica napus*). The plants were grown for approximately fourteen days, then sprayed postemergence with the chemicals dissolved in a nonphytotoxic solvent.

Preemergence

Three round pans (25 cm diameter by 12.5 cm deep) were filled with Sassafras sand loam soil. One pan was planted with nutsedge tubers, crabgrass, sicklepod, jimsonweed, velvetleaf, lambsquarters, rice, and teaweed. The second pod was planted with green foxtail, cocklebur, morningglory, cotton, johnsongrass, barnyardgrass, corn, soybean, and giant foxtail. The third pot was planted with wheat, barley, wild buckwheat, cheatgrass, sugarbeet, wild oat, viola, blackgrass, and rape. The three pans were sprayed preemergence with the chemicals dissolved in a non-phytotoxic solvent.

Treated plants and controls were maintained in the greenhouse for approximately 24 days, then all rated plants were compared to controls and visually rated for plant response.

Response ratings are based on a scale of 0 to 100 where 0=no effect, and 100=complete control. A dash (-) response means no test.

Response ratings are contained in Table B.

TABLE B

POSTEMERGENCE

| RATE = G/HA | CMPD 7 | | | | CMPD 8 | | | | CMPD 9 | | | | CMPD 10 | | | | CMPD 11 | | |
|---|---|---|---|---|---|---|---|---|---|---|---|---|---|---|---|---|---|---|---|
| RATE | 0001 | 0004 | 0016 | 0062 | 0001 | 0004 | 0016 | 0062 | 0001 | 0004 | 0016 | 0062 | 0001 | 0004 | 0016 | 0062 | 0004 | 0016 | 0062 |
| GIANT FOXTAIL | 30 | 50 | 70 | 100 | 0 | 0 | 0 | 30 | 0 | 0 | 0 | 30 | 0 | 30 | 60 | 100 | 0 | 30 | 60 |
| VELVETLEAF | 0 | 0 | 30 | 60 | 30 | 60 | 90 | 100 | 0 | 30 | 70 | 100 | 30 | 50 | 0 | 100 | 50 | 80 | 100 |
| SUGAR BEETS | 0 | 70 | 100 | 70 | 0 | 50 | 80 | 0 | 0 | 0 | 0 | 0 | 0 | 0 | 70 | 0 | 30 | 60 | 100 |
| CRABGRASS | 0 | 30 | 50 | 70 | 30 | 30 | 50 | 70 | 0 | 0 | 0 | 30 | 30 | 30 | 30 | 70 | 30 | 50 | 70 |
| TEAWEED | 0 | 30 | 50 | 70 | 0 | 50 | 70 | 90 | 0 | 0 | 30 | 60 | 0 | 30 | 70 | 60 | 50 | 70 | 90 |
| JIMSONWEED | 30 | 50 | 70 | 90 | 30 | 50 | 70 | 100 | 30 | 0 | 30 | 30 | 30 | 50 | 90 | 100 | 50 | 70 | 100 |
| RICE | 30 | 60 | 100 | 100 | 30 | 50 | 70 | 100 | 0 | 0 | 50 | 70 | 30 | 60 | 50 | 100 | 70 | 100 | 100 |
| COCKLEBUR | 30 | 50 | 70 | 100 | 30 | 40 | 80 | 100 | 30 | 0 | 30 | 50 | 0 | 30 | 90 | 100 | 50 | 80 | 100 |
| COTTON | 30 | 0 | 20 | 40 | 60 | 90 | 100 | 100 | 0 | 30 | 40 | 60 | 0 | 30 | 50 | 70 | 30 | 90 | 100 |
| SOYBEAN | 50 | 80 | 100 | 100 | 0 | 40 | 70 | 100 | 0 | 0 | 20 | 40 | 0 | 30 | 60 | 70 | 70 | 70 | 100 |
| BARNYARD GRASS | 30 | 60 | 100 | 100 | 60 | 90 | 100 | 100 | 0 | 0 | 0 | 0 | 30 | 30 | 50 | 70 | 30 | 70 | 100 |
| WILD OATS | 30 | 60 | 90 | 100 | 0 | 40 | 70 | 100 | 0 | 0 | 0 | 30 | 30 | 30 | 60 | 100 | 30 | 50 | 100 |
| MORNINGGLORY | 0 | 0 | 0 | 40 | 0 | 0 | 0 | 0 | 0 | 0 | 0 | 50 | 0 | 0 | 70 | 90 | 30 | 0 | 30 |
| WHEAT | 40 | 60 | 80 | 100 | 30 | 30 | 60 | 100 | 30 | 30 | 30 | 50 | 30 | 50 | 70 | 100 | 50 | 70 | 100 |
| CASSIA | 0 | 30 | 60 | 90 | 60 | 70 | 80 | 90 | 0 | 30 | 50 | 80 | 30 | 50 | 70 | 100 | 50 | 80 | 100 |
| JOHNSONGRASS | 30 | 60 | 90 | 100 | 30 | 60 | 70 | 100 | 30 | 0 | 0 | 30 | 0 | 30 | 50 | 80 | 50 | 90 | 90 |
| NUTSEDGE | 0 | 30 | 60 | 100 | 30 | 50 | 70 | 100 | 0 | 30 | 40 | 30 | 30 | 50 | 70 | 100 | 0 | 50 | 50 |
| CORN | 70 | 80 | 100 | 100 | 50 | 0 | 0 | 70 | 0 | 0 | 0 | 30 | 0 | 0 | 30 | 100 | 30 | 100 | 100 |
| WILD BUCKWHEAT | 30 | 40 | 50 | 70 | 0 | 30 | 50 | 60 | 0 | 0 | 0 | 0 | 0 | 0 | 20 | 40 | 0 | 30 | 70 |
| BLACK GRASS | 30 | 50 | 70 | 100 | 30 | 100 | 100 | 100 | 0 | 30 | 70 | 100 | 70 | 100 | 100 | 60 | 30 | 60 | 100 |
| RAPESEED | 30 | 50 | 60 | 100 | 0 | 30 | 60 | 70 | 0 | 0 | 0 | 30 | 0 | 30 | 30 | 60 | 30 | 60 | 100 |
| BARLEY | 30 | 50 | 70 | 100 | 100 | 100 | 70 | 100 | 50 | 70 | 100 | 100 | 30 | 50 | 70 | 100 | 30 | 50 | 70 |
| GREEN FOXTAIL | 0 | 30 | 60 | 100 | 0 | 30 | 50 | 60 | 0 | 0 | 0 | 30 | 0 | 50 | 70 | 100 | 0 | 30 | 30 |
| CHEAT GRASS | 30 | 60 | 80 | 100 | 50 | 0 | 70 | 100 | 0 | 0 | 0 | 30 | 30 | 0 | 0 | 70 | 50 | 60 | 100 |
| VIOLA | 70 | 100 | 100 | 100 | 30 | 30 | 60 | 100 | 0 | 0 | 30 | 0 | 30 | 0 | 30 | 100 | 30 | 50 | 60 |
| LAMBSQUARTER | 50 | 70 | 100 | 100 | 0 | 30 | 50 | 70 | 0 | 0 | 0 | 0 | 30 | 40 | 50 | 70 | 50 | 100 | 100 |

| RATE = G/HA | CMPD 13 | | | | CMPD 12 | | | | CMPD 14 | | | | CMPD 16 | | | CMPD 17 | | | |
|---|---|---|---|---|---|---|---|---|---|---|---|---|---|---|---|---|---|---|---|
| RATE | 0001 | 0004 | 0016 | 0062 | 0001 | 0004 | 0016 | 0062 | 0001 | 0004 | 0016 | 0062 | 0062 | 0250 | 0500 | 0004 | 0016 | 0250 | 0500 |
| GIANT FOXTAIL | 0 | 0 | 30 | 60 | 0 | 0 | 0 | 30 | 0 | 0 | 0 | 0 | 40 | 40 | 70 | 0 | 0 | 0 | 30 |
| VELVETLEAF | 0 | 0 | 50 | 100 | 30 | 50 | 70 | 100 | 0 | 0 | 0 | 0 | 0 | 0 | 20 | 0 | 0 | 30 | 30 |
| SUGAR BEETS | 0 | 30 | 50 | 70 | 0 | 0 | 0 | 0 | 0 | 50 | 0 | 0 | 10 | 30 | 70 | 20 | 30 | 30 | 50 |
| CRABGRASS | 30 | 30 | 50 | 70 | 0 | 0 | 30 | 50 | 0 | 0 | 0 | 0 | 0 | 0 | 60 | 0 | 0 | 0 | 0 |
| TEAWEED | 0 | 30 | 50 | 70 | 0 | 30 | 30 | 60 | 0 | 0 | 0 | 0 | 0 | 20 | 60 | 0 | 30 | 30 | 40 |
| JIMSONWEED | 30 | 50 | 50 | 100 | 0 | 30 | 30 | 70 | 0 | 30 | 50 | 0 | 0 | 50 | 90 | 0 | 30 | 30 | 70 |
| RICE | 50 | 70 | 100 | 100 | 0 | 30 | 50 | 90 | 0 | 0 | 30 | 0 | 60 | 40 | 80 | 20 | 30 | 30 | 0 |
| COCKLEBUR | 0 | 50 | 70 | 100 | 30 | 30 | 60 | 70 | 30 | 30 | 30 | 50 | 40 | 40 | 60 | 0 | 30 | 40 | 0 |
| COTTON | 0 | 30 | 50 | 90 | 0 | 30 | 50 | 90 | 0 | 0 | 30 | 10 | 0 | 10 | 20 | 0 | 0 | 20 | 70 |
| SOYBEAN | 70 | 100 | 100 | 100 | 0 | 30 | 50 | 70 | 0 | 0 | 0 | 0 | 50 | 60 | 70 | 0 | 0 | 30 | 30 |
| BARNYARD GRASS | 30 | 60 | 100 | 100 | 0 | 30 | 30 | 50 | 0 | 0 | 10 | 0 | 40 | 80 | 80 | 0 | 0 | 0 | 40 |
| WILD OATS | 0 | 30 | 30 | 50 | 0 | 30 | 0 | 0 | 0 | 20 | 0 | 0 | 0 | 0 | 10 | 0 | 0 | 30 | 0 |
| MORNINGGLORY | 0 | 0 | 0 | 50 | 0 | 0 | 30 | 50 | 0 | 20 | 0 | 40 | 0 | 0 | 0 | 0 | 0 | 0 | 50 |
| WHEAT | 30 | 50 | 70 | 100 | 0 | 30 | 30 | 50 | 0 | 0 | 10 | 0 | 40 | 60 | 100 | 0 | 20 | 30 | 0 |
| CASSIA | 30 | 60 | 90 | 70 | 30 | 30 | 60 | 80 | 0 | 0 | 60 | 0 | 0 | 40 | 50 | 0 | 40 | 40 | 60 |
| JOHNSONGRASS | 30 | 50 | 70 | 90 | 0 | 0 | 0 | 30 | 30 | 30 | 0 | 0 | 70 | 0 | 70 | 0 | 0 | 0 | 40 |
| NUTSEDGE | 30 | 60 | 100 | 100 | 30 | 30 | 30 | 30 | 0 | 0 | 0 | 0 | 0 | 40 | 50 | 0 | 0 | 0 | 0 |
| CORN | 80 | 90 | 100 | 100 | 0 | 40 | 60 | 60 | 0 | 0 | 0 | 50 | 50 | 0 | 100 | 0 | 0 | 0 | 0 |
| WILD BUCKWHEAT | 0 | 0 | 0 | 30 | 0 | 0 | 30 | 50 | 0 | 0 | 0 | 0 | 0 | 0 | 0 | 0 | 0 | 0 | 0 |
| BLACK GRASS | 0 | 30 | 60 | 90 | 0 | 0 | 0 | 30 | 0 | 30 | 0 | 40 | 40 | 50 | 80 | 0 | 0 | 30 | 50 |

TABLE B-continued

| | CMPD 19 | | | | CMPD 23 | | | | |
|---|---|---|---|---|---|---|---|---|---|
| RATE RATE = G/HA | 0004 | 0016 | 0062 | 0250 | 0500 | 0004 | 0016 | 0062 | 0250 | 0500 |
| RAPESEED | 50 | 100 | 100 | 100 | 100 | 50 | 100 | 100 | 100 | 50 |
| BARLEY | 0 | 0 | 0 | 60 | 60 | 0 | 0 | 0 | 0 | 0 |
| GREEN FOXTAIL | 0 | 30 | 50 | 70 | 70 | 0 | 30 | 60 | 30 | 0 |
| CHEAT GRASS | 30 | 60 | 100 | 100 | 100 | 0 | 30 | 50 | 30 | 0 |
| VIOLA | 50 | 70 | 100 | 100 | 100 | 0 | 0 | 0 | 0 | 30 |
| LAMBSQUARTER | 60 | 80 | 90 | 100 | 100 | 0 | 0 | 40 | 0 | 0 |
| GIANT FOXTAIL | 0 | 20 | 20 | 20 | 30 | 0 | 0 | 0 | 0 | 30 |
| VELVETLEAF | 20 | 30 | 30 | 30 | 30 | 0 | 0 | 0 | 20 | 30 |
| SUGAR BEETS | 0 | 0 | 0 | 50 | 50 | 0 | 0 | 50 | 50 | 50 |
| CRABGRASS | 0 | 0 | 0 | 0 | 30 | 0 | 0 | 0 | 30 | 0 |
| TEAWEED | 0 | 30 | 70 | 70 | 70 | 0 | 0 | 30 | 80 | 40 |
| JIMSONWEED | 0 | 40 | 60 | 30 | 70 | 30 | 50 | 80 | 0 | 80 |
| RICE | | | | 90 | 90 | 0 | 0 | 0 | 0 | 0 |
| COCKLEBUR | 0 | 30 | 70 | 70 | 70 | 0 | 0 | 0 | 0 | 40 |
| COTTON | 20 | 50 | 50 | 70 | 80 | 0 | 0 | 60 | 60 | 0 |
| SOYBEAN | 70 | 70 | 80 | 80 | 80 | 50 | 50 | 60 | 50 | 60 |
| BARNYARD GRASS | 0 | 0 | 0 | 0 | 20 | 30 | 30 | 30 | 30 | 50 |
| WILD OATS | 50 | 50 | 50 | 50 | 60 | 30 | 30 | 40 | 40 | 30 |
| MORNINGGLORY | 20 | 40 | 40 | 70 | 75 | 0 | 0 | 0 | 0 | 0 |
| WHEAT | 0 | 0 | 0 | 20 | 20 | 0 | 30 | 0 | 40 | 40 |
| CASSIA | 20 | 30 | 40 | 50 | 50 | 30 | 50 | 80 | 20 | 30 |
| JOHNSONGRASS | 0 | 50 | 50 | 60 | 60 | 30 | 50 | 60 | 50 | 50 |
| NUTSEDGE | 0 | 20 | 30 | 40 | 40 | 0 | 0 | 0 | 30 | 30 |
| CORN | 70 | 80 | 80 | 80 | 80 | 60 | 60 | 60 | 50 | 50 |
| WILD BUCKWHEAT | 0 | 0 | 50 | 50 | 60 | 0 | 0 | 0 | 0 | 0 |
| BLACK GRASS | 0 | 40 | 40 | 40 | 60 | 0 | 0 | 0 | 0 | 0 |
| RAPESEED | 60 | 80 | 90 | 90 | 90 | 40 | 40 | 40 | 60 | 60 |
| BARLEY | 0 | 20 | 30 | 30 | 30 | 0 | 0 | 0 | 0 | 0 |
| GREEN FOXTAIL | 0 | 20 | 30 | 40 | 50 | 0 | 0 | 30 | 30 | 30 |
| CHEAT GRASS | 50 | 50 | 50 | 60 | 70 | 0 | 0 | 30 | 60 | 30 |
| VIOLA | 0 | 0 | 50 | 50 | 80 | 0 | 0 | 30 | 50 | 30 |
| LAMBSQUARTER | 0 | 30 | 30 | 50 | 60 | 0 | 20 | 30 | 30 | 30 |

| | CMPD 24 | | | | CMPD 27 | | | | |
|---|---|---|---|---|---|---|---|---|---|
| RATE RATE = G/HA | 0001 | 0004 | 0016 | 0062 | 0250 | 0062 | 0125 | 0250 | 0500 |
| GIANT FOXTAIL | 0 | 0 | 0 | 30 | 0 | 0 | 0 | 0 | 40 |
| VELVETLEAF | 0 | 0 | 30 | 60 | 80 | 0 | 0 | 0 | 20 |
| SUGAR BEETS | 0 | 80 | 70 | 80 | 90 | 0 | 0 | 0 | 30 |
| CRABGRASS | 0 | 0 | 20 | 40 | 40 | 0 | 0 | 20 | 50 |
| TEAWEED | 0 | 20 | 30 | 70 | 70 | 0 | 30 | 30 | 30 |
| JIMSONWEED | 0 | 0 | 30 | 30 | 50 | 0 | 0 | 30 | 30 |
| RICE | 0 | 20 | 40 | 40 | 80 | 0 | 0 | 0 | 20 |
| COCKLEBUR | 0 | 20 | 20 | 70 | 0 | 0 | 0 | 20 | 40 |
| COTTON | 0 | 20 | 40 | 50 | 10 | 0 | 20 | 30 | 0 |
| SOYBEAN | 0 | 30 | 20 | 70 | 90 | 0 | 30 | 30 | 50 |
| BARNYARD GRASS | 0 | 0 | 40 | 40 | 40 | 0 | 0 | 20 | 40 |
| WILD OATS | 0 | 0 | 0 | 40 | 0 | 0 | 0 | 0 | 0 |
| MORNINGGLORY | 0 | 0 | 20 | 30 | 0 | 0 | 0 | 0 | 20 |
| WHEAT | 0 | 0 | 0 | 30 | 0 | 0 | 0 | 0 | 20 |
| CASSIA | 0 | 0 | 20 | 30 | 70 | 0 | 0 | 0 | 0 |
| JOHNSONGRASS | 0 | 30 | 0 | 80 | 10 | 0 | 0 | 0 | 50 |
| NUTSEDGE | 0 | 0 | 30 | 50 | 90 | 0 | 0 | 50 | 50 |
| CORN | 0 | 20 | 30 | 70 | 40 | 0 | 0 | 60 | 60 |
| WILD BUCKWHEAT | 0 | 0 | 20 | 50 | 90 | 0 | 0 | 0 | 0 |
| BLACK GRASS | 0 | 0 | 20 | 30 | 30 | 0 | 0 | 0 | 60 |
| RAPESEED | 0 | 40 | 80 | 90 | 80 | 0 | 40 | 40 | 50 |
| BARLEY | 0 | 0 | 0 | 30 | 10 | 0 | 0 | 50 | 40 |
| GREEN FOXTAIL | 0 | 0 | 0 | 40 | 90 | 0 | 0 | 0 | 0 |
| CHEAT GRASS | 0 | 0 | 30 | 30 | 40 | 0 | 30 | 30 | 0 |
| VIOLA | 0 | 0 | 40 | 50 | 90 | 0 | 0 | 0 | 0 |
| LAMBSQUARTER | 0 | 30 | 40 | 50 | 80 | 0 | 0 | 0 | 0 |

| | CMPD 35 | | | | CMPD 41 | | | | CMPD 50 | | |
|---|---|---|---|---|---|---|---|---|---|---|---|
| RATE RATE = G/HA | 0001 | 0004 | 0016 | 0062 | 0250 | 0500 | 1000 | 0004 | 0016 | 0062 |
| GIANT FOXTAIL | 0 | 20 | 30 | 30 | 40 | 60 | 60 | 0 | 20 | 40 |
| VELVETLEAF | 0 | 20 | 50 | 80 | 80 | 90 | 100 | 0 | 20 | 30 |
| SUGAR BEETS | 0 | 0 | 20 | 80 | 90 | 100 | 100 | 0 | 20 | 70 |
| CRABGRASS | 0 | 0 | 0 | 20 | 70 | 30 | 40 | 0 | 0 | 0 |
| TEAWEED | 0 | 0 | 20 | 70 | 50 | 70 | 90 | 0 | 0 | 20 |
| JIMSONWEED | 20 | 30 | 40 | 80 | 90 | 60 | 90 | 40 | 30 | 30 |
| RICE | 0 | 0 | 30 | 40 | 90 | | 100 | 0 | 0 | 80 |
| COCKLEBUR | 20 | 0 | 0 | 70 | 100 | 90 | 90 | 0 | 50 | 0 |
| COTTON | 0 | 60 | 70 | 20 | 70 | 90 | 100 | 40 | 0 | 40 |
| SOYBEAN | 50 | 20 | 60 | 90 | 80 | 100 | 70 | 0 | 30 | 40 |
| BARNYARD GRASS | 0 | 20 | 40 | 70 | 60 | 70 | 90 | 0 | 0 | 40 |
| WILD OATS | 0 | 0 | 0 | 70 | 70 | 90 | 70 | 0 | 30 | 30 |
| MORNINGGLORY | 0 | 30 | 40 | 30 | 80 | 60 | 60 | 0 | 0 | 0 |
| WHEAT | 0 | 20 | 0 | 90 | 50 | 60 | 60 | 0 | 0 | 30 |
| CASSIA | 0 | 0 | 30 | 30 | 0 | | | | | |

| | | CMPD 19 | | | | CMPD 23 | | | | |
|---|---|---|---|---|---|---|---|---|---|---|
| RAPESEED | 50 | 100 | 100 | 100 | 100 | 50 | 100 | 100 | 100 | 50 |

TABLE B-continued

|  | JOHNSONGRASS | NUTSEDGE | CORN | WILD BUCKWHEAT | BLACK GRASS | RAPESEED | BARLEY | GREEN FOXTAIL | CHEAT GRASS | VIOLA | LAMBSQUARTER |
|---|---|---|---|---|---|---|---|---|---|---|---|
| (col a) | 40 | 30 | 40 | 0 | 0 | 30 | 0 | 60 | 0 | 60 | 30 | 30 | 0 |
| (col b) | 0 | 30 | 20 | 30 | 0 | 0 | 20 | 0 | 20 | 0 | 50 | 20 | 20 |

PREEMERGENCE

| | CMPD 7 | | CMPD 8 | | | CMPD 9 | | | CMPD 10 | | | CMPD 11 | | | CMPD 12 | |
|---|---|---|---|---|---|---|---|---|---|---|---|---|---|---|---|---|
| RATE RATE = G/HA | 0016 | 0062 | 0250 | 0016 | 0062 | 0250 | 0016 | 0062 | 0250 | 0016 | 0062 | 0500 | 0016 | 0062 | 0250 | 0016 | 0062 | 0250 |
| GIANT FOXTAIL | 0 | 0 | 30 | 0 | 30 | 50 | 0 | 0 | 0 | 0 | 0 | 20 | 0 | 30 | 50 | 0 | 0 | 30 |
| VELVETLEAF | 0 | 0 | 30 | 0 | 30 | 60 | 0 | 0 | 30 | 0 | 0 | 30 | 30 | 50 | 70 | 0 | 0 | 20 |
| SUGAR BEETS | 30 | 50 | 70 | 50 | 70 | 90 | 50 | 30 | 0 | 0 | 30 | 10 | 50 | 50 | 80 | 0 | 0 | 30 |
| CRABGRASS | 0 | 0 | 0 | 30 | 50 | 70 | 30 | 0 | 50 | 30 | 30 | 0 | 30 | 50 | 80 | 0 | 0 | 40 |
| TEAWEED | 0 | 0 | 30 | 0 | 30 | 70 | 0 | 30 | 60 | 30 | 30 | 0 | 50 | 70 | 90 | 0 | 0 | 50 |
| JIMSONWEED | 0 | 0 | 30 | 0 | 30 | 60 | 0 | 0 | 30 | 0 | 0 | 0 | 30 | 30 | 50 | 0 | 0 | 40 |
| RICE | 0 | 30 | 80 | 30 | 70 | 90 | 30 | 30 | 30 | 30 | 60 | 30 | 50 | 90 | 100 | 30 | 30 | 90 |
| COCKLEBUR | 0 | 30 | 30 | 30 | 50 | 90 | 0 | 0 | 60 | 0 | 30 | 30 | 50 | 70 | 50 | 0 | 50 | 50 |
| COTTON | 0 | 0 | 0 | 30 | 50 | 80 | 0 | 0 | 30 | 30 | 30 | 0 | 30 | 50 | 70 | 0 | 30 | 30 |
| SOYBEAN | 0 | 0 | 0 | 30 | 50 | 50 | 0 | 0 | 50 | 0 | 0 | 0 | 0 | 30 | 60 | 0 | 0 | 0 |
| BARNYARD GRASS | 0 | 0 | 40 | 0 | 30 | 60 | 0 | 0 | 30 | 30 | 0 | 30 | 30 | 30 | 70 | 0 | 30 | 60 |
| WILD OATS | 0 | 0 | 0 | 0 | 30 | 30 | 0 | 0 | 0 | 0 | 0 | 0 | 0 | 30 | 50 | 0 | 0 | 0 |
| MORNINGGLORY | 0 | 0 | 0 | 30 | 30 | 50 | 0 | 30 | 30 | 0 | 0 | 0 | 30 | 30 | 70 | 0 | 0 | 0 |
| WHEAT | 0 | 0 | 0 | 0 | 30 | 30 | 0 | 30 | 40 | 0 | 30 | 0 | 30 | 30 | 80 | 0 | 0 | 0 |
| CASSIA | 0 | 30 | 60 | 30 | 50 | 70 | 0 | 0 | 30 | 0 | 30 | 0 | 30 | 50 | 90 | 0 | 30 | 30 |
| JOHNSONGRASS | 0 | 30 | 70 | 30 | 70 | 90 | 0 | 0 | 40 | 30 | 50 | 0 | 50 | 70 | 80 | 0 | 30 | 60 |
| NUTSEDGE | 0 | 0 | 0 | 30 | 50 | 70 | 0 | 0 | 0 | 0 | 0 | 0 | 30 | 50 | 90 | 0 | 30 | 50 |
| CORN | 0 | 0 | 0 | 30 | 30 | 60 | 0 | 0 | 0 | 0 | 0 | 0 | 0 | 30 | 80 | 0 | 0 | 0 |
| WILD BUCKWHEAT | 0 | 30 | 60 | 30 | 50 | 80 | 30 | 30 | 50 | 30 | 30 | 20 | 30 | 60 | 80 | 0 | 30 | 60 |
| BLACK GRASS | 0 | 30 | 60 | 50 | 70 | 90 | 0 | 0 | 60 | 30 | 30 | 10 | 50 | 70 | 90 | 0 | 60 | 80 |
| RAPESEED | 30 | 50 | 70 | 50 | 70 | 90 | 0 | 30 | 30 | 30 | 50 | 0 | 30 | 70 | 80 | 0 | 50 | 70 |
| BARLEY | 0 | 0 | 0 | 30 | 30 | 70 | 0 | 0 | 40 | 0 | 0 | 30 | 30 | 30 | 70 | 0 | 0 | 30 |
| GREEN FOXTAIL | 0 | 30 | 30 | 0 | 60 | 90 | 0 | 0 | 60 | 30 | 30 | 0 | 30 | 60 | 90 | 0 | 30 | 30 |
| CHEAT GRASS | 0 | 30 | 50 | 30 | 70 | 90 | 0 | 0 | 0 | 0 | 0 | 20 | 30 | 50 | 80 | 0 | 30 | 0 |
| VIOLA | 0 | 50 | 50 | 50 | 90 | 100 | 30 | 30 | 70 | 50 | 70 | 20 | 70 | 90 | 100 | 0 | 100 | 100 |
| LAMBSQUARTER | 0 | 30 | 70 | 50 | 100 | 70 | 0 | 0 | 90 | 60 | 60 | 0 | 50 | 100 | 100 | 0 | 30 | 60 |

| | CMPD 13 | | CMPD 14 | | CMPD 16 | | CMPD 17 | | CMPD 19 | | CMPD 23 | |
|---|---|---|---|---|---|---|---|---|---|---|---|---|
| RATE RATE = G/HA | 0016 | 0062 | 0250 | 0062 | 0016 | 0062 | 0250 | 0500 | 0062 | 0250 | 0062 | 0500 | 0016 | 0062 | 0250 | 0062 | 0250 | 0016 | 0062 | 0250 |
| GIANT FOXTAIL | 0 | 0 | 30 | 0 | 0 | 30 | 50 | 90 | 0 | 0 | 0 | 40 | 0 | 30 | 40 | 20 | 0 | 0 | 0 | 30 |
| VELVETLEAF | 30 | 50 | 70 | 0 | 0 | 30 | 70 | 30 | 20 | 20 | 0 | 30 | 0 | 30 | 70 | 0 | 0 | 0 | 10 | 20 |
| SUGAR BEETS | 30 | 50 | 60 | 0 | 50 | 50 | 70 | 100 | 0 | 30 | 30 | 40 | 50 | 50 | 80 | 40 | 40 | 0 | 0 | 20 |
| CRABGRASS | 30 | 50 | 70 | 0 | 30 | 30 | 50 | 70 | 30 | 70 | 30 | 80 | 30 | 50 | 50 | 0 | 0 | 10 | 0 | 20 |
| TEAWEED | 30 | 30 | 70 | 40 | 0 | 30 | 50 | 70 | 0 | 0 | 30 | 80 | 50 | 70 | 80 | 40 | 50 | 0 | 0 | 20 |
| JIMSONWEED | 0 | 30 | 50 | 0 | 0 | 0 | 20 | 50 | 50 | 30 | 30 | 90 | 50 | 60 | 40 | 0 | 10 | 0 | 0 | 40 |
| RICE | 50 | 70 | 90 | 0 | 50 | 60 | 60 | 100 | 0 | 0 | 30 | 40 | 0 | 70 | 20 | 20 | 0 | 0 | 20 | 10 |
| COCKLEBUR | 30 | 50 | 70 | 0 | 30 | 20 | 90 | 50 | 0 | 0 | 30 | 0 | 70 | 80 | 100 | 0 | 10 | 0 | 0 | 20 |
| COTTON | 0 | 30 | 60 | 0 | 50 | 30 | 30 | 60 | 10 | 10 | 0 | 60 | 0 | 40 | 30 | 10 | 0 | 0 | 0 | 10 |

TABLE B-continued

| | CMPD 24 | | | CMPD 27 | | | | CMPD 35 | | | | CMPD 41 | | | | CMPD 50 | |
|---|---|---|---|---|---|---|---|---|---|---|---|---|---|---|---|---|---|
| RATE RATE = G/HA | 0004 | 0016 | 0062 | 0250 | 0062 | 0125 | 0250 | 0500 | 0016 | 0062 | 0250 | 0500 | 0062 | 0250 | 0500 | 1000 | 0016 | 0062 |
| SOYBEAN | 0 | 0 | 60 | | 0 | 0 | 20 | 50 | 0 | 0 | 0 | 20 | 0 | 0 | 20 | 70 | 0 | 10 |
| BARNYARD GRASS | 0 | 30 | 60 | | 0 | 0 | 30 | 60 | 0 | 0 | 0 | 60 | 0 | 30 | 50 | 70 | 0 | 0 |
| WILD OATS | 0 | 0 | 0 | | 0 | 0 | 0 | 30 | 0 | 0 | 10 | 30 | 10 | 30 | 50 | 90 | 10 | 30 |
| MORNINGGLORY | 0 | 0 | 0 | 20 | 0 | 10 | 20 | 30 | 0 | 0 | 30 | 0 | 30 | 50 | 50 | 30 | 0 | 0 |
| WHEAT | 0 | 0 | 50 | 40 | 0 | 30 | 50 | 70 | 0 | 0 | 0 | 0 | 40 | 20 | 20 | 0 | 0 | 30 |
| CASSIA | 30 | 30 | 90 | | 0 | 0 | 30 | 50 | 0 | 0 | 0 | 0 | 0 | 0 | 0 | 30 | 0 | 0 |
| JOHNSONGRASS | 0 | 60 | 60 | 20 | 0 | 30 | 60 | 90 | 0 | 30 | 60 | 80 | 30 | 90 | 90 | 100 | 0 | 20 |
| NUTSEDGE | 0 | 40 | 0 | | 0 | 0 | 30 | 70 | 0 | 0 | 60 | 50 | 10 | 20 | 80 | 100 | 10 | 30 |
| CORN | 0 | 0 | 50 | | 0 | 0 | 0 | 20 | 0 | 0 | 10 | 30 | 0 | 20 | 70 | 70 | 60 | 20 |
| WILD BUCKWHEAT | 0 | 30 | | 50 | 30 | 50 | 70 | 0 | 0 | 0 | 30 | 0 | 0 | 80 | 80 | 90 | 0 | 80 |
| BLACK GRASS | | | | | 20 | 30 | 60 | 90 | 0 | 10 | 20 | 30 | 40 | 60 | 90 | 70 | 0 | 20 |
| RAPESEED | 0 | 0 | 0 | | 0 | 20 | 30 | 60 | 0 | 40 | 50 | 0 | 10 | 10 | 40 | 40 | 0 | 70 |
| BARLEY | 0 | 30 | 50 | 50 | 0 | 40 | 50 | 80 | 30 | 40 | 40 | 0 | 60 | 60 | 80 | 80 | 30 | 20 |
| GREEN FOXTAIL | 0 | 30 | 50 | | 20 | 30 | 30 | 70 | 10 | 40 | 40 | 50 | 30 | 30 | 50 | 60 | 20 | 30 |
| CHEAT GRASS | | | | | 0 | 0 | 30 | 50 | 0 | 30 | 0 | 60 | 0 | 50 | 20 | 50 | 30 | 0 |
| VIOLA | 50 | 70 | 90 | | 0 | 0 | 0 | 40 | 20 | 30 | 0 | 50 | 50 | 60 | 80 | 90 | 0 | 60 |
| LAMBSQUARTER | | | | | | | | | | | | | | | | | | |
| GIANT FOXTAIL | 20 | 30 | 60 | 100 | 0 | 0 | 0 | 40 | 0 | 0 | 20 | 20 | 0 | 50 | 50 | 70 | | |
| VELVETLEAF | 0 | 30 | 40 | 90 | 0 | 0 | 0 | 0 | 0 | 40 | 50 | 50 | 20 | 30 | 90 | 70 | | |
| SUGAR BEETS | 70 | 80 | 90 | 100 | 0 | 0 | 0 | 0 | 10 | 20 | 60 | 70 | 70 | 80 | 20 | 90 | | |
| CRABGRASS | 0 | 0 | 50 | 70 | 0 | 0 | 0 | 50 | 0 | 0 | 30 | 80 | 0 | 0 | 20 | 30 | | |
| TEAWEED | 20 | 70 | 70 | 80 | 0 | 0 | 0 | 40 | 0 | 30 | 70 | 90 | 0 | 0 | 0 | 30 | | |
| JIMSONWEED | 0 | 20 | 40 | 80 | 0 | 0 | 0 | 0 | 0 | 30 | 80 | 80 | 40 | 90 | 95 | 100 | | |
| RICE | 70 | 80 | 90 | 100 | 0 | 0 | 0 | 50 | 0 | 30 | 80 | 80 | 0 | 20 | | 70 | | |
| COCKLEBUR | 20 | 40 | 50 | 80 | 0 | 0 | 0 | 0 | 0 | 20 | 30 | 50 | 0 | 20 | 60 | 90 | | |
| COTTON | 0 | 0 | 40 | 90 | 0 | 0 | 0 | 0 | 0 | 10 | 20 | 40 | 0 | 80 | 60 | 70 | | |
| SOYBEAN | 0 | 0 | 20 | 70 | 0 | 0 | 20 | 0 | 0 | 0 | 0 | 30 | 30 | 60 | 90 | 90 | | |
| BARNYARD GRASS | 0 | 10 | 50 | 90 | 0 | 0 | 0 | 0 | 0 | 10 | 30 | 30 | 30 | 0 | 70 | 70 | | |
| WILD OATS | 0 | 20 | 50 | 80 | 0 | 0 | 0 | 0 | 0 | 20 | 50 | 50 | 0 | 50 | 50 | 40 | | |
| MORNINGGLORY | 30 | 40 | 40 | 50 | 0 | 0 | 0 | 20 | 0 | 30 | 30 | 40 | 20 | 0 | 20 | 80 | | |
| WHEAT | 10 | 10 | 40 | 50 | 0 | 0 | 0 | 0 | 10 | 20 | 50 | 60 | 0 | 50 | 40 | 60 | | |
| CASSIA | 0 | 30 | 50 | 90 | 0 | 0 | 0 | 0 | 20 | 50 | 60 | 70 | 30 | 60 | 60 | 50 | | |
| JOHNSONGRASS | 60 | 80 | 90 | 100 | 0 | 0 | 0 | 20 | 30 | 70 | 90 | 90 | 0 | 0 | 20 | 60 | | |
| NUTSEDGE | 0 | 10 | 70 | 90 | 0 | 0 | 0 | 0 | 0 | 60 | 60 | 80 | 0 | 0 | 40 | 50 | | |
| CORN | 0 | 20 | 80 | 90 | 0 | 0 | 0 | 0 | 0 | 20 | 50 | 60 | 50 | 80 | 80 | 90 | | |
| WILD BUCKWHEAT | 70 | 70 | 80 | 90 | 0 | 0 | 20 | 0 | 30 | 20 | 50 | 70 | 0 | 70 | 70 | 100 | | |
| BLACK GRASS | 30 | 70 | 80 | 100 | 0 | 0 | 0 | 0 | 40 | 40 | 80 | 80 | 80 | 80 | 70 | 100 | | |
| RAPESEED | 20 | 80 | 90 | 50 | 0 | 0 | 0 | 40 | 0 | 40 | 80 | 10 | 0 | 80 | 0 | 0 | | |
| BARLEY | 0 | 20 | 40 | 100 | 0 | 0 | 0 | 0 | 0 | 20 | 0 | 50 | 0 | 0 | 30 | 70 | | |
| GREEN FOXTAIL | 0 | 30 | 70 | 80 | 0 | 0 | 20 | 0 | 20 | 50 | 30 | 80 | 60 | 20 | 60 | 70 | | |
| CHEAT GRASS | 40 | 50 | 50 | 100 | 0 | 0 | 0 | 0 | 0 | 40 | 70 | 80 | 40 | 40 | 20 | 50 | | |
| VIOLA | 20 | 50 | 70 | 80 | 0 | 0 | 0 | | 0 | 40 | 60 | 80 | 0 | 0 | 80 | 90 | | |
| LAMBSQUARTER | 40 | 60 | 80 | 90 | 0 | 0 | 0 | 0 | 40 | 40 | 80 | 100 | 50 | 60 | 80 | 90 | | |

TEST C

The purpose of this screen is to identify and characterize potential sugarbeet herbicides.

Seeds of the following crops and weeds are sown into 18 cm diameter plastic pots containing steam-sterilized Sassafras sandy loam soil (0.8% organic soil, pH 6.7): spring wheat (*Triticum gestivum*), spring barley (*Hordeum vulgare*), sugarbeets (*Beta vulgaris*), black nightshade (*Solanum nigrum*), chickweed (*Stellaria media*), cleavers (*Galium aparine*), common lambsquarters (*Chenopodium album*), knotweed (*Polygonum aviculare*), kockia (*Kochia scoparia*), matricaria (*Matricaria indora*), redroot pigweed (*Amaranthus retroflexus*), speedwell (*Veronica persica*), wild mustard (*Sinapis arvensis*), wild radish (*Raphinus raphinistrum*), smartweed (*Polygonum pericaria*), black bindweed (*Polygonum convolvulus*), annual bluegrass (*Poa annua*), annual ryegrass (*Lolium multiflorum*), blackgrass (*Alopecurus myosuroides*), green foxtail (*Setaria viridis*), and wild oats (*Avena fatua*).

The compound tested is formulated in a non-phytotoxic solvent and applied as a spray to the soil (preemergence) or to the foliage and soil (postemergence). Plants are treated at three stages: (1) preemergence, (2) postemergence when the sugarbeets are in the 1–2 leaf stage (Postemergence 1), and (3) postemergence when the sugarbeets are in the 3–4 leaf stage (Postemergence 2). Plants are grown in a temperature-controlled greenhouse for the duration of the experiment.

Weed control and crop injury are evaluated visually (38 days after the Pre treatment, 28 days after Post treatment 1, and 11 days after Post treatment 2). Ratings are expressed using a scale of 0 to 100, where 0 means no injury or control and 100 means complete death of the plants. The ratings are summarized in Table C.

TABLE C

| RATE RATE GM/HA | CMPD 9 | | | | CMPD 10 | | | | CMPD 12 | | | |
|---|---|---|---|---|---|---|---|---|---|---|---|---|
| | 0030 | 0063 | 0125 | 0250 | 0030 | 0063 | 0125 | 0250 | 0030 | 0063 | 0125 | 0250 |
| PREEMERGENCE | | | | | | | | | | | | |
| WHEAT | 0 | 20 | 20 | 25 | 20 | 45 | 50 | 80 | 0 | 25 | 30 | 65 |
| BARLEY | 0 | 25 | 35 | 50 | 20 | 50 | 60 | 90 | 0 | 15 | 45 | 85 |
| BLCK NIGHTSHADE | 20 | 0 | 20 | 20 | 20 | 65 | 90 | 95 | 20 | 20 | 20 | 20 |
| CHICK WEED | 0 | 20 | 0 | 0 | 0 | 0 | 20 | 20 | 0 | 0 | 0 | 20 |
| LAMBSQUARTER | 80 | 80 | 80 | 80 | 70 | 50 | 100 | 100 | 50 | 50 | 60 | 80 |
| GALIUM | 0 | 50 | 50 | 100 | 100 | 100 | 100 | 100 | 20 | 20 | 60 | 100 |
| MATRA INDORA | 0 | 0 | 0 | 0 | 35 | 80 | 100 | 100 | 0 | 30 | 20 | 75 |
| PIG WEED | 20 | 0 | 20 | 20 | 0 | 20 | 30 | 20 | 30 | 20 | 25 | 35 |
| SMART WEED | 25 | 0 | 20 | 20 | 0 | 90 | 80 | 100 | 0 | 20 | 100 | 0 |
| SPEEDWELL | 30 | 35 | 25 | 30 | 0 | 0 | 20 | 0 | 25 | 20 | 20 | 30 |
| BUCKWHEAT | 25 | 45 | 25 | 25 | 30 | 55 | 90 | 100 | 0 | 0 | 25 | 100 |
| MUSTARD | 50 | 50 | 70 | 90 | 50 | 90 | 100 | 100 | 0 | 95 | 100 | 100 |
| WILD RADISH | 0 | 20 | 50 | 50 | 0 | 70 | 95 | 100 | 50 | 60 | 50 | 95 |
| BLUE GRASS | 0 | 0 | 20 | 50 | 0 | 60 | 75 | 90 | 0 | 15 | 50 | 80 |
| RYE GRASS | 0 | 0 | 0 | 0 | 0 | 20 | 40 | 80 | 0 | 0 | 20 | 45 |
| BLACK GRASS | 0 | 60 | 70 | 25 | 0 | 0 | 100 | 100 | 0 | 20 | 30 | 90 |
| GREEN FOXTAIL | 20 | 50 | 20 | 20 | 30 | 65 | 80 | 80 | 0 | 0 | 20 | 20 |
| WILD OATS | 0 | 0 | 30 | 0 | 50 | 35 | 20 | 80 | 0 | 0 | 20 | 50 |
| SUGARBEET C/TOL | 40 | 20 | 40 | 25 | 0 | 25 | 40 | 10 | 0 | 10 | 25 | 10 |

| RATE RATE GM/HA | CMPD 9 | | | | CMPD 10 | | | | CMPD 12 | | | |
|---|---|---|---|---|---|---|---|---|---|---|---|---|
| | 0016 | 0030 | 0063 | 0125 | 0016 | 0030 | 0063 | 0125 | 0016 | 0030 | 0063 | 0125 |
| POSTEMERGENCE 1 | | | | | | | | | | | | |
| WHEAT | 25 | 60 | 75 | 85 | 70 | 90 | 100 | 95 | 70 | 70 | 70 | 80 |
| BARLEY | 25 | 60 | 80 | 80 | 70 | 80 | 90 | 95 | 30 | 70 | 85 | 80 |
| BLCK NIGHTSHADE | 0 | 40 | 40 | 40 | 70 | 90 | 90 | 100 | 0 | 30 | 30 | 30 |
| CHICK WEED | 30 | 0 | 30 | 20 | 25 | 25 | 25 | 0 | 0 | 0 | 0 | 0 |
| LAMBSQUARTER | 20 | 0 | 0 | 0 | 70 | 80 | 80 | 90 | 30 | 0 | 0 | 50 |
| GALIUM | 20 | 50 | 100 | 40 | 85 | 100 | 100 | 100 | 0 | 20 | 0 | 60 |
| MATRA INDORA | 0 | 20 | 35 | 40 | 80 | 95 | 100 | 100 | 20 | 20 | 0 | 80 |
| PIG WEED | 40 | 60 | 30 | 70 | 50 | 60 | 50 | 80 | 0 | 30 | 40 | 60 |
| SMART WEED | 0 | 0 | 0 | 0 | 85 | 100 | 90 | 100 | 0 | 20 | 20 | 20 |
| SPEEDWELL | 0 | 20 | 20 | 20 | 25 | 0 | 0 | 25 | 0 | 0 | 0 | 25 |
| BUCKWHEAT | 0 | 30 | 30 | 30 | 70 | 80 | 90 | 100 | 30 | 20 | 20 | 70 |
| MUSTARD | 100 | 100 | 100 | 100 | 100 | 100 | 100 | 100 | 100 | 100 | 100 | 100 |
| WILD RADISH | 70 | 100 | 100 | 100 | 100 | 100 | 100 | 100 | 90 | 100 | 100 | 100 |
| BLUE GRASS | 0 | 0 | 15 | 30 | 50 | 80 | 90 | 90 | 0 | 0 | 0 | 60 |
| RYE GRASS | 20 | 20 | 30 | 60 | 0 | 100 | 95 | 100 | 20 | 40 | 40 | 60 |
| BLACK GRASS | 0 | 0 | 20 | 90 | 50 | 95 | 100 | 100 | 20 | 80 | 80 | 100 |
| GREEN FOXTAIL | 0 | 0 | 30 | 20 | 60 | 70 | 90 | 95 | 20 | 0 | 20 | 30 |
| WILD OATS | 10 | 25 | 20 | 40 | 90 | 100 | 100 | 100 | 20 | 20 | 20 | 50 |
| SUGARBEET C/TOL | 15 | 20 | 20 | 25 | 20 | 30 | 20 | 50 | 0 | 0 | 20 | 25 |

| RATE GM/HA | CMPD 9 | | | | CMPD 10 | | | | CMPD 12 | |
|---|---|---|---|---|---|---|---|---|---|---|
| | 0016 | 0030 | 0063 | 0125 | 0016 | 0030 | 0063 | 0125 | 0063 | 0125 |
| POSTEMERGENCE 2 | | | | | | | | | | |
| WHEAT | 30 | 25 | 30 | 30 | 20 | 60 | 40 | 50 | 20 | 40 |
| BARLEY | 35 | 45 | 30 | 25 | 30 | 50 | 50 | 40 | 20 | 50 |
| SUGARBEET CROPS | | | | | | | | | | |
| BLCK NIGHTSHADE | 50 | 50 | 50 | 50 | 25 | 50 | 50 | 50 | 20 | 60 |
| CHICK WEED | 80 | 80 | 85 | 90 | 60 | 50 | 65 | 80 | 20 | 25 |
| LAMBSQUARTER | 0 | 20 | 20 | 20 | 30 | 50 | 50 | 50 | 0 | 30 |
| GALIUM | 20 | 40 | 65 | 70 | 30 | 60 | 50 | 70 | 55 | 30 |
| KNOT WEED | | | | | | | | | | |

TABLE C-continued

| KOCHIA | | | | | | | | | | |
|---|---|---|---|---|---|---|---|---|---|---|
| MATRA INDORA | 0 | 0 | 0 | 0 | 20 | 20 | 0 | 20 | 0 | 0 |
| PIG WEED | 50 | 50 | 70 | 65 | 60 | 50 | 60 | 80 | 0 | 30 |
| SMART WEED | 0 | 30 | 0 | 30 | 0 | 20 | 40 | 60 | 0 | 0 |
| SPEEDWELL | 25 | 20 | 25 | 20 | 20 | 25 | 25 | 20 | 30 | 25 |
| BUCKWHEAT | 0 | 30 | 70 | 80 | 30 | 50 | 50 | 50 | 0 | 25 |
| MUSTARD | 70 | 70 | 60 | 85 | 60 | 50 | 90 | 30 | 30 | 80 |
| WILD RADISH | 25 | 20 | 50 | 25 | 0 | 20 | 50 | 25 | 0 | 50 |
| BLUE GRASS | 0 | 0 | 0 | 15 | 0 | 0 | 0 | 20 | 0 | 0 |
| RYE GRASS | 0 | 15 | 25 | 35 | 50 | 35 | 20 | 10 | 30 | 70 |
| BLACK GRASS | 25 | 50 | 30 | 70 | 40 | 20 | 50 | 80 | 20 | 40 |
| GREEN FOXTAIL | 20 | 20 | 0 | 0 | 20 | 20 | 20 | 20 | 0 | 0 |
| WILD OATS | 0 | 10 | 50 | 20 | 60 | 60 | 20 | 25 | 20 | 20 |
| SUGARBEET C/TOL | 10 | 15 | 15 | 20 | 15 | 15 | 20 | 25 | 15 | 20 |

TEST D

This test was conducted to evaluate compounds for potential utility in fallow weed control. This test was comprised of a preemergence segment and a postemergence segment. Both segments were conducted in 26 cm plastic pans containing pasteurized Sassafras sandy loam soil (pH 6.5, 1% organic matter). The postemergence fallow segment was planted in two parts with a separation of seven days between the first and second plantings. The common name, botanical name, and size at herbicide application are presented in the following tables.

| Common Name | Botanical Name | Size (cm) |
|---|---|---|
| Downy brome | Bromus tectorum | 7.0 |
| Kochia, Fireweed | Kochia scoparia | 3.0 |
| Russian thistle | Salsoa kali | 3.0 |
| Wild oats | Avena fatua | 6.0 |
| Field bindweed | Convolvulus arvensis | 4.0 |
| Cereal rye | Secale cereale | 7.0 |
| Green foxtail | Setaria viridis | 5.0 |
| Winter wheat | Triticum aestivum | 8.0 |

The postemergence segment of the screen was grown in the greenhouse for approximately 18 days until treatment. The preemergence segment was planted immediately before herbicidal application using the following species.

| Common Name | Botanical Name |
|---|---|
| Jointed goatgrass | Aegilops cylindrica |
| Redroot pigweed | Amaranthus retroflexus |
| Wild oats | Avena fatua |
| Common lambsquarters | Chenopodium album |
| Field bindweed | Convolvulus arvensis |
| Downy brome | Bromus tectorum |
| Spring barley | Hordeum vulgare |
| Kochia, Fireweed | Kochia scoparia |
| Wild buckwheat | Polygonum convolvulus |
| Russian thistle | Salsoa kali |
| Cereal rye | Secale cereale |
| Green foxtail | Setaria viridis |
| Sorghum | Sorghum bicolor |
| Spring wheat | Triticum aestivum |
| Winter wheat | Triticum aestivum |
| Corn | Zea mays |

All herbicides were applied to pots and plants using a belt sprayer with the compound dissolved in AGWT, a non-phytotoxic solvent system. All treatments were maintained in the greenhouse for 21 days at which time they were rated on a scale of 0 to 100 for each species (0=no control, 100=complete control). The response data are summarized in Table D. "Cheat grass" recited in this table was actually downy brome, a related Bromus species.

TABLE D

| | CMPD 13 | | | | |
|---|---|---|---|---|---|
| RATE RATE = G/H | 64. | 125. | 250. | 500. | 1000. |
| PREEMERGENCE | | | | | |
| WINE WHEAT | 0 | 20 | 40 | 60 | 60 |
| RUSSIAN THSTL | 0 | 0 | 0 | 20 | 40 |
| KOCHIA | 20 | 50 | 60 | 80 | 100 |
| CHEAT GRASS | 10 | 20 | 40 | 60 | 70 |
| GREEN FXTL | 0 | 10 | 30 | 40 | 60 |
| WHEAT | 40 | 60 | 90 | 90 | 90 |
| WILD OATS | 0 | 0 | 30 | 50 | 70 |
| RYE | 0 | 0 | 0 | 20 | 30 |
| BARLEY | 30 | 50 | 70 | 90 | 90 |
| CORN | 20 | 40 | 70 | 100 | 100 |
| SORGHUM | 60 | 70 | 90 | 100 | 100 |
| FIELD BINDWEED | 0 | 0 | 0 | 20 | 50 |
| JOINT GOATGRASS | 0 | 0 | 20 | 30 | 40 |
| WILD BUCKWHEAT | 0 | 0 | 30 | 50 | 70 |
| LAMBSQUARTER | 40 | 60 | 70 | 70 | 90 |
| PIG WEED | 20 | 30 | 80 | 80 | 90 |

| | CMPD 13 | | | | |
|---|---|---|---|---|---|
| RATE RATE = G/H | 64. | 125. | 250. | 500. | 1000. |
| POSTEMERGENCE | | | | | |
| RUSSIAN THISTLE | 0 | 70 | 100 | 100 | 100 |
| KOCHIA | 100 | 100 | 100 | 100 | 100 |
| CHEAT GRASS | 90 | 90 | 90 | 90 | 90 |
| GREEN FOXTAIL | 60 | 70 | 80 | 90 | 100 |
| WILD OATS | 40 | 40 | 70 | 90 | 100 |
| WHEAT | 90 | 90 | 100 | 100 | 100 |
| RYE | 90 | 90 | 100 | 100 | 100 |
| FIELD BINDWEED | 60 | 100 | 100 | 100 | 100 |

What is claimed is:

1. A compound selected from

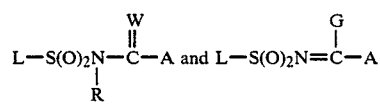

wherein

R is H; $C_1$-$C_3$ alkyl optionally substituted with halogen; $C_1$-$C_3$ thioalkyl optionally substituted with halogen; benzyl optionally substituted with F, Cl, $OCH_3$, $SCH_3$ or $NO_2$; allyl; propargyl; —C(O)(-$C_1$-$C_3$ alkyl); $CO_2CH_3$; or $CO_2CH_2CH_3$;

G is Cl, OR' or SR';

R' is $C_1$-$C_3$ alkyl optionally substituted with halogen;

W is O, S, NR" or NOR";

R" is H or $C_1$-$C_3$ alkyl optionally substituted with halogen;

L is

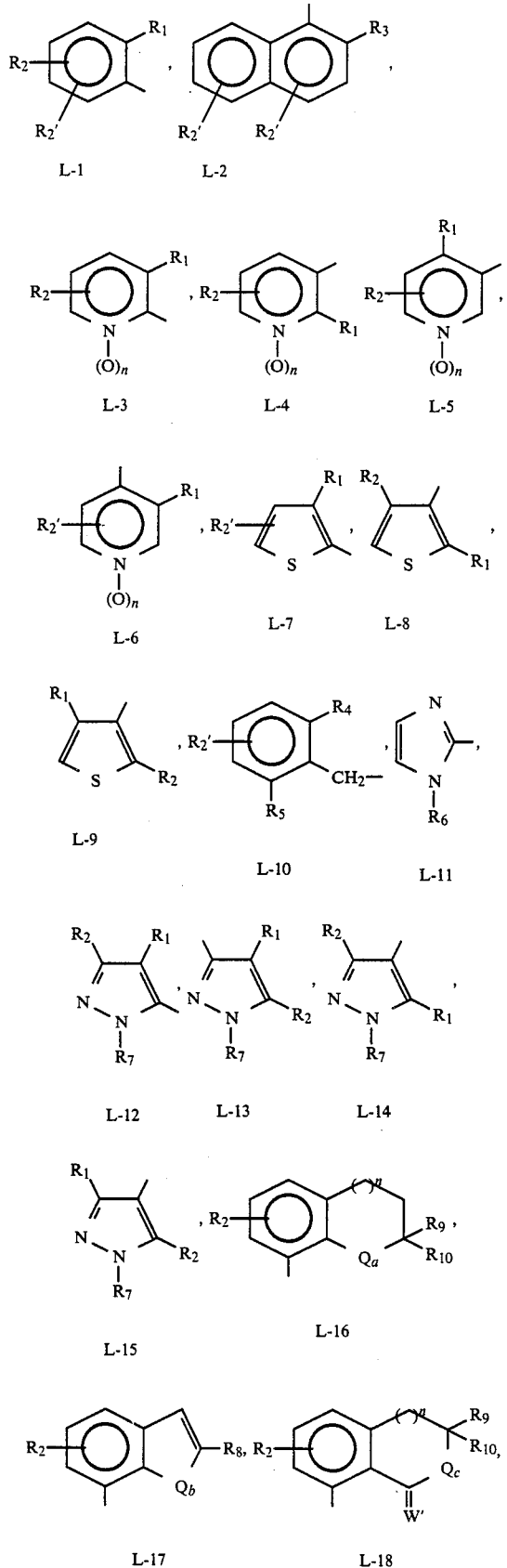
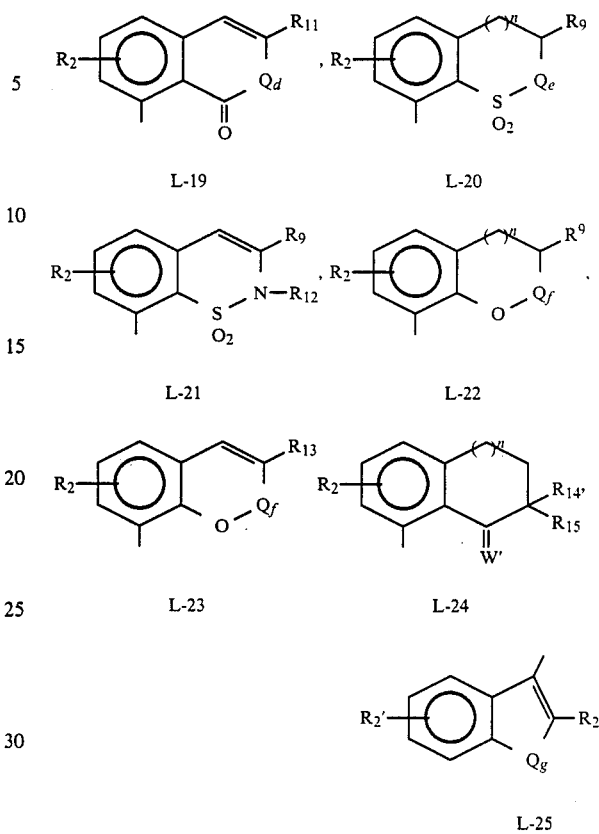

R₁ is H; halogen; NO₂; CH; C₁–C₄ alkyl optionally substituted with F, Cl, Br, CN, OCH₃ or SCH₃; C₂–C₄ alkenyl optionally substituted with F, Cl, Br, OCH₃ or SMe; C₃–C₄ alkynyl; C₃–C₅ cycloalkyl optionally substituted with F, Cl or CH₃; C(O)R₁₆; C(OCH₂CH₂O)R₁₆; C(R₁₆)(OR₁₇)(OR₁₈); CO₂R₁₉; C(O)NR₂₀R₂₁; N₃; S(O)₂NR₂₂R₂₃; S(O)₂OR₂₄; OS(O)₂R₂₅; phenyl optionally substituted by F, Cl, Br, CH₃ or OCH₃; ER₂₆; (CH₂)ₙQ or (CH₂)ₙQ₁;

R₂ is H, halogen, CN, NO₂, C₁–C₃ alkyl optionally substituted with halogen, CO₂R₁₉, S(O)₂NR₂₇R₂₈; NR₂₉R₃₀; ER₃₁; or C₁–C₂ alkyl substituted with C₁–C₂ alkoxy, C₁–C₂ haloalkoxy, C₁–C₂ alkylthio, C₁–C₂ haloalkylthio, CN, OH or SH;

R₂' is independently H, F, Cl, Br, CH₃, OCH₃, or SCH₃;

R₃ is H, CH₃, OCH₃, OCF₂H, F, Cl, Br, CO₂R₁₉, S(O)₂N(CH₃)₂, OS(O)₂CH₃ or S(O)ₚCH₃;

R₄ is Cl, NO₂, CO₂CH₃, CO₂CH₂CH₃, C(O)N(CH₃)₂, OS(O)₂CH₃, S(O)₂CH₃, S(O)₂CH₂CH₃, OCH₃ or OCH₂CH₃;

R₅ is H, C₁–C₃ alkyl, F, Cl, Br, NO₂, S(O)₂NR₃₂R₃₃, S(O)₂N(OCH₃)CH₃ or S(O)ₚR₃₄;

R₆ is C₁–C₃ alkyl or phenyl;

R₇ is H, C₁–C₃ alkyl optionally substituted with halogen, C₃–C₄ alkenyl, or phenyl;

R₈ is H or CH₃;

R₉ is H, CH₃ or CH₂CH₃;

R₁₀ is H, CH₃ or CH₂CH₃;

R₁₁ is H, Cl or C₁–C₃ alkyl;

R₁₂ is H, C₁–C₄ alkyl optionally substituted with F, Cl, Br or OCH₃; C₃–C₅ cycloalkyl optionally substituted with F, Cl or OCH$_3$; C$_3$-C$_4$ alkenyl; or C$_3$-C$_4$ alkynyl;

R$_{13}$ is H or C$_1$-C$_3$ alkyl;

R$_{14}$ is H, F, Cl, Br, CH$_3$ or CH$_2$CH$_3$;

R$_{15}$ is H, F, Cl, Br, CH$_3$ or CH$_2$CH$_3$;

R$_{16}$ is C$_1$-C$_4$ alkyl optionally substituted with F, Cl, Br or OCH$_3$; C$_3$-C$_5$ cycloalkyl optionally substituted with F or Cl; or C$_3$-C$_4$ alkenyl;

R$_{17}$ and R$_{18}$ are independently C$_1$-C$_3$ alkyl;

R$_{19}$ is C$_1$-C$_4$ alkyl, C$_3$-C$_4$ alkenyl, C$_3$-C$_4$ alkynyl; C$_2$-C$_4$ haloalkyl, C$_2$-C$_3$ cyanoalkyl, C$_3$-C$_6$ cycloalkyl, C$_4$-C$_7$ cycloalkylalkyl or C$_2$-C$_4$ alkoxyalkyl;

R$_{20}$ is H, CH$_3$ or CH$_2$CH$_3$;

R$_{21}$ is CH$_3$, CH$_2$CH$_3$, CH$_2$CH$_2$CH$_3$, OCH$_3$ or OCH$_2$CH$_3$; or R$_{20}$ and R$_{21}$ may be taken together to form —(CH$_2$)$_2$(CH$_2$)$_n$(CH$_2$)$_2$— and —CH$_2$CH$_2$OCH$_2$CH$_2$—;

R$_{22}$ is C$_1$-C$_4$ alkyl, C$_2$-C$_3$ cyanoalkyl, OCH$_3$, OCH$_2$CH$_3$, N(CH$_3$)$_2$, C$_3$-C$_4$ alkenyl, C$_3$-C$_4$ alkynyl, cyclopropylmethyl or C$_3$-C$_4$ cycloalkyl;

R$_{23}$ is H, C$_1$-C$_4$ alkyl or C$_3$-C$_4$ alkenyl; or

R$_{22}$ and R$_{23}$ may be taken together as —(CH$_2$)$_3$—, —(CH$_2$)$_4$— or —CH$_2$CH$_2$OCH$_2$CH$_2$—;

R$_{24}$ is C$_1$-C$_3$ alkyl or C$_1$-C$_3$ haloalkyl;

R$_{25}$ is C$_1$-C$_3$ alkyl or N(CH$_3$)$_2$;

R$_{26}$ is C$_1$-C$_4$ alkyl, C$_1$-C$_4$ haloalkyl, C$_2$-C$_4$ alkoxyalkyl, C$_3$-C$_4$ alkenyl, C$_3$-C$_4$ alkynyl, phenyl optionally substituted by F, Cl, Br, CH$_3$ or OCH$_3$, or C$_2$-C$_4$ haloalkenyl;

R$_{27}$ is C$_1$-C$_3$ alkyl;

R$_{28}$ is H, C$_1$-C$_4$ alkyl or methoxy;

R$_{27}$ and R$_{28}$ may be taken together to form —(CH$_2$)$_4$—, —(CH$_2$)$_5$— or —CH$_2$CH$_2$OCH$_2$CH$_2$—;

R$_{29}$ and R$_{30}$ are independently H, CH$_3$ or CH$_2$CH$_3$;

R$_{31}$ is C$_1$-C$_4$ alkyl optionally substituted with F, Cl or OCH$_3$;

R$_{32}$ is CH$_3$ or CH$_2$CH$_3$;

R$_{33}$ is H, CH$_3$ or CH$_2$CH$_3$;

R$_{34}$ is C$_1$-C$_3$ alkyl, C$_3$-C$_4$ alkenyl or C$_3$-C$_4$ alkynyl;

Q$_a$ is O, S, S(O), S(O)$_2$ or NCH$_3$;

Q$_b$ is O, S, or S(O)$_2$;

Q$_c$ is O, S, NH, N(C$_1$-C$_3$ alkyl), NCH$_2$CH=CH$_2$ or NCH$_2$C≡CH;

Q$_d$ is O, NH, N(C$_1$-C$_3$ alkyl), NCH$_2$CH=CH$_2$ or NCH$_2$C≡CH;

Q$_e$ is O or NR$_{12}$;

Q$_f$ is C(O) or S(O)$_2$;

Q$_g$ is O, S, NH or N(C$_1$-C$_3$ alkyl);

n is 0 or 1;

p is 0, 1 or 2;

W' is O or S;

E is O, S, S(O) or S(O)$_2$;

Q is

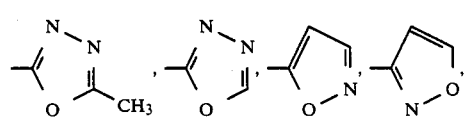

Q-1　Q-2　Q-3　Q-4

-continued

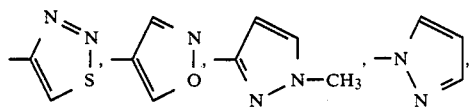

Q-5　Q-6　Q-7　Q-8

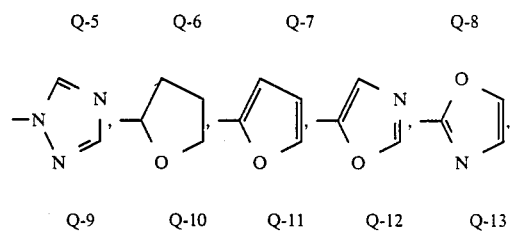

Q-9　Q-10　Q-11　Q-12　Q-13

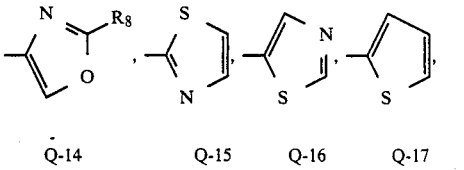

Q-14　Q-15　Q-16　Q-17

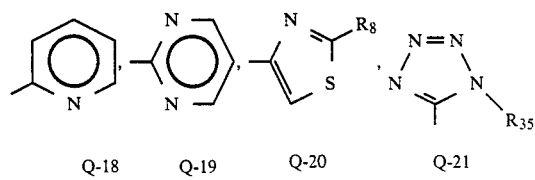

Q-18　Q-19　Q-20　Q-21

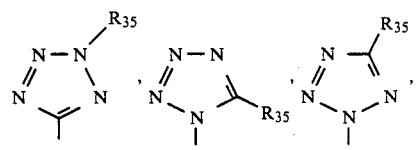

Q-22　Q-23　Q-24

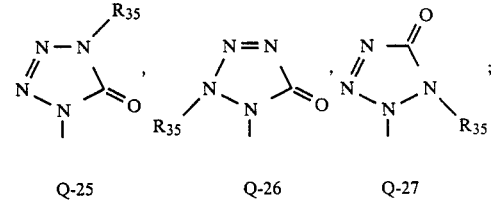

Q-25　Q-26　Q-27

Q$_1$ is

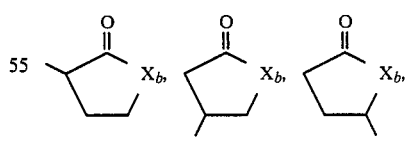

Q$_1$-1　Q$_1$-2　Q$_1$-3

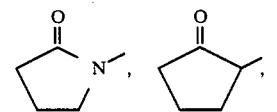

Q$_1$-4　Q$_1$-5　Q$_1$-6

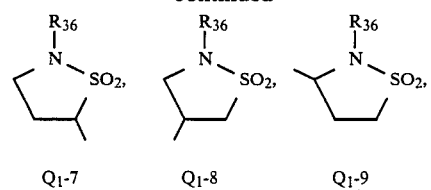
Q₁-7, Q₁-8, Q₁-9
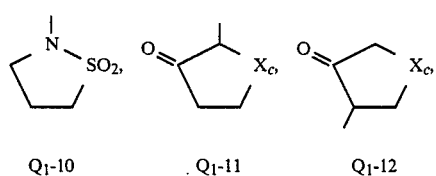
Q₁-10, Q₁-11, Q₁-12
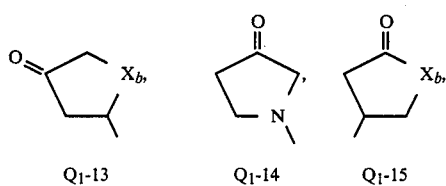
Q₁-13, Q₁-14, Q₁-15
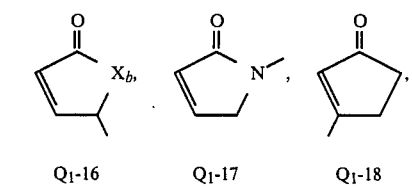
Q₁-16, Q₁-17, Q₁-18
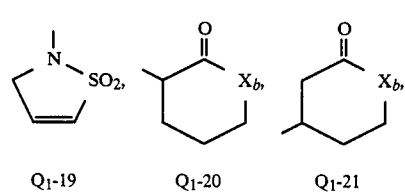
Q₁-19, Q₁-20, Q₁-21
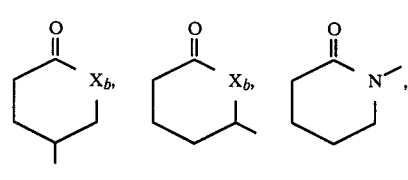
Q₁-22, Q₁-23, Q₁-24
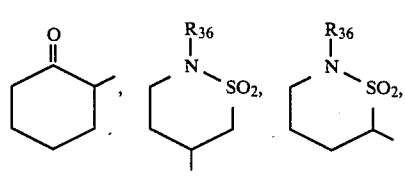
Q₁-25, Q₁-26, Q₁-27
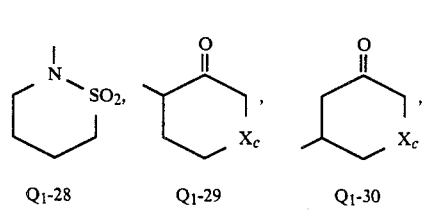
Q₁-28, Q₁-29, Q₁-30
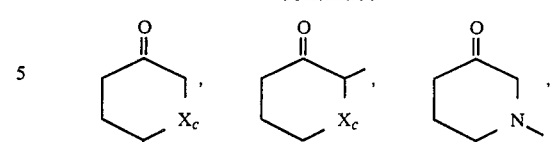
Q₁-31, Q₁-32, Q₁-33
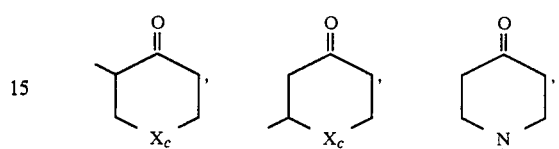
Q₁-34, Q₁-35, Q₁-36
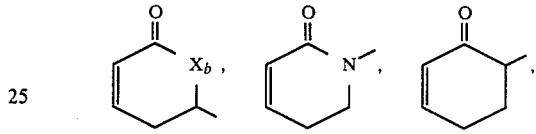
Q₁-37, Q₁-38, Q₁-39
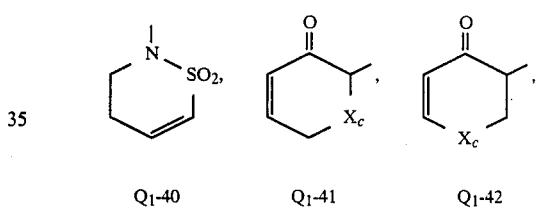
Q₁-40, Q₁-41, Q₁-42
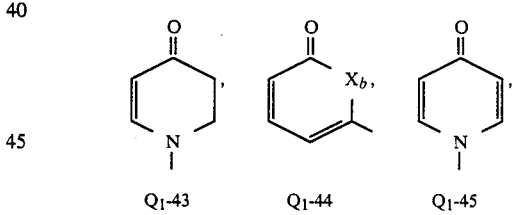
Q₁-43, Q₁-44, Q₁-45
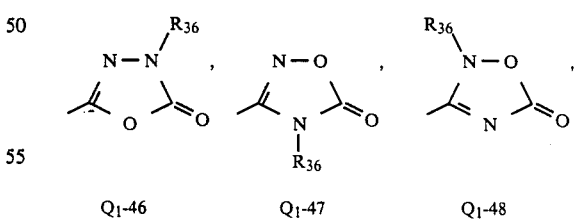
Q₁-46, Q₁-47, Q₁-48
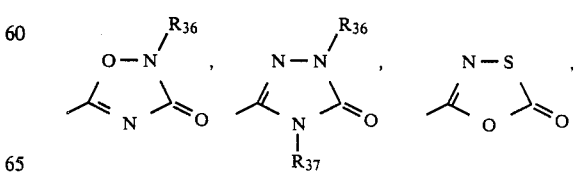
Q₁-49, Q₁-50, Q₁-51

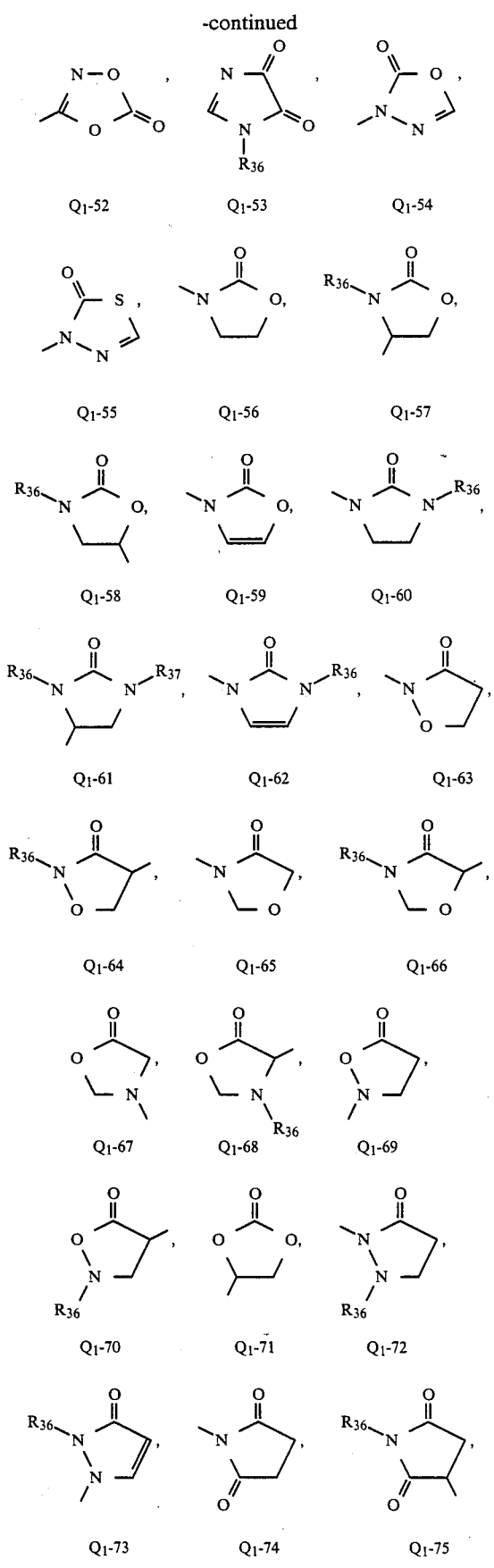
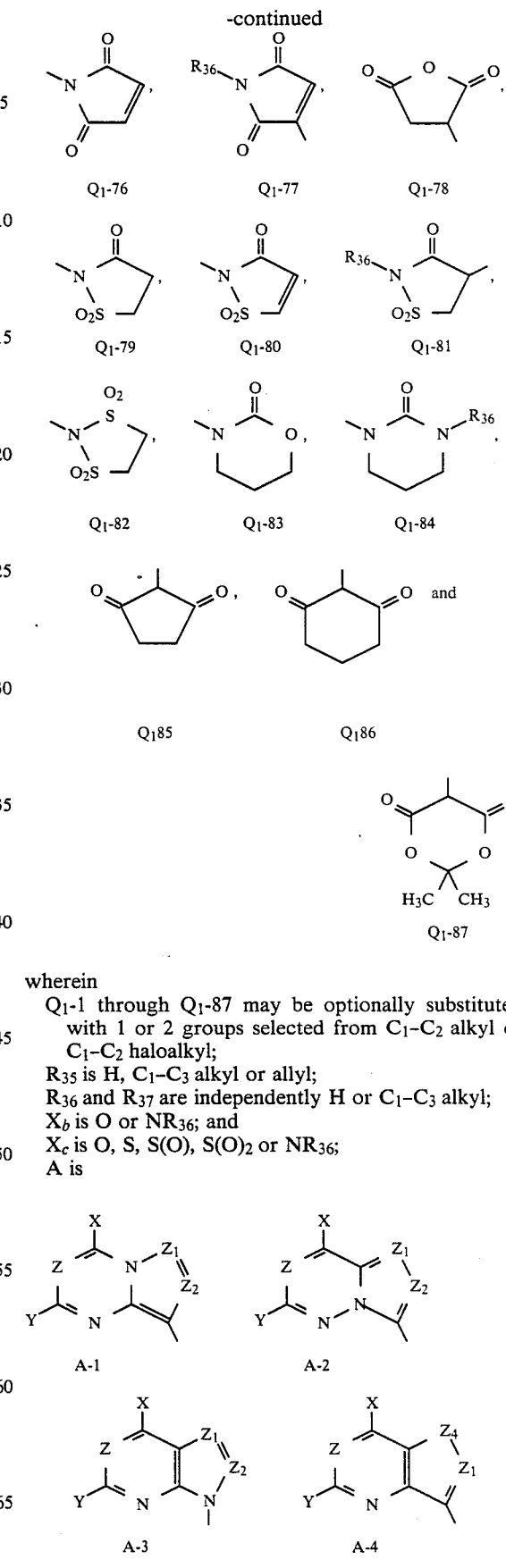
wherein
Q₁-1 through Q₁-87 may be optionally substituted with 1 or 2 groups selected from $C_1$–$C_2$ alkyl or $C_1$–$C_2$ haloalkyl;
$R_{35}$ is H, $C_1$–$C_3$ alkyl or allyl;
$R_{36}$ and $R_{37}$ are independently H or $C_1$–$C_3$ alkyl;
$X_b$ is O or $NR_{36}$; and
$X_c$ is O, S, S(O), S(O)$_2$ or $NR_{36}$;
A is -continued

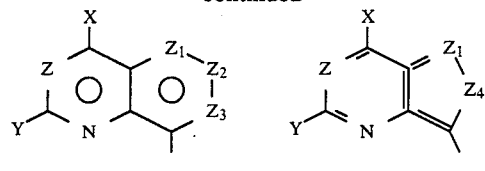

A-5  A-6

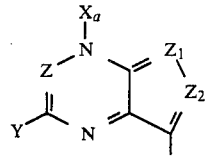   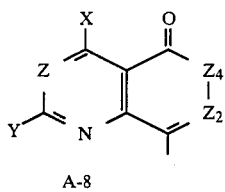

A-7  A-8

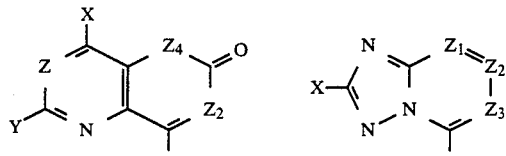

A-9  A-11

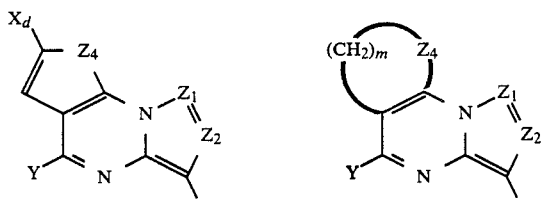

A-12  A-13

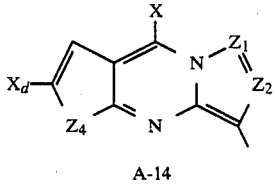

A-14

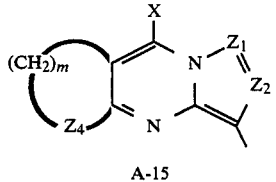

A-15

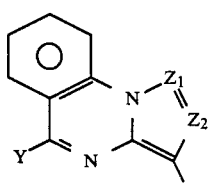

A-17

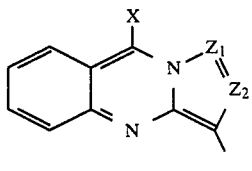

A-18

-continued

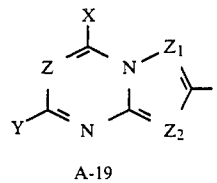

A-19

X or Y is H, halogen, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylsulfinylalkyl, $C_1$–$C_4$ haloalkyl, $C_2$–$C_5$ alkylsulfonylalkyl, $C_3$–$C_5$ cycloalkyl, $C_2$–$C_4$ alkynyl, $C_2$–$C_5$ alkylthioalkyl,

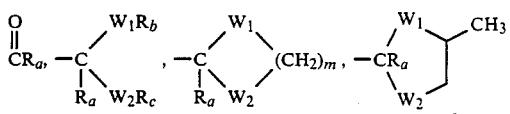

or $N(OCH_3)CH_3$;

$W_1$ and $W_2$ are independently O or S;

m and m' are independently 2 or 3;

$R_a$ is H or $CH_3$;

$R_b$ and $R_c$ are independently $C_1$–$C_2$ alkyl;

Z is CH, N, $CCH_3$, $CCH_2CH_3$, CCl or CBr;

$Z_1$ is C—U, N or N—O;

$Z_2$ and $Z_3$ are independently N or C—U;

$Z_4$ is $NCH_3$, O, S or $CH_2$;

U is H, F, Cl, Br, $C_1$–$C_2$ alkyl optionally substituted by F, Cl, Br or $OCH_3$, CN, $NO_2$, $NMe_2$, OR''', SR''' or $CO_2CH_3$;

R''' is $C_1$–$C_2$ alkyl optionally substituted with F, Cl, Br or $OCH_3$;

$X_a$ is $CH_3$, $CH_2CH_3$ or $CH_2CF_3$; and $X_d$ is H or $CH_3$;

and their agriculturally suitable salts; provided that (1) the total number of carbon atoms of $R_{22}$ and $R_{23}$ is less than or equal to five;

(2) when X or Y is Cl, F, Br or I, then Z is CH and the remaining X or Y is $OCH_3$, $OCH_2CH_3$, $N(OCH_3)CH_3$, $NHCH_3$, $N(CH_3)_2$ or $OCF_2H$;

(3) when X or Y is $C_1$ haloalkoxy, then Z is CH;

(4) at least one of X or Y is X' where X' is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, $C_2$–$C_5$ alkoxyalkoxy, amino, $C_1$–$C_3$ alkylamino or di($C_1$–$C_3$ alkyl)amino;

(5) the total number of carbon atoms of $R_{27}$ and $R_{28}$ is less than or equal to five;

(6) when A is A-1, A-2, A-7 or A-19 then Z is a carbon value, and when A is A-3, A-4, A-5, A-6, A-8 and A-9 then Z is N; and (7) when A is A-11 then one of $Z_1$, $Z_2$ or $Z_3$ is N.

2. A compound of claim 1 where A is A-1, A-2, A-4, A-6, A-7, A-8, A-9, A-11, or A-19.

3. A compound of claim 2 where
Formula I is Formula Ia;
W is O; and
R is H.

4. A compound of claim 2 where
Formula I is Formula Ib;
G is $OR^4$ or SR'.

5. A compound of claim 3 where $R_2'$ is H;

X' is $C_1$-$C_2$ alkyl, $C_1$-$C_2$ alkoxy, $OCF_2H$, $CH_2F$, $CF_3$, $OCH_2CH_2F$, $OCH_2CHF_2$, $OCH_2CF_3$, $CH_2Cl$ or $CH_2Br$;

X or Y is H, $C_1$-$C_2$ alkyl, $C_1$-$C_2$ alkoxy, $CH_2OCH_3$, Cl, F, Br, I, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

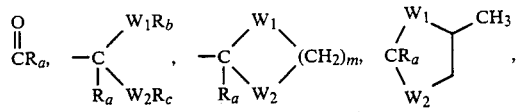

$OCF_2H$, $SCF_2H$, cyclopropyl, $C\equiv CH$ or $C\equiv CCH_3$; and

Z is CH.

6. A compound of claim 5 where $R_1$ is halogen; $NO_2$; CH; $C_1$-$C_3$ alkyl optionally substituted with F, Cl, Br, CN, $OCH_3$ or $SCH_3$; $C_3$ alkenyl optionally substituted with F, Cl or Br; $C_3$ alkynyl; $C_3$ cycloalkyl optionally substituted with F, Cl or $CH_3$; $C(O)R_{16}$; $C(OCH_2CH_2O)R_{16}$; $C(R_{16})(OR_{17})(OR_{18})$; $CO_2R_{19}$; $C(O)NR_{20}R_{21}$; $N_3$; $S(O)_2NR_{22}R_{23}$; $OS(O)_2R_{25}$; $ER_{26}$; $(CH_2)_nQ$ or $(CH_2)_nQ_1$;

$R_{16}$ is $C_1$-$C_3$ alkyl, $C_3$ cycloalkyl or $C_3$ alkenyl;

$R_{17}$ and $R_{18}$ are $C_1$-$C_2$ alkyl;

$R_{19}$ is $C_1$-$C_3$ alkyl, $C_3$ alkenyl, $CH_2CH_2F$, $CH_2CH_2Cl$, $CH_2CH_2OCH_3$ or cyclopropyl methyl;

$R_{20}$ is H or $CH_3$;

$R_{21}$ is $CH_3$, $CH_2CH_3$ or $OCH_3$;

$R_{22}$ is $C_1$-$C_3$ alkyl, $OCH_3$, $OCH_2CH_3$, allyl, propargyl or cyclopropyl;

$R_{23}$ is H, $CH_3$ or $CH_2CH_3$;

$R_{26}$ is $C_1$-$C_3$ alkyl optionally substituted by halogen, $C_2$-$C_3$ alkoxyalkyl, allyl, propargyl or $C_2$-$C_3$ haloalkenyl;

n is 0; and $Q_1$ is $Q_1$-1, $Q_1$-4, $Q_1$-5, $Q_1$-7, $Q_1$-10, $Q_1$-11, $Q_1$-12, $Q_1$-17, $Q_1$-19, $Q_1$-20, $Q_1$-24, $Q_1$-25, $Q_1$-27, $Q_1$-28, $Q_1$-36, $Q_1$-38, $Q_1$-46, $Q_1$-47, $Q_1$-54, $Q_1$-56, $Q_1$-59, $Q_1$-60, $Q_1$-63, $Q_1$-71, $Q_1$-74, $Q_1$-76, $Q_1$-78 or $Q_1$-79.

7. A compound of claim 6 where $R_2$ is H; halogen; CN; $NO_2$; $CH_3$; $CF_3$; $ER_{31}$; or $C_1$-$C_2$ alkyl substituted with $C_1$-$C_2$ alkoxy, $C_1$-$C_2$ haloalkoxy, $C_1$-$C_2$ alkylthio, $C_1$-$C_2$ haloalkylthio or CN;

E is O or S; and $R_{31}$ is $C_1$-$C_2$ alkyl optionally substituted with F, Cl or $OCH_3$.

8. A compound of claim 7 where

W' is O;

$Q_e$ is $NR_{12}$;

$Q_c$ is O, NH, N($C_1$-$C_3$ alkyl), $NCH_2CH=CH_2$, or $NCH_2C\equiv CH$;

$Q_f$ is $S(O)_2$;

$Q_g$ is O or S;

$R_{11}$ is H or $CH_3$; and $R_{13}$ is H or $CH_3$.

9. A compound of claim 8 where

X' is $CH_3$, $OCH_3$, $OCH_2CH_3$ or $OCF_2H$; and

X or Y is $CH_3$, $OCH_3$, $C_2H_5$, $CH_2OCH_3$, $NHCH_3$, $CH(OCH_3)$, Cl or cyclopropyl.

10. A compound of claim 9 where A is A-1.

11. A compound of claim 9 where A is A-2.

12. A compound of claim 9 where A is A-4.

13. A compound of claim 9 where A is A-6.

14. A compound of claim 9 where A is A-7.

15. A compound of claim 9 where A is A-8.

16. A compound of claim 9 where A is A-9.

17. A compound of claim 9 where A is A-11.

18. A compound of claim 9 where A is A-19.

19. A compound of claim 9 where

A is A-1;

L is L-1, L-3, L-4, L-5, L-6, L-7, L-8, L-9, L-11, L-12, L-13, L-14, L-15 or L-16;

$Z_1$ is CH or N; and $Z_2$ is CH or N.

20. A compound of claim 19 where $Z_1$ and $Z_2$ are N.

21. A compound of claim 9 where

A is A-4;

L is L-1, L-3, L-4, L-5, L-6, L-7, L-8, L-9, L-11, L-12, L-13, L-14, L-15 or L-16;

$Z_4$ is O or S; and $Z_1$ is N, CH or $CCH_3$.

22. The compound of claim 1 which is 5,7-Dimethyl-N-[[2-(methylsulfonyl)phenyl]sulfonyl]pyrazolo[1,5-a]pyrimidine-3-carboxamide.

23. The compound of claim 1 which is methyl 2-[[[(5,7-dimethylpyrazolo[1,5-a]pyrimidin-3-yl)carbonyl]amino]sulfonyl]benzoate.

24. The compound of claim 1 which is methyl 2-[[[(5,7-dimethyl[1,2,3]triazolo[1,5-a]pyrimidin-3-yl)carbonyl]amino]sulfonyl]benzoate.

25. The compound of claim 1 which is N-[[2-(1-ethyl-1H-tetrazol-5-yl)phenyl]sulfonyl]-5,7-dimethyl-pyrazolo[1,5-a]pyrimidine-3-carbamate.

26. The compound of claim 1 which is N-[[2-[(dimethylamino)sulfonyl]phenyl]sulfonyl]-5,7-dimethyl[1,2,3]triazolo[1,5-a]pyrimidine-3-carboxamide.

27. The compound of claim 1 which is N-[(2-chlorophenyl)sulfonyl]-5,7-dimethyl[1,2,3]triazolo[1,5-a]pyrimidine-3-carboxamide.

28. The compound of claim 1 which is N-[(2,6-dibromophenyl)sulfonyl]-5,7-dimethyl[1,2,3]-triazolo[1,5-a]pyrimidine-3-carboxamide.

29. A composition suitable for controlling the growth of undesired vegetation which comprises an effective amount of a compound of claim 1 and at least one of the following: surfactant, solid diluent, liquid diluent and mixtures of the foregoing.

30. A composition suitable for controlling the growth of undesired vegetation which comprises an effective amount of a compound of claim 2 and at least one of the following: surfactant, solid diluent, liquid diluent and mixtures of the foregoing.

31. A composition suitable for controlling the growth of undesired vegetation which comprises an effective amount of a compound of claim 3 and at least one of the following: surfactant, solid diluent, liquid diluent and mixtures of the foregoing.

32. A composition suitable for controlling the growth of undesired vegetation which comprises an effective amount of a compound of claim 4 and at least one of the following: surfactant, solid diluent, liquid diluent and mixtures of the foregoing.

33. A composition suitable for controlling the growth of undesired vegetation which comprises an effective amount of a compound of claim 5 and at least one of the following: surfactant, solid diluent, liquid diluent and mixtures of the foregoing.

34. A composition suitable for controlling the growth of undesired vegetation which comprises an effective amount of a compound of claim 6 and at least one of the following: surfactant, solid diluent, liquid diluent and mixtures of the foregoing.

35. A composition suitable for controlling the growth of undesired vegetation which comprises an effective amount of a compound of claim 7 and at least one of the following: surfactant, solid diluent, liquid diluent and mixtures of the foregoing.

36. A composition suitable for controlling the growth of undesired vegetation which comprises an effective amount of a compound of claim 8 and at least one of the following: surfactant, solid diluent, liquid diluent and mixtures of the foregoing.

37. A method for controlling the growth of undesired vegetation which comprises applying to the locus to be protected an effective amount of a compound of claim 1.

38. A method for controlling the growth of undesired vegetation which comprises applying to the locus to be protected an effective amount of a compound of claim 2.

39. A method for controlling the growth of undesired vegetation which comprises applying to the locus to be protected an effective amount of a compound of claim 3.

40. A method for controlling the growth of undesired vegetation which comprises applying to the locus to be protected an effective amount of a compound of claim 4.

41. A method for controlling the growth of undesired vegetation which comprises applying to the locus to be protected an effective amount of a compound of claim 5.

42. A method for controlling the growth of undesired vegetation which comprises applying to the locus to be protected an effective amount of a compound of claim 6.

43. A method for controlling the growth of undesired vegetation which comprises applying to the locus to be protected an effective amount of a compound of claim 7.

44. A method for controlling the growth of undesired vegetation which comprises applying to the locus to be protected an effective amount of a compound of claim 8.

* * * * *